US009005940B2

(12) United States Patent
Zhu et al.

(10) Patent No.: US 9,005,940 B2
(45) Date of Patent: Apr. 14, 2015

(54) DOWN-REGULATION OF A POLYNUCLEOTIDE ENCODING A SOU2 SORBITOL UTILIZATION PROTEIN TO MODIFY LIPID PRODUCTION IN MICROBIAL CELLS

(71) Applicant: E I du Pont de Nemours and Company, Wilmington, DE (US)

(72) Inventors: Quinn Qun Zhu, West Chester, PA (US); Seung-Pyo Hong, Hockessin (DE); Dongming Xie, Newark, DE (US); Zhixiong Xue, Chadds Ford, PA (US); Hyeryoung Yoon, Wilmington, DE (US); Michael Dauner, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 14/132,051

(22) Filed: Dec. 18, 2013

(65) Prior Publication Data

US 2014/0220645 A1    Aug. 7, 2014

Related U.S. Application Data

(60) Provisional application No. 61/740,506, filed on Dec. 21, 2012.

(51) Int. Cl.
*C12P 7/64* (2006.01)
*C12N 9/02* (2006.01)

(52) U.S. Cl.
CPC ............. *C12P 7/6427* (2013.01); *C12P 7/6472* (2013.01); *C12N 9/0036* (2013.01)

(58) Field of Classification Search
None
See application file for complete search history.

(56) References Cited

U.S. PATENT DOCUMENTS

| | | |
|---|---|---|
| 7,238,482 B2 | 7/2007 | Picataggio et al. |
| 7,267,976 B2 | 9/2007 | Yadav et al. |
| 7,732,155 B2 | 6/2010 | Zou et al. |
| 7,932,077 B2 | 4/2011 | Damude et al. |
| 2008/0145867 A1 | 6/2008 | Zou et al. |
| 2009/0093543 A1 | 4/2009 | Xue et al. |
| 2010/0068789 A1 | 3/2010 | Xue et al. |
| 2010/0317072 A1 | 12/2010 | Hong et al. |
| 2010/0317882 A1 | 12/2010 | Yadav et al. |
| 2011/0059496 A1 | 3/2011 | Zhu |
| 2012/0052537 A1 | 3/2012 | Hong et al. |
| 2012/0252079 A1 | 10/2012 | Zhu et al. |
| 2012/0252093 A1 | 10/2012 | Zhu |
| 2013/0089910 A1 | 4/2013 | Zhu |
| 2013/0089911 A1 | 4/2013 | Zhu et al. |

FOREIGN PATENT DOCUMENTS

| | | |
|---|---|---|
| CA | 2517253 | 9/2004 |
| WO | 2004076617 | 9/2004 |

OTHER PUBLICATIONS

Garcera et al., Anchorage of *Candida albicans* SSR1 to the Cell Wall, and Transcript Profiling of the Null Mutant, Research Microbiology (2005), vol. 156, No. 9, pp. 911-920.
Chen et al., The Yeast Acylglycerol Acyltransferase LCA1 is a Key Component of Lands Cycle for Phosphatidylcholine Turnover, FEBS Letters (2007), vol. 581, pp. 5511-5516.
Benghezal et al., SLC1 and SLC4 Encode Partially Redundant Acyl-Coenzyme A 1-Acylglycerol-3-Phosphate O-Acyltransferases of Budding Yeast, J. Biol. Chemistry (2007), vol. 282, No. 42, pp. 30845-30855.
Dahlqvist et al., Phospholipid: Diacylglycerol Acyltransferase: An Enzyme That Catalyzes the Acyl-COA-Independent Formation of Triacylglycerol in Yeast and Plants, PNAS (2000) vol. 97, No. 12, pp. 6487-6492.
Hishikawa et al., Discovery of a Lysophospholipid Acyltransferase Family Essential for Membrane Assymetry and Diversity, PNAS (2008), vol. 105, No. 8, pp. 2830-2835.
Jami et al., The *Penicillium chrysogenum* Extracellular Proteome, Conversion From a Food-Rotting Strain to a Versatile Cell Factory for White Biotechnology, Molecular & Cellular Proteomics (2010), vol. 9, pp. 2729-2744.
Janbon et al., Monosomy of a Specific Chromosome Determins L-Sorbose Utilization: A Novel Regulatory Mechanism in *Candida albicans*, PNAS (1998), vol. 95, pp. 5150-5155.
Lee et al., *Caenorhabditis elegans* MBOA-7, a Member of the MBOAT Family, Is Required for Selective Incorporation of Polyunsaturated Fatty Acids Into Phosphatidylinositol, Molecular Biology of the Cell (2008), vol. 19, pp. 1174-1184.
Oelkers et al., A Lecithin Cholesterol Acyltransferase-Like Gene Mediates Diacylglycerol Esterification in Yeast, J. Biol. Chemistry (2000), vol. 275, No. 21, pp. 15609-15612.
Riekhof et al., Identification and Characterization of the Major Lysophosphatidylethanolamine Acyltransferase in *Saccharomyces cerevisiae*, J. Biol. Chemistry (2007), vol. 282, No. 39, pp. 28344-28352.
Shindou et al., Identification of Membrane O-Acyltransferase Family Motifs, Biochemical and Biophysical Research Communications (2009), vol. 383, pp. 320-325.
Stahl et al., A Family of Eukaryotic Lysophospholipid Acyltransferases With Broad Specificity, FEBS Letters (2008), vol. 582, pp. 305-309.
Tamaki et al., LPT1 Encodes a Membrane-Bound O-Acyltransferase Involved in the Acylation of Lysophospholipids in the Yeast *Saccharomyces cerevisiae* (2007), vol. 282, No. 47, pp. 34288-34298.

*Primary Examiner* — Nashaat Nashed

(57) ABSTRACT

Recombinant microbial cells are disclosed herein that comprise (i) a down-regulation of an endogenous polynucleotide sequence encoding Sou2 sorbitol utilization protein, and (ii) a polyunsaturated fatty acid (PUFA) biosynthetic pathway. The down-regulation of the polynucleotide sequence encoding Sou2 sorbitol utilization protein can increase the lipid content of the microbial cells and/or decrease the total amount of sugar alcohols produced by the microbial cells. Also disclosed are methods of using the recombinant microbial cells to produce oil containing omega-3 polyunsaturated fatty acids such as EPA.

14 Claims, 11 Drawing Sheets

Figure 1:
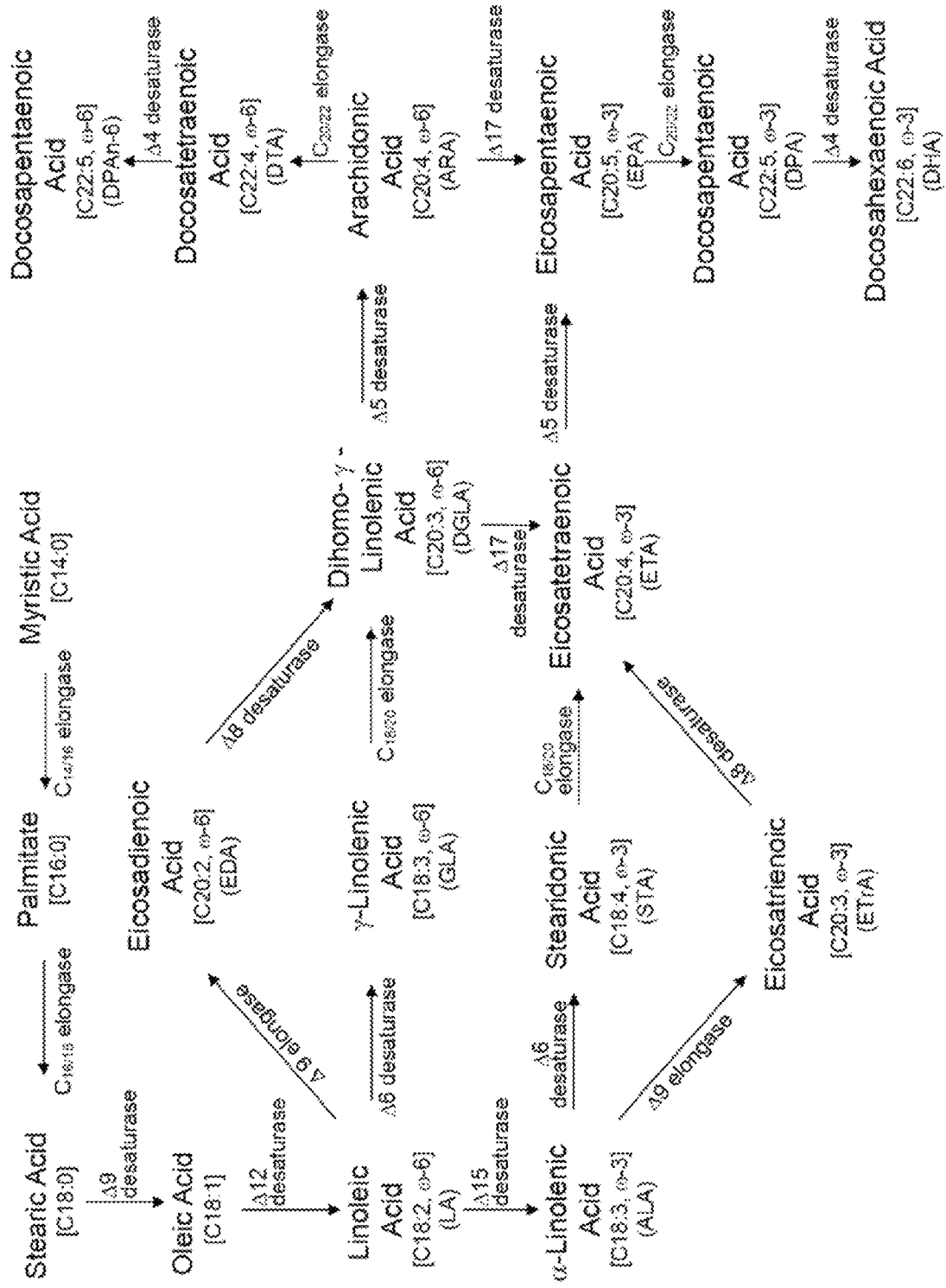

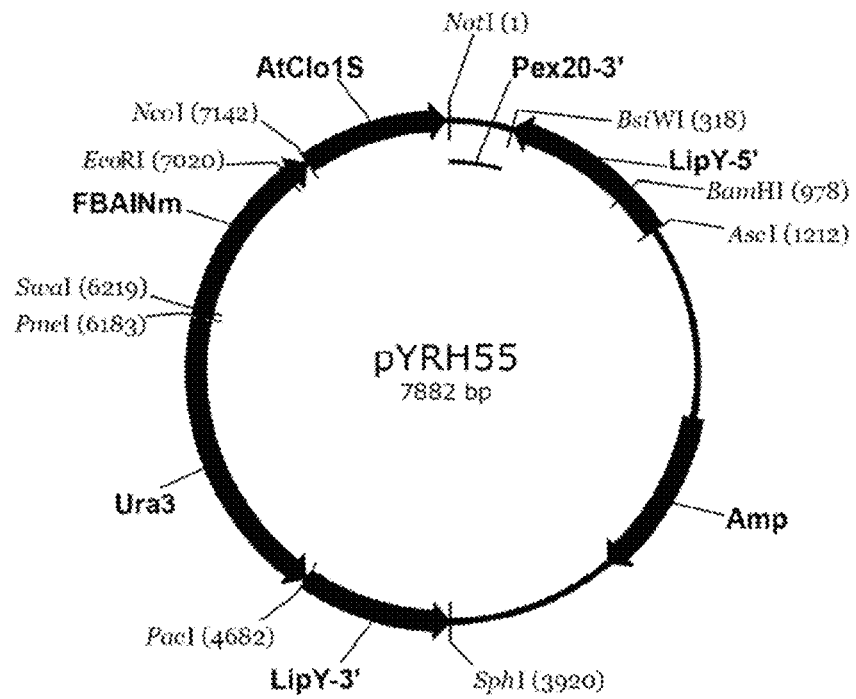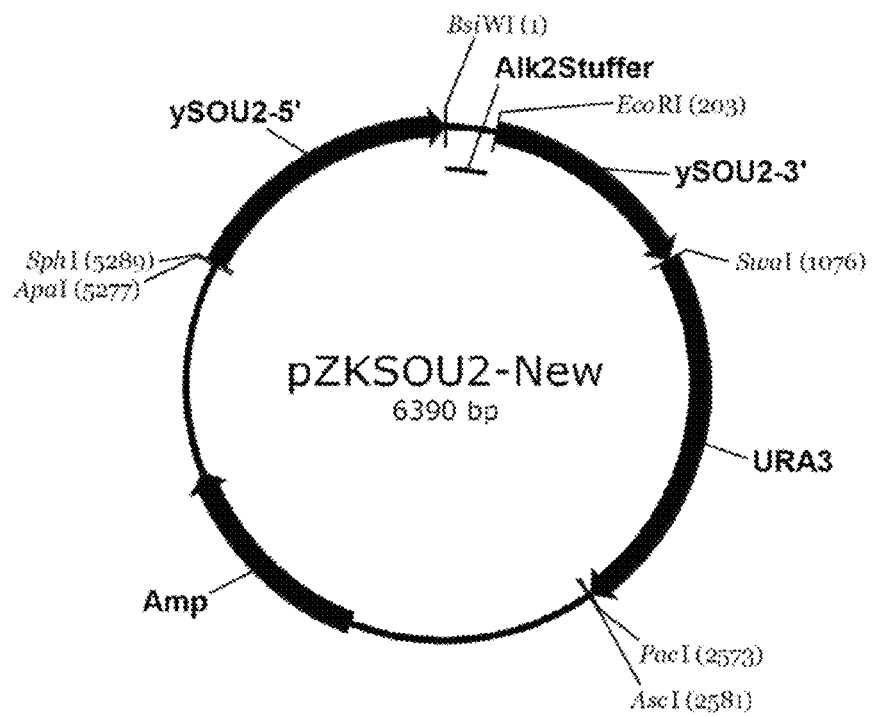
Figure 4

TGACGAGGGGTGTTTGGGCGCTGGAAGCGTAATTTTCGTCTTGAATGGGCCGTCGAGACTTGGGGTTCGACCCGACTAAATGGGC
ACCGCTAGATTCTCTCTTTTGGCGACTTCGGGATTCTAGTCACCCGCAATGTTCCAGCTTACGGTTTGAGACAGTACACGACTG
GCTAGCGAGTGTTGAAGTCGTAGCGTAGAGGTGGAGGCATGACGTGCGTGCACCGGACAGCTGCGCTGCACCACGCAGGCAATTGA
CCTCATTTGAGTGGTGTGGCTTGGCGTTCTAGCGGTTGGCGGGCGTTGTCGAGCGTTCTACTTGTAGTGAGATTATGTCGACGAGCG
GGGGGACTTCCATTGTGCTTGCTGCCACTGCTAGTGCAGTACAACTGAAAGCTAAACCCAAACTGCATGTCCGCCTTA
ACTCTGATATGTTATCAAGAGAGTGGTTGGTGTGAGGTGAGGTGACGTGAGGTGACAAGTTGATGGGGAGTTGGGCATTGACAAAA
GGGAAATTGCAGGGGATTCCGCCGGTACATAATCTTATGTCTGTCACTCATCCATTCCGCTCCACACAAAACCAAGATACCACA
CCATCATGGTCACACGGGTACACATAACTAACCTCCCCGAAAATTAACTTCACTGACATGGCCAGCTATTAAGGCTAAAGTGAATGCATGGCTCATC
TCGGCGCGGTCCCCAGGGCGACAAATCACGAGTGACTTCCGAAAGCCGCGTTCCAACACA▲CCCCCAAAATCCCCCC
CTCAAACACGTCAGCACCTGTCCCCGAAAATTAACTTCACTGACATGGCCAGCTATTAAGGCTAAAGTGAATGCATGGCTCATC
TTTGTTTGCTGGTTGCTACTGTGACTGAGGTAAAACCCTGCTCAATCATGTCTCCCTTCCACCCTCGCCACGGGACTGCACCCTC
CGTCACAGTAAACTACTACCTCCATACACAGCACCACTCAATCATGTCTCCCTTCAAGGTGTTGCCTCAGCGTGACGCAAAG
CCCACAGAGACCCCAAAGTTCCCACCAAGCATCATGGACCGATTCTCCCTTCAAGGTAAGGTTGCCTCCAGCGTGACGCAAAG
GGTATCGGCTACTGCCGTGCCGAGGCCTACGCCGGTGCCATCGTCCAGTGCCATCTGTACAACTCCACCGGACGCCGCC▲CGTGGAGTCCACCAT
GCTGAGCACCTCGCTAAGAAGACCTACGGCGTCAAGGCCTACAAGTGCCCCTGTCCACCGAAGTGCCCGGCCGACCCGGCCCCATGATCGACGT
CCAGCAGATCGAGAAGGACTTTGGCACCATTGACATTGACATCTTCGTCGTGTGCCCTGGATCTCAACCTGGCCTACGCCGGTGCCACGGGCCAAGTAGCCGGCCAAGTACGCCGGCCTGCTACAACGC
GAAGAAGGGCAAGGGCGCTCTGCTGCCCGACTTGTGTCCCAAGGAGACCAAGGAGACCAAGGAGTGGTGGCCGGCCCTTGCCCGATGCAACACAGTCTCCCCTGGCTA
CGGCCAAGGCCACCGAGATCTCCGACTTGTGTCCCAAGGAGACCAAGGAGACCAAGGAGTGGTGGCCGGCCCATGGGCCGAGAGGGAGACCC
CATGGCCACCGAGATCTCCGACTTGTGTCCCAAGGAGACCAAGGAGACCAAGGAGTGGTGGCCGGCCCATGGGCCGAGAGGGAGACCC
CTCCGAGCTCTACCTCTACCTTGCCCTGATGCTGCCACCACTGGTTCGTCATTATCGTGGTGTGCTACTGCG
CTCCTTAGAGGATGTATAGATACATTGATTGTTTATGAATGATCTCGAATACATTGAATTACATAACAAGTGACAGCAATTAGCAGTCAGATAGGCAACG
AAGATCATCCAAGTCTGAATACAGCACATACATATACAAATCATACATATACAAGTCATAAATGATGAATTACTACATATAAGTATGATATTACTTGTACC
GAATTGCCAATGAATGTCAATCAGAACGCCAGTATGTCACAACGCCACTATCATAAGGCACTCGAATGT (SEQ ID NO:8)

Figure 5

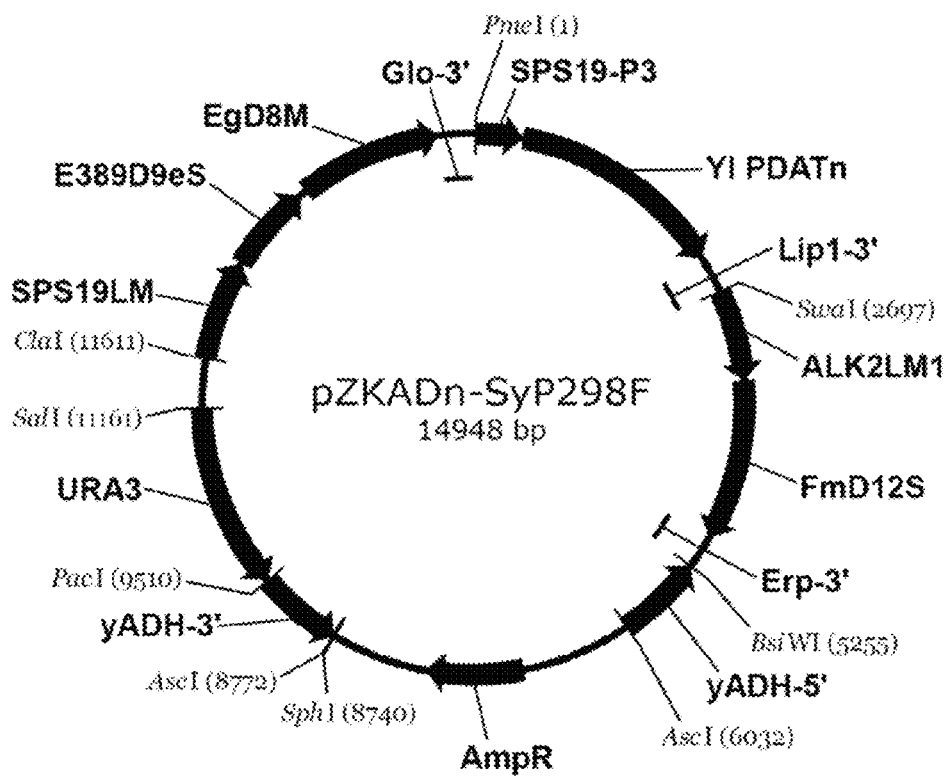
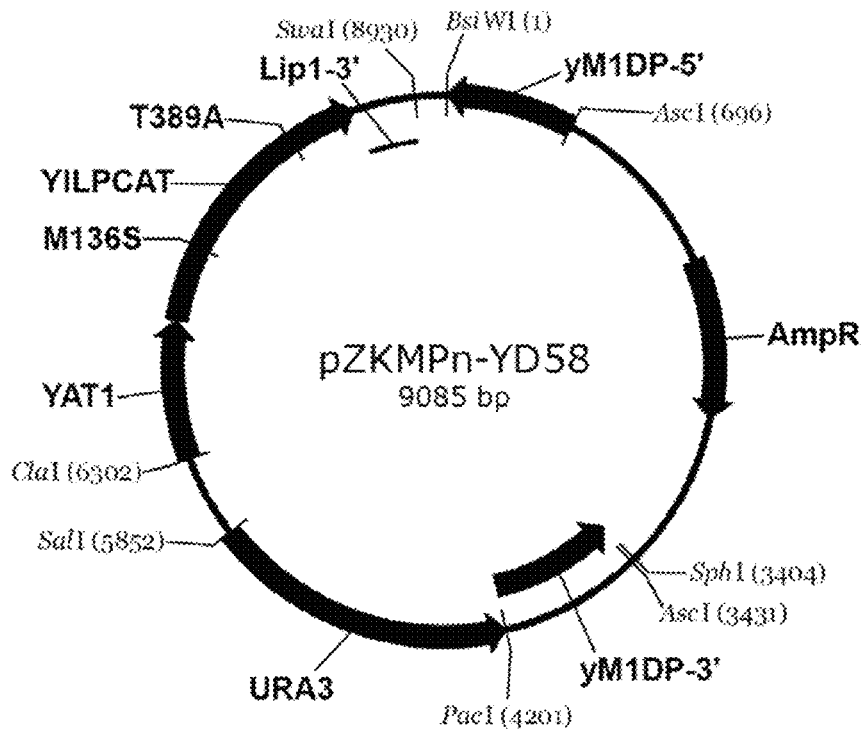
Figure 7

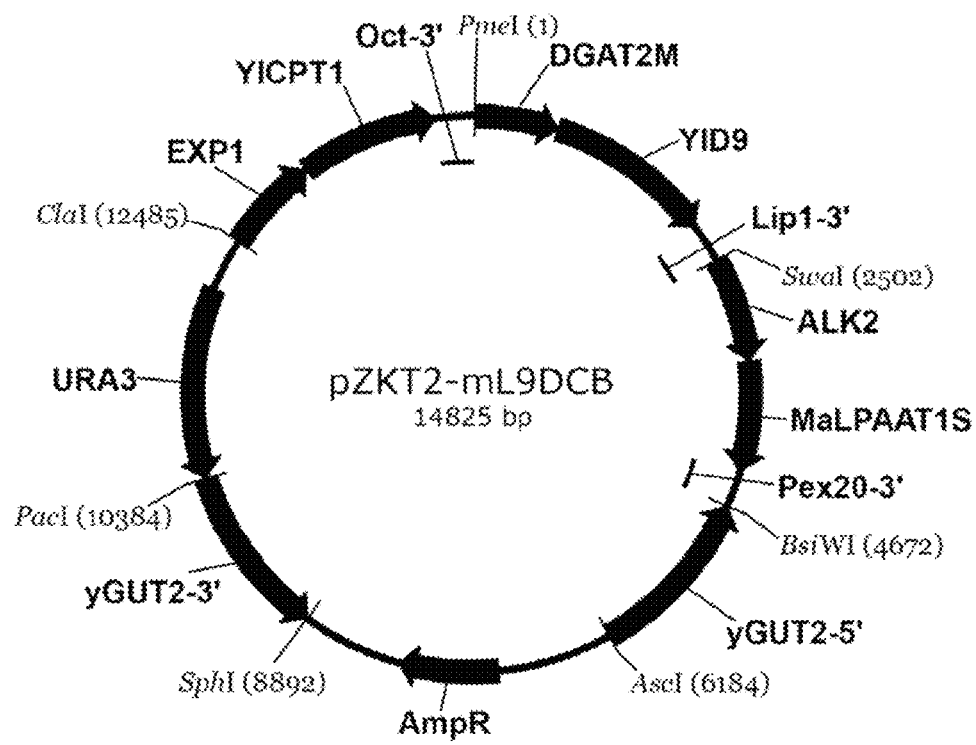
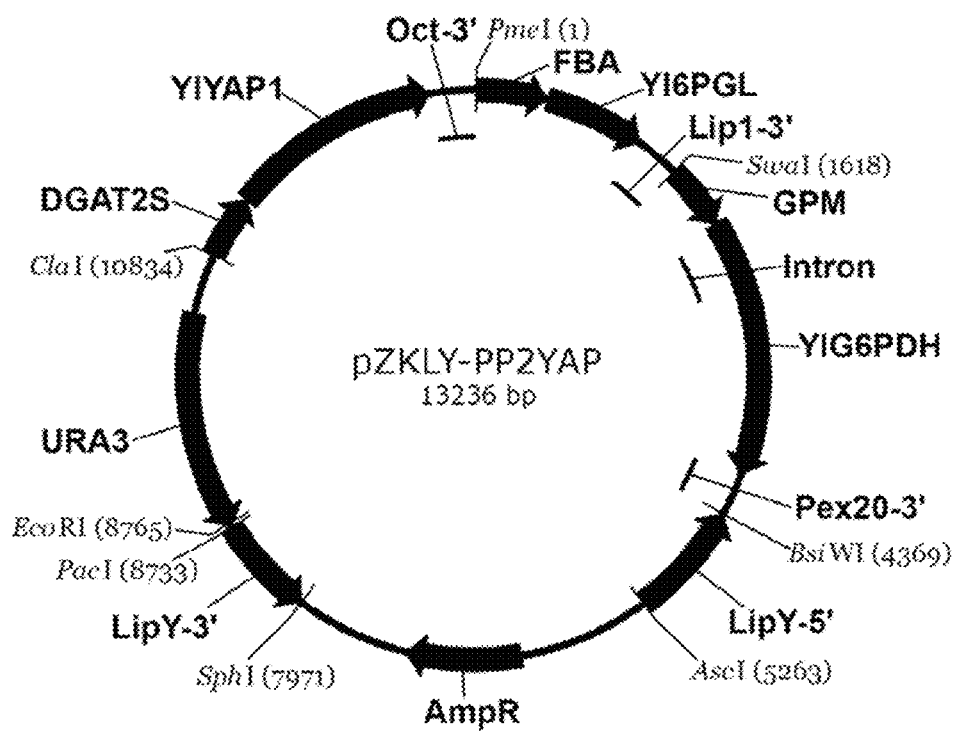
Figure 9

SEQUENCE LISTING

```
<160> NUMBER OF SEQ ID NOS: 106

<210> SEQ ID NO 1
<211> LENGTH: 7880
<212> TYPE: DNA
<213> ORGANISM: Artificial sequence
<220> FEATURE:
<223> OTHER INFORMATION: Construct pYRH55 for expressing AtClo1S

<400> SEQUENCE: 1
ggccgcaagt gtggatgggg aagtgagtgc ccggttctgt gtgcacaatt ggcaatccaa      60
gatggatgga ttcaacacag ggatatagcg agctacgtgg tggtgcgagg atatagcaac     120
ggatatttat gtttgacact tgagaatgta cgatacaagc actgtccaag tacaatacta     180
aacatactgt acatactcat actcgtaccc gggcaacggt tcacttgag tgcagtggct      240 agtgctctta ctcgtacagt gtgcaatact gcgtatcata gtctttgatg tatatcgtat     300
tcattcatgt tagttgcgta cgttgattga ggtgagcca gatgggctat tgtttcatat     360
atagactggc agccacctct ttggcccagc atgtttgtat acctggaagg gaaaactaaa     420
gaagctggct agtttagttt gattattata gtagatgtcc taatcactag agattagaat     480
gtcttggcga tgattagtcg tcgtcccctg tatcatgtct agaccaactg tgtcatgaag    540
```

-continued

```
ttggtgctgg tgttttacct gtgtactaca agtaggtgtc ctagatctag tgtacagagc    600
cgtttagacc catgtggact tcaccattaa cgatggaaaa tgttcattat atgacagtat    660
attacaatgg acttgctcca tttcttcctt gcatcacatg ttctccacct ccatagttga    720
tcaacacatc atagtagcta aggctgctgc tctcccacta cagtccacca caagttaagt    780
agcaccgtca gtacagctaa agtacacgt ctagtacgtt tcataactag tcaagtagcc    840
cctattacag atatcagcac tatcacgcac gagttttct ctgtgctatc taatcaactt    900
gccaagtatt cggagaagat acactttctt ggcatcaggt atacgaggga gcctatcaga    960
tgaaaaaggg tatattggat ccattcatat ccacctacac gttgtcataa tctcctcatt    1020
cacgtgattc atttcgtgac actagtttct cactttcccc cccgcaccta tagtcaactt    1080
ggcggacacg ctacttgtag ctgacgttga tttatagacc caatcaaagc gggttatcgg    1140
tcaggtagca cttatcattc atcgttcata ctacgatgag caatctcggg catgtccgga    1200
aaagtgtcgg gcgcgccagc tgcattaatg aatcggccaa cgcgcgggga gaggcggttt    1260
gcgtattggg cgctcttccg cttcctcgct cactgactcg ctgcgctcgg tcgttcggct    1320
gcggcgagcg gtatcagctc actcaaaggc ggtaatacgg ttatccacag aatcagggga    1380
taacgcagga aagaacatgt gagcaaaagg ccagcaaaag gccaggaacc gtaaaaaggc    1440
cgcgttgctg gcgttttcc ataggctccg cccccctgac gagcatcaca aaaatcgacg    1500
ctcaagtcag aggtggcgaa acccgacagg actataaaga taccaggcgt ttccccctgg    1560
aagctccctc gtgcgctctc ctgttccgac cctgccgctt accggatacc tgtccgcctt    1620
tctcccttcg ggaagcgtgg cgctttctca tagctcacgc tgtaggtatc tcagttcggt    1680
gtaggtcgtt cgctccaagc tgggctgtgt gcacgaaccc cccgttcagc ccgaccgctg    1740
cgccttatcc ggtaactatc gtcttgagtc caacccggta agacacgact tatcgccact    1800
ggcagcagcc actggtaaca ggattagcag agcgaggtat gtaggcggtg ctacagagtt    1860
cttgaagtgg tggcctaact acggctacac tagaagaaca gtatttggta tctgcgctct    1920
gctgaagcca gttaccttcg gaaaaagagt tggtagctct tgatccggca aacaaaccac    1980
cgctggtagc ggtggttttt tgtttgcaa gcagcagatt acgcgcagaa aaaaaggatc    2040
tcaagaagat cctttgatct tttctacggg gtctgacgct cagtggaacg aaaactcacg    2100
ttaagggatt ttggtcatga gattatcaaa aaggatcttc acctagatcc ttttaaatta    2160
aaaatgaagt tttaaatcaa tctaaagtat atatgagtaa acttggtctg acagttacca    2220
atgcttaatc agtgaggcac ctatctcagc gatctgtcta tttcgttcat ccatagttgc    2280
ctgactcccc gtcgtgtaga taactacgat acgggagggc ttaccatctg gccccagtgc    2340
tgcaatgata ccgcgagacc cacgctcacc ggctccagat ttatcagcaa taaaccagcc    2400
agccggaagg gccgagcgca gaagtggtcc tgcaactta ccgcctcca tccagtctat    2460 taattgttgc cgggaagcta gagtaagtag ttcgccagtt aatagtttgc gcaacgttgt    2520
tgccattgct acaggcatcg tggtgtcacg ctcgtcgttt ggtatggctt cattcagctc    2580
cggttcccaa cgatcaaggc gagttacatg atcccccatg ttgtgcaaaa aagcggttag    2640
ctccttcggt cctccgatcg ttgtcagaag taagttggcc gcagtgttat cactcatggt    2700
tatggcagca ctgcataatt ctcttactgt catgccatcc gtaagatgct tttctgtgac    2760
tggtgagtac tcaaccaagt cattctgaga atagtgtatg cggcgaccga gttgctcttg    2820
cccggcgtca atacgggata ataccgcgcc acatagcaga actttaaaag tgctcatcat    2880
tggaaaacgt tcttcggggc gaaaactctc aaggatctta ccgctgttga tccagttc    2940
```

```
gatgtaaccc actcgtgcac ccaactgatc ttcagcatct tttactttca ccagcgtttc   3000
tgggtgagca aaaacaggaa ggcaaaatgc cgcaaaaaag ggaataaggg cgacacggaa   3060
atgttgaata ctcatactct tccttttca atattattga agcatttatc agggttattg   3120
tctcatgagc ggatacatat ttgaatgtat ttagaaaaat aaacaaatag gggttccgcg   3180
cacatttccc cgaaaagtgc cacctgatgc ggtgtgaaat accgcacaga tgcgtaagga   3240
gaaaataccg catcaggaaa ttgtaagcgt taatattttg ttaaaattcg cgttaaattt   3300
ttgttaaatc agctcatttt ttaaccaata ggccgaaatc ggcaaaatcc cttataaatc   3360
aaaagaatag accgagatag ggttgagtgt tgttccagtt tggaacaaga gtccactatt   3420
aaagaacgtg gactccaacg tcaaagggcg aaaaccgtc tatcagggcg atggcccact   3480
acgtgaacca tcaccctaat caagtttttt ggggtcgagg tgccgtaaag cactaaatcg   3540
gaaccctaaa gggagccccc gatttagagc ttgacgggga agccggcga acgtggcgag   3600 aaaggaaggg aagaaagcga aaggagcggg cgctagggcg ctggcaagtg tagcggtcac   3660
gctgcgcgta accaccacac ccgccgcgct taatgcgccg ctacagggcg cgtccattcg   3720
ccattcaggc tgcgcaactg ttgggaaggg cgatcggtgc gggcctcttc gctattacgc   3780
cagctggcga aggggggatg tgctgcaagg cgattaagtt gggtaacgcc agggttttcc   3840
cagtcacgac gttgtaaaac gacggccagt gaattgtaat acgactcact atagggcgaa   3900
ttgggcccga cgtcgcatgc attccgacag cagcgactgg gcaccatgat caagcgaaac   3960
accttccccc agctgccctg gcaaaccatc aagaacccta ctttcatcaa gtgcaagaac   4020
ggttctactc ttctcacctc cggtgtctac ggctggtgcc gaaagcctaa ctacaccgct   4080
gatttcatca tgtgcctcac ctgggctctc atgtgcggtg ttgcttctcc cctgccttac   4140
ttctacccgg tcttcttctt cctggtgctc atccaccgag cttaccgaga ctttgagcga   4200
ctggagcgaa agtacggtga ggactaccag gagttcaagc gacaggtccc cttggatcttc   4260 atcccttatg ttttctaaac gataagctta gtgagcgaat ggtgaggtta cttaattgag   4320
tggccagcct atgggattgt ataacagaca gtcaatatat tactgaaaag actgaacagc   4380
cagacggagt gaggttgtga gtgaatcgta gagggcggct attacagcaa gtctactcta   4440
cagtgtacta acacagcaga gaacaaatac aggtgtgcat tcggctatct gagaattagt   4500
tggagagctc gagaccctcg gcgataaact gctcctcggt tttgtgtcca tacttgtacg   4560
gaccattgta atggggcaag tcgttgagtt ctcgtcgtcc gacgttcaga gcacagaaac   4620
caatgtaatc aatgtagcag agatggttct gcaaaagatt gatttgtgcg agcaggttaa   4680
ttaagtcata cacaagtcag ctttcttcga gcctcatata agtataagta gttcaacgta   4740
ttagcactgt acccagcatc tccgtatcga gaaacacaac aacatgcccc attggacaga   4800
tcatgcggat acacaggttg tgcagtatca tacatactcg atcagacagg tcgtctgacc   4860
atcatacaag ctgaacaagc gctccatact tgcacgctct ctatatacac agttaaatta   4920
catatccata gtctaacctc taacagttaa tcttctggta agcctcccag ccagccttct   4980
ggtatcgctt ggcctcctca ataggatctc ggttctggcc gtacagacct cggccgacaa   5040
ttatgatatc cgttccggta gacatgacat cctcaacagt tcggtactgc tgtccgagag   5100
cgtctccctt gtcgtcaaga cccaccccgg gggtcagaat aagccagtcc tcagagtcgc   5160
ccttaggtcg gttctgggca atgaagccaa ccacaaactc ggggtcggat cgggcaagct   5220
caatggtctg cttggagtac tcgccagtgg ccagagagcc cttgcaagac agctcggcca   5280
```

```
gcatgagcag acctctggcc agcttctcgt tgggagaggg gactaggaac tccttgtact   5340
gggagttctc gtagtcagag acgtcctcct tcttctgttc agagacagtt tcctcggcac   5400
cagctcgcag gccagcaatg attccggttc cgggtacacc gtgggcgttg gtgatatcgg   5460
accactcggc gattcggtga caccggtact ggtgcttgac agtgttgcca atatctgcga   5520
actttctgtc ctcgaacagg aagaaaccgt gcttaagagc aagttccttg aggggagca   5580
cagtgccggc gtaggtgaag tcgtcaatga tgtcgatatg ggttttgatc atgcacacat   5640
aaggtccgac cttatcggca agctcaatga gctccttggt ggtggtaaca tccagagaag   5700
cacacaggtt ggttttcttg gctgccacga gcttgagcac tcgagcggca aggcggact    5760
tgtggacgtt agctcgagct tcgtaggagg gcattttggt ggtgaagagg agactgaaat   5820
aaatttagtc tgcagaactt tttatcggaa ccttatctgg ggcagtgaag tatatgttat    5880
ggtaatagtt acgagttagt tgaacttata gatagactgg actatacggc tatcggtcca   5940
aattagaaag aacgtcaatg gctctctggg cgtcgccttt gccgacaaaa atgtgatcat   6000
gatgaaagcc agcaatgacg ttgcagctga tattgttgtc ggccaaccgc gccgaaaacg   6060
cagctgtcag acccacagcc tccaacgaag aatgtatcgt caaagtgatc caagcacact   6120
catagttgga gtcgtactcc aaaggcggca atgacgagtc agacagatac tcgtcgacgt   6180
ttaaacagtg tacgcagatc tactatagag gaacatttaa attgccccgg agaagacggc   6240
caggccgcct agatgacaaa ttcaacaact cacagctgac tttctgccat gccactagg    6300
gggggggcctt tttatatggc caagccaagc tctccacgtc ggttgggctg cacccaacaa   6360
taaatgggta gggttgcacc aacaaaggga tgggatgggg ggtagaagat acgaggataa   6420
cggggctcaa tggcacaaat aagaacgaat actgccatta agactcgtga tccagcgact   6480
gacaccattg catcatctaa gggcctcaaa actacctcgg aactgctgcg ctgatctgga   6540
caccacagag gttccgagca ctttaggttg caccaaatgt cccaccaggt gcaggcagaa   6600
aacgctggaa cagcgtgtac agtttgtctt aacaaaaagt gagggcgctg aggtcgagca   6660
gggtggtgtg acttgttata gcctttagag ctgcgaaagc gcgtatggat ttggctcatc   6720
aggccagatt gagggtctgt ggacacatgt catgttagtg tacttcaatc gccccctgga   6780
tatagccccg acaataggcc gtggcctcat ttttttgcct tccgcacatt tccattgctc   6840
gatacccaca ccttgcttct cctgcacttg ccaaccttaa tactggttta cattgaccaa   6900
catcttacaa gcgggggggct tgtctagggt atatataaac agtggctctc ccaatcggtt   6960
gccagtctct ttttcctttt ctttccccac agattcgaaa tctaaactac acatcacaga   7020
attccgagcc gtgagtatcc acgacaagat cagtgtcgag acgacgcgtt ttgtgtaatg   7080
acacaatccg aaagtcgcta gcaacacaca ctctctacac aaactaaccc agctctggta   7140
ccatgggctc caagaccgag atgatggagc gagacgctat ggccaccgtc gctccttacg   7200
cacccgttac ctaccaccga agagcccgag tcgacctgga cgatcgactt cccaaacctt   7260
acatgcctcg agccctgcag gctcctgacc gagagcatcc ctacgaaact cctggtcaca   7320
agaactacgg cctctccgtg ctgcagcagc atgtctcttt ctttgacatt gatgacaacg   7380
gaatcattta ccctgggag acctactccg gtctgcggat gctcggcttc aacatcattg   7440
gatctctgat cattgccgct gtcatcaacc ttacactcag ctacgccacc ctgcctggtt   7500
ggcttccctc tcccttcttt cccatctaca ttcacaacat tcataagtcc aagcacggct   7560
ccgacagcaa gacttacgac aatgaaggac gattcatgcc cgtcaacctc gagctgatct   7620
tctcgaagta cgccaagacc ctgcccgaca agctctcctt gggagagctg tgggagatga   7680
```

```
ccgaaggcaa ccgagatgct tgggacatct ttggatggat tgccggcaag atcgagtggg   7740
gtctgctcta cctgctcgct cgagacgagg aaggcttctt gtccaaggag gccattcgaa   7800
gatgctttga cggttctctg ttcgagtact gtgccaagat ctatgctggt atcagcgagg   7860
ataagaccgc atactattaa                                                7880

<210> SEQ ID NO 2
<211> LENGTH: 738
<212> TYPE: DNA
<213> ORGANISM: Artificial sequence
<220> FEATURE:
<223> OTHER INFORMATION: A. thaliana caleosin-1 codon-omptimized for
      expression in Y. lipolytica

<400> SEQUENCE: 2
atgggctcca agaccgagat gatggagcga gacgctatgg ccaccgtcgc tccttacgca    60
cccgttacct accaccgaag agcccgagtc gacctggacg atcgacttcc caaaccttac   120
atgcctcgag ccctgcaggc tcctgaccga gagcatccct acggaactcc tggtcacaag   180
aactacggcc tctccgtgct gcagcagcat gtctctttct tgacattga tgacaacgga   240 atcatttacc cctgggagac ctactccggt ctgcggatgc tcggcttcaa catcattgga   300
tctctgatca ttgccgctgt catcaacctt acactcagct acgccaccct gcctggttgg   360
cttcccctct ccttctttcc catctacatt acaacattc ataagtccaa gcacggctcc    420
gacagcaaga cttacgacaa tgaaggacga ttcatgcccg tcaacctcga gctgatcttc   480
tcgaagtacg ccaagaccct gcccgacaag ctctccttgg gagagctgtg ggagatgacc   540
gaaggcaacc gagatgcttg ggacatcttt ggatggattg ccggcaagat cgagtggggt   600
ctgctctacc tgctcgctcg agacgaggaa ggcttcttgt ccaaggaggc cattcgaaga   660
tgctttgacg gttctctgtt cgagtactgt gccaagatct atgctggtat cagcgaggat   720
aagaccgcat actattaa                                                 738

<210> SEQ ID NO 3
<211> LENGTH: 245
<212> TYPE: PRT
<213> ORGANISM: Arabidopsis thaliana

<400> SEQUENCE: 3

Met Gly Ser Lys Thr Glu Met Met Glu Arg Asp Ala Met Ala Thr Val
1               5                   10                  15

Ala Pro Tyr Ala Pro Val Thr Tyr His Arg Arg Ala Arg Val Asp Leu
            20                  25                  30

Asp Asp Arg Leu Pro Lys Pro Tyr Met Pro Arg Ala Leu Gln Ala Pro
        35                  40                  45

Asp Arg Glu His Pro Tyr Gly Thr Pro Gly His Lys Asn Tyr Gly Leu
    50                  55                  60

Ser Val Leu Gln Gln His Val Ser Phe Phe Asp Ile Asp Asp Asn Gly
65                  70                  75                  80

Ile Ile Tyr Pro Trp Glu Thr Tyr Ser Gly Leu Arg Met Leu Gly Phe
                85                  90                  95

Asn Ile Ile Gly Ser Leu Ile Ala Ala Val Ile Asn Leu Thr Leu
            100                 105                 110

Ser Tyr Ala Thr Leu Pro Gly Trp Leu Pro Ser Pro Phe Phe Pro Ile
        115                 120                 125

Tyr Ile His Asn Ile His Lys Ser Lys His Gly Ser Asp Ser Lys Thr
```

```
            130                 135                 140
Tyr Asp Asn Glu Gly Arg Phe Met Pro Val Asn Leu Glu Leu Ile Phe
145                 150                 155                 160

Ser Lys Tyr Ala Lys Thr Leu Pro Asp Lys Leu Ser Leu Gly Glu Leu
                165                 170                 175

Trp Glu Met Thr Glu Gly Asn Arg Asp Ala Trp Asp Ile Phe Gly Trp
            180                 185                 190

Ile Ala Gly Lys Ile Glu Trp Gly Leu Leu Tyr Leu Leu Ala Arg Asp
        195                 200                 205

Glu Glu Gly Phe Leu Ser Lys Glu Ala Ile Arg Arg Cys Phe Asp Gly
    210                 215                 220

Ser Leu Phe Glu Tyr Cys Ala Lys Ile Tyr Ala Gly Ile Ser Glu Asp
225                 230                 235                 240

Lys Thr Ala Tyr Tyr
            245

<210> SEQ ID NO 4
<211> LENGTH: 6390
<212> TYPE: DNA
<213> ORGANISM: Artificial sequence
<220> FEATURE:
<223> OTHER INFORMATION: Construct pZKSOU2-New for down-regulating
      endogenous Y. lipolytica SOU2 expression

<400> SEQUENCE: 4
gtacgggcgg atgttgactc aattgaagct agatcaacag gactttatta ttcagctcca      60
aaaaatcctc acattacata aatttctctc cccccgtaac ctggatgtgc tccaaatcag     120
cttctctcgg ggacagagat gtatcacctc ggagaatatc tgtccgattt gaatgatatc     180
aactgtaatg gacttaaccg ggaattcgtg gagtccacca tccagcagat cgagaaggac     240
tttggcacca ttgacatctt cgtcgccaac gctggtgtcc cctggaccgc cggccccatg     300
atcgacgtgc ccgacaacaa ggagtgggac aaggtcatca acctggatct caacggtgcc     360
tactactgcg ccaagtacgc cggccagatc ttcaagaaga agggcaaggg atccttcatc     420
ttcaccgcct ccatgtccgg ccacattgtc aacatccccc agatgcaggc ctgctacaac     480
gccgccaagg ccgctctgct gcacctgtct cgatcgctgg ccgtcgagtg ggccggcttt     540
gcccgatgca acacagtctc ccctggctac atggccaccg agatctccga ctttgtcccc     600
aaggagacca aggagaagtg gtggcagctc attcccatgg ccgagaggg agacccctcc     660 gagctctacc tacctctacc ttgcctctga tgctgccacc tacaccactg gtgccgacat     720
tatcgtcgat ggtggctact gcgctcctta gaggatgtat atagataatg attgtttatg     780
attagacatt gattgagtgt agttggacat tagcagtcag ataggcaacg aagatcatcc     840
aagtctgaat acatacccat acaaatcata caagtaaatg atggaattac tcatataagt     900
atgtacttac ttgtaccgaa ttgccaatga atgtcaatca gaacgcagta tgtacaagta     960
ctcgcacaat atcataaggc actcgaatgt tcaagaagtc atcattttgg tgattcgggg    1020
aaatacttga caccttttgtt gatgcaactt gactccataa gtaggaaacc catttaaatg    1080
agtatctgtc tgactcgtca ttgccgcctt tggagtacga ctccaactat gagtgtgctt    1140
ggatcacttt gacgatacat tcttcgttgg aggctgtggg tctgacagct gcgttttcgg    1200
cgcggttggc cgacaacaat atcagctgca acgtcattgc tggctttcat catgatcaca    1260
tttttgtcgg caaaggcgac gcccagagag ccattgacgt tctttctaat ttggaccgat    1320
agccgtatag tccagtctat ctataagttc aactaactcg taactattac cataacatat    1380
```

```
acttcactgc cccagataag gttccgataa aaagttctgc agactaaatt tatttcagtc    1440
tcctcttcac caccaaaatg ccctcctacg aagctcgagc taacgtccac aagtccgcct    1500
ttgccgctcg agtgctcaag ctcgtggcag ccaagaaaac caacctgtgt gcttctctgg    1560
atgttaccac caccaaggag ctcattgagc ttgccgataa ggtcggacct tatgtgtgca    1620
tgatcaaaac ccatatcgac atcattgacg acttcaccta cgccggcact gtgctccccc    1680
tcaaggaact tgctcttaag cacggtttct tcctgttcga ggacagaaag ttcgcagata    1740
ttggcaacac tgtcaagcac cagtaccggt gtcaccgaat cgccgagtgg tccgatatca    1800
ccaacgccca cggtgtaccc ggaaccggaa tcattgctgg cctgcgagct ggtgccgagg    1860
aaactgtctc tgaacagaag aaggaggacg tctctgacta cgagaactcc cagtacaagg    1920
agttcctagt cccctctccc aacgagaagc tggccagagg tctgctcatg ctggccgagc    1980
tgtcttgcaa gggctctctg gccactggcg agtactccaa gcagaccatt gagcttgccc    2040
gatccgaccc cgagtttgtg gttggcttca ttgcccagaa ccgacctaag ggcgactctg    2100
aggactggct tattctgacc cccggggtgg gtcttgacga caagggagac gctctcggac    2160
agcagtaccg aactgttgag gatgtcatgt ctaccggaac ggatatcata attgtcggcc    2220
gaggtctgta cggccagaac cgagatccta ttgaggaggc caagcgatac cagaaggctg    2280
gctgggaggc ttaccagaag attaactgtt agaggttaga ctatggatat gtaatttaac    2340
tgtgtatata gagagcgtgc aagtatggag cgcttgttca gcttgtatga tggtcagacg    2400
acctgtctga tcgagtatgt atgatactgc acaacctgtg tatccgcatg atctgtccaa    2460
tggggcatgt tgttgtgttt ctcgatacgg agatgctggg tacagtgcta atacgttgaa    2520
ctacttatac ttatatgagg ctcgaagaaa gctgacttgt gtatgactta attaacgcgg    2580
cgcgccagct gcattaatga atcggccaac gcgcggggag aggcggtttg cgtattgggc    2640
gctcttccgc ttcctcgctc actgactcgc tgcgctcggt cgttcggctg cggcgagcgg    2700
tatcagctca ctcaaaggcg gtaatacggt tatccacaga atcaggggat aacgcaggaa    2760
agaacatgtg agcaaaaggc cagcaaaagg ccaggaaccg taaaaaggcc gcgttgctgg    2820
cgttttccca taggctccgc cccccctgacg agcatcacaa aaatcgacgc tcaagtcaga    2880
ggtggcgaaa cccgacagga ctataaagat accaggcgtt tccccctgga agctccctcg    2940
tgcgctctcc tgttccgacc ctgccgctta ccggatacct gtccgccttt ctcccttcgg    3000
gaagcgtggc gctttctcat agctcacgct gtaggtatct cagttcggtg taggtcgttc    3060
gctccaagct gggctgtgtg cacgaacccc cgttcagcc cgaccgctgc gccttatccg    3120
gtaactatcg tcttgagtcc aacccggtaa gacacgactt atcgccactg gcagcagcca    3180
ctggtaacag gattagcaga gcgaggtatg taggcggtgc tacagagttc ttgaagtggt    3240
ggcctaacta cggctacact agaagaacag tatttggtat ctgcgctctg ctgaagccag    3300
ttaccttcgg aaaaagagtt ggtagctctt gatccggcaa acaaaccacc gctggtagcg    3360
gtggtttttt tgtttgcaag cagcagatta cgcgcagaaa aaaaggatct caagaagatc    3420
ctttgatctt ttctacgggg tctgacgctc agtggaacga aaactcacgt taagggattt    3480
tggtcatgag attatcaaaa aggatcttca cctagatcct tttaaattaa aaatgaagtt    3540
ttaaatcaat ctaaagtata tatgagtaaa cttggtctga cagttaccaa tgcttaatca    3600
gtgaggcacc tatctcagcg atctgtctat ttcgttcatc catagttgcc tgactccccg    3660
tcgtgtagat aactacgata cgggagggct taccatctgg ccccagtgct gcaatgatac    3720
```

```
cgcgagaccc acgctcaccg gctccagatt tatcagcaat aaaccagcca gccggaaggg      3780
ccgagcgcag aagtggtcct gcaactttat ccgcctccat ccagtctatt aattgttgcc      3840
gggaagctag agtaagtagt tcgccagtta atagtttgcg caacgttgtt gccattgcta      3900
caggcatcgt ggtgtcacgc tcgtcgtttg gtatggcttc attcagctcc ggttcccaac      3960
gatcaaggcg agttacatga tcccccatgt tgtgcaaaaa agcggttagc tccttcggtc      4020
ctccgatcgt tgtcagaagt aagttggccg cagtgttatc actcatggtt atggcagcac      4080
tgcataattc tcttactgtc atgccatccg taagatgctt ttctgtgact ggtgagtact      4140
caaccaagtc attctgagaa tagtgtatgc ggcgaccgag ttgctcttgc ccggcgtcaa      4200
tacgggataa taccgcgcca catagcagaa ctttaaaagt gctcatcatt ggaaaacgtt      4260
cttcggggcg aaaactctca aggatcttac cgctgttgag atccagttcg atgtaaccca      4320
ctcgtgcacc caactgatct tcagcatctt ttactttcac cagcgtttct gggtgagcaa      4380
aaacaggaag gcaaaatgcc gcaaaaaagg gaataagggc gacacggaaa tgttgaatac      4440
tcatactctt cctttttcaa tattattgaa gcatttatca gggttattgt ctcatgagcg      4500
gatacatatt tgaatgtatt tagaaaaata aacaaatagg ggttccgcgc acatttcccc      4560
gaaaagtgcc acctgatgcg gtgtgaaata ccgcacagat gcgtaaggag aaaataccgc      4620
atcaggaaat tgtaagcgtt aatattttgt taaaattcgc gttaaatttt tgttaaatca      4680
gctcattttt taaccaatag gccgaaatcg gcaaaatccc ttataaatca aagaatagac      4740
cgagataggg ttgagtgtt gttccagttt ggaacaagag tccactatta agaacgtgg       4800 actccaacgt caaagggcga aaaccgtct atcaggcga tggcccacta cgtgaaccat       4860
caccctaatc aagttttttg gggtcgaggt gccgtaaagc actaaatcgg aaccctaaag      4920 ggagccccg atttagagct tgacgggaa agccggcgaa cgtggcgaga aggaaggga       4980 agaaagcgaa aggagcgggc gctagggcgc tggcaagtgt agcggtcacg ctgcgcgtaa      5040
ccaccacacc cgccgcgctt aatgcgccgc tacagggcgc gtccattcgc cattcaggct      5100
gcgcaactgt tgggaagggc gatcggtgcg ggcctcttcg ctattacgcc agctggcgaa      5160
agggggatgt gctgcaaggc gattaagttg ggtaacgcca gggttttccc agtcacgacg      5220
ttgtaaaacg acggccagtg aattgtaata cgactcacta tagggcgaat tgggcccgac      5280
gtcgcatgct cctctgtgac ccgagtgttg ctggacgttc gatgttcgat gctcggcaca      5340
tgccggttcg aacaggaatt atagcgttca tctggagttg gacgcaagca aaaaagcaaa      5400
tgagggagtt atgggagggt tccgagaagt gaaaaatcgg tcaatgggtt agtttgaagt      5460
ctcgttttgt tcgtgttggc gagacaagaa gaatggtata attttcgcac caaaaagaga      5520
ccgtttatcg tggattatgg gggtgtgatg tgggggagg ggggagatgc ccatctctg       5580 gcaaccctat ttgacgatag ttgctggagg cttgacagga cttggtgacg aggggtgttt      5640
gggcgctgga agcgtaattt tcgtcttgaa tgggccgtcg agacttgggg ttcgaccccg      5700
actaaatggc gcaccgctag attctctttt ggcgactttc tcgggattct agtcaccccc      5760
gcaatgttcc agcttacggt ttgagacagt acacgactgg ctaggcgagt tgttgaagtc      5820
gtagcgtaga gtgggaggca tgacgtcacg ggacagctgc gtgcaccacg cgagcaggtc      5880
aattgacctc atttgagtgg tgtggcttgg cgttctagcg gtggcggcgt tgtcgagctc      5940
cctctacttg tagtgagatt atgtcgacga gcgggggga cttccattgt gcttgccact      6000
gctagtgcag tacaactgaa agctaaaccg caatcaatcc caaactgcat gtccgcctta      6060
actctgatat gttatcaaga gagtggtgtg gtgaggtgag gtgaggtgac gtggacaagt      6120
```

```
tgatggggag ttggggcatt gacaaaaggg aaattgcagg gggattccgc cggctatata    6180
tatcttatgt ctgctcaatt cccagacggc tccacacaaa accaagatac cacaccatca    6240
tggtcacacc gggtacataa ctcccatcca tctcatccca cttgcatggc gaccggagag    6300
agaaagcccg gggagagcac gtcggcgcgg tccccagggc gacaaccaaa acaaaatcac    6360
cgagtgactc cgaaagccgc gttccaacac                                     6390
```

<210> SEQ ID NO 5
<211> LENGTH: 14948
<212> TYPE: DNA
<213> ORGANISM: Artificial sequence
<220> FEATURE:
<223> OTHER INFORMATION: Construct pZKADn-SyP298F for expressing YlPDAT,
      FmD12S, and E389D9eS/EgD8M

<400> SEQUENCE: 5

```
aaactttttt caccccccagg ctgttattcc ggggaataag gctggtcatg atggggttgg      60
aaagtctaaa ttttgtggg acaaagaaag caggtatcgt gccactaaga aaatagactt     120
ttaggcaccc cagattttg gaaaccttaa taggagacta cttccgtttc ctaattagga     180
cttccgcgac cccagacaaa gcggcttgga gtaggcctcg tgtccggcct agggcagaaa     240
cagctccgga actcgattga aagccgtac tctggaaagt ctagaggaag ttccaaggtc     300
gagtctcttc gatataaaag gacgccatcg aagctctgta gttcgatatc aaatactgac     360
aacagtttcc aaacacacaa acacacacac acacacacac acacatacaa ccatggccac     420
acaacctgtg aatcggaagg cgactgtcga gcgggtcgag ccagcagtgg aggtggctga     480
ctccgagtcc gaggccaaga ccgacgtcca cgttcaccac catcatcacc accacaagcg     540
aaaatccgtc aagggcaaga ttctcaactt cttcacccga gtcgacgta tcaccttcgt     600 cctcggcgcc gtggtcggtg tgatagccgc gggatactac gctgcgccac cggagctcag     660
cattgatatc gacgctcttc tcggcgactt gccctcgttc gactttgacg ctctatctct     720
cgacaacttg tcgatggaca gtgtgtcgga cttttgtacaa gacatgaaat cgcggtttcc     780
gaccaagatt ctgcaggagg cggccaagat cgagaagcac cagaaaagcg aacagaaggc     840
tgcccctttt gctgtgggca aggctatgaa gagcgaggga ctcaacgcca gtacccggt     900 ggtgctggtg cccggcgtca tctccacggg actggagagc tggtccctgg agggaaccga     960
ggagtgtccc accgagtcgc acttcagaaa gcgaatgtgg ggctcctggt acatgatccg    1020
agtcatgctg ctggacaagt actgctggct gcagaacctg atgctggaca cagagaccgg    1080 tctagacccct ccccatttca agctgcgagc cgcccaggga tttgcctccg ccgacttctt    1140
tatggcaggc tactgctgt ggaacaagct gctcgagaac ctggctgtta ttggatacga    1200
tacggataca atgtctgctg cggcctacga ctggagactg tcctaccctg atttggagca    1260
ccgagacgga tacttctcca agctcaaagc ttcaatcgaa gagactaagc gtatgacagg    1320
tgagaagaca gttctgacgg gccattcgat gggctcccag gtcatcttct acttcatgaa    1380
gtgggctgag gccgagggat atgaggagg aggtcccaac tgggtcaatg accatattga    1440
atcctttgtc gacatttccg gctccatgct gggtactccc aagacccctgg ttgctcttct    1500 gtctggagaa atgaaggata ccgtgcagct gaacgcgatg gctgtgtatg gactggagca    1560
gttcttctct cgacgagagc gagccgatct gctgcgaaca tggggagggaa ttgcttccat    1620 gattcccaag ggtggtaagg ctatctgggg tgatcattct ggagcccctg atgacgagcc    1680
cggccagaat gtcacctttg gcaacttcat caagttcaag gagtccttga ccgagtactc    1740
```

```
tgctaagaac ctcactatgg atgaaaccgt tgacttcctg tatttctcagt ctcccgagtg   1800
gtttgtgaac cgaaccgagg gtgcttactc ctttggaatt gccaagactc gaaagcaggt   1860
tgagcagaat gagaagcgac cttctacctg gagcaaccct ctggaagctg ctctccccaa   1920
tgcccccgat ctcaagatct actgcttcta tggagtcggt aaggataccg agcgagccta   1980
ctactaccag gatgagccca atcccgagca gaccaacttg aacgtcagta cgctggaaa    2040
cgaccctgat ggtgtgctta tgggtcaggg cgatggaacc gtctcccttg tgacccatac   2100
catgtgtcac cgatggaagg acgagaactc caagttcaac cctggtaacg cccaggtcaa   2160
ggttgtggag atgttgcacc agcctgatcg acttgatatt cgaggcggtg ctcagactgc   2220
cgagcatgtg gacattctgg ggcgttctga gttgaacgag atggttctga aggtggctag   2280
tggaaaggga aatgagattg aagagagagt catctccaac attgatgagt gggtgtggaa   2340
gattgatctc ggcagcaatt aggcggccgc atgagaagat aaatatataa atacattgag   2400
atattaaatg cgctagatta gagagcctca tactgctcgg agagaagcca agacgagtac   2460
tcaaagggga ttacaccatc catatccaca gacacaagct ggggaaaggt tctatataca   2520
ctttccggaa taccgtagtt tccgatgtta tcaatggggg cagccaggat ttcaggcact   2580
tcggtgtctc ggggtgaaat ggcgttcttg gcctccatca agtcgtacca tgtcttcatt   2640
tgcctgtcaa agtaaaacag aagcagatga agaatgaact tgaagtgaag gaatttaaat   2700
cacatggaac ctttgctatt tcggggataa ccccctttgc cattgcacga tggacgtggc   2760
aaaagaaaga tcgccctgcg gggatactta tcatgtggtc acatgctgtg attagaaata   2820
aagaaaaagg tgcttttttg gcgctgtgat taacatctcg tctgccgtgc tctactagtc   2880
gcaatagcaa aaactcgctt aatagtgtgc atagtgcggg gtagcaggat actgaactac   2940
agtacgattt gcttgctact gcttgtagca attaccttta ctgtagggac cacacctcct   3000
ggtttcaatg tctttcctcg cctcgacaaa gcaaaactgt cacccaatca caccttgttc   3060
atattcatta gtgcatccgt taaccttgac atgacacttc tcatactagt gatagggctg   3120
tagttgagac aagttgattc acacggatac atacaaagcc tcagagagca atgttatat   3180
actcagggac cgaccaatca aaaaaacaca ctcctaataa ccaccatttc catctacgcg   3240
tactcactct gtcagctgcc ccacattgcc caatgcacaa tgcacaatga tgtgtgcaaa   3300
caacgcaatc aaaagtctat ggatgctgac caaactctga tcaccaagtt gcgaacatga   3360
aaagaagac  ctgtgtatat ataagtaagg gggagagccc taactagatc tttcgaaaac   3420
cccccgacct tcaccttcca caaccatgat catcttatac gttttggccg ttgcggtctc   3480
cttcctcatc ttcaagagag tcacctacac catggcctcc acctcggctc tgcccaagca   3540
gaaccctgcc ctccgacgaa ccgtcacttc caccactgtg accgactcgg agtctgctgc   3600
cgtctctccc tccgattctc ccagacactc ggcctcctct acatcgctgt cttccatgtc   3660
cgaggtggac attgccaagc ccaagtccga gtacggtgtc atgctggata cctacggcaa   3720
ccagttcgaa gttcccgact tcaccatcaa ggacatctac aacgctattc caagcactg    3780
cttcaagcga tctgctctca agggatacgc ctacattctt cgagacattg tcctcctgac   3840
taccactttc agcatctggt acaactttgt gacacccgag tacattccct ccactcctgc   3900
tcgagccggt ctgtgggctg tgtacaccgt tcttcaggga ctcttcggta ctggactgtg   3960
ggtcattgcc cacgagtgtg gacatggtgc tttctccgat tcccgaatca tcaacgacat   4020
tactggctgg gtgcttcact cttccctgct tgttccctac ttcagctggc aaatctccca   4080
```

-continued

```
ccggaagcat cacaaggcca ctggaaacat ggagcgagac atggtcttcg ttcctcgaac   4140
ccgagagcag caagctactc gactcggcaa gatgacccac gaactcgccc atcttaccga   4200
ggaaactcct gctttcaccc tgctcatgct tgtgcttcag caactggtcg gttggcccaa   4260
ctatctcatt accaacgtta ctggacacaa ctaccatgag cggcagcgag agggtcgagg   4320
caagggaaag cacaacggtc ttggcggtgg agttaaccat ttcgatcccc gatctcctct   4380
gtacgagaac agcgacgcca agctcatcgt gctctccgac attggcattg gtcttatggc   4440
caccgctctg tactttctcg ttcagaagtt cggattctac aacatggcca tctggtactt   4500
cgttccctac ttgtgggtta accactggct cgtcgccatt acctttctgc agcacacaga   4560
tcctactctt ccccactaca ccaacgacga gtggaacttt gtgcgaggtg ccgctgcaac   4620
catcgaccga gagatgggct tcattggacg tcatctgctc cacggcatta tcgagactca   4680
cgtcctgcat cactacgtct cttccattcc cttctacaat gcggacgaag ctaccgaggc   4740
catcaaacct atcatgggca agcactatcg agctgatgtc caggacggtc ctcgaggatt   4800
cattcgagcc atgtaccgat ctgcacgaat gtgccagtgg gttgaaccct ccgctggtgc   4860
cgagggagct ggcaagggtg tcctgttctt tcgaaaccga aacaatgtgg gcactcctcc   4920
cgctgtcatc aagcccgttg cctaagcggc cgcaaataga ttaaggaaga tgttattgtt   4980
gagagtgggt agactagaga tacgccttgg atacgtcacg tgatgcgagg caatgagaca   5040
gacagatttt cgtgtacccg cacgttagta gacgtaggaa acgtcgacga atatgacagt   5100
gtgatccatt ctatacaacg accttgtttt cagactacag tacagtacag taatcaacag   5160
tttcattatc tattcactgt cgaaactcta agctcgcgat agctgcaagt tagtttataa   5220
aaaatggagt ttcaaatttc aagacactct acacgtacga acgcacggta tcggagcatc   5280 ggataccccca cattgagcca acctactttg tagtgtacat actgtagaga agagggacgc   5340
ttcgacatga ttggccgatg tgggcatgta gaaacacgat atatggtgct tactaatgga   5400
cacttgcaca accatttctc ttctagggta acctcgacag tgacagccgt tttttctgcg   5460
ctagcgtgtc gtcgtatttt tggtttcgac atgttaagat ttgtggggca atcgagcgac   5520
attaaggtgc atcggatcat cggcccaagg gagagtcact ggagtctcgt agggtggagg   5580
aaaagagcaa tttgggacga tttggggcga tttgaagacg gattggggca ggtgtttgtc   5640
acgtgactgt ggtattacta ttactaatcg tcattgttcg aaagtcctgt caattgtatc   5700
actttggtgg gtctaccaaa acactggtca aatctacgcc acatgaaaat ataaagtttc   5760
acattagcca cattgagggg taccctagt tggaatctac aaggagggat gcagtgaaaa   5820
atgttccttt gatccttcag agatgaaaat gccattgacc aatcacagcg ggtttaaaga   5880
gtggcgaaaa gagcccctt tttgcaccgg ttggcccagc agccacgtga ctggccctt   5940 ccccatccca ctcaactgtt gaggaggtgg gatgccaaga tgcaccgtca atgtacttcc   6000
gtgtatcctt ctgcaattga tccgagatag gcgcgccagc tgcattaatg aatcggccaa   6060
cgcgcgggga gaggcggttt gcgtattggg cgctcttccg cttcctcgct cactgactcg   6120
ctgcgctcgg tcgttcggct gcggcgagcg gtatcagctc actcaaaggc ggtaatacgg   6180
ttatccacag aatcagggga taacgcagga aagaacatgt gagcaaaagg ccagcaaaag   6240
gccaggaacc gtaaaaaggc cgcgttgctg gcgttttttcc ataggctccg ccccctgac   6300 gagcatcaca aaaatcgacg ctcaagtcag aggtggcgaa acccgacagg actataaaga   6360
taccaggcgt ttccccctgg aagctccctc gtgcgctctc ctgttccgac cctgccgctt   6420
accggatacc tgtccgcctt tctcccttcg ggaagcgtgg cgctttctca tagctcacgc   6480
```

```
tgtaggtatc tcagttcggt gtaggtcgtt cgctccaagc tgggctgtgt gcacgaaccc    6540
cccgttcagc ccgaccgctg cgccttatcc ggtaactatc gtcttgagtc caacccggta    6600
agacacgact tatcgccact ggcagcagcc actggtaaca ggattagcag agcgaggtat    6660
gtaggcggtg ctacagagtt cttgaagtgg tggcctaact acggctacac tagaagaaca    6720
gtatttggta tctgcgctct gctgaagcca gttaccttcg gaaaagagt tggtagctct     6780 tgatccggca acaaaccac cgctggtagc ggtggttttt ttgtttgcaa gcagcagatt     6840
acgcgcagaa aaaaggatc tcaagaagat cctttgatct tttctacggg gtctgacgct     6900
cagtggaacg aaaactcacg ttaagggatt ttggtcatga gattatcaaa aaggatcttc     6960
acctagatcc ttttaaatta aaaatgaagt tttaaatcaa tctaaagtat atatgagtaa     7020
acttggtctg acagttacca atgcttaatc agtgaggcac ctatctcagc gatctgtcta     7080
tttcgttcat ccatagttgc ctgactcccc gtcgtgtaga taactacgat acgggagggc     7140
ttaccatctg gccccagtgc tgcaatgata ccgcgagacc cacgctcacc ggctccagat     7200
ttatcagcaa taaaccagcc agccggaagg gccgagcgca gaagtggtcc tgcaacttta     7260
tccgcctcca tccagtctat taattgttgc cgggaagcta gagtaagtag ttcgccagtt     7320
aatagtttgc gcaacgttgt tgccattgct acaggcatcg tggtgtcacg ctcgtcgttt     7380
ggtatggctt cattcagctc cggttcccaa cgatcaaggc gagttacatg atcccccatg     7440
ttgtgcaaaa aagcggttag ctccttcggt cctccgatcg ttgtcagaag taagttggcc     7500
gcagtgttat cactcatggt tatggcagca ctgcataatt ctcttactgt catgccatcc     7560
gtaagatgct tttctgtgac tggtgagtac tcaaccaagt cattctgaga atagtgtatg     7620
cggcgaccga gttgctcttg cccggcgtca atacgggata ataccgcgcc acatagcaga     7680
actttaaaag tgctcatcat tggaaaacgt tcttcgggc gaaaactctc aaggatctta     7740
ccgctgttga tccagttc gatgtaaccc actcgtgcac ccaactgatc ttcagcatct     7800
tttactttca ccagcgtttc tgggtgagca aaaacaggaa ggcaaaatgc cgcaaaaaag     7860
ggaataaggg cgacacggaa atgttgaata ctcatactct tcctttttca atattattga     7920
agcatttatc agggttattg tctcatgagc ggatacatat ttgaatgtat ttagaaaaat     7980
aaacaaatag gggttccgcg cacatttccc cgaaaagtgc cacctgatgc ggtgtgaaat     8040
accgcacaga tgcgtaagga gaaaataccg catcaggaaa ttgtaagcgt taatattttg     8100
ttaaaattcg cgttaaattt ttgttaaatc agctcatttt ttaaccaata ggccgaaatc     8160
ggcaaaatcc cttataaatc aaaagaatag accgagatag ggttgagtgt tgttccagtt     8220
tggaacaaga gtccactatt aaagaacgtg gactccaacg tcaaagggcg aaaaaccgtc     8280
tatcagggcg atggcccact acgtgaacca tcaccctaat caagtttttt ggggtcgagg     8340
tgccgtaaag cactaaatcg gaaccctaaa gggagccccc gatttagagc ttgacgggga     8400
aagccggcga acgtggcgag aaaggaaggg aagaaagcga aaggagcggg cgctagggcg     8460
ctggcaagtg tagcggtcac gctgcgcgta accaccacac ccgccgcgct taatgcgccg     8520
ctacagggcg cgtccattcg ccattcaggc tgcgcaactg ttgggaaggg cgatcggtgc     8580
gggcctcttc gctattacgc cagctggcga aggggatg tgctgcaagg cgattaagtt      8640
gggtaacgcc agggttttcc cagtcacgac gttgtaaaac gacggccagt gaattgtaat     8700
acgactcact atagggcgaa ttgggcccga cgtcgcatgc tacaagtatc gcaccatact     8760
tttgctgacg gcgcgccttc ttgcagtgat ataatcggtt tcttggagct gatggggtga     8820
```

```
gcatcataca agtatgagta cgagaagtcg cacttgtact ccaagtacaa atgcccggaa    8880
tggcagacac acaagtccta cgggtgttca gagactactg actggagatt gcaactacaa    8940
gtactgtaca cacagtacaa cacacaagtt aactcatcat tcataattat cataaactag    9000
acggccaaaa agtcgtggcc gctcctcagc gtcaatagcc gcgcttactt ggagcagtcc    9060
agaacgtatc gaccggcaat cttgccctcc tccatgagct tgtagacgga ttcgagctcg    9120
gagagaccaa caataatgat gggggacttg accagtcctc gggcaaagaa ctcaatggcc    9180
tcctgggagt cggctcggtt tccgacgtaa gagcccttga tctgaataga tcgagcaacc    9240
tgctggaaga tgggcgactt gcagacggca ccggcgggca gaccgaccag aacaacggtt    9300
cccagggttc gcacgtactc aacagactgg ttgacggcaa actcggagac agacacgttg    9360 atgacgcgt ggggtccgcc cttggtggcc tcctggacgt ccttgaccag atccttggac     9420
ttggcaaagt cgatgaagac ctcggcgccg agctccttgc acatcttctc cttgtcagcg    9480
ccagtgtcaa tggccagcac tcggttaatt aagttgcgac acatgtcttg atagtatctt    9540
gaattctctc tcttgagctt ttccataaca agttcttctg cctccaggaa gtccatcggt    9600
ggtttgatca tggttttggt gtagtggtag tgcagtggtg gtattgtgac tggggatgta    9660
gttgagaata agtcatacac aagtcagctt tcttcgagcc tcatataagt ataagtagtt    9720
caacgtatta gcactgtacc cagcatctcc gtatcgagaa acacaacaac atgccccatt    9780
ggacagatca tgcggataca caggttgtgc agtatcatac atactcgatc agacaggtcg    9840
tctgaccatc atacaagctg aacaagcgct ccatacttgc acgctctcta tatacacagt    9900
taaattacat atccatagtc taacctctaa cagttaatct tctggtaagc ctcccagcca    9960
gccttctggt atcgcttggc ctcctcaata ggatctcggt tctggccgta cagacctcgg    10020
ccgacaatta tgatatccgt tccggtagac atgacatcct caacagttcg gtactgctgt    10080
ccgagagcgt ctcccttgtc gtcaagaccc accccggggg tcagaataag ccagtcctca    10140
gagtcgccct taggtcggtt ctgggcaatg aagccaacca caaactcggg gtcggatcgg    10200
gcaagctcaa tggtctgctt ggagtactcg ccagtggcca gagagccctt gcaagacagc    10260
tcggccagca tgagcagacc tctgccagc ttctcgttgg gagaggggac taggaactcc     10320
ttgtactggg agttctcgta gtcagagacg tcctccttct tctgttcaga gacagtttcc    10380
tcggcaccag ctcgcaggcc agcaatgatt ccggttccgg gtacaccgtg gcgttggtg     10440 atatcggacc actcggcgat tcggtgacac cggtactggt gcttgacagt gttgccaata    10500
tctgcgaact ttctgtcctc gaacaggaag aaaccgtgct taagagcaag ttccttgagg    10560
gggagcacag tgccggcgta ggtgaagtcg tcaatgatgt cgatatgggt tttgatcatg    10620
cacacataag gtccgacctt atcggcaagc tcaatgagct ccttggtggt ggtaacatcc    10680
agagaagcac acaggttggt tttcttggct gccacgagct tgagcactcg agcggcaaag    10740
gcggacttgt ggacgttagc tcgagcttcg taggagggca ttttggtggt gaagaggaga    10800
ctgaaataaa tttagtctgc agaacttttt atcggaacct tatctggggc agtgaagtat    10860
atgttatggt aatagttacg agttagttga acttatagat agactggact atacggctat    10920
cggtccaaat tagaaagaac gtcaatggct ctctgggcgt cgcctttgcc gacaaaaatg    10980
tgatcatgat gaaagccagc aatgacgttg cagctgatat tgttgtcggc aaccgcgcc     11040 gaaaacgcag ctgtcagacc cacagcctcc aacgaagaat gtatcgtcaa agtgatccaa    11100
gcacactcat agttggagtc gtactccaaa ggcggcaatg acgagtcaga cagatactcg    11160 tcgaccttt ccttgggaac caccaccgtc agcccttctg actcacgtat tgtagccacc     11220
```

```
gacacaggca acagtccgtg gatagcagaa tatgtcttgt cggtccattt ctcaccaact    11280
ttaggcgtca agtgaatgtt gcagaagaag tatgtgcctt cattgagaat cggtgttgct    11340
gatttcaata aagtcttgag atcagtttgg ccagtcatgt tgtgggggt aattggattg    11400 agttatcgcc tacagtctgt acaggtatac tcgctgccca ctttatactt tttgattccg    11460
ctgcacttga agcaatgtcg tttaccaaaa gtgagaatgc tccacagaac acccccagg    11520 gtatggttga gcaaaaaata aacactccga tacggggaat cgaaccccgg tctccacggt    11580
tctcaagaag tattcttgat gagagcgtat cgatattctg aaactagagc catctcaaca    11640
caacagtctc tttgtgtagc tacttgtacc ctttttctct tcctctctcc agccagacat    11700
ctttgctagc gcctataatg taacccatca agacatgcac aggagatgct taatcggagt    11760
gtgtggtctg taggggagat cgagagagac tgcaattgac agagagatcg aagttggaat    11820
gagagagact gaaaattaag cgagcttggg tgtttgcccc tcccctcaca ccctcggata    11880
ctgtacctac atatccaggc cggtttggca cggcatcaaa agcctcctac aagaatgtat    11940
atgcgactct tctacaagta gatttccgcg cttgcaccaa cggctacgcc caagacgggg    12000
ctcgtacccg tccgtctatg gttcagccgc caacgaaaaa aaaaaaaagg atggctgtaa    12060
ttttattatg cttctgtgtt tgtgtttgtc ggtccgtttt tgcttttttc accccaggc    12120 tgttattccg gggaataagg ctggtcatga tggggttgga aagtctaaat ttttgtggga    12180
caaagaaagc aggtatcgtg ccactaagaa aatagacttt taggcacccc agattttttgg    12240 aaaccttaat aggagactac ttccgtttcc taattaggac ttccgcgacc ccagacaaag    12300
cggcttggag taggcctcgt gtccggccta gggcagaaac agctccggaa ctcgattgag    12360
aagccgtact ctggaaagtc tagaggaagt tccaaggtcg agtctcttcg atataaaagg    12420
acgccatcga agctctgtag ttcgatatca aatactgaca acagtttcca aacacacaaa    12480
cacacacaca cacacacaca cacatacaac catggctgcc gtcatcgagg tggccaacga    12540
gttcgtcgct atcactgccg agacccttcc caaggtggac tatcagcgac tctggcgaga    12600
catctactcc tgcgagctcc tgtacttctc cattgctttc gtcatcctca agtttaccct    12660
tggcgagctc tcggattctg gcaaaaagat tctgcgagtg ctgttcaagt ggtacaacct    12720
cttcatgtcc gtcttttcgc tggtgtcctt cctctgtatg ggttacgcca tctacaccgt    12780
tggactgtac tccaacgaat gcgacagagc tttcgacaac agcttgttcc gatttgccac    12840
caaggtcttc tactattcca agtttctgga gtacatcgac tctttctacc ttcccctcat    12900
ggccaagcct ctgtcctttc tgcagttctt tcatcacttg ggagctccta tggacatgtg    12960
gctcttcgtg cagtactctg gcgaatccat ttggatcttt gtgttcctga acggattcat    13020
tcactttgtc atgtacggct actattggac acggctgatg aagttcaact ttcccatgcc    13080
caagcagctc attaccgcaa tgcagatcac ccagttcaac gttggcttct acctcgtgtg    13140
gtggtacaag gacattccct gttaccgaaa ggatcccatg cgaatgctgg cctggatctt    13200
caactactgg tacgtcggta ccgttcttct gctcttcatc aacttctttg tcaagtccta    13260
cgtgtttccc aagcctaaga ctgccgacaa aaaggtccag ggcgccggtc ccgctcgacc    13320
tgccggactt cctcccgcta cctactacga ctctctggcc gtcatgggat ccgtgaaggc    13380
ttctcgacag gctctgcccc tcgtcatcga cggaaaggtg tacgacgtct ccgcttgggt    13440
gaacttccac cctggtggag ctgaaatcat tgagaactac cagggacgag atgctactga    13500
cgccttcatg gttatgcact ctcaggaagc cttcgacaag ctcaagcgaa tgcccaagat    13560
```

```
caaccaggct tccgagctgc ctccccaggc tgccgtcaac gaagctcagg aggatttccg     13620
aaagctccga gaagagctga tcgccactgg catgtttgac gcctctcccc tctggtactc     13680
gtacaagatc ttgaccaccc tgggtcttgg cgtgcttgcc ttcttcatgc tggtccagta     13740
ccacctgtac ttcattggtg ctctcgtgct cggtatgcac taccagcaaa tgggatggct     13800
gtctcatgac atctgccacc accagacctt caagaaccga actggaata cgtcctggg      13860 tctggtcttt ggcaacggac tccagggctt ctccgtgacc tggtggaagg acagacacaa     13920
cgcccatcat tctgctacca acgttcaggg tcacgatccc gacattgata acctgcctct     13980
gctcgcctgg tccgaggacg atgtcactcg agcttctccc atctcccgaa agctcattca     14040
gttccaacag tactatttcc tggtcatctg tattctcctg cgattcatct ggtgtttcca     14100
gtctgtgctg accgttcgat ccctcaagga ccgagacaac cagttctacc gatctcagta     14160
caagaaagag gccattggac tcgctctgca ctggactctc aagaccctgt ccacctctt     14220 ctttatgccc tccatcctga cctcgatgct ggtgttcttt gtttccgagc tcgtcggtgg     14280
cttcggaatt gccatcgtgg tcttcatgaa ccactaccct ctggagaaga tcggtgattc     14340
cgtctgggac ggacatggct tctctgtggg tcagatccat gagaccatga acattcgacg     14400
aggcatcatt actgactggt tctttggagg cctgaactac cagatcgagc accatctctg     14460 gcccacccctg cctcgacaca acctcactgc cgtttcctac caggtggaac agctgtgcca     14520
gaagcacaac ctcccctacc gaaaccctct gccccatgaa ggtctcgtca tcctgctccg     14580
atacctgtcc cagttcgctc gaatggccga gaagcagccc ggtgccaagg ctcagtaagc     14640
ggccgcacag cgaatggatc atcagcaact agctggtgca accgatacga tgagaacgga     14700
aaacaacata cttggtgcgc aacaaagacc aacaagtgag catcttcgat tctgaaagtc     14760
cgataagacg agggtatata tttaattgta ttgattagtt ttgagtattg tgtgagtagt     14820
cataaccaag atcaagttac agtaaatata caatacatag tcttcttgtt actacttgta     14880
gcagatatat acaattatat tcaatgatta taggtacaaa atataaatag gggaatgtac     14940
aatggttt                                                              14948

<210> SEQ ID NO 6
<211> LENGTH: 300
<212> TYPE: DNA
<213> ORGANISM: Yarrowia lipolytica

<400> SEQUENCE: 6
aaatagatta aggaagatgt tattgttgag agtgggtaga ctagagatac gccttggata      60
cgtcacgtga tgcgaggcaa tgagacagac agattttcgt gtacccgcac gttagtagac     120
gtaggaaacg tcgacgaata tgacagtgtg atccattcta tacaacgacc ttgttttcag     180
actacagtac agtacagtaa tcaacagttt cattatctat tcactgtcga aactctaagc     240
tcgcgatagc tgcaagttag tttataaaaa atggagtttc aaatttcaag cactctaca      300

<210> SEQ ID NO 7
<211> LENGTH: 300
<212> TYPE: DNA
<213> ORGANISM: Yarrowia lipolytica

<400> SEQUENCE: 7
acagcgaatg gatcatcagc aactagctgg tgcaaccgat acgatgagaa cggaaaacaa      60
catacttggt gcgcaacaaa gaccaacaag tgagcatctt cgattctgaa agtccgataa     120
gacgagggta tatatttaat tgtattgatt agttttgagt attgtgtgag tagtcataac     180
```

```
caagatcaag ttacagtaaa tatacaatac atagtcttct tgttactact tgtagcagat    240
atatacaatt atattcaatg attataggta caaaatataa atagggaat gtacaatggt     300
```

<210> SEQ ID NO 8
<211> LENGTH: 2071
<212> TYPE: DNA
<213> ORGANISM: Yarrowia lipolytica

<400> SEQUENCE: 8

```
tgacgagggg tgtttgggcg ctggaagcgt aattttcgtc ttgaatgggc cgtcgagact     60
tggggttcga ccccgactaa atggcgcacc gctagattct cttttggcga ctttctcggg   120
attctagtca cccccgcaat gttccagctt acggtttgag acagtacacg actggctagg   180
cgagttgttg aagtcgtagc gtagagtggg aggcatgacg tcacgggaca gctgcgtgca   240
ccacgcgagc aggtcaattg acctcatttg agtggtgtgg cttggcgttc tagcggtggc   300
ggcgttgtcg agctccctct acttgtagtg agattatgtc gacgagcggg ggggacttcc   360
attgtgcttg ccactgctag tgcagtacaa ctgaaagcta aaccgcaatc aatcccaaac   420
tgcatgtccg ccttaactct gatatgttat caagagagtg gtgtggtgag gtgaggtgag   480
gtgacgtgga caagttgatg gggagttggg gcattgacaa aagggaaatt gcagggggat   540
tccgccggct atatatatct tatgtctgct caattcccag acggtccac acaaaaccaa    600 gataccacac catcatggtc acccgggta cataactccc atccatctca tcccacttgc    660
atggcgaccg gagagagaaa gcccggggag agcacgtcgg cgcggtcccc agggcgacaa   720
ccaaaacaaa atcaccgagt gactccgaaa gccgcgttcc aacaccccc caaaatcccc    780 ccctcaaaca cgtcagccac ctgtcccccg aaaattaact tcactgacat ggcgcagcta   840
ttaaggctaa agtgaatgca tggctcatct ttgtttgctg gttgctactg tgactgaggt   900
aaaaaccctc gctcccaagt ctatatatac ctgggtgtgc ccctcgaac agacccgtca    960 cagtaaaact actacctcca tacacagcac cacctcaatc atgtctggac cttccaccct  1020
cgccacggga ctgcaccctc tccccacaga accccaaag ttcccacca acatcatgga   1080 ccgattctcc ctcaagggta aggttgcctc cgtcaccggc tcctcgtcag gtatcggcta  1140
ctgcgtggcc gaggcctacg cccaggccgg tgccgacgtg ccatctggt acaactccca   1200 ccccgccgac gcaaaggctg agcacctcgc taagacctac ggcgtcaagg ccaaggccta  1260
caagtgccct gtcaccgacg ccgccgccgt ggagtccacc atccagcaga tcgagaagga  1320 cttttggcacc attgacatct tcgtcgccaa cgctggtgtc cctggaccg ccggccccat   1380 gatcgacgtg cccgacaaca aggagtggga caaggtcatc aacctggatc tcaacggtgc  1440
ctactactgc gccaagtacg ccggccagat cttcaagaag aagggcaagg gatccttcat  1500
cttcaccgcc tccatgtccg gccacattgt caacatcccc cagatgcagg cctgctacaa  1560
cgccgccaag gccgctctgc tgcacctgtc tcgatcgctg gccgtcgagt gggcggctt    1620 tgcccgatgc aacacagtct cccctggcta catggccacc gagatctccg actttgtccc  1680
caaggagacc aaggagaagt ggtggcagct cattcccatg ggccgagagg gagacccctc  1740
cgagctctac ctacctctac cttgcctctg atgctgccac ctacaccact ggtgccgaca  1800
ttatcgtcga tggtggctac tgcgctcctt agaggatgta tatagataat gattgtttat  1860
gattagacat tgattgagtg tagttggaca tttagcagtca gataggcaac gaagatcatc  1920
caagtctgaa tacatacccca tacaaatcat acaagtaaat gatggaatta ctcatataag  1980
```

```
tatgtactta cttgtaccga attgccaatg aatgtcaatc agaacgcagt atgtacaagt    2040
actcgcacaa tatcataagg cactcgaatg t                                   2071

<210> SEQ ID NO 9
<211> LENGTH: 771
<212> TYPE: DNA
<213> ORGANISM: Yarrowia lipolytica

<400> SEQUENCE: 9
atgtctggac cttccaccct cgccacggga ctgcaccctc tccccacaga daccccaaag      60
ttccccacca acatcatgga ccgattctcc ctcaagggta aggttgcctc cgtcaccggc    120
tcctcgtcag gtatcggcta ctgcgtggcc gaggcctacg cccaggccgg tgccgacgtg    180
gccatctggt acaactccca ccccgccgac gcaaaggctg agcacctcgc taagacctac    240
ggcgtcaagg ccaaggccta caagtgccct gtcaccgacg ccgccgccgt ggagtccacc    300
atccagcaga tcgagaagga ctttggcacc attgacatct cgtcgccaa cgctggtgtc    360 ccctggaccg ccggccccat gatcgacgtg cccgacaaca aggagtggga caaggtcatc    420
aacctggatc tcaacggtgc ctactactgc gccaagtacg ccggccagat cttcaagaag    480
aagggcaagg gatccttcat cttcaccgcc tccatgtccg gccacattgt caacatcccc    540
cagatgcagg cctgctacaa cgccgccaag gccgctctgc tgcacctgtc tcgatcgctg    600
gccgtcgagt gggccggctt tgcccgatgc aacacagtct cccctggcta catggccacc    660
gagatctccg actttgtccc caaggagacc aaggagaagt ggtggcagct cattcccatg    720
ggccgagagg gagaccccct cgagctctac ctacctctac cttgcctctg a             771

<210> SEQ ID NO 10
<211> LENGTH: 256
<212> TYPE: PRT
<213> ORGANISM: Yarrowia lipolytica

<400> SEQUENCE: 10

Met Ser Gly Pro Ser Thr Leu Ala Thr Gly Leu His Pro Leu Pro Thr
 1               5                  10                  15

Glu Thr Pro Lys Phe Pro Thr Asn Ile Met Asp Arg Phe Ser Leu Lys
            20                  25                  30

Gly Lys Val Ala Ser Val Thr Gly Ser Ser Ser Gly Ile Gly Tyr Cys
        35                  40                  45

Val Ala Glu Ala Tyr Ala Gln Ala Gly Ala Asp Val Ala Ile Trp Tyr
    50                  55                  60

Asn Ser His Pro Ala Asp Ala Lys Ala Glu His Leu Ala Lys Thr Tyr
65                  70                  75                  80

Gly Val Lys Ala Lys Ala Tyr Lys Cys Pro Val Thr Asp Ala Ala Ala
                85                  90                  95

Val Glu Ser Thr Ile Gln Gln Ile Glu Lys Asp Phe Gly Thr Ile Asp
           100                 105                 110

Ile Phe Val Ala Asn Ala Gly Val Pro Trp Thr Ala Gly Pro Met Ile
       115                 120                 125

Asp Val Pro Asp Asn Lys Glu Trp Asp Lys Val Ile Asn Leu Asp Leu
   130                 135                 140

Asn Gly Ala Tyr Tyr Cys Ala Lys Tyr Ala Gly Gln Ile Phe Lys Lys
145                 150                 155                 160

Lys Gly Lys Gly Ser Phe Ile Phe Thr Ala Ser Met Ser Gly His Ile
                165                 170                 175
```

```
Val Asn Ile Pro Gln Met Gln Ala Cys Tyr Asn Ala Ala Lys Ala Ala
            180                 185                 190

Leu Leu His Leu Ser Arg Ser Leu Ala Val Glu Trp Ala Gly Phe Ala
        195                 200                 205

Arg Cys Asn Thr Val Ser Pro Gly Tyr Met Ala Thr Glu Ile Ser Asp
    210                 215                 220

Phe Val Pro Lys Glu Thr Lys Glu Lys Trp Trp Gln Leu Ile Pro Met
225                 230                 235                 240

Gly Arg Glu Gly Asp Pro Ser Glu Leu Tyr Leu Pro Leu Pro Cys Leu
                245                 250                 255

<210> SEQ ID NO 11
<211> LENGTH: 2771
<212> TYPE: DNA
<213> ORGANISM: Yarrowia lipolytica

<400> SEQUENCE: 11
```

| | | | | | |
|---|---|---|---|---|---|
| tgacgagggg | tgtttgggcg | ctggaagcgt | aattttcgtc | ttgaatgggc | cgtcgagact | 60 |
| tggggttcga | ccccgactaa | atggcgcacc | gctagattct | cttttggcga | ctttctcggg | 120 |
| attctagtca | ccccgcaat | gttccagctt | acggtttgag | acagtacacg | actggctagg | 180 |
| cgagttgttg | aagtcgtagc | gtagagtggg | aggcatgacg | tcacgggaca | gctgcgtgca | 240 |
| ccacgcgagc | aggtcaattg | acctcatttg | agtggtgtgg | cttggcgttc | tagcggtggc | 300 |
| ggcgttgtcg | agctccctct | acttgtagtg | agattatgtc | gacgagcggg | ggggacttcc | 360 |
| attgtgcttg | ccactgctag | tgcagtacaa | ctgaaagcta | aaccgcaatc | aatcccaaac | 420 |
| tgcatgtccg | ccttaactct | gatatgttat | caagagagtg | gtgtggtgag | gtgaggtgag | 480 |
| gtgacgtgga | caagttgatg | gggagttggg | gcattgacaa | agggaaatt | gcagggggat | 540 |
| tccgccggct | atatatatct | tatgtctgct | caattcccag | acggctccac | acaaaaccaa | 600 |
| gataccacac | catcatggtc | acaccgggta | cataactccc | atccatctca | tcccacttgc | 660 |
| atggcgaccg | gagagagaaa | gcccggggag | agcacgtcgg | cgcggtcccc | agggcgacaa | 720 |
| ccaaaacaaa | atcaccgagt | gactccgaaa | gccgcgttcc | aacacccccc | caaaatcccc | 780 |
| ccctcaaaca | cgtcagccac | ctgtccccccg | aaaattaact | tcactgacat | ggcgcagcta | 840 |
| ttaaggctaa | agtgaatgca | tggctcatct | ttgtttgctg | gttgctactg | tgactgaggt | 900 |
| aaaaaccctc | gctcccaagt | ctatatatac | ctgggtgtgc | tccctcgaac | agaccccgtca | 960 |
| cagtaaaact | actacctcca | tacacagcac | cacctcaatc | atgtctggac | cttccaccct | 1020 |
| cgccacggga | ctgcaccctc | tccccacaga | gaccccaaag | ttccccacca | acatcatgga | 1080 |
| ccgattctcc | ctcaagggta | aggttgcctc | cgtcaccggc | tcctcgtcag | gtatcggcta | 1140 |
| ctgcgtggcc | gaggcctacg | cccaggccgg | tgccgacgtg | gccatctggt | acaactccca | 1200 |
| ccccgccgac | gcaaaggctg | agcacctcgc | taagacctac | ggcgtcaagg | ccaaggccta | 1260 |
| caagtgccct | gtcaccgacg | ccgccgccgt | ggagtccacc | atccagcaga | tcgagaagga | 1320 |
| cttttggcacc | attgacatct | tcgtcgccaa | cgctggtgtc | cctggaccg | ccggccccat | 1380 |
| gatcgacgtg | cccgacaaca | aggagtggga | caaggtcatc | aacctggatc | tcaacgtgc | 1440 |
| ctactactgc | gccaagtacg | ccggccagat | cttcaagaag | aagggcaagg | gatccttcat | 1500 |
| cttcaccgcc | tccatgtccg | gccacattgt | caacatcccc | cagatgcagg | cctgctacaa | 1560 |
| cgccgccaag | gccgctctgc | tgcacctgtc | tcgatcgctg | gccgtcgagt | gggcggctt | 1620 |
| tgcccgatgc | aacacagtct | cccctggcta | catggccacc | gagatctccg | actttgtccc | 1680 |

| | |
|---|---|
| caaggagacc aaggagaagt ggtggcagct cattcccatg ggccgagagg gagacccctc | 1740 |
| cgagctctac ctacctctac cttgcctctg atgctgccac ctacaccact ggtgccgaca | 1800 |
| ttatcgtcga tggtggctac tgcgctcctt agaggatgta tatagataat gattgtttat | 1860 |
| gattagacat tgattgagtg tagttggaca ttagcagtca gataggcaac gaagatcatc | 1920 |
| caagtctgaa tacataccca tacaaatcat acaagtaaat gatggaatta ctcatataag | 1980 |
| tatgtactta cttgtaccga attgccaatg aatgtcaatc agaacgcagt atgtacaagt | 2040 |
| actcgcacaa tatcataagg cactcgaatg ttcaagaagt catcattttg gtgattcggg | 2100 |
| gaaatacttg acacctttgt tgatgcaact tgactccata agtaggaaac ccatagtata | 2160 |
| tcttttttgtc gctttatatt cacctgttcc cttctttcta tggactataa gttaatttag | 2220 |
| ttgaccttgt caagtaatac ctcaacaaac tgtaaagaaa taggagatta ttgcttttgg | 2280 |
| tttttgagaa gagatctgga tagcaccaca caaataatgc gtcaaaatca gttcaaaatc | 2340 |
| caacccacag aacaaccaac actccccgaa ccgctcataa cctgtatagg atgctgctcc | 2400 |
| actcacacct cttgtccagc cctaacctgc gatctaggtt ggggaaattt tgtatgcagg | 2460 |
| aaaaatatat gcaagatttg ggattttatt tgtgttcatc aaccacgtcg atttacacag | 2520 |
| ctatcatggt ccgagaacga tctggaacgg tggcgtacac gcccaaaaag cagcagaagc | 2580 |
| ctctggtgga cgacgcccac ttgtcctctg ctgaggagga cgatttcaag accccagaga | 2640 |
| gtgcaaagag caagaagcct gaagcgtcac aacaggagcc ggcggtgtca gaaacgccag | 2700 |
| tcaagggcaa ggccaagaag atcacctttg acgaggacgg aatgagtgcc gagcccatcg | 2760 |
| ttgagaagaa a | 2771 |

<210> SEQ ID NO 12
<211> LENGTH: 1434
<212> TYPE: DNA
<213> ORGANISM: Artificial sequence
<220> FEATURE:
<223> OTHER INFORMATION: Fusarium moniliforme delta-12 desaturase
      codon-omptimized for expression in Y. lipolytica

<400> SEQUENCE: 12

| | |
|---|---|
| atggcctcca cctcggctct gcccaagcag aaccctgccc tccgacgaac cgtcacttcc | 60 |
| accactgtga ccgactcgga gtctgctgcc gtctctccct ccgattctcc cagacactcg | 120 |
| gcctcctcta catcgctgtc ttccatgtcc gaggtggaca ttgccaagcc caagtccgag | 180 |
| tacggtgtca tgctggatac ctacggcaac cagttcgaag ttcccgactt caccatcaag | 240 |
| gacatctaca acgctattcc caagcactgc ttcaagcgat ctgctctcaa gggatacggc | 300 |
| tacattcttc gagacattgt cctcctgact accactttca gcatctggta caactttgtg | 360 |
| acacccgagt acattccctc cactcctgct cgagccggtc tgtgggctgt gtacaccgtt | 420 |
| cttcagggac tcttcggtac tggactgtgg gtcattgccc acgagtgtgg acatggtgct | 480 |
| ttctccgatt cccgaatcat caacgacatt actggctggg tgcttcactc ttccctgctt | 540 |
| gttccctact tcagctggca aatctcccac cggaagcatc acaaggccac tggaaacatg | 600 |
| gagcgagaca tggtcttcgt tcctcgaacc cgagagcagc aagctactcg actcggcaag | 660 |
| atgacccacg aactcgccca tcttaccgag gaaactcctg ctttcacccct gctcatgctt | 720 |
| gtgcttcagc aactggtcgg ttggcccaac tatctcatta ccaacgttac tggacacaac | 780 |
| taccatgagc ggcagcgaga gggtcgaggc aagggaaagc acaacggtct ggcggtggaa | 840 |
| gttaaccatt tcgatccccg atctcctctg tacgagaaca gcgacgccaa gctcatcgtg | 900 |

```
ctctccgaca ttggcattgg tcttatggcc accgctctgt actttctcgt tcagaagttc      960
ggattctaca acatggccat ctggtacttc gttccctact tgtgggttaa ccactggctc     1020
gtcgccatta cctttctgca gcacacagat cctactcttc cccactacac caacgacgag     1080
tggaactttg tgcgaggtgc cgctgcaacc atcgaccgag agatgggctt cattggacgt     1140
catctgctcc acggcattat cgagactcac gtcctgcatc actacgtctc ttccattccc     1200
ttctacaatg cggacgaagc taccgaggcc atcaaaccta tcatgggcaa gcactatcga     1260
gctgatgtcc aggacggtcc tcgaggattc attcgagcca tgtaccgatc tgcacgaatg     1320
tgccagtggg ttgaaccctc cgctggtgcc gagggagctg gcaagggtgt cctgttcttt     1380
cgaaaccgaa acaatgtggg cactcctccc gctgtcatca gcccgttgc ctaa            1434
```

<210> SEQ ID NO 13
<211> LENGTH: 477
<212> TYPE: PRT
<213> ORGANISM: Fusarium moniliforme

<400> SEQUENCE: 13

```
Met Ala Ser Thr Ser Ala Leu Pro Lys Gln Asn Pro Ala Leu Arg Arg
1               5                   10                  15

Thr Val Thr Ser Thr Val Thr Asp Ser Glu Ser Ala Ala Val Ser
            20                  25                  30

Pro Ser Asp Ser Pro Arg His Ser Ala Ser Ser Thr Ser Leu Ser Ser
        35                  40                  45

Met Ser Glu Val Asp Ile Ala Lys Pro Lys Ser Glu Tyr Gly Val Met
    50                  55                  60

Leu Asp Thr Tyr Gly Asn Gln Phe Glu Val Pro Asp Phe Thr Ile Lys
65                  70                  75                  80

Asp Ile Tyr Asn Ala Ile Pro Lys His Cys Phe Lys Arg Ser Ala Leu
                85                  90                  95

Lys Gly Tyr Gly Tyr Ile Leu Arg Asp Ile Val Leu Leu Thr Thr Thr
            100                 105                 110

Phe Ser Ile Trp Tyr Asn Phe Val Thr Pro Glu Tyr Ile Pro Ser Thr
        115                 120                 125

Pro Ala Arg Ala Gly Leu Trp Ala Val Tyr Thr Val Leu Gln Gly Leu
    130                 135                 140

Phe Gly Thr Gly Leu Trp Val Ile Ala His Glu Cys Gly His Gly Ala
145                 150                 155                 160

Phe Ser Asp Ser Arg Ile Ile Asn Asp Ile Thr Gly Trp Val Leu His
                165                 170                 175

Ser Ser Leu Leu Val Pro Tyr Phe Ser Trp Gln Ile Ser His Arg Lys
            180                 185                 190

His His Lys Ala Thr Gly Asn Met Glu Arg Asp Met Val Phe Val Pro
        195                 200                 205

Arg Thr Arg Glu Gln Gln Ala Thr Arg Leu Gly Lys Met Thr His Glu
    210                 215                 220

Leu Ala His Leu Thr Glu Glu Thr Pro Ala Phe Thr Leu Leu Met Leu
225                 230                 235                 240

Val Leu Gln Gln Leu Val Gly Trp Pro Asn Tyr Leu Ile Thr Asn Val
                245                 250                 255

Thr Gly His Asn Tyr His Glu Arg Gln Arg Glu Gly Arg Gly Lys Gly
            260                 265                 270

Lys His Asn Gly Leu Gly Gly Val Asn His Phe Asp Pro Arg Ser
        275                 280                 285
```

```
Pro Leu Tyr Glu Asn Ser Asp Ala Lys Leu Ile Val Leu Ser Asp Ile
    290                 295                 300

Gly Ile Gly Leu Met Ala Thr Ala Leu Tyr Phe Leu Val Gln Lys Phe
305                 310                 315                 320

Gly Phe Tyr Asn Met Ala Ile Trp Tyr Phe Val Pro Tyr Leu Trp Val
                325                 330                 335

Asn His Trp Leu Val Ala Ile Thr Phe Leu Gln His Thr Asp Pro Thr
                340                 345                 350

Leu Pro His Tyr Thr Asn Asp Glu Trp Asn Phe Val Arg Gly Ala Ala
            355                 360                 365

Ala Thr Ile Asp Arg Glu Met Gly Phe Ile Gly Arg His Leu Leu His
    370                 375                 380

Gly Ile Ile Glu Thr His Val Leu His His Tyr Val Ser Ser Ile Pro
385                 390                 395                 400

Phe Tyr Asn Ala Asp Glu Ala Thr Glu Ala Ile Lys Pro Ile Met Gly
                405                 410                 415

Lys His Tyr Arg Ala Asp Val Gln Asp Gly Pro Arg Gly Phe Ile Arg
                420                 425                 430

Ala Met Tyr Arg Ser Ala Arg Met Cys Gln Trp Val Glu Pro Ser Ala
            435                 440                 445

Gly Ala Glu Gly Ala Gly Lys Gly Val Leu Phe Phe Arg Asn Arg Asn
    450                 455                 460

Asn Val Gly Thr Pro Pro Ala Val Ile Lys Pro Val Ala
465                 470                 475

<210> SEQ ID NO 14
<211> LENGTH: 1950
<212> TYPE: DNA
<213> ORGANISM: Artificial sequence
<220> FEATURE:
<223> OTHER INFORMATION: Y. lipolytica PDAT, but with an added alanine
      at amino acid position 2

<400> SEQUENCE: 14
atggccacac aacctgtgaa tcggaaggcg actgtcgagc gggtcgagcc agcagtggag      60
gtggctgact ccgagtccga ggccaagacc gacgtccacg ttcaccacca tcatcaccac     120
cacaagcgaa atccgtcaa gggcaagatt ctcaacttct tcacccgaag tcgacgtatc     180
accttcgtcc tcggcgccgt ggtcggtgtg atagccgcgg atactacgc tgcgccaccg      240 gagctcagca ttgatatcga cgctcttctc ggcgacttgc cctcgttcga ctttgacgct     300
ctatctctcg acaacttgtc gatggacagt gtgtcggact tgtacaaga catgaaatcg      360 cggtttccga ccaagattct gcaggaggcg gccaagatcg agaagcacca gaaaagcgaa     420
cagaaggctg ccccttttgc tgtgggcaag gctatgaaga gcgagggact caacgccaag     480
tacccggtgg tgctggtgcc cggcgtcatc tccacgggac tggagagctg gtccctggag     540
ggaaccgagg agtgtcccac cgagtcgcac ttcagaaagc gaatgtgggg ctcctggtac     600
atgatccgag tcatgctgct ggacaagtac tgctggctgc agaacctgat gctggacaca     660
gagaccggtc tagaccctcc ccatttcaag ctgcgagccg cccagggatt tgcctccgcc     720
gacttcttta tggcaggcta ctggctgtgg aacaagctgc tcgagaacct ggctgttatt     780
ggatacgata cggatacaat gtctgctgcg gcctacgact ggagactgtc ctaccctgat     840
ttggagcacc gagacggata cttctccaag ctcaaagctt caatcgaaga gactaagcgt     900
atgacaggtg agaagacagt tctgacgggc cattcgatgg ctcccaggt catcttctac      960
```

-continued

```
ttcatgaagt gggctgaggc cgagggatat ggaggaggag gtcccaactg ggtcaatgac    1020
catattgaat cctttgtcga catttccggc tccatgctgg gtactcccaa gaccctggtt    1080
gctcttctgt ctggagaaat gaaggatacc gtgcagctga acgcgatggc tgtgtatgga    1140
ctggagcagt tcttctctcg acgagagcga gccgatctgc tgcgaacatg gggaggaatt    1200
gcttccatga ttcccaaggg tggtaaggct atctggggtg atcattctgg agcccctgat    1260
gacgagcccg gccagaatgt cacctttggc aacttcatca agttcaagga gtccttgacc    1320
gagtactctg ctaagaacct cactatggat gaaaccgttg acttcctgta ttctcagtct    1380
cccgagtggt ttgtgaaccg aaccgagggt gcttactcct ttggaattgc caagactcga    1440
aagcaggttg agcagaatga gaagcgacct tctacctgga gcaaccctct ggaagctgct    1500
ctccccaatg cccccgatct caagatctac tgcttctatg gagtcggtaa ggataccgag    1560
cgagcctact actaccagga tgagcccaat cccgagcaga ccaacttgaa cgtcagtatc    1620
gctggaaacg accctgatgg tgtgcttatg ggtcagggcg atggaaccgt ctcccttgtg    1680
acccatacca tgtgtcaccg atggaaggac gagaactcca agttcaaccc tggtaacgcc    1740
caggtcaagg ttgtggagat gttgcaccag cctgatcgac ttgatattcg aggcggtgct    1800
cagactgccg agcatgtgga cattctgggg cgttctgagt tgaacgagat ggttctgaag    1860
gtggctagtg aaagggaaa tgagattgaa gagagagtca tctccaacat tgatgagtgg    1920
gtgtggaaga ttgatctcgg cagcaattag                                    1950
```

<210> SEQ ID NO 15
<211> LENGTH: 649
<212> TYPE: PRT
<213> ORGANISM: Artificial sequence
<220> FEATURE:
<223> OTHER INFORMATION: Y. lipolytica PDAT, but with an added alanine
      at amino acid position 2

<400> SEQUENCE: 15

```
Met Ala Thr Gln Pro Val Asn Arg Lys Ala Thr Val Glu Arg Val Glu
1               5                   10                  15

Pro Ala Val Glu Val Ala Asp Ser Glu Ser Ala Lys Thr Asp Val
            20                  25                  30

His Val His His His His His His Lys Arg Lys Ser Val Lys Gly
        35                  40                  45

Lys Ile Leu Asn Phe Phe Thr Arg Ser Arg Arg Ile Thr Phe Val Leu
    50                  55                  60

Gly Ala Val Val Gly Val Ile Ala Ala Gly Tyr Tyr Ala Ala Pro Pro
65                  70                  75                  80

Glu Leu Ser Ile Asp Ile Asp Ala Leu Leu Gly Asp Leu Pro Ser Phe
                85                  90                  95

Asp Phe Asp Ala Leu Ser Leu Asp Asn Leu Ser Met Asp Ser Val Ser
            100                 105                 110

Asp Phe Val Gln Asp Met Lys Ser Arg Phe Pro Thr Lys Ile Leu Gln
        115                 120                 125

Glu Ala Ala Lys Ile Glu Lys His Gln Lys Ser Glu Gln Lys Ala Ala
    130                 135                 140

Pro Phe Ala Val Gly Lys Ala Met Lys Ser Glu Gly Leu Asn Ala Lys
145                 150                 155                 160

Tyr Pro Val Val Leu Val Pro Gly Val Ile Ser Thr Gly Leu Glu Ser
                165                 170                 175
```

-continued

```
Trp Ser Leu Glu Gly Thr Glu Glu Cys Pro Thr Glu Ser His Phe Arg
                180                 185                 190
Lys Arg Met Trp Gly Ser Trp Tyr Met Ile Arg Val Met Leu Leu Asp
            195                 200                 205
Lys Tyr Cys Trp Leu Gln Asn Leu Met Leu Asp Thr Glu Thr Gly Leu
        210                 215                 220
Asp Pro Pro His Phe Lys Leu Arg Ala Ala Gln Gly Phe Ala Ser Ala
225                 230                 235                 240
Asp Phe Phe Met Ala Gly Tyr Trp Leu Trp Asn Lys Leu Leu Glu Asn
                245                 250                 255
Leu Ala Val Ile Gly Tyr Asp Thr Asp Thr Met Ser Ala Ala Ala Tyr
            260                 265                 270
Asp Trp Arg Leu Ser Tyr Pro Asp Leu Glu His Arg Asp Gly Tyr Phe
        275                 280                 285
Ser Lys Leu Lys Ala Ser Ile Glu Glu Thr Lys Arg Met Thr Gly Glu
    290                 295                 300
Lys Thr Val Leu Thr Gly His Ser Met Gly Ser Gln Val Ile Phe Tyr
305                 310                 315                 320
Phe Met Lys Trp Ala Glu Ala Glu Gly Tyr Gly Gly Gly Pro Asn
                325                 330                 335
Trp Val Asn Asp His Ile Glu Ser Phe Val Asp Ile Ser Gly Ser Met
            340                 345                 350
Leu Gly Thr Pro Lys Thr Leu Val Ala Leu Leu Ser Gly Glu Met Lys
        355                 360                 365
Asp Thr Val Gln Leu Asn Ala Met Ala Val Tyr Gly Leu Glu Gln Phe
    370                 375                 380
Phe Ser Arg Arg Glu Arg Ala Asp Leu Leu Arg Thr Trp Gly Gly Ile
385                 390                 395                 400
Ala Ser Met Ile Pro Lys Gly Lys Ala Ile Trp Gly Asp His Ser
                405                 410                 415
Gly Ala Pro Asp Asp Glu Pro Gly Gln Asn Val Thr Phe Gly Asn Phe
            420                 425                 430
Ile Lys Phe Lys Glu Ser Leu Thr Glu Tyr Ser Ala Lys Asn Leu Thr
        435                 440                 445
Met Asp Glu Thr Val Asp Phe Leu Tyr Ser Gln Ser Pro Glu Trp Phe
    450                 455                 460
Val Asn Arg Thr Glu Gly Ala Tyr Ser Phe Gly Ile Ala Lys Thr Arg
465                 470                 475                 480
Lys Gln Val Glu Gln Asn Glu Lys Arg Pro Ser Thr Trp Ser Asn Pro
                485                 490                 495
Leu Glu Ala Ala Leu Pro Asn Ala Pro Asp Leu Lys Ile Tyr Cys Phe
            500                 505                 510
Tyr Gly Val Gly Lys Asp Thr Glu Arg Ala Tyr Tyr Gln Asp Glu
        515                 520                 525
Pro Asn Pro Glu Gln Thr Asn Leu Asn Val Ser Ile Ala Gly Asn Asp
    530                 535                 540
Pro Asp Gly Val Leu Met Gly Gln Gly Asp Gly Thr Val Ser Leu Val
545                 550                 555                 560
Thr His Thr Met Cys His Arg Trp Lys Asp Glu Asn Ser Lys Phe Asn
                565                 570                 575
Pro Gly Asn Ala Gln Val Lys Val Val Glu Met Leu His Gln Pro Asp
            580                 585                 590
Arg Leu Asp Ile Arg Gly Gly Ala Gln Thr Ala Glu His Val Asp Ile
```

```
                    595                 600                 605
Leu Gly Arg Ser Glu Leu Asn Glu Met Val Leu Lys Val Ala Ser Gly
    610                 615                 620

Lys Gly Asn Glu Ile Glu Glu Arg Val Ile Ser Asn Ile Asp Glu Trp
625                 630                 635                 640

Val Trp Lys Ile Asp Leu Gly Ser Asn
                645

<210> SEQ ID NO 16
<211> LENGTH: 2127
<212> TYPE: DNA
<213> ORGANISM: Artificial sequence
<220> FEATURE:
<223> OTHER INFORMATION: E389D9eS/EgD8M fusion

<400> SEQUENCE: 16
atggctgccg tcatcgaggt ggccaacgag ttcgtcgcta tcactgccga gacccttccc        60
aaggtggact atcagcgact ctggcgagac atctactcct gcgagctcct gtacttctcc       120
attgctttcg tcatcctcaa gtttacccct ggcgagctct cggattctgg caaaaagatt       180
ctgcgagtgc tgttcaagtg gtacaacctc ttcatgtccg tcttttcgct ggtgtccttc       240
ctctgtatgg gttacgccat ctacaccgtt ggactgtact ccaacgaatg cgacagagct       300
ttcgacaaca gcttgttccg atttgccacc aaggtcttct actattccaa gtttctggag       360
tacatcgact ctttctacct tcccctcatg gccaagcctc tgtcctttct gcagttcttt       420
catcacttgg gagctcctat ggacatgtgg ctcttcgtgc agtactctgg cgaatccatt       480
tggatctttg tgttcctgaa cggattcatt cactttgtca tgtacggcta ctattggaca       540
cggctgatga agttcaactt ccccatgccc aagcagctca ttaccgcaat gcagatcacc       600
cagttcaacg ttggcttcta cctcgtgtgg tggtacaagg acattccctg ttaccgaaag       660
gatcccatgc gaatgctggc ctggatcttc aactactggt acgtcggtac cgttcttctg       720
ctcttcatca acttctttgt caagtcctac gtgtttccca gcctaagact gccgacaaa       780 aaggtccagg cgccggtcc cgctcgacct gccggactt cctcccgcta ctactacgac       840
tctctggccg tcatgggatc cgtgaaggct ctcgacagg ctctgccct cgtcatcgac       900 ggaaaggtgt acgacgtctc cgcttgggtg aacttccacc tggtggagc tgaaatcatt       960 gagaactacc agggacgaga tgctactgac gccttcatgg ttatgcactc tcaggaagcc      1020
ttcgacaagc tcaagcgaat gcccaagatc aaccaggctt ccgagctgcc tccccaggct      1080
gccgtcaacg aagctcagga ggatttccga agctccgag aagagctgat cgccactggc      1140
atgtttgacg cctctcccct ctggtactcg tacaagatct tgaccaccct gggtcttggc      1200
gtgcttgcct tcttcatgct ggtccagtac cacctgtact tcattggtgc tctcgtgctc      1260
ggtatgcact accagcaaat gggatggctg tctcatgaca tctgccacca ccagaccttc      1320
aagaaccgaa actggaataa cgtcctgggt ctggtctttg caacggact ccagggcttc      1380 tccgtgacct ggtggaagga cagacacaac gcccatcatt ctgctaccaa cgttcagggt      1440
cacgatcccg acattgataa cctgcctctg ctcgcctggt ccgaggacga tgtcactcga      1500
gcttctccca tctcccgaaa gctcattcag ttccaacagt actatttcct ggtcatctgt      1560
attctcctgc gattcatctg gtgtttccag tctgtgctga ccgttcgatc cctcaaggac      1620
cgagacaacc agttctaccg atctcagtac aagaaagagg ccattggact cgctctgcac      1680
tggactctca agaccctgtt ccacctcttc tttatgccct ccatcctgac ctcgatgctg      1740
```

-continued

```
gtgttctttg tttccgagct cgtcggtggc ttcggaattg ccatcgtggt cttcatgaac    1800
cactaccctc tggagaagat cggtgattcc gtctgggacg acatggcttc tctgtgggt     1860 cagatccatg agaccatgaa cattcgacga ggcatcatta ctgactggtt ctttggaggc    1920
ctgaactacc agatcgagca ccatctctgg cccacccctgc ctcgacacaa cctcactgcc   1980
gtttcctacc aggtggaaca gctgtgccag aagcacaacc tccctaccg aaaccctctg     2040 ccccatgaag gtctcgtcat cctgctccga tacctgtccc agttcgctcg aatggccgag    2100
aagcagcccg gtgccaaggc tcagtaa                                         2127
```

<210> SEQ ID NO 17
<211> LENGTH: 708
<212> TYPE: PRT
<213> ORGANISM: Artificial sequence
<220> FEATURE:
<223> OTHER INFORMATION: E389D9eS/EgD8M fusion

<400> SEQUENCE: 17

```
Met Ala Val Ile Glu Val Ala Asn Glu Phe Val Ala Ile Thr Ala
1               5                   10                  15

Glu Thr Leu Pro Lys Val Asp Tyr Gln Arg Leu Trp Arg Asp Ile Tyr
                20                  25                  30

Ser Cys Glu Leu Leu Tyr Phe Ser Ile Ala Phe Val Ile Leu Lys Phe
            35                  40                  45

Thr Leu Gly Glu Leu Ser Asp Ser Gly Lys Lys Ile Leu Arg Val Leu
        50                  55                  60

Phe Lys Trp Tyr Asn Leu Phe Met Ser Val Phe Ser Leu Val Ser Phe
65                  70                  75                  80

Leu Cys Met Gly Tyr Ala Ile Tyr Thr Val Gly Leu Tyr Ser Asn Glu
                85                  90                  95

Cys Asp Arg Ala Phe Asp Asn Ser Leu Phe Arg Phe Ala Thr Lys Val
                100                 105                 110

Phe Tyr Tyr Ser Lys Phe Leu Glu Tyr Ile Asp Ser Tyr Leu Pro
            115                 120                 125

Leu Met Ala Lys Pro Leu Ser Phe Leu Gln Phe Phe His His Leu Gly
        130                 135                 140

Ala Pro Met Asp Met Trp Leu Phe Val Gln Tyr Ser Gly Glu Ser Ile
145                 150                 155                 160

Trp Ile Phe Val Phe Leu Asn Gly Phe Ile His Phe Val Met Tyr Gly
                165                 170                 175

Tyr Tyr Trp Thr Arg Leu Met Lys Phe Asn Pro Met Pro Lys Gln
            180                 185                 190

Leu Ile Thr Ala Met Gln Ile Thr Gln Phe Asn Val Gly Phe Tyr Leu
        195                 200                 205

Val Trp Trp Tyr Lys Asp Ile Pro Cys Tyr Arg Lys Asp Pro Met Arg
210                 215                 220

Met Leu Ala Trp Ile Phe Asn Tyr Trp Tyr Val Gly Thr Val Leu Leu
225                 230                 235                 240

Leu Phe Ile Asn Phe Phe Val Lys Ser Tyr Val Phe Pro Lys Pro Lys
                245                 250                 255

Thr Ala Asp Lys Lys Val Gln Gly Ala Gly Pro Ala Arg Pro Ala Gly
            260                 265                 270

Leu Pro Pro Ala Thr Tyr Tyr Asp Ser Leu Ala Val Met Gly Ser Val
        275                 280                 285

Lys Ala Ser Arg Gln Ala Leu Pro Leu Val Ile Asp Gly Lys Val Tyr
```

-continued

```
            290                 295                 300
Asp Val Ser Ala Trp Val Asn Phe His Pro Gly Gly Ala Glu Ile Ile
305                 310                 315                 320

Glu Asn Tyr Gln Gly Arg Asp Ala Thr Asp Ala Phe Met Val Met His
                325                 330                 335

Ser Gln Glu Ala Phe Asp Lys Leu Lys Arg Met Pro Lys Ile Asn Gln
            340                 345                 350

Ala Ser Glu Leu Pro Pro Gln Ala Ala Val Asn Glu Ala Gln Glu Asp
        355                 360                 365

Phe Arg Lys Leu Arg Glu Glu Leu Ile Ala Thr Gly Met Phe Asp Ala
    370                 375                 380

Ser Pro Leu Trp Tyr Ser Tyr Lys Ile Leu Thr Thr Leu Gly Leu Gly
385                 390                 395                 400

Val Leu Ala Phe Phe Met Leu Val Gln Tyr His Leu Tyr Phe Ile Gly
                405                 410                 415

Ala Leu Val Leu Gly Met His Tyr Gln Gln Met Gly Trp Leu Ser His
            420                 425                 430

Asp Ile Cys His His Gln Thr Phe Lys Asn Arg Asn Trp Asn Asn Val
        435                 440                 445

Leu Gly Leu Val Phe Gly Asn Gly Leu Gln Gly Phe Ser Val Thr Trp
    450                 455                 460

Trp Lys Asp Arg His Asn Ala His His Ser Ala Thr Asn Val Gln Gly
465                 470                 475                 480

His Asp Pro Asp Ile Asp Asn Leu Pro Leu Leu Ala Trp Ser Glu Asp
                485                 490                 495

Asp Val Thr Arg Ala Ser Pro Ile Ser Arg Lys Leu Ile Gln Phe Gln
            500                 505                 510

Gln Tyr Tyr Phe Leu Val Ile Cys Ile Leu Leu Arg Phe Ile Trp Cys
        515                 520                 525

Phe Gln Ser Val Leu Thr Val Arg Ser Leu Lys Asp Arg Asp Asn Gln
    530                 535                 540

Phe Tyr Arg Ser Gln Tyr Lys Lys Glu Ala Ile Gly Leu Ala Leu His
545                 550                 555                 560

Trp Thr Leu Lys Thr Leu Phe His Leu Phe Phe Met Pro Ser Ile Leu
                565                 570                 575

Thr Ser Met Leu Val Phe Phe Val Ser Glu Leu Val Gly Gly Phe Gly
            580                 585                 590

Ile Ala Ile Val Val Phe Met Asn His Tyr Pro Leu Glu Lys Ile Gly
        595                 600                 605

Asp Ser Val Trp Asp Gly His Gly Phe Ser Val Gly Gln Ile His Glu
    610                 615                 620

Thr Met Asn Ile Arg Arg Gly Ile Ile Thr Asp Trp Phe Phe Gly Gly
625                 630                 635                 640

Leu Asn Tyr Gln Ile Glu His His Leu Trp Pro Thr Leu Pro Arg His
                645                 650                 655

Asn Leu Thr Ala Val Ser Tyr Gln Val Glu Gln Leu Cys Gln Lys His
            660                 665                 670

Asn Leu Pro Tyr Arg Asn Pro Leu Pro His Glu Gly Leu Val Ile Leu
        675                 680                 685

Leu Arg Tyr Leu Ser Gln Phe Ala Arg Met Ala Glu Lys Gln Pro Gly
    690                 695                 700

Ala Lys Ala Gln
705
```

<210> SEQ ID NO 18
<211> LENGTH: 1269
<212> TYPE: DNA
<213> ORGANISM: Artificial sequence
<220> FEATURE:
<223> OTHER INFORMATION: mutant E. gracilis delta-8 desaturase

<400> SEQUENCE: 18

```
atggtgaagg cttctcgaca ggctctgccc ctcgtcatcg acggaaaggt gtacgacgtc      60
tccgcttggg tgaacttcca ccctggtgga gctgaaatca ttgagaacta ccagggacga     120
gatgctactg acgccttcat ggttatgcac tctcaggaag ccttcgacaa gctcaagcga     180
atgcccaaga tcaaccaggc ttccgagctg cctccccagg ctgccgtcaa cgaagctcag     240
gaggatttcc gaaagctccg agaagagctg atcgccactg gcatgtttga cgcctctccc     300
ctctggtact cgtacaagat cttgaccacc ctgggtcttg gcgtgcttgc cttcttcatg     360
ctggtccagt accacctgta cttcattggt gctctcgtgc tcggtatgca ctaccagcaa     420
atgggatggc tgtctcatga catctgccac accagacct tcaagaaccg aaactggaat      480
aacgtcctgg gtctggtctt tggcaacgga ctccagggct ctccgtgac ctggtggaag      540
gacagacaca acgcccatca ttctgctacc aacgttcagg gtcacgatcc cgacattgat     600
aacctgcctc tgctcgcctg gtccgaggac gatgtcactc gagcttctcc catctcccga     660
aagctcattc agttccaaca gtactatttc ctggtcatct gtattctcct gcgattcatc     720
tggtgtttcc agtctgtgct gaccgttcga tccctcaagg accgagacaa ccagttctac     780
cgatctcagt acaagaaaga ggccattgga ctcgctctgc actggactct caagaccctg     840
ttccacctct ctttatgcc ctccatcctg acctcgatgc tggtgttctt tgtttccgag      900
ctcgtcggtg gcttcggaat tgccatcgtg gtcttcatga accactaccc tctggagaag     960
atcggtgatt ccgtctggga cggacatggc ttctctgtgg gtcagatcca tgagaccatg    1020
aacattcgac gaggcatcat tactgactgg ttctttggag gcctgaacta ccagatcgag    1080
caccatctct ggcccaccct gcctcgacac aacctcactg ccgtttccta ccaggtggaa    1140
cagctgtgcc agaagcacaa cctcccctac cgaaaccctc tgccccatga aggtctcgtc    1200
atcctgctcc gatacctgtc ccagttcgct cgaatggccg agaagcagcc cggtgccaag    1260
gctcagtaa                                                             1269
```

<210> SEQ ID NO 19
<211> LENGTH: 422
<212> TYPE: PRT
<213> ORGANISM: Artificial sequence
<220> FEATURE:
<223> OTHER INFORMATION: mutant E. gracilis delta-8 desaturase

<400> SEQUENCE: 19

Met Val Lys Ala Ser Arg Gln Ala Leu Pro Leu Val Ile Asp Gly Lys
1               5                   10                  15

Val Tyr Asp Val Ser Ala Trp Val Asn Phe His Pro Gly Gly Ala Glu
            20                  25                  30

Ile Ile Glu Asn Tyr Gln Gly Arg Asp Ala Thr Asp Ala Phe Met Val
        35                  40                  45

Met His Ser Gln Glu Ala Phe Asp Lys Leu Lys Arg Met Pro Lys Ile
    50                  55                  60

Asn Gln Ala Ser Glu Leu Pro Pro Gln Ala Ala Val Asn Glu Ala Gln
65                  70                  75                  80

```
Glu Asp Phe Arg Lys Leu Arg Glu Glu Leu Ile Ala Thr Gly Met Phe
                 85                  90                  95

Asp Ala Ser Pro Leu Trp Tyr Ser Tyr Lys Ile Leu Thr Thr Leu Gly
            100                 105                 110

Leu Gly Val Leu Ala Phe Phe Met Leu Val Gln Tyr His Leu Tyr Phe
        115                 120                 125

Ile Gly Ala Leu Val Leu Gly Met His Tyr Gln Gln Met Gly Trp Leu
130                 135                 140

Ser His Asp Ile Cys His His Gln Thr Phe Lys Asn Arg Asn Trp Asn
145                 150                 155                 160

Asn Val Leu Gly Leu Val Phe Gly Asn Gly Leu Gln Gly Phe Ser Val
                165                 170                 175

Thr Trp Trp Lys Asp Arg His Asn Ala His His Ser Ala Thr Asn Val
            180                 185                 190

Gln Gly His Asp Pro Asp Ile Asp Asn Leu Pro Leu Leu Ala Trp Ser
        195                 200                 205

Glu Asp Asp Val Thr Arg Ala Ser Pro Ile Ser Arg Lys Leu Ile Gln
210                 215                 220

Phe Gln Gln Tyr Tyr Phe Leu Val Ile Cys Ile Leu Leu Arg Phe Ile
225                 230                 235                 240

Trp Cys Phe Gln Ser Val Leu Thr Val Arg Ser Leu Lys Asp Arg Asp
                245                 250                 255

Asn Gln Phe Tyr Arg Ser Gln Tyr Lys Lys Glu Ala Ile Gly Leu Ala
            260                 265                 270

Leu His Trp Thr Leu Lys Thr Leu Phe His Leu Phe Phe Met Pro Ser
        275                 280                 285

Ile Leu Thr Ser Met Leu Val Phe Phe Val Ser Glu Leu Val Gly Gly
290                 295                 300

Phe Gly Ile Ala Ile Val Val Phe Met Asn His Tyr Pro Leu Glu Lys
305                 310                 315                 320

Ile Gly Asp Ser Val Trp Asp Gly His Gly Phe Ser Val Gly Gln Ile
                325                 330                 335

His Glu Thr Met Asn Ile Arg Arg Gly Ile Ile Thr Asp Trp Phe Phe
            340                 345                 350

Gly Gly Leu Asn Tyr Gln Ile Glu His His Leu Trp Pro Thr Leu Pro
        355                 360                 365

Arg His Asn Leu Thr Ala Val Ser Tyr Gln Val Glu Gln Leu Cys Gln
370                 375                 380

Lys His Asn Leu Pro Tyr Arg Asn Pro Leu Pro His Glu Gly Leu Val
385                 390                 395                 400

Ile Leu Leu Arg Tyr Leu Ser Gln Phe Ala Arg Met Ala Glu Lys Gln
                405                 410                 415

Pro Gly Ala Lys Ala Gln
            420

<210> SEQ ID NO 20
<211> LENGTH: 1518
<212> TYPE: DNA
<213> ORGANISM: Artificial sequence
<220> FEATURE:
<223> OTHER INFORMATION: Rhizobium leguminosarum bv. viciae 3841
      malonyl-CoA synthetase codon-opmtimized for expression in Y.
      lipolytica

<400> SEQUENCE: 20
```

```
atggtctcca accacctgtt cgacgccatg cgagctgccg ctcccggaga cgcacctttc    60
attcgaatcg acaacgctcg gacctggact tacgatgacg ccattgctct ttccggtcga   120
atcgctggag ctatggacgc actcggcatt cgacccggag acagagttgc cgtgcaggtc   180
gagaagtctg ccgaggcgtt gattctctac ctggcctgtc ttcgaaccgg agctgtctac   240
ctgcctctca cactgcctca caccctggcc gagctcgact acttcatcgg cgatgccgaa   300
ccgcgtctgg tggtcgttgc tcccgcagct cgaggtggcg tggagacaat tgccaagcga   360
cacggtgcta tcgtcgaaac cctcgacgcc gatggacgag gctccttgct ggaccttgct   420
agagatgagc ctgccgactt tgtcgatgct tcgcgatctg ccgacgatct ggctgctatt   480
ctctacactt ccggtacaac cggacgatcg aagggtgcca tgcttactca tggcaatctg   540
ctctccaacg ctctcacctt gcgagactat tggagagtta ccgcagacga tcgactcatc   600
catgccttgc aatctttca cactcatggt ctgttcgttg ctacgaacgt cacactgctt   660
gcaggagcct cgatgtttct gctctccaag ttcgatgccg acgaggtcgt ttctctcatg   720
ccacaggcca ccatgcttat gggcgtgccc acattctacg ttcgattgct gcagagtcct   780
cgactcgaga agggtgctgt ggccagcatc agactgttca tttctggatc agctcccttg   840
cttgccgaaa cccacgccga gtttcatgct cgtactggtc acgccattct cgagcgatac   900
ggcatgacgg aaaccaacat gaatacttcc aacccctacg agggcaagcg tattgccgga   960
accgttggtt ttcctctgcc cgacgtcact gtgcgagtca ccgatcccgc caccggtctc  1020
gttcttccac tgaagagac tggcatgatc gagatcaagg acccaacgt cttcaagggc  1080
tattggcgaa tgcccgaaaa gaccgctgcc gagtttaccg cagacggttt ctttatctct  1140
ggagatctcg gcaagatcga ccgagaaggt tacgttcaca ttgtgggacg aggcaaggac  1200
ctggtcattt ccggtggcta caacatctat cccaaagagg tcgaaggcga gatcgaccag  1260
atcgagggtg tggtcgagtc tgctgtcatt ggtgttcctc atcccgattt cggagaaggt  1320
gtcaccgctg ttgtcgtgtg caaacctggt gccgttctcg acgaaaagac catcgtgtct  1380
gctctgcagg accgtcttgc ccgatacaag caacccaagc ggattatctt tgccgacgat  1440
ctgcctcgaa acactatggg aaaggttcag aagaacattc ttcgacagca atacgccgat  1500
ctctacacca gacgataa                                                 1518
```

<210> SEQ ID NO 21
<211> LENGTH: 505
<212> TYPE: PRT
<213> ORGANISM: Artificial sequence
<220> FEATURE:
<223> OTHER INFORMATION: Rhizobium leguminosarum bv. viciae 3841
      malonyl-CoA synthetase codon-omptimized for expression in Y.
      lipolytica

<400> SEQUENCE: 21

```
Met Val Ser Asn His Leu Phe Asp Ala Met Arg Ala Ala Ala Pro Gly
1               5                   10                  15

Asp Ala Pro Phe Ile Arg Ile Asp Asn Ala Arg Thr Trp Thr Tyr Asp
            20                  25                  30

Asp Ala Ile Ala Leu Ser Gly Arg Ile Ala Gly Ala Met Asp Ala Leu
        35                  40                  45

Gly Ile Arg Pro Gly Asp Arg Val Ala Val Gln Val Glu Lys Ser Ala
    50                  55                  60

Glu Ala Leu Ile Leu Tyr Leu Ala Cys Leu Arg Thr Gly Ala Val Tyr
65                  70                  75                  80
```

```
Leu Pro Leu Asn Thr Ala Tyr Thr Leu Ala Glu Leu Asp Tyr Phe Ile
                 85                  90                  95
Gly Asp Ala Glu Pro Arg Leu Val Val Val Ala Pro Ala Ala Arg Gly
            100                 105                 110
Gly Val Glu Thr Ile Ala Lys Arg His Gly Ala Ile Val Glu Thr Leu
        115                 120                 125
Asp Ala Asp Gly Arg Gly Ser Leu Leu Asp Leu Ala Arg Asp Glu Pro
    130                 135                 140
Ala Asp Phe Val Asp Ala Ser Arg Ser Ala Asp Leu Ala Ala Ile
145                 150                 155                 160
Leu Tyr Thr Ser Gly Thr Thr Gly Arg Ser Lys Gly Ala Met Leu Thr
                165                 170                 175
His Gly Asn Leu Leu Ser Asn Ala Leu Thr Leu Arg Asp Tyr Trp Arg
            180                 185                 190
Val Thr Ala Asp Asp Arg Leu Ile His Ala Leu Pro Ile Phe His Thr
        195                 200                 205
His Gly Leu Phe Val Ala Thr Asn Val Thr Leu Ala Gly Ala Ser
    210                 215                 220
Met Phe Leu Leu Ser Lys Phe Asp Ala Asp Glu Val Val Ser Leu Met
225                 230                 235                 240
Pro Gln Ala Thr Met Leu Met Gly Val Pro Thr Phe Tyr Val Arg Leu
                245                 250                 255
Leu Gln Ser Pro Arg Leu Glu Lys Gly Ala Val Ala Ser Ile Arg Leu
            260                 265                 270
Phe Ile Ser Gly Ser Ala Pro Leu Leu Ala Glu Thr His Ala Glu Phe
        275                 280                 285
His Ala Arg Thr Gly His Ala Ile Leu Glu Arg Tyr Gly Met Thr Glu
    290                 295                 300
Thr Asn Met Asn Thr Ser Asn Pro Tyr Glu Gly Lys Arg Ile Ala Gly
305                 310                 315                 320
Thr Val Gly Phe Pro Leu Pro Asp Val Thr Val Arg Val Thr Asp Pro
                325                 330                 335
Ala Thr Gly Leu Val Leu Pro Glu Glu Thr Gly Met Ile Glu Ile
            340                 345                 350
Lys Gly Pro Asn Val Phe Lys Gly Tyr Trp Arg Met Pro Glu Lys Thr
        355                 360                 365
Ala Ala Glu Phe Thr Ala Asp Gly Phe Phe Ile Ser Gly Asp Leu Gly
    370                 375                 380
Lys Ile Asp Arg Glu Gly Tyr Val His Ile Val Gly Arg Gly Lys Asp
385                 390                 395                 400
Leu Val Ile Ser Gly Gly Tyr Asn Ile Tyr Pro Lys Glu Val Glu Gly
                405                 410                 415
Glu Ile Asp Gln Ile Glu Gly Val Val Glu Ser Ala Val Ile Gly Val
            420                 425                 430
Pro His Pro Asp Phe Gly Glu Gly Val Thr Ala Val Val Cys Lys
        435                 440                 445
Pro Gly Ala Val Leu Asp Glu Lys Thr Ile Val Ser Ala Leu Gln Asp
    450                 455                 460
Arg Leu Ala Arg Tyr Lys Gln Pro Lys Arg Ile Ile Phe Ala Asp Asp
465                 470                 475                 480
Leu Pro Arg Asn Thr Met Gly Lys Val Gln Lys Asn Ile Leu Arg Gln
                485                 490                 495
Gln Tyr Ala Asp Leu Tyr Thr Arg Arg
```

-continued

```
              500           505
```

<210> SEQ ID NO 22
<211> LENGTH: 849
<212> TYPE: DNA
<213> ORGANISM: Yarrowia lipolytica

<400> SEQUENCE: 22

```
atgtccgttg catccaagct cgtcttctac gtccgcgccg ccatcgccgt ggtcatcttt      60
gccgcctgtg ccacctacgg cgtgctggcg tccaccattc tcaccgccat cggcaagcag     120
ggcctggccc aatggaccgt tgccagagcc ttctactact cggtgcgcat cttcctgggt     180
atcagcatca agctgcgtag ccggcaggtg accggaaccg ccggtctgga tgcctccaag     240
atccaggtcg ccaacaccac caagcccatt gacgacatca ccaaacacct gccccgacca     300
tgcattctga tttccaacca ccagaacgaa atggacattc tggtgctcgg tcgcatcttc     360
ccccagtact gctccgtcac cgccaaaaag gccctcaagt ggtaccctct gctgggccag     420
ttcatggcgc tgtccggcac catcttcctg gaccgaaagg accgaaccaa gtccgtgcag     480
accctcggcg gcgccgtcaa gaccatccag agcggcaacg gaggcaaggg ccagagcgtc     540
ttcatgttcc ccgagggaac ccgatcctac tccaaggacg tcggcatcat gcccttcaag     600
aagggctgtt ccacctggc ggtccagtcg ggcgctccca ttgtccccgt ggtggtccag     660
aacacctccc gaatgttttc tttcggccga ggcaagctgg acgccggaga gatccttgtc     720
gacgtcctga gccccattga gaccaagggt ctggacgcca gcaacgtcga cgctctcatg     780
gccaccactt ataaggccat gtgcgagact gccgaccaga ttggctacgc tggccagaag     840
actcagtag                                                              849
```

<210> SEQ ID NO 23
<211> LENGTH: 282
<212> TYPE: PRT
<213> ORGANISM: Yarrowia lipolytica

<400> SEQUENCE: 23

```
Met Ser Val Ala Ser Lys Leu Val Phe Tyr Val Arg Ala Ala Ile Ala
1               5                   10                  15

Val Val Ile Phe Ala Ala Cys Ala Thr Tyr Gly Val Leu Ala Ser Thr
            20                  25                  30

Ile Leu Thr Ala Ile Gly Lys Gln Gly Leu Ala Gln Trp Thr Val Ala
        35                  40                  45

Arg Ala Phe Tyr Tyr Ser Val Arg Ile Phe Leu Gly Ile Ser Ile Lys
    50                  55                  60

Leu Arg Ser Arg Gln Val Thr Gly Thr Ala Gly Leu Asp Ala Ser Lys
65                  70                  75                  80

Ile Gln Val Ala Asn Thr Thr Lys Pro Ile Asp Asp Ile Thr Lys His
                85                  90                  95

Leu Pro Arg Pro Cys Ile Leu Ile Ser Asn His Gln Asn Glu Met Asp
            100                 105                 110

Ile Leu Val Leu Gly Arg Ile Phe Pro Gln Tyr Cys Ser Val Thr Ala
        115                 120                 125

Lys Lys Ala Leu Lys Trp Tyr Pro Leu Leu Gly Gln Phe Met Ala Leu
    130                 135                 140

Ser Gly Thr Ile Phe Leu Asp Arg Lys Asp Arg Thr Lys Ser Val Gln
145                 150                 155                 160

Thr Leu Gly Gly Ala Val Lys Thr Ile Gln Ser Gly Asn Gly Gly Lys
```

```
                   165                 170                 175
Gly Gln Ser Val Phe Met Phe Pro Glu Gly Thr Arg Ser Tyr Ser Lys
            180                 185                 190

Asp Val Gly Ile Met Pro Phe Lys Lys Gly Cys Phe His Leu Ala Val
        195                 200                 205

Gln Ser Gly Ala Pro Ile Val Pro Val Val Gln Asn Thr Ser Arg
    210                 215                 220

Met Phe Ser Phe Gly Arg Gly Lys Leu Asp Ala Gly Glu Ile Leu Val
225                 230                 235                 240

Asp Val Leu Ser Pro Ile Glu Thr Lys Gly Leu Asp Ala Ser Asn Val
            245                 250                 255

Asp Ala Leu Met Ala Thr Thr Tyr Lys Ala Met Cys Glu Thr Ala Asp
            260                 265                 270

Gln Ile Gly Tyr Ala Gly Gln Lys Thr Gln
            275                 280
```

<210> SEQ ID NO 24
<211> LENGTH: 9085
<212> TYPE: DNA
<213> ORGANISM: Artificial sequence
<220> FEATURE:
<223> OTHER INFORMATION: Construct pZKMPn-YD58 for expressing mutant
      YlLPCAT (M136S_T389A)

<400> SEQUENCE: 24

```
gtacgactga tgtgtatgta agctcaatga gcagcgtgct cctcggtcta ctatatggcg     60
acatatctct tcgcttctgt ttaccctta catacggtac agctcttaca atgacattta    120
tccactggcg tcgatccata aaccacacga accctgtttt gttagtcacc atgaccgggg   180
cgtgtcgtgt tacgttccac cgtttcacct cagccggtta cgattcaact tgccgcgtca   240
ttctgcgttg ctagcggagc gagtacgagt aactagactt tcgataagct gaatgacttc   300
agggtgcatg agaggcgcag atcggtattt tcggacttgt tcttctagaa gactggtttg   360
agagcaatcg cggaagagtt gggaaccgct ggagagcaga atgggttagt acagagacta   420
tctgatctcc cccgcttgtg tctagcccca ctttatactc tatttggcag ttgttgcttg   480
ttattcaagc acagcatgtc tgctcgtatc actttggaga catccctaac ctctaaacct   540
ttatagatgc cttaccttct gagcttgcag agagcattcc acagcgaacc cagttgacat   600
tatcagttga catcttacgc tcacaccaca ttacgcatct cacacacaat cacacgcaca   660
agtacacacg caagcacatc atacaatggt caaggcgcgc cagctgcatt aatgaatcgg   720
ccaacgcgcg gggagaggcg gtttgcgtat tgggcgctct tccgcttcct cgctcactga   780
ctcgctgcgc tcggtcgttc ggctgcggcg agcggtatca gctcactcaa aggcggtaat   840
acggttatcc acagaatcag gggataacgc aggaaagaac atgtgagcaa aaggccagca   900
aaaggccagg aaccgtaaaa aggccgcgtt gctggcgttt ttccataggc tccgccccc    960
tgacgagcat cacaaaaatc gacgctcaag tcagaggtgg cgaaacccga caggactata  1020
aagataccag gcgtttcccc ctggaagctc cctcgtgcgc tctcctgttc cgaccctgcc  1080
gcttaccgga tacctgtccg cctttctccc ttcgggaagc gtggcgcttt ctcatagctc  1140
acgctgtagg tatctcagtt cggtgtaggt cgttcgctcc aagctgggct gtgtgcacga  1200
accccccgtt cagcccgacc gctgcgcctt atccggtaac tatcgtcttg agtccaaccc  1260
ggtaagacac gacttatcgc cactggcagc agccactggt aacaggatta gcagagcgag  1320
gtatgtaggc ggtgctacag agttcttgaa gtggtggcct aactacggct acactagaag  1380
```

```
aacagtattt ggtatctgcg ctctgctgaa gccagttacc ttcggaaaaa gagttggtag    1440
ctcttgatcc ggcaaacaaa ccaccgctgg tagcggtggt ttttttgttt gcaagcagca    1500
gattacgcgc agaaaaaaag gatctcaaga agatcctttg atcttttcta cggggtctga    1560
cgctcagtgg aacgaaaact cacgttaagg gattttggtc atgagattat caaaaaggat    1620
cttcacctag atccttttaa attaaaaatg aagttttaaa tcaatctaaa gtatatatga    1680
gtaaacttgg tctgacagtt accaatgctt aatcagtgag gcacctatct cagcgatctg    1740
tctatttcgt tcatccatag ttgcctgact ccccgtcgtg tagataacta cgatacggga    1800
gggcttacca tctggcccca gtgctgcaat gataccgcga gacccacgct caccggctcc    1860
agatttatca gcaataaacc agccagccgg aagggccgag cgcagaagtg gtcctgcaac    1920
tttatccgcc tccatccagt ctattaattg ttgccgggaa gctagagtaa gtagttcgcc    1980
agttaatagt ttgcgcaacg ttgttgccat tgctacaggc atcgtggtgt cacgctcgtc    2040
gtttggtatg gcttcattca gctccggttc ccaacgatca aggcgagtta catgatcccc    2100
catgttgtgc aaaaaagcgg ttagctcctt cggtcctccg atcgttgtca gaagtaagtt    2160
ggccgcagtg ttatcactca tggttatggc agcactgcat aattctctta ctgtcatgcc    2220
atccgtaaga tgcttttctg tgactggtga gtactcaacc aagtcattct gagaatagtg    2280
tatgcggcga ccgagttgct cttgcccggc gtcaatacgg gataataccg cgccacatag    2340
cagaacttta aaagtgctca tcattggaaa acgttcttcg gggcgaaaac tctcaaggat    2400
cttaccgctg ttgagatcca gttcgatgta acccactcgt gcacccaact gatcttcagc    2460
atcttttact ttcaccagcg tttctgggtg agcaaaaaca ggaaggcaaa atgccgcaaa    2520
aaagggaata agggcgacac ggaaatgttg aatactcata ctcttccttt ttcaatatta    2580
ttgaagcatt tatcagggtt attgtctcat gagcggatac atatttgaat gtatttagaa    2640
aaataaacaa ataggggttc cgcgcacatt tccccgaaaa gtgccacctg atgcggtgtg    2700
aaataccgca cagatgcgta aggagaaaat accgcatcag gaaattgtaa gcgttaatat    2760
tttgttaaaa ttcgcgttaa attttttgtta aatcagctca ttttttaacc aataggccga    2820
aatcggcaaa atcccttata aatcaaaaga atagaccgag atagggttga gtgttgttcc    2880
agtttggaac aagagtccac tattaaagaa cgtggactcc aacgtcaaag ggcgaaaaac    2940
cgtctatcag ggcgatggcc cactacgtga accatcaccc taatcaagtt ttttggggtc    3000
gaggtgccgt aaagcactaa atcggaaccc taaagggagc ccccgattta gagcttgacg    3060
gggaaagccg gcgaacgtgg cgagaaagga agggaagaaa gcgaaaggag cgggcgctag    3120
ggcgctggca agtgtagcgg tcacgctgcg cgtaaccacc acacccgccg cgcttaatgc    3180
gccgctacag ggcgcgtcca ttcgccattc aggctgcgca actgttggga agggcgatcg    3240
gtgcgggcct cttcgctatt acgccagctg gcgaaagggg gatgtgctgc aaggcgatta    3300
agttgggtaa cgccagggtt ttcccagtca cgacgttgta aaacgacggc cagtgaattg    3360
taatacgact cactataggg cgaattgggc ccgacgtcgc atgctaggag agtctgtcgt    3420
tcgcgagtgg cgcgccaatg tcatgagtta cacctgattc aaatagtgaa taataatata    3480
acagccacaa atgaaagatg tatccacggg tagatatggc tttaattact gatgattgaa    3540
tgattatctg agtgctacag ttgtaacgag tacgagttat tacctgctac tattgtactc    3600
ctaaatcaaa gtactcgtac atgcaatgaa ttacttgtac ttgcgccaat cagatctatc    3660
ggttgtattg tatataatac tagtctattc ttttgcttac cagatggtgt aacctccatc    3720
```

```
gacaatgaga tcgtggccgg tcatgtagct ggaggcgtcg gaagccatga agacaatagg      3780
gcctccaaac tcctcgggct cagccattcg tcggaaagga attcgtcgct cccagtcgtt      3840
tcggagctct ccgtcagtct cgatgatgtg acgggtcaga ggagtaagaa tgtagccggg      3900
agacagagtg ttgactcgga tgttgtactg ggcccactcg gcagccagag acttggccat      3960
gtggatgaca cctgccttgg acatgttgta gggggtctgg ggctgggggt cgttgacaat      4020
ggagccactc atggatgcaa ccagaatcag agatccagga gactcgtcca ggacaagcga      4080
cttggccacc tcggtagcga agttgtagga tcccatgagg ttgacgtcca gcagtcgctt      4140
gacctggggg ttgggataat caaaggcagt catattctcg cagaatccgg cacagttaat      4200
taagttgcga cacatgtctt gatagtatct tgaattctct ctcttgagct tttccataac      4260
aagttcttct gcctccagga agtccatcgg tggtttgatc atggttttgg tgtagtggta      4320
gtgcagtggt ggtattgtga ctggggatgt agttgagaat aagtcataca caagtcagct      4380
ttcttcgagc ctcatataag tataagtagt tcaacgtatt agcactgtac ccagcatctc      4440
cgtatcgaga aacacaacaa catgccccat tggacagatc atgcggatac acaggttgtg      4500
cagtatcata catactcgat cagacaggtc gtctgaccat catacaagct gaacaagcgc      4560
tccatacttg cacgctctct atatacacag ttaaattaca tatccatagt ctaacctcta      4620
acagttaatc ttctggtaag cctcccagcc agccttctgg tatcgcttgg cctcctcaat      4680
aggatctcgg ttctggccgt acagacctcg gccgacaatt atgatatccg ttccggtaga      4740
catgacatcc tcaacagttc ggtactgctg tccgagagcg tctcccttgt cgtcaagacc      4800
cacccgggg gtcagaataa gccagtcctc agagtcgccc ttaggtcggt tctgggcaat      4860
gaagccaacc acaaactcgg ggtcggatcg ggcaagctca atggtctgct tggagtactc      4920
gccagtggcc agagagccct tgcaagacag ctcggccagc atgagcagac ctctggccag      4980
cttctcgttg ggagagggga ctaggaactc cttgtactgg gagttctcgt agtcagagac      5040
gtcctccttc ttctgttcag agacagtttc ctcggcacca gctcgcaggc cagcaatgat      5100
tccggttccg ggtacaccgt gggcgttggt gatatcggac cactcggcga ttcggtgaca      5160
ccggtactgg tgcttgacag tgttgccaat atctgcgaac tttctgtcct cgaacaggaa      5220
gaaaccgtgc ttaagagcaa gttccttgag ggggagcaca gtgccggcgt aggtgaagtc      5280
gtcaatgatg tcgatatggg ttttgatcat gcacacataa ggtccgacct tatcggcaag      5340
ctcaatgagc tccttggtgg tggtaacatc cagagaagca cacaggttgg ttttcttggc      5400
tgccacgagc ttgagcactc gagcggcaaa ggcggacttg tggacgttag ctcgagcttc      5460
gtaggagggc attttggtgg tgaagaggag actgaaataa atttagtctg cagaactttt      5520
tatcggaacc ttatctgggg cagtgaagta tatgttatgg taatagttac gagttagttg      5580
aacttataga tagactggac tatacggcta tcggtccaaa ttagaaagaa cgtcaatggc      5640
tctctgggcg tcgcctttgc cgacaaaaat gtgatcatga tgaaagccag caatgacgtt      5700
gcagctgata ttgttgtcgg ccaaccgcgc cgaaaacgca gctgtcagac ccacagcctc      5760
caacgaagaa tgtatcgtca agtgatcca agcacactca tagttggagt cgtactccaa      5820
aggcggcaat gacgagtcag acagatactc gtcgaccttt tccttgggaa ccaccaccgt      5880
cagcccttct gactcacgta ttgtagccac cgacacaggc aacagtccgt ggatagcaga      5940
atatgtcttg tcggtccatt tctcaccaac tttaggcgtc aagtgaatgt tgcagaagaa      6000
gtatgtgcct tcattgagaa tcggtgttgc tgatttcaat aaagtcttga gatcagtttg      6060
gccagtcatg ttgtgggggg taattggatt gagttatcgc ctacagtctg tacaggtata      6120
```

| | |
|---|---|
| ctcgctgccc actttatact ttttgattcc gctgcacttg aagcaatgtc gtttaccaaa | 6180 |
| agtgagaatg ctccacagaa cacaccccag ggtatggttg agcaaaaaat aaacactccg | 6240 |
| atacggggaa tcgaaccccg gtctccacgg ttctcaagaa gtattcttga tgagagcgta | 6300 |
| tcgatagttg gagcaaggga gaaatgtaga gtgtgaaaga ctcactatgg tccgggctta | 6360 |
| tctcgaccaa tagccaaagt ctggagtttc tgagagaaaa aggcaagata cgtatgtaac | 6420 |
| aaagcgacgc atggtacaat aataccggag gcatgtatca tagagagtta gtggttcgat | 6480 |
| gatggcactg gtgcctggta tgactttata cggctgacta catatttgtc ctcagacata | 6540 |
| caattacagt caagcactta cccttggaca tctgtaggta cccccggcc aagacgatct | 6600 |
| cagcgtgtcg tatgtcggat tggcgtagct ccctcgctcg tcaattggct cccatctact | 6660 |
| ttcttctgct tggctacacc cagcatgtct gctatggctc gttttcgtgc cttatctatc | 6720 |
| ctcccagtat taccaactct aaatgacatg atgtgattgg gtctacactt tcatatcaga | 6780 |
| gataaggagt agcacagttg cataaaaagc ccaactctaa tcagcttctt cctttcttgt | 6840 |
| aattagtaca aaggtgatta gcgaaatctg gaagcttagt tggccctaaa aaaatcaaaa | 6900 |
| aaagcaaaaa acgaaaaacg aaaaaccaca gttttgagaa cagggaggta acgaaggatc | 6960 |
| gtatatatat atatatatat atataccac ggatcccgag accggccttt gattcttccc | 7020 |
| tacaaccaac cattctcacc accctaattc acaaccatgg cctttccttg ggcagataag | 7080 |
| tgggcagccg atgcgtctgc atctacaggg ctgcctccgg acctcctcaa gattgcattc | 7140 |
| actctggtca tgtcttatcc gctgagttct ctcatgaaac ggctgccaga tgacgccaaa | 7200 |
| aacctcaaga tcatctatat catctccgtg tccatcttct acatggtggg tgtcttctcc | 7260 |
| ctctatggcg gagctgccac tctgctcttc tcctcaatgg gtaccttctt catcacccaa | 7320 |
| tggaagagcc cttacatgcc ctgggtcaat tttggttttg tcatgaccca tctcttcgtc | 7380 |
| aatcacctgc gttcgcagtt ttccccgaa acatacgacc ccaatgtcat tgacatcacc | 7440 |
| ggagcacaga tggttctgtg ttccaagcta tcgtcttttg gatggaacgt ctacgatgga | 7500 |
| tggcagattg agaagggtga gcagctcagc gagttccaga ctaaaagggc tgttctcaag | 7560 |
| caccccagtc ttatggactt cctagctttt gtgttctact tcccttccat tctgacaggt | 7620 |
| ccttcttacg actatatgga gttccataac tggctcgatc tcagcctgtt caaggagctg | 7680 |
| gagaaagata aggaccccaa gcgagctgct cgacgaaagc gacacaagat ccccgatct | 7740 |
| ggaatcgctg cttccaagaa actcgccgct ggtatcttct ggatcgttct gtggacccag | 7800 |
| gtggactctc gaatctccac cgcctacgct tactcagacg cattcaccaa ggagcacaac | 7860 |
| atctttggac gaattgtgta cctctacatg ctcggtttca tgtaccgact caagtactac | 7920 |
| ggagcctggt ccatttccga gggagcctgc atcttgtctg gctcggatt ccacggcgtg | 7980 |
| gaccccaaaa ctggcaagta caagtgggac cgtgtccaga acgtggaccc gtgggattc | 8040 |
| gaaactggtc aaaacacaaa ggctctgctg gaggcctgga accagaacac taacaagtgg | 8100 |
| ctacgaaact atgtgtacct ccgagtggtg cccaaaggcc aaaagcctgg attccgagcc | 8160 |
| actatcttca catttgtggt ttccgccttc tggcatggaa ctcgacctgg ctactatctc | 8220 |
| gcctttgtga ccgctgccat gtaccagtct gttggtaagt tcttccgacg atacctgcga | 8280 |
| cccttcttca tggagtctga tggaaagact gccggtccct ataagatcta ctacgacatt | 8340 |
| gtgtgttgga tcgttgtcca aaccgcattt ggatacgcta cccagtcctt tatgattcta | 8400 |
| gacttctggc tgtcgctcaa gtgttggaag aactcctggt tcctgtacca cattgctctg | 8460 |

-continued

| | |
|---|---|
| ggcgccatct tgcaattttc tagcccctac aaggcatggg cgattcccaa gatcaagaaa | 8520 |
| aagcaggctg agccgtcac tgacaagaag gacgccaagg aggaggtgaa gaaggacacc | 8580 |
| atcaagacca agtaagcggc cgcatgagaa gataaatata taaatacatt gagatattaa | 8640 |
| atgcgctaga ttagagagcc tcatactgct cggagagaag ccaagacgag tactcaaagg | 8700 |
| ggattacacc atccatatcc acagacacaa gctggggaaa ggttctatat acactttccg | 8760 |
| gaataccgta gtttccgatg ttatcaatgg gggcagccag gatttcaggc acttcggtgt | 8820 |
| ctcggggtga atggcgttc ttggcctcca tcaagtcgta ccatgtcttc atttgcctgt | 8880 |
| caaagtaaaa cagaagcaga tgaagaatga acttgaagtg aaggaattta aatgtaacga | 8940 |
| aactgaaatt tgaccagata ttgtgtccgc ggtggagctc cagcttttgt tccctttagt | 9000 |
| gagggttaat ttcgagcttg gcgtaatcat ggtcatagct gtttcctgtg tgaaattgtt | 9060 |
| atccgctcac aagcttccac acaac | 9085 |

<210> SEQ ID NO 25
<211> LENGTH: 1539
<212> TYPE: DNA
<213> ORGANISM: Artificial sequence
<220> FEATURE:
<223> OTHER INFORMATION: Y. lipolytica LPCAT containing M136S and T389A
      mutations

<400> SEQUENCE: 25

| | |
|---|---|
| atggcctttc cttgggcaga taagtgggca gccgatgcgt ctgcatctac agggctgcct | 60 |
| ccggacctcc tcaagattgc attcactctg gtcatgtctt atccgctgag ttctctcatg | 120 |
| aaacggctgc cagatgacgc caaaaacctc aagatcatct atatcatctc cgtgtccatc | 180 |
| ttctacatgg tgggtgtctt ctccctctat ggcggagctg ccactctgct cttctcctca | 240 |
| atgggtacct tcttcatcac ccaatggaag agcccttaca tgccctgggt caattttggt | 300 |
| tttgtcatga cccatctctt cgtcaatcac ctgcgttcgc agttttttccc cgaaacatac | 360 |
| gaccccaatg tcattgacat caccggagca cagatggttc tgtgttccaa gctatcgtct | 420 |
| tttggatgga cgtctacga tggatggcag attgagaagg gtgagcagct cagcgagttc | 480 |
| cagactaaaa gggctgttct caagcacccc agtcttatgg acttcctagc ttttgtgttc | 540 |
| tacttccctt ccattctgac aggtcccttct tacgactata tggagttcca taactggctc | 600 |
| gatctcagcc tgttcaagga gctggagaaa gataaggacc ccaagcgagc tgctcgacga | 660 |
| aagcgacaca agatccccg atctggaatc gctgcttcca agaaactcgc cgctggtatc | 720 |
| ttctggatcg ttctgtggac ccaggtggac tctcgaatct ccaccgccta cgcttactca | 780 |
| gacgcattca ccaaggagca caacatcttt ggacgaattg tgtacctcta catgctcggt | 840 |
| ttcatgtacc gactcaagta ctacggagcc tggtccattt ccgagggagc ctgcatcttg | 900 |
| tctggcctcg gattccacgg cgtggacccc aaaactggca agtacaagtg ggaccgtgtc | 960 |
| cagaacgtgg acccgtgggg attcgaaact ggtcaaaaca caaaggctct gctggaggcc | 1020 |
| tggaaccaga acactaacaa gtggctacga aactatgtgt acctccgagt ggtgcccaaa | 1080 |
| ggccaaaagc ctggattccg agccactatc ttcacatttg tggtttccgc cttctggcat | 1140 |
| ggaactcgac ctggctacta tctcgccttt gtgaccgctg ccatgtacca gtctgttggt | 1200 |
| aagttcttcc gacgatacct gcgaccttc ttcatggagt ctgatggaaa gactgccggt | 1260 |
| ccctataaga tctactacga cattgtgtgt tggatcgttg tccaaaccgc atttggatac | 1320 |
| gctacccagt cctttatgat tctagacttc tggctgtcgc tcaagtgttg gaagaactcc | 1380 |

```
tggttcctgt accacattgc tctgggcgcc atctttgcaa tttctagccc ctacaaggca   1440
tgggcgattc ccaagatcaa gaaaaagcag gctggagccg tcactgacaa gaaggacgcc   1500
aaggaggagg tgaagaagga caccatcaag accaagtaa                          1539
```

<210> SEQ ID NO 26
<211> LENGTH: 512
<212> TYPE: PRT
<213> ORGANISM: Artificial sequence
<220> FEATURE:
<223> OTHER INFORMATION: Y. lipolytica LPCAT containing M136S and T389A
      mutations

<400> SEQUENCE: 26

| Met | Ala | Phe | Pro | Trp | Ala | Asp | Lys | Trp | Ala | Asp | Ala | Ser | Ala | Ser |
|---|---|---|---|---|---|---|---|---|---|---|---|---|---|---|
| 1 | | | | 5 | | | | | 10 | | | | | 15 |

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
50                  55                  60

Gly Val Phe Ser Leu Tyr Gly Gly Ala Ala Thr Leu Leu Phe Ser Ser
65                  70                  75                  80

Met Gly Thr Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Ser Lys Leu Ser Ser Phe Gly Trp Asn
    130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

```
Leu Leu Glu Ala Trp Asn Gln Asn Thr Asn Lys Trp Leu Arg Asn Tyr
                340                 345                 350

Val Tyr Leu Arg Val Val Pro Lys Gly Gln Lys Pro Gly Phe Arg Ala
            355                 360                 365

Thr Ile Phe Thr Phe Val Val Ser Ala Phe Trp His Gly Thr Arg Pro
        370                 375                 380

Gly Tyr Tyr Leu Ala Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Gln Ala Gly Ala Val Thr Asp
                485                 490                 495

Lys Lys Asp Ala Lys Glu Glu Val Lys Lys Asp Thr Ile Lys Thr Lys
                500                 505                 510
```

<210> SEQ ID NO 27
<211> LENGTH: 14825
<212> TYPE: DNA
<213> ORGANISM: Artificial sequence
<220> FEATURE:
<223> OTHER INFORMATION: Construct pZKT2-ML9DCB for expressing YlCPT1, YlD9, and MaLPAAT1S

<400> SEQUENCE: 27

```
aaaccacgcc aactgatatc cccttacgtt acccccctcat cacctggtga ggcaaaactg    60
taaggtgaaa gctaaaaatg acatctcagc tgcacgaagg accggggctt aaaagacggg   120
ctggtgcttg tgatttaaaa ctggacaaat ctcagcttgc ttgaaatttt ggtctccaac   180
tgtttccgag cgaatcgcac acaaaccggg cttctctctg cagaccacgc ccccgaaact   240
ctttctccca ccaccaccaa cactcccttt ccattcccac accgttcctc tctcatcctc   300
gcgcaatcat cttcgtctgc gacatattgt acgacataca gtaccacgga acgtttcaga   360
ccgtcgacgt gaacacatct taggaacagc aacctgagct acagaaatct atctataggc   420
ggataaaaaa acgcacccac tgctcgtcct ccttgctcct cgaaaccgac tcctctacac   480
acgtcaaatc cgaggttgaa atcttcccca catttggcag ccaaaccagc acatcccagc   540
aacctcgcac agcgccgaaa tcgacctgtc gacttggcca caaaaaaaag caccggctct   600
gcaacagttc tcacgaccaa ttacgtacaa gtacgaaatc gttcgtggac cgtgactgat   660
aagctcccac ttttcttct aacaacaggc aacagacaag tcacacaaaa caaaagccat   720
ggtgaaaaac gtggaccaag tggatctctc gcaggtcgac accattgcct ccggccgaga   780
tgtcaactac aaggtcaagt acacctccgg cgttaagatg agccagggcg cctacgacga   840
caagggccgc cacatttccg agcagccctt cacctgggcc aactggcacc agcacatcaa   900
ctggctcaac ttcattctgg tgattgcgct gcctctgtcg tcctttgctg ccgctccctt   960
cgtctccttc aactggaaga ccgccgcgtt tgctgtcggc tattacatgt gcaccggtct  1020
```

```
cggtatcacc gccggctacc accgaatgtg ggcccatcga gcctacaagg ccgctctgcc    1080
cgttcgaatc atccttgctc tgtttggagg aggagctgtc gagggctcca tccgatggtg    1140
ggcctcgtct caccgagtcc accaccgatg gaccgactcc aacaaggacc cttacgacgc    1200
ccgaaaggga ttctggttct cccactttgg ctggatgctg cttgtgccca accccaagaa    1260
caagggccga actgacattt ctgacctcaa caacgactgg gttgtccgac tccagcacaa    1320
gtactacgtt tacgttctcg tcttcatggc cattgttctg cccaccctcg tctgtggctt    1380
tggctggggc gactggaagg gaggtcttgt ctacgccggt atcatgcgat acacctttgt    1440
gcagcaggtg actttctgtg tcaactccct tgcccactgg attggagagc agcccttcga    1500
cgaccgacga actccccgag accacgctct taccgccctg gtcacctttg agagggcta    1560
ccacaacttc caccacgagt tcccctcgga ctaccgaaac gccctcatct ggtaccagta    1620
cgaccccacc aagtggctca tctggaccct caagcaggtt ggtctcgcct gggacctcca    1680
gaccttctcc cagaacgcca tcgagcaggg tctcgtgcag cagcgacaga gaagctgga    1740
caagtggcga acaaacctca actgggggtat ccccattgag cagctgcctg tcattgagtt    1800
tgaggagttc caagagcagg ccaagacccg agatctggtt ctcatttctg cattgtcca    1860
cgacgtgtct gcctttgtcg agcaccaccc tggtggaaag gccctcatta tgagcgccgt    1920
cggcaaggac ggtaccgctg tcttcaacgg aggtgtctac cgacactcca acgctggcca    1980
caacctgctt gccaccatgc gagtttcggt cattcgaggc ggcatggagg ttgaggtgtg    2040
gaagactgcc cagaacgaaa agaaggacca gaacattgtc tccgatgaga gtggaaaccg    2100
aatccaccga gctggtctcc aggccacccg ggtcgagaac cccggtatgt ctggcatggc    2160
tgcttaggcg gccgcatgag aagataaata tataaataca ttgagatatt aaatgcgcta    2220
gattagagag cctcatactg ctcggagaga agccaagacg agtactcaaa ggggattaca    2280
ccatccatat ccacagacac aagctgggga aaggttctat atacactttc cggaataccg    2340
tagttttccga tgttatcaat gggggcagcc aggatttcag gcacttcggt gtctcggggt    2400
gaaatggcgt tcttggcctc catcaagtcg taccatgtct tcatttgcct gtcaaagtaa    2460
aacagaagca gatgaagaat gaacttgaag tgaaggaatt taaattttcg agattttaca    2520
gatatttctc gcagtttttc acgtccccctt gtccttgtcc tattgtttca ataaactct    2580
cgtctactga tttcacatgg aacctttgct atttcgggga taacccccctt tgccattgca    2640
cgatggacgt ggcaaaagaa agatcgccct gcggggatac ttatcatgtg gtcacatgct    2700
gtgattagaa ataagaaaa aggtgctttt ttggcgctgt gattaacatc tcgtctgccg    2760
tgctctacta gtcgcaatag caaaaactcg cttaatagtg tgcatagtgc ggggtagcag    2820
gatactgaac tacagtacga tttgcttgct actgcttgta gcaattacct ttactgtagg    2880
gaccacacct cctggtttca atgtcttttcc tcgcctcgac aaagcaaaac tgtcacccaa    2940
tcacaccttg ttcatattca ttagtgcatc cgttaacctt gacatgacac ttctcatact    3000
agtgataggg ctgtagttga gacaagttga ttcacacgga tacatacaaa gcctcagaga    3060
gcaaatgtta tatactcagg gaccgaccaa tcaaaaaaac acactcctaa taaccaccat    3120
ttccatctac gcgtactcac tctgtcagct gccccacatt gcccaatgca caatgcacaa    3180
tgatgtgtgc aaacaacgca atcaaaagtc tatggatgct gaccaaactc tgatcaccaa    3240
gttgcgaaca tgaaaaagaa gacctgtgta tatataagta aggggagag ccctaactag    3300
atctttcgaa aaccccccga ccttcacctt ccacaaccat gatcatctta tacgttttgg    3360
ccgttgcggt ctccttcctc atcttcaaga gagtcaccta caccatggct tctattggtt    3420
```

-continued

```
cgtccaaccc cgtgctcttg gctgcgattc ccttcgtcta cctgtttgtc ctcccacgag   3480
tcctggcttt cctgcctcag aaggctcagt tcctggccaa atgtattgtg gtcctgattg   3540
ccacgcttat catgtccgtt gcaggctgct tcatctcgat cgtgtgcgct cttctggaca   3600
agagatacgt catcaattac gttgtgtcgc gattgttctc cttccttgcc gctcgaccgt   3660
gtggtgtgac ctataagatt gttggtgagg aacacctcga taagtaccct gctatcgtgg   3720
tctgtaacca tcaatcctct atggatatga tggttttggg acgagttttt ccaaagcact   3780
gcgttgtcat ggcgaagaag gaactcctgt actttccctt tttgggaatg tttatgaaac   3840
tgagcaacgc tatcttcatc gaccggaaga accacaagaa agccatcgag tctaccaccc   3900
aagccgtggc ggacatgaag aagcacaact ctggaatctg gattttccca gagggcaccc   3960
ggtctagact ggacaaggca gacctgctgc ccttcaagaa aggtgccttt catcttgcaa   4020
ttcaggccca gctccctatt ctccccatta tctcgcaggg ctattcccat atctacgact   4080
cttcgaagcg gtacttcccc ggtggagagc tcgagatcag agtcctggag cccattccta   4140
caactggcct cactactgat gatgtgaacg acctgatgga caagacacga aaccttatgc   4200
tcaagcactt gaaggagatg gattcccagt attcgtcgag cactgctgaa atggatccaa   4260
cgcacatcga cgccgatatt gccaagtcta cagccaccag cattggcaac actgacgacg   4320
caattacaaa acgtcgtacc cctaaggaat aagcggccgc aagtgtggat ggggaagtga   4380
gtgcccggtt ctgtgtgcac aattggcaat ccaagatgga tggattcaac acagggatat   4440
agcgagctac gtggtggtgc gaggatatag caacggatat ttatgtttga cacttgagaa   4500
tgtacgatac aagcactgtc caagtacaat actaaacata ctgtacatac tcatactcgt   4560
acccgggcaa cggtttcact tgagtgcagt ggctagtgct cttactcgta cagtgtgcaa   4620
tactgcgtat catagtcttt gatgtatatc gtattcattc atgttagttg cgtacgtcta   4680
cattgagtgg gttaagtatg ctttgcggtg gtgcgctttg tttgaatttt aaatggaagt   4740
gtgctgtgag cagaccagac gaacggcttg tggggcgtgt ctatttatcc gggcttgtgg   4800
gggggttccg gcagaaacga tgaggtcaat caattgcgcg ggcaattgac tacaacaagc   4860
cctccagacg gactcttgtc gcctctgttc acattggcca atccttcacc ttattttcct   4920
acaacgtgct gcacttggac atctgtcaca aaggctcaaa gtctacgttg ctactgactc   4980
atgcaactct aagctgttgg atgaagggtc cggaaaaact ctcggctgtg tgattggtga   5040
ataaatcccg ctagccgagg tatgcaagga cgagtgcaga gaaatcctcc ggtcgagcac   5100 gcgagggggtc ggatgtgaga ctggtcagta attgacctga cgtgaccatc gtttggtttt   5160
tatggtcctt ctcggcccca tgacaaagtg tctctagacc ttgttgtgaa cctctgaccg   5220
ggccgctgtc gcaactaaaa aattgaaaat ggtaggctca aacgaagaga acctccaatt   5280
ttgacacaat tgagtttgga cgttttgcga gtggaagagc aggaggggga tgaggaggag   5340
acgttgcggc gtggctgatg tggcggagaa tcagagggcg acagaatggt aggactgtat   5400
aagtgtacgc gagcccattt gtatattgtc caacccgtat cccaagacca ataaccacta   5460
ttcttgaaac caactaacgc ctctagtgcg accttatcgt gaccgttgag cgtgtgtgag   5520
ctgagtgagg cctttacaaa tggcctgttt tagtaccgtg ctgttggata caacataaaa   5580
aatggcgtca tgtgacagca tcatccgttg tcaccgttga atagccgttg gcagcttgcg   5640
tcaacaacat gccatagaaa acaaaccgct cttgtatgta gaggtcatcc aggtgtgaca   5700
tattcacatg actccctagc ctctatcaca tgatgcgtgg cggacagact cggcttgaca   5760
```

```
gtggatctgc gttgccccg tcattccggt tcattctcgt gtttaaaatt cgccaaccag    5820
cattggatac tgtatgtacc atacagacac gttttttcct cttcgtagta ggcacagaag    5880
acgtgcaata gatgtacata acctctgctt gtgaaaaaga aatgagcagc agcttaagcg    5940
gctgaattat gtgtgcactt tggcactact tgcacctggt atctttgttg acttcaatga    6000
gacaggatgt tacgcattca ccacttcaca ctaatccgat tgtaccgcag tggtggttgg    6060
acacactcta gaccgctgtt tccactcaca acacctatcc tcggcttatg aagagaaagg    6120
gtcggcttat gcaatgcagg acacgcgtga agttgaaaa acttgcgatt cagtaagaac     6180
aggcgcgcca gctgcattaa tgaatcggcc aacgcgcggg gagaggcggt ttgcgtattg    6240
ggcgctcttc cgcttcctcg ctcactgact cgctgcgctc ggtcgttcgg ctgcggcgag    6300
cggtatcagc tcactcaaag gcggtaatac ggttatccac agaatcaggg gataacgcag    6360
gaaagaacat gtgagcaaaa ggccagcaaa aggccaggaa ccgtaaaaag gccgcgttgc    6420
tggcgttttt ccataggctc cgcccccctg acgagcatca aaaaatcga cgctcaagtc     6480
agaggtggcg aaacccgaca ggactataaa gataccaggc gtttccccct ggaagctccc    6540
tcgtgcgctc tcctgttccg accctgccgc ttaccggata cctgtccgcc tttctccctt    6600
cgggaagcgt ggcgctttct catagctcac gctgtaggta tctcagttcg gtgtaggtcg    6660
ttcgctccaa gctgggctgt gtgcacgaac cccccgttca gcccgaccgc tgcgccttat    6720
ccggtaacta tcgtcttgag tccaacccgg taagacacga cttatcgcca ctggcagcag    6780
ccactggtaa caggattagc agagcgaggt atgtaggcgg tgctacagag ttcttgaagt    6840
ggtggcctaa ctacggctac actagaagaa cagtatttgg tatctgcgct ctgctgaagc    6900
cagttacctt cggaaaaaga gttggtagct cttgatccgg caaacaaacc accgctggta    6960
gcggtggttt ttttgtttgc aagcagcaga ttacgcgcag aaaaaaagga tctcaagaag    7020
atcctttgat cttttctacg ggtctgacg ctcagtggaa cgaaaactca cgttaaggga     7080
ttttggtcat gagattatca aaaaggatct cacctagat cctttttaaat taaaaatgaa    7140
gttttaaatc aatctaaagt atatatgagt aaacttggtc tgacagttac caatgcttaa    7200
tcagtgaggc acctatctca gcgatctgtc tatttcgttc atccatagtt gcctgactcc    7260
ccgtcgtgta gataactacg atacgggagg gcttaccatc tggccccagt gctgcaatga    7320
taccgcgaga cccacgctca ccggctccag atttatcagc aataaaccag ccagccggaa    7380
gggccgagcg cagaagtggt cctgcaactt tatccgcctc catccagtct attaattgtt    7440
gccgggaagc tagagtaagt agttcgccag ttaatagttt cgcaacgtt gttgccattg      7500
ctacaggcat cgtggtgtca cgctcgtcgt ttggtatggc ttcattcagc tccggttccc    7560
aacgatcaag gcgagttaca tgatccccca tgttgtgcaa aaaagcggtt agctccttcg    7620
gtcctccgat cgttgtcaga agtaagttgg ccgcagtgtt atcactcatg gttatggcag    7680
cactgcataa ttctcttact gtcatgccat ccgtaagatg cttttctgtg actggtgagt    7740
actcaaccaa gtcattctga gaatagtgta tgcggcgacc gagttgctct tgcccggcgt    7800
caatacggga taataccgcg ccacatagca gaactttaaa agtgctcatc attggaaaac    7860
gttcttcggg gcgaaaactc tcaaggatct taccgctgtt gagatccagt tcgatgtaac    7920
ccactcgtgc acccaactga tcttcagcat cttttacttt caccagcgtt tctgggtgag    7980
caaaaacagg aaggcaaaat gccgcaaaaa agggaataag ggcgacacgg aaatgttgaa    8040
tactcatact cttcctttt caatattatt gaagcattta tcagggttat tgtctcatga     8100
gcggatacat atttgaatgt atttagaaaa ataaacaaat aggggttccg cgcacatttc    8160
```

```
cccgaaaagt gccacctgat gcggtgtgaa ataccgcaca gatgcgtaag gagaaaatac    8220
cgcatcagga aattgtaagc gttaatattt tgttaaaatt cgcgttaaat ttttgttaaa    8280
tcagctcatt ttttaaccaa taggccgaaa tcggcaaaat cccttataaa tcaaaagaat    8340
agaccgagat agggttgagt gttgttccag tttggaacaa gagtccacta ttaaagaacg    8400
tggactccaa cgtcaaaggg cgaaaaaccg tctatcaggg cgatggccca ctacgtgaac    8460
catcacccta atcaagtttt tggggtcga ggtgccgtaa agcactaaat cggaacccta    8520
aagggagccc ccgatttaga gcttgacggg gaaagccggc gaacgtggcg agaaaggaag    8580
ggaagaaagc gaaaggagcg gcgctaggg cgctggcaag tgtagcggtc acgctgcgcg    8640
taaccaccac acccgccgcg cttaatgcgc cgctacaggg cgcgtccatt cgccattcag    8700
gctgcgcaac tgttgggaag gcgatcggt gcgggcctct tcgctattac gccagctggc    8760
gaaaggggga tgtgctgcaa ggcgattaag ttgggtaacg ccagggtttt cccagtcacg    8820
acgttgtaaa acgacggcca gtgaattgta atacgactca ctatagggcg aattgggccc    8880
gacgtcgcat gcaaggaagt cgatggcggt ggtggcatac tcgtacttca tagagtactt    8940
gcactcggca tcgaggtagg ggtaggggta caggattcgc ttacccttg tgagagtaga    9000
ctgggggatc acccgggtt cggggtggg catctcagca agagaagcaa cggtgaaagc    9060
tcgagatccg tagttctcag aaaggtgctt agcaacctcg ggtcaaggt cctcctgctg    9120
gatcagatca atgtaagtga gaggagtcca gtccttagca ccgatgagct tgacgtctcg    9180
ggtgacggcc ttggcggaga tttcaggctt gagaccgaac ttggcaatgc aggcatcgac    9240
agtctcctca gccatctgtc ggtaagtggt ccactttccg ccagcaatgg tgacaagacc    9300
agactcggag taggtgatga gatggtttcg gacaagagac tcggtgttct tggcgtgggg    9360
gtcccggaca aggggtcgga ttccggacca ggcggccaga acgtcctctc gtcgcacatc    9420
aaccttgccc tcaacgtagt gtcggacctc gttgagaatg aagtcaatgt cctcctcgga    9480
ggggataggg ttagcagtga tcttggtagg ctggtcagta gtaccggcaa gggtgtttcc    9540
ctgccagggg aggaagaaga taactcggcc gtcagaagta gcgggtcaa ggagtcccat    9600
cttcttgggg gagtagtaac cggggagaat gatgtgaaca ccggaggaag gagcacagat    9660
ctccttggtg ttcttgtcgt ccatctgtcg cagagagtca gtgaagggtc cagtagcatt    9720
aacgacacac ttggccttga tgttgaagga tccagcgttt ccgtcagtat ccttggcaac    9780
aacaccgttg agctggccat ggcgcccctt ggtgagctcg gtgacctcgc aatggttcag    9840
gatggtggca ccccttctcaa cagcagtcat aataagagaa acgttcattc gagagtcgtt    9900
ctggagccca tcatagtaga caatggcgcc cttgagcttg tcatcggaaa gcatggggaa    9960
ggcatcgaga gcacgggatc gggagagcat gtaagaggac tcgaggttct gtcggccggc   10020
aagcagatcg tagcacttga cacccatcca gaagtaggga agctgccacc aggtgtagac   10080
ggggatcatg atgggcagag caaaggtgag gtggggagca atgtcgagga agacctttcg   10140
ctcgtgcagg gcctccttga ccagctcgta ctggttgtag tcgaggttcc acacagcctt   10200
ctcgaggtat cggacacctc cgtggatgag cttggtggat cgggacgagg ttccgcagga   10260
gaaatcgtct cgctcgacca gagcaacctt gaggcctcgt gtgacagcgt cgaggcgat   10320
accggatccg gtagctcctc caccaacaac gacgagatca aactcctcgg tcttcatctt   10380
aattaagttg cgacacatgt cttgatagta tcttgaattc tctctcttga gcttttccat   10440
aacaagttct tctgcctcca ggaagtccat gggtggtttg atcatggttt tggtgtagtg   10500
```

```
gtagtgcagt ggtggtattg tgactgggga tgtagttgag aataagtcat acacaagtca    10560
gctttcttcg agcctcatat aagtataagt agttcaacgt attagcactg tacccagcat    10620
ctccgtatcg agaaacacaa caacatgccc cattggacag atcatgcgga tacacaggtt    10680
gtgcagtatc atacatactc gatcagacag gtcgtctgac catcatacaa gctgaacaag    10740
cgctccatac ttgcacgctc tctatataca cagttaaatt acatatccat agtctaacct    10800
ctaacagtta atcttctggt aagcctccca gccagccttc tggtatcgct tggcctcctc    10860
aataggatct cggttctggc cgtacagacc tcggccgaca attatgatat ccgttccggt    10920
agacatgaca tcctcaacag ttcggtactg ctgtccgaga gcgtctccct tgtcgtcaag    10980 acccacccccg ggggtcagaa taagccagtc ctcagagtcg cccttaggtc ggttctgggc    11040
aatgaagcca accacaaact cggggtcgga tcggcaagc tcaatggtct gcttggagta     11100
ctcgccagtg gccagagagc ccttgcaaga cagctcggcc agcatgagca gacctctggc    11160
cagcttctcg ttgggagagg ggactaggaa ctccttgtac tgggagttct cgtagtcaga    11220
gacgtcctcc ttcttctgtt cagagacagt ttcctcggca ccagctcgca ggccagcaat    11280
gattccggtt ccgggtacac cgtgggcgtt ggtgatatcg gaccactcgg cgattcggtg    11340
acaccggtac tggtgcttga cagtgttgcc aatatctgcg aactttctgt cctcgaacag    11400
gaagaaaccg tgcttaagag caagttcctt gaggggagc acagtgccgg cgtaggtgaa      11460
gtcgtcaatg atgtcgatat gggttttgat catgcacaca taaggtccga ccttatcggc    11520
aagctcaatg agctccttgg tggtggtaac atccagagaa gcacacaggt tggttttctt    11580
ggctgccacg agcttgagca ctcgagcggc aaaggcggac ttgtggacgt tagctcgagc    11640
ttcgtaggag ggcattttgg tggtgaagag gagactgaaa taaatttagt ctgcagaact    11700
ttttatcgga accttatctg gggcagtgaa gtatatgtta tggtaatagt tacgagttag    11760
ttgaacttat agatagactg gactatacgg ctatcggtcc aaattagaaa gaacgtcaat    11820
ggctctctgg gcgtcgcctt tgccgacaaa aatgtgatca tgatgaaagc cagcaatgac    11880
gttgcagctg atattgttgt cggccaaccg cgccgaaaac gcagctgtca gacccacagc    11940
ctccaacgaa gaatgtatcg tcaaagtgat ccaagcacac tcatagttgg agtcgtactc    12000
caaaggcggc aatgacgagt cagacagata tcgtcgacc tttttccttgg gaaccaccac    12060 cgtcagccct tctgactcac gtattgtagc caccgacaca ggcaacagtc cgtggatagc    12120
agaatatgtc ttgtcggtcc atttctcacc aactttaggc gtcaagtgaa tgttgcagaa    12180
gaagtatgtg ccttcattga gaatcggtgt tgctgatttc aataaagtct tgagatcagt    12240
ttggccagtc atgttgtggg gggtaattgg attgagttat cgcctacagt ctgtacaggt    12300
atactcgctg cccactttat acttttttgat tccgctgcac ttgaagcaat gtcgtttacc    12360
aaaagtgaga atgctccaca gaacacaccc cagggtatgg ttgagcaaaa aataaacact    12420
ccgatacggg gaatcgaacc ccggtctcca cggttctcaa gaagtattct tgatgagagc    12480
gtatcgatgg ttaatgctgc tgtgtgctgt gtgtgtgtgt tgtttggcgc tcattgttgc    12540
gttatgcagc gtacaccaca atattggaag cttattagcc tttctatttt ttcgtttgca    12600
aggcttaaca acattgctgt ggagagggat ggggatatgg aggccgctgg agggagtcgg    12660
agaggcgttt tggagcggct tggcctggcg cccagctcgc gaaacgcacc taggacccttt   12720 tggcacgccg aaatgtgcca cttttcagtc tagtaacgcc ttacctacgt cattccatgc    12780
gtgcatgttt gcgccttttt tcccttgccc ttgatcgcca cacagtacag tgcactgtac    12840
agtggaggtt ttgggggggt cttagatggg agctaaaagc ggcctagcgg tacactagtg    12900
```

```
ggattgtatg gagtggcatg gagcctaggt ggagcctgac aggacgcacg accggctagc   12960
ccgtgacaga cgatgggtgg ctcctgttgt ccaccgcgta caaatgtttg ggccaaagtc   13020
ttgtcagcct tgcttgcgaa cctaattccc aattttgtca cttcgcaccc ccattgatcg   13080
agccctaacc cctgcccatc aggcaatcca attaagctcg cattgtctgc cttgtttagt   13140
ttggctcctg cccgtttcgg cgtccacttg cacaaacaca aacaagcatt atatataagg   13200
ctcgtctctc cctcccaacc acactcactt ttttgcccgt cttcccttgc taacacaaaa   13260
gtcaagaaca caaacaacca ccccaacccc cttacacaca agacatatct acagcaatgg   13320
ccatgggcgt attcattaaa caggagcagc ttccggctct caagaagtac aagtactccg   13380
ccgaggatca ctcgttcatc tccaacaaca ttctgcgccc cttctggcga cagtttgtca   13440
aaatcttccc tctgtggatg ccccccaaca tggtgactct gctgggcttc ttctttgtca   13500
ttgtgaactt catcaccatg ctcattgttg atcccaccca cgaccgcgag cctcccagat   13560
gggtctacct cacctacgct ctgggtctgt tcctttacca gacatttgat gcctgtgacg   13620
gatcccatgc ccgacgaact ggccagagtg gaccccttgg agagctgttt gaccactgtg   13680
tcgacgccat gaatacctct ctgattctca cggtggtggt gtccaccacc catatgggat   13740
ataacatgaa gctactgatt gtgcagattg ccgctctcgg aaacttctac ctgtcgacct   13800
gggagaccta ccataccgga actctgtacc tttctggctt ctctggtcct gttgaaggta   13860
tcttgattct ggtggctctt ttcgtcctca ccttcttcac tggtcccaac gtgtacgctc   13920
tgaccgtcta cgaggctctt cccgagtcca tcacttcgct gctgcctgcc agcttcctgg   13980
acgtcaccat cacccagatc tacattggat tcggagtgct gggcatggtg ttcaacatct   14040
acggcgcctg cggaaacgtg atcaagtact acaacaacaa gggcaagagc gctctccccg   14100
ccattctcgg aatcgccccc tttggcatct tctacgtcgg cgtctttgcc tgggcccatg   14160
ttgctcctct gcttctctcc aagtacgcca tcgtctatct gtttgccatt ggggctgcct   14220
ttgccatgca agtcggccag atgattcttg cccatctcgt gcttgctccc tttccccact   14280
ggaacgtgct gctcttcttc ccctttgtgg gactggcagt gcactacatt gcaccgtgt    14340 ttggctggga cgccgatatc gtgtcggtta acactctctt cacctgtttt ggcgccaccc   14400
tctccattta cgccttcttt gtgcttgaga tcatcgacga gatcaccaac tacctcgata   14460
tctggtgtct gcgaatcaag taccctcagg agaagaagac cgaataagcg gccgcatgta   14520
catacaagat tatttataga aatgaatcgc gatcgaacaa agagtacgag tgtacgagta   14580
ggggatgatg ataaaagtgg aagaagttcc gcatctttgg atttatcaac gtgtaggacg   14640
atacttcctg taaaaatgca atgtctttac cataggttct gctgtagatg ttattaacta   14700
ccattaacat gtctacttgt acagttgcag accagttgga gtatagaatg gtacacttac   14760
caaaaagtgt tgatggttgt aactacgata tataaaactg ttgacgggat ctgcgtacac   14820
tgttt                                                              14825
```

<210> SEQ ID NO 28
<211> LENGTH: 13236
<212> TYPE: DNA
<213> ORGANISM: Artificial sequence
<220> FEATURE:
<223> OTHER INFORMATION: Construct pZKLY-PP2YAP for expressing YlYAP1, Yl6PGL, and YlG6PDH

<400> SEQUENCE: 28

```
aaaccatcat ctaagggcct caaaactacc tcggaactgc tgcgctgatc tggacaccac      60
```

```
agaggttccg agcactttag gttgcaccaa atgtcccacc aggtgcaggc agaaaacgct    120
ggaacagcgt gtacagtttg tcttaacaaa aagtgagggc gctgaggtcg agcagggtgg    180
tgtgacttgt tatagccttt agagctgcga aagcgcgtat ggatttggct catcaggcca    240
gattgagggt ctgtggacac atgtcatgtt agtgtacttc aatcgccccc tggatatagc    300
cccgacaata ggccgtggcc tcattttttt gccttccgca catttccatt gctcggtacc    360
cacaccttgc ttctcctgca cttgccaacc ttaatactgg tttacattga ccaacatctt    420
acaagcgggg ggcttgtcta gggtatatat aaacagtggc tctcccaatc ggttgccagt    480 ctctttttc ctttctttcc ccacagattc gaaatctaaa ctacacatca caccatggct    540
cccaaggtca tctctaagaa cgaatcgcaa ctggtcgctg aggctgctgc cgctgagatc    600
attcgactcc agaacgagtc aattgctgcc actggagctt ccatgttgc cgtatctgga    660 ggctctctgg tgtctgctct ccgaaagggt ctggtcaaca actcggagac caagttcccc    720
aagtggaaga ttttcttctc cgacgaacgg ctggtcaagc tggacgatgc cgactccaac    780
tacggtctcc tcaagaagga tctgctcgat cacatcccca aggatcagca accacaggtc    840
ttcaccgtca aggagtctct tctgaacgac tctgatgccg tctccaagga ctaccaggag    900
cagattgtca agaatgtgcc tctcaacggc cagggagtgc ctgttttcga tctcattctg    960
ctcggatgcg gtcctgatgg ccacacttgc tcgctgttcc ctggacacgc tctgctcaag   1020
gaggagacca gtttgtcgc caccattgag gactctccca gcctcctcc tcgacgaatc    1080 accatcactt tccccgttct caaggctgcc aaggccatcg ctttcgtcgc cgagggagcc   1140
ggaaaggccc ctgtcctcaa gcagatcttc gaggagcccg agcccactct tccctctgcc   1200
attgtcaaca aggtcgctac cggacccgtt ttctggtttg tttccgactc tgccgttgag   1260
ggcgtcaacc tctccaagat ctagcggccg catgagaaga taaatatata aatacattga   1320
gatattaaat gcgctagatt agagagcctc atactgctcg gagagaagcc aagacgagta   1380
ctcaaagggg attacaccat ccatatccac agacacaagc tggggaaagg ttctatatac   1440
actttccgga ataccgtagt ttccgatgtt atcaatgggg gcagccagga tttcaggcac   1500
ttcggtgtct cggggtgaaa tggcgttctt ggcctccatc aagtcgtacc atgtcttcat   1560
ttgcctgtca aagtaaaaca gaagcagatg aagaatgaac ttgaagtgaa ggaatttaaa   1620
tgcgtttgga tagcactagt ctatgaggag cgttttatgt gcggtgagg gcgattggtg    1680 ctcatatggg ttcaattgag gtggcggaac gagcttagtc ttcaattgag gtgcgagcga   1740
cacaattggg tgtcacgtgg cctaattgac ctcgggtcgt ggagtcccca gttatacagc   1800
aaccacgagg tgcatgggta ggagacgtca ccagacaata gggtttttt tggactggag   1860 agggttgggc aaaagcgctc aacgggctgt ttggggagct gtggggagg aattggcgat   1920 atttgtgagg ttaacggctc cgatttgcgt gttttgtcgc tcctgcatct ccccataccc   1980
atatcttccc tccccacctc tttcacgat aattttacgg atcagcaata aggttccttc   2040
tcctagtttc cacgtccata tatatctatg ctgcgtcgtc cttttcgtga catcaccaaa   2100
acacatacaa ccatggctgg caccttaccc aagttcggcg acggaaccac cattgtggtt   2160
cttggagcct ccgcgacct cgctaagaag aagaccgtga gtattgaacc agactgaggt   2220
caattgaaga gtaggagagt ctgagaacat cgacggacc tgattgtgct ctggaccact   2280
caattgactc gttgagagcc ccaatgggtc ttggctagcc gagtcgttga cttgttgact   2340
tgttgagccc agaaccccca acttttgcca ccatacaccg ccatcaccat gacacccaga   2400
```

```
tgtgcgtgcg tatgtgagag tcaattgttc cgtggcaagg cacagcttat tccaccgtgt    2460
tccttgcaca ggtggtcttt acgctctccc actctatccg agcaataaaa gcggaaaaac    2520
agcagcaagt cccaacagac ttctgctccg aataaggcgt ctagcaagtg tgcccaaaac    2580
tcaattcaaa aatgtcagaa acctgatatc aacccgtctt caaaagctaa ccccagttcc    2640
ccgccctctt cggcctttac cgaaacggcc tgctgcccaa aaatgttgaa atcatcggct    2700
acgcacggtc gaaaatgact caggaggagt accacgagcg aatcagccac tacttcaaga    2760
cccccgacga ccagtccaag gagcaggcca agaagttcct tgagaacacc tgctacgtcc    2820 agggcccta cgacggtgcc gagggctacc agcgactgaa tgaaaagatt gaggagtttg    2880
agaagaagaa gcccgagccc cactaccgtc ttttctacct ggctctgccc cccagcgtct    2940
tccttgaggc tgccaacggt ctgaagaagt atgtctaccc cggcgagggc aaggcccgaa    3000
tcatcatcga gaagcccttt ggccacgacc tggcctcgtc acgagagctc caggacggcc    3060
ttgctcctct ctggaaggag tctgagatct ccgaatcga ccactacctc ggaaaggaga    3120
tggtcaagaa cctcaacatt ctgcgatttg caaccagtt cctgtccgcc gtgtgggaca    3180
agaacaccat ttccaacgtc cagatctcct tcaaggagcc ctttggcact gagggccgag    3240
gtggatactt caacgacatt ggaatcatcc gagacgttat tcagaaccat ctgttgcagg    3300
ttctgtccat tctagccatg gagcgacccg tcactttcgg cgccgaggac attcgagatg    3360
agaaggtcaa ggtgctccga tgtgtcgaca ttctcaacat tgacgacgtc attctcggcc    3420
agtacggccc ctctgaagac ggaaagaagc ccggatacac cgatgacgat ggcgttcccg    3480
atgactcccg agctgtgacc tttgctgctc tccatctcca gatccacaac gacagatggg    3540
agggtgttcc tttcatcctc cgagccggta aggctctgga cgagggcaag gtcgagatcc    3600
gagtgcagtt ccgagacgtg accaagggcg ttgtggacca tctgcctcga aatgagctcg    3660
tcatccgaat ccagccctcc gagtccatct acatgaagat gaactccaag ctgcctggcc    3720
ttactgccaa gaacattgtc accgacctgg atctgaccta caaccgacga tactcggacg    3780
tgcgaatccc tgaggcttac gagtctctca ttctggactg cctcaagggt gaccacacca    3840
actttgtgcg aaacgacgag ctggacattt cctggaagat tttcaccgat ctgctgcaca    3900
agattgacga ggacaagagc attgtgcccg agaagtacgc ctacggctct cgtggccccg    3960
agcgactcaa gcagtggctc cgagaccgag gctacgtgcg aaacggcacc gagctgtacc    4020
aatggcctgt caccaagggc tcctcgtgag cggccgcaag tgtggatggg gaagtgagtg    4080
cccggttctg tgtgcacaat tggcaatcca agatggatgg attcaacaca gggatatagc    4140
gagctacgtg gtggtgcgag gatatagcaa cggatattta tgtttgacac ttgagaatgt    4200
acgatacaag cactgtccaa gtacaatact aaacatactg tacatactca tactcgtacc    4260
cgggcaacgg tttcacttga gtgcagtggc tagtgctctt actcgtacag tgtgcaatac    4320
tgcgtatcat agtctttgat gtatatcgta ttcattcatg ttagttgcgt acgttgattg    4380
aggtggagcc agatgggcta ttgtttcata tatagactgg cagccacctc tttggcccag    4440
catgtttgta tacctggaag ggaaaactaa agaagctggc tagtttagtt tgattattat    4500
agtagatgtc ctaatcacta gagattagaa tgtcttggcg atgattagtc gtcgtccct    4560 gtatcatgtc tagaccaact gtgtcatgaa gttggtgctg gtgttttacc tgtgtactac    4620
aagtaggtgt cctagatcta gtgtacagag ccgtttagac ccatgtggac ttcaccatta    4680
acgatggaaa atgttcatta tatgacagta tattacaatg gacttgctcc atttcttcct    4740
tgcatcacat gttctccacc tccatagttg atcaacacat catagtagct aaggctgctg    4800
```

```
ctctcccact acagtccacc acaagttaag tagcaccgtc agtacagcta aaagtacacg    4860
tctagtacgt ttcataacta gtcaagtagc ccctattaca gatatcagca ctatcacgca    4920 cgagttttc tctgtgctat ctaatcaact tgccaagtat tcggagaaga tacactttct    4980
tggcatcagg tatacgaggg agcctatcag atgaaaaagg gtatattgga tccattcata    5040
tccacctaca cgttgtcata atctcctcat tcacgtgatt catttcgtga cactagtttc    5100
tcactttccc ccccgcacct atagtcaact tggcggacac gctacttgta gctgacgttg    5160
atttatagac ccaatcaaag cgggttatcg gtcaggtagc acttatcatt catcgttcat    5220
actacgatga gcaatctcgg gcatgtccgg aaaagtgtcg ggcgcgccag ctgcattaat    5280
gaatcggcca acgcgcgggg agaggcggtt tgcgtattgg gcgctcttcc gcttcctcgc    5340
tcactgactc gctgcgctcg gtcgttcggc tgcggcgagc ggtatcagct cactcaaagg    5400
cggtaatacg gttatccaca gaatcagggg ataacgcagg aaagaacatg tgagcaaaag    5460
gccagcaaaa ggccaggaac cgtaaaaagg ccgcgttgct ggcgtttttc cataggctcc    5520
gcccccctga cgagcatcac aaaaatcgac gctcaagtca gaggtggcga aacccgacag    5580
gactataaag ataccaggcg tttccccctg gaagctccct cgtgcgctct cctgttccga    5640
ccctgccgct taccggatac ctgtccgcct ttctcccttc gggaagcgtg gcgctttctc    5700
atagctcacg ctgtaggtat ctcagttcgg tgtaggtcgt tcgctccaag ctgggctgtg    5760
tgcacgaacc ccccgttcag cccgaccgct gcgccttatc cggtaactat cgtcttgagt    5820
ccaacccggt aagacacgac ttatcgccac tggcagcagc cactggtaac aggattagca    5880
gagcgaggta tgtaggcggt gctacagagt tcttgaagtg gtggcctaac tacggctaca    5940
ctagaagaac agtatttggt atctgcgctc tgctgaagcc agttaccttc ggaaaaagag    6000
ttggtagctc ttgatccggc aaacaaacca ccgctggtag cggtggtttt tttgtttgca    6060
agcagcagat tacgcgcaga aaaaaaggat ctcaagaaga tcctttgatc ttttctacgg    6120
ggtctgacgc tcagtggaac gaaaactcac gttaagggat tttggtcatg agattatcaa    6180
aaaggatctt cacctagatc cttttaaatt aaaaatgaag ttttaaatca atctaaagta    6240
tatatgagta aacttggtct gacagttacc aatgcttaat cagtgaggca cctatctcag    6300
cgatctgtct atttcgttca tccatagttg cctgactccc cgtcgtgtag ataactacga    6360
tacgggaggg cttaccatct ggccccagtg ctgcaatgat accgcgagac ccacgctcac    6420
cggctccaga tttatcagca ataaaccagc cagccggaag ggccgagcgc agaagtggtc    6480
ctgcaacttt atccgcctcc atccagtcta ttaattgttg ccgggaagct agagtaagta    6540
gttcgccagt taatagtttg cgcaacgttg ttgccattgc tacaggcatc gtggtgtcac    6600
gctcgtcgtt tggtatggct tcattcagct ccggttccca acgatcaagg cgagttacat    6660 gatccccat gttgtgcaaa aaagcggtta gctccttcgg tcctccgatc gttgtcagaa    6720
gtaagttggc cgcagtgtta tcactcatgg ttatggcagc actgcataat tctcttactg    6780
tcatgccatc cgtaagatgc ttttctgtga ctggtgagta ctcaaccaag tcattctgag    6840
aatagtgtat gcggcgaccg agttgctctt gcccggcgtc aatacgggat aataccgcgc    6900
cacatagcag aactttaaaa gtgctcatca ttggaaaacg ttcttcgggg cgaaaactct    6960
caaggatctt accgctgttg agatccagtt cgatgtaacc cactcgtgca cccaactgat    7020
cttcagcatc ttttactttc accagcgttt ctgggtgagc aaaaacagga aggcaaaatg    7080
ccgcaaaaaa gggaataagg gcgacacgga aatgttgaat actcatactc ttccttttc    7140
```

```
aatattattg aagcatttat cagggttatt gtctcatgag cggatacata tttgaatgta    7200
tttagaaaaa taaacaaata ggggttccgc gcacatttcc ccgaaaagtg ccacctgatg    7260
cggtgtgaaa taccgcacag atgcgtaagg agaaaatacc gcatcaggaa attgtaagcg    7320
ttaatatttt gttaaaattc gcgttaaatt tttgttaaat cagctcattt tttaaccaat    7380
aggccgaaat cggcaaaatc ccttataaat caaaagaata gaccgagata gggttgagtg    7440
ttgttccagt ttggaacaag agtccactat taaagaacgt ggactccaac gtcaaagggc    7500
gaaaaaccgt ctatcagggc gatggcccac tacgtgaacc atcaccctaa tcaagttttt    7560
tggggtcgag gtgccgtaaa gcactaaatc ggaaccctaa agggagcccc cgatttagag    7620
cttgacgggg aaagccggcg aacgtggcga gaaaggaagg gaagaaagcg aaaggagcgg    7680
gcgctagggc gctggcaagt gtagcggtca cgctgcgcgt aaccaccaca cccgccgcgc    7740
ttaatgcgcc gctacagggc gcgtccattc gccattcagg ctgcgcaact gttgggaagg    7800
gcgatcggtg cgggcctctt cgctattacg ccagctggcg aaaggggat gtgctgcaag    7860 gcgattaagt tgggtaacgc cagggttttc ccagtcacga cgttgtaaaa cgacggccag    7920
tgaattgtaa tacgactcac tatagggcga attgggcccg acgtcgcatg cattccgaca    7980
gcagcgactg ggcaccatga tcaagcgaaa caccttcccc cagctgccct ggcaaaccat    8040
caagaaccct actttcatca agtgcaagaa cggttctact cttctcacct ccggtgtcta    8100
cggctggtgc cgaaagccta actacaccgc tgatttcatc atgtgcctca cctgggctct    8160
catgtgcggt gttgcttctc ccctgcctta cttctacccg gtcttcttct tcctggtgct    8220
catccaccga gcttaccgag actttgagcg actggagcga aagtacgtg aggactacca    8280 ggagttcaag cgacaggtcc cttggatctt catcccttat gttttctaaa cgataagctt    8340
agtgagcgaa tggtgaggtt acttaattga gtggccagcc tatgggattg tataacagac    8400
agtcaatata ttactgaaaa gactgaacag ccagacggag tgaggttgtg agtgaatcgt    8460
agagggcggc tattacagca agtctactct acagtgtact aacacagcag agaacaaata    8520
caggtgtgca ttcggctatc tgagaattag ttggagagct cgagaccctc ggcgataaac    8580
tgctcctcgg ttttgtgtcc atacttgtac ggaccattgt aatggggcaa gtcgttgagt    8640
tctcgtcgtc cgacgttcag agcacagaaa ccaatgtaat caatgtagca gagatggttc    8700
tgcaaaagat tgatttgtgc gagcaggtta attaagttgc gacacatgtc ttgatagtat    8760
cttgaattct ctctcttgag cttttccata acaagttctt ctgcctccag gaagtccatg    8820
ggtggtttga tcatggtttt ggtgtagtgg tagtgcagtg gtggtattgt gactggggat    8880
gtagttgaga ataagtcata cacaagtcag ctttcttcga gcctcatata agtataagta    8940
gttcaacgta ttagcactgt acccagcatc tccgtatcga gaaacacaac aacatgcccc    9000
attggacaga tcatgcggat acacaggttg tgcagtatca tacatactcg atcagacagg    9060
tcgtctgacc atcatacaag ctgaacaagc gctccatact tgcacgctct ctatatacac    9120
agttaaatta catatcccata gtctaacctc taacagttaa tcttctggta agcctcccag    9180
ccagccttct ggtatcgctt ggcctcctca ataggatctc ggttctggcc gtacagacct    9240
cggccgacaa ttatgatatc cgttccggta gacatgacat cctcaacagt tcggtactgc    9300
tgtccgagag cgtctcccett gtcgtcaaga cccacccccgg gggtcagaat aagccagtcc    9360
tcagagtcgc ccttaggtcg gttctgggca atgaagccaa ccacaaactc ggggtcggat    9420
cgggcaagct caatggtctg cttggagtac tcgccagtgg ccagagagcc cttgcaagac    9480
agctcggcca gcatgagcag acctctggcc agcttctcgt tgggagaggg gactaggaac    9540
```

```
tccttgtact gggagttctc gtagtcagag acgtcctcct tcttctgttc agagacagtt   9600
tcctcggcac cagctcgcag gccagcaatg attccggttc cgggtacacc gtgggcgttg   9660
gtgatatcgg accactcggc gattcggtga caccggtact ggtgcttgac agtgttgcca   9720
atatctgcga actttctgtc ctcgaacagg aagaaaccgt gcttaagagc aagttccttg   9780 aggggagca cagtgccggc gtaggtgaag tcgtcaatga tgtcgatatg ggttttgatc    9840
atgcacacat aaggtccgac cttatcggca agctcaatga gctccttggt ggtggtaaca   9900
tccagagaag cacacaggtt ggttttcttg gctgccacga gcttgagcac tcgagcggca   9960
aaggcggact tgtggacgtt agctcgagct tcgtaggagg gcattttggt ggtgaagagg  10020
agactgaaat aaatttagtc tgcagaactt tttatcggaa ccttatctgg ggcagtgaag  10080
tatatgttat ggtaatagtt acgagttagt tgaacttata gatagactgg actatacggc  10140
tatcggtcca aattagaaag aacgtcaatg gctctctggg cgtcgccttt gccgacaaaa  10200
atgtgatcat gatgaaagcc agcaatgacg ttgcagctga tattgttgtc ggccaaccgc  10260
gccgaaaacg cagctgtcag acccacagcc tccaacgaag aatgtatcgt caaagtgatc  10320
caagcacact catagttgga gtcgtactcc aaaggcggca atgacgagtc agacagatac  10380
tcgtcgacct tttccttggg aaccaccacc gtcagcccct ctgactcacg tattgtagcc  10440
accgacacag gcaacagtcc gtggatagca gaatatgtct tgtcggtcca tttctcacca  10500
actttaggcg tcaagtgaat gttgcagaag aagtatgtgc cttcattgag aatcggtgtt  10560
gctgatttca ataaagtctt gagatcagtt tggccagtca tgttgtgggg ggtaattgga  10620
ttgagttatc gcctacagtc tgtacaggta tactcgctgc ccactttata cttttgatt   10680 ccgctgcact tgaagcaatg tcgtttacca aaagtgagaa tgctccacag aacacacccc  10740
agggtatggt tgagcaaaaa ataaacactc cgatacgggg aatcgaaccc cggtctccac  10800
ggttctcaag aagtattctt gatgagagcg tatcgatttc tcccaccacc accaacactc  10860
cctttccatt cccacaccgt tcctctctca tccttgcgca atcatcttcg tctgcgacat  10920
attgtacgac atacagtacc acggaacgtt tcagaccgtc gacgtgaaca catcttagga  10980
acagcaacct gagctacaga aatctatcta taggcggata aaaaaacgca cccactgctc  11040
gtcctccttg ctcctcgaaa ccgactcctc tacacacgtc aaatccgagg ttgaaatctt  11100
ccccacattt ggcagccaaa ccagcacatc ccagcaacct cgcacagcgc cgaaatcgac  11160
ctgtcgactt ggccacaaaa aaaagcaccg gctctgcaac agttctcacg accaattacg  11220
tacaagtacg aaatcgttcg tggaccgtga ctgataagcc cccacttttt cttctaacaa  11280
caggcaacag acaagtcaca caaaacaaaa gccatgtact cagactacaa cattcctggt  11340
gccatgccgg cgtccatggc catgcctccg ttcaaacagg agtttgacta cgcccaatac  11400
gaccttaacc agcccctgcc cccgcagcag caacaacagc ctatcgacct gacccctgga  11460
gggcccctcc ccgtctcgga ttactcgacg tcgtcataca ccctgacaa cgactcacag    11520 aagcgaaaaa tgtccccggg agagtccacc agtgacggag gcgccgacga cgagtctcca  11580
gaaggagatg acggtgaggc cgaccccaag aagcccgaa agcccggccg aaagcccgaa   11640
accaccatcc ccgcgtccaa acgcaaggct cagaaccggg ctgcccaaag ggccttcaga  11700
gagcgaaagg aaaagcatct gcgcgacctg gaaaccaaaa tatctcagct cgagggcgag  11760
acggcagcca aaaactcgga aaacgagttc ctgcgcttcc aggtccagcg gcttcagaac  11820
gagctcaagc tttaccgtga gaagcctgcc ggcacttcgg gagcctctgg agtctctgga  11880
```

| | |
|---|---|
| gccggagcac ccgcttcaaa cgtgcattcg gctcccatcc cggagatgtc gtccaaaccg | 11940 |
| ttcacgttcg agttcccctc gtacaacgtg cccaagccga ccgatgtgga gcgagaggca | 12000 |
| cgcgagcaac tgcaacgaga gcagatccga ggctacttgc agcgcaagcc ctcatctgtg | 12060 |
| gcctccgaca ccacttctcc tgcatctcaa acctcgtgca accagtctcc ctgcaccaac | 12120 |
| ccctcggcat acacttcgcc ccagagccag agtggaagtg tgagccagca gaagcccctg | 12180 |
| ttgggtgcta ccatcgctgc catgaacggc aagcccgacc cccatgctgt tgacttttgt | 12240 |
| gctgagctct ccaaggcctg tgtaaacaag gccgagctgc tgcagcgatc cgccacagcc | 12300 |
| agtgcatctc ccacaacctc caacacggtg gtaccgtccg cagctgcacc gggtagcact | 12360 |
| cagcagtcgg caggccagcc ctctgtatcc actcctacct cctccacaac tgcccctcct | 12420 |
| caattgtctg catctgtcgc tacagccggc tctgatcttc ccggatcgga cttcctgttt | 12480 |
| gacatgccct tcgacatgga ctttatgtcg taccgagacc ccgtttccga dacggcacat | 12540 |
| ctggacgact tttcgctgcc cgagctcacg acagaaacat ccatgtttga tcctctggac | 12600 |
| ccccattcca gcagcgacgt tatttctggc aagcctctgt ctaccatggg cgctacacac | 12660 |
| agtggtgtca acaacggaca gggaagtggt gctcccgaag tcaagaagga ggaggatgag | 12720 |
| gacctgctca tgttctccaa gcccaagacg ctcatgaact gcaccgctgt gtgggaccgt | 12780 |
| atcacgtcgc atcccaagtt tggcgatatc gacatcgagg gcctgtgttc ggagctgcga | 12840 |
| aacaaggcaa agtgcagtga gagtggcgtc gtgttgacgg agttggacgt ggatggtgtc | 12900 |
| ctgtcaacgt tccagtaagc ggccgcatgt acatacaaga ttatttatag aaatgaatcg | 12960 |
| cgatcgaaca aagagtacga gtgtacgagt aggggatgat gataaaagtg gaagaagttc | 13020 |
| cgcatctttg gatttatcaa cgtgtaggac gatacttcct gtaaaaatgc aatgtcttta | 13080 |
| ccataggttc tgctgtagat gttattaact accattaaca tgtctacttg tacagttgca | 13140 |
| gaccagttgg agtatagaat ggtacactta ccaaaaagtg ttgatggttg taactacgat | 13200 |
| atataaaact gttgacggga tctgcgtaca ctgttt | 13236 |

<210> SEQ ID NO 29
<211> LENGTH: 843
<212> TYPE: DNA
<213> ORGANISM: Candida albicans

<400> SEQUENCE: 29

| | |
|---|---|
| atgagcaaag aaacaacttc atataccaat gctaaattag gtccattacc aaccaaagca | 60 |
| gcaaccattc ctgataatat tttagatgca ttttcattaa aggtaaagt tgcttctgta | 120 |
| actggttcct ctggaggaat tggttgggca gtagctgaag ggtatgcaca agctggtgct | 180 |
| gatgttgcca tctggtataa ttctcatcct gctgatgata aagctgaata tttaaccaag | 240 |
| acttatgggg ttaaatccaa agcatacaaa tgtaatgtta ctgatttcca agatgttgaa | 300 |
| aaagttgtca acaaattga actggatttc ggtaccattg atatctttgt tgccaatgct | 360 |
| ggtgttgcct ggaccgaagg gcccgaaatt gatgtcaagg gagttgacaa atggaacaaa | 420 |
| gttgttgatg ttgatttaaa cagtgtttat tattgtgctc atgttgttgg tccaattttc | 480 |
| agaaaaaagg gtaaagggtc attcattttc actgccagta tgtcggcttc aattgttaat | 540 |
| gtcccacaat tacaagcagc ttacaacgct gctaaagctg gggtcaaaca tttgtccaaa | 600 |
| tcattgagtg ttgaatgggc accatttgct agagtcaatt ctgtttctcc aggttacatc | 660 |
| gctactcatc ttagtgaatt tgctgatcca gatgtcaaga gtaaatggtt gcaacttaca | 720 |
| ccacttggta gagaagccaa accaagagag cttgttggtg cctacttgta tttggcttcc | 780 |

```
gatgctgcat cttatacaac tggtgctgat cttgctgttg atggtggtta cacagttgtt    840
taa                                                                  843
```

<210> SEQ ID NO 30
<211> LENGTH: 280
<212> TYPE: PRT
<213> ORGANISM: Candida albicans

<400> SEQUENCE: 30

```
Met Ser Lys Glu Thr Thr Ser Tyr Thr Asn Ala Lys Leu Gly Pro Leu
1               5                   10                  15

Pro Thr Lys Ala Ala Thr Ile Pro Asp Asn Ile Leu Asp Ala Phe Ser
            20                  25                  30

Leu Lys Gly Lys Val Ala Ser Val Thr Gly Ser Ser Gly Ile Gly
        35                  40                  45

Trp Ala Val Ala Glu Gly Tyr Ala Gln Ala Gly Ala Asp Val Ala Ile
    50                  55                  60

Trp Tyr Asn Ser His Pro Ala Asp Asp Lys Ala Glu Tyr Leu Thr Lys
65                  70                  75                  80

Thr Tyr Gly Val Lys Ser Lys Ala Tyr Lys Cys Asn Val Thr Asp Phe
                85                  90                  95

Gln Asp Val Glu Lys Val Val Lys Gln Ile Glu Ser Asp Phe Gly Thr
            100                 105                 110

Ile Asp Ile Phe Val Ala Asn Ala Gly Val Ala Trp Thr Glu Gly Pro
        115                 120                 125

Glu Ile Asp Val Lys Gly Val Asp Lys Trp Asn Lys Val Val Asp Val
    130                 135                 140

Asp Leu Asn Ser Val Tyr Tyr Cys Ala His Val Val Gly Pro Ile Phe
145                 150                 155                 160

Arg Lys Lys Gly Lys Gly Ser Phe Ile Phe Thr Ala Ser Met Ser Ala
                165                 170                 175

Ser Ile Val Asn Val Pro Gln Leu Gln Ala Ala Tyr Asn Ala Ala Lys
            180                 185                 190

Ala Gly Val Lys His Leu Ser Lys Ser Leu Ser Val Glu Trp Ala Pro
        195                 200                 205

Phe Ala Arg Val Asn Ser Val Ser Pro Gly Tyr Ile Ala Thr His Leu
    210                 215                 220

Ser Glu Phe Ala Asp Pro Asp Val Lys Ser Lys Trp Leu Gln Leu Thr
225                 230                 235                 240

Pro Leu Gly Arg Glu Ala Lys Pro Arg Glu Leu Val Gly Ala Tyr Leu
                245                 250                 255

Tyr Leu Ala Ser Asp Ala Ala Ser Tyr Thr Thr Gly Ala Asp Leu Ala
            260                 265                 270

Val Asp Gly Gly Tyr Thr Val Val
        275                 280
```

<210> SEQ ID NO 31
<211> LENGTH: 648
<212> TYPE: PRT
<213> ORGANISM: Yarrowia lipolytica

<400> SEQUENCE: 31

```
Met Thr Gln Pro Val Asn Arg Lys Ala Thr Val Glu Arg Val Glu Pro
1               5                   10                  15

Ala Val Glu Val Ala Asp Ser Glu Ser Glu Ala Lys Thr Asp Val His
```

```
                 20                  25                  30
Val His His His His His His Lys Arg Lys Ser Val Lys Gly Lys
         35                  40                  45
Ile Leu Asn Phe Phe Thr Arg Ser Arg Arg Ile Thr Phe Val Leu Gly
 50                  55                  60
Ala Val Val Gly Val Ile Ala Ala Gly Tyr Tyr Ala Pro Pro Glu
 65                  70                  75                  80
Leu Ser Ile Asp Ile Asp Ala Leu Leu Gly Asp Leu Pro Ser Phe Asp
                 85                  90                  95
Phe Asp Ala Leu Ser Leu Asp Asn Leu Ser Met Asp Ser Val Ser Asp
         100                 105                 110
Phe Val Gln Asp Met Lys Ser Arg Phe Pro Thr Lys Ile Leu Gln Glu
         115                 120                 125
Ala Ala Lys Ile Glu Lys His Gln Lys Ser Gln Lys Ala Ala Pro
         130                 135                 140
Phe Ala Val Gly Lys Ala Met Lys Ser Glu Gly Leu Asn Ala Lys Tyr
145                 150                 155                 160
Pro Val Val Leu Val Pro Gly Val Ile Ser Thr Gly Leu Glu Ser Trp
                 165                 170                 175
Ser Leu Glu Gly Thr Glu Cys Pro Thr Glu Ser His Phe Arg Lys
         180                 185                 190
Arg Met Trp Gly Ser Trp Tyr Met Ile Arg Val Met Leu Leu Asp Lys
         195                 200                 205
Tyr Cys Trp Leu Gln Asn Leu Met Leu Asp Thr Glu Thr Gly Leu Asp
         210                 215                 220
Pro Pro His Phe Lys Leu Arg Ala Ala Gln Gly Phe Ala Ser Ala Asp
225                 230                 235                 240
Phe Phe Met Ala Gly Tyr Trp Leu Trp Asn Lys Leu Leu Glu Asn Leu
                 245                 250                 255
Ala Val Ile Gly Tyr Asp Thr Asp Thr Met Ser Ala Ala Tyr Asp
         260                 265                 270
Trp Arg Leu Ser Tyr Pro Asp Leu Glu His Arg Asp Gly Tyr Phe Ser
         275                 280                 285
Lys Leu Lys Ala Ser Ile Glu Glu Thr Lys Arg Met Thr Gly Glu Lys
         290                 295                 300
Thr Val Leu Thr Gly His Ser Met Gly Ser Gln Val Ile Phe Tyr Phe
305                 310                 315                 320
Met Lys Trp Ala Glu Ala Glu Gly Tyr Gly Gly Gly Pro Asn Trp
                 325                 330                 335
Val Asn Asp His Ile Glu Ser Phe Val Asp Ile Ser Gly Ser Met Leu
         340                 345                 350
Gly Thr Pro Lys Thr Leu Val Ala Leu Leu Ser Gly Glu Met Lys Asp
         355                 360                 365
Thr Val Gln Leu Asn Ala Met Ala Val Tyr Gly Leu Glu Gln Phe Phe
         370                 375                 380
Ser Arg Arg Glu Arg Ala Asp Leu Leu Arg Thr Trp Gly Gly Ile Ala
385                 390                 395                 400
Ser Met Ile Pro Lys Gly Gly Lys Ala Ile Trp Gly Asp His Ser Gly
                 405                 410                 415
Ala Pro Asp Asp Glu Pro Gly Gln Asn Val Thr Phe Gly Asn Phe Ile
         420                 425                 430
Lys Phe Lys Glu Ser Leu Thr Glu Tyr Ser Ala Lys Asn Leu Thr Met
         435                 440                 445
```

```
Asp Glu Thr Val Asp Phe Leu Tyr Ser Gln Ser Pro Glu Trp Phe Val
        450                 455                 460

Asn Arg Thr Glu Gly Ala Tyr Ser Phe Gly Ile Ala Lys Thr Arg Lys
465                 470                 475                 480

Gln Val Glu Gln Asn Glu Lys Arg Pro Ser Thr Trp Ser Asn Pro Leu
                485                 490                 495

Glu Ala Ala Leu Pro Asn Ala Pro Asp Leu Lys Ile Tyr Cys Phe Tyr
            500                 505                 510

Gly Val Gly Lys Asp Thr Glu Arg Ala Tyr Tyr Gln Asp Glu Pro
        515                 520                 525

Asn Pro Glu Gln Thr Asn Leu Asn Val Ser Ile Ala Gly Asn Asp Pro
530                 535                 540

Asp Gly Val Leu Met Gly Gln Gly Asp Gly Thr Val Ser Leu Val Thr
545                 550                 555                 560

His Thr Met Cys His Arg Trp Lys Asp Glu Asn Ser Lys Phe Asn Pro
                565                 570                 575

Gly Asn Ala Gln Val Lys Val Val Glu Met Leu His Gln Pro Asp Arg
                580                 585                 590

Leu Asp Ile Arg Gly Gly Ala Gln Thr Ala Glu His Val Asp Ile Leu
                595                 600                 605

Gly Arg Ser Glu Leu Asn Glu Met Val Leu Lys Val Ala Ser Gly Lys
            610                 615                 620

Gly Asn Glu Ile Glu Glu Arg Val Ile Ser Asn Ile Asp Glu Trp Val
625                 630                 635                 640

Trp Lys Ile Asp Leu Gly Ser Asn
                645

<210> SEQ ID NO 32
<211> LENGTH: 419
<212> TYPE: PRT
<213> ORGANISM: Yarrowia lipolytica

<400> SEQUENCE: 32

Met Asp Ser Thr Thr Gln Thr Asn Thr Gly Thr Gly Lys Val Ala Val
1               5                   10                  15

Gln Pro Pro Thr Ala Phe Ile Lys Pro Ile Glu Lys Val Ser Glu Pro
                20                  25                  30

Val Tyr Asp Thr Phe Gly Asn Glu Phe Thr Pro Pro Asp Tyr Ser Ile
            35                  40                  45

Lys Asp Ile Leu Asp Ala Ile Pro Gln Glu Cys Tyr Lys Arg Ser Tyr
50                  55                  60

Val Lys Ser Tyr Ser Tyr Val Ala Arg Asp Cys Phe Phe Ile Ala Val
65                  70                  75                  80

Phe Ala Tyr Met Ala Tyr Ala Tyr Leu Pro Leu Ile Pro Ser Ala Ser
                85                  90                  95

Gly Arg Ala Val Ala Trp Ala Met Tyr Ser Ile Val Gln Gly Leu Phe
                100                 105                 110

Gly Thr Gly Leu Trp Val Leu Ala His Glu Cys Gly His Ser Ala Phe
            115                 120                 125

Ser Asp Ser Asn Thr Val Asn Asn Val Thr Gly Trp Val Leu His Ser
            130                 135                 140

Ser Met Leu Val Pro Tyr Tyr Ala Trp Lys Leu Thr His Ser Met His
145                 150                 155                 160

His Lys Ser Thr Gly His Leu Thr Arg Asp Met Val Phe Val Pro Lys
```

```
                165                 170                 175
Asp Arg Lys Glu Phe Met Glu Asn Arg Gly Ala His Asp Trp Ser Glu
            180                 185                 190

Leu Ala Glu Asp Ala Pro Leu Met Thr Leu Tyr Gly Leu Ile Thr Gln
        195                 200                 205

Gln Val Phe Gly Trp Pro Leu Tyr Leu Ser Tyr Val Thr Gly Gln
    210                 215                 220

Lys Tyr Pro Lys Leu Asn Lys Trp Ala Val Asn His Phe Asn Pro Asn
225                 230                 235                 240

Ala Pro Leu Phe Glu Lys Lys Asp Trp Phe Asn Ile Trp Ile Ser Asn
                245                 250                 255

Val Gly Ile Gly Ile Thr Met Ser Val Ile Ala Tyr Ser Ile Asn Arg
            260                 265                 270

Trp Gly Leu Ala Ser Val Thr Leu Tyr Tyr Leu Ile Pro Tyr Leu Trp
        275                 280                 285

Val Asn His Trp Leu Val Ala Ile Thr Tyr Leu Gln His Thr Asp Pro
    290                 295                 300

Thr Leu Pro His Tyr His Ala Asp Gln Trp Asn Phe Thr Arg Gly Ala
305                 310                 315                 320

Ala Ala Thr Ile Asp Arg Glu Phe Gly Phe Ile Gly Ser Phe Cys Phe
                325                 330                 335

His Asp Ile Ile Glu Thr His Val Leu His His Tyr Val Ser Arg Ile
            340                 345                 350

Pro Phe Tyr Asn Ala Arg Ile Ala Thr Glu Lys Ile Lys Lys Val Met
        355                 360                 365

Gly Lys His Tyr Arg His Asp Asp Thr Asn Phe Ile Lys Ser Leu Tyr
    370                 375                 380

Thr Val Ala Arg Thr Cys Gln Phe Val Glu Gly Lys Glu Gly Ile Gln
385                 390                 395                 400

Met Phe Arg Asn Val Asn Gly Val Gly Val Ala Pro Asp Gly Leu Pro
                405                 410                 415

Ser Lys Lys

<210> SEQ ID NO 33
<211> LENGTH: 263
<212> TYPE: PRT
<213> ORGANISM: Eutreptiella sp. CCMP389

<400> SEQUENCE: 33

Met Ala Ala Val Ile Glu Val Asn Glu Phe Val Ala Ile Thr Ala
1               5                   10                  15

Glu Thr Leu Pro Lys Val Asp Tyr Gln Arg Leu Trp Arg Asp Ile Tyr
            20                  25                  30

Ser Cys Glu Leu Leu Tyr Phe Ser Ile Ala Phe Val Ile Leu Lys Phe
        35                  40                  45

Thr Leu Gly Glu Leu Ser Asp Ser Gly Lys Lys Ile Leu Arg Val Leu
    50                  55                  60

Phe Lys Trp Tyr Asn Leu Phe Met Ser Val Phe Ser Leu Val Ser Phe
65                  70                  75                  80

Leu Cys Met Gly Tyr Ala Ile Tyr Thr Val Gly Leu Tyr Ser Asn Glu
                85                  90                  95

Cys Asp Arg Ala Phe Asp Asn Ser Leu Phe Arg Phe Ala Thr Lys Val
            100                 105                 110

Phe Tyr Tyr Ser Lys Phe Leu Glu Tyr Ile Asp Ser Phe Tyr Leu Pro
```

```
                  115                 120                 125
Leu Met Ala Lys Pro Leu Ser Phe Leu Gln Phe Phe His His Leu Gly
    130                 135                 140

Ala Pro Met Asp Met Trp Leu Phe Val Gln Tyr Ser Gly Glu Ser Ile
145                 150                 155                 160

Trp Ile Phe Val Phe Leu Asn Gly Phe Ile His Phe Val Met Tyr Gly
                165                 170                 175

Tyr Tyr Trp Thr Arg Leu Met Lys Phe Asn Phe Pro Met Pro Lys Gln
            180                 185                 190

Leu Ile Thr Ala Met Gln Ile Thr Gln Phe Asn Val Gly Phe Tyr Leu
        195                 200                 205

Val Trp Trp Tyr Lys Asp Ile Pro Cys Tyr Arg Lys Asp Pro Met Arg
    210                 215                 220

Met Leu Ala Trp Ile Phe Asn Tyr Trp Tyr Val Gly Thr Val Leu Leu
225                 230                 235                 240

Leu Phe Ile Asn Phe Phe Val Lys Ser Tyr Val Phe Pro Lys Pro Lys
                245                 250                 255

Thr Ala Asp Lys Lys Val Gln
            260

<210> SEQ ID NO 34
<211> LENGTH: 24
<212> TYPE: PRT
<213> ORGANISM: Artificial sequence
<220> FEATURE:
<223> OTHER INFORMATION: Linker comprised in E389D9eS/EgD8M multizyme

<400> SEQUENCE: 34

Gly Ala Gly Pro Ala Arg Pro Ala Gly Leu Pro Pro Ala Thr Tyr Tyr
1               5                  10                  15

Asp Ser Leu Ala Val Met Gly Ser
            20

<210> SEQ ID NO 35
<211> LENGTH: 701
<212> TYPE: PRT
<213> ORGANISM: Artificial sequence
<220> FEATURE:
<223> OTHER INFORMATION: EgD9eS/EgD8M fusion

<400> SEQUENCE: 35

Met Glu Val Val Asn Glu Ile Val Ser Ile Gly Gln Glu Val Leu Pro
1               5                  10                  15

Lys Val Asp Tyr Ala Gln Leu Trp Ser Asp Ala Ser His Cys Glu Val
                20                  25                  30

Leu Tyr Leu Ser Ile Ala Phe Val Ile Leu Lys Phe Thr Leu Gly Pro
            35                  40                  45

Leu Gly Pro Lys Gly Gln Ser Arg Met Lys Phe Val Phe Thr Asn Tyr
        50                  55                  60

Asn Leu Leu Met Ser Ile Tyr Ser Leu Gly Ser Phe Leu Ser Met Ala
65                  70                  75                  80

Tyr Ala Met Tyr Thr Ile Gly Val Met Ser Asp Asn Cys Glu Lys Ala
                85                  90                  95

Phe Asp Asn Asn Val Phe Arg Ile Thr Thr Gln Leu Phe Tyr Leu Ser
            100                 105                 110

Lys Phe Leu Glu Tyr Ile Asp Ser Phe Tyr Leu Pro Leu Met Gly Lys
        115                 120                 125
```

```
Pro Leu Thr Trp Leu Gln Phe Phe His His Leu Gly Ala Pro Met Asp
    130                 135                 140
Met Trp Leu Phe Tyr Asn Tyr Arg Asn Glu Ala Val Trp Ile Phe Val
145                 150                 155                 160
Leu Leu Asn Gly Phe Ile His Trp Ile Met Tyr Gly Tyr Tyr Trp Thr
                165                 170                 175
Arg Leu Ile Lys Leu Lys Phe Pro Met Pro Lys Ser Leu Ile Thr Ser
            180                 185                 190
Met Gln Ile Ile Gln Phe Asn Val Gly Phe Tyr Ile Val Trp Lys Tyr
        195                 200                 205
Arg Asn Ile Pro Cys Tyr Arg Gln Asp Gly Met Arg Met Phe Gly Trp
    210                 215                 220
Phe Phe Asn Tyr Phe Tyr Val Gly Thr Val Leu Cys Leu Phe Leu Asn
225                 230                 235                 240
Phe Tyr Val Gln Thr Tyr Ile Val Arg Lys His Lys Gly Ala Lys Lys
                245                 250                 255
Ile Gln Gly Ala Gly Pro Ala Arg Pro Ala Gly Leu Pro Pro Ala Thr
            260                 265                 270
Tyr Tyr Asp Ser Leu Ala Val Met Val Lys Ala Ser Arg Gln Ala Leu
        275                 280                 285
Pro Leu Val Ile Asp Gly Lys Val Tyr Asp Val Ser Ala Trp Val Asn
    290                 295                 300
Phe His Pro Gly Gly Ala Glu Ile Ile Glu Asn Tyr Gln Gly Arg Asp
305                 310                 315                 320
Ala Thr Asp Ala Phe Met Val Met His Ser Gln Glu Ala Phe Asp Lys
                325                 330                 335
Leu Lys Arg Met Pro Lys Ile Asn Gln Ala Ser Glu Leu Pro Pro Gln
            340                 345                 350
Ala Ala Val Asn Glu Ala Gln Glu Asp Phe Arg Lys Leu Arg Glu Glu
        355                 360                 365
Leu Ile Ala Thr Gly Met Phe Asp Ala Ser Pro Leu Trp Tyr Ser Tyr
    370                 375                 380
Lys Ile Leu Thr Thr Leu Gly Leu Gly Val Leu Ala Phe Phe Met Leu
385                 390                 395                 400
Val Gln Tyr His Leu Tyr Phe Ile Gly Ala Leu Val Leu Gly Met His
                405                 410                 415
Tyr Gln Gln Met Gly Trp Leu Ser His Asp Ile Cys His His Gln Thr
            420                 425                 430
Phe Lys Asn Arg Asn Trp Asn Asn Val Leu Gly Leu Val Phe Gly Asn
        435                 440                 445
Gly Leu Gln Gly Phe Ser Val Thr Trp Trp Lys Asp Arg His Asn Ala
    450                 455                 460
His His Ser Ala Thr Asn Val Gln Gly His Asp Pro Asp Ile Asp Asn
465                 470                 475                 480
Leu Pro Leu Leu Ala Trp Ser Glu Asp Val Thr Arg Ala Ser Pro
                485                 490                 495
Ile Ser Arg Lys Leu Ile Gln Phe Gln Gln Tyr Tyr Phe Leu Val Ile
            500                 505                 510
Cys Ile Leu Leu Arg Phe Ile Trp Cys Phe Gln Ser Val Leu Thr Val
        515                 520                 525
Arg Ser Leu Lys Asp Arg Asp Asn Gln Phe Tyr Arg Ser Gln Tyr Lys
    530                 535                 540
Lys Glu Ala Ile Gly Leu Ala Leu His Trp Thr Leu Lys Thr Leu Phe
```

```
            545                 550                 555                 560
        His Leu Phe Phe Met Pro Ser Ile Leu Thr Ser Met Leu Val Phe Phe
                        565                 570                 575

Val Ser Glu Leu Val Gly Gly Phe Gly Ile Ala Ile Val Val Phe Met
                        580                 585                 590

Asn His Tyr Pro Leu Glu Lys Ile Gly Asp Ser Val Trp Asp Gly His
                        595                 600                 605

Gly Phe Ser Val Gly Gln Ile His Glu Thr Met Asn Ile Arg Arg Gly
                        610                 615                 620

Ile Ile Thr Asp Trp Phe Phe Gly Gly Leu Asn Tyr Gln Ile Glu His
        625                 630                 635                 640

His Leu Trp Pro Thr Leu Pro Arg His Asn Leu Thr Ala Val Ser Tyr
                        645                 650                 655

Gln Val Glu Gln Leu Cys Gln Lys His Asn Leu Pro Tyr Arg Asn Pro
                        660                 665                 670

Leu Pro His Glu Gly Leu Val Ile Leu Leu Arg Tyr Leu Ser Gln Phe
                        675                 680                 685

Ala Arg Met Ala Glu Lys Gln Pro Gly Ala Lys Ala Gln
        690                 695                 700

<210> SEQ ID NO 36
<211> LENGTH: 702
<212> TYPE: PRT
<213> ORGANISM: Artificial sequence
<220> FEATURE:
<223> OTHER INFORMATION: EaD9eS/EaD8S fusion

<400> SEQUENCE: 36

Met Glu Ala Ala Lys Glu Leu Val Ser Ile Val Gln Glu Glu Leu Pro
        1               5                   10                  15

Lys Val Asp Tyr Ala Gln Leu Trp Gln Asp Ala Ser Ser Cys Glu Val
                        20                  25                  30

Leu Tyr Leu Ser Val Ala Phe Val Ala Ile Lys Phe Met Leu Arg Pro
                        35                  40                  45

Leu Asp Leu Lys Arg Gln Ala Thr Leu Lys Lys Leu Phe Thr Ala Tyr
                        50                  55                  60

Asn Phe Leu Met Ser Ile Tyr Ser Phe Gly Ser Phe Leu Ala Met Ala
        65                  70                  75                  80

Tyr Ala Leu Ser Val Thr Gly Ile Leu Ser Gly Asp Cys Glu Thr Ala
                        85                  90                  95

Phe Asn Asn Asp Val Phe Arg Ile Thr Thr Gln Leu Phe Tyr Leu Ser
                        100                 105                 110

Lys Phe Val Glu Tyr Ile Asp Ser Phe Tyr Leu Pro Leu Met Asp Lys
                        115                 120                 125

Pro Leu Ser Phe Leu Gln Phe Phe His His Leu Gly Ala Pro Ile Asp
                        130                 135                 140

Met Trp Leu Phe Tyr Lys Tyr Arg Asn Glu Gly Val Trp Ile Phe Val
        145                 150                 155                 160

Leu Leu Asn Gly Phe Ile His Trp Ile Met Tyr Gly Tyr Tyr Trp Thr
                        165                 170                 175

Arg Leu Ile Lys Leu Asn Phe Pro Met Pro Lys Asn Leu Ile Thr Ser
                        180                 185                 190

Met Gln Ile Ile Gln Phe Asn Val Gly Phe Tyr Ile Val Trp Lys Tyr
                        195                 200                 205

Arg Asn Val Pro Cys Tyr Arg Gln Asp Gly Met Arg Met Phe Ala Trp
```

```
            210                 215                 220
Ile Phe Asn Tyr Trp Tyr Val Gly Thr Val Leu Leu Phe Leu Asn
225                 230                 235                 240

Phe Tyr Val Gln Thr Tyr Ile Arg Lys Pro Arg Lys Asn Arg Gly Lys
                245                 250                 255

Lys Glu Gly Ala Gly Pro Ala Arg Pro Ala Gly Leu Pro Pro Ala Thr
                260                 265                 270

Tyr Tyr Asp Ser Leu Ala Val Met Gly Ser Met Val Lys Arg Pro Ala
                275                 280                 285

Leu Pro Leu Thr Val Asp Gly Val Thr Tyr Asp Val Ser Ala Trp Leu
                290                 295                 300

Asn His His Pro Gly Gly Ala Asp Ile Ile Glu Asn Tyr Arg Gly Arg
305                 310                 315                 320

Asp Ala Thr Asp Val Phe Met Val Met His Ser Glu Asn Ala Val Ser
                325                 330                 335

Lys Leu Arg Arg Met Pro Ile Met Glu Pro Ser Ser Pro Leu Thr Pro
                340                 345                 350

Thr Pro Pro Lys Pro Asn Ser Asp Glu Pro Gln Glu Asp Phe Arg Lys
                355                 360                 365

Leu Arg Asp Glu Leu Ile Ala Ala Gly Met Phe Asp Ala Ser Pro Met
                370                 375                 380

Trp Tyr Ala Tyr Lys Thr Leu Ser Thr Leu Gly Leu Gly Val Leu Ala
385                 390                 395                 400

Val Leu Leu Met Thr Gln Trp His Trp Tyr Leu Val Gly Ala Ile Val
                405                 410                 415

Leu Gly Ile His Phe Gln Gln Met Gly Trp Leu Ser His Asp Ile Cys
                420                 425                 430

His His Gln Leu Phe Lys Asp Arg Ser Ile Asn Asn Ala Ile Gly Leu
                435                 440                 445

Leu Phe Gly Asn Val Leu Gln Gly Phe Ser Val Thr Trp Trp Lys Asp
                450                 455                 460

Arg His Asn Ala His His Ser Ala Thr Asn Val Gln Gly His Asp Pro
465                 470                 475                 480

Asp Ile Asp Asn Leu Pro Leu Leu Ala Trp Ser Lys Glu Asp Val Glu
                485                 490                 495

Arg Ala Gly Pro Phe Ser Arg Arg Met Ile Lys Tyr Gln Gln Tyr Tyr
                500                 505                 510

Phe Phe Phe Ile Cys Ala Leu Leu Arg Phe Ile Trp Cys Phe Gln Ser
                515                 520                 525

Ile His Thr Ala Thr Gly Leu Lys Asp Arg Ser Asn Gln Tyr Tyr Arg
                530                 535                 540

Arg Gln Tyr Glu Lys Glu Ser Val Gly Leu Ala Leu His Trp Gly Leu
545                 550                 555                 560

Lys Ala Leu Phe Tyr Tyr Phe Tyr Met Pro Ser Phe Leu Thr Gly Leu
                565                 570                 575

Met Val Phe Phe Val Ser Glu Leu Leu Gly Gly Phe Gly Ile Ala Ile
                580                 585                 590

Val Val Phe Met Asn His Tyr Pro Leu Glu Lys Ile Gln Asp Ser Val
                595                 600                 605

Trp Asp Gly His Gly Phe Cys Ala Gly Gln Ile His Glu Thr Met Asn
                610                 615                 620

Val Gln Arg Gly Leu Val Thr Asp Trp Phe Phe Gly Gly Leu Asn Tyr
625                 630                 635                 640
```

```
Gln Ile Glu His His Leu Trp Pro Thr Leu Pro Arg His Asn Leu Thr
                645                 650                 655

Ala Ala Ser Ile Lys Val Glu Gln Leu Cys Lys Lys His Asn Leu Pro
            660                 665                 670

Tyr Arg Ser Pro Pro Met Leu Glu Gly Val Gly Ile Leu Ile Ser Tyr
        675                 680                 685

Leu Gly Thr Phe Ala Arg Met Val Ala Lys Ala Asp Lys Ala
    690                 695                 700

<210> SEQ ID NO 37
<211> LENGTH: 420
<212> TYPE: PRT
<213> ORGANISM: Euglena anabaena

<400> SEQUENCE: 37

Met Val Lys Arg Pro Ala Leu Pro Leu Thr Val Asp Gly Val Thr Tyr
1               5                   10                  15

Asp Val Ser Ala Trp Leu Asn His His Pro Gly Gly Ala Asp Ile Ile
            20                  25                  30

Glu Asn Tyr Arg Gly Arg Asp Ala Thr Asp Val Phe Met Val Met His
        35                  40                  45

Ser Glu Asn Ala Val Ser Lys Leu Arg Arg Met Pro Ile Met Glu Pro
    50                  55                  60

Ser Ser Pro Leu Thr Pro Thr Pro Lys Pro Asn Ser Asp Glu Pro
65                  70                  75                  80

Gln Glu Asp Phe Arg Lys Leu Arg Asp Glu Leu Ile Ala Ala Gly Met
            85                  90                  95

Phe Asp Ala Ser Pro Met Trp Tyr Ala Tyr Lys Thr Leu Ser Thr Leu
            100                 105                 110

Gly Leu Gly Val Leu Ala Val Leu Leu Met Thr Gln Trp His Trp Tyr
        115                 120                 125

Leu Val Gly Ala Ile Val Leu Gly Ile His Phe Gln Gln Met Gly Trp
    130                 135                 140

Leu Ser His Asp Ile Cys His His Gln Leu Phe Lys Asp Arg Ser Ile
145                 150                 155                 160

Asn Asn Ala Ile Gly Leu Leu Phe Gly Asn Val Leu Gln Gly Phe Ser
            165                 170                 175

Val Thr Trp Trp Lys Asp Arg His Asn Ala His His Ser Ala Thr Asn
        180                 185                 190

Val Gln Gly His Asp Pro Asp Ile Asp Asn Leu Pro Leu Leu Ala Trp
    195                 200                 205

Ser Lys Glu Asp Val Glu Arg Ala Gly Pro Phe Ser Arg Arg Met Ile
    210                 215                 220

Lys Tyr Gln Gln Tyr Tyr Phe Phe Ile Cys Ala Leu Leu Arg Phe
225                 230                 235                 240

Ile Trp Cys Phe Gln Ser Ile His Thr Ala Thr Gly Leu Lys Asp Arg
            245                 250                 255

Ser Asn Gln Tyr Tyr Arg Arg Gln Tyr Glu Lys Glu Ser Val Gly Leu
        260                 265                 270

Ala Leu His Trp Gly Leu Lys Ala Leu Phe Tyr Tyr Phe Met Pro
    275                 280                 285

Ser Phe Leu Thr Gly Leu Met Val Phe Val Ser Glu Leu Leu Gly
    290                 295                 300

Gly Phe Gly Ile Ala Ile Val Val Phe Met Asn His Tyr Pro Leu Glu
```

```
              305                 310                 315                 320
Lys Ile Gln Asp Ser Val Trp Asp Gly His Gly Phe Cys Ala Gly Gln
                325                 330                 335

Ile His Glu Thr Met Asn Val Gln Arg Gly Leu Val Thr Asp Trp Phe
                340                 345                 350

Phe Gly Gly Leu Asn Tyr Gln Ile Glu His His Leu Trp Pro Thr Leu
                355                 360                 365

Pro Arg His Asn Leu Thr Ala Ala Ser Ile Lys Val Glu Gln Leu Cys
                370                 375                 380

Lys Lys His Asn Leu Pro Tyr Arg Ser Pro Met Leu Glu Gly Val
385                 390                 395                 400

Gly Ile Leu Ile Ser Tyr Leu Gly Thr Phe Ala Arg Met Val Ala Lys
                405                 410                 415

Ala Asp Lys Ala
                420

<210> SEQ ID NO 38
<211> LENGTH: 314
<212> TYPE: PRT
<213> ORGANISM: Mortierella alpina

<400> SEQUENCE: 38

Met Ser Ile Gly Ser Ser Asn Pro Val Leu Ala Ala Ile Pro Phe
1               5                   10                  15

Val Tyr Leu Phe Val Leu Pro Arg Val Leu Ala Phe Leu Pro Gln Lys
                20                  25                  30

Ala Gln Phe Leu Ala Lys Cys Ile Val Leu Ile Ala Thr Leu Ile
                35                  40                  45

Met Ser Val Ala Gly Cys Phe Ile Ser Ile Val Cys Ala Leu Leu Asp
50                  55                  60

Lys Arg Tyr Val Ile Asn Tyr Val Val Ser Arg Leu Phe Ser Phe Leu
65                  70                  75                  80

Ala Ala Arg Pro Cys Gly Val Thr Tyr Lys Ile Val Gly Glu Glu His
                85                  90                  95

Leu Asp Lys Tyr Pro Ala Ile Val Val Cys Asn His Gln Ser Ser Met
                100                 105                 110

Asp Met Met Val Leu Gly Arg Val Phe Pro Lys His Cys Val Val Met
                115                 120                 125

Ala Lys Lys Glu Leu Leu Tyr Phe Pro Phe Leu Gly Met Phe Met Lys
130                 135                 140

Leu Ser Asn Ala Ile Phe Ile Asp Arg Lys Asn His Lys Lys Ala Ile
145                 150                 155                 160

Glu Ser Thr Thr Gln Ala Val Ala Asp Met Lys Lys His Asn Ser Gly
                165                 170                 175

Ile Trp Ile Phe Pro Glu Gly Thr Arg Ser Arg Leu Asp Lys Ala Asp
                180                 185                 190

Leu Leu Pro Phe Lys Lys Gly Ala Phe His Leu Ala Ile Gln Ala Gln
                195                 200                 205

Leu Pro Ile Leu Pro Ile Ile Ser Gln Gly Tyr Ser His Ile Tyr Asp
                210                 215                 220

Ser Ser Lys Arg Tyr Phe Pro Gly Gly Glu Leu Glu Ile Arg Val Leu
225                 230                 235                 240

Glu Pro Ile Pro Thr Thr Gly Leu Thr Thr Asp Asp Val Asn Asp Leu
                245                 250                 255
```

Met Asp Lys Thr Arg Asn Leu Met Leu Lys His Leu Lys Glu Met Asp
                    260                 265                 270

Ser Gln Tyr Ser Ser Ser Thr Ala Glu Asn Gly Ser Thr His Ile Asp
                275                 280                 285

Ala Asp Ile Ala Lys Ser Thr Ala Thr Ser Ile Gly Asn Thr Asp Asp
            290                 295                 300

Ala Ile Thr Lys Arg Arg Thr Pro Lys Glu
305                 310

<210> SEQ ID NO 39
<211> LENGTH: 1539
<212> TYPE: DNA
<213> ORGANISM: Yarrowia lipolytica

<400> SEQUENCE: 39

| | | |
|---|---|---|
| atggccttc catgggcaga taagtgggca gccgatgcgt ctgcatctac agggctgcct | 60 |
| ccggacctcc tcaagattgc attcactctg gtcatgtctt atccgctgag ttctctcatg | 120 |
| aaacggctgc cagatgacgc caaaaacctc aagatcatct atatcatctc cgtgtccatc | 180 |
| ttctacatgg tgggtgtctt ctccctctat ggcggagctg ccactctgct cttctcctca | 240 |
| atgggtacct tcttcatcac ccaatggaag agcccttaca tgccctgggt caattttggt | 300 |
| tttgtcatga cccatctctt cgtcaatcac ctgcgttcgc agttttttcc cgaaacatac | 360 |
| gaccccaatg tcattgacat caccggagca cagatggttc tgtgtatgaa gctatcgtct | 420 |
| tttggatgga acgtctacga tggatggcag attgagaagg gtgagcagct cagcgagttc | 480 |
| cagactaaaa gggctgttct caagcacccc agtcttatgg acttcctagc ttttgtgttc | 540 |
| tacttcccctt ccattctgac aggtccttct tacgactata tggagttcca taactggctc | 600 |
| gatctcagcc tgttcaagga gctggagaaa gataaggacc ccaagcgagc tgctcgacga | 660 |
| aagcgacaca gatcccccg atctggaatc gctgcttcca agaaactcgc cgctggtatc | 720 |
| ttctggatcg ttctgtggac ccaggtggac tctcgaatct ccaccgccta cgcttactca | 780 |
| gacgcattca ccaaggagca caacatcttt ggacgaattg tgtacctcta catgctcggt | 840 |
| ttcatgtacc gactcaagta ctacggagcc tggtccattt ccgagggagc ctgcatcttg | 900 |
| tctggcctcg gattccatgg cgtggacccc aaaactggca agtacaagtg ggaccgtgtc | 960 |
| cagaacgtgg acccgtgggg attcgaaact ggtcaaaaca caaaggctct gctggaggcc | 1020 |
| tggaaccaga acactaacaa gtggctacga actatgtgt acctccgagt ggtgcccaaa | 1080 |
| ggccaaaagc ctggattccg agccactatc ttcacatttg tggtttccgc cttctggcat | 1140 |
| ggaactcgac ctggctacta tctcaccttt gtgaccgctg ccatgtacca gtctgttggt | 1200 |
| aagttcttcc gacgataccct gcgacccttc ttcatggagt ctgatggaaa gactgccggt | 1260 |
| ccctataaga tctactacga cattgtgtgt tggatcgttg tccaaaccgc atttggatac | 1320 |
| gctacccagt cctttatgat tctagacttc tggctgtcgc tcaagtgttg gaagaactcc | 1380 |
| tggttcctgt accacattgc tctgggcgcc atctttgcaa tttctagccc ctacaaggca | 1440 |
| tgggcgattc ccaagatcaa gaaaaagcag gctggagccg tcactgacaa gaaggacgcc | 1500 |
| aaggaggagg tgaagaagga caccatcaag accaagtaa | 1539 |

<210> SEQ ID NO 40
<211> LENGTH: 512
<212> TYPE: PRT
<213> ORGANISM: Yarrowia lipolytica

<400> SEQUENCE: 40

```
Met Ala Phe Pro Trp Ala Asp Lys Trp Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Ala Ala Thr Leu Leu Phe Ser Ser
65                  70                  75                  80

Met Gly Thr Phe Phe Ile Thr Gln Trp Lys Ser Pro Tyr Met Pro Trp
                    85                  90                  95

Val Asn Phe Gly Phe Val Met Thr His Leu Phe Val Asn His Leu Arg
                100                 105                 110

Ser Gln Phe Phe Pro Glu Thr Tyr Asp Pro Asn Val Ile Asp Ile Thr
            115                 120                 125

Gly Ala Gln Met Val Leu Cys Met Lys Leu Ser Ser Phe Gly Trp Asn
    130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
                180                 185                 190

Tyr Met Glu Phe His Asn Trp Leu Asp Leu Ser Leu Phe Lys Glu Leu
            195                 200                 205

Glu Lys Asp Lys Asp Pro Lys Arg Ala Ala Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
            325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
            355                 360                 365

Thr Ile Phe Thr Phe Val Val Ser Ala Phe Trp His Gly Thr Arg Pro
    370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Met Glu Ser Asp Gly
                405                 410                 415
```

| Lys | Thr | Ala | Gly | Pro | Tyr | Lys | Ile | Tyr | Tyr | Asp | Ile | Val | Cys | Trp | Ile |
|---|---|---|---|---|---|---|---|---|---|---|---|---|---|---|---|
| | | | 420 | | | | 425 | | | | 430 | | | | |

| Val | Val | Gln | Thr | Ala | Phe | Gly | Tyr | Ala | Thr | Gln | Ser | Phe | Met | Ile | Leu |
|---|---|---|---|---|---|---|---|---|---|---|---|---|---|---|---|
| | | | 435 | | | | 440 | | | | 445 | | | | |

| Asp | Phe | Trp | Leu | Ser | Leu | Lys | Cys | Trp | Lys | Asn | Ser | Trp | Phe | Leu | Tyr |
|---|---|---|---|---|---|---|---|---|---|---|---|---|---|---|---|
| | | 450 | | | | 455 | | | | 460 | | | | | |

| His | Ile | Ala | Leu | Gly | Ala | Ile | Phe | Ala | Ile | Ser | Ser | Pro | Tyr | Lys | Ala |
|---|---|---|---|---|---|---|---|---|---|---|---|---|---|---|---|
| 465 | | | | 470 | | | | 475 | | | | | | | 480 |

| Trp | Ala | Ile | Pro | Lys | Ile | Lys | Lys | Gln | Ala | Gly | Ala | Val | Thr | Asp |
|---|---|---|---|---|---|---|---|---|---|---|---|---|---|---|
| | | | 485 | | | | 490 | | | | | | 495 | |

| Lys | Lys | Asp | Ala | Lys | Glu | Glu | Val | Lys | Lys | Asp | Thr | Ile | Lys | Thr | Lys |
|---|---|---|---|---|---|---|---|---|---|---|---|---|---|---|---|
| | | | 500 | | | | 505 | | | | 510 | | | | |

<210> SEQ ID NO 41
<211> LENGTH: 1539
<212> TYPE: DNA
<213> ORGANISM: Artificial sequence
<220> FEATURE:
<223> OTHER INFORMATION: YlLPCAT lacking two internal NcoI restriction
      sites with respect to SEQ ID NO:39, but encoding wild type YlLPCAT
      protein

<400> SEQUENCE: 41

```
atggccttcc cttgggcaga taagtgggca gccgatgcgt ctgcatctac agggctgcct       60
ccggacctcc tcaagattgc attcactctg gtcatgtctt atccgctgag ttctctcatg      120
aaacggctgc cagatgacgc caaaaacctc aagatcatct atatcatctc cgtgtccatc      180
ttctacatgg tgggtgtctt ctccctctat ggcggagctg ccactctgct cttctcctca      240
atgggtacct tcttcatcac ccaatggaag agcccttaca tgccctgggt caattttggt      300
tttgtcatga cccatctctt cgtcaatcac ctgcgttcgc agttttttccc cgaaacatac      360
gaccccaatg tcattgacat caccggagca cagatggttc tgtgtatgaa gctatcgtct      420
tttggatgga cgtctacga tggatggcag attgagaagg gtgagcagct cagcgagttc      480
cagactaaaa gggctgttct caagcacccc agtcttatgg acttcctagc ttttgtgttc      540
tacttccctt ccattctgac aggtcctttct tacgactata tggagttcca taactggctc      600
gatctcagcc tgttcaagga gctggagaaa gataaggacc ccaagcgagc tgctcgacga      660
aagcgacaca gatcccccg atctggaatc gctgcttcca agaaactcgc cgctggtatc      720
ttctggatcg ttctgtggac ccaggtggac tctcgaatct ccaccgccta cgcttactca      780
gacgcattca ccaaggagca caacatcttt ggacgaattg tgtacctcta catgctcggt      840
ttcatgtacc gactcaagta ctacggagcc tggtccattt ccgagggagc ctgcatcttg      900
tctggcctcg gattccacgg cgtggacccc aaaactggca agtacaagtg ggaccgtgtc      960
cagaacgtgg acccgtgggg attcgaaact ggtcaaaaca caaggctct gctggaggcc     1020
tggaaccaga cactaacaa gtggctacga actatgtgt acctccgagt ggtgcccaaa      1080
ggccaaaagc ctggattccg agccactatc ttcacatttg tggtttccgc cttctggcat     1140
ggaactcgac ctggctacta tctcaccttt gtgaccgctg ccatgtacca gtctgttggt     1200
aagttcttcc gacgatacct gcgacccttc ttcatggagt ctgatggaaa gactgccggt     1260
ccctataaga tctactacga cattgtgtgt tggatcgttg tccaaaccgc atttggatac     1320
gctacccagt cctttatgat tctagacttc tggctgtcgc tcaagtgttg gaagaactcc     1380
tggttcctgt accacattgc ctctggcgcc atctttgcaa tttctagccc ctacaaggca     1440
tgggcgattc ccaagatcaa gaaaaagcag gctggagccg tcactgacaa gaaggacgcc     1500
```

```
aaggaggagg tgaagaagga caccatcaag accaagtaa                    1539
```

<210> SEQ ID NO 42
<211> LENGTH: 8518
<212> TYPE: DNA
<213> ORGANISM: Artificial sequence
<220> FEATURE:
<223> OTHER INFORMATION: Construct pY306-N, containing YlLPCAT*
      nucleotide sequence

<400> SEQUENCE: 42

```
catggccttt ccttgggcag ataagtgggc agccgatgcg tctgcatcta cagggctgcc      60
tccggacctc ctcaagattg cattcactct ggtcatgtct tatccgctga gttctctcat     120
gaaacggctg ccagatgacg ccaaaaacct caagatcatc tatatcatct ccgtgtccat     180
cttctacatg gtgggtgtct ctccctcta tggcggagct gccactctgc tcttctcctc      240
aatgggtacc ttcttcatca cccaatggaa gagcccttac atgccctggg tcaattttgg     300
ttttgtcatg acccatctct tcgtcaatca cctgcgttcg cagttttcc ccgaaacata      360
cgaccccaat gtcattgaca tcaccggagc acagatggtt ctgtgtatga agctatcgtc     420
ttttggatgg aacgtctacg atggatgca gattgagaag ggtgagcagc tcagcgagtt      480
ccagactaaa agggctgttc tcaagcaccc cagtcttatg gacttcctag cttttgtgtt     540
ctacttccct tccattctga caggtccttc ttacgactat atggagttcc ataactggct     600
cgatctcagc ctgttcaagg agctggagaa agataaggac cccaagcgag ctgctcgacg     660
aaagcgacac aagatccccc gatctggaat cgctgcttcc aagaaactcg ccgctggtat     720
cttctggatc gttctgtgga cccaggtgga ctctcgaatc tccaccgcct acgcttactc     780
agacgcattc accaaggagc acaacatctt tggacgaatt gtgtacctct acatgctcgg     840
tttcatgtac cgactcaagt actacggagc ctggtccatt tccgagggag cctgcatctt     900
gtctggcctc ggattccacg gcgtggaccc caaaactggc aagtacaagt gggaccgtgt     960
ccagaacgtg gacccgtggg gattcgaaac tggtcaaaac acaaaggctc tgctggaggc    1020
ctggaaccag aacactaaca agtggctacg aaactatgtg tacctccgag tggtgcccaa    1080
aggccaaaag cctggattcc gagccactat cttcacattt gtggtttccg ccttctggca    1140
tggaactcga cctggctact atctcacctt tgtgaccgct gccatgtacc agtctgttgg    1200
taagttcttc cgacgatacc tgcgaccctt cttcatggag tctgatggaa agactgccgg    1260
tcctataag atctactacg acattgtgtg ttggatcgtt gtccaaccg catttggata      1320
cgctacccag tcctttatga ttctagactt ctggctgtcg ctcaagtgtt ggaagaactc    1380
ctggttcctg taccacattg ctctgggcgc catctttgca atttctagcc cctacaaggc    1440
atgggcgatt cccaagatca agaaaaagca ggctggagcc gtcactgaca agaaggacgc    1500
caaggaggag gtgaagaagg acaccatcaa gaccaagtaa gcggccgcat gagaagataa    1560
atatataaat acattgagat attaaatgcg ctagattaga gagcctcata ctgctcggag    1620
agaagccaag acgagtactc aaaggggatt acaccatcca tatccacaga cacaagctgg    1680
ggaaaggttc tatatacact ttccggaata ccgtagtttc cgatgttatc aatgggggca    1740
gccaggattt caggcacttc ggtgtctcgg ggtgaaatgg cgttcttggc ctccatcaag    1800
tcgtaccatg tcttcatttg cctgtcaaag taaaacagaa gcagatgaag aatgaacttg    1860
aagtgaagga atttaaatgt aacgaaactg aaatttgacc agatattgtg tccgcggtgg    1920
agctccagct tttgttccct ttagtgaggg ttaatttcga gcttggcgta atcatggtca    1980
```

```
tagctgtttc ctgtgtgaaa ttgttatccg ctcacaagct tccacacaac gtacgagccg    2040
gaagcataaa gtgtaaagcc tggggtgcct aatgagtgag ctaactcaca ttaattgcgt    2100
tgcgctcact gcccgctttc cagtcgggaa acctgtcgtg ccagctgcat taatgaatcg    2160
gccaacgcgc ggggagaggc ggtttgcgta ttgggcgctc ttccgcttcc tcgctcactg    2220
actcgctgcg ctcggtcgtt cggctgcggc gagcggtatc agctcactca aaggcggtaa    2280
tacggttatc cacagaatca ggggataacg caggaaagaa catgtgagca aaaggccagc    2340
aaaaggccag gaaccgtaaa aaggccgcgt tgctggcgtt tttccatagg ctccgccccc    2400
ctgacgagca tcacaaaaat cgacgctcaa gtcagaggtg gcgaaacccg acaggactat    2460
aaagatacca ggcgtttccc cctggaagct ccctcgtgcg ctctcctgtt ccgaccctgc    2520
cgcttaccgg atacctgtcc gcctttctcc cttcgggaag cgtggcgctt tctcatagct    2580
cacgctgtag gtatctcagt tcggtgtagg tcgttcgctc caagctgggc tgtgtgcacg    2640
aaccccccgt tcagcccgac cgctgcgcct tatccggtaa ctatcgtctt gagtccaacc    2700
cggtaagaca cgacttatcg ccactggcag cagccactgg taacaggatt agcagagcga    2760
ggtatgtagg cggtgctaca gagttcttga agtggtggcc taactacggc tacactagaa    2820
ggacagtatt tggtatctgc gctctgctga agccagttac cttcggaaaa agagttggta    2880
gctcttgatc cggcaaacaa accaccgctg gtagcggtgg tttttttgtt tgcaagcagc    2940
agattacgcg cagaaaaaaa ggatctcaag aagatccttt gatcttttct acggggtctg    3000
acgctcagtg gaacgaaaac tcacgttaag ggattttggt catgagatta tcaaaaagga    3060
tcttcaccta gatcctttta aattaaaaat gaagttttaa atcaatctaa agtatatatg    3120
agtaaacttg gtctgacagt taccaatgct taatcagtga ggcacctatc tcagcgatct    3180
gtctatttcg ttcatccata gttgcctgac tccccgtcgt gtagataact acgatacggg    3240
agggcttacc atctggcccc agtgctgcaa tgataccgcg agaccacgc tcaccggctc    3300 cagatttatc agcaataaac cagccagccg gaagggccga gcgcagaagt ggtcctgcaa    3360
ctttatccgc ctccatccag tctattaatt gttgccggga agctagagta agtagttcgc    3420
cagttaatag tttgcgcaac gttgttgcca ttgctacagg catcgtggtg tcacgctcgt    3480
cgtttggtat ggcttcattc agctccggtt cccaacgatc aaggcgagtt acatgatccc    3540
ccatgttgtg caaaaaagcg gttagctcct tcggtcctcc gatcgttgtc agaagtaagt    3600
tggccgcagt gttatcactc atggttatgg cagcactgca taattctctt actgtcatgc    3660
catccgtaag atgcttttct gtgactggtg agtactcaac caagtcattc tgagaatagt    3720
gtatgcggcg accgagttgc tcttgcccgg cgtcaatacg ggataatacc gcgccacata    3780
gcagaacttt aaaagtgctc atcattggaa aacgttcttc gggcgaaaa ctctcaagga    3840 tcttaccgct gttgagatcc agttcgatgt aacccactcg tgcacccaac tgatcttcag    3900
catcttttac tttcaccagc gtttctgggt gagcaaaaac aggaaggcaa aatgccgcaa    3960
aaaagggaat aagggcgaca cggaaatgtt gaatactcat actcttcctt tttcaatatt    4020
attgaagcat ttatcagggt tattgtctca tgagcggata catatttgaa tgtatttaga    4080
aaaataaaca aataggggtt ccgcgcacat ttccccgaaa agtgccacct gacgcgccct    4140
gtagcggcgc attaagcgcg gcgggtgtgg tggttacgcg cagcgtgacc gctacacttg    4200
ccagcgccct agcgcccgct cctttcgctt tcttcccttc ctttctcgcc acgttcgccg    4260
gctttccccg tcaagctcta aatcgggggc tccctttagg gttccgattt agtgctttac    4320
```

```
                                              -continued
ggcacctcga ccccaaaaaa cttgattagg gtgatggttc acgtagtggg ccatcgccct    4380
gatagacggt ttttcgccct ttgacgttgg agtccacgtt ctttaatagt ggactcttgt    4440
tccaaactgg aacaacactc aaccctatct cggtctattc ttttgattta aagggattt    4500 tgccgatttc ggcctattgg ttaaaaaatg agctgattta acaaaaattt aacgcgaatt    4560
ttaacaaaat attaacgctt acaatttcca ttcgccattc aggctgcgca actgttggga    4620
agggcgatcg gtgcgggcct cttcgctatt acgccagctg gcgaaagggg gatgtgctgc    4680
aaggcgatta agttgggtaa cgccagggtt ttcccagtca cgacgttgta aaacgacggc    4740
cagtgaattg taatacgact cactataggg cgaattgggt accgggcccc ccctcgaggt    4800
cgatggtgtc gataagcttg atatcgaatt catgtcacac aaaccgatct tcgcctcaag    4860
gaaacctaat tctacatccg agagactgcc gagatccagt ctacactgat taattttcgg    4920
gccaataatt taaaaaaatc gtgttatata atattatatg tattatatat atacatcatg    4980
atgatactga cagtcatgtc ccattgctaa atagacagac tccatctgcc gcctccaact    5040
gatgttctca atatttaagg ggtcatctcg cattgtttaa taataaacag actccatcta    5100
ccgcctccaa atgatgttct caaaatatat tgtatgaact tatttttatt acttagtatt    5160
attagacaac ttacttgctt tatgaaaaac acttcctatt taggaaacaa tttataatgg    5220
cagttcgttc atttaacaat ttatgtagaa taaatgttat aaatgcgtat gggaaatctt    5280
aaatatggat agcataaatg atatctgcat tgcctaattc gaaatcaaca gcaacgaaaa    5340
aaatcccttg tacaacataa atagtcatcg agaaatatca actatcaaag aacagctatt    5400
cacacgttac tattgagatt attattggac gagaatcaca cactcaactg tctttctctc    5460
ttctagaaat acaggtacaa gtatgtacta ttctcattgt tcatacttct agtcatttca    5520
tcccacatat tccttggatt tctctccaat gaatgacatt ctatcttgca aattcaacaa    5580
ttataataag ataccaaa gtagcggtat agtggcaatc aaaaagcttc tctggtgtgc    5640
ttctcgtatt tatttttatt ctaatgatcc attaaaggta tatatttatt tcttgttata    5700
taatcctttt gtttattaca tgggctggat acataaaggt attttgattt aattttttgc    5760
ttaaattcaa tcccccctcg ttcagtgtca actgtaatgg taggaaatta ccatactttt    5820
gaagaagcaa aaaaatgaa agaaaaaaaa aatcgtattt ccaggttaga cgttccgcag    5880
aatctagaat gcggtatgcg gtacattgtt cttcgaacgt aaaagttgcg ctccctgaga    5940
tattgtacat ttttgctttt acaagtacaa gtacatcgta caactatgta ctactgttga    6000
tgcatccaca acagtttgtt ttgtttttt ttgttttttt ttttctaat gattcattac    6060 cgctatgtat acctacttgt acttgtagta agccgggtta ttggcgttca attaatcata    6120
gacttatgaa tctgcacggt gtgcgctgcg agttactttt agcttatgca tgctacttgg    6180
gtgtaatatt gggatctgtt cggaaatcaa cggatgctca atcgatttcg acagtaatta    6240
attaagtcat acacaagtca gctttcttcg agcctcatat aagtataagt agttcaacgt    6300
attagcactg tacccagcat ctccgtatcg agaaacacaa caacatgccc cattggacag    6360
atcatgcgga tacacaggtt gtgcagtatc atacatactc gatcagacag gtcgtctgac    6420
catcatacaa gctgaacaag cgctccatac ttgcacgctc tctatataca cagttaaatt    6480
acatatccat agtctaacct ctaacagtta atcttctggt aagcctccca gccagccttc    6540
tggtatcgct tggcctcctc aataggatct cggttctggc cgtacagacc tcggccgaca    6600
attatgatat ccgttccggt agacatgaca tcctcaacag ttcggtactg ctgtccgaga    6660
gcgtctccct tgtcgtcaag acccacccgg ggggtcagaa taagccagtc ctcagagtcg    6720
```

```
cccttaggtc ggttctgggc aatgaagcca accacaaact cggggtcgga tcgggcaagc   6780
tcaatggtct gcttggagta ctcgccagtg gccagagagc ccttgcaaga cagctcggcc   6840
agcatgagca gacctctggc cagcttctcg ttgggagagg ggactaggaa ctccttgtac   6900
tgggagttct cgtagtcaga gacgtcctcc ttcttctgtt cagagacagt ttcctcggca   6960
ccagctcgca ggccagcaat gattccggtt ccgggtacac cgtgggcgtt ggtgatatcg   7020
gaccactcgg cgattcggtg acaccggtac tggtgcttga cagtgttgcc aatatctgcg   7080
aactttctgt cctcgaacag gaagaaaccg tgcttaagag caagttcctt gaggggagc    7140 acagtgccgg cgtaggtgaa gtcgtcaatg atgtcgatat gggttttgat catgcacaca   7200
taaggtccga ccttatcggc aagctcaatg agctccttgg tggtggtaac atccagagaa   7260
gcacacaggt tggttttctt ggctgccacg agcttgagca ctcgagcggc aaaggcggac   7320
ttgtggacgt tagctcgagc ttcgtaggag ggcattttgg tggtgaagag gagactgaaa   7380
taaatttagt ctgcagaact ttttatcgga accttatctg gggcagtgaa gtatatgtta   7440
tggtaatagt tacgagttag ttgaacttat agatagactg gactatacgg ctatcggtcc   7500
aaattagaaa gaacgtcaat ggctctctgg gcgtcgcctt tgccgacaaa aatgtgatca   7560
tgatgaaagc cagcaatgac gttgcagctg atattgttgt cggccaaccg cgccgaaaac   7620
gcagctgtca gacccacagc ctccaacgaa gaatgtatcg tcaaagtgat ccaagcacac   7680
tcatagttgg agtcgtactc caaaggcggc aatgacgagt cagacagata ctcgtcgacc   7740
gtacgatagt tagtagacaa caatcgatag ttggagcaag ggagaaatgt agagtgtgaa   7800
agactcacta tggtccgggc ttatctcgac caatagccaa agtctggagt ttctgagaga   7860
aaaaggcaag atacgtatgt aacaaagcga cgcatggtac aataataccg gaggcatgta   7920
tcatagagag ttagtggttc gatgatggca ctggtgcctg gtatgacttt atacggctga   7980
ctacatattt gtcctcagac atacaattac agtcaagcac ttaccctttgg acatctgtag   8040 gtaccccccg gccaagacga tctcagcgtg tcgtatgtcg gattggcgta gctccctcgc   8100
tcgtcaattg gctcccatct actttcttct gcttggctac acccagcatg tctgctatgg   8160
ctcgttttcg tgccttatct atcctcccag tattaccaac tctaaatgac atgatgtgat   8220
tgggtctaca ctttcatatc agagataagg agtagcacag ttgcataaaa agcccaactc   8280
taatcagctt cttcctttct tgtaattagt acaaaggtga ttagcgaaat ctggaagctt   8340
agttggccct aaaaaaatca aaaaagcaa aaaacgaaaa acgaaaaacc acagttttga    8400
gaacagggag gtaacgaagg atcgtatata tatatatata tatatatacc cacggatccc   8460
gagaccggcc tttgattctt ccctacaacc aaccattctc accaccctaa ttcacaac     8518
```

<210> SEQ ID NO 43
<211> LENGTH: 8518
<212> TYPE: DNA
<213> ORGANISM: Artificial sequence
<220> FEATURE:
<223> OTHER INFORMATION: Construct pY306, containing wild type YlLPCAT
      nucleotide sequence

<400> SEQUENCE: 43

```
ggccgcatga gaagataaat atataaatac attgagatat taaatgcgct agattagaga    60
gcctcatact gctcggagag aagccaagac gagtactcaa aggggattac accatccata   120
tccacagaca caagctgggg aaaggttcta tatacacttt ccggaatacc gtagtttccg   180
atgttatcaa tggggggcagc caggatttca ggcacttcgg tgtctcgggg tgaaatggcg   240
```

```
ttcttggcct ccatcaagtc gtaccatgtc ttcatttgcc tgtcaaagta aaacagaagc    300
agatgaagaa tgaacttgaa gtgaaggaat ttaaatgtaa cgaaactgaa atttgaccag    360
atattgtgtc cgcggtggag ctccagcttt tgttcccttt agtgagggtt aatttcgagc    420
ttggcgtaat catggtcata gctgtttcct gtgtgaaatt gttatccgct cacaagcttc    480
cacacaacgt acgagccgga agcataaagt gtaaagcctg gggtgcctaa tgagtgagct    540
aactcacatt aattgcgttg cgctcactgc ccgctttcca gtcgggaaac ctgtcgtgcc    600
agctgcatta atgaatcggc caacgcgcgg ggagaggcgg tttgcgtatt gggcgctctt    660
ccgcttcctc gctcactgac tcgctgcgct cggtcgttcg gctgcggcga gcggtatcag    720
ctcactcaaa ggcggtaata cggttatcca gaatcagg ggataacgca ggaaagaaca     780
tgtgagcaaa aggccagcaa aaggccagga accgtaaaaa ggccgcgttg ctggcgtttt    840
tccataggct ccgcccccct gacgagcatc acaaaaatcg acgctcaagt cagaggtggc    900
gaaacccgac aggactataa agataccagg cgtttccccc tggaagctcc ctcgtgcgct    960
ctcctgttcc gaccctgccg cttaccggat acctgtccgc ctttctccct tcgggaagcg   1020
tggcgctttc tcatagctca cgctgtaggt atctcagttc ggtgtaggtc gttcgctcca   1080
agctgggctg tgtgcacgaa ccccccgttc agcccgaccg ctgcgcctta ccggtaact    1140 atcgtcttga gtccaacccg gtaagacacg acttatcgcc actggcagca gccactggta   1200
acaggattag cagagcgagg tatgtaggcg gtgctacaga gttcttgaag tggtggccta   1260
actacggcta cactagaagg acagtatttg gtatctgcgc tctgctgaag ccagttacct   1320
tcggaaaaag agttggtagc tcttgatccg gcaaacaaac caccgctggt agcggtggtt   1380
tttttgtttg caagcagcag attacgcgca gaaaaaagg atctcaagaa gatcctttga    1440
tcttttctac ggggtctgac gctcagtgga acgaaaactc acgttaaggg attttggtca   1500
tgagattatc aaaaaggatc ttcacctaga tccttttaaa ttaaaaatga agttttaaat   1560
caatctaaag tatatatgag taaacttggt ctgacagtta ccaatgctta atcagtgagg   1620
cacctatctc agcgatctgt ctatttcgtt catccatagt tgcctgactc cccgtcgtgt   1680
agataactac gatacgggag ggcttaccat ctggccccag tgctgcaatg ataccgcgag   1740
acccacgctc accggctcca gatttatcag caataaacca gccagccgga agggccgagc   1800
gcagaagtgg tcctgcaact ttatccgcct ccatccagtc tattaattgt tgccgggaag   1860
ctagagtaag tagttcgcca gttaatagtt tgcgcaacgt tgttgccatt gctacaggca   1920
tcgtggtgtc acgctcgtcg tttggtatgg cttcattcag ctccggttcc caacgatcaa   1980
ggcgagttac atgatccccc atgttgtgca aaaaagcggt tagctccttc ggtcctccga   2040
tcgttgtcag aagtaagttg gccgcagtgt tatcactcat ggttatggca gcactgcata   2100
attctcttac tgtcatgcca tccgtaagat gcttttctgt gactggtgag tactcaacca   2160
agtcattctg agaatagtgt atgcggcgac cgagttgctc ttgcccggcg tcaatacggg   2220
ataataccgc gccacatagc agaactttaa aagtgctcat cattggaaaa cgttcttcgg   2280
ggcgaaaact ctcaaggatc ttaccgctgt tgagatccag ttcgatgtaa cccactcgtg   2340
cacccaactg atcttcagca tcttttactt tcaccagcgt ttctgggtga gcaaaaacag   2400
gaaggcaaaa tgccgcaaaa aagggaataa gggcgacacg gaaatgttga atactcatac   2460
tcttcctttt tcaatattat tgaagcattt atcagggtta ttgtctcatg agcggataca   2520
tatttgaatg tatttagaaa aataaacaaa taggggttcc gcgcacattt ccccgaaaag   2580
```

```
tgccacctga cgcgccctgt agcggcgcat taagcgcggc gggtgtggtg gttacgcgca    2640
gcgtgaccgc tacacttgcc agcgccctag cgcccgctcc tttcgctttc ttcccttcct    2700
ttctcgccac gttcgccggc tttccccgtc aagctctaaa tcggggctc cctttagggt    2760 tccgatttag tgctttacgg cacctcgacc ccaaaaaact tgattagggt gatggttcac    2820
gtagtgggcc atcgccctga tagacggttt ttcgcccttt gacgttggag tccacgttct    2880
ttaatagtgg actcttgttc caaactggaa caacactcaa ccctatctcg gtctattctt    2940
ttgatttata agggattttg ccgatttcgg cctattggtt aaaaaatgag ctgatttaac    3000
aaaaatttaa cgcgaatttt aacaaaatat taacgcttac aatttccatt cgccattcag    3060
gctgcgcaac tgttgggaag ggcgatcggt gcgggcctct tcgctattac gccagctggc    3120
gaaaggggga tgtgctgcaa ggcgattaag ttgggtaacg ccagggtttt cccagtcacg    3180
acgttgtaaa acgacggcca gtgaattgta atacgactca ctatagggcg aattgggtac    3240
cgggcccccc ctcgaggtcg atggtgtcga taagcttgat atcgaattca tgtcacacaa    3300
accgatcttc gcctcaagga aacctaattc tacatccgag agactgccga gatccagtct    3360
acactgatta attttcgggc caataattta aaaaaatcgt gttatataat attatatgta    3420
ttatatatat acatcatgat gatactgaca gtcatgtccc attgctaaat agacagactc    3480
catctgccgc ctccaactga tgttctcaat atttaagggg tcatctcgca ttgtttaata    3540
ataaacagac tccatctacc gcctccaaat gatgttctca aaatatattg tatgaactta    3600
tttttattac ttagtattat tagacaactt acttgcttta tgaaaacac ttcctattta    3660 ggaaacaatt tataatggca gttcgttcat ttaacaattt atgtagaata aatgttataa    3720
atgcgtatgg gaaatcttaa atatggatag cataaatgat atctgcattg cctaattcga    3780
aatcaacagc aacgaaaaaa atcccttgta caacataaat agtcatcgag aaatatcaac    3840
tatcaaagaa cagctattca cacgttacta ttgagattat tattggacga gaatcacaca    3900
ctcaactgtc tttctctctt ctagaaatac aggtacaagt atgtactatt ctcattgttc    3960
atacttctag tcatttcatc ccacatattc cttggatttc tctccaatga atgacattct    4020
atcttgcaaa ttcaacaatt ataataagat ataccaaagt agcggtatag tgcaatcaa    4080 aaagcttctc tggtgtgctt ctcgtatta tttttattct aatgatccat taaaggtata    4140
tatttatttc ttgttatata atccttttgt ttattacatg ggctggatac ataaaggtat    4200
tttgatttaa ttttttgctt aaattcaatc cccctcgtt cagtgtcaac tgtaatggta    4260
ggaaattacc atactttga agaagcaaaa aaatgaaag aaaaaaaaa tcgtatttcc    4320 aggttagacg ttccgcagaa tctagaatgc ggtatgcggt acattgttct tcgaacgtaa    4380
aagttgcgct ccctgagata ttgtacattt ttgcttttac aagtacaagt acatcgtaca    4440
actatgtact actgttgatg catccacaac agtttgtttt gttttttttt gtttttttt    4500 tttctaatga ttcattaccg ctatgtatac ctacttgtac ttgtagtaag ccgggttatt    4560
ggcgttcaat taatcataga cttatgaatc tgcacggtgt gcgctgcgag ttacttttag    4620
cttatgcatg ctacttgggt gtaatattgg gatctgttcg gaaatcaacg gatgctcaat    4680
cgatttcgac agtaattaat taagtcatac acaagtcagc tttcttcgag cctcatataa    4740
gtataagtag ttcaacgtat tagcactgta cccagcatct ccgtatcgag aaacacaaca    4800
acatgcccca ttggacagat catgcggata cacaggttgt gcagtatcat acatactcga    4860
tcagacaggt cgtctgacca tcatacaagc tgaacaagcg ctccatactt gcacgctctc    4920
tatatacaca gttaaattac atatccatag tctaacctct aacagttaat cttctggtaa    4980
```

-continued

```
gcctcccagc cagccttctg gtatcgcttg gcctcctcaa taggatctcg gttctggccg   5040
tacagacctc ggccgacaat tatgatatcc gttccggtag acatgacatc ctcaacagtt   5100
cggtactgct gtccgagagc gtctcccttg tcgtcaagac ccaccccggg ggtcagaata   5160
agccagtcct cagagtcgcc cttaggtcgg ttctgggcaa tgaagccaac cacaaactcg   5220
gggtcggatc gggcaagctc aatggtctgc ttggagtact cgccagtggc cagagagccc   5280
ttgcaagaca gctcggccag catgagcaga cctctggcca gcttctcgtt gggagagggg   5340
actaggaact ccttgtactg ggagttctcg tagtcagaga cgtcctcctt cttctgttca   5400
gagacagttt cctcggcacc agctcgcagg ccagcaatga ttccggttcc gggtacaccg   5460
tgggcgttgg tgatatcgga ccactcggcg attcggtgac accggtactg gtgcttgaca   5520
gtgttgccaa tatctgcgaa ctttctgtcc tcgaacagga agaaaccgtg cttaagagca   5580
agttccttga gggggagcac agtgccggcg taggtgaagt cgtcaatgat gtcgatatgg   5640
gttttgatca tgcacacata aggtccgacc ttatcggcaa gctcaatgag ctccttggtg   5700
gtggtaacat ccagagaagc acacaggttg gttttcttgg ctgccacgag cttgagcact   5760
cgagcggcaa aggcggactt gtggacgtta gctcgagctt cgtaggaggg cattttggtg   5820
gtgaagagga gactgaaata aatttagtct gcagaacttt ttatcggaac cttatctggg   5880
gcagtgaagt atatgttatg gtaatagtta cgagttagtt gaacttatag atagactgga   5940
ctatacggct atcggtccaa attagaaaga acgtcaatgg ctctctgggc gtcgcctttg   6000
ccgacaaaaa tgtgatcatg atgaaagcca gcaatgacgt tgcagctgat attgttgtcg   6060
gccaaccgcg ccgaaaacgc agctgtcaga cccacagcct caacgaaga atgtatcgtc   6120 aaagtgatcc aagcacactc atagttggag tcgtactcca aaggcggcaa tgacgagtca   6180
gacagatact cgtcgaccgt acgatagtta gtagacaaca atcgatagtt ggagcaaggg   6240
agaaatgtag agtgtgaaag actcactatg gtccgggctt atctcgacca atagccaaag   6300
tctggagttt ctgagagaaa aaggcaagat acgtatgtaa caaagcgacg catggtacaa   6360
taataccgga ggcatgtatc atagagagtt agtggttcga tgatggcact ggtgcctggt   6420
atgactttat acggctgact acatatttgt cctcagacat acaattacag tcaagcactt   6480
acccttggac atctgtaggt accccccggc caagacgatc tcagcgtgtc gtatgtcgga   6540
ttggcgtagc tccctcgctc gtcaattggc tcccatctac tttcttctgc ttggctacac   6600
ccagcatgtc tgctatggct cgttttcgtg ccttatctat cctcccagta ttaccaactc   6660
taaatgacat gatgtgattg ggtctacact ttcatatcag agataaggag tagcacagtt   6720
gcataaaaag cccaactcta atcagcttct tcctttcttg taattagtac aaaggtgatt   6780
agcgaaatct ggaagcttag ttggccctaa aaaatcaaa aaaagcaaaa acgaaaaac     6840 gaaaaaccac agttttgaga acagggaggt aacgaaggat cgtatatata tatatatata   6900
tatataccca cggatcccga gaccggcctt tgattcttcc ctacaaccaa ccattctcac   6960
caccctaatt cacaaccatg gcctttccat gggcagataa gtgggcagcc gatgcgtctg   7020
catctacagg gctgcctccg gacctcctca agattgcatt cactctggtc atgtcttatc   7080
cgctgagttc tctcatgaaa cggctgccag atgacgccaa aaacctcaag atcatctata   7140
tcatctccgt gtccatcttc tacatggtgg gtgtcttctc cctctatggc ggagctgcca   7200
ctctgctctt ctcctcaatg ggtaccttct tcatcaccca atggaagagc ccttacatgc   7260
cctgggtcaa ttttggtttt gtcatgaccc atctcttcgt caatcacctg cgttcgcagt   7320
```

-continued

```
ttttccccga aacatacgac cccaatgtca ttgacatcac cggagcacag atggttctgt    7380
gtatgaagct atcgtctttt ggatggaacg tctacgatgg atggcagatt gagaagggtg    7440
agcagctcag cgagttccag actaaaaggg ctgttctcaa gcaccccagt cttatggact    7500
tcctagcttt tgtgttctac ttcccttcca ttctgacagg tccttcttac gactatatgg    7560
agttccataa ctggctcgat ctcagcctgt tcaaggagct ggagaaagat aaggacccca    7620
agcgagctgc tcgacgaaag cgacacaaga tcccccgatc tggaatcgct gcttccaaga    7680
aactcgccgc tggtatcttc tggatcgttc tgtggaccca ggtggactct cgaatctcca    7740
ccgcctacgc ttactcagac gcattcacca aggagcacaa catctttgga cgaattgtgt    7800
acctctacat gctcggtttc atgtaccgac tcaagtacta cggagcctgg tccatttccg    7860
agggagcctg catcttgtct ggcctcggat tccatggcgt ggaccccaaa actggcaagt    7920
acaagtggga ccgtgtccag aacgtggacc cgtggggatt cgaaactggt caaaacacaa    7980
aggctctgct ggaggcctgg aaccagaaca ctaacaagtg gctacgaaac tatgtgtacc    8040
tccgagtggt gcccaaaggc caaaagcctg gattccgagc cactatcttc acatttgtgg    8100
tttccgcctt ctggcatgga actcgacctg ctactatct caccttttgtg accgctgcca    8160
tgtaccagtc tgttggtaag ttcttccgac gatacctgcg accttcttc atggagtctg    8220
atggaaagac tgccggtccc tataagatct actacgacat tgtgtgttgg atcgttgtcc    8280
aaaccgcatt tggatacgct acccagtcct ttatgattct agacttctgg ctgtcgctca    8340
agtgttggaa gaactcctgg ttcctgtacc acattgctct gggcgccatc tttgcaattt    8400
ctagccccta caaggcatgg gcgattccca agatcaagaa aaagcaggct ggagccgtca    8460
ctgacaagaa ggacgccaag gaggaggtga agaaggacac catcaagacc aagtaagc     8518
```

```
<210> SEQ ID NO 44
<211> LENGTH: 512
<212> TYPE: PRT
<213> ORGANISM: Artificial sequence
<220> FEATURE:
<223> OTHER INFORMATION: Mutant YlLPCAT_M132X
<220> FEATURE:
<221> NAME/KEY: MISC_FEATURE
<222> LOCATION: (132)..(132)
<223> OTHER INFORMATION: Xaa = Ala [A], Asn [N], Cys [C], Gly [G],
      Gln [Q], His [H], Ile [I], Leu [L], Phe [F], Pro [P], Ser [S],
      Thr [T], Trp [W], Tyr [Y] or Val [V]

<400> SEQUENCE: 44

Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
                20                  25                  30

Ser Tyr Pro Leu Ser Ser Leu Met Lys Arg Leu Pro Asp Ala Lys
            35                  40                  45

Asn Leu Lys Ile Ile Tyr Ile Ile Ser Val Ser Ile Phe Tyr Met Val
        50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125
```

Gly Ala Gln Xaa Val Leu Cys Met Lys Leu Ser Ser Phe Gly Trp Asn
            130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Lys Arg His Lys
210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510

<210> SEQ ID NO 45
<211> LENGTH: 512
<212> TYPE: PRT
<213> ORGANISM: Artificial sequence
<220> FEATURE:

<223> OTHER INFORMATION: Mutant Y1LPCAT_V133X
<220> FEATURE:
<221> NAME/KEY: MISC_FEATURE
<222> LOCATION: (133)..(133)
<223> OTHER INFORMATION: Xaa = Ala [A], Asn [N], Cys [C], Gly [G],
      Gln [Q], His [H], Leu [L], Met [M], Phe [F], Pro [P], Ser [S],
      Thr [T], Trp [W] or Tyr [Y]

<400> SEQUENCE: 45

Met Ala Phe Pro Trp Ala Asp Lys Trp Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Ala Lys
        35                  40                  45

Asn Leu Lys Ile Ile Tyr Ile Ile Ser Val Ser Ile Phe Tyr Met Val
        50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
                100                 105                 110

Ser Gln Phe Phe Pro Glu Thr Tyr Asp Pro Asn Val Ile Asp Ile Thr
            115                 120                 125

Gly Ala Gln Met Xaa Leu Cys Met Lys Leu Ser Ser Phe Gly Trp Asn
130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Lys Arg His Lys
210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

```
Thr Ile Phe Thr Phe Val Val Ser Ala Phe Trp His Gly Thr Arg Pro
        370                 375                 380

Gly Tyr Tyr Leu Thr Phe Val Thr Ala Ala Met Tyr Gln Ser Val Gly
385                 390                 395                 400

Lys Phe Arg Arg Tyr Leu Arg Pro Phe Phe Met Glu Ser Asp Gly
            405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
            435                 440                 445

Asp Phe Trp Leu Ser Leu Lys Cys Trp Lys Asn Ser Trp Phe Leu Tyr
450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Gln Ala Gly Ala Val Thr Asp
            485                 490                 495

Lys Lys Asp Ala Lys Glu Glu Val Lys Lys Asp Thr Ile Lys Thr Lys
            500                 505                 510
```

<210> SEQ ID NO 46
<211> LENGTH: 512
<212> TYPE: PRT
<213> ORGANISM: Artificial sequence
<220> FEATURE:
<223> OTHER INFORMATION: Mutant Y1LPCAT_L134X
<220> FEATURE:
<221> NAME/KEY: MISC_FEATURE
<222> LOCATION: (134)..(134)
<223> OTHER INFORMATION: Xaa = Ala [A], Asn [N], Cys [C], Gly [G], Gln [Q], His [H], Met [M], Phe [F], Pro [P], Ser [S], Thr [T], Trp [W], Tyr [Y] or Val [V]

<400> SEQUENCE: 46

```
Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Ala Lys
        35                  40                  45

Asn Leu Lys Ile Ile Tyr Ile Ile Ser Val Ser Ile Phe Tyr Met Val
50                  55                  60

Gly Val Phe Ser Leu Tyr Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Xaa Cys Met Lys Leu Ser Ser Phe Gly Trp Asn
            130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Pro Ser Ile Leu Thr Gly Pro Ser Tyr Asp
            180                 185                 190
```

```
Tyr Met Glu Phe His Asn Trp Leu Asp Leu Ser Leu Phe Lys Glu Leu
            195                 200                 205

Glu Lys Asp Lys Asp Pro Lys Arg Ala Ala Arg Lys Arg His Lys
210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
                260                 265                 270

Ile Val Tyr Leu Tyr Met Leu Gly Phe Met Tyr Arg Leu Lys Tyr Tyr
                275                 280                 285

Gly Ala Trp Ser Ile Ser Glu Gly Ala Cys Ile Leu Ser Gly Leu Gly
290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
                340                 345                 350

Val Tyr Leu Arg Val Val Pro Lys Gly Gln Lys Pro Gly Phe Arg Ala
                355                 360                 365

Thr Ile Phe Thr Phe Val Val Ser Ala Phe Trp His Gly Thr Arg Pro
370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
                420                 425                 430

Val Val Gln Thr Ala Phe Gly Tyr Ala Thr Gln Ser Phe Met Ile Leu
                435                 440                 445

Asp Phe Trp Leu Ser Leu Lys Cys Trp Lys Asn Ser Trp Phe Leu Tyr
450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Gln Ala Gly Ala Val Thr Asp
                485                 490                 495

Lys Lys Asp Ala Lys Glu Glu Val Lys Lys Asp Thr Ile Lys Thr Lys
                500                 505                 510

<210> SEQ ID NO 47
<211> LENGTH: 512
<212> TYPE: PRT
<213> ORGANISM: Artificial sequence
<220> FEATURE:
<223> OTHER INFORMATION: Mutant YlLPCAT_C135X
<220> FEATURE:
<221> NAME/KEY: MISC_FEATURE
<222> LOCATION: (135)..(135)
<223> OTHER INFORMATION: Xaa = Arg [R], Asn [N], Asp [D], Glu [E],
      Gly [G], Gln [Q], His [H], Ile [I], Leu [L], Lys [K], Met [M],
      Phe [F], Pro [P], Ser [S], Trp [W] or Tyr [Y]

<400> SEQUENCE: 47

Met Ala Phe Pro Trp Ala Asp Lys Trp Ala Ala Asp Ala Ser Ala Ser
1               5                   10                  15
```

```
Thr Gly Leu Pro Pro Asp Leu Leu Lys Ile Ala Phe Thr Leu Val Met
             20                  25                  30

Ser Tyr Pro Leu Ser Ser Leu Met Lys Arg Leu Pro Asp Asp Ala Lys
         35                  40                  45

Asn Leu Lys Ile Ile Tyr Ile Ile Ser Val Ser Ile Phe Tyr Met Val
     50                  55                  60

Gly Val Phe Ser Leu Tyr Gly Ala Ala Thr Leu Leu Phe Ser Ser
 65                  70                  75                  80

Met Gly Thr Phe Phe Ile Thr Gln Trp Lys Ser Pro Tyr Met Pro Trp
                 85                  90                  95

Val Asn Phe Gly Phe Val Met Thr His Leu Phe Val Asn His Leu Arg
             100                 105                 110

Ser Gln Phe Phe Pro Glu Thr Tyr Asp Pro Asn Val Ile Asp Ile Thr
         115                 120                 125

Gly Ala Gln Met Val Leu Xaa Met Lys Leu Ser Ser Phe Gly Trp Asn
 130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                 165                 170                 175

Ala Phe Val Phe Tyr Phe Pro Ser Ile Leu Thr Gly Pro Ser Tyr Asp
             180                 185                 190

Tyr Met Glu Phe His Asn Trp Leu Asp Leu Ser Leu Phe Lys Glu Leu
         195                 200                 205

Glu Lys Asp Lys Asp Pro Lys Arg Ala Ala Arg Arg Lys Arg His Lys
 210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                 245                 250                 255

Tyr Ala Tyr Ser Asp Ala Phe Thr Lys Glu His Asn Ile Phe Gly Arg
             260                 265                 270

Ile Val Tyr Leu Tyr Met Leu Gly Phe Met Tyr Arg Leu Lys Tyr Tyr
         275                 280                 285

Gly Ala Trp Ser Ile Ser Glu Gly Ala Cys Ile Leu Ser Gly Leu Gly
 290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                 325                 330                 335

Leu Leu Glu Ala Trp Asn Gln Asn Thr Asn Lys Trp Leu Arg Asn Tyr
             340                 345                 350

Val Tyr Leu Arg Val Val Pro Lys Gly Gln Lys Pro Gly Phe Arg Ala
         355                 360                 365

Thr Ile Phe Thr Phe Val Val Ser Ala Phe Trp His Gly Thr Arg Pro
 370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Met Glu Ser Asp Gly
                 405                 410                 415

Lys Thr Ala Gly Pro Tyr Lys Ile Tyr Tyr Asp Ile Val Cys Trp Ile
             420                 425                 430

Val Val Gln Thr Ala Phe Gly Tyr Ala Thr Gln Ser Phe Met Ile Leu
```

```
                    435                 440                 445
Asp Phe Trp Leu Ser Leu Lys Cys Trp Lys Asn Ser Trp Phe Leu Tyr
            450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Gln Ala Gly Ala Val Thr Asp
                    485                 490                 495

Lys Lys Asp Ala Lys Glu Glu Val Lys Lys Asp Thr Ile Lys Thr Lys
                500                 505                 510

<210> SEQ ID NO 48
<211> LENGTH: 512
<212> TYPE: PRT
<213> ORGANISM: Artificial sequence
<220> FEATURE:
<223> OTHER INFORMATION: Mutant Y1LPCAT_M136X
<220> FEATURE:
<221> NAME/KEY: MISC_FEATURE
<222> LOCATION: (136)..(136)
<223> OTHER INFORMATION: Xaa = Ala [A], Asn [N], Cys [C], Gly [G],
      His [H], Ile [I], Phe [F], Pro [P], Ser [S], Thr [T], Trp [W],
      Tyr [Y] or Val [V]

<400> SEQUENCE: 48

Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
                20                  25                  30

Ser Tyr Pro Leu Ser Ser Leu Met Lys Arg Leu Pro Asp Asp Ala Lys
            35                  40                  45

Asn Leu Lys Ile Ile Tyr Ile Ile Ser Val Ser Ile Phe Tyr Met Val
50                  55                  60

Gly Val Phe Ser Leu Tyr Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Xaa Lys Leu Ser Ser Phe Gly Trp Asn
130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Lys Arg His Lys
210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
```

-continued

```
                  260                 265                 270
    Ile Val Tyr Leu Tyr Met Leu Gly Phe Met Tyr Arg Leu Lys Tyr Tyr
                275                 280                 285
    Gly Ala Trp Ser Ile Ser Glu Gly Ala Cys Ile Leu Ser Gly Leu Gly
                290                 295                 300
    Phe His Gly Val Asp Pro Lys Thr Gly Lys Tyr Lys Trp Asp Arg Val
    305                 310                 315                 320
    Gln Asn Val Asp Pro Trp Gly Phe Glu Thr Gly Gln Asn Thr Lys Ala
                    325                 330                 335
    Leu Leu Glu Ala Trp Asn Gln Asn Thr Asn Lys Trp Leu Arg Asn Tyr
                340                 345                 350
    Val Tyr Leu Arg Val Val Pro Lys Gly Gln Lys Pro Gly Phe Arg Ala
                355                 360                 365
    Thr Ile Phe Thr Phe Val Val Ser Ala Phe Trp His Gly Thr Arg Pro
                370                 375                 380
    Gly Tyr Tyr Leu Thr Phe Val Thr Ala Ala Met Tyr Gln Ser Val Gly
    385                 390                 395                 400
    Lys Phe Phe Arg Arg Tyr Leu Arg Pro Phe Phe Met Glu Ser Asp Gly
                    405                 410                 415
    Lys Thr Ala Gly Pro Tyr Lys Ile Tyr Tyr Asp Ile Val Cys Trp Ile
                420                 425                 430
    Val Val Gln Thr Ala Phe Gly Tyr Ala Thr Gln Ser Phe Met Ile Leu
                435                 440                 445
    Asp Phe Trp Leu Ser Leu Lys Cys Trp Lys Asn Ser Trp Phe Leu Tyr
    450                 455                 460
    His Ile Ala Leu Gly Ala Ile Phe Ala Ile Ser Ser Pro Tyr Lys Ala
    465                 470                 475                 480
    Trp Ala Ile Pro Lys Ile Lys Lys Gln Ala Gly Ala Val Thr Asp
                    485                 490                 495
    Lys Lys Asp Ala Lys Glu Glu Val Lys Lys Asp Thr Ile Lys Thr Lys
                    500                 505                 510

<210> SEQ ID NO 49
<211> LENGTH: 512
<212> TYPE: PRT
<213> ORGANISM: Artificial sequence
<220> FEATURE:
<223> OTHER INFORMATION: Mutant YlLPCAT_K137X
<220> FEATURE:
<221> NAME/KEY: MISC_FEATURE
<222> LOCATION: (137)..(137)
<223> OTHER INFORMATION: Xaa = Ala [A], Arg [R], Asn [N], Gly [G],
      His [H], Pro [P], Ser [S], Thr [T] or Tyr [Y]

<400> SEQUENCE: 49

Met Ala Phe Pro Trp Ala Asp Lys Trp Ala Ala Asp Ala Ser Ala Ser
    1               5                   10                  15
    Thr Gly Leu Pro Pro Asp Leu Leu Lys Ile Ala Phe Thr Leu Val Met
                20                  25                  30
    Ser Tyr Pro Leu Ser Ser Leu Met Lys Arg Leu Pro Asp Asp Ala Lys
                35                  40                  45
    Asn Leu Lys Ile Ile Tyr Ile Ile Ser Val Ser Ile Phe Tyr Met Val
            50                  55                  60
    Gly Val Phe Ser Leu Tyr Gly Gly Ala Ala Thr Leu Leu Phe Ser Ser
    65                  70                  75                  80
    Met Gly Thr Phe Phe Ile Thr Gln Trp Lys Ser Pro Tyr Met Pro Trp
                85                  90                  95
```

```
Val Asn Phe Gly Phe Val Met Thr His Leu Phe Val Asn His Leu Arg
            100                 105                 110

Ser Gln Phe Pro Glu Thr Tyr Asp Pro Asn Val Ile Asp Ile Thr
            115                 120                 125

Gly Ala Gln Met Val Leu Cys Met Xaa Leu Ser Ser Phe Gly Trp Asn
130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
            165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
            195                 200                 205

Glu Lys Asp Lys Asp Pro Lys Arg Ala Ala Arg Lys Arg His Lys
            210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
            245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
            275                 280                 285

Gly Ala Trp Ser Ile Ser Glu Gly Ala Cys Ile Leu Ser Gly Leu Gly
            290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
            325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
            355                 360                 365

Thr Ile Phe Thr Phe Val Val Ser Ala Phe Trp His Gly Thr Arg Pro
370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Met Glu Ser Asp Gly
            405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
            435                 440                 445

Asp Phe Trp Leu Ser Leu Lys Cys Trp Lys Asn Ser Trp Phe Leu Tyr
            450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Gln Ala Gly Ala Val Thr Asp
            485                 490                 495

Lys Lys Asp Ala Lys Glu Glu Val Lys Lys Asp Thr Ile Lys Thr Lys
            500                 505                 510
```

```
<210> SEQ ID NO 50
<211> LENGTH: 512
<212> TYPE: PRT
<213> ORGANISM: Artificial sequence
<220> FEATURE:
<223> OTHER INFORMATION: Mutant Y1LPCAT_L138X
<220> FEATURE:
<221> NAME/KEY: MISC_FEATURE
<222> LOCATION: (138)..(138)
<223> OTHER INFORMATION: Xaa = Ala [A], Asn [N], Cys [C], Gly [G],
      Gln [Q], His [H], Ile [I], Met [M], Phe [F], Pro [P], Ser [S],
      Thr [T], Trp [W] or Tyr [Y]

<400> SEQUENCE: 50
```

| | | | | | | | | | | | | | | |
|---|---|---|---|---|---|---|---|---|---|---|---|---|---|---|
| Met | Ala | Phe | Pro | Trp | Ala | Asp | Lys | Trp | Ala | Ala | Asp | Ala | Ser | Ala | Ser |
| 1 | | | | 5 | | | | | 10 | | | | | 15 | |
| Thr | Gly | Leu | Pro | Pro | Asp | Leu | Leu | Lys | Ile | Ala | Phe | Thr | Leu | Val | Met |
| | | | 20 | | | | | 25 | | | | | 30 | | |
| Ser | Tyr | Pro | Leu | Ser | Ser | Leu | Met | Lys | Arg | Leu | Pro | Asp | Asp | Ala | Lys |
| | | | | 35 | | | | | 40 | | | | | 45 | |
| Asn | Leu | Lys | Ile | Ile | Tyr | Ile | Ile | Ser | Val | Ser | Ile | Phe | Tyr | Met | Val |
| | 50 | | | | | 55 | | | | | 60 | | | | |
| Gly | Val | Phe | Ser | Leu | Tyr | Gly | Ala | Ala | Thr | Leu | Leu | Phe | Ser | Ser |
| 65 | | | | | 70 | | | | | 75 | | | | | 80 |
| Met | Gly | Thr | Phe | Phe | Ile | Thr | Gln | Trp | Lys | Ser | Pro | Tyr | Met | Pro | Trp |
| | | | | 85 | | | | | 90 | | | | | 95 | |
| Val | Asn | Phe | Gly | Phe | Val | Met | Thr | His | Leu | Phe | Val | Asn | His | Leu | Arg |
| | | | 100 | | | | | 105 | | | | | 110 | | |
| Ser | Gln | Phe | Phe | Pro | Glu | Thr | Tyr | Asp | Pro | Asn | Val | Ile | Asp | Ile | Thr |
| | | | | 115 | | | | | 120 | | | | | 125 | |
| Gly | Ala | Gln | Met | Val | Leu | Cys | Met | Lys | Xaa | Ser | Ser | Phe | Gly | Trp | Asn |
| | 130 | | | | | 135 | | | | | 140 | | | | |
| Val | Tyr | Asp | Gly | Trp | Gln | Ile | Glu | Lys | Gly | Glu | Gln | Leu | Ser | Glu | Phe |
| 145 | | | | | 150 | | | | | 155 | | | | | 160 |
| Gln | Thr | Lys | Arg | Ala | Val | Leu | Lys | His | Pro | Ser | Leu | Met | Asp | Phe | Leu |
| | | | | 165 | | | | | 170 | | | | | 175 | |
| Ala | Phe | Val | Phe | Tyr | Phe | Pro | Ser | Ile | Leu | Thr | Gly | Pro | Ser | Tyr | Asp |
| | | | 180 | | | | | 185 | | | | | 190 | | |
| Tyr | Met | Glu | Phe | His | Asn | Trp | Leu | Asp | Leu | Ser | Leu | Phe | Lys | Glu | Leu |
| | | | | 195 | | | | | 200 | | | | | 205 | |
| Glu | Lys | Asp | Lys | Asp | Pro | Lys | Arg | Ala | Ala | Arg | Lys | Arg | His | Lys |
| | 210 | | | | | 215 | | | | | 220 | | | | |
| Ile | Pro | Arg | Ser | Gly | Ile | Ala | Ala | Ser | Lys | Lys | Leu | Ala | Ala | Gly | Ile |
| 225 | | | | | 230 | | | | | 235 | | | | | 240 |
| Phe | Trp | Ile | Val | Leu | Trp | Thr | Gln | Val | Asp | Ser | Arg | Ile | Ser | Thr | Ala |
| | | | | 245 | | | | | 250 | | | | | 255 | |
| Tyr | Ala | Tyr | Ser | Asp | Ala | Phe | Thr | Lys | Glu | His | Asn | Ile | Phe | Gly | Arg |
| | | | 260 | | | | | 265 | | | | | 270 | | |
| Ile | Val | Tyr | Leu | Tyr | Met | Leu | Gly | Phe | Met | Tyr | Arg | Leu | Lys | Tyr | Tyr |
| | | | | 275 | | | | | 280 | | | | | 285 | |
| Gly | Ala | Trp | Ser | Ile | Ser | Glu | Gly | Ala | Cys | Ile | Leu | Ser | Gly | Leu | Gly |
| | 290 | | | | | 295 | | | | | 300 | | | | |
| Phe | His | Gly | Val | Asp | Pro | Lys | Thr | Gly | Lys | Tyr | Lys | Trp | Asp | Arg | Val |
| 305 | | | | | 310 | | | | | 315 | | | | | 320 |
| Gln | Asn | Val | Asp | Pro | Trp | Gly | Phe | Glu | Thr | Gly | Gln | Asn | Thr | Lys | Ala |
| | | | | 325 | | | | | 330 | | | | | 335 | |

```
Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
    370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510

<210> SEQ ID NO 51
<211> LENGTH: 512
<212> TYPE: PRT
<213> ORGANISM: Artificial sequence
<220> FEATURE:
<223> OTHER INFORMATION: Mutant YlLPCAT_S139X
<220> FEATURE:
<221> NAME/KEY: MISC_FEATURE
<222> LOCATION: (139)..(139)
<223> OTHER INFORMATION: Xaa = Ala [A], Asn [N], Cys [C], Gly [G],
      His [H], Leu [L], Met [M], Phe [F], Pro [P], Trp [W] or Val [V]

<400> SEQUENCE: 51

Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Lys Leu Xaa Ser Phe Gly Trp Asn
    130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
```

```
                    165                 170                 175
Ala Phe Val Phe Tyr Phe Pro Ser Ile Leu Thr Gly Pro Ser Tyr Asp
                180                 185                 190

Tyr Met Glu Phe His Asn Trp Leu Asp Leu Ser Leu Phe Lys Glu Leu
            195                 200                 205

Glu Lys Asp Lys Asp Pro Lys Arg Ala Ala Arg Lys Arg His Lys
        210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
                260                 265                 270

Ile Val Tyr Leu Tyr Met Leu Gly Phe Met Tyr Arg Leu Lys Tyr Tyr
                275                 280                 285

Gly Ala Trp Ser Ile Ser Glu Gly Ala Cys Ile Leu Ser Gly Leu Gly
            290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
                355                 360                 365

Thr Ile Phe Thr Phe Val Val Ser Ala Phe Trp His Gly Thr Arg Pro
370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
                420                 425                 430

Val Val Gln Thr Ala Phe Gly Tyr Ala Thr Gln Ser Phe Met Ile Leu
            435                 440                 445

Asp Phe Trp Leu Ser Leu Lys Cys Trp Lys Asn Ser Trp Phe Leu Tyr
                450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Gln Ala Gly Ala Val Thr Asp
                485                 490                 495

Lys Lys Asp Ala Lys Glu Glu Val Lys Lys Asp Thr Ile Lys Thr Lys
                500                 505                 510

<210> SEQ ID NO 52
<211> LENGTH: 512
<212> TYPE: PRT
<213> ORGANISM: Artificial sequence
<220> FEATURE:
<223> OTHER INFORMATION: Mutant YlLPCAT_S140X
<220> FEATURE:
<221> NAME/KEY: MISC_FEATURE
<222> LOCATION: (140)..(140)
<223> OTHER INFORMATION: Xaa = Asn [N], Cys [C], His [H], Ile [I],
      Leu [L], Phe [F], Pro [P], Trp [W], Tyr [Y] or Val [V]

<400> SEQUENCE: 52
```

```
Met Ala Phe Pro Trp Ala Asp Lys Trp Ala Asp Ala Ser Ala Ser
1               5                  10                 15

Thr Gly Leu Pro Pro Asp Leu Leu Lys Ile Ala Phe Thr Leu Val Met
            20                  25                 30

Ser Tyr Pro Leu Ser Ser Leu Met Lys Arg Leu Pro Asp Ala Lys
        35                  40                 45

Asn Leu Lys Ile Ile Tyr Ile Ile Ser Val Ser Ile Phe Tyr Met Val
    50                  55                 60

Gly Val Phe Ser Leu Tyr Gly Ala Ala Thr Leu Leu Phe Ser Ser
65              70                  75                 80

Met Gly Thr Phe Phe Ile Thr Gln Trp Lys Ser Pro Tyr Met Pro Trp
                85                  90                 95

Val Asn Phe Gly Phe Val Met Thr His Leu Phe Val Asn His Leu Arg
            100                 105                110

Ser Gln Phe Phe Pro Glu Thr Tyr Asp Pro Asn Val Ile Asp Ile Thr
        115                 120                125

Gly Ala Gln Met Val Leu Cys Met Lys Leu Ser Xaa Phe Gly Trp Asn
    130                 135                 140

Val Tyr Asp Gly Trp Gln Ile Glu Lys Gly Glu Gln Leu Ser Glu Phe
145                 150                 155                160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Lys Arg His Lys
210                 215                 220

Ile Pro Arg Ser Gly Ile Ala Ala Ser Lys Lys Leu Ala Ala Gly Ile
225                 230                 235                240

Phe Trp Ile Val Leu Trp Thr Gln Val Asp Ser Arg Ile Ser Thr Ala
            245                 250                 255

Tyr Ala Tyr Ser Asp Ala Phe Thr Lys Glu His Asn Ile Phe Gly Arg
        260                 265                 270

Ile Val Tyr Leu Tyr Met Leu Gly Phe Met Tyr Arg Leu Lys Tyr Tyr
    275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                320

Gln Asn Val Asp Pro Trp Gly Phe Glu Thr Gly Gln Asn Thr Lys Ala
            325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
            355                 360                 365

Thr Ile Phe Thr Phe Val Val Ser Ala Phe Trp His Gly Thr Arg Pro
    370                 375                 380

Gly Tyr Tyr Leu Thr Phe Val Thr Ala Ala Met Tyr Gln Ser Val Gly
385                 390                 395                400

Lys Phe Pro Arg Arg Tyr Leu Arg Pro Phe Met Glu Ser Asp Gly
                405                 410                 415
```

```
Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
            435                 440                 445

Asp Phe Trp Leu Ser Leu Lys Cys Trp Lys Asn Ser Trp Phe Leu Tyr
450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510

<210> SEQ ID NO 53
<211> LENGTH: 512
<212> TYPE: PRT
<213> ORGANISM: Artificial sequence
<220> FEATURE:
<223> OTHER INFORMATION: Mutant YlLPCAT_F141X
<220> FEATURE:
<221> NAME/KEY: MISC_FEATURE
<222> LOCATION: (141)..(141)
<223> OTHER INFORMATION: Xaa = Ala [A], Asn [N], Gly [G], His [H],
      Ile [I], Met [M], Pro [P], Ser [S], Thr [T], Trp [W] or Val [V]

<400> SEQUENCE: 53

Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
                35                  40                  45

Asn Leu Lys Ile Ile Tyr Ile Ile Ser Val Ser Ile Phe Tyr Met Val
50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Lys Leu Ser Ser Xaa Gly Trp Asn
130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
```

245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
    370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510

<210> SEQ ID NO 54
<211> LENGTH: 512
<212> TYPE: PRT
<213> ORGANISM: Artificial sequence
<220> FEATURE:
<223> OTHER INFORMATION: Mutant YlLPCAT_G142X
<220> FEATURE:
<221> NAME/KEY: MISC_FEATURE
<222> LOCATION: (142)..(142)
<223> OTHER INFORMATION: Xaa = Asn [N], His [H], Ile [I], Leu [L],
      Met [M], Phe [F], Pro [P], Thr [T], Trp [W], Tyr [Y] or Val [V]

<400> SEQUENCE: 54

Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

```
Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Lys Leu Ser Ser Phe Xaa Trp Asn
130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Gln Ala Gly Ala Val Thr Asp
                485                 490                 495
```

```
Lys Lys Asp Ala Lys Glu Glu Val Lys Asp Thr Ile Lys Thr Lys
            500                 505                 510

<210> SEQ ID NO 55
<211> LENGTH: 512
<212> TYPE: PRT
<213> ORGANISM: Artificial sequence
<220> FEATURE:
<223> OTHER INFORMATION: Mutant YlLPCAT_W143X
<220> FEATURE:
<221> NAME/KEY: MISC_FEATURE
<222> LOCATION: (143)..(143)
<223> OTHER INFORMATION: Xaa = Ala [A], Gly [G], His [H], Leu [L],
      Lys [K], Pro [P], Ser [S], Thr [T] or Val [V]

<400> SEQUENCE: 55

Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
50                  55                  60

Gly Val Phe Ser Leu Tyr Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Lys Leu Ser Ser Phe Gly Xaa Asn
130                 135                 140

Val Tyr Asp Gly Trp Gln Ile Glu Lys Gly Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
```

```
                     325                 330                 335
Leu Leu Glu Ala Trp Asn Gln Asn Thr Asn Lys Trp Leu Arg Asn Tyr
                340                 345                 350

Val Tyr Leu Arg Val Val Pro Lys Gly Gln Lys Pro Gly Phe Arg Ala
                355                 360                 365

Thr Ile Phe Thr Phe Val Val Ser Ala Phe Trp His Gly Thr Arg Pro
        370                 375                 380

Gly Tyr Tyr Leu Thr Phe Val Thr Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
                420                 425                 430

Val Val Gln Thr Ala Phe Gly Tyr Ala Thr Gln Ser Phe Met Ile Leu
                435                 440                 445

Asp Phe Trp Leu Ser Leu Lys Cys Trp Lys Asn Ser Trp Phe Leu Tyr
        450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Gln Ala Gly Ala Val Thr Asp
                485                 490                 495

Lys Lys Asp Ala Lys Glu Glu Val Lys Lys Asp Thr Ile Lys Thr Lys
                500                 505                 510

<210> SEQ ID NO 56
<211> LENGTH: 512
<212> TYPE: PRT
<213> ORGANISM: Artificial sequence
<220> FEATURE:
<223> OTHER INFORMATION: Mutant YlLPCAT_N144X
<220> FEATURE:
<221> NAME/KEY: MISC_FEATURE
<222> LOCATION: (144)..(144)
<223> OTHER INFORMATION: Xaa = Ala [A], Arg [R], Gly [G], His [H],
      Lys [K], Phe [F], Pro [P], Thr [T] or Val [V]

<400> SEQUENCE: 56

Met Ala Phe Pro Trp Ala Asp Lys Trp Ala Ala Asp Ala Ser Ala Ser
1               5                  10                  15

Thr Gly Leu Pro Pro Asp Leu Leu Lys Ile Ala Phe Thr Leu Val Met
                20                  25                  30

Ser Tyr Pro Leu Ser Ser Leu Met Lys Arg Leu Pro Asp Asp Ala Lys
            35                  40                  45

Asn Leu Lys Ile Ile Tyr Ile Ile Ser Val Ser Ile Phe Tyr Met Val
50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Lys Leu Ser Ser Phe Gly Trp Xaa
130                 135                 140

Val Tyr Asp Gly Trp Gln Ile Glu Lys Gly Glu Gln Leu Ser Glu Phe
145                 150                 155                 160
```

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
    370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510

<210> SEQ ID NO 57
<211> LENGTH: 512
<212> TYPE: PRT
<213> ORGANISM: Artificial sequence
<220> FEATURE:
<223> OTHER INFORMATION: Mutant YlLPCAT_V145X
<220> FEATURE:
<221> NAME/KEY: MISC_FEATURE
<222> LOCATION: (145)..(145)
<223> OTHER INFORMATION: Xaa = Ala [A], Cys [C], Gly [G], Glu [E],
      His [H], Met [M], Phe [F], Pro [P], Ser [S], Thr [T] or Trp [W]

<400> SEQUENCE: 57

Met Ala Phe Pro Trp Ala Asp Lys Trp Ala Asp Ala Ser Ala Ser
1               5                   10                  15

Thr Gly Leu Pro Pro Asp Leu Leu Lys Ile Ala Phe Thr Leu Val Met
                20                  25                  30

Ser Tyr Pro Leu Ser Ser Leu Met Lys Arg Leu Pro Asp Asp Ala Lys
            35                  40                  45

Asn Leu Lys Ile Ile Tyr Ile Ile Ser Val Ser Ile Phe Tyr Met Val
50                  55                  60

Gly Val Phe Ser Leu Tyr Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
                100                 105                 110

Ser Gln Phe Phe Pro Glu Thr Tyr Asp Pro Asn Val Ile Asp Ile Thr
            115                 120                 125

Gly Ala Gln Met Val Leu Cys Met Lys Leu Ser Ser Phe Gly Trp Asn
130                 135                 140

Xaa Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
                180                 185                 190

Tyr Met Glu Phe His Asn Trp Leu Asp Leu Ser Leu Phe Lys Glu Leu
            195                 200                 205

Glu Lys Asp Lys Asp Pro Lys Arg Ala Ala Arg Arg Lys Arg His Lys
210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
                260                 265                 270

Ile Val Tyr Leu Tyr Met Leu Gly Phe Met Tyr Arg Leu Lys Tyr Tyr
            275                 280                 285

Gly Ala Trp Ser Ile Ser Glu Gly Ala Cys Ile Leu Ser Gly Leu Gly
290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
                340                 345                 350

Val Tyr Leu Arg Val Val Pro Lys Gly Gln Lys Pro Gly Phe Arg Ala
            355                 360                 365

Thr Ile Phe Thr Phe Val Val Ser Ala Phe Trp His Gly Thr Arg Pro
            370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly

```
                     405                 410                 415
Lys Thr Ala Gly Pro Tyr Lys Ile Tyr Tyr Asp Ile Val Cys Trp Ile
                420                 425                 430

Val Val Gln Thr Ala Phe Gly Tyr Ala Thr Gln Ser Phe Met Ile Leu
            435                 440                 445

Asp Phe Trp Leu Ser Leu Lys Cys Trp Lys Asn Ser Trp Phe Leu Tyr
        450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Gln Ala Gly Ala Val Thr Asp
                485                 490                 495

Lys Lys Asp Ala Lys Glu Glu Val Lys Lys Asp Thr Ile Lys Thr Lys
                500                 505                 510
```

<210> SEQ ID NO 58
<211> LENGTH: 512
<212> TYPE: PRT
<213> ORGANISM: Artificial sequence
<220> FEATURE:
<223> OTHER INFORMATION: Mutant YlLPCAT_Y146X
<220> FEATURE:
<221> NAME/KEY: MISC_FEATURE
<222> LOCATION: (146)..(146)
<223> OTHER INFORMATION: Xaa = Arg [R], Asn [N], Asp [D], Gly [G],
      Glu [E], Gln [Q], Ile [I], Leu [L], Met [M], Phe [F], Pro [P],
      Trp [W] or Val [V]

<400> SEQUENCE: 58

```
Met Ala Phe Pro Trp Ala Asp Lys Trp Ala Asp Ala Ser Ala Ser
1               5                   10                  15

Thr Gly Leu Pro Pro Asp Leu Leu Lys Ile Ala Phe Thr Leu Val Met
                20                  25                  30

Ser Tyr Pro Leu Ser Ser Leu Met Lys Arg Leu Pro Asp Asp Ala Lys
            35                  40                  45

Asn Leu Lys Ile Ile Tyr Ile Ile Ser Val Ser Ile Phe Tyr Met Val
        50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
                100                 105                 110

Ser Gln Phe Phe Pro Glu Thr Tyr Asp Pro Asn Val Ile Asp Ile Thr
            115                 120                 125

Gly Ala Gln Met Val Leu Cys Met Lys Leu Ser Ser Phe Gly Trp Asn
        130                 135                 140

Val Xaa Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Lys Glu Leu
        195                 200                 205

Glu Lys Asp Lys Asp Pro Lys Arg Ala Ala Arg Arg Lys Arg His Lys
210                 215                 220

Ile Pro Arg Ser Gly Ile Ala Ala Ser Lys Lys Leu Ala Ala Gly Ile
```

```
                    225                 230                 235                 240
            Phe Trp Ile Val Leu Trp Thr Gln Val Asp Ser Arg Ile Ser Thr Ala
                            245                 250                 255

Tyr Ala Tyr Ser Asp Ala Phe Thr Lys Glu His Asn Ile Phe Gly Arg
                            260                 265                 270

Ile Val Tyr Leu Tyr Met Leu Gly Phe Met Tyr Arg Leu Lys Tyr Tyr
                            275                 280                 285

Gly Ala Trp Ser Ile Ser Glu Gly Ala Cys Ile Leu Ser Gly Leu Gly
                            290                 295                 300

Phe His Gly Val Asp Pro Lys Thr Gly Lys Tyr Lys Trp Asp Arg Val
            305                 310                 315                 320

Gln Asn Val Asp Pro Trp Gly Phe Glu Thr Gly Gln Asn Thr Lys Ala
                            325                 330                 335

Leu Leu Glu Ala Trp Asn Gln Asn Thr Asn Lys Trp Leu Arg Asn Tyr
                            340                 345                 350

Val Tyr Leu Arg Val Val Pro Lys Gly Gln Lys Pro Gly Phe Arg Ala
                            355                 360                 365

Thr Ile Phe Thr Phe Val Val Ser Ala Phe Trp His Gly Thr Arg Pro
                            370                 375                 380

Gly Tyr Tyr Leu Thr Phe Val Thr Ala Ala Met Tyr Gln Ser Val Gly
            385                 390                 395                 400

Lys Phe Phe Arg Arg Tyr Leu Arg Pro Phe Phe Met Glu Ser Asp Gly
                            405                 410                 415

Lys Thr Ala Gly Pro Tyr Lys Ile Tyr Tyr Asp Ile Val Cys Trp Ile
                            420                 425                 430

Val Val Gln Thr Ala Phe Gly Tyr Ala Thr Gln Ser Phe Met Ile Leu
                            435                 440                 445

Asp Phe Trp Leu Ser Leu Lys Cys Trp Lys Asn Ser Trp Phe Leu Tyr
                            450                 455                 460

His Ile Ala Leu Gly Ala Ile Phe Ala Ile Ser Ser Pro Tyr Lys Ala
            465                 470                 475                 480

Trp Ala Ile Pro Lys Ile Lys Lys Gln Ala Gly Ala Val Thr Asp
                            485                 490                 495

Lys Lys Asp Ala Lys Glu Val Lys Lys Asp Thr Ile Lys Thr Lys
                            500                 505                 510

<210> SEQ ID NO 59
<211> LENGTH: 512
<212> TYPE: PRT
<213> ORGANISM: Artificial sequence
<220> FEATURE:
<223> OTHER INFORMATION: Mutant Y1LPCAT_D147X
<220> FEATURE:
<221> NAME/KEY: MISC_FEATURE
<222> LOCATION: (147)..(147)
<223> OTHER INFORMATION: Xaa = Ala [A], Asn [N], Gly [G], Glu [E],
      Gln [Q], His [H], Phe [F], Ser [S] or Thr [T]

<400> SEQUENCE: 59

Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
                20                  25                  30

Ser Tyr Pro Leu Ser Ser Leu Met Lys Arg Leu Pro Asp Asp Ala Lys
            35                  40                  45

Asn Leu Lys Ile Ile Tyr Ile Ile Ser Val Ser Ile Phe Tyr Met Val
        50                  55                  60
```

```
Gly Val Phe Ser Leu Tyr Gly Ala Ala Thr Leu Leu Phe Ser Ser
 65                  70                  75                  80

Met Gly Thr Phe Phe Ile Thr Gln Trp Lys Ser Pro Tyr Met Pro Trp
                 85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Lys Leu Ser Ser Phe Gly Trp Asn
130                 135                 140

Val Tyr Xaa Gly Trp Gln Ile Glu Lys Gly Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Lys Arg His Lys
210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
450                 455                 460

His Ile Ala Leu Gly Ala Ile Phe Ala Ile Ser Ser Pro Tyr Lys Ala
465                 470                 475                 480
```

```
Trp Ala Ile Pro Lys Ile Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510

<210> SEQ ID NO 60
<211> LENGTH: 512
<212> TYPE: PRT
<213> ORGANISM: Artificial sequence
<220> FEATURE:
<223> OTHER INFORMATION: Mutant YlLPCAT_G148X
<220> FEATURE:
<221> NAME/KEY: MISC_FEATURE
<222> LOCATION: (148)..(148)
<223> OTHER INFORMATION: Xaa = Ala [A], Asn [N], His [H], Leu [L],
      Met [M], Phe [F], Ser [S], Thr [T] or Val [V]

<400> SEQUENCE: 60

Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Lys Leu Ser Ser Phe Gly Trp Asn
    130                 135                 140

Val Tyr Asp Xaa Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
```

```
            305                 310                 315                 320
        Gln Asn Val Asp Pro Trp Gly Phe Glu Thr Gly Gln Asn Thr Lys Ala
                        325                 330                 335

Leu Leu Glu Ala Trp Asn Gln Asn Thr Asn Lys Trp Leu Arg Asn Tyr
                        340                 345                 350

Val Tyr Leu Arg Val Val Pro Lys Gly Gln Lys Pro Gly Phe Arg Ala
                        355                 360                 365

Thr Ile Phe Thr Phe Val Val Ser Ala Phe Trp His Gly Thr Arg Pro
                    370                 375                 380

Gly Tyr Tyr Leu Thr Phe Val Thr Ala Ala Met Tyr Gln Ser Val Gly
        385                 390                 395                 400

Lys Phe Phe Arg Arg Tyr Leu Arg Pro Phe Met Glu Ser Asp Gly
                        405                 410                 415

Lys Thr Ala Gly Pro Tyr Lys Ile Tyr Tyr Asp Ile Val Cys Trp Ile
                        420                 425                 430

Val Val Gln Thr Ala Phe Gly Tyr Ala Thr Gln Ser Phe Met Ile Leu
                        435                 440                 445

Asp Phe Trp Leu Ser Leu Lys Cys Trp Lys Asn Ser Trp Phe Leu Tyr
                    450                 455                 460

His Ile Ala Leu Gly Ala Ile Phe Ala Ile Ser Ser Pro Tyr Lys Ala
        465                 470                 475                 480

Trp Ala Ile Pro Lys Ile Lys Lys Gln Ala Gly Ala Val Thr Asp
                        485                 490                 495

Lys Lys Asp Ala Lys Glu Glu Val Lys Lys Asp Thr Ile Lys Thr Lys
                        500                 505                 510

<210> SEQ ID NO 61
<211> LENGTH: 512
<212> TYPE: PRT
<213> ORGANISM: Artificial sequence
<220> FEATURE:
<223> OTHER INFORMATION: Mutant YlLPCAT_S376X
<220> FEATURE:
<221> NAME/KEY: MISC_FEATURE
<222> LOCATION: (376)..(376)
<223> OTHER INFORMATION: Xaa = Ala [A], Gly [G], His [H], Leu [L],
      Phe [F], Pro [P], Thr [T] or Val [V]

<400> SEQUENCE: 61

Met Ala Phe Pro Trp Ala Asp Lys Trp Ala Asp Ala Ser Ala Ser
        1               5                   10                  15

Thr Gly Leu Pro Pro Asp Leu Leu Lys Ile Ala Phe Thr Leu Val Met
                        20                  25                  30

Ser Tyr Pro Leu Ser Ser Leu Met Lys Arg Leu Pro Asp Asp Ala Lys
                        35                  40                  45

Asn Leu Lys Ile Ile Tyr Ile Ile Ser Val Ser Ile Phe Tyr Met Val
                    50                  55                  60

Gly Val Phe Ser Leu Tyr Gly Gly Ala Ala Thr Leu Leu Phe Ser Ser
        65                  70                  75                  80

Met Gly Thr Phe Phe Ile Thr Gln Trp Lys Ser Pro Tyr Met Pro Trp
                        85                  90                  95

Val Asn Phe Gly Phe Val Met Thr His Leu Val Asn His Leu Arg
                        100                 105                 110

Ser Gln Phe Phe Pro Glu Thr Tyr Asp Pro Asn Val Ile Asp Ile Thr
                        115                 120                 125

Gly Ala Gln Met Val Leu Cys Met Lys Leu Ser Ser Phe Gly Trp Asn
                    130                 135                 140
```

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
            165                 170                 175

Ala Phe Val Phe Tyr Phe Pro Ser Ile Leu Thr Gly Pro Ser Tyr Asp
        180                 185                 190

Tyr Met Glu Phe His Asn Trp Leu Asp Leu Ser Leu Phe Lys Glu Leu
    195                 200                 205

Glu Lys Asp Lys Asp Pro Lys Arg Ala Ala Arg Arg Lys Arg His Lys
210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
            245                 250                 255

Tyr Ala Tyr Ser Asp Ala Phe Thr Lys Glu His Asn Ile Phe Gly Arg
        260                 265                 270

Ile Val Tyr Leu Tyr Met Leu Gly Phe Met Tyr Arg Leu Lys Tyr Tyr
    275                 280                 285

Gly Ala Trp Ser Ile Ser Glu Gly Ala Cys Ile Leu Ser Gly Leu Gly
290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
            325                 330                 335

Leu Leu Glu Ala Trp Asn Gln Asn Thr Asn Lys Trp Leu Arg Asn Tyr
        340                 345                 350

Val Tyr Leu Arg Val Val Pro Lys Gly Gln Lys Pro Gly Phe Arg Ala
    355                 360                 365

Thr Ile Phe Thr Phe Val Val Xaa Ala Phe Trp His Gly Thr Arg Pro
370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
            405                 410                 415

Lys Thr Ala Gly Pro Tyr Lys Ile Tyr Tyr Asp Ile Val Cys Trp Ile
        420                 425                 430

Val Val Gln Thr Ala Phe Gly Tyr Ala Thr Gln Ser Phe Met Ile Leu
    435                 440                 445

Asp Phe Trp Leu Ser Leu Lys Cys Trp Lys Asn Ser Trp Phe Leu Tyr
450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Gln Ala Gly Ala Val Thr Asp
            485                 490                 495

Lys Lys Asp Ala Lys Glu Glu Val Lys Lys Asp Thr Ile Lys Thr Lys
        500                 505                 510

<210> SEQ ID NO 62
<211> LENGTH: 512
<212> TYPE: PRT
<213> ORGANISM: Artificial sequence
<220> FEATURE:
<223> OTHER INFORMATION: Mutant Y1LPCAT_A377X
<220> FEATURE:
<221> NAME/KEY: MISC_FEATURE
<222> LOCATION: (377)..(377)
<223> OTHER INFORMATION: Xaa = Asn [N], Gly [G], His [H], Leu [L],
    Phe [F], Pro [P], Ser [S], Thr [T] or Val [V]

<400> SEQUENCE: 62

```
Met Ala Phe Pro Trp Ala Asp Lys Trp Ala Asp Ala Ser Ala Ser
1               5                  10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Ala Lys
        35                  40                  45

Asn Leu Lys Ile Ile Tyr Ile Ile Ser Val Ser Ile Phe Tyr Met Val
50                  55                  60

Gly Val Phe Ser Leu Tyr Gly Ala Ala Thr Leu Leu Phe Ser Ser
65              70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Lys Leu Ser Ser Phe Gly Trp Asn
130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Arg Arg Lys Arg His Lys
210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Pro Lys Gly Gln Lys Pro Gly Phe Arg Ala
        355                 360                 365

Thr Ile Phe Thr Phe Val Val Ser Xaa Phe Trp His Gly Thr Arg Pro
370                 375                 380

Gly Tyr Tyr Leu Thr Phe Val Thr Ala Ala Met Tyr Gln Ser Val Gly
```

```
                385                 390                 395                 400
Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
                420                 425                 430

Val Val Gln Thr Ala Phe Gly Tyr Ala Thr Gln Ser Phe Met Ile Leu
                435                 440                 445

Asp Phe Trp Leu Ser Leu Lys Cys Trp Lys Asn Ser Trp Phe Leu Tyr
            450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510

<210> SEQ ID NO 63
<211> LENGTH: 512
<212> TYPE: PRT
<213> ORGANISM: Artificial sequence
<220> FEATURE:
<223> OTHER INFORMATION: Mutant YlLPCAT_F378X
<220> FEATURE:
<221> NAME/KEY: MISC_FEATURE
<222> LOCATION: (378)..(378)
<223> OTHER INFORMATION: Xaa = Ala [A], Asn [N], Cys [C], Gly [G],
      His [H], Leu [L], Pro [P], Ser [S], Thr [T], Trp [W] or Tyr [Y]

<400> SEQUENCE: 63

Met Ala Phe Pro Trp Ala Asp Lys Trp Ala Asp Ala Ser Ala Ser
1               5                   10                  15

Thr Gly Leu Pro Pro Asp Leu Leu Lys Ile Ala Phe Thr Leu Val Met
                20                  25                  30

Ser Tyr Pro Leu Ser Ser Leu Met Lys Arg Leu Pro Asp Asp Ala Lys
            35                  40                  45

Asn Leu Lys Ile Ile Tyr Ile Ile Ser Val Ser Ile Phe Tyr Met Val
        50                  55                  60

Gly Val Phe Ser Leu Tyr Gly Gly Ala Ala Thr Leu Leu Phe Ser Ser
65                  70                  75                  80

Met Gly Thr Phe Ile Thr Gln Trp Lys Ser Pro Tyr Met Pro Trp
                85                  90                  95

Val Asn Phe Gly Phe Val Met Thr His Leu Phe Val Asn His Leu Arg
                100                 105                 110

Ser Gln Phe Phe Pro Glu Thr Tyr Asp Pro Asn Val Ile Asp Ile Thr
            115                 120                 125

Gly Ala Gln Met Val Leu Cys Met Lys Leu Ser Ser Phe Gly Trp Asn
        130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
                180                 185                 190

Tyr Met Glu Phe His Asn Trp Leu Asp Leu Ser Leu Phe Lys Glu Leu
            195                 200                 205

Glu Lys Asp Lys Asp Pro Lys Arg Ala Ala Arg Arg Lys Arg His Lys
        210                 215                 220
```

```
Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Xaa Trp His Gly Thr Arg Pro
370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510
```

<210> SEQ ID NO 64
<211> LENGTH: 512
<212> TYPE: PRT
<213> ORGANISM: Artificial sequence
<220> FEATURE:
<223> OTHER INFORMATION: Mutant YlLPCAT_T382X
<220> FEATURE:
<221> NAME/KEY: MISC_FEATURE
<222> LOCATION: (382)..(382)
<223> OTHER INFORMATION: Xaa = Ala [A], Asn [N], Gly [G], Gln [Q],
      His [H], Ile [I], Met [M], Pro [P], Ser [S], Trp [W] or Tyr [Y]

<400> SEQUENCE: 64

```
Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Ala Lys
        35                  40                  45
```

```
Asn Leu Lys Ile Ile Tyr Ile Ile Ser Val Ser Ile Phe Tyr Met Val
 50                  55                  60

Gly Val Phe Ser Leu Tyr Gly Ala Ala Thr Leu Leu Phe Ser Ser
 65                  70                  75                  80

Met Gly Thr Phe Phe Ile Thr Gln Trp Lys Ser Pro Tyr Met Pro Trp
                     85                  90                  95

Val Asn Phe Gly Phe Val Met Thr His Leu Phe Val Asn His Leu Arg
                    100                 105                 110

Ser Gln Phe Pro Glu Thr Tyr Asp Pro Asn Val Ile Asp Ile Thr
                115                 120                 125

Gly Ala Gln Met Val Leu Cys Met Lys Leu Ser Ser Phe Gly Trp Asn
130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
                180                 185                 190

Tyr Met Glu Phe His Asn Trp Leu Asp Leu Ser Leu Phe Lys Glu Leu
                195                 200                 205

Glu Lys Asp Lys Asp Pro Lys Arg Ala Ala Arg Arg Lys Arg His Lys
210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
                260                 265                 270

Ile Val Tyr Leu Tyr Met Leu Gly Phe Met Tyr Arg Leu Lys Tyr Tyr
                275                 280                 285

Gly Ala Trp Ser Ile Ser Glu Gly Ala Cys Ile Leu Ser Gly Leu Gly
                290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
                340                 345                 350

Val Tyr Leu Arg Val Val Pro Lys Gly Gln Lys Pro Gly Phe Arg Ala
                355                 360                 365

Thr Ile Phe Thr Phe Val Val Ser Ala Phe Trp His Gly Xaa Arg Pro
370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
                420                 425                 430

Val Val Gln Thr Ala Phe Gly Tyr Ala Thr Gln Ser Phe Met Ile Leu
                435                 440                 445

Asp Phe Trp Leu Ser Leu Lys Cys Trp Lys Asn Ser Trp Phe Leu Tyr
450                 455                 460

His Ile Ala Leu Gly Ala Ile Phe Ala Ile Ser Ser Pro Tyr Lys Ala
```

```
                465                 470                 475                 480
Trp Ala Ile Pro Lys Ile Lys Lys Gln Ala Gly Ala Val Thr Asp
            485                 490                 495
Lys Lys Asp Ala Lys Glu Glu Val Lys Lys Asp Thr Ile Lys Thr Lys
        500                 505                 510

<210> SEQ ID NO 65
<211> LENGTH: 512
<212> TYPE: PRT
<213> ORGANISM: Artificial sequence
<220> FEATURE:
<223> OTHER INFORMATION: Mutant YlLPCAT_R383X
<220> FEATURE:
<221> NAME/KEY: MISC_FEATURE
<222> LOCATION: (383)..(383)
<223> OTHER INFORMATION: Xaa = Ala [A], Asn [N], Asp [D], Gly [G],
      Glu [E], Gln [Q], His [H], Ile [I], Leu [L], Lys [K], Met [M],
      Phe [F], Pro [P], Thr [T], Trp [W] or Val [V]

<400> SEQUENCE: 65

Met Ala Phe Pro Trp Ala Asp Lys Trp Ala Ala Asp Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Ala Ala Thr Leu Leu Phe Ser Ser
65              70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Lys Leu Ser Ser Phe Gly Trp Asn
    130                 135                 140

Val Tyr Asp Gly Trp Gln Ile Glu Lys Gly Glu Gln Leu Ser Glu Phe
145             150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225             230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
```

```
                290                 295                 300
Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
                340                 345                 350

Val Tyr Leu Arg Val Val Pro Lys Gly Gln Lys Pro Gly Phe Arg Ala
                355                 360                 365

Thr Ile Phe Thr Phe Val Val Ser Ala Phe Trp His Gly Thr Xaa Pro
370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
                420                 425                 430

Val Val Gln Thr Ala Phe Gly Tyr Ala Thr Gln Ser Phe Met Ile Leu
                435                 440                 445

Asp Phe Trp Leu Ser Leu Lys Cys Trp Lys Asn Ser Trp Phe Leu Tyr
                450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Gln Ala Gly Ala Val Thr Asp
                485                 490                 495

Lys Lys Asp Ala Lys Glu Val Lys Lys Asp Thr Ile Lys Thr Lys
                500                 505                 510

<210> SEQ ID NO 66
<211> LENGTH: 512
<212> TYPE: PRT
<213> ORGANISM: Artificial sequence
<220> FEATURE:
<223> OTHER INFORMATION: Mutant YlLPCAT_P384X
<220> FEATURE:
<221> NAME/KEY: MISC_FEATURE
<222> LOCATION: (384)..(384)
<223> OTHER INFORMATION: Xaa = Ala [A], Arg [R], Gly [G], His [H],
      Ile [I], Leu [L], Lys [K], Met [M], Phe [F], Ser [S], Thr [T],
      Trp [W], Tyr [Y] or Val [V]

<400> SEQUENCE: 66

Met Ala Phe Pro Trp Ala Asp Lys Trp Ala Asp Ala Ser Ala Ser
1                   5                  10                  15

Thr Gly Leu Pro Pro Asp Leu Leu Lys Ile Ala Phe Thr Leu Val Met
                20                  25                  30

Ser Tyr Pro Leu Ser Ser Leu Met Lys Arg Leu Pro Asp Asp Ala Lys
                35                  40                  45

Asn Leu Lys Ile Ile Tyr Ile Ile Ser Val Ser Ile Phe Tyr Met Val
                50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
                100                 105                 110

Ser Gln Phe Phe Pro Glu Thr Tyr Asp Pro Asn Val Ile Asp Ile Thr
```

```
                    115                 120                 125
        Gly Ala Gln Met Val Leu Cys Met Lys Leu Ser Ser Phe Gly Trp Asn
        130                 135                 140

Val Tyr Asp Gly Trp Gln Ile Glu Lys Gly Glu Gln Leu Ser Glu Phe
    145                 150                 155                 160

Gln Thr Lys Arg Ala Val Leu Lys His Pro Ser Leu Met Asp Phe Leu
                        165                 170                 175

Ala Phe Val Phe Tyr Phe Pro Ser Ile Leu Thr Gly Pro Ser Tyr Asp
                        180                 185                 190

Tyr Met Glu Phe His Asn Trp Leu Asp Leu Ser Leu Phe Lys Glu Leu
                        195                 200                 205

Glu Lys Asp Lys Asp Pro Lys Arg Ala Ala Arg Arg Lys Arg His Lys
                    210                 215                 220

Ile Pro Arg Ser Gly Ile Ala Ala Ser Lys Lys Leu Ala Ala Gly Ile
    225                 230                 235                 240

Phe Trp Ile Val Leu Trp Thr Gln Val Asp Ser Arg Ile Ser Thr Ala
                        245                 250                 255

Tyr Ala Tyr Ser Asp Ala Phe Thr Lys Glu His Asn Ile Phe Gly Arg
                        260                 265                 270

Ile Val Tyr Leu Tyr Met Leu Gly Phe Met Tyr Arg Leu Lys Tyr Tyr
                        275                 280                 285

Gly Ala Trp Ser Ile Ser Glu Gly Ala Cys Ile Leu Ser Gly Leu Gly
                    290                 295                 300

Phe His Gly Val Asp Pro Lys Thr Gly Lys Tyr Lys Trp Asp Arg Val
    305                 310                 315                 320

Gln Asn Val Asp Pro Trp Gly Phe Glu Thr Gly Gln Asn Thr Lys Ala
                        325                 330                 335

Leu Leu Glu Ala Trp Asn Gln Asn Thr Asn Lys Trp Leu Arg Asn Tyr
                        340                 345                 350

Val Tyr Leu Arg Val Val Pro Lys Gly Gln Lys Pro Gly Phe Arg Ala
                        355                 360                 365

Thr Ile Phe Thr Phe Val Val Ser Ala Phe Trp His Gly Thr Arg Xaa
                    370                 375                 380

Gly Tyr Tyr Leu Thr Phe Val Thr Ala Ala Met Tyr Gln Ser Val Gly
    385                 390                 395                 400

Lys Phe Phe Arg Arg Tyr Leu Arg Pro Phe Phe Met Glu Ser Asp Gly
                        405                 410                 415

Lys Thr Ala Gly Pro Tyr Lys Ile Tyr Tyr Asp Ile Val Cys Trp Ile
                        420                 425                 430

Val Val Gln Thr Ala Phe Gly Tyr Ala Thr Gln Ser Phe Met Ile Leu
                        435                 440                 445

Asp Phe Trp Leu Ser Leu Lys Cys Trp Lys Asn Ser Trp Phe Leu Tyr
                    450                 455                 460

His Ile Ala Leu Gly Ala Ile Phe Ala Ile Ser Ser Pro Tyr Lys Ala
    465                 470                 475                 480

Trp Ala Ile Pro Lys Ile Lys Lys Gln Ala Gly Ala Val Thr Asp
                        485                 490                 495

Lys Lys Asp Ala Lys Glu Glu Val Lys Lys Asp Thr Ile Lys Thr Lys
                    500                 505                 510

<210> SEQ ID NO 67
<211> LENGTH: 512
<212> TYPE: PRT
<213> ORGANISM: Artificial sequence
```

<220> FEATURE:
<223> OTHER INFORMATION: Mutant YlLPCAT_G385X
<220> FEATURE:
<221> NAME/KEY: MISC_FEATURE
<222> LOCATION: (385)..(385)
<223> OTHER INFORMATION: Xaa = Ala [A], Asn [N], Cys [C], Gly [G],
      His [H], Ile [I], Leu [L], Lys [K], Met [M], Phe [F], Ser [S],
      Thr [T], Trp [W], Tyr [Y] or Val [V]

<400> SEQUENCE: 67

```
Met Ala Phe Pro Trp Ala Asp Lys Trp Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Lys Leu Ser Ser Phe Gly Trp Asn
130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
210                 215                 220

Ile Pro Arg Ser Gly Ile Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365
```

```
Thr Ile Phe Thr Phe Val Val Ser Ala Phe Trp His Gly Thr Arg Pro
            370                 375                 380

Xaa Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
                420                 425                 430

Val Val Gln Thr Ala Phe Gly Tyr Ala Thr Gln Ser Phe Met Ile Leu
                435                 440                 445

Asp Phe Trp Leu Ser Leu Lys Cys Trp Lys Asn Ser Trp Phe Leu Tyr
        450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Gln Ala Gly Ala Val Thr Asp
                485                 490                 495

Lys Lys Asp Ala Lys Glu Glu Val Lys Asp Thr Ile Lys Thr Lys
                500                 505                 510
```

<210> SEQ ID NO 68
<211> LENGTH: 512
<212> TYPE: PRT
<213> ORGANISM: Artificial sequence
<220> FEATURE:
<223> OTHER INFORMATION: Mutant YlLPCAT_Y386X
<220> FEATURE:
<221> NAME/KEY: MISC_FEATURE
<222> LOCATION: (386)..(386)
<223> OTHER INFORMATION: Xaa = Ala [A], Gly [G], His [H], Leu [L],
      Phe [F], Pro [P], Ser [S], Thr [T] or Val [V]

<400> SEQUENCE: 68

```
Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
                20                  25                  30

Ser Tyr Pro Leu Ser Ser Leu Met Lys Arg Leu Pro Asp Asp Ala Lys
            35                  40                  45

Asn Leu Lys Ile Ile Tyr Ile Ile Ser Val Ser Ile Phe Tyr Met Val
        50                  55                  60

Gly Val Phe Ser Leu Tyr Gly Gly Ala Ala Thr Leu Leu Phe Ser Ser
65              70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
                100                 105                 110

Ser Gln Phe Phe Pro Glu Thr Tyr Asp Pro Asn Val Ile Asp Ile Thr
            115                 120                 125

Gly Ala Gln Met Val Leu Cys Met Lys Leu Ser Ser Phe Gly Trp Asn
        130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Pro Ser Ile Leu Thr Gly Pro Ser Tyr Asp
            180                 185                 190
```

Tyr Met Glu Phe His Asn Trp Leu Asp Leu Ser Leu Phe Lys Glu Leu
         195                 200                 205

Glu Lys Asp Lys Asp Pro Lys Arg Ala Ala Arg Lys Arg His Lys
210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
370                 375                 380

Gly Xaa Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510

<210> SEQ ID NO 69
<211> LENGTH: 512
<212> TYPE: PRT
<213> ORGANISM: Artificial sequence
<220> FEATURE:
<223> OTHER INFORMATION: Mutant Y1LPCAT_Y387X
<220> FEATURE:
<221> NAME/KEY: MISC_FEATURE
<222> LOCATION: (387)..(387)
<220> FEATURE:
<221> NAME/KEY: MISC_FEATURE
<222> LOCATION: (387)..(387)
<223> OTHER INFORMATION: Xaa = Ala [A], Gly [G], His [H], Leu [L],
      Phe [F], Pro [P], Ser [S], Thr [T], Trp [W] or Val [V]

<400> SEQUENCE: 69

Met Ala Phe Pro Trp Ala Asp Lys Trp Ala Ala Asp Ala Ser Ala Ser

```
1               5                   10                  15
Thr Gly Leu Pro Pro Asp Leu Leu Lys Ile Ala Phe Thr Leu Val Met
                20                  25                  30

Ser Tyr Pro Leu Ser Ser Leu Met Lys Arg Leu Pro Asp Asp Ala Lys
                35                  40                  45

Asn Leu Lys Ile Ile Tyr Ile Ile Ser Val Ser Ile Phe Tyr Met Val
50                      55                  60

Gly Val Phe Ser Leu Tyr Gly Ala Ala Thr Leu Leu Phe Ser Ser
65                  70                  75                  80

Met Gly Thr Phe Phe Ile Thr Gln Trp Lys Ser Pro Tyr Met Pro Trp
                    85                  90                  95

Val Asn Phe Gly Phe Val Met Thr His Leu Phe Val Asn His Leu Arg
                100                 105                 110

Ser Gln Phe Phe Pro Glu Thr Tyr Asp Pro Asn Val Ile Asp Ile Thr
                115                 120                 125

Gly Ala Gln Met Val Leu Cys Met Lys Leu Ser Ser Phe Gly Trp Asn
            130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                    165                 170                 175

Ala Phe Val Phe Tyr Phe Pro Ser Ile Leu Thr Gly Pro Ser Tyr Asp
                180                 185                 190

Tyr Met Glu Phe His Asn Trp Leu Asp Leu Ser Leu Phe Lys Glu Leu
                195                 200                 205

Glu Lys Asp Lys Asp Pro Lys Arg Ala Ala Arg Lys Arg His Lys
210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                    245                 250                 255

Tyr Ala Tyr Ser Asp Ala Phe Thr Lys Glu His Asn Ile Phe Gly Arg
                260                 265                 270

Ile Val Tyr Leu Tyr Met Leu Gly Phe Met Tyr Arg Leu Lys Tyr Tyr
                275                 280                 285

Gly Ala Trp Ser Ile Ser Glu Gly Ala Cys Ile Leu Ser Gly Leu Gly
                290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                    325                 330                 335

Leu Leu Glu Ala Trp Asn Gln Asn Thr Asn Lys Trp Leu Arg Asn Tyr
                340                 345                 350

Val Tyr Leu Arg Val Val Pro Lys Gly Gln Lys Pro Gly Phe Arg Ala
                355                 360                 365

Thr Ile Phe Thr Phe Val Val Ser Ala Phe Trp His Gly Thr Arg Pro
370                 375                 380

Gly Tyr Xaa Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                    405                 410                 415

Lys Thr Ala Gly Pro Tyr Lys Ile Tyr Tyr Asp Ile Val Cys Trp Ile
                420                 425                 430
```

```
Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Gln Ala Gly Ala Val Thr Asp
                485                 490                 495

Lys Lys Asp Ala Lys Glu Glu Val Lys Lys Asp Thr Ile Lys Thr Lys
                500                 505                 510
```

<210> SEQ ID NO 70
<211> LENGTH: 512
<212> TYPE: PRT
<213> ORGANISM: Artificial sequence
<220> FEATURE:
<223> OTHER INFORMATION: Mutant YlLPCAT_L388X
<220> FEATURE:
<221> NAME/KEY: MISC_FEATURE
<222> LOCATION: (388)..(388)
<223> OTHER INFORMATION: Xaa = Ala [A], Gly [G], His [H], Pro [P],
      Ser [S], Thr [T], Trp [W], Tyr [Y] or Val [V]

<400> SEQUENCE: 70

```
Met Ala Phe Pro Trp Ala Asp Lys Trp Ala Asp Ala Ser Ala Ser
1               5                   10                  15

Thr Gly Leu Pro Pro Asp Leu Leu Lys Ile Ala Phe Thr Leu Val Met
                20                  25                  30

Ser Tyr Pro Leu Ser Ser Leu Met Lys Arg Leu Pro Asp Asp Ala Lys
                35                  40                  45

Asn Leu Lys Ile Ile Tyr Ile Ile Ser Val Ser Ile Phe Tyr Met Val
50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
                100                 105                 110

Ser Gln Phe Phe Pro Glu Thr Tyr Asp Pro Asn Val Ile Asp Ile Thr
                115                 120                 125

Gly Ala Gln Met Val Leu Cys Met Lys Leu Ser Ser Phe Gly Trp Asn
            130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
                180                 185                 190

Tyr Met Glu Phe His Asn Trp Leu Asp Leu Ser Leu Phe Lys Glu Leu
                195                 200                 205

Glu Lys Asp Lys Asp Pro Lys Arg Ala Ala Arg Arg Lys Arg His Lys
            210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255
```

```
Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
    370                 375                 380

Gly Tyr Tyr Xaa Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510
```

<210> SEQ ID NO 71
<211> LENGTH: 512
<212> TYPE: PRT
<213> ORGANISM: Artificial sequence
<220> FEATURE:
<223> OTHER INFORMATION: Mutant Y1LPCAT_T389X
<220> FEATURE:
<221> NAME/KEY: MISC_FEATURE
<222> LOCATION: (389)..(389)
<223> OTHER INFORMATION: Xaa = Ala [A], Cys [C], Gly [G], His [H], Ile [I], Leu [L], Met [M], Phe [F], Pro [P], Ser [S], Trp [W], Tyr [Y] or Val [V]

<400> SEQUENCE: 71

```
Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80
```

```
Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
            115                 120                 125

Gly Ala Gln Met Val Leu Cys Met Lys Leu Ser Ser Phe Gly Trp Asn
            130                 135                 140

Val Tyr Asp Gly Trp Gln Ile Glu Lys Gly Gln Leu Ser Glu Phe
145                 150                 155                 160

Gln Thr Lys Arg Ala Val Leu Lys His Pro Ser Leu Met Asp Phe Leu
            165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
            195                 200                 205

Glu Lys Asp Lys Asp Pro Lys Arg Ala Ala Arg Lys Arg His Lys
            210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
            245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
            275                 280                 285

Gly Ala Trp Ser Ile Ser Glu Gly Ala Cys Ile Leu Ser Gly Leu Gly
            290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
            325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
            355                 360                 365

Thr Ile Phe Thr Phe Val Val Ser Ala Phe Trp His Gly Thr Arg Pro
            370                 375                 380

Gly Tyr Tyr Leu Xaa Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
            405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
            435                 440                 445

Asp Phe Trp Leu Ser Leu Lys Cys Trp Lys Asn Ser Trp Phe Leu Tyr
            450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Gln Ala Gly Ala Val Thr Asp
            485                 490                 495

Lys Lys Asp Ala Lys Glu Glu Val Lys Lys Asp Thr Ile Lys Thr Lys
```

-continued

```
                500                 505                 510
```

<210> SEQ ID NO 72
<211> LENGTH: 512
<212> TYPE: PRT
<213> ORGANISM: Artificial sequence
<220> FEATURE:
<223> OTHER INFORMATION: Mutant YlLPCAT_F390X
<220> FEATURE:
<221> NAME/KEY: MISC_FEATURE
<222> LOCATION: (390)..(390)
<223> OTHER INFORMATION: Ala [A], Asn [N], Cys [C], Gly [G], His [H],
      Leu [L], Met [M], Pro [P], Ser [S], Thr [T] or Val [V]

<400> SEQUENCE: 72

```
Met Ala Phe Pro Trp Ala Asp Lys Trp Ala Asp Ala Ser Ala Ser
 1               5                  10                  15

Thr Gly Leu Pro Pro Asp Leu Leu Lys Ile Ala Phe Thr Leu Val Met
                20                  25                  30

Ser Tyr Pro Leu Ser Ser Leu Met Lys Arg Leu Pro Asp Asp Ala Lys
            35                  40                  45

Asn Leu Lys Ile Ile Tyr Ile Ile Ser Val Ser Ile Phe Tyr Met Val
 50                  55                  60

Gly Val Phe Ser Leu Tyr Gly Gly Ala Ala Thr Leu Leu Phe Ser Ser
 65                  70                  75                  80

Met Gly Thr Phe Ile Thr Gln Trp Lys Ser Pro Tyr Met Pro Trp
                85                  90                  95

Val Asn Phe Gly Phe Val Met Thr His Leu Phe Val Asn His Leu Arg
                100                 105                 110

Ser Gln Phe Phe Pro Glu Thr Tyr Asp Pro Asn Val Ile Asp Ile Thr
            115                 120                 125

Gly Ala Gln Met Val Leu Cys Met Lys Leu Ser Ser Phe Gly Trp Asn
130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335
```

```
Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
    370                 375                 380

Gly Tyr Tyr Leu Thr Xaa Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Gln Ala Gly Ala Val Thr Asp
                485                 490                 495

Lys Lys Asp Ala Lys Glu Glu Val Lys Lys Asp Thr Ile Lys Thr Lys
                500                 505                 510
```

<210> SEQ ID NO 73
<211> LENGTH: 512
<212> TYPE: PRT
<213> ORGANISM: Artificial sequence
<220> FEATURE:
<223> OTHER INFORMATION: Mutant YlLPCAT protein generic
<220> FEATURE:
<221> NAME/KEY: MISC_FEATURE
<222> LOCATION: (133)..(133)
<223> OTHER INFORMATION: Xaa = Val [V] or Cys [C]
<220> FEATURE:
<221> NAME/KEY: MISC_FEATURE
<222> LOCATION: (134)..(134)
<223> OTHER INFORMATION: Xaa = Leu [L] or Ala [A] or Cys [C] or Gly [G]
<220> FEATURE:
<221> NAME/KEY: MISC_FEATURE
<222> LOCATION: (135)..(135)
<223> OTHER INFORMATION: Xaa = Cys [C] or Asp [D] or Ile [I] or Phe [F]
<220> FEATURE:
<221> NAME/KEY: MISC_FEATURE
<222> LOCATION: (136)..(136)
<223> OTHER INFORMATION: Xaa = Met [M] or Gly [G] or Pro [P] or Ser [S]
      or Val [V] or Asn [N] or Thr [T]
<220> FEATURE:
<221> NAME/KEY: MISC_FEATURE
<222> LOCATION: (137)..(137)
<223> OTHER INFORMATION: Xaa = Lys [K] or Asn [N] or Gly [G] or His [H]
      or Tyr [Y]
<220> FEATURE:
<221> NAME/KEY: MISC_FEATURE
<222> LOCATION: (138)..(138)
<223> OTHER INFORMATION: Xaa = Leu [L] or Ala [A] or His [H] or Met [M]
      or Gly [G] or Ile [I] or Asn [N]
<220> FEATURE:
<221> NAME/KEY: MISC_FEATURE
<222> LOCATION: (139)..(139)
<223> OTHER INFORMATION: Xaa = Ser [S] or Leu [L] or Trp [W] or Gly [G]
      or Asn [N]
<220> FEATURE:
<221> NAME/KEY: MISC_FEATURE
<222> LOCATION: (140)..(140)
<223> OTHER INFORMATION: Xaa = Ser [S] or Asn [N] or His [H] or Pro [P]
      or Trp [W] or Tyr [Y] or Ile [I]
<220> FEATURE:

```
<221> NAME/KEY: MISC_FEATURE
<222> LOCATION: (141)..(141)
<223> OTHER INFORMATION: Xaa = Phe [F] or Ala [A] or Met [M] or Trp [W]
      or Val [V]
<220> FEATURE:
<221> NAME/KEY: MISC_FEATURE
<222> LOCATION: (142)..(142)
<223> OTHER INFORMATION: Xaa = Gly [G] or His [H] or Ile [I] or Val [V]
<220> FEATURE:
<221> NAME/KEY: MISC_FEATURE
<222> LOCATION: (143)..(143)
<223> OTHER INFORMATION: Xaa = Trp [W] or Leu [L] or His [H]
<220> FEATURE:
<221> NAME/KEY: MISC_FEATURE
<222> LOCATION: (144)..(144)
<223> OTHER INFORMATION: Xaa = Asn [N] or Ala [A] or Lys [K] or Phe [F]
      or Thr [T] or Val [V]
<220> FEATURE:
<221> NAME/KEY: MISC_FEATURE
<222> LOCATION: (145)..(145)
<223> OTHER INFORMATION: Xaa = Val [V] or Ala [A] or Gly [G] or Glu [E]
      or Met [M] or Phe [F] or Trp [W]
<220> FEATURE:
<221> NAME/KEY: MISC_FEATURE
<222> LOCATION: (146)..(146)
<223> OTHER INFORMATION: Xaa = Tyr (Y) or Gly [G] or Leu [L] or Met [M]
<220> FEATURE:
<221> NAME/KEY: MISC_FEATURE
<222> LOCATION: (147)..(147)
<223> OTHER INFORMATION: Xaa = Asp [D] or Asn [N] or Gln [Q] or His [H]
      or Glu [E]
<220> FEATURE:
<221> NAME/KEY: MISC_FEATURE
<222> LOCATION: (148)..(148)
<223> OTHER INFORMATION: Xaa = Gly [G] or Ala [A] or Asn [N] or Val [V]
<220> FEATURE:
<221> NAME/KEY: MISC_FEATURE
<222> LOCATION: (378)..(378)
<223> OTHER INFORMATION: Xaa = Phe [F] or Tyr [Y]
<220> FEATURE:
<221> NAME/KEY: MISC_FEATURE
<222> LOCATION: (382)..(382)
<223> OTHER INFORMATION: Xaa = Thr [T] or Ile [I] or Pro [P] or Tyr [Y]
<220> FEATURE:
<221> NAME/KEY: MISC_FEATURE
<222> LOCATION: (383)..(383)
<223> OTHER INFORMATION: Xaa = Arg [R] or Ala [A] or Met [M]
<220> FEATURE:
<221> NAME/KEY: MISC_FEATURE
<222> LOCATION: (388)..(388)
<223> OTHER INFORMATION: Xaa = Leu [L] or Gly [G] or Tyr [Y] or His [H]
      or Thr [T]
<220> FEATURE:
<221> NAME/KEY: MISC_FEATURE
<222> LOCATION: (389)..(389)
<223> OTHER INFORMATION: Xaa = Thr [T] or Ala [A] or Cys [C] or Ser [S]
<220> FEATURE:
<221> NAME/KEY: MISC_FEATURE
<222> LOCATION: (390)..(390)
<223> OTHER INFORMATION: Xaa = Phe [F] or Cys [C] or Gly [G] or Asn [N]
      or Ser [S] or Thr [T]

<400> SEQUENCE: 73

Met Ala Phe Pro Trp Ala Asp Lys Trp Ala Asp Ala Ser Ala Ser
1               5                   10                  15

Thr Gly Leu Pro Pro Asp Leu Leu Lys Ile Ala Phe Thr Leu Val Met
                20                  25                  30

Ser Tyr Pro Leu Ser Ser Leu Met Lys Arg Leu Pro Asp Asp Ala Lys
            35                  40                  45

Asn Leu Lys Ile Ile Tyr Ile Ile Ser Val Ser Ile Phe Tyr Met Val
        50                  55                  60

Gly Val Phe Ser Leu Tyr Gly Gly Ala Ala Thr Leu Leu Phe Ser Ser
65                  70                  75                  80
```

```
Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Xaa Xaa Xaa Xaa Xaa Xaa Xaa Xaa Xaa Xaa Xaa Xaa
130                 135                 140

Xaa Xaa Xaa Xaa Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Xaa Trp His Gly Xaa Xaa Pro
370                 375                 380

Gly Tyr Tyr Xaa Xaa Xaa Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Gln Ala Gly Ala Val Thr Asp
                485                 490                 495

Lys Lys Asp Ala Lys Glu Glu Val Lys Lys Asp Thr Ile Lys Thr Lys
```

-continued

<210> SEQ ID NO 74
<211> LENGTH: 512
<212> TYPE: PRT
<213> ORGANISM: Artificial sequence
<220> FEATURE:
<223> OTHER INFORMATION: Mutant YlLPCAT protein double generic
<220> FEATURE:
<221> NAME/KEY: MISC_FEATURE
<222> LOCATION: (134)..(134)
<223> OTHER INFORMATION: Xaa = Leu [L] or Ala [A] or Gly [G]
<220> FEATURE:
<221> NAME/KEY: MISC_FEATURE
<222> LOCATION: (136)..(136)
<223> OTHER INFORMATION: Xaa = Met [M] or Ser [S] or Val [V]
<220> FEATURE:
<221> NAME/KEY: MISC_FEATURE
<222> LOCATION: (137)..(137)
<223> OTHER INFORMATION: Xaa = Lys [K] or Asn [N] or His [H]
<220> FEATURE:
<221> NAME/KEY: MISC_FEATURE
<222> LOCATION: (140)..(140)
<223> OTHER INFORMATION: Xaa = Ser [S] or His [H] or Trp [W]
<220> FEATURE:
<221> NAME/KEY: MISC_FEATURE
<222> LOCATION: (141)..(141)
<223> OTHER INFORMATION: Xaa = Phe [F] or Met [M] or Trp [W]
<220> FEATURE:
<221> NAME/KEY: MISC_FEATURE
<222> LOCATION: (144)..(144)
<223> OTHER INFORMATION: Xaa = Asn [N] or Ala [A] or Thr [T]
<220> FEATURE:
<221> NAME/KEY: MISC_FEATURE
<222> LOCATION: (145)..(145)
<223> OTHER INFORMATION: Xaa = Val [V] or Met [M] or Trp [W]
<220> FEATURE:
<221> NAME/KEY: MISC_FEATURE
<222> LOCATION: (147)..(147)
<223> OTHER INFORMATION: Xaa = Asp [D] or Gln [Q] or His [H]
<220> FEATURE:
<221> NAME/KEY: MISC_FEATURE
<222> LOCATION: (148)..(148)
<223> OTHER INFORMATION: Xaa = Gly [G] or Ala [A] or Asn [N]
<220> FEATURE:
<221> NAME/KEY: MISC_FEATURE
<222> LOCATION: (378)..(378)
<223> OTHER INFORMATION: Xaa = Phe [F] or Tyr [Y]
<220> FEATURE:
<221> NAME/KEY: MISC_FEATURE
<222> LOCATION: (382)..(382)
<223> OTHER INFORMATION: Xaa = Thr [T] or Ile [I] or Pro [P] or Tyr [Y]
<220> FEATURE:
<221> NAME/KEY: MISC_FEATURE
<222> LOCATION: (383)..(383)
<223> OTHER INFORMATION: Xaa = Arg [R] or Met [M]
<220> FEATURE:
<221> NAME/KEY: MISC_FEATURE
<222> LOCATION: (384)..(384)
<223> OTHER INFORMATION: Xaa = Pro [P] or Ala [A] or Gly [G]
<220> FEATURE:
<221> NAME/KEY: MISC_FEATURE
<222> LOCATION: (388)..(388)
<223> OTHER INFORMATION: Xaa = Leu [L] or Gly [G] or Tyr [Y] or Thr [T]
<220> FEATURE:
<221> NAME/KEY: MISC_FEATURE
<222> LOCATION: (389)..(389)
<223> OTHER INFORMATION: Xaa = Thr [T] or Ala [A] or Cys [C] or Ser [S]
<220> FEATURE:
<221> NAME/KEY: MISC_FEATURE
<222> LOCATION: (390)..(390)
<223> OTHER INFORMATION: Xaa = Phe [F] or Gly [G] or Ser [S] or Thr [T]

<400> SEQUENCE: 74

Met Ala Phe Pro Trp Ala Asp Lys Trp Ala Asp Ala Ser Ala Ser
1               5                   10                  15

```
Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
            35                  40                  45

Asn Leu Lys Ile Ile Tyr Ile Ile Ser Val Ser Ile Phe Tyr Met Val
 50                  55                  60

Gly Val Phe Ser Leu Tyr Gly Ala Ala Thr Leu Leu Phe Ser Ser
 65                  70                  75                  80

Met Gly Thr Phe Phe Ile Thr Gln Trp Lys Ser Pro Tyr Met Pro Trp
                 85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
            115                 120                 125

Gly Ala Gln Met Val Xaa Cys Xaa Xaa Leu Ser Xaa Xaa Gly Trp Xaa
130                 135                 140

Xaa Tyr Xaa Xaa Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
            195                 200                 205

Glu Lys Asp Lys Asp Pro Lys Arg Ala Arg Arg Lys Arg His Lys
210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
            275                 280                 285

Gly Ala Trp Ser Ile Ser Glu Gly Ala Cys Ile Leu Ser Gly Leu Gly
290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
            355                 360                 365

Thr Ile Phe Thr Phe Val Val Ser Ala Xaa Trp His Gly Xaa Xaa Xaa
            370                 375                 380

Gly Tyr Tyr Xaa Xaa Xaa Val Thr Ala Ala Met Tyr Gln Ser Val Gly
385                 390                 395                 400

Lys Phe Phe Arg Arg Tyr Leu Arg Pro Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
```

```
            435                 440                 445
Asp Phe Trp Leu Ser Leu Lys Cys Trp Lys Asn Ser Trp Phe Leu Tyr
450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Gln Ala Gly Ala Val Thr Asp
                    485                 490                 495

Lys Lys Asp Ala Lys Glu Glu Val Lys Lys Asp Thr Ile Lys Thr Lys
                500                 505                 510

<210> SEQ ID NO 75
<211> LENGTH: 512
<212> TYPE: PRT
<213> ORGANISM: Artificial sequence
<220> FEATURE:
<223> OTHER INFORMATION: Y. lipolytica LPCAT containing M136S and T389C
      mutations

<400> SEQUENCE: 75

Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
                20                  25                  30

Ser Tyr Pro Leu Ser Ser Leu Met Lys Arg Leu Pro Asp Asp Ala Lys
            35                  40                  45

Asn Leu Lys Ile Ile Tyr Ile Ile Ser Val Ser Ile Phe Tyr Met Val
        50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Ser Lys Leu Ser Ser Phe Gly Trp Asn
    130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285
```

-continued

```
Gly Ala Trp Ser Ile Ser Glu Gly Ala Cys Ile Leu Ser Gly Leu Gly
        290                 295                 300
Phe His Gly Val Asp Pro Lys Thr Gly Lys Tyr Lys Trp Asp Arg Val
305                 310                 315                 320
Gln Asn Val Asp Pro Trp Gly Phe Glu Thr Gly Gln Asn Thr Lys Ala
                325                 330                 335
Leu Leu Glu Ala Trp Asn Gln Asn Thr Asn Lys Trp Leu Arg Asn Tyr
            340                 345                 350
Val Tyr Leu Arg Val Val Pro Lys Gly Gln Lys Pro Gly Phe Arg Ala
        355                 360                 365
Thr Ile Phe Thr Phe Val Val Ser Ala Phe Trp His Gly Thr Arg Pro
    370                 375                 380
Gly Tyr Tyr Leu Cys Phe Val Thr Ala Ala Met Tyr Gln Ser Val Gly
385                 390                 395                 400
Lys Phe Phe Arg Arg Tyr Leu Arg Pro Phe Phe Met Glu Ser Asp Gly
                405                 410                 415
Lys Thr Ala Gly Pro Tyr Lys Ile Tyr Tyr Asp Ile Val Cys Trp Ile
            420                 425                 430
Val Val Gln Thr Ala Phe Gly Tyr Ala Thr Gln Ser Phe Met Ile Leu
        435                 440                 445
Asp Phe Trp Leu Ser Leu Lys Cys Trp Lys Asn Ser Trp Phe Leu Tyr
    450                 455                 460
His Ile Ala Leu Gly Ala Ile Phe Ala Ile Ser Ser Pro Tyr Lys Ala
465                 470                 475                 480
Trp Ala Ile Pro Lys Ile Lys Lys Gln Ala Gly Ala Val Thr Asp
                485                 490                 495
Lys Lys Asp Ala Lys Glu Glu Val Lys Lys Asp Thr Ile Lys Thr Lys
            500                 505                 510

<210> SEQ ID NO 76
<211> LENGTH: 512
<212> TYPE: PRT
<213> ORGANISM: Artificial sequence
<220> FEATURE:
<223> OTHER INFORMATION: Y. lipolytica LPCAT containing M136S and T389S
      mutations

<400> SEQUENCE: 76

Met Ala Phe Pro Trp Ala Asp Lys Trp Ala Ala Asp Ala Ser Ala Ser
1               5                   10                  15
Thr Gly Leu Pro Pro Asp Leu Leu Lys Ile Ala Phe Thr Leu Val Met
            20                  25                  30
Ser Tyr Pro Leu Ser Ser Leu Met Lys Arg Leu Pro Asp Asp Ala Lys
        35                  40                  45
Asn Leu Lys Ile Ile Tyr Ile Ile Ser Val Ser Ile Phe Tyr Met Val
    50                  55                  60
Gly Val Phe Ser Leu Tyr Gly Ala Ala Thr Leu Leu Phe Ser Ser
65                  70                  75                  80
Met Gly Thr Phe Phe Ile Thr Gln Trp Lys Ser Pro Tyr Met Pro Trp
                85                  90                  95
Val Asn Phe Gly Phe Val Met Thr His Leu Val Asn His Leu Arg
                100                 105                 110
Ser Gln Phe Phe Pro Glu Thr Tyr Asp Pro Asn Val Ile Asp Ile Thr
        115                 120                 125
Gly Ala Gln Met Val Leu Cys Ser Lys Leu Ser Ser Phe Gly Trp Asn
    130                 135                 140
```

```
Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
370                 375                 380

Gly Tyr Tyr Leu Ser Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510

<210> SEQ ID NO 77
<211> LENGTH: 512
<212> TYPE: PRT
<213> ORGANISM: Artificial sequence
<220> FEATURE:
<223> OTHER INFORMATION: Y. lipolytica LPCAT containing M136V and T389C
      mutations
```

<400> SEQUENCE: 77

Met Ala Phe Pro Trp Ala Asp Lys Trp Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Val Lys Leu Ser Ser Phe Gly Trp Asn
130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Arg Arg Lys Arg His Lys
210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
370                 375                 380

Gly Tyr Tyr Leu Cys Phe Val Thr Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

```
Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
            435                 440                 445

Asp Phe Trp Leu Ser Leu Lys Cys Trp Lys Asn Ser Trp Phe Leu Tyr
450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Gln Ala Gly Ala Val Thr Asp
            485                 490                 495

Lys Lys Asp Ala Lys Glu Glu Val Lys Lys Asp Thr Ile Lys Thr Lys
500                 505                 510
```

<210> SEQ ID NO 78
<211> LENGTH: 512
<212> TYPE: PRT
<213> ORGANISM: Artificial sequence
<220> FEATURE:
<223> OTHER INFORMATION: Y. lipolytica LPCAT containing N144A and F390S
      mutations

<400> SEQUENCE: 78

```
Met Ala Phe Pro Trp Ala Asp Lys Trp Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
            35                  40                  45

Asn Leu Lys Ile Ile Tyr Ile Ile Ser Val Ser Ile Phe Tyr Met Val
        50                  55                  60

Gly Val Phe Ser Leu Tyr Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Lys Leu Ser Ser Phe Gly Trp Ala
    130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
```

```
                  260                 265                 270
Ile Val Tyr Leu Tyr Met Leu Gly Phe Met Tyr Arg Leu Lys Tyr Tyr
                275                 280                 285

Gly Ala Trp Ser Ile Ser Glu Gly Ala Cys Ile Leu Ser Gly Leu Gly
            290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Ser Ala Phe Trp His Gly Thr Arg Pro
    370                 375                 380

Gly Tyr Tyr Leu Thr Ser Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510

<210> SEQ ID NO 79
<211> LENGTH: 512
<212> TYPE: PRT
<213> ORGANISM: Artificial sequence
<220> FEATURE:
<223> OTHER INFORMATION: Y. lipolytica LPCAT containing G148A and F390S
      mutations

<400> SEQUENCE: 79

Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110
```

Ser Gln Phe Phe Pro Glu Thr Tyr Asp Pro Asn Val Ile Asp Ile Thr
                115                 120                 125

Gly Ala Gln Met Val Leu Cys Met Lys Leu Ser Ser Phe Gly Trp Asn
130                 135                 140

Val Tyr Asp Ala Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
                180                 185                 190

Tyr Met Glu Phe His Asn Trp Leu Asp Leu Ser Leu Phe Lys Glu Leu
            195                 200                 205

Glu Lys Asp Lys Asp Pro Lys Arg Ala Ala Arg Arg Lys Arg His Lys
210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
                260                 265                 270

Ile Val Tyr Leu Tyr Met Leu Gly Phe Met Tyr Arg Leu Lys Tyr Tyr
            275                 280                 285

Gly Ala Trp Ser Ile Ser Glu Gly Ala Cys Ile Leu Ser Gly Leu Gly
            290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
                340                 345                 350

Val Tyr Leu Arg Val Val Pro Lys Gly Gln Lys Pro Gly Phe Arg Ala
            355                 360                 365

Thr Ile Phe Thr Phe Val Val Ser Ala Phe Trp His Gly Thr Arg Pro
370                 375                 380

Gly Tyr Tyr Leu Thr Ser Val Thr Ala Ala Met Tyr Gln Ser Val Gly
385                 390                 395                 400

Lys Phe Phe Arg Arg Tyr Leu Arg Pro Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
            435                 440                 445

Asp Phe Trp Leu Ser Leu Lys Cys Trp Lys Asn Ser Trp Phe Leu Tyr
450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510

<210> SEQ ID NO 80
<211> LENGTH: 512
<212> TYPE: PRT

<213> ORGANISM: Artificial sequence
<220> FEATURE:
<223> OTHER INFORMATION: Y. lipolytica LPCAT containing G148N and T382I mutations

<400> SEQUENCE: 80

```
Met Ala Phe Pro Trp Ala Asp Lys Trp Ala Asp Ala Ser Ala Ser
1               5                   10                  15

Thr Gly Leu Pro Pro Asp Leu Leu Lys Ile Ala Phe Thr Leu Val Met
                20                  25                  30

Ser Tyr Pro Leu Ser Ser Leu Met Lys Arg Leu Pro Asp Asp Ala Lys
            35                  40                  45

Asn Leu Lys Ile Ile Tyr Ile Ser Val Ser Ile Phe Tyr Met Val
50                  55                  60

Gly Val Phe Ser Leu Tyr Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Lys Leu Ser Ser Phe Gly Trp Asn
130                 135                 140

Val Tyr Asp Asn Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Ile Arg Pro
370                 375                 380
```

```
Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
            405                 410                 415

Lys Thr Ala Gly Pro Tyr Lys Ile Tyr Tyr Asp Ile Val Cys Trp Ile
        420                 425                 430

Val Val Gln Thr Ala Phe Gly Tyr Ala Thr Gln Ser Phe Met Ile Leu
            435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Gln Ala Gly Ala Val Thr Asp
            485                 490                 495

Lys Lys Asp Ala Lys Glu Glu Val Lys Asp Thr Ile Lys Thr Lys
        500                 505                 510

<210> SEQ ID NO 81
<211> LENGTH: 512
<212> TYPE: PRT
<213> ORGANISM: Artificial sequence
<220> FEATURE:
<223> OTHER INFORMATION: Y. lipolytica LPCAT containing G148N and F390S
      mutations

<400> SEQUENCE: 81

Met Ala Phe Pro Trp Ala Asp Lys Trp Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Lys Leu Ser Ser Phe Gly Trp Asn
    130                 135                 140

Val Tyr Asp Asn Trp Gln Ile Glu Lys Gly Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Arg Arg Lys Arg His Lys
    210                 215                 220

Ile Pro Arg Ser Gly Ile Ala Ala Ser Lys Lys Leu Ala Ala Gly Ile
225                 230                 235                 240
```

```
Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
    370                 375                 380

Gly Tyr Tyr Leu Thr Ser Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510

<210> SEQ ID NO 82
<211> LENGTH: 17
<212> TYPE: PRT
<213> ORGANISM: Yarrowia lipolytica

<400> SEQUENCE: 82

Met Val Leu Cys Met Lys Leu Ser Ser Phe Gly Trp Asn Val Tyr Asp
1               5                   10                  15

Gly

<210> SEQ ID NO 83
<211> LENGTH: 15
<212> TYPE: PRT
<213> ORGANISM: Yarrowia lipolytica

<400> SEQUENCE: 83

Ser Ala Phe Trp His Gly Thr Arg Pro Gly Tyr Tyr Leu Thr Phe
1               5                   10                  15

<210> SEQ ID NO 84
<211> LENGTH: 512
```

```
<212> TYPE: PRT
<213> ORGANISM: Artificial sequence
<220> FEATURE:
<223> OTHER INFORMATION: Mutant YlLPCAT protein generic Xaa only
<220> FEATURE:
<221> NAME/KEY: MISC_FEATURE
<222> LOCATION: (133)..(148)
<223> OTHER INFORMATION: Xaa can be any naturally occurring amino acid
<220> FEATURE:
<221> NAME/KEY: MISC_FEATURE
<222> LOCATION: (378)..(378)
<223> OTHER INFORMATION: Xaa can be any naturally occurring amino acid
<220> FEATURE:
<221> NAME/KEY: MISC_FEATURE
<222> LOCATION: (382)..(383)
<223> OTHER INFORMATION: Xaa can be any naturally occurring amino acid
<220> FEATURE:
<221> NAME/KEY: MISC_FEATURE
<222> LOCATION: (385)..(385)
<223> OTHER INFORMATION: Xaa can be any naturally occurring amino acid
<220> FEATURE:
<221> NAME/KEY: MISC_FEATURE
<222> LOCATION: (388)..(390)
<223> OTHER INFORMATION: Xaa can be any naturally occurring amino acid

<400> SEQUENCE: 84

Met Ala Phe Pro Trp Ala Asp Lys Trp Ala Ala Asp Ala Ser Ala Ser
1               5                  10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
50                  55                  60

Gly Val Phe Ser Leu Tyr Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Xaa Xaa Xaa Xaa Xaa Xaa Xaa Xaa Xaa Xaa Xaa Xaa
    130                 135                 140

Xaa Xaa Xaa Xaa Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
```

```
            275                 280                 285
Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Xaa Trp His Gly Xaa Xaa Pro
    370                 375                 380

Xaa Tyr Tyr Xaa Xaa Xaa Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510

<210> SEQ ID NO 85
<211> LENGTH: 285
<212> TYPE: PRT
<213> ORGANISM: Scheffersomyces stipitis

<400> SEQUENCE: 85

Met Thr Val Glu Thr Ala Thr Ala Pro Gln Ser Met Cys Asn Thr Asp
1               5                   10                  15

Ile Gly Ser Leu Pro Ala Ala Asp Pro Val Leu Pro Thr Asn Val Leu
            20                  25                  30

Asp Phe Phe Lys Leu Asp Gly Lys Thr Ala Ala Ile Thr Gly Gly Ala
        35                  40                  45

Arg Gly Ile Gly Tyr Ala Ile Ser Glu Ala Tyr Leu Gln Ala Gly Ile
    50                  55                  60

Ser Lys Leu Ala Ile Ile Asp Tyr Ala Pro Asn Glu Ala Ala Leu Asp
65                  70                  75                  80

Glu Leu Arg Ser Arg Phe Leu Lys Ser Thr Ile Val Tyr His Asn Cys
                85                  90                  95

Asp Val Arg Lys Ala Asp Gln Val Lys Ser Val Ile Asp Lys Ile Glu
            100                 105                 110

Glu Glu Phe Lys Val Ile Asp Ile Phe Val Ala Asn Ala Gly Ile Ala
        115                 120                 125

Trp Thr Ser Gly Pro Met Ile Asp Gln Glu Thr Asp Asp Asp Trp His
    130                 135                 140
```

```
Asn Val Met Asn Val Asp Leu Asn Gly Val Tyr Tyr Cys Ala Lys Asn
145                 150                 155                 160

Ile Gly Lys Ile Phe Arg Lys Gln Gly Lys Gly Ser Leu Val Met Thr
            165                 170                 175

Ala Ser Met Ser Ala His Ile Val Asn Val Pro Gln Leu Gln Ala Ala
            180                 185                 190

Tyr Asn Ala Ala Lys Ala Gly Val Leu His Leu Gly Lys Ser Leu Ala
            195                 200                 205

Val Glu Trp Ala Pro Phe Ala Arg Val Asn Thr Val Ser Pro Gly Tyr
            210                 215                 220

Ile Ser Thr Glu Leu Ser Asp Phe Val Pro Thr Glu Met Lys Asn Lys
225                 230                 235                 240

Trp Tyr Ala Leu Thr Pro Gln Gly Arg Gln Gly Ala Pro Arg Glu Leu
            245                 250                 255

Cys Gly Ala Tyr Leu Tyr Leu Ala Ser Asp Ala Ser Thr Tyr Thr Thr
            260                 265                 270

Gly Ser Asp Ile Arg Val Asp Gly Gly Tyr Cys Ser Val
            275                 280                 285

<210> SEQ ID NO 86
<211> LENGTH: 280
<212> TYPE: PRT
<213> ORGANISM: Candida dubliniensis

<400> SEQUENCE: 86

Met Ser Lys Glu Thr Ile Ser Tyr Thr Asn Asp Ala Leu Gly Pro Leu
1               5                   10                  15

Pro Thr Lys Pro Ala Thr Ile Pro Asp Asn Ile Leu Asp Ala Phe Ser
            20                  25                  30

Leu Lys Gly Lys Val Ala Ser Val Thr Gly Ser Ser Gly Gly Ile Gly
            35                  40                  45

Trp Ala Val Ala Glu Gly Tyr Ala Gln Ala Gly Ala Asp Val Ala Ile
        50                  55                  60

Trp Tyr Asn Ser His Pro Ala Asp Asp Lys Ala Glu Tyr Leu Ala Lys
65                  70                  75                  80

Thr Tyr Gly Val Lys Ser Lys Ala Tyr Lys Cys Asn Val Thr Asp Phe
                85                  90                  95

Gln Asp Val Glu Lys Val Val Lys Gln Ile Glu Ser Asp Phe Gly Thr
            100                 105                 110

Ile Asp Ile Phe Val Ala Asn Ala Gly Val Ala Trp Thr Asp Gly Pro
            115                 120                 125

Glu Ile Asp Val Lys Gly Val Asp Lys Trp Asn Lys Val Val Asn Val
            130                 135                 140

Asp Leu Asn Ser Val Tyr Tyr Cys Ala His Val Val Gly Pro Ile Phe
145                 150                 155                 160

Arg Lys His Gly Lys Gly Ser Phe Ile Phe Thr Ala Ser Met Ser Ala
            165                 170                 175

Ser Ile Val Asn Val Pro Gln Leu Gln Ala Ala Tyr Asn Ala Ala Lys
            180                 185                 190

Ala Gly Val Lys His Leu Ser Lys Ser Leu Ser Val Glu Trp Ala Pro
            195                 200                 205

Phe Ala Arg Val Asn Ser Val Ser Pro Gly Tyr Ile Ala Thr His Leu
            210                 215                 220

Ser Glu Phe Ala Asp Pro Asp Val Lys Asn Lys Trp Leu Gln Leu Thr
225                 230                 235                 240
```

```
Pro Leu Gly Arg Glu Ala Lys Pro Arg Glu Leu Val Gly Ala Tyr Leu
            245                 250                 255

Tyr Leu Ala Ser Asp Ala Ala Ser Tyr Thr Thr Gly Ala Asp Leu Ala
            260                 265                 270

Val Asp Gly Gly Tyr Thr Val Val
        275                 280

<210> SEQ ID NO 87
<211> LENGTH: 160
<212> TYPE: PRT
<213> ORGANISM: Glarea lozoyensis

<400> SEQUENCE: 87

Met Thr Thr Asp Val Asp Ser Val Phe Tyr Cys Ala Arg Ala Ala Gly
1               5                   10                  15

Leu His Trp Arg Arg Gln Lys Leu Glu Gln Thr Thr Ile Asp Gly Lys
            20                  25                  30

Lys Leu Glu Pro Ala Phe Arg Gln Gly Ser Phe Val Thr Ala Ser
        35                  40                  45

Met Ser Gly Ser Ile Val Asn Val Pro Gln Gln Gln Ala Ala Tyr Asn
50                  55                  60

Ala Ala Lys Ala Gly Val Ile His Leu Cys Lys Ser Leu Ala Val Glu
65                  70                  75                  80

Phe Val Gly Phe Ala Arg Val Asn Thr Val Ser Pro Gly Tyr Ile Ala
                85                  90                  95

Thr Glu Ile Ser Ser Phe Ala Pro Ser Glu Thr Lys Asp Val Trp Arg
            100                 105                 110

Lys Lys Thr Pro Met Gly Arg Glu Gly Glu Cys His Glu Leu Lys Gly
        115                 120                 125

Ala Phe Leu Tyr Leu Ala Ser Asp Ala Ala Ser Tyr Thr Thr Gly Ala
    130                 135                 140

Asp Leu Ile Val Asp Gly Gly Leu Ser Asn Met Val Phe Asn Val Glu
145                 150                 155                 160

<210> SEQ ID NO 88
<211> LENGTH: 254
<212> TYPE: PRT
<213> ORGANISM: Enterobacter hormaechei

<400> SEQUENCE: 88

Met Thr Leu Leu Gln Thr Pro Ser Phe Thr Leu His Gly Lys Arg Ala
1               5                   10                  15

Leu Val Thr Gly Gly Ser Lys Gly Ile Gly Phe Ala Ala Ala Val Ala
            20                  25                  30

Leu Ala Gln Ala Gly Ala Glu Val Trp Ile Ala Ala Arg His Arg Asp
        35                  40                  45

Ala Leu Asp Gly Ala Val Ala Leu Ala Ala Ala His Gln Leu Ser Leu
    50                  55                  60

His Pro Val Val Leu Asp Ile Thr Leu Thr Asp Asp Val Glu Arg Val
65                  70                  75                  80

Leu Ala Thr Leu Pro Glu Phe Asp Ile Leu Val Asn Ser Ala Gly Leu
                85                  90                  95

Ala Arg His Gln Pro Phe Leu Glu Val Ser Glu Glu Asn Phe Asp Ala
            100                 105                 110

Val Met Ala Leu Asn Leu Arg Ala Thr Phe Phe Ile Ser Gln Arg Val
        115                 120                 125
```

```
Ala Arg Asn Met Arg Ala Gly Gly Lys Glu Gly Ser Ile Ile His Ile
            130                 135                 140

Ser Ser Gln Met Gly His Val Gly Gly Pro Glu Arg Ser Val Tyr Cys
145                 150                 155                 160

Ala Ser Lys Phe Ala Leu Glu Gly Leu Thr Arg Thr Met Ala Leu Glu
                165                 170                 175

Leu Gly Asp Ala Gly Ile Arg Val Asn Thr Leu Cys Pro Thr Phe Ile
            180                 185                 190

Glu Thr Asp Leu Thr Arg Ala Ser Leu Ala Asp Pro Ala Phe Arg Arg
        195                 200                 205

Tyr Val Leu Asp Asn Ile Lys Leu Arg Arg Pro Gly Thr Leu Glu Asp
    210                 215                 220

Ile Met Gly Pro Val Val Phe Leu Ala Ser Asp Ala Ala Gly Leu Ile
225                 230                 235                 240

Thr Gly Ser Ala Leu Met Val Asp Gly Gly Trp Thr Ala Thr
                245                 250
```

<210> SEQ ID NO 89
<211> LENGTH: 281
<212> TYPE: PRT
<213> ORGANISM: Candida orthopsilosis

<400> SEQUENCE: 89

```
Met Ser Lys Asp Glu Thr Ile Ser Tyr Cys Asn Ala Glu Leu Gly Pro
1               5                   10                  15

Leu Pro Thr Thr Ala Pro Lys Val Ser Asp Asn Ile Thr Asp Leu Phe
            20                  25                  30

Ser Phe Lys Gly Lys Val Val Ser Val Thr Gly Ser Ser Gly Gly Ile
        35                  40                  45

Gly Trp Ala Val Ala Glu Gly Phe Ala Gln Ala Gly Ala Asp Val Ala
    50                  55                  60

Ile Trp Tyr His Ser His Asn Ala Asp Glu Lys Ala Lys Tyr Leu Ala
65                  70                  75                  80

Glu Lys Tyr Gly Val Lys Ser Ile Ala Tyr Gly Cys Asn Ile Gly Ile
                85                  90                  95

Ala Glu Glu Val Gln Lys Thr Val Lys Gln Ile Glu Ser Asp Phe Gly
            100                 105                 110

Lys Ile Asp Val Phe Val Ala Asn Ala Gly Val Ala Trp Thr Glu Gly
        115                 120                 125

Pro Glu Ile Asp Val Glu Asp Leu Ser Lys Trp Asn Lys Ile Ile Asp
    130                 135                 140

Thr Asp Leu Asn Ser Val Phe Tyr Cys Ala His Ala Ile Gly Pro Ile
145                 150                 155                 160

Phe Arg Lys Gln Gly Lys Gly Ser Leu Val Leu Thr Gly Ser Met Ser
                165                 170                 175

Ala Thr Ile Val Asn Ile Pro Gln Leu Gln Ala Ala Tyr Asn Val Ala
            180                 185                 190

Lys Ala Gly Val Lys His Leu Ala Lys Ser Leu Ala Val Glu Trp Ala
        195                 200                 205

Pro Phe Ala Arg Val Asn Ala Val Ser Pro Gly Tyr Ile Ala Thr Asp
    210                 215                 220

Ile Ser Asp Phe Val Asp Lys Asp Met Lys Ala Lys Trp Trp Gln Leu
225                 230                 235                 240

Thr Pro Leu Gly Arg Glu Gly His Pro Lys Glu Leu Val Gly Ala Tyr
```

```
                    245                 250                 255

Leu Tyr Leu Ala Ser Asp Ala Ala Thr Tyr Thr Thr Gly Cys Asp Leu
                260                 265                 270

Ala Val Asp Gly Gly Tyr Thr Val Pro
            275                 280

<210> SEQ ID NO 90
<211> LENGTH: 255
<212> TYPE: PRT
<213> ORGANISM: Mycobacterium smegmatis

<400> SEQUENCE: 90

Met Asp Val Arg Ser Ala Phe Asp Leu Ser Gly Arg Thr Ala Leu Val
1               5                   10                  15

Thr Gly Gly Asn Gln Gly Leu Gly Lys Ala Phe Ala Ile Ala Leu Ala
                20                  25                  30

Gln Ala Gly Ala Arg Val Ser Phe Ser Gly Arg Asn Ala Glu Arg Asn
            35                  40                  45

Glu Lys Thr Ala Ala Glu Ala Ala Ala Gly His Gln Leu His Ala
    50                  55                  60

Ile Thr Ala Asp Ile Thr Arg Ala Glu Asp Val Glu Arg Met Thr Ala
65              70                  75                  80

Glu Ala Ile Glu Ala Leu Gly His Ile Asp Ile Leu Val Asn Asn Ala
                85                  90                  95

Gly Thr Cys His His Gly Glu Ser Trp Thr Val Thr Glu Glu Gln Trp
            100                 105                 110

Asp Asp Val Phe Asp Leu Asn Val Lys Ala Leu Trp Ala Cys Ser Leu
        115                 120                 125

Ala Val Gly Ala His Met Arg Glu Arg Gly Ser Gly Ser Val Val Asn
    130                 135                 140

Ile Gly Ser Met Ser Gly Ile Ile Val Asn Arg Pro Gln Met Gln Pro
145             150                 155                 160

Ala Tyr Asn Ala Ser Lys Ala Ala Val His His Leu Thr Lys Ser Leu
                165                 170                 175

Ala Ala Glu Trp Ala Pro Leu Gly Ile Arg Val Asn Ala Leu Ala Pro
            180                 185                 190

Gly Tyr Val Lys Thr Asp Met Ala Pro Val Asp Arg Pro Glu Phe Lys
        195                 200                 205

Arg Tyr Trp Ile Asp Asp Thr Pro Gln Leu Arg Tyr Ala Val Pro Glu
    210                 215                 220

Glu Ile Ala Pro Ser Val Val Phe Leu Ala Ser Asp Ala Ala Ser Phe
225             230                 235                 240

Ile Thr Gly Ser Val Leu Val Ala Asp Gly Gly Tyr Thr Ala Trp
                245                 250                 255

<210> SEQ ID NO 91
<211> LENGTH: 265
<212> TYPE: PRT
<213> ORGANISM: Gaeumannomyces graminis

<400> SEQUENCE: 91

Met Ile Glu Val Pro Lys Thr Glu Arg Leu Thr Asp Met Phe Ser Leu
1               5                   10                  15

Lys Gly Lys Val Val Val Thr Gly Ala Ser Gly Pro Gly Gly Ile
                20                  25                  30

Gly Leu Glu Ala Ala Arg Gly Cys Ala Glu Met Gly Ala Thr Val Ile
```

```
            35                  40                  45
Val Thr Ala Phe Ser Arg Leu Glu Gly Ala Gln Lys Asn Ala Glu Ala
 50                  55                  60

Leu Ala Lys Glu Tyr Gly Val Lys Thr Gly Ala Tyr Gln Cys Asp Ile
 65                  70                  75                  80

Arg Ser Trp Glu Ala Val Lys Gly Phe Val Lys Val Ile Ala Asp
                 85                  90                  95

Phe Gly Gln Ile Asp Val Phe Ile Ala Asn Ser Gly Arg Thr Ala Asp
                100                 105                 110

Ala Gly Val Ile Asp Ser Thr Ala Glu Glu Trp Asp Gln Val Ile Gln
                115                 120                 125

Ser Asp Leu Ser Gly Thr Ala Tyr Cys Ala Lys Ala Val Gly Glu His
130                 135                 140

Phe Arg Lys Arg Gly Lys Gly Ser Leu Val Ile Thr Ala Ser Met Ser
145                 150                 155                 160

Gly His Ile Ala Asn Phe Pro Gln Glu Gln Thr Ser Tyr Asn Val Ala
                165                 170                 175

Lys Ala Gly Cys Ile His Met Ala Lys Ser Leu Ala Asn Glu Trp Arg
                180                 185                 190

Glu Phe Ala Arg Val Asn Ser Val Ser Pro Gly Tyr Ile Asp Thr Gly
                195                 200                 205

Leu Ser Asp Phe Ile Asp Gln Lys Thr Gln Asp Leu Trp Lys Ser Met
210                 215                 220

Ile Pro Met Gly Arg Asn Gly Ala Pro Lys Glu Leu Arg Gly Ala Tyr
225                 230                 235                 240

Val Tyr Leu Ala Ser Asp Ala Ser Thr Tyr Thr Gly Ala Asp Ile
                245                 250                 255

Val Val Asp Gly Gly Tyr Thr Thr Arg
                260                 265

<210> SEQ ID NO 92
<211> LENGTH: 292
<212> TYPE: PRT
<213> ORGANISM: Neurospora tetrasperma

<400> SEQUENCE: 92

Met Ala Ala Glu Met Lys Asp Gly Arg Phe Ala His Asp Ile Thr Val
 1                   5                  10                  15

Ala Pro Gln Thr Asn Ser Val Met Ser Leu Phe Ser Leu Lys Gly Lys
                 20                  25                  30

Thr Ala Ile Val Thr Gly Ala Ala Gly Ile Gly Tyr Gly Val Ala
                 35                  40                  45

Glu Ala Phe Ala Glu Ala Gly Ala Asn Val Ala Ile Trp Tyr Asn Ser
 50                  55                  60

Asn Lys Lys Ala Leu Asp Ala Ala Asp Ile Glu Lys Arg Tyr Gly
 65                  70                  75                  80

Val Lys Cys Lys Ala Tyr Gln Val Asn Val Thr Ser Leu Glu Ala Val
                 85                  90                  95

Glu Ser Val Val Thr Glu Ile Ile Lys Glu Phe Asn Gly Arg Leu Asp
                100                 105                 110

Ile Phe Val Ala Asn Ser Gly Ile Pro Trp Thr Asp Gly Ala Ala Leu
                115                 120                 125

Asp Gly Pro Pro Glu Ser Tyr Lys Arg Val Met Ala Thr Asn Val Asp
130                 135                 140
```

```
Gly Thr Phe Trp Cys Ala Gln Val Ala Gly Arg His Trp Arg Arg Gln
145                 150                 155                 160

Lys Gln Glu Gly Thr Thr Met Asp Gly Lys Lys Leu Glu Gly Phe Ala
                165                 170                 175

Tyr Gly Ser Phe Ile Ala Thr Ala Ser Met Ser Gly His Ile Ala Asn
            180                 185                 190

Ile Pro Gln Leu Gln Ala Ala Tyr Asn Ala Ser Lys Ala Ala Val Ile
            195                 200                 205

His Leu Cys Arg Ser Leu Ala Val Glu Trp Val Gly Phe Ala Arg Ala
        210                 215                 220

Asn Thr Ile Ser Pro Gly Tyr Ile Arg Thr Asp Ile Ser Glu Phe Cys
225                 230                 235                 240

Ser Pro Glu Val Lys Asn Ala Trp Lys Asp Lys Ile Pro Met Gly Arg
                245                 250                 255

Glu Gly Glu Val Asn Glu Leu Lys Gly Ala Tyr Leu Tyr Phe Ala Ser
            260                 265                 270

Asp Ala Ser Ser Tyr Thr Gly Ala Asp Leu Leu Val Asp Gly Gly
            275                 280                 285

Tyr Cys Ala Pro
    290

<210> SEQ ID NO 93
<211> LENGTH: 292
<212> TYPE: PRT
<213> ORGANISM: Metarhizium anisopliae

<400> SEQUENCE: 93

Met Ala Thr Asp Met Lys Asn Gly Ala Phe Glu His Asp Asn Met Asp
1               5                   10                  15

Ile Pro Lys Gly Asp Arg Val Leu Pro Met Phe Ser Leu Lys Gly Arg
                20                  25                  30

Thr Ala Ile Val Ser Gly Ala Gly Ala Gly Ile Gly Leu Gly Val Ala
            35                  40                  45

Gln Ala Phe Ala Glu Ala Gly Ala Asn Val Ala Ile Trp Tyr Asn Ser
    50                  55                  60

Asn Lys Gln Ala Val Thr Glu Ala Glu Asn Ile Gln Lys Thr Tyr Ser
65                  70                  75                  80

Val Lys Cys Lys Ala Tyr Gln Val Asn Val Ile Ser Ala Asp Ala Val
                85                  90                  95

Asp Lys Ala Ile Gly Glu Ile Ile Arg Glu Phe Asn Gly Arg Leu Asp
            100                 105                 110

Ile Phe Val Ala Asn Ser Gly Ile Ala Trp Glu Asp Gly Pro Phe Leu
            115                 120                 125

Asp Gly His Val Glu Thr Ala Lys Lys Val Met Ala Val Asn Val Asp
        130                 135                 140

Gly Val Met Trp Cys Ala Lys Ser Ala Gly Ile His Phe Arg Arg Gln
145                 150                 155                 160

Lys Lys Glu Gly Lys Thr Ile Asp Gly Lys Pro Leu Glu Asn Tyr Ile
                165                 170                 175

Cys Gly Ser Phe Ile Ala Thr Ala Ser Met Ser Gly Lys Ile Val Asn
            180                 185                 190

Val Pro Lys Leu Gln Ala Val Tyr Asn Gly Ser Lys Ala Ala Val Ile
            195                 200                 205

His Phe Cys Lys Ser Leu Ala Val Glu Trp Thr Gly Phe Ala Arg Val
        210                 215                 220
```

```
Asn Thr Val Ser Pro Gly Tyr Ile Lys Thr Glu Val Ser Ser Phe Ala
225                 230                 235                 240

Glu Ala Glu Thr Glu Glu Gln Arg Lys Asn Lys Ile Pro Met Gly Arg
            245                 250                 255

Glu Gly Gln Val Ser Glu Leu Lys Gly Ser Tyr Leu Tyr Leu Ala Ser
            260                 265                 270

Asp Ala Ala Ser Tyr Ile Thr Gly Leu Asp Met Ile Val Asp Gly Gly
            275                 280                 285

Tyr Ser Leu Leu
        290

<210> SEQ ID NO 94
<211> LENGTH: 292
<212> TYPE: PRT
<213> ORGANISM: Cordyceps militaris

<400> SEQUENCE: 94

Met Ala Asn Ala Met Lys His Gly Val Phe Arg Arg Asn Asn Thr Ala
1               5                   10                  15

Ala Pro Ala Gly Ser Ala Val Met Pro Leu Phe Ser Leu Ala Gly Lys
            20                  25                  30

Thr Ala Ile Val Ala Gly Ala Gly Gln Gly Ile Gly Phe Ala Ala Ala
            35                  40                  45

Glu Ala Phe Ala Glu Ala Gly Ala Asn Val Ala Leu Trp Tyr Asn Arg
    50                  55                  60

Asn Ser Glu Ala Val Thr Lys Ala Lys Met Glu Ala Asn Tyr Gly
65                  70                  75                  80

Val Lys Cys Lys Ala His Lys Val Asp Val Thr Ser Tyr Asp Glu Val
                85                  90                  95

Glu Arg Ala Val Ser Ser Ala Val Gln Asp Leu Asn Gly Arg Leu Asp
            100                 105                 110

Val Phe Val Ala Asn Ser Gly Ile Ser Trp Gly Asp Glu Ala Phe Leu
            115                 120                 125

Asp Ala Ser Val Ala Arg Tyr His Gly Leu Met Ser Ile Asn Thr Asp
130                 135                 140

Gly Val Ala Tyr Cys Ala His Val Ala Gly Gln His Phe Arg Arg Gln
145                 150                 155                 160

Lys Leu Glu Gly Ile Thr Thr His Gly Thr Lys Leu Glu Asp Phe Ala
                165                 170                 175

Asn Gly Ser Phe Ile Ala Lys Ala Ser Met Ser Gly His Ile Val Asn
            180                 185                 190

Ile Pro Arg Gln Gln Ala Val Tyr Asn Thr Ser Lys Ala Ala Ile Ile
            195                 200                 205

His Leu Cys Lys Ser Leu Ala Ile Glu Trp Leu Gly Phe Ala Arg Val
210                 215                 220

Asn Ser Val Ser Pro Gly Phe Phe Asn Thr Gly Ile Ser Gly Pro Ile
225                 230                 235                 240

Ala Glu Glu Val Met Ser Ala Ile Met Asp Lys Val Pro Met Gly Arg
            245                 250                 255

Phe Gly Glu Thr Val Glu Leu Lys Ala Val Tyr Leu Phe Leu Ala Ser
            260                 265                 270

Asn Ala Ser Ser Tyr Val Thr Gly Thr Asp Ile Leu Val Asp Gly Gly
            275                 280                 285

Tyr Thr Ala Thr
```

<210> SEQ ID NO 95
<211> LENGTH: 255
<212> TYPE: PRT
<213> ORGANISM: Metarhizium acridum

<400> SEQUENCE: 95

Met Ala Thr Asp Met Lys Asn Gly Ala Phe Glu His Asp Asn Met Asp
1               5                   10                  15

Ile Pro Lys Gly Asp Arg Val Leu Pro Met Phe Ser Leu Lys Gly Arg
            20                  25                  30

Thr Ala Ile Val Ser Gly Ala Gly Ile Gly Leu Gly Val Ala
        35                  40                  45

Gln Ala Phe Ala Glu Ala Gly Ala Asn Val Ala Ile Trp Tyr Asn Ser
    50                  55                  60

Asn Lys Gln Ala Val Thr Glu Ala Glu Lys Ile Gln Lys Thr Tyr Gly
65                  70                  75                  80

Val Lys Cys Lys Ala Tyr Gln Val Asp Val Ile Ser Ala Asp Ala Val
                85                  90                  95

Asp Lys Thr Val Gly Glu Ile Ile Arg Glu Phe Asn Gly Arg Leu Asp
            100                 105                 110

Ile Phe Val

```
                 65                  70                  75                  80
Ser Ala Ala Ser Thr Ala Ala Leu Gln Ser Leu Arg Gln Ala Tyr Pro
                     85                  90                  95

His Ala Ala Ile Ile Leu Ala Glu Val Asp Val Thr Ser Glu Asp Ala
                100                 105                 110

Val Gly Ala Ala Thr Ala Ala Phe Cys Ala Ala Gln Pro Pro Asp Gly
            115                 120                 125

Gly Ile Asp Ala Leu Val Cys Thr Ala Gly Val Ala Cys Ala Pro
        130                 135                 140

Ser Leu Asp Ala Pro Pro Ala Ala Phe Arg Arg Thr Leu Asp Val Asn
145                 150                 155                 160

Ala Thr Gly Thr Phe Leu Cys Ala Gln Ala Val Ala Arg Thr Met Val
                165                 170                 175

Ala Arg Gly Arg Gly Arg Leu Val Phe Thr Ala Ser Ile Ser Gly
                180                 185                 190

Ser Arg Val Asn Phe Pro Gln Pro Gln Ala Ala Tyr Asn Ala Ser Lys
                195                 200                 205

Ala Ala Val Val Met Leu Gly Arg Ser Leu Ala Ala Glu Trp Ala Arg
        210                 215                 220

Tyr Gly Ile Arg Val Asn Val Val Ser Pro Gly Tyr Leu Asp Thr Val
225                 230                 235                 240

Leu Asn Ala Gly Ala Gly Leu Ala Glu Ala Arg Ala Val Trp Thr Gly
                245                 250                 255

Arg Asn Pro Leu Gly Arg Met Gly Arg Val Glu Glu Val Ala Ala Val
                260                 265                 270

Val Leu Met Leu Val Gly Arg Ala Gly Ser Tyr Val Asn Gly Ala Glu
        275                 280                 285

Ile Val Val Asp Gly Gly Thr Val Phe
        290                 295

<210> SEQ ID NO 97
<211> LENGTH: 293
<212> TYPE: PRT
<213> ORGANISM: Paracoccidioides brasiliensis

<400> SEQUENCE: 97

Met Ser Gly Pro Ile Val Asp Gly Lys Phe Arg Ile Asp Asn Thr Ser
1               5                   10                  15

Pro Pro Ser Ala Ser Ser Gly Ile Leu Ala Leu Phe Ser Leu Lys Gly
                20                  25                  30

Lys Thr Ala Ile Val Thr Gly Ala Gly Ala Gly Ile Gly Leu Ala Val
            35                  40                  45

Ala His Ala Leu Ala Glu Ala Gly Ala Asn Val Ala Ile Trp Phe Asn
        50                  55                  60

Arg Asn Lys Ala Ala Ile Glu Arg Ala Ala Glu Ile Glu Asn Lys Tyr
65                  70                  75                  80

Gly Val Lys Cys Arg Ala Tyr Gln Val Asn Val Thr Asp Pro Gln Val
                85                  90                  95

Val Ser Asp Ala Val Asp Ser Ile Val Lys Glu Phe Asn Gly Arg Leu
                100                 105                 110

Asp Ile Phe Val Ala Asn Ser Gly Ile Pro Trp Thr Gln Gly Pro Met
            115                 120                 125

Thr Glu Gly His Leu Asp His Tyr Arg Lys Val Val Thr Thr Asp Ile
        130                 135                 140
```

-continued

```
Asp Gly Val Phe Tyr Ser Ala Arg Ala Ala Val His Trp Lys Arg
145                 150                 155                 160

Gln Lys Glu Glu Gly Thr Asp Ile Asn Gly Lys Lys Leu Glu Asn Phe
                165                 170                 175

Ser Tyr Gly Ser Phe Ile Ala Thr Ala Ser Met Ser Gly His Ile Val
            180                 185                 190

Asn Phe Pro Gln Leu Gln Ala Ala Tyr Asn Ala Ala Lys Ala Ala Val
        195                 200                 205

Val His Leu Cys Lys Ser Leu Ala Val Glu Trp Val Gln Phe Ala Arg
    210                 215                 220

Ala Asn Ser Val Ser Pro Gly Tyr Met Ala Thr Glu Ile Ser Asn Phe
225                 230                 235                 240

Ile Pro Ser Ser Thr Lys Asp Ile Trp Arg Ser Lys Ile Pro Met Gly
                245                 250                 255

Arg Glu Gly Glu Pro His Glu Leu Ala Gly Thr Tyr Leu Tyr Leu Ala
                260                 265                 270

Ser Asp Ala Ser Ser Tyr Thr Gly Ala Asp Ile Ile Val Asp Gly
            275                 280                 285

Gly Tyr Thr Leu Pro
    290

<210> SEQ ID NO 98
<211> LENGTH: 292
<212> TYPE: PRT
<213> ORGANISM: Magnaporthe oryzae

<400> SEQUENCE: 98

Met Ala Glu Thr Met Lys Asp Gly Lys Phe Pro His Asp Asn Met Val
1               5                   10                  15

Ala Pro Lys Ser Asn Arg Val Met Pro Leu Phe Ser Leu Lys Gly Arg
                20                  25                  30

Thr Ala Ile Val Ser Gly Ala Gly Ala Gly Ile Gly Leu Ala Val Ala
            35                  40                  45

Glu Ala Phe Ala Glu Ala Gly Ala Asn Val Ala Ile Trp Phe Asn Ser
50                  55                  60

Asn Lys Glu Ala His Glu Arg Ala Lys Asp Ile Glu Arg Glu Tyr Gly
65                  70                  75                  80

Val Thr Cys Lys Ala Tyr Gln Val Asn Val Thr Ser Tyr Glu Glu Val
                85                  90                  95

Glu Lys Ala Ile Asn Gln Gly Val Lys Asp Leu Asn Gly Arg Leu Asp
            100                 105                 110

Val Phe Val Ala Asn Ser Gly Val Ala Trp Glu Gln Gly Pro Leu Ile
        115                 120                 125

Asp Gly Gly Leu Asp His Tyr Lys Lys Val Met Thr Thr Asn Met Asp
    130                 135                 140

Gly Thr Ile Tyr Cys Ala Arg Val Ala Gly Gln His Trp Arg Arg Gln
145                 150                 155                 160

Lys Lys Glu Gly Thr Thr Ile Asp Gly Lys Pro Leu Glu Asn Tyr Thr
                165                 170                 175

Tyr Gly Ser Phe Ile Ala Thr Gly Ser Met Ser Gly His Ile Val Asn
            180                 185                 190

Val Pro Gln Leu Gln Thr Ala Tyr Asn Ala Ala Lys Ala Gly Ile Ile
        195                 200                 205

His Met Cys Arg Ser Leu Gly Val Glu Trp Thr Gly Phe Ala Arg Ala
    210                 215                 220
```

```
Asn Ser Val Ser Pro Gly Tyr Ile Asn Thr Glu Ile Ser Ser Phe Ala
225                 230                 235                 240

Pro Ala Glu Val Lys Asn Ala Trp Lys Asp Lys Ile Pro Met Gly Arg
            245                 250                 255

Glu Gly Glu Thr Ser Glu Leu Lys Gly Val Tyr Leu Tyr Leu Ala Ser
            260                 265                 270

Asp Ala Ala Ser Tyr Thr Thr Gly Thr Asp Ile Cys Val Asp Gly Gly
            275                 280                 285

Tyr Ala Ala Pro
        290

<210> SEQ ID NO 99
<211> LENGTH: 295
<212> TYPE: PRT
<213> ORGANISM: Uncinocarpus reesii

<400> SEQUENCE: 99

Met Asp Thr Ala Leu Ser Ser Asn Gly Ala Ser Trp Ser Gln Gln Asn
1               5                   10                  15

Thr Gln Pro Pro Ala Glu Arg Gly Tyr Met Ala Leu Phe Ser Leu
            20                  25                  30

Lys Gly Lys Thr Ala Ile Ile Ala Gly Ala Ala Ala Gly Ile Gly Leu
            35                  40                  45

Ile Val Ala Gln Ala Tyr Ala Glu Ala Gly Ala Asn Val Ala Leu Trp
50                  55                  60

Tyr His Ser Asn Lys Thr Ala His Asp Arg Ala Lys Glu Ile Glu Lys
65                  70                  75                  80

Gln Tyr Gly Val Lys Ala Arg Ala Tyr Gln Val Asn Val Gln Glu Pro
                85                  90                  95

Gln Glu Val Glu Asn Ala Val Gln Gly Val Val Lys Glu Phe Asn Gly
            100                 105                 110

Arg Leu Asp Ile Phe Val Ala Asn Ser Gly Ile Pro Trp Lys Gln Gly
            115                 120                 125

Ala Met Thr Glu Gly Thr Leu Asp His Tyr Arg Lys Val Ile Ser Thr
130                 135                 140

Asp Leu Asp Gly Val Tyr Tyr Ala Ala Arg Ala Val Ala Pro Val Trp
145                 150                 155                 160

Arg Arg Gln Lys Gln Glu Gly Thr Asp Ile Asn Gly Asn Arg Leu Glu
                165                 170                 175

Asn Phe Ser Tyr Gly Ser Phe Ile Ala Thr Gly Ser Met Ser Gly His
            180                 185                 190

Ile Val Asn Val Pro Gln Leu Gln Ser Ala Tyr Asn Ala Ala Lys Ala
            195                 200                 205

Gly Val Ile His Leu Cys Lys Ser Leu Ala Leu Glu Trp Val Gln Phe
210                 215                 220

Ala Arg Ala Asn Ser Val Ser Pro Gly Tyr Ile Ser Thr Glu Leu Thr
225                 230                 235                 240

Glu Phe Leu Ser Gln Glu Thr Ile Thr Leu Leu Asn Gly Lys Ile Pro
            245                 250                 255

Met Gly Arg Gln Gly Gln Ala His Glu Leu Ala Gly Ala Tyr Ile Phe
            260                 265                 270

Leu Ala Ser Asp Ala Ser Ser Tyr Ala Thr Gly Thr Asp Ile Ile Ile
            275                 280                 285

Asp Gly Gly Tyr Thr Ser Gln
```

-continued

```
                290                 295

<210> SEQ ID NO 100
<211> LENGTH: 292
<212> TYPE: PRT
<213> ORGANISM: Neurospora crassa

<400> SEQUENCE: 100

Met Ala Ala Glu Met Lys Asp Gly Arg Phe Ala His Asp Ile Thr Val
1               5                   10                  15

Ala Pro Gln Thr Asn Ser Val Met Ser Leu Phe Ser Leu Lys Gly Lys
            20                  25                  30

Thr Ala Ile Val Thr Gly Ala Ala Gly Ile Gly Tyr Gly Val Ala
        35                  40                  45

Glu Ala Phe Ala Glu Ala Gly Ala Asn Val Ala Ile Trp Tyr Asn Ser
    50                  55                  60

Asn Lys Lys Ala Leu Asp Ala Ala Asp Ile Glu Lys Arg Tyr Gly
65              70                  75                  80

Val Lys Cys Lys Ala Tyr Gln Val Asn Val Thr Ser Leu Glu Ala Val
                85                  90                  95

Glu Ser Ala Val Thr Glu Ile Val Lys Glu Phe Asn Gly Arg Leu Asp
            100                 105                 110

Ile Phe Val Ala Asn Ser Gly Ile Pro Trp Thr Asp Gly Ala Ala Leu
        115                 120                 125

Asp Gly Pro Pro Glu Ser Tyr Lys Arg Val Met Ala Thr Asn Val Asp
    130                 135                 140

Gly Thr Phe Trp Cys Ala Gln Val Ala Gly Arg His Trp Arg Arg Gln
145                 150                 155                 160

Lys Gln Glu Gly Thr Thr Met Asp Gly Lys Lys Leu Glu Gly Phe Thr
                165                 170                 175

Tyr Gly Ser Phe Ile Ala Thr Ala Ser Met Ser Gly His Ile Ala Asn
            180                 185                 190

Ile Pro Gln Leu Gln Ala Val Tyr Asn Ala Ser Lys Ala Ala Val Ile
        195                 200                 205

His Leu Cys Arg Ser Leu Ala Val Glu Trp Val Gly Phe Ala Arg Ala
    210                 215                 220

Asn Thr Ile Ser Pro Gly Tyr Ile Arg Thr Asp Ile Ser Glu Phe Cys
225                 230                 235                 240

Ser Pro Glu Val Lys Asn Ala Trp Lys Asp Lys Ile Pro Met Gly Arg
                245                 250                 255

Glu Gly Glu Val Asn Glu Leu Lys Gly Ala Tyr Leu Tyr Phe Ala Ser
            260                 265                 270

Asp Ala Ser Ser Tyr Thr Thr Gly Ala Asp Leu Leu Val Asp Gly Gly
        275                 280                 285

Tyr Cys Ala Pro
    290

<210> SEQ ID NO 101
<211> LENGTH: 284
<212> TYPE: PRT
<213> ORGANISM: Lodderomyces elongisporus

<400> SEQUENCE: 101

Met Ser Arg Glu Asn Pro Asp Ile Gln Ser Tyr Ala Asn Pro Glu Leu
1               5                   10                  15

Gly Asn Leu Pro Arg Pro Ile Pro Ser Tyr Ile Asp Asp Asn Ile Leu
```

```
            20                  25                  30
Ser Leu Phe Ser Leu Lys Gly Lys Thr Ala Ile Thr Gly Ser Ser
            35                  40                  45

Gly Gly Ile Gly Trp Cys Val Ala Glu Gly Phe Ala Gln Ala Gly
        50                  55                  60

Asp Val Ile Ile Trp Tyr Asn Ser His Pro Ala Asp Glu Lys Ala Thr
65                  70                  75                  80

Tyr Leu Ser Glu Lys Tyr Gly Ile Lys Ser Lys Ala Tyr Lys Cys Asp
                85                  90                  95

Ile Ser Asp Ala Asp Asp Val Lys Arg Thr Ile Ala Glu Gln Leu Lys
            100                 105                 110

Glu Phe Gly Lys Ile Asp Ile Phe Val Ala Asn Ala Gly Ile Pro Trp
        115                 120                 125

Thr Ser Gly Pro Leu Ile Asp Glu Pro Asp Met Asn Lys Trp Lys Lys
    130                 135                 140

Val Ile Asp Thr Asp Leu Asn Ser Val Phe Tyr Cys Ala His Ala Ile
145                 150                 155                 160

Gly Pro Val Phe Arg Lys Gln Gly His Gly Ser Leu Val Ile Thr Ala
                165                 170                 175

Ser Met Ser Gly Ser Ile Val Asn Ile Pro Gln Met Gln Ala Ala Tyr
            180                 185                 190

Asn Ala Ala Lys Ala Ala Val Lys His Leu Ser Lys Ser Leu Ala Val
        195                 200                 205

Glu Trp Ala Pro Phe Ala Arg Val Asn Ser Val Ser Pro Gly Tyr Ile
    210                 215                 220

Ala Thr Asn Leu Thr Thr Phe Ala Asp Ala Glu Leu Thr Lys Lys Trp
225                 230                 235                 240

Leu Gln Leu Thr Pro Ile Gly Arg Glu Gly Lys Pro Arg Glu Leu Val
                245                 250                 255

Gly Ala Tyr Leu Tyr Leu Ala Ser Asp Ala Ala Ser Phe Thr Thr Gly
            260                 265                 270

Cys Asp Leu Ala Val Asp Gly Gly Tyr Thr Val Pro
        275                 280

<210> SEQ ID NO 102
<211> LENGTH: 293
<212> TYPE: PRT
<213> ORGANISM: Aspergillus niger

<400> SEQUENCE: 102

Met Ala Ala Asn Pro Val Glu Asn Gly Leu Phe Val His Asn Asn Thr
1               5                   10                  15

Thr Ala Pro Ala His Pro Gly Leu Leu Ser Met Phe Ser Leu Lys Gly
            20                  25                  30

Lys Thr Ala Ile Val Thr Gly Ala Gly Ala Gly Ile Gly Leu Ser Val
        35                  40                  45

Ala Ile Gly Leu Ala Glu Ala Gly Ala Asn Val Ala Leu Trp Tyr Ser
    50                  55                  60

Ser Asn Pro Asn Cys Ile Glu Arg Ala Ala Glu Ile Ala Ser Lys Tyr
65                  70                  75                  80

Gly Val Gln Ala Gln Ala Tyr Lys Val Glu Ile Thr Lys Pro Glu Ala
                85                  90                  95

Val Gln Ala Val Asp Gln Val Lys Asp Phe Asn Gly Arg Leu
            100                 105                 110
```

```
Asp Val Phe Ile Ala Asn Ala Gly Ile Pro Trp Thr Lys Gly Pro Met
            115                 120                 125

Val Asp Gly Pro Leu Asp His Tyr Ser Ser Val Asp Val Asp Leu
    130                 135                 140

Asn Gly Thr Phe Tyr Cys Ala Arg Ala Ala Thr His Trp Arg Arg
145                 150                 155                 160

Gln Lys Glu Glu Gly Thr Asp Ile Asn Gly Asn Ala Leu Asn Asn Phe
                165                 170                 175

Thr Tyr Gly Ser Phe Val Ala Thr Ser Met Ser Gly His Ile Val
            180                 185                 190

Asn Phe Pro Gln Met Gln Ala Ala Tyr Asn Ala Ser Lys Ala Gly Val
                195                 200                 205

Ile His Leu Cys Lys Ser Leu Ala Val Glu Trp Val Lys Phe Ala Arg
    210                 215                 220

Ala Asn Thr Val Ser Pro Gly Tyr Ile Ala Thr Glu Ile Ser Asn Phe
225                 230                 235                 240

Ile Pro Asp Asp Val Lys Gly Ile Trp Lys Asp Lys Ile Pro Met Gly
                245                 250                 255

Arg Glu Gly Glu Pro Glu Glu Leu Lys Gly Ala Tyr Leu Tyr Leu Ala
                260                 265                 270

Ser Asp Ala Ser Ser Tyr Thr Thr Gly Ala Asp Ile Val Val Asp Gly
    275                 280                 285

Gly Tyr Cys Ala Pro
        290

<210> SEQ ID NO 103
<211> LENGTH: 266
<212> TYPE: PRT
<213> ORGANISM: Penicillium chrysogenum

<400> SEQUENCE: 103

Met Pro Ile Pro Val Pro Lys Ala Asp Arg Leu Leu Asp Leu Leu Ser
1               5                   10                  15

Leu Lys Gly Lys Val Val Val Thr Gly Ala Ser Gly Ala Arg Gly
            20                  25                  30

Met Gly Ile Glu Ala Ala Arg Gly Cys Ala Glu Met Gly Ala Asp Leu
            35                  40                  45

Ala Ile Thr Tyr Ser Ser Arg Arg Glu Gly Gly Glu Lys Asn Ala Lys
        50                  55                  60

Glu Leu Ser Glu Glu Tyr Gly Val Lys Val Lys Pro Tyr Lys Cys Asp
65                  70                  75                  80

Val Gly Ser Trp Glu Ser Val Glu Thr Leu Val Lys Asp Val Leu Lys
                85                  90                  95

Asp Phe Gly Lys Ile Asp Ala Phe Ile Ala Asn Ala Gly Arg Thr Ala
            100                 105                 110

Asp Ser Gly Ile Leu Asp Gly Ser Val Glu Asp Trp Asn Glu Val Ile
        115                 120                 125

Asn Thr Asp Leu Thr Gly Thr Phe His Cys Ala Lys Ala Val Gly Ala
    130                 135                 140

His Phe Lys Glu Arg Gly Thr Gly Ser Phe Val Ile Thr Ser Ser Met
145                 150                 155                 160

Ser Gly His Ile Ala Asn Phe Pro Gln Glu Gln Thr Ser Tyr Asn Val
                165                 170                 175

Ala Lys Ala Gly Thr Ile His Leu Ala Arg Ser Leu Ala Asn Glu Trp
            180                 185                 190
```

```
Arg Asp Phe Ala Arg Val Asn Ser Ile Ser Pro Gly Tyr Ile Asp Thr
            195                 200                 205

Gly Leu Ser Asp Phe Val Ala Lys Asp Val Gln Asp Leu Trp Asn Ser
        210                 215                 220

Met Ile Pro Met Gly Arg Asn Gly Asp Ala Lys Glu Leu Lys Gly Ala
225                 230                 235                 240

Tyr Val Tyr Leu Val Ser Asp Ala Ser Thr Tyr Met Thr Gly Asn Asp
                245                 250                 255

Leu Leu Ile Asp Gly Gly Tyr Thr Val Arg
            260                 265

<210> SEQ ID NO 104
<211> LENGTH: 289
<212> TYPE: PRT
<213> ORGANISM: Debaryomyces hansenii

<400> SEQUENCE: 104

Met Thr Leu Pro Asp Lys Arg Glu Thr Asp Ile Thr Val Val Ser Tyr
1               5                   10                  15

Ile Ser Asn Glu Phe Thr Asp Glu Leu Pro Arg Ala Ser Pro Pro Lys
            20                  25                  30

Arg His Ile Met Asp Leu Leu Ser Leu Lys Gly Lys Val Ala Val Val
        35                  40                  45

Thr Gly Ala Ala Arg Gly Ile Gly Leu Ala Ile Ala Glu Thr Phe Ala
    50                  55                  60

Glu Ala Gly Ala Ala Val Ala Leu Val Asp Tyr Thr Asp Cys Ser Glu
65                  70                  75                  80

Gln Ala Leu Lys Leu Ala Thr Arg Leu Lys Val Cys Thr Lys Ala Phe
                85                  90                  95

Gln Cys Asp Val Ala Asp Leu Lys Arg Val Glu Gly Thr Val Gln Ala
            100                 105                 110

Ile Glu Lys Glu Phe Gly Thr Ile Asp Val Phe Val Ala Asn Ala Gly
        115                 120                 125

Ile Val Trp Lys Thr Gly Asn Ile Ile Asp Glu Val Asn Arg Asp Gly
    130                 135                 140

Lys Thr Trp Gln Thr Ile Met Asp Val Asn Leu Asn Gly Ala Tyr Tyr
145                 150                 155                 160

Cys Ala Gln Ala Val Gly Arg Ile Phe Lys Lys Asn Gly Lys Gly Ser
                165                 170                 175

Phe Ile Val Thr Ser Ser Met Ser Ala Ser Ile Val Asn Ile Pro Met
            180                 185                 190

Asn Leu Thr Pro Tyr Asn Val Ser Lys Ala Gly Val Lys His Leu Ala
        195                 200                 205

Lys Ser Leu Ala Ile Glu Trp Ala Gly Phe Ala Arg Ala Asn Ser Ile
    210                 215                 220

Ser Pro Gly Tyr Cys Asp Thr Gly Leu Asn Asp His Leu Pro Arg Glu
225                 230                 235                 240

Ser Arg Gly Lys Met Trp Ala Leu Ile Pro Ala Gly Arg Glu Ala Leu
                245                 250                 255

Pro Tyr Glu Ile Ala Ser Ala Tyr Leu Tyr Leu Ala Ser Asp Ala Ala
            260                 265                 270

Ser Tyr Ile Thr Gly Ser Asp Ile Ala Ile Asp Gly Gly Tyr Thr Ser
        275                 280                 285

Ile
```

<210> SEQ ID NO 105
<211> LENGTH: 281
<212> TYPE: PRT
<213> ORGANISM: Candida parapsilosis

<400> SEQUENCE: 105

Met Ser Lys Asp Glu Thr Ile Ser Tyr Cys Asn Asp Gln Leu Gly Pro
1               5                   10                  15

Leu Pro Thr Thr Ala Pro Lys Val Ser Asp Asn Val Thr Asp Leu Phe
            20                  25                  30

Ser Phe Lys Gly Lys Val Val Ser Val Thr Gly Ser Ser Gly Gly Ile
        35                  40                  45

Gly Trp Ala Val Ala Glu Gly Phe Ala Gln Ala Gly Ala Asp Val Ala
    50                  55                  60

Ile Trp Tyr His Ser His Asn Ala Asp Glu Lys Ala Lys Tyr Leu Gln
65                  70                  75                  80

Glu Lys Tyr Gly Val Lys Ser Ile Ala Tyr Gly Cys Asn Ile Gly Val
                85                  90                  95

Ala Glu Glu Val Gln Lys Thr Val Asp Gln Ile Glu Ser Asp Phe Gly
            100                 105                 110

Lys Ile Asp Val Phe Val Ala Asn Ala Gly Ile Pro Trp Thr Asp Gly
        115                 120                 125

Pro Glu Ile Asp Val Gln Asp Leu Ser Lys Trp Thr Lys Ile Ile Asp
    130                 135                 140

Thr Asp Leu Asn Ser Val Tyr Tyr Cys Ala His Ala Ile Gly Pro Ile
145                 150                 155                 160

Phe Arg Lys Gln Gly Lys Gly Ser Leu Val Ile Thr Ala Ser Met Ser
                165                 170                 175

Ala Thr Ile Val Asn Val Pro Gln Leu Gln Ala Ala Tyr Asn Val Ala
            180                 185                 190

Lys Ala Gly Val Lys His Leu Ser Lys Ser Leu Ala Val Glu Trp Ala
        195                 200                 205

Pro Phe Ala Arg Val Asn Ser Val Ser Pro Gly Tyr Ile Ser Thr Asn
    210                 215                 220

Leu Thr Thr Phe Ala Asn Pro Asp Leu Gln Lys Lys Trp Val Gln Leu
225                 230                 235                 240

Thr Pro Leu Gly Arg Glu Gly His Pro Lys Glu Leu Val Gly Ala Tyr
                245                 250                 255

Leu Tyr Leu Ala Ser Asp Ala Thr Phe Thr Thr Gly Cys Asp Leu
            260                 265                 270

Ala Val Asp Gly Gly Tyr Thr Val Pro
        275                 280

<210> SEQ ID NO 106
<211> LENGTH: 287
<212> TYPE: PRT
<213> ORGANISM: Bifidobacterium dentium

<400> SEQUENCE: 106

Met Ile Lys Gln Val Gly Lys Ala Ala Leu Arg Leu Ser Arg Ala Cys
1               5                   10                  15

Ser Ala Phe Val Gln Thr Leu Lys Ala Gly Gly Val Asn Thr Ile Ala
            20                  25                  30

Leu Asn Gln Ile Gln Asn His Asp Ala Leu Ser Gly Lys Arg Ile Val
        35                  40                  45

-continued

```
Ile Thr Gly Gly Ser Gly Ile Gly Phe Ala Ile Ala Lys Gln Cys
    50              55              60
Val Glu Ser Gly Ala Thr Val Leu Ile Thr Gly Arg Asn Glu Lys Lys
65              70              75              80
Leu Lys Thr Ala Ala Ala Lys Leu Asp Glu Lys Arg Met Arg Tyr Leu
            85              90              95
Val Trp Asp Ile Ala Asp Ser Ser Gln Ala Asp Ala Lys Val Ala Gln
            100             105             110
Cys Val Asp Leu Leu Asp Gly His Val Asp Ala Val Ile Asn Asn Ala
            115             120             125
Gly Met Gln Pro His Glu Phe Phe Pro Asn Val Ser Val Asp Glu Trp
    130             135             140
Asn Arg Ile Tyr Glu Thr Asn Ser Arg Gly Thr Phe Phe Val Ser Gln
145             150             155             160
Ala Phe Cys Lys His Trp Met Glu His Pro Ser His Ser Tyr Arg His
            165             170             175
Leu Val Asn Ile Ser Ser Gln Gly Gly Phe Val Gly Ala Ile Tyr Pro
            180             185             190
Tyr Arg Met Ser Lys Trp Asp Ile Arg Gly Leu Thr Val Gly Leu Gly
    195             200             205
Leu Gln Met Ala Pro Tyr Gly Val Leu Val Asn Gly Val Ala Pro Gly
    210             215             220
Val Val Lys Thr Ala Met Gln Gly Phe Ala Met Lys Gln Gly Asp Asn
225             230             235             240
Gly Tyr Cys Asn Gln Asn Pro Leu Gly Arg Val Ala Leu Pro Glu Glu
            245             250             255
Ile Ala Gln Phe Val Val Phe Met Leu Ser Gly Ala Cys Asn Phe Met
            260             265             270
Val Gly Gln Thr Val Val Leu Asp Gly Gly Tyr Ser Leu Lys Asn
    275             280             285
```

DOWN-REGULATION OF A POLYNUCLEOTIDE ENCODING A SOU2 SORBITOL UTILIZATION PROTEIN TO MODIFY LIPID PRODUCTION IN MICROBIAL CELLS

This application claims the benefit of U.S. Provisional Application Nos. 61/740,502 and 61/740,506, each filed Dec. 21, 2012, both of which are incorporated herein by reference in their entireties.

FIELD OF THE INVENTION

This invention is in the field of biotechnology. More specifically, this invention pertains to recombinant microbial cells comprising (i) a down-regulated endogenous polynucleotide sequence encoding Sou2 sorbitol utilization protein, and (ii) a polyunsaturated fatty acid biosynthetic pathway.

BACKGROUND OF THE INVENTION

A variety of different hosts including plants, algae, fungi, stramenopiles and yeast have been and continue to be investigated as means for commercial production of polyunsaturated fatty acids (PUFA). Genetic engineering has demonstrated that the natural abilities of some hosts, even those natively limited to linoleic acid (LA, 18:2 omega-6) or alpha-linolenic acid (ALA, 18:3 omega-3) fatty acid production, can be substantially altered to result in high-level production of various long-chain omega-3/omega-6 PUFAs.

Although the literature reports a number of recent examples whereby various portions of the omega-3/omega-6 PUFA biosynthetic pathway responsible for eicosapentaenoic acid (EPA) production have been introduced into plants and non-oleaginous yeast, significant efforts have focused on the use of the oleaginous yeast, *Yarrowia lipolytica* (U.S. Pat. Nos. 7,238,482 and 7,932,077; U.S. Pat. Appl. Publ. Nos. 2009-0093543 and 2010-0317072). Oleaginous yeast are defined as those yeast that are naturally capable of oil synthesis and accumulation, wherein oil accumulation is at least 25% of the cellular dry weight, or those yeast genetically engineered such that they become capable of oil synthesis and accumulation, wherein oil accumulation is at least 25% of the cellular dry weight.

Emphasis has been placed on the development of transgenic oleaginous *Y. lipolytica* strains that can produce enhanced amounts of EPA. This focus on EPA production is due in part to the recognized salutary effects of EPA. For example, EPA has been shown to play a role in maintaining brain, retina and cardiovascular health. EPA is also known to have anti-inflammatory properties and may be useful in treating or preventing diseases linked to inflammation, such as cardiovascular disease and arthritis. Thus, the clinical and pharmaceutical value of EPA is well known (U.S. Pat. Appl. Publ. No. 2009-0093543). Similarly, the advantages of producing EPA in microbes using recombinant means, as opposed to producing EPA from natural microbial sources or via isolation from fish oil and marine plankton, are also well recognized. Interest in EPA production in yeast has also been due to the drive to develop sustainable sources of EPA as alternatives to producing EPA from fish, which would help alleviate problems associated with overfishing.

Enhanced EPA production in *Y. lipolytica* has been targeted in two general ways. First, attempts have been made to increase the amount of EPA present in the oil produced by *Y. lipolytica*. Such oil, which may not necessarily constitute a large percentage of the dry cell weight of *Y. lipolytica* biomass, can be purified away from the biomass, then used in EPA dietary supplements and/or used for further concentration for pharmaceutical applications. Attempts have also been made to increase the amount of EPA in the dry cell weight of *Y. lipolytica*. This entails trying to (i) increase the level of oil in *Y. lipolytica* while also (ii) increasing the amount of EPA present in the oil. The resulting biomass can be used directly in feeding schemes to deliver a high quantity of EPA in the diet while side-stepping issues of oil purification. Of course, such biomass can also serve as a source of oil in EPA supplements and the oil can also be used for further concentration for pharmaceutical applications, requiring less biomass per unit of EPA produced compared to *Y. lipolytica* biomass containing a lower amount of oil.

U.S. Pat. Appl. Publ. No. 2010-0317072 discloses a transgenic *Y. lipolytica* strain that produces oil containing 61.8% by weight EPA of the total fatty acids of the oil. However, this strain contains 26.5% oil on a dry cell weight basis. So, while the EPA content in the oil is high (61.8%), the EPA content in the disclosed *Y. lipolytica* strain on a dry cell weight basis is lower at about 16.4%.

A transgenic *Y. lipolytica* strain is disclosed in U.S. Pat. Appl. Publ. No. 2012-0052537 that produces oil containing 58.7% by weight EPA of the total fatty acids of the oil. This strain contains 38.3% oil on a dry cell weight basis. So, while the EPA content in the oil is high (58.7%), the EPA content in the disclosed *Y. lipolytica* strain on a dry cell weight basis is lower at about 22.5%.

U.S. Pat. Appl. Publ. No. 2012-0052537 also discloses a transgenic *Y. lipolytica* strain that produces oil containing 48.3% by weight EPA of the total fatty acids of the oil. On a dry cell weight basis, this strain contains 56.2% oil and an EPA content of about 27.1%.

These disclosed examples indicate that as improvements are made in developing transgenic *Y. lipolytica* strains for enhanced EPA and/or oil production, an inverse correlation arises between the total amount of oil produced and the amount of EPA present in the total fatty acids of the oil. Strains engineered to produce higher amounts of oil on a dry cell basis generally have lower amounts of EPA as a percentage of the fatty acids in the oil.

Increases in the total amount of EPA produced on a dry cell weight basis have been realized, even though there has been an inverse relationship between oil production and the amount of EPA produced as a percentage of the total fatty acids in oil. Despite this achievement, there is still a need to develop *Y. lipolytica* strains that can produce greater total amounts of EPA. Achieving this goal will likely entail the development of new strain modifications that enhance the amount of EPA as a percentage of the total fatty acids in oil, while not compromising the total amount of oil produced by the strain.

Polynucleotide sequences encoding the Sou2 sorbitol utilization protein have been identified by others. Information regarding the function of this protein, however, appears to be limited. For example, Jami et al. (2010, *Molecular & Cellular Proteomics* 9:2729-2744) disclosed that a "probable" Sou2 protein was present in the extra-cellular fraction of the filamentous fungus *Penicillium chrysogenum*. The characterization of several amino acid sequences in online databases as Sou2 sorbitol utilization protein appears to be based on sequence homology only without the disclosure of functional studies. The amino acid sequence of the Sou2 protein in *Candida albicans* is about 72% identical to the amino acid sequence of *C. albicans* Sou1 protein, which has been disclosed by Janbon et al. (1998, *Proc. Natl. Acad. Sci. U.S.A.* 95:5150-5155) and Greenberg et al. (2005, *Yeast* 22:957-969)

to be a sorbose reductase required for L-sorbose utilization. However, despite the homology between *C. albicans* Sou1 and -2 proteins, Janbon et al. disclosed that the Sou2 protein is not required for sorbose utilization. The roles of the Sou1 and Sou2 proteins in lipid metabolism, if any, are believed to be unknown.

Studies are disclosed herein detailing the development of *Y. lipolytica* strains that can produce more than 28% EPA as dry cell weight. The modifications used to generate such strains included down-regulating a gene encoding Sou2 sorbitol utilization protein.

SUMMARY OF THE INVENTION

In one embodiment, the invention concerns a recombinant microbial cell comprising: (i) a down-regulation of an endogenous polynucleotide sequence encoding Sou2 sorbitol utilization protein, and (ii) a polyunsaturated fatty acid (PUFA) biosynthetic pathway, wherein the down-regulation of the endogenous polynucleotide sequence encoding Sou2 sorbitol utilization protein increases the lipid content of the microbial cell and/or decreases the total amount of sugar alcohols produced by the microbial cell.

In a second embodiment, the down-regulation is due to a mutation of the endogenous polynucleotide sequence encoding Sou2 sorbitol utilization protein. In a third embodiment, this mutation is selected from the group consisting of a substitution, deletion and insertion.

In a fourth embodiment, the mutation of the endogenous polynucleotide sequence encoding Sou2 sorbitol utilization protein is a deletion that removes: (i) one or more nucleotides from an open reading frame encoding the Sou2 sorbitol utilization protein, and/or (ii) one or more nucleotides of a non-protein-coding sequence located within 500 base pairs of the 5'-end of the open reading frame.

In a fifth embodiment, the mutation of the endogenous polynucleotide sequence encoding Sou2 sorbitol utilization protein is an insertion that occurs within: (i) an open reading frame encoding the Sou2 sorbitol utilization protein, or (ii) a non-protein-coding sequence located within 500 base pairs of the 5'-end of the open reading frame.

In a sixth embodiment, the PUFA pathway of the recombinant microbial cell produces at least one PUFA selected from the group consisting of linoleic acid, alpha-linolenic acid, gamma-linolenic acid, stearidonic acid, eicosadienoic acid, dihomo-gamma-linolenic acid, arachidonic acid, eicosatrienoic acid, eicosatetraenoic acid, eicosapentaenoic acid, docosatetraenoic acid, omega-3 docosapentaenoic acid, omega-6 docosapentaenoic acid and docosahexaenoic acid. In a seventh embodiment, the PUFA pathway produces eicosapentaenoic acid.

In an eighth embodiment, arabitol or mannitol are comprised in the total amount of sugar alcohols that are decreased in the recombinant microbial cell.

In a ninth embodiment, the recombinant microbial cell is an oleaginous yeast cell. In a tenth embodiment, this oleaginous yeast cell is a *Yarrowia* cell.

In an eleventh embodiment, the Sou2 sorbitol utilization protein encoded by the endogenous polynucleotide sequence comprises an amino acid sequence that is at least 95% identical to SEQ ID NO:10. In a twelfth embodiment, the endogenous polynucleotide sequence comprises a nucleotide sequence that is at least 95% identical to SEQ ID NO:9.

In a thirteenth embodiment, the invention concerns a method of producing a microbial oil comprising a polyunsaturated fatty acid (PUFA). This method comprises: a) culturing a recombinant microbial cell of the invention, wherein a microbial oil comprising a PUFA is produced; and b) optionally recovering the microbial oil of step (a). In a fourteenth embodiment, the microbial oil produced by this method comprises eicosapentaenoic acid.

BIOLOGICAL DEPOSITS

The following biological material has been deposited with the American Type Culture Collection (ATCC), 10801 University Boulevard, Manassas, Va. 20110-2209, and bears the following designation, accession number and date of deposit.

| Biological Material | Accession No. | Date of Deposit |
|---|---|---|
| *Yarrowia lipolytica* Y8412 | ATCC PTA-10026 | May 14, 2009 |

The biological material listed above was deposited under the terms of the Budapest Treaty on the International Recognition of the Deposit of Microorganisms for the Purposes of Patent Procedure. The listed deposit will be maintained in the indicated international depository for at least 30 years and will be made available to the public upon the grant of a patent disclosing it. The availability of a deposit does not constitute a license to practice the subject invention in derogation of patent rights granted by government action.

*Y. lipolytica* strain Y9502 was derived from *Y. lipolytica* strain Y8412 as described in U.S. Pat. Appl. Publ. No. 2010-0317072, which is incorporated herein by reference. *Y. lipolytica* strain Z5585 was derived from *Y. lipolytica* strain Y9502 as described in U.S. Pat. Appl. Publ. No. 2012-0052537, which is incorporated herein by reference.

BRIEF DESCRIPTION OF THE DRAWINGS AND SEQUENCES

FIG. 1: Biosynthetic pathways for producing omega-3 and omega-6 fatty acids in *Yarrowia* are shown.

FIG. 2: Diagrammed are (A) the steps of developing *Y. lipolytica* strain Y9502 from wild type strain ATCC #20362, and (B) the steps of developing *Y. lipolytica* strains Z5627 and Z5585 from strain Y9502. The percent fatty acid (E.g., EPA) values listed under certain strains represent the percentage of the particular fatty acid in the fatty acids of the oil produced by the strain. The percent oil values listed under certain strains represent the oil as a percent of dry cell weight of the strain.

Figure 3:
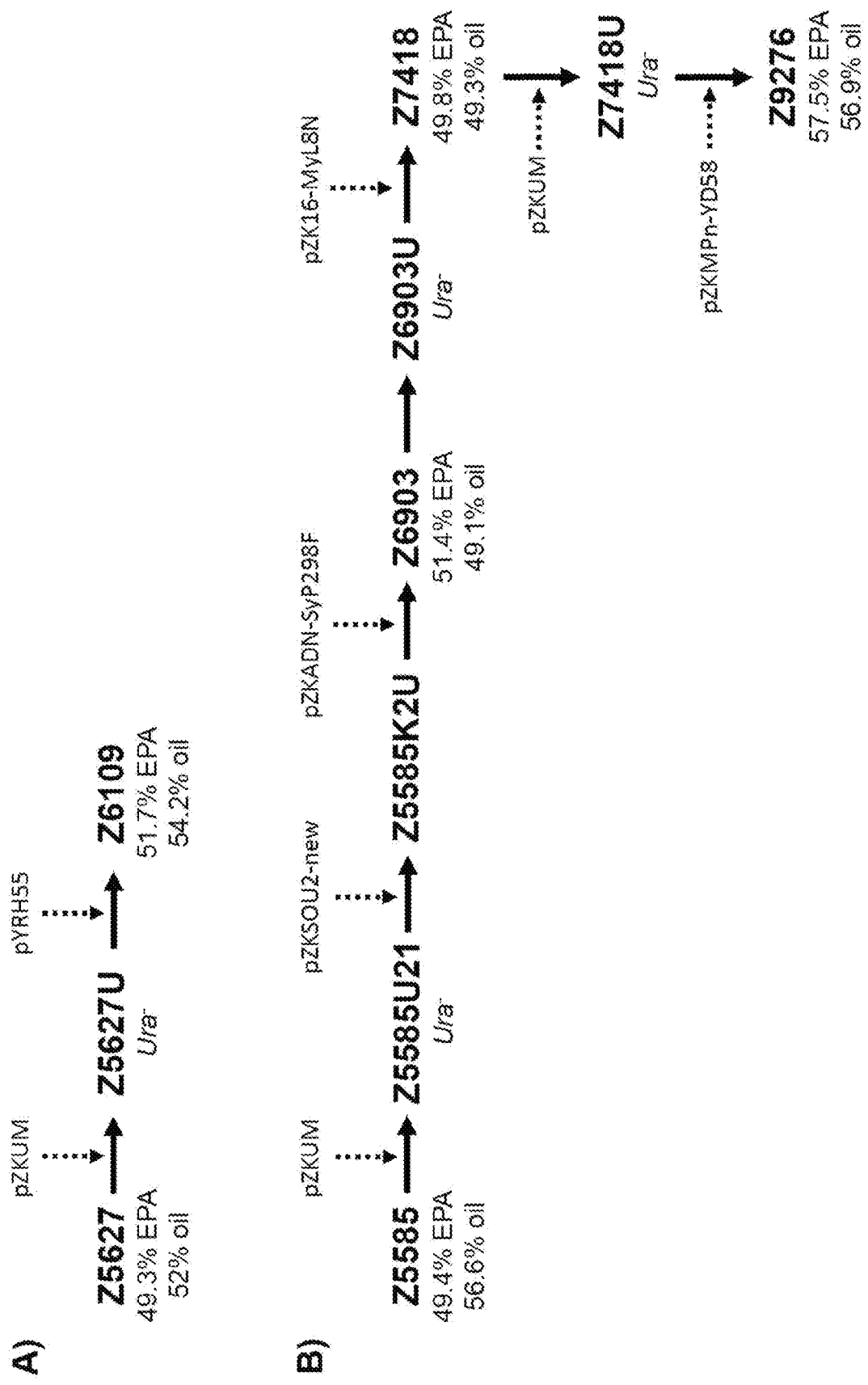

FIG. 3: Diagrammed are (A) the steps of developing *Y. lipolytica* strain Z6109 from strain Z5627, and (B) the steps of developing *Y. lipolytica* strain Z9276 from strain Z5585. The percent EPA values listed under certain strains represent the percentage of the EPA in the fatty acids of the oil produced by the strain. The percent oil values listed under certain strains represent the oil as a percent of dry cell weight of the strain.

FIG. 4: Diagrammed are plasmid constructs (A) pYRH55 and (B) pZKSOU2-New.

FIG. 5: Genomic DNA sequence (SEQ ID NO:8) containing the *Y. lipolytica* SOU2 gene locus (GenBank Accession No. XM_503010, YALI0D18964g) is shown. The Sou2 amino acid coding region (SEQ ID NO:9) is indicated with bold, underlined text. Two adjacent cytosine residues, which are located at positions 2400349 and 2400350 of chromosome D, are shown in large bold font and are just downstream an apparent TATA box (bold). The mutational insertion observed in strain Z3041 impairing Sou2 expression occurred between these two cytosine residues. The sequence indicated between the two opposing triangles was targeted for removal by the 5'- and 3'-homology sequences of plasmid pZKSOU2-New.

Figure 6:
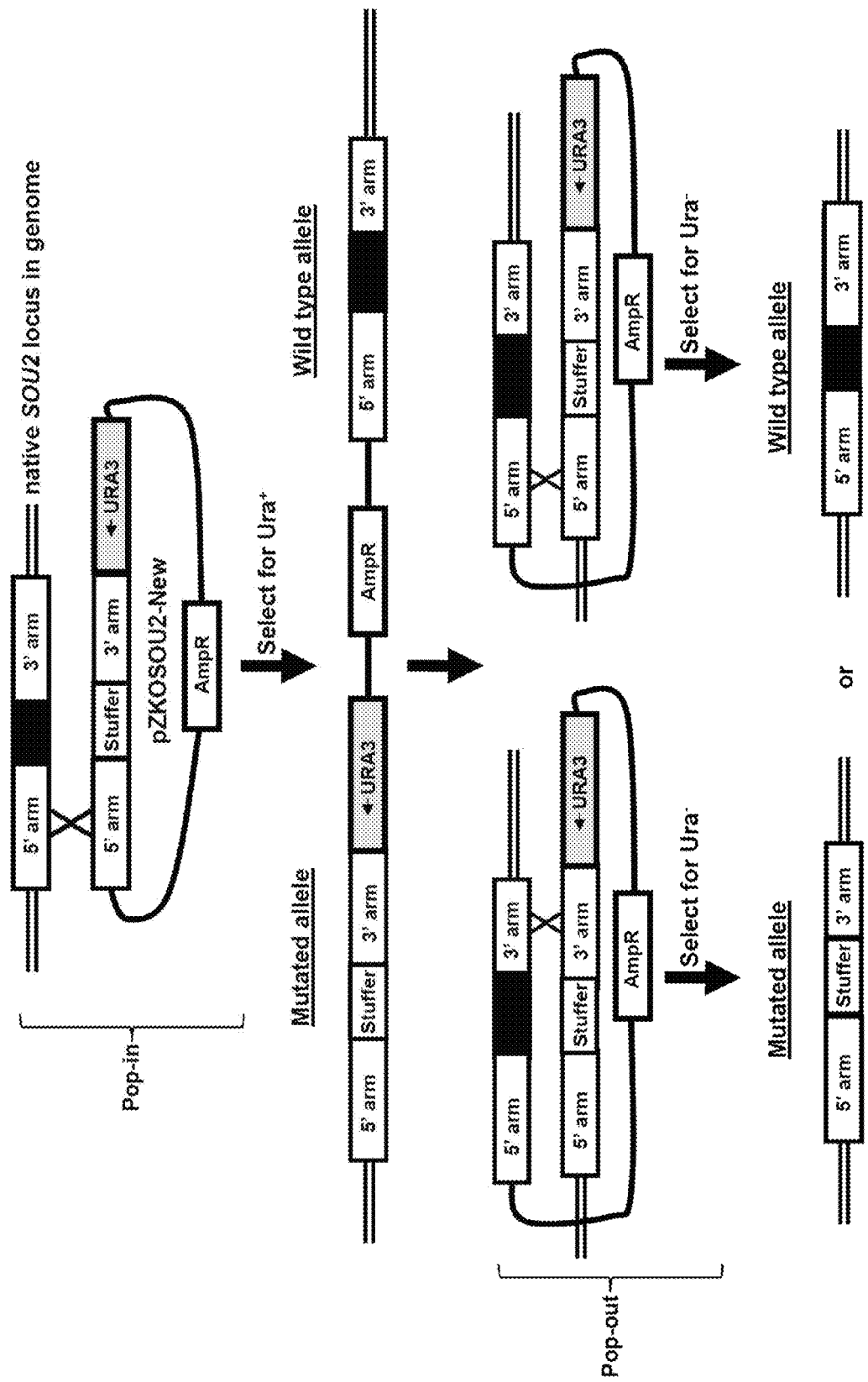

FIG. 6: Diagrammed is the genetic targeting strategy used to knock-out the endogenous SOU2 gene in *Y. lipolytica* using construct pZKSOU2-New. The "X"s shown between certain 5'- and 3'-homology arm sequences denotes sites of homologous recombination. The pop-in event resulting from homologous recombination at the 5'-homology arms results in the juxtaposition of a mutated SOU2 allele with the wild type SOU2 allele. Two different pop-out events are shown. The left-hand pop-out event occurs as a result of homologous recombination at the 3'-homology arms of the gene structure formed from the 5'-arm pop-in event. This process results in a mutated SOU2 allele and removal of the wild type allele. The right-hand pop-out event occurs as a result of homologous recombination at the 5'-homology arms. This pop-out event results in the wild type SOU2 allele.

FIG. 7: Diagrammed are plasmid constructs (A) pZKADn-SyP298F and (B) pZKMPn-YD58.

Figure 8:
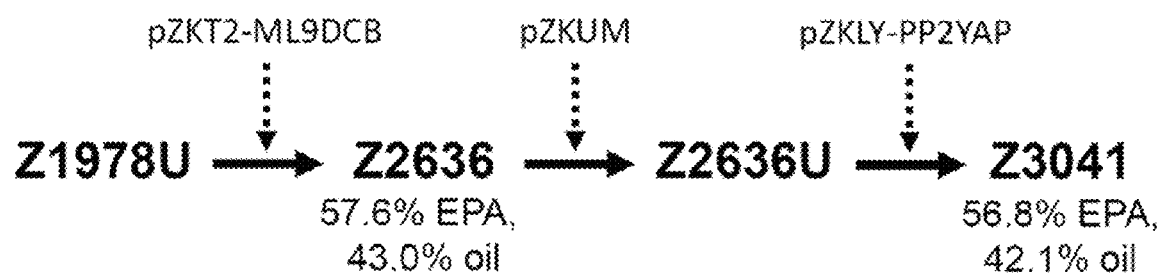

FIG. 8: Diagrammed are the steps of developing *Y. lipolytica* strain Z3041 from strain Z1978U. The percent EPA values listed under certain strains represent the percentage of the EPA in the fatty acids of the oil produced by the strain. The percent oil values listed under certain strains represent the oil as a percent of dry cell weight of the strain.

FIG. 9: Diagrammed are plasmid constructs (A) pZKT2-ML9DCB and (B) pZKLY-PP2YAP.

Figure 10:
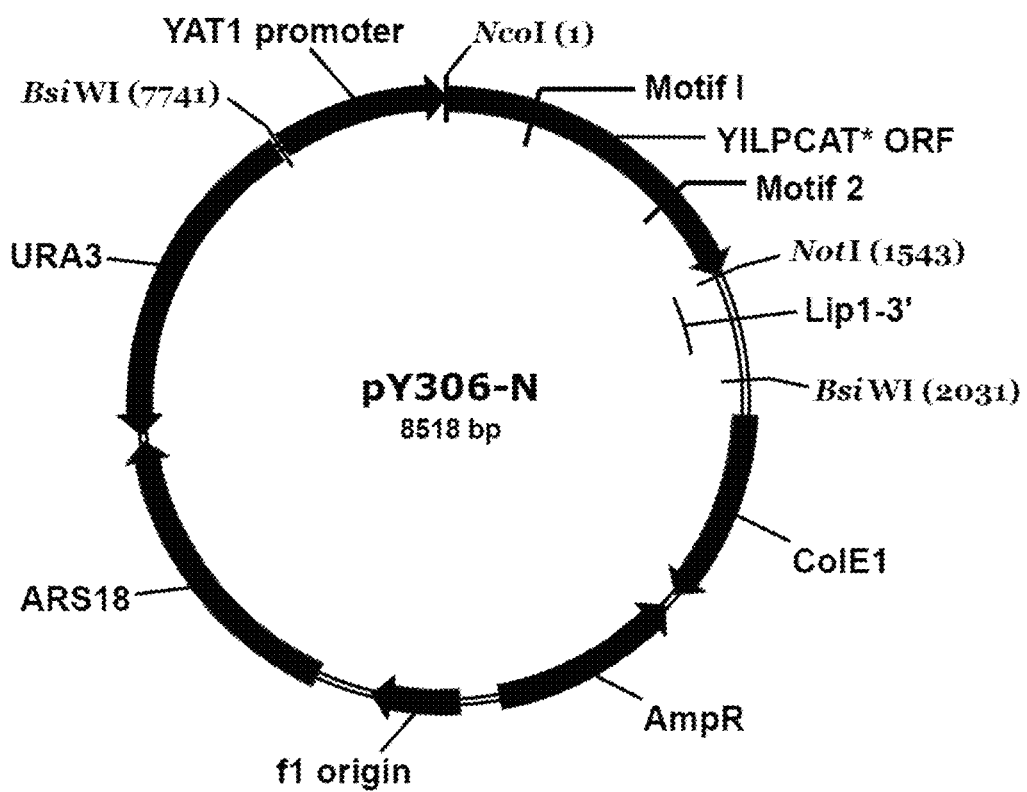

FIG. 10: Diagrammed is the plasmid construct pY306-N.

TABLE 1

Summary of Gene and Protein SEQ ID Numbers

| Description | Nucleic acid SEQ ID NO. | Protein SEQ ID NO. |
|---|---|---|
| Construct pYRH55 for expressing codon-optimized *Arabidopsis thaliana* caleosin-1 (AtClo1S) | 1 | |
| AtClo1S, *A. thaliana* caleosin-1 codon-optimized for expression in *Y. lipolytica* (U.S. Appl. Publ. No. 2012-0301932) | 2 | 3 (245 aa) |
| Construct pZKSOU2-New for down-regulating endogenous *Y. lipolytica* SOU2 expression | 4 | |
| Construct pZKADn-SyP298F for expressing YIPDAT, FmD12S, and E389D9eS/EgD8M | 5 | |
| Erp, terminator sequence from *Y. lipolytica* ERP gene | 6 | |
| Glo terminator sequence from *Y. lipolytica* GLO gene | 7 | |
| Genomic DNA sequence containing the *Y. lipolytica* SOU2 gene locus, FIG. 5, 2071-bp (1000-bp upstream Sou2 ATG start codon, 771-bp Sou2 coding sequence, 300-bp downstream Sou2 TGA stop codon) | 8 | |
| *Y. lipolytica* Sou2 sorbitol utilization protein | 9 | 10 (256 aa) |
| Genomic DNA sequence containing the *Y. lipolytica* SOU2 gene locus, 2771-bp (1000-bp upstream Sou2 ATG start codon, 771-bp Sou2 coding sequence, 1000-bp downstream Sou2 TGA stop codon) | 11 | |
| FmD12S, *Fusarium moniliforme* delta-12 desaturase (U.S. Pat. No. 7,504,259) codon-optimized for expression in *Y. lipolytica* | 12 | 13 (477 aa) |
| YIPDAT, *Y. lipolytica* PDAT (U.S. Pat. Appl. Publ. No. 2012-0052537), but with an added alanine at amino acid position 2 | 14 | 15 (649 aa) |
| E389D9eS/EgD8M: gene fusion comprising a codon-optimized delta-9 elongase derived from *Eutreptiella* sp. CCMP389 (E389D9eS), a linker, and a codon-optimized mutant delta-8 desaturase derived from *Euglena gracilis* (EgD8M) (U.S. Pat. Appl. Publ. No. 2008-0254191) | 16 | 17 (708 aa) |
| EgD8M, mutant *E. gracilis* delta-8 desaturase (U.S. Pat. No. 7,709,239) | 18 | 19 (422 aa) |
| MCS, *Rhizobium leguminosarum* bv. *viciae* 3841 malonyl-CoA synthetase (U.S. Pat. Appl. Publ. No. 2010/0159558) codon-optimized for expression in *Y. lipolytica* | 20 | 21 (505 aa) |
| YILPAAT1, *Y. lipolytica* LPAAT1 (U.S. Pat. Appl. Publ. No. 2012-0052537) | 22 | 23 (282 aa) |
| Construct pZKMPn-YD58 for expressing mutant YILPCAT (M136S_T389A) | 24 | |
| Mutant YILPCAT (M136S_T389A), *Y. lipolytica* LPCAT containing M136S and T389A mutations | 25 | 26 (512 aa) |
| Construct pZKT2-ML9DCB for expressing YICPT1, YID9, and MaLPAAT1S | 27 | |
| Construct pZKLY-PP2YAP for expressing YIYAP1, YI6PGL, and YIG6PDH | 28 | |
| *Candida albicans* Sou2 sorbitol utilization protein | 29 | 30 (280 aa) |
| YIPDAT, *Y. lipolytica* PDAT (U.S. Pat. No. 7,267,976) | | 31 (648 aa) |
| YID12, *Y. lipolytica* delta-12 desaturase (U.S. Pat. No. 7,504,259) | | 32 (419 aa) |
| E389D9eS, delta-9 elongase derived from *Eutreptiella* | | 33 |

TABLE 1-continued

Summary of Gene and Protein SEQ ID Numbers

| Description | Nucleic acid SEQ ID NO. | Protein SEQ ID NO. |
|---|---|---|
| sp. CCMP389 (E389D9eS) (U.S. Pat. Appl. Publ. No. 2008-0254191) | | (263 aa) |
| Linker comprised in E389D9eS/EgD8M multizyme | | 34 (24 aa) |
| EgD9eS/EgD8M: gene fusion comprising a delta-9 elongase derived from *Euglena gracilis* (EgD9eS), a linker, and a mutant delta-8 desaturase derived from *Euglena gracilis* (EgD8M) (U.S. Pat. Appl. Publ. No. 2008-0254191) | | 35 (701 aa) |
| EaD9eS/EaD8S: gene fusion comprising a delta-9 elongase derived from *Euglena anabaena* (EaD9eS), a linker, and a delta-8 desaturase derived from *Euglena anabaena* (EaD8S) (U.S. Pat. Appl. Publ. No. 2008-0254191) | | 36 (702 aa) |
| EaD8, *E. anabaena* delta-8 desaturase (U.S. Pat. No. 7,790,156) | | 37 (420 aa) |
| MaLPAAT1, *M. alpina* lysophosphatidic acid acyltransferase-1 (U.S. Pat. No. 7,879,591) | | 38 (314 aa) |
| YlLPCAT, wild type *Y. lipolytica* LPCAT (YALI0F19514p, GenBank Accession No. XP_505624) | 39 | 40 (512 aa) |
| YlLPCAT*, YlLPCAT lacking two internal NcoI restriction sites with respect to SEQ ID NO: 39, but encoding wild type YlLPCAT protein | 41 | 40 (512 aa) |
| Construct pY306-N, containing YlLPCAT* nucleotide sequence | 42 | |
| Construct pY306, containing wild type YlLPCAT nucleotide sequence | 43 | |
| Mutant YlLPCAT_M132X, comprising M132A, M132N, M132C, M132G, M132Q, M132H, M132I, M132L, M132F, M132P, M132S, M132T, M132W, M132Y or M132V mutation in Motif I | | 44 (512 aa) |
| Mutant YlLPCAT_V133X, comprising V133A, V133N, V133C, V133G, V133Q, V133H, V133L, V133M, V133F, V133P, V133S, V133T, V133W or V133Y mutation in Motif I | | 45 (512 aa) |
| Mutant YlLPCAT_L134X, comprising L134A, L134N, L134C, L134G, L134Q, L134H, L134M, L134F, L134P, L134S, L134T, L134W, L134Y or L134V mutation in Motif I | | 46 (512 aa) |
| Mutant YlLPCAT_C135X, comprising C135R, C135N, C135D, C135G, C135E, C135Q, C135H, C135I, C135L, C135K, C135M, C135F, C135P, C135S, C135W or C135Y mutation in Motif I | | 47 (512 aa) |
| Mutant YlLPCAT_M136X, comprising M136A, M136N, M136C, M136G, M136H, M136I, M136F, M136P, M136S, M136T, M136W, M136Y or M136V mutation in Motif I | | 48 (512 aa) |
| Mutant YlLPCAT_K137X, comprising K137A, K137R, K137N, K137G, K137H, K137P, K137S, K137T, or K137Y mutation in Motif I | | 49 (512 aa) |
| Mutant YlLPCAT_L138X, comprising L138A, L138N, L138C, L138G, L138Q, L138H, L138I, L138M, L138F, L138P, L138S, L138T, L138W, or L138Y mutation in Motif I | | 50 (512 aa) |
| Mutant YlLPCAT_S139X, comprising S139A, S139N, S139C, S139G, S139H, S139L, S139M, S139F, S139P, S139W, or S139V mutation in Motif I | | 51 (512 aa) |
| Mutant YlLPCAT_S140X, comprising S140N, S140C, S140H, S140I, S140L, S140F, S140P, S140W, S140Y or S140V mutation in Motif I | | 52 (512 aa) |
| Mutant YlLPCAT_F141X, comprising F141A, F141N, F141G, F141H, F141I, F141M, F141P, F141S, F141T, F141W, or F141V mutation in Motif I | | 53 (512 aa) |
| Mutant YlLPCAT_G142X, comprising G142N, G142H, G142I, G142L, G142M, G142F, G142P, G142T, G142W, G142Y or G142V mutation in Motif I | | 54 (512 aa) |
| Mutant YlLPCAT_W143X, comprising W143A, W143G, W143H, W143L, W143K, W143P, W143S, W143T or W143V mutation in Motif I | | 55 (512 aa) |
| Mutant YlLPCAT_N144X, comprising N144A, N144R, N144G, N144H, N144K, N144F, N144P, N144T or N144V mutation in Motif I | | 56 (512 aa) |

TABLE 1-continued

Summary of Gene and Protein SEQ ID Numbers

| Description | Nucleic acid SEQ ID NO. | Protein SEQ ID NO. |
|---|---|---|
| Mutant YlLPCAT_V145X, comprising V145A, V145C, V145G, V145E, V145H, V145M, V145F, V145P, V145S, V145T, or V145W mutation in Motif I | | 57 (512 aa) |
| Mutant YlLPCAT_Y146X, comprising Y146R, Y146N, Y146D, Y146G, Y146E, Y146Q, Y146I, Y146L, Y146M, Y146F, Y146P, Y146W or Y146V mutation in Motif I | | 58 (512 aa) |
| Mutant YlLPCAT_D147X, comprising D147A, D147N, D147G, D147E, D147Q, D147H, D147F, D147S, or D147T mutation in Motif I | | 59 (512 aa) |
| Mutant YlLPCAT_G148X, comprising G148A, G148N, G148H, G148L, G148M, G148F, G148S, G148T or G148V mutation in Motif I | | 60 (512 aa) |
| Mutant YlLPCAT_S376X, comprising S376A, S376G, S376H, S376L, S376F, S376P, S376T or S376V mutation in Motif II | | 61 (512 aa) |
| Mutant YlLPCAT_A377X, comprising A377N, A377G, A377H, A377L, A377F, A377P, A377S, A377T or A377V mutation in Motif II | | 62 (512 aa) |
| Mutant YlLPCAT_F378X, comprising F378A, F378N, F378C, F378G, F378H, F378L, F378P, F378S, F378T, F378W, or F378Y mutation in Motif II | | 63 (512 aa) |
| Mutant YlLPCAT_T382X, comprising T382A, T382N, T382G, T382Q, T382H, T382I, T382M, T382P, T382S, T382W or T382Y mutation in Motif II | | 64 (512 aa) |
| Mutant YlLPCAT_R383X, comprising R383A, R383N, R383D, R383G, R383E, R383Q, R383H, R383I, R383L, R383K, R383M, R383F, R383P, R383T, R383W or R383V mutation in Motif II | | 65 (512 aa) |
| Mutant YlLPCAT_P384X, comprising P384A, P384R, P384G, P384H, P384I, P384L, P384K, P384M, P384F, P384S, P384T, P384W, P384Y or P384V mutation in Motif II | | 66 (512 aa) |
| Mutant YlLPCAT_G385X, comprising G385A, G385N, G385C, G385G, G385H, G385I, G385L, G385K, G385M, G385F, G385S, G385T, G385W, G385Y or G385V mutation in Motif II | | 67 (512 aa) |
| Mutant YlLPCAT_Y386X, comprising Y386A, Y386G, Y386H, Y386L, Y386F, Y386P, Y386S, Y386T or Y386V mutation in Motif II | | 68 (512 aa) |
| Mutant YlLPCAT_Y387X, comprising Y387A, Y387G, Y387H, Y387L, Y387F, Y387P, Y387S, Y387T, Y387W or Y387V mutation in Motif II | | 69 (512 aa) |
| Mutant YlLPCAT_L388X, comprising L388A, L388G, L388H, L388P, L388S, L388T, L388W, L388Y or L388V mutation in Motif II | | 70 (512 aa) |
| Mutant YlLPCAT_T389X, comprising T389A, T389C, T389G, T389H, T389I, T389L, T389M, T389F, T389P, T389S, T389W, T389Y or T389V mutation in Motif II | | 71 (512 aa) |
| Mutant YlLPCAT_F390X, comprising F390A, F390N, F390C, F390G, F390H, F390L, F390M, F390P, F390S, F390T or F390V mutation in Motif II | | 72 (512 aa) |
| Mutant YlLPCAT, comprising single mutations in Motif I and/or Motif II | | 73 (512 aa) |
| Mutant YlLPCAT, comprising a single mutation in Motif I and a single mutation in Motif II | | 74 (512 aa) |
| Mutant YlLPCAT (M136S_T389C), *Y. lipolytica* LPCAT containing M136S and T389C mutations | | 75 (512 aa) |
| Mutant YlLPCAT (M136S_T389S), *Y. lipolytica* LPCAT containing M136S and T389S mutations | | 76 (512 aa) |
| Mutant YlLPCAT (M136V_T389C), *Y. lipolytica* LPCAT containing M136V and T389C mutations | | 77 (512 aa) |
| Mutant YlLPCAT (N144A_F390S), *Y. lipolytica* LPCAT containing N144A and F390S mutations | | 78 (512 aa) |
| Mutant YlLPCAT (G148A_F390S), *Y. lipolytica* LPCAT containing G148A and F390S mutations | | 79 (512 aa) |
| Mutant YlLPCAT (G148N_T382I), *Y. lipolytica* LPCAT containing G148N and T382I mutations | | 80 (512 aa) |
| Mutant YlLPCAT (G148N_F390S), *Y. lipolytica* LPCAT containing G148N and F390S mutations | | 81 (512 aa) |
| MBOAT Motif I of YlLPCAT | | 82 (17 aa) |
| MBOAT Motif II of YlLPCAT | | 83 (15 aa) |
| Mutant YlLPCAT, comprising a mutant Motif I and/or a | | 84 |

TABLE 1-continued

Summary of Gene and Protein SEQ ID Numbers

| Description | Nucleic acid SEQ ID NO. | Protein SEQ ID NO. |
|---|---|---|
| mutant Motif II | | (512 aa) |
| *Scheffersomyces stipitis* Sou2 sorbitol utilization protein | | 85 (285 aa) |
| *Candida dubliniensis* Sou2 sorbitol utilization protein | | 86 (280 aa) |
| *Glarea lozoyensis* Sou2 sorbitol utilization protein | | 87 (160 aa) |
| *Enterobacter hormaechei* Sou2 sorbitol utilization protein | | 88 (254 aa) |
| *Candida orthopsilosis* Sou2 sorbitol utilization protein | | 89 (281 aa) |
| *Mycobacterium smegmatis* Sou2 sorbitol utilization protein | | 90 (255 aa) |
| *Gaeumannomyces graminis* Sou2 sorbitol utilization protein | | 91 (265 aa) |
| *Neurospora tetrasperma* Sou2 sorbitol utilization protein | | 92 (292 aa) |
| *Metarhizium anisopliae* Sou2 sorbitol utilization protein | | 93 (292 aa) |
| *Cordyceps militaris* Sou2 sorbitol utilization protein | | 94 (292 aa) |
| *Metarhizium acridum* Sou2 sorbitol utilization protein | | 95 (255 aa) |
| *Verticillium dahliae* Sou2 sorbitol utilization protein | | 96 (298 aa) |
| *Paracoccidioides brasiliensis* Sou2 sorbitol utilization protein | | 97 (293 aa) |
| *Magnaporthe oryzae* Sou2 sorbitol utilization protein | | 98 (292 aa) |
| *Uncinocarpus reesii* Sou2 sorbitol utilization protein | | 99 (295 aa) |
| *Neurospora crassa* Sou2 sorbitol utilization protein | | 100 (292 aa) |
| *Lodderomyces elongisporus* Sou2 sorbitol utilization protein | | 101 (284 aa) |
| *Aspergillus niger* Sou2 sorbitol utilization protein | | 102 (293 aa) |
| *Penicillium chrysogenum* Sou2 sorbitol utilization protein | | 103 (266 aa) |
| *Debaryomyces hansenii* Sou2 sorbitol utilization protein | | 104 (289 aa) |
| *Candida parapsilosis* Sou2 sorbitol utilization protein | | 105 (281 aa) |
| *Bifidobacterium dentium* Sou2 sorbitol utilization protein | | 106 (287 aa) |

DETAILED DESCRIPTION OF THE INVENTION

All patents, patent applications, and publications cited are incorporated herein by reference in their entirety.

As used herein the term "invention" or "present invention" is intended to refer to all aspects and embodiments of the invention as described in the claims and specification herein and should not be read so as to be limited to any particular embodiment or aspect.

The terms "SOU2", "SOU2 gene" and "endogenous polynucleotide sequence encoding Sou2 sorbitol utilization protein" are used interchangeably herein. The "Sou2 sorbitol utilization protein" (Sou2p) is encoded by the SOU2 gene.

The Sou2 sorbitol utilization protein of *Y. lipolytica* (SEQ ID NO:10) has about 66% amino acid sequence identity (according to a BLAST alignment) with *Candida albicans* Sou2 sorbitol utilization protein (SEQ ID NO:30). Thus, a Sou2 sorbitol utilization protein in certain embodiments has at least 60% amino acid sequence identity with SEQ ID NO:30. A Sou2 sorbitol utilization protein may alternatively have at least 65%, 70%, 75%, or 80% amino acid sequence identity with SEQ ID NO:30.

The term "lipids" as used herein refers to any fat-soluble (i.e., lipophilic), naturally-occurring molecule. A general overview of lipids is provided in U.S. Pat. Appl. Publ. No. 2009-0093543 (see Table 2 therein).

The term "oil" as used herein refers to a lipid substance that is liquid at 25° C.; oil is hydrophobic and soluble in organic solvents. In oleaginous organisms, oil constitutes a major part of the total lipids. Oil is composed primarily of triacylglycerols, but may also contain other neutral lipids, phospholipids and free fatty acids. The fatty acid composition in the oil and the fatty acid composition of the total lipids are generally similar; thus, an increase or decrease in the concentration of fatty acids in the total lipids will correspond with an increase or decrease in the concentration of fatty acids in the oil, and vice versa. The terms "oil", "total lipids", "total lipid content", "total fatty acids", and "total fatty acid methyl esters" are used interchangeable herein.

The term "triacylglycerols" (TAG or TAGs) as used herein refers to neutral lipids composed of three fatty acyl residues esterified to a glycerol molecule. TAGs can contain long-chain polyunsaturated and saturated fatty acids, as well as shorter chain unsaturated and saturated fatty acids.

The term "total fatty acids" (TFA or TFAs) as used herein refers to the sum of all cellular fatty acids that can be derivatized to fatty acid methyl esters (FAME or FAMES) by base transesterification of a given sample, which may be biomass or oil, for example. Thus, total fatty acids include fatty acids from neutral lipids (monoacylglycerols, diacylglycerols, TAGs) and polar lipids (e.g., phosphatidylcholine, phosphatidylethanolamine).

The term "total lipid content" of cells as used herein refers to a measure of TFAs as a percent of the dry cell weight (DCW) and can be expressed as "TFAs % DCW"; e.g., milligrams TFA per 100 milligrams of DCW. For example, 50 TFAs % DCW means that 50% of the dry cell weight is lipid or oil. Total lipid content can be approximated as a measure of FAMEs as a percent of the DCW (FAMEs % DCW).

The concentration of a fatty acid in the total lipids is expressed herein as a weight percent of TFAs (% TFAs); e.g., milligrams of a given fatty acid per 100 milligrams of TFAs. Unless otherwise specifically stated herein, reference to the percent of a given fatty acid with respect to total lipids or oil is equivalent to the concentration of the fatty acid as % TFAs (e.g., % EPA of total lipids or oil is equivalent to EPA % TFAs). For example, 50% by weight of EPA in the total fatty acids of an oil is expressed as 50 EPA % TFAs.

It can also useful to express the content of a given fatty acid(s) in a cell as its weight percent of the dry cell weight (% DCW). A measure of total EPA production (EPA % DCW), for example, can be determined using the formula: (EPA % TFAs)*(TFAs % DCW)]/100. A measurement of 30% by weight EPA in the dry cell weight, for example, is expressed by 30 EPA % DCW. The content of a fatty acid(s) such as EPA in the dry cell weight can be approximated using the formula: (EPA % FAMEs)*(FAMEs % DCW)]/100.

The terms "lipid profile", "lipid composition", and "fatty acid profile" are used interchangeably herein and refer to the amount of each individual fatty acid contained in the total lipids or oil, wherein the amount is expressed as a wt % of TFAs. The sum of each individual fatty acid present in the mixture should be 100.

The term "oleaginous" as used herein describes those organisms that tend to store their energy source in the form of lipid (Weete, In: Fungal Lipid Biochemistry, 2nd Ed., Plenum, 1980). An oleaginous microorganism can comprise, or can accumulate or produce, about 25% or more of its dry cell weight as oil (i.e., ≥25 TFAs % DCW).

The term "oleaginous yeast" as used in certain embodiments refers to those microorganisms classified as yeasts that can produce a high amount of oil. Examples of oleaginous yeast include, for example, the genera *Yarrowia, Candida, Rhodotorula, Rhodosporidium, Cryptococcus, Trichosporon* and *Lipomyces*. Preferably, an oleaginous yeast can accumulate in excess of about 25% of its dry cell weight as oil.

The term "fatty acids" as used herein refers to long-chain aliphatic acids (alkanoic acids) of varying chain lengths, from about $C_{12}$ to $C_{22}$. The predominant chain lengths are between $C_{16}$ and $C_{22}$. The structure of a fatty acid is represented by a simple notation system of "X:Y", where X is the total number of carbon (C) atoms in the fatty acid and Y is the number of double bonds. Additional details concerning the differentiation between "saturated fatty acids" versus "unsaturated fatty acids", "monounsaturated fatty acids" versus "polyunsaturated fatty acids" (PUFAs), and "omega-6 fatty acids" (n-6) versus "omega-3 fatty acids" (n-3) are provided in U.S. Pat. No. 7,238,482, which is incorporated herein by reference.

The nomenclature used to describe PUFAs herein is given in Table 2. In the "Shorthand Notation" column, the omega-reference system is used to indicate the number of carbons, the number of double bonds and the position of the double bond closest to the omega carbon, counting from the omega carbon. The remainder of Table 2 summarizes the common names of omega-3 and omega-6 fatty acids, abbreviations that will be used throughout the specification, and the chemical name of each compound.

TABLE 2

Nomenclature of Polyunsaturated Fatty Acids

| Common Name | Abbreviation | Chemical Name | Shorthand Notation |
|---|---|---|---|
| Myristic | — | tetradecanoic | 14:0 |
| Palmitic | — | hexadecanoic | 16:0 |
| Palmitoleic | — | 9-hexadecenoic | 16:1 |
| Stearic | — | octadecanoic | 18:0 |
| Oleic | — | cis-9-octadecenoic | 18:1 |
| Linoleic | LA | cis-9,12-octadecadienoic | 18:2 n-6 |
| gamma-Linolenic | GLA | cis-6,9,12-octadecatrienoic | 18:3 n-6 |
| Eicosadienoic | EDA | cis-11,14-eicosadienoic | 20:2 n-6 |
| Dihomo-gamma-Linolenic | DGLA | cis-8,11,14-eicosatrienoic | 20:3 n-6 |
| Arachidonic | ARA | cis-5,8,11,14-eicosatetraenoic | 20:4 n-6 |
| alpha-Linolenic | ALA | cis-9,12,15-octadecatrienoic | 18:3 n-3 |
| Stearidonic | STA | cis-6,9,12,15-octadecatetraenoic | 18:4 n-3 |
| Eicosatrienoic | ETrA | cis-11,14,17-eicosatrienoic | 20:3 n-3 |
| Eicosatetraenoic | ETA | cis-8,11,14,17-eicosatetraenoic | 20:4 n-3 |
| Eicosapentaenoic | EPA | cis-5,8,11,14,17-eicosapentaenoic | 20:5 n-3 |
| Docosatetraenoic | DTA | cis-7,10,13,16-docosatetraenoic | 22:4 n-6 |
| Docosapentaenoic | DPAn-6 | cis-4,7,10,13,16-docosapentaenoic | 22:5 n-6 |
| Docosapentaenoic | DPA | cis-7,10,13,16,19-docosapentaenoic | 22:5 n-3 |
| Docosahexaenoic | DHA | cis-4,7,10,13,16,19-docosahexaenoic | 22:6 n-3 |

The term "PUFA biosynthetic pathway" as used herein refers to a metabolic pathway or process that converts oleic acid to omega-6 fatty acids such as LA, EDA, GLA, DGLA, ARA, DTA and DPAn-6 and omega-3 fatty acids such as ALA, STA, ETrA, ETA, EPA, DPA and DHA. This pathway is described in the literature (e.g., U.S. Pat. No. 7,932,077; U.S. Pat. Appl. Publ. No. 2009-0093543-A1). Briefly, a PUFA biosynthetic pathway involves elongation of the carbon chain through the addition of carbon atoms and desaturation of the molecule through the addition of double bonds, via a series of special elongation and desaturation enzymes termed "PUFA biosynthetic pathway enzymes". More specifically, "PUFA biosynthetic pathway enzymes" refer to any of the following enzymes (and genes encoding these enzymes) associated with the biosynthesis of a PUFA, including: delta-4 desaturase, delta-5 desaturase, delta-6 desaturase, delta-12 desaturase, delta-15 desaturase, delta-17 desaturase, delta-9 desaturase, delta-8 desaturase, delta-9 elongase, $C_{14/16}$ elongase, $C_{16/18}$ elongase, $C_{18/20}$ elongase and/or $C_{20/22}$ elongase. FIG. 1 illustrates certain PUFA biosynthetic pathways.

A PUFA biosynthetic pathway may be "engineered" in certain embodiments. Such a pathway would comprise one or more foreign or heterologous PUFA biosynthetic pathway enzymes. Such enzymes could be expressed in the cell through the introduction of one or more transgenes encoding the enzymes.

The terms "conversion efficiency" and "percent substrate conversion" herein refer to the efficiency by which a particular enzyme, such as a desaturase or elongase, can convert its respective substrate to product. The conversion efficiency is measured according to the following formula: ([product]/[substrate+product])*100, where "product" refers to the immediate product and all products derived from it. More specifically, since each PUFA biosynthetic pathway enzyme rarely functions with 100% efficiency to convert substrate to product, the final lipid profile of unpurified oils produced in a host cell will typically be a mixture of various PUFAs consisting of the desired omega-3/omega-6 fatty acid, as well as various upstream intermediary PUFAs.

The term "$C_{18}$ to $C_{20}$ elongation conversion efficiency" refers herein to the efficiency by which $C_{18/20}$ elongases can convert $C_{18}$ substrates (i.e., LA, ALA, GLA, STA, etc.) to $C_{20}$ products (i.e., EDA, ETrA, DGLA, ETA, EPA, etc.). These $C_{18/20}$ elongases can be either delta-9 elongases or delta-6 elongases.

The terms "delta-9 elongation conversion efficiency" and "delta-9 elongase conversion efficiency" herein refer to the efficiency by which delta-9 elongase can convert $C_{18}$ substrates (e.g., LA, ALA) to $C_{20}$ products (e.g., EDA, ETrA, DGLA, ETA, ARA, EPA). Delta-9 elongase conversion efficiency is referred to herein as "% Cony." or "d9e CE (%)".

The terms "membrane-bound O-acyltransferase motif" and "MBOAT motif" are used interchangeably herein. MBOAT motifs are contained in LPLATs such as LPCAT and play a role in the enzymatic activity of these proteins (Shindou et al., 2009, *Biochem. Biophys. Res. Comm.* 383:320-325; U.S. Pat. No. 7,732,155; U.S. Pat. Appl. Publ. Nos. 2008-0145867 and 2010-0317882).

The terms "polynucleotide", "polynucleotide sequence", "nucleic acid sequence", "nucleic acid fragment" and "isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

The term "isolated" as used herein refers to a polynucleotide or polypeptide molecule that has been completely or partially purified from its native source. In some instances, the isolated polynucleotide or polypeptide molecule is part of a greater composition, buffer system or reagent mix. For example, the isolated polynucleotide or polypeptide molecule can be comprised within a cell or organism in a heterologous manner.

The term "gene" as used herein refers to a polynucleotide sequence that expresses a protein, and which may refer to the coding region alone or may include regulatory sequences upstream and/or downstream to the coding region (e.g., 5' untranslated regions upstream of the transcription start site of the coding region). A gene that is "native" or "endogenous" refers to a gene as found in nature with its own regulatory sequences; this gene is located in its natural location in the genome of an organism. An "endogenous polynucleotide encoding" a particular protein is an example of an endogenous gene. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A "foreign" or "heterologous" gene herein refers to a gene that is introduced into the host organism by gene transfer. Foreign genes can comprise native genes inserted into a non-native organism, native genes introduced into a new location within the native host, or chimeric genes. The polynucleotide sequences in certain embodiments disclosed herein are heterologous. A "transgene" is a gene that has been introduced into the genome by a transformation procedure. A "codon-optimized gene" is a gene having its frequency of codon usage designed to mimic the frequency of preferred codon usage of the host cell.

"Coding sequence" as used herein refers to a DNA sequence that codes for a specific amino acid sequence. "Regulatory sequences" as used herein refer to nucleotide sequences located upstream of the coding sequence's transcription start site, 5' untranslated regions and 3' non-coding regions, and which may influence the transcription, RNA processing or stability, or translation of the associated coding sequence. Regulatory sequences may include promoters, enhancers, silencers, 5' untranslated leader sequence, introns, polyadenylation recognition sequences, RNA processing sites, effector binding sites, stem-loop structures and other elements involved in regulation of gene expression.

A "promoter" as used herein refers to a DNA sequence capable of controlling the expression of a coding sequence or functional RNA. In general, a promoter sequence is 5' upstream of the transcription start site of a gene. Promoters may be derived in their entirety from a native gene, or be composed of different elements derived from different promoters found in nature, or even comprise synthetic DNA segments. Promoters that cause a gene to be expressed in most cell types at most times are commonly referred to as "constitutive promoters".

The terms "3' non-coding sequence", "transcription terminator" and "terminator" as used herein refer to DNA sequences located 3' downstream of a coding sequence. This includes polyadenylation recognition sequences and other sequences encoding regulatory signals capable of affecting mRNA processing or gene expression.

The term "expression" as used herein refers to the transcription from a gene to produce RNA such as messenger RNA (mRNA). This term can also refer to translation of mRNA into a polypeptide.

When used to describe the expression of a gene or polynucleotide sequence, the terms "down-regulation", "disruption", and "inhibition" are used interchangeably herein to refer to instances when the transcription of the polynucleotide sequence is reduced or eliminated. This results in the reduction or elimination of RNA transcripts from the polynucleotide sequence, which results in a reduction or elimination of protein expression derived from the polynucleotide sequence. Alternatively, down-regulation can refer to instances where protein translation from transcripts produced by the polynucleotide sequence is reduced or eliminated. Alternatively still, down-regulation can refer to instances where a protein expressed by the polynucleotide sequence has reduced activity. The reduction in any of the above processes (transcription, translation, protein activity) in a cell can by about 40%, 50%, 60%, 70%, 80%, 90%, 95%, or 100% relative to the transcription, translation, or protein activity of a suitable control cell. Down-regulation can be the result of a mutation as disclosed herein (e.g., knock-out) or through the use of antisense or RNAi technology, for example.

The terms "control cell" and "suitable control cell" are used interchangeably herein and may be referenced with respect to a cell in which a particular modification (e.g., over-expression of a polynucleotide, down-regulation of a polynucleotide) has been made (i.e., an "experimental cell"). A control cell may be any cell that does not have or does not express the particular modification of the experimental cell. Thus, a control cell may be an untransformed wild type cell or may be genetically transformed but does not express the genetic transformation. For example, a control cell may be a direct parent of the experimental cell, which direct parent cell does not have the particular modification that is in the experimental cell. Alternatively, a control cell may be a parent of the experimental cell that is removed by one or more generations. Alternatively still, a control cell may be a sibling of the experimental cell, which sibling does not comprise the particular modification that is present in the experimental cell. A sibling cell that could serve as a control cell could be a cell in which a plasmid for protein over-expression is inserted, but not expressed, in the sibling cell, whereas the plasmid is expressed in the experimental cell. It is well within the skill in the art to determine if a cell can be a control cell.

The term "increased" as used herein means having a greater quantity, for example a quantity only slightly greater than the original quantity, or for example a quantity in large excess compared to the original quantity, and including all quantities in between. Alternatively, "increased" may refer to a quantity or activity that is at least 1%, 2%, 3%, 4%, 5%, 6%, 7%, 8%, 9%, 10%, 11%, 12%, 13%, 14%, 15%, 16%, 17%, 18%, 19% or 20% more than the quantity or activity for which the increased quantity or activity is being compared. The terms "increased", "greater than", and "improved" are used interchangeably herein. The term "increased" can be used to characterize the expression of a polynucleotide encoding a protein, for example, where "increased expression" can also mean "over-expression".

The term "operably linked" as used herein refers to the association of two or more nucleic acid sequences such that that the function of one is affected by the other. For example, a promoter is operably linked with a coding sequence when it is capable of affecting the expression of that coding sequence. That is, the coding sequence is under the transcriptional control of the promoter. Coding sequences can be operably linked to regulatory sequences in sense or antisense orientation.

The term "recombinant" as used herein refers to an artificial combination of two otherwise separated segments of sequence, e.g., by chemical synthesis or by the manipulation of isolated segments of nucleic acids by genetic engineering techniques. The terms "recombinant", "transgenic", "transformed", "engineered" or "modified for exogenous gene expression" are used interchangeably herein.

The term "transformation" as used herein refers to the transfer of a nucleic acid molecule into a host organism. The nucleic acid molecule may be a plasmid that replicates autonomously, or it may integrate into the genome of the host organism. Host organisms containing the transformed nucleic acid fragments are referred to as "transgenic" or "recombinant" or "transformed" organisms or "transformants".

The terms "microbial cell" and "microbial organism" are used interchangeably herein and refer to a microorganism capable of receiving foreign or heterologous genes and capable of expressing those genes. A "recombinant microbial cell" refers to a microbial cell that has been recombinantly engineered.

The term "expression cassette" as used herein refers to a polynucleotide sequence comprising a promoter and the coding sequence of a selected gene as well as some other regulatory sequences preceding (5' non-coding sequences) and following (3' non-coding sequences) the coding sequence that are required for expression of the selected gene product. Thus, an expression cassette is typically composed of: 1) a promoter; 2) a coding sequence (i.e., open reading frame [ORF]); and 3) a terminator that usually contains a polyadenylation site. Different expression cassettes can be transformed into different organisms including bacteria, yeast, plants and mammalian cells, as long as the correct regulatory sequences are used for each host. As used herein, an "open reading frame" refers to a sequence of DNA or RNA that encodes the amino acid sequence of a polypeptide. The open reading frame begins at the translation initiation start codon (ATG) and ends at the codon immediately 5' to the translation termination codon (stop codon).

The terms "sequence identity" or "identity" as used herein with respect to nucleic acid or polypeptide sequences refer to the nucleic acid bases or amino acid residues in two sequences that are the same when aligned for maximum correspondence over a specified comparison window. Thus, "percentage of sequence identity" or "percent identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity.

The Basic Local Alignment Search Tool (BLAST) algorithm, which is available online at the National Center for Biotechnology Information (NCBI) website, may be used, for example, to measure percent identity between or among two or more of the polynucleotide sequences (BLASTN algorithm) or polypeptide sequences (BLASTP algorithm) disclosed herein. Alternatively, percent identity between sequences may be performed using a Clustal algorithm (e.g., ClustalW or ClustalV). For multiple alignments using a Clustal method of alignment, the default values may correspond to GAP PENALTY=10 and GAP LENGTH PENALTY=10. Default parameters for pairwise alignments and calculation of percent identity of protein sequences using a Clustal method may be KTUPLE=1, GAP PENALTY=3, WINDOW=5 and DIAGONALS SAVED=5. For nucleic acids, these parameters may be KTUPLE=2, GAP PENALTY=5, WINDOW=4 and DIAGONALS SAVED=4.

Various polypeptide amino acid sequences and polynucleotide sequences are disclosed herein as features of certain embodiments of the disclosed invention. Variants of these sequences that are at least about 70-85%, 85-90%, or 90%-95% identical to the sequences disclosed herein may be used in certain embodiments. Alternatively, a variant amino acid sequence or polynucleotide sequence in certain embodiments can have at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identity with a sequence disclosed herein. The variant amino acid sequence or polynucleotide sequence has the same function of the disclosed sequence, or at least about 85%, 86%, 87%, 88%, 89%, 90%, 91%, 92%, 93%, 94%, 95%, 96%, 97%, 98%, or 99% of the function of the disclosed sequence.

As discussed in the Background section (above), previous work has shown that as improvements are made in developing transgenic *Y. lipolytica* strains for enhanced EPA and/or oil production, an inverse correlation generally arises between the total amount of oil produced and the amount of EPA present in the total fatty acids of the oil. Strains that have been engineered to produce higher amounts of oil on a dry cell weight basis generally have lower amounts of EPA as a percentage of the fatty acids in the oil.

The Examples disclosed herein show that certain modifications in *Y. lipolytica* strains maintain or increase total oil content in a manner that does not decrease the EPA content in the total fatty acids of the oil. Interestingly, such modified *Y. lipolytica* strains are capable of producing oil comprising at least about 28 percent EPA measured as a weight percent of the dry cell weight of each strain (i.e., 28 EPA % DCW).

Thus, one aspect of the disclosed invention is drawn to a recombinant microbial cell that produces an oil comprising at least about 28 percent EPA measured as a weight percent of dry cell weight. The recombinant microbial cell can be a cell of a yeast, mold, fungus, oomycete, bacteria, algae, stramenopile, or protist (e.g., euglenoid). In certain embodiments, the recombinant microbial cell is an oleaginous microbial cell, such as an oleaginous yeast cell. Examples of oleaginous yeast include species of the genera *Yarrowia, Candida, Rhodotorula, Rhodosporidium, Cryptococcus, Trichosporon* and *Lipomyces*. More specific examples of oleaginous yeast include *Rhodosporidium toruloides, Lipomyces starkeyii, L. lipoferus, Candida revkaufi, C. pulcherrima, C. tropicalis, C. utilis, Trichosporon pullans, T. cutaneum, Rhodotorula glutinus* and *R. graminis*, for example. Examples of fungal cells in certain embodiments include species of the genera *Fusarium* (e.g., *Fusarium lateritium*), *Mortierella* (e.g., *Mortierella alpina*) and *Mucor* (e.g., *Mucor rouxii* and *Mucor circinelloides*). The microbial cell can be of the genera *Entomophthora, Pythium* and *Porphyridium* in other embodiments of the disclosed invention.

A *Yarrowia* cell can be the oleaginous yeast cell in certain embodiments of the disclosed invention. Examples of *Yarrowia* cells that can be modified to produce an oil with at least 28% EPA as a percent of dry cell weight include the following wild type *Y. lipolytica* isolates available from the American Type Culture Collection (ATCC, Manassas, Va.): strain designations ATCC #20362, #8862, #8661, #8662, #9773, #15586, #16617, #16618, #18942, #18943, #18944, #18945, #20114, #20177, #20182, #20225, #20226, #20228, #20327, #20255, #20287, #20297, #20315, #20320, #20324, #20336, #20341, #20346, #20348, #20363, #20364, #20372, #20373, #20383.

The recombinant microbial cell in certain embodiments may be one that has been genetically engineered to produce an increased amount of total lipids and/or fatty acids such as PUFAs. For example, a fatty acid or PUFA biosynthetic pathway, or portion thereof, may be introduced to the organism by inserting coding sequences for certain pathway enzymes, such as fatty acid desaturases and elongases. Examples of PUFA biosynthetic pathways that can be used herein are shown in FIG. 1. One or a combination of the following enzymes may be genetically introduced to the oleaginous yeast cell to provide a PUFA biosynthetic pathway therein: delta-4 desaturase, delta-5 desaturase, delta-6 desaturase, delta-12 desaturase, delta-15 desaturase, delta-17 desaturase, delta-9 desaturase, delta-8 desaturase, delta-9 elongase, $C_{14/16}$ elongase, $C_{16/18}$ elongase, $C_{18/20}$ elongase, $C_{20/22}$ elongase. One or more of these enzymes may be from a heterologous source. Example PUFA biosynthetic pathways may contain both a delta-9 elongase and delta-8 desaturase (e.g., refer to U.S. Pat. Appl. Publ. No. 2011-0055973, herein incorporated by reference), or both a delta-6 desaturase and delta-6 elongase. Alternatively, the recombinant microbial cell may be modified to have increased total lipids and/or PUFA levels by introducing or deleting genes, other than those encoding desaturases or elongases, that regulate fatty acid biosynthesis.

The PUFAs generated by the PUFA biosynthetic pathway expressed by a recombinant microbial cell of the disclosed invention may include omega-3 and/or omega-6 PUFAs; examples of such PUFAs are linoleic acid (LA), gamma-linolenic acid (GLA), dihomo-gamma-linolenic acid (DGLA), arachidonic acid (ARA), alpha-linolenic acid (ALA), stearidonic acid (STA), eicosatetraenoic acid (ETA), eicosapentaenoic acid (EPA), omega-6 docosapentaenoic acid (DPAn-6), omega-3 docosapentaenoic acid (DPAn-3), eicosadienoic acid (EDA), eicosatrienoic acid (ETrA), docosatetraenoic acid (DTA) and docosahexaenoic acid (DHA). One or more of these PUFAs in the recombinant microbial cell may be produced from a substrate that is endogenously produced by the recombinant microbial cell or exogenously supplied to the recombinant microbial cell.

The recombinant microbial cell of the disclosed invention may be a *Yarrowia* strain containing a PUFA biosynthetic pathway that produces a PUFA in addition to linoleic acid. For example, the *Yarrowia* cell may contain enzymes for producing alpha-linolenic acid, gamma-linolenic acid, and/or eicosadienoic acid, none of which PUFAs are produced in wild type *Yarrowia*. Beyond the fatty acid biosynthetic pathway enzymes normally expressed in *Yarrowia* to generate linoleic acid, a delta-9 elongase, delta-6 desaturase, and/or delta-15 desaturase may be exogenously expressed for production of eicosadienoic acid, gamma-linolenic acid, and/or alpha-linolenic acid, respectively. These three PUFAs can be further modified (desaturation and/or elongation) to produce downstream PUFAs by expressing additional PUFA pathway enzymes.

The recombinant microbial cell used in certain embodiments of the disclosed invention may be one that has been genetically engineered to produce an elevated amount of lipids compared to its wild type form. Examples of such genetically engineered cells are certain *Yarrowia* strains disclosed in U.S. Pat. Appl. Publ. Nos. 2009-0093543, 2010-0317072 and 2012-0052537, which are herein incorporated by reference.

The recombinant microbial cell in certain embodiments of the disclosed invention comprises or produces an oil comprising at least about 28% EPA measured as a weight percent of the dry cell weight of the microbial cell. Alternatively, the recombinant microbial cell comprises or produces an oil comprising at least about 30% EPA measured as a weight percent of the dry cell weight of the microbial cell. Still, in other embodiments of the disclosed invention, the recombinant microbial cell produces an oil comprising at least about 28%, 28.5%, 29%, 29.5%, 30%, 30.5%, 31%, 31.5%, 32%, 32.5%, 33%, 33.5%, 34%, 34.5%, or 35% EPA measured as a weight percent of the dry cell weight of the microbial cell.

An increase in the level of EPA measured as a weight percent of the dry cell weight (EPA % DCW) of the recombinant microbial cell in certain embodiments may be at least about 1%, 2%, 3%, 4%, 5%, 6%, 7%, 8%, 9%, 10%, 11%, 12%, 13%, 14%, 15%, 16%, 17%, or 18% over the EPA % DCW of a control cell. In certain embodiments, this increase in EPA % DCW is coupled with a maintenance or increase in oil content (TFAs % DCW) relative to the oil content of a control cell. A maintenance in oil content in certain embodiments refers to less than about a −3%, −2%, −1%, or 0% change in oil content of the recombinant microbial cell relative to the oil content of a control cell. An increase in oil content in certain embodiments refers to an increase of more than about 3%, 4%, 5%, 6%, 7%, 8%, 9%, or 10% over the oil content of a control cell.

The recombinant microbial cell in certain embodiments of the disclosed invention has an oil content (TFAs % DCW) of at least about 50%, 51%, 52%, 53%, 54%, 55%, 56%, 57%, 58%, 59%, 60%, 61%, 62%, 63%, 64%, or 65% of the dry cell weight of the microbial cell.

The recombinant microbial cell in certain embodiments of the disclosed invention has an EPA content in the total fatty acids of the oil (EPA % TFAs) of at least about 50%, 51%, 52%, 53%, 54%, 55%, 56%, 57%, 58%, 59%, 60%, 61%, 62%, 63%, 64%, or 65% by weight.

The recombinant microbial cell in certain embodiments of the disclosed invention produces oil that is devoid of gamma-linolenic acid (GLA). By devoid, it is meant that GLA is below the threshold of detection in the oil, or alternatively, it is meant that the amount of GLA in the oil is less than 0.1% by weight of the TFAs of the oil.

The recombinant microbial cell in certain embodiments of the disclosed invention has a stearic acid (C18:0) content in the total fatty acids of the oil (18:0% TFAs) that is less than about 2.5%, 2.4%, 2.3%, 2.2%, 2.1%, 1.9%, 1.8%, 1.7%, 1.6%, 1.5%, 1.4%, 1.3%, 1.2%, 1.1%, or 1.0% by weight of the TFAs of the oil.

In certain embodiments of the disclosed invention, the dry cell weight of the recombinant microbial cell grown in a culture is at least about 5.5 grams per liter of the culture. Alternatively, the dry cell weight of the recombinant microbial cell grown in a culture is at least 5.0, 5.2, 5.4, 5.6, 5.8, 6.0, 6.2, 6.4, 6.6, 6.8, 7.0, or 7.2 grams per liter of the culture. The dry cell weight of the microbial cell can be measured in certain embodiments by growing the microbial cell in a culture that is nitrogen-limited for a period of about 120 hours. Such a culture may comprise glucose as the only carbon source or as the predominant carbon source (e.g., other carbon sources less than 5% by weight of the culture). The starting inoculum of the culture for determining dry cell weight of the recombinant microbial cell can be from a culture in which the cells have grown to an $OD_{600}$ of about 0.3. All the cells of a certain volume (e.g., 6 mL) of this $OD_{600}$ ~0.3 culture are then used to inoculate a volume (e.g., 25 mL) of a nitrogen-limited culture medium. This culture is then incubated for a period of about 120 hours, after which the dry cell weight of the culture is determined.

An increase in the dry cell weight of the recombinant microbial cell in certain embodiments may be at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, or 38% over the dry cell weight of a control cell. The dry cell weights can be measured as above, for example, in making this comparison.

The recombinant microbial cell in certain embodiments of the disclosed invention comprises at least one polynucleotide sequence encoding an acyl-CoA:lysophosphatidylcholine acyltransferase (LPCAT) comprising at least one amino acid mutation in a membrane-bound O-acyltransferase (MBOAT) motif, wherein the LPCAT has LPCAT activity. The polynucleotide encoding the LPCAT is operably linked to at least one regulatory sequence. Thus, certain embodiments are drawn to a recombinant microbial cell that produces an oil comprising at least 28 percent eicosapentaenoic acid (EPA) measured as a weight percent of dry cell weight, wherein the cell comprises at least one polynucleotide sequence encoding an LPCAT comprising at least one amino acid mutation in an MBOAT motif, wherein the LPCAT has LPCAT activity.

The term "acyl-CoA:lysophosphatidylcholine acyltransferase" (LPCAT, EC 2.3.1.23) as used herein refers to an enzyme that catalyzes the following enzymatic reaction: acyl-CoA+1-acyl-sn-glycero-3-phosphocholine=CoA+1,2-diacyl-sn-glycero-3-phosphocholine. LPCAT activity has been described in two structurally distinct protein families, namely the LPAAT protein family (Hishikawa et al., 2008, *Proc. Natl. Acad. Sci. U.S.A.* 105:2830-2835; Intl. App. Publ. No. WO 2004/076617) and the Ale1 protein family (Tamaki et al., Ståhl et al., Chen et al., Benghezal et al., Riekhof et al.).

Polynucleotide sequences encoding mutant LPCAT enzymes as disclosed in U.S. Pat. Appl. No. 61/661,623 (incorporated herein by reference) may be used in certain embodiments disclosed herein. The mutant LPCAT is non-naturally occurring.

Membrane-bound O-acyltransferase (MBOAT) motifs are contained in LPLATs such as LPCAT and play a role in the enzymatic activity of these proteins. Examples of MBOAT motifs that can be mutated in certain embodiments of the disclosed invention are disclosed in Shindou et al. (2009, *Biochem. Biophys. Res. Comm.* 383:320-325), U.S. Pat. No. 7,732,155, and U.S. Pat. Appl. Publ. Nos. 2008-0145867 and 2010-0317882, which are incorporated herein by reference. In certain embodiments, either one or two MBOAT motifs of the LPCAT enzyme are mutated. Since the mutant LPCAT has LPCAT activity, the mutation(s) in the MBOAT motif(s) should not significantly reduce the activity of the enzyme.

The mutated LPCAT in certain embodiments of the disclosed invention is a *Yarrowia lipolytica* LPCAT (YlLPCAT, SEQ ID NO:40) that has been mutated. The terms "Motif I" and "Motif II" are used herein to refer to two different MBOAT motifs of YlLPCAT that can be mutated in certain embodiments. Motif I is represented by the amino acid sequence MVLCMKLSSFGWNVYDG (SEQ ID NO:82), which is located at positions 132-148 of SEQ ID NO:40, whereas Motif II is represented by the amino acid sequence SAFWHGTRPGYYLTF (SEQ ID NO:83), which is located at positions 376-390 of SEQ ID NO:40; both these sequences are contained in wild type YlLPCAT.

Motif I and/or Motif II of YlLPCAT (SEQ ID NO:40) can be mutated in certain embodiments. Alternatively, Motif I and/or Motif II can be mutated and be comprised within an amino acid sequence that is at least 90%, or 95%, identical to SEQ ID NO:40 and has LPCAT activity. The mutations may be, for example, one or more amino acid substitutions, deletions, and/or insertions in Motif I (SEQ ID NO:40 residues 132, 133, 134, 135, 136, 137, 138, 139, 140, 141, 142, 143, 144, 145, 146, 147, 148) and/or Motif II (SEQ ID NO:40 residues 376, 377, 378, 382, 383, 384, 385, 386, 387, 389, 390). Substitution mutations may be any of those described herein, for example. In alternative embodiments, mutations in Motif II can be to residues 376 to 378 and 382-390 of SEQ ID NO:40. Preferably, the activity of a mutant LPCAT polypeptide encoded by a polynucleotide in certain embodiments is equal to or greater than the activity of wild type YlLPCAT (e.g., SEQ ID NO:40). Such activity can be determined by comparing the EPA % TFAs and/or d9e CE (%) in a recombinant microbial cell over-expressing a mutant LPCAT with the EPA % TFAs and/or d9e CE (%) in a control cell.

In the below examples, YlLPCAT mutants having equivalent or increased activity were generated by mutating amino acid residues 133, 134, 135, 136, 137, 138, 139, 140, 141, 142, 143, 144, 145, 146, 147 or 148 within Motif I, thereby demonstrating that only the methionine residue at position 132 of SEQ ID NO:40 may be unable to tolerate variation.

Similarly, YILPCAT mutants having equivalent or increased activity were generated by mutating amino acid residues 378, 382, 383, 385, 388, 389 or 390 within Motif II, thereby demonstrating that the serine, alanine, proline and with tyrosines of SEQ ID NO:83 may be unable to tolerate variation. The amino acids at residues 379-381 (i.e., WHG) of SEQ ID NO:40 were not subjected to mutation, since the histidine of other LPCATs corresponding to H380 of YILPCAT has been reported to be a likely active site residue (Lee et al., 2008, *Mol. Biol. Cell* 19:1174-1184).

Thus, in certain embodiments of the disclosed invention, the mutant LPCAT comprises an amino acid sequence as set forth in SEQ ID NO:84, wherein SEQ ID NO:84 differs from SEQ ID NO:40 (YILPCAT) by at least one amino acid mutation, wherein:

(i) the amino acid mutation is an amino acid substitution at a residue selected from the group consisting of: residue 133, residue 134, residue 135, residue 136, residue 137, residue 138, residue 139, residue 140, residue 141, residue 142, residue 143, residue 144, residue 145, residue 146, residue 147 and residue 148;

(ii) the amino acid mutation is in an amino acid substitution at a residue selected from the group consisting of: residue 378, residue 382, residue 383, residue 385, residue 388, residue 389 and residue 390; or (iii) there are at least two amino acid mutations, wherein a first amino acid mutation is an amino acid substitution selected from the group set forth in part (i), and the second amino acid mutation is an amino acid substitution selected from the group set forth in part (ii).

A mutant YILPCAT in certain embodiments can comprise an amino acid sequence as set forth in SEQ ID NO:73, wherein SEQ ID NO:73 differs from SEQ ID NO:40 by at least one amino acid mutation selected from the group consisting of: V133C, L134A, L134C, L134G, C135F, C135D, C135I, M136T, M136N, M136G, M136P, M136S, M136V, K137N, K137G, K137H, K137Y, L138G, L138I, L138N, L138A, L138H, L138M, S139G, S139N, S139L, S139W, S140Y, S140I, S140N, S140H, S140P, S140W, F141V, F141A, F141M, F141W, G142I, G142V, G142H, W143H, W143L, N144A, N144K, N144F, N144T, N144V, V145A, V145G, V145E, V145M, V145F, V145W, Y146G, Y146L, Y146M, D147E, D147N, D147Q, D147H, G148V, G148A, G148N, F378Y, T382Y, T382I, T382P, R383A, R383M, L388H, L388T, L388G, L388Y, T389A, T389C, T389S, F390C, F390G, F390N, F390T and F390S.

A mutant YILPCAT in certain embodiments can comprise a mutated MBOAT motif. Examples of mutated MBOAT motifs are mutated variants of motifs I (SEQ ID NO:82) and II (SEQ ID NO:83). In certain embodiments, a YILPCAT comprises a Motif I having one or more of the following amino acid substitutions: V2C, L3A, L3C, L3G, K6H, K6G, K6N, K6Y, L7A, L7N, L7G, L7H, L7I, L7M, D16Q, D16N, D16H, G17A, G17V and G17N; and/or a Motif II having one or more of the following amino acid substitutions: F15N, F15C, F15G and F15T.

The mutated YILPCAT in certain embodiments of the disclosed invention comprises mutations at (i) amino acid position 136 changing methionine to a different amino acid, and (ii) amino acid position 389 changing threonine to a different amino acid. An example of such a mutated YILPCAT is one in which the position 136 methionine is changed to a serine and the position 389 threonine is changed to an alanine (SEQ ID NO:26). Alternatively, the mutated YILPCAT may comprise the amino acid sequence of any one of SEQ ID NOs:75-81, which contain other combinations of mutations in both Motifs I and II. Alternatively, a mutated YILPCAT in certain embodiments may comprise an amino acid sequence that is at least about 90%, 91%, 92%, 93%, 94%, 95%, 96%, 97%, 98%, or 99% identical to any one of SEQ ID NOs:26, 75-81 (or any other mutant LPCAT disclosed herein) and have LPCAT function (above). Alternatively still, a mutated YILPCAT may comprise an amino acid sequence that (i) is at least about 90%, 91%, 92%, 93%, 94%, 95%, 96%, 97%, 98%, or 99% identical to any one of SEQ ID NOs:26, 75-81; (ii) contains both mutations listed in Table 1 for the mutated YILPCAT of (i); and (iii) has LPCAT function (above). For example, a mutated YILPCAT may comprise an amino acid sequence that is at least about 90%, 91%, 92%, 93%, 94%, 95%, 96%, 97%, 98%, or 99% identical to SEQ ID NO:26, where the amino acid sequence has a serine at position 136 and an alanine at position 389.

Further regarding mutations in both Motifs I and II, a mutant YILPCAT in certain embodiments can comprise an amino acid sequence as set forth in SEQ ID NO:74, wherein SEQ ID NO:74 differs from SEQ ID NO:40 by at least one of the pairs of mutations set forth in Table 3 (e.g., an L134A mutation in Motif I may be combined with either a T382I mutation, L388G mutation, F390G mutation or F390T mutation in Motif II, thereby generating mutants L134A_T382I, L134A_L388G, L134A_F390G and L134A_F390T, respectively).

TABLE 3

YILPCAT Double Mutations Demonstrating Equivalent or Improved EPA % TFAs and/or Equivalent or Improved % Delta-9 Conversion

| Amino Acid Mutation in Motif I | Amino Acid Mutation in Motif II |
|---|---|
| L134A | T382I[b], L388G, F390G[a], F390T |
| L134G | L388G[a], F390G[a], F390T[a] |
| M136S | F378Y, T382I, T382P, T382Y, R383M, P384A, L388Y, T389A, T389C, T389S |
| M136V | T382P, T382Y, P384A, L388Y, T389A, T389C, T389S |
| K137H | T382I[a], P384G, L388G[b], L388T, F390G[a], F390S, F390T |
| K137N | F378Y, T382P, R383M, P384G, L388G, L388T, T389A, T389C[b], T389S, F390G[b], F390S, F390T |
| S140H | T382I[b], P384G, L388G[b], L388T, F390G, F390S |
| S140W | T382I, T382P, T382Y, R383M, P384A, L388Y, T389A, T389C, T389S[a] |
| F141M | F378Y, T382P[b], T382Y, R383M, P384A, T389A[a], T389C |
| F141W | F378Y, T382I[b], T382P, T382Y, R383M, P384A, L388Y[b], T389A, T389C, T389S |
| N144A | T382I[a], P384G, L388G, L388T, F390G, F390S, F390T |
| N144T | F378Y, T382P, T382Y, R383M, P384A, L388Y, T389A, T389C, T389S |
| V145M | F378Y[b], T382Y[b], T382I, R383M, T389A, T389C |
| V145W | F378Y[b], T382I, T389A[a], T389S[a] |
| D147H | T382I[b], L388G, L388T, F390S, F390T[a] |
| D147Q | T382I, L388G[a], L388T[a], F390S |
| G148A | F378Y, T382I, T382Y, R383M, P384A[b], P384G, L388G, L388Y, T389A, T389C, F390S, F390T |
| G148N | T382I, P384G[a], L388T, F390G, F390S |

Notes:
Pairs of mutations comprising a first mutation in Motif I and a second mutation in Motif II lacking a superscript (a or b) resulted in equivalent or improved EPA % TFAs and equivalent or improved % Conv.
[a]Indicates a pair of mutations comprising a first mutation in Motif I and a second mutation in Motif II that resulted in equivalent or improved EPA % TFAs (but not equivalent or improved % Conv.).
[b]Indicates a pair of mutations comprising a first mutation in Motif I and a second mutation in Motif II that resulted in equivalent or improved % Conv. (but not equivalent or improved EPA % TFAs).

Although certain combinations of LPCAT amino acid mutations are disclosed herein, one of skill in the art would readily recognize that other combinations of the Motif I and Motif II mutations disclosed herein may be combined as well. Accordingly, one or more of the disclosed Motif I mutations may be used in combination with one or more of the disclosed Motif II mutations in preparing a polynucleotide encoding a mutant LPCAT polypeptide.

In certain embodiments of the disclosed invention, the recombinant microbial cell comprising a polynucleotide sequence encoding an active LPCAT enzyme with at least one amino acid mutation in an MBOAT motif also comprises:

(a) an amount of at least one long-chain polyunsaturated fatty acid measured as a weight percent of total fatty acids that is at least the same as or greater than the amount produced by a control cell, and/or (b) a $C_{18}$ to $C_{20}$ elongation conversion efficiency (e.g., delta-9 elongase conversion efficiency or delta-6 elongase conversion efficiency) that is at least the same as or greater than the conversion efficiency of a control cell.

An increase in the amount of the at least one long-chain PUFA (e.g., EPA) measured as a weight percent of total fatty acids of the recombinant cell over-expressing a mutant LPCAT (containing a mutation in Motif I and/or Motif II) may be at least about 1%, 2%, 3%, 4%, 5%, 6%, 7%, 8%, 9%, 10%, 11%, 12%, 13%, 14%, 15%, 16%, 17%, 18%, 19%, or 20% over the amount of the at least one long-chain PUFA measured as a weight percent of total fatty acids of a control cell.

An increase in the $C_{18}$ to $C_{20}$ elongation conversion efficiency, delta-9 elongase conversion efficiency, and/or delta-6 elongase conversion efficiency of the recombinant cell over-expressing a mutant LPCAT (containing a mutation in Motif I and/or Motif II) may be at least about 1%, 2%, 3%, 4%, 5%, 6%, 7%, 8%, 9%, 10%, 11%, 12%, 13%, 14%, or 15% over the $C_{18}$ to $C_{20}$ elongation conversion efficiency, delta-9 elongase conversion efficiency, and/or delta-6 elongase conversion efficiency, respectively, of a control cell.

The control cell in certain embodiments may be a wild type or recombinant cell that corresponds to the recombinant cell, but that does not comprise, or does not over-express, a polynucleotide encoding an active LPCAT enzyme comprising a mutated MBOAT motif. For example, the control cell does not over-express a mutant LPCAT by virtue of not comprising recombinant polynucleotide sequences encoding mutant LPCAT. Also for example, the control cell does not over-express mutant LPCAT by virtue of comprising, but not expressing, a polynucleotide sequence encoding mutant LPCAT. The control cell may be the recombinant cell as it existed before it was modified to over-express a mutant LPCAT polypeptide (i.e., a parent cell), or may be a recombinant cell that has been modified to contain a recombinant polynucleotide encoding mutant LPCAT, but does not over-express the mutant LPCAT polypeptide (e.g., a cell prepared in parallel with the recombinant cell that over-expresses a mutant LPCAT).

The recombinant microbial cell in certain embodiments of the disclosed invention comprises a down-regulation of an endogenous polynucleotide sequence encoding Sou2 sorbitol utilization protein. In other embodiments, the recombinant microbial cell comprises (i) a down-regulation of an endogenous polynucleotide sequence encoding Sou2 sorbitol utilization protein, and (ii) a PUFA biosynthetic pathway. The down-regulation of the endogenous polynucleotide sequence encoding the Sou2 sorbitol utilization protein in certain embodiments increases the lipid content of the recombinant microbial cell and/or decreases the total amount of sugar alcohols produced by the cell.

The Sou2 sorbitol utilization protein is encoded by the SOU2 gene. The terms "SOU2", "SOU2 gene" and "endogenous polynucleotide sequence encoding Sou2 sorbitol utilization protein" are used interchangeably herein.

The Sou2 sorbitol utilization protein (Sou2p) of *Y. lipolytica* (SEQ ID NO:10) has about 66% amino acid sequence identity (according to a BLAST alignment) with *Candida albicans* Sou2 sorbitol utilization protein (SEQ ID NO:30). *C. albicans* Sou2 sorbitol utilization protein was described by Janbon et al. (1998, *Proc. Natl. Acad. Sci. U.S.A.* 95:5150-5155) as being similar to Sou1 sorbitol utilization protein (Sou1p), but as not being required for sorbose utilization. Sou1 sorbitol utilization protein has been described by Janbon et al. and Greenberg et al. (2005, Yeast 22:957-969) to be a sorbose reductase required for L-sorbose utilization. The amino acid sequences of *C. albicans* Sou1 and Sou2 proteins have about 72% identity with each other. Given this degree of similarity, it was proposed by Greenberg et al. that Sou2 protein "is probably an oxidoreductase which utilizes NADP (H) as a co-factor and overlaps with Sou1p in substrate specificity.

Examples of microbial cell Sou2 sorbitol utilization protein sequences that can be down-regulated in certain embodiments include the sequences disclosed in the following GenBank Accession Nos.: P87218 (*Candida albicans*, SEQ ID NO:30), EAZ63262 (*Scheffersomyces stipitis*, SEQ ID NO:85), CAX42453 (*Candida dubliniensis*, SEQ ID NO:86), EHK97934 (*Glarea lozoyensis*, SEQ ID NO:87), ZP_08499267 (*Enterobacter hormaechei*, SEQ ID NO:88), CCG21852 (*Candida orthopsilosis*, SEQ ID NO:89), YP_887907 (*Mycobacterium smegmatis*, SEQ ID NO:90), EJT74900 (*Gaeumannomyces graminis*, SEQ ID NO:91), EGZ74878 (*Neurospora tetrasperma*, SEQ ID NO:92), EFY96110 (*Metarhizium anisopliae*, SEQ ID NO:93), EGX88960 (*Cordyceps militaris*, SEQ ID NO:94), EFY85020 (*Metarhizium acridum*, SEQ ID NO:95), EGY16179 (*Verticillium dahliae*, SEQ ID NO:96), EEH42615 (*Paracoccidioides brasiliensis*, SEQ ID NO:97), EHA51546 (*Magnaporthe oryzae*, SEQ ID NO:98), EEP78930 (*Uncinocarpus reesii*, SEQ ID NO:99), XP_961192 (*Neurospora crassa*, SEQ ID NO:100), XP_001523181 (*Lodderomyces elongisporus*, SEQ ID NO:101), CAK39371 (*Aspergillus niger*, SEQ ID NO:102), XP_002556984 (*Penicillium chrysogenum*, SEQ ID NO:103), CAG81202 (*Yarrowia lipolytica*, SEQ ID NO:10), CAG84844 (*Debaryomyces hansenii*, SEQ ID NO:104), CCE43891 (*Candida parapsilosis*, SEQ ID NO:105) and ZP_02917979 (*Bifidobacterium dentium*, SEQ ID NO:106).

In certain embodiments of the disclosed invention, the down-regulation of the endogenous polynucleotide sequence encoding Sou2 sorbitol utilization protein is due to a mutation of the polynucleotide sequence. This mutation is a substitution, deletion or an insertion in certain embodiments. A deletion in certain embodiments removes (i) one or more nucleotides from an open reading frame encoding the Sou2 sorbitol utilization protein, and/or (ii) one or more nucleotides of a non-protein-coding sequence located within 500 base pairs of the 5'-end of the open reading frame encoding the Sou2 sorbitol utilization protein.

Examples of a deletion in an SOU2 open reading frame are those removing one or two nucleotides, thereby resulting in a frame-shift mutation; the amino acid sequence encoded downstream such a deletion would be different from the endogenous amino acid sequence. One of ordinary skill in the art would understand that other deletions can be made to create a frame-shift mutation (e.g., any deletion removing a number of base pairs that is not divisible by three). Other deletion examples include those removing the entire SOU2 open reading frame or a portion thereof (e.g., a "knock-out" of SOU2). Where a portion of the SOU2 open reading frame is deleted, or removed by virtue of introducing a frame-shift, down-regulation may occur if the deleted amino acids are necessary for proper Sou2 protein function and/or localization. Alternatively, a deletion in the SOU2 open reading frame may affect proper transcription and/or translation of SOU2. In certain embodiments, the deletion in the SOU2 open reading frame is at least 50, 100, 150, 200, 250, 300, 350, 400, 450, 500, 550, 600, 650, 700, 750, or 800 base pairs. The deletion may be made beginning at the first codon or any downstream codon (e.g., a 250-bp deletion could begin at the tenth codon).

Deletions in certain embodiments of the disclosed invention remove portions of the 5'- and/or 3'-regulatory, non-translated sequences of SOU2. Certain deletions may remove sequences from both of these regulatory sequences; such deletions in most instances would remove the entire SOU2 open reading frame. Other deletions may affect one SOU2 regulatory region and the open reading frame (e.g., deletion of certain 5'-regulatory sequence and 5'-end of the open reading frame). Deletions affecting a 5'-regulatory sequence may down-regulate SOU2 by disrupting proper promoter activity, thereby reducing or eliminating SOU2 transcription. Deletions affecting a 3'-regulatory sequence may down-regulate SOU2 by disrupting proper transcription termination and/or transcript stability.

A deletion in certain embodiments removes one or more nucleotides of a non-protein-coding sequence located within 500 base pairs of the 5'-end of the SOU2 open reading frame. Such a deletion removes sequence from the 5'-non-translated region of the SOU2 transcribed sequence and/or the SOU2 promoter, and may down-regulate SOU2 by reducing transcription and/or translation. The deletion in certain embodiments removes base pairs −10 to −1, −20 to −1, −30 to −1, −40 to −1, −50 to −1, −60 to −1, −70 to −1, −80 to −1, −90 to −1, −100 to −1, −150 to −1, −200 to −1, −250 to −1, −300 to −1, −350 to −1, −400 to −1, −450 to −1, or −500 to −1 of the non-protein-coding sequence upstream the SOU2 open reading frame, where the −1 position is the nucleotide immediately 5'-adjacent the SOU2 start codon (ATG). A deletion in other embodiments removes about 10, 20, 30, 40, 50, 60, 70, 80, 90, 100, 150, 200, 250, 300, 350, 400, or 450 consecutive base pairs from any one of these aforementioned regions (e.g., 300 consecutive base pairs deleted within the −500 to −1 region).

In other embodiments a deletion removes one or more regulatory elements in the SOU2 promoter such as a TATA box consensus sequence or a TATA-like sequence (Basehoar et al., 2004, Cell 116:699-709, which is incorporated by reference). This type of promoter consensus sequence is usually located within 100 base pairs of the non-protein-coding sequence upstream of the SOU2 open reading frame. Where such a deletion is made to the SOU2 gene promoter in a Yarrowia cell, for example, the TATA box consensus could be removed by deleting one or more base pairs of the −79 to −72 region with respect to the SOU2 start codon (FIG. 5).

In those embodiments in which the recombinant microbial cell is a Yarrowia cell, the down-regulated endogenous polynucleotide sequence may encode a Sou2 sorbitol utilization protein that comprises an amino acid sequence that is at least 95% identical to SEQ ID NO:10. In alternative embodiments, the Sou2 sorbitol utilization protein comprises an amino acid sequence that is at least 96%, 97%, 98%, or 99% identical to SEQ ID NO:10, or the amino acid sequence comprises SEQ ID NO:10. In other embodiments, the down-regulated endogenous polynucleotide sequence encoding a Sou2 sorbitol utilization protein comprises a nucleotide sequence that is at least 95% identical to SEQ ID NO:9. The polynucleotide sequence may alternatively comprise a nucleotide sequence that is at least 96%, 97%, 98%, or 99% identical to SEQ ID NO:9, or the polynucleotide sequence comprises SEQ ID NO:9.

Y. lipolytica in the below Examples was genetically modified to have a deletion that removed the first 287 base pairs of an endogenous SOU2 open reading frame, as well as 235 base pairs of non-protein coding sequence immediately upstream the SOU2 start codon (i.e., positions −235 to −1 were deleted). SEQ ID NO:8 (FIG. 5) is an example of genomic DNA sequence containing the Y. lipolytica SOU2 gene locus. This sequence contains 1000 base pairs of non-protein coding sequence upstream the SOU2 start codon, 771 base pairs of SOU2 open reading frame (corresponding to SEQ ID NO:9), and 300 base pairs of non-protein coding sequence downstream of the SOU2 stop codon.

Thus, any of the deletions disclosed herein that can be used to down-regulate SOU2 in Yarrowia may be characterized with respect to nucleotide positions in SEQ ID NOs:8 or 9, or a polynucleotide sequence having at least 95%, 96%, 97%, 98%, or 99% identity thereto (accounting for natural sequence variability that might exist across different Yarrowia strains). Such deletions may similarly be characterized with respect to amino acid positions in SEQ ID NO:10, or an amino acid sequence having at least 95%, 96%, 97%, 98%, or 99% identity thereto. For example, a deletion can remove at least nucleotide positions 1-768 (an entire Yarrowia SOU2 open reading frame removed) or 1-287 of SEQ ID NO:9 (i.e., base pairs 1-287 of a Yarrowia SOU2 open reading frame), or alternatively a deletion can remove at least nucleotide positions 1001-1768 (an entire Yarrowia SOU2 open reading frame removed) or 1001-1287 of SEQ ID NO:8 (i.e., base pairs 1-287 of a Yarrowia SOU2 open reading frame). As another example, a deletion can remove at least nucleotide positions 501-1000 of SEQ ID NO:8 (i.e., −500 to −1 with respect to a Yarrowia SOU2 start codon) or 766-1000 (i.e., −235 to −1 with respect to a Yarrowia SOU2 start codon). As yet another example, a deletion can remove at least nucleotide positions 766-1287 of SEQ ID NO:8 (i.e., −235 to +287, corresponding to the deletion noted in FIG. 5).

An insertion in certain embodiments occurs within (i) an open reading frame encoding the Sou2 sorbitol utilization protein, or (ii) a non-protein-coding sequence located within 500 base pairs of the 5'-end of the open reading frame. As used herein, the terms "insertion" and "integration" are used interchangeably herein to refer to one or more consecutive nucleotides inserted into a genetic sequence. If an insertion is in an open reading frame, it will be disrupted during transcription and/or translation. This may result in an altered sequence of amino acids, extra amino acids in a chain, or premature termination. The newly synthesized protein produced from such a mutated open reading frame may be abnormally short, abnormally long, and/or contain the wrong amino acids, and will most likely not be functional.

In certain embodiments, an insertion in an SOU2 open reading frame adds one or two nucleotides, thereby resulting in a frame-shift mutation; the amino acid sequence encoded downstream such an insertion would be different from the endogenous amino acid sequence. One of ordinary skill in the art would understand that other insertions can be made to create a frame-shift mutation (e.g., any insertion adding a number of base pairs that is not divisible by three). Down-regulation of SOU2 may occur if the amino acids affected by the insertion are necessary for proper Sou2 protein function and/or localization. Alternatively, an insertion in the SOU2 open reading frame may affect proper transcription and/or translation of SOU2. In certain embodiments, the insertion in the SOU2 open reading frame can be of any length that results in down-regulation of the SOU2 gene. Alternatively, the length of the insertion can be at least 50, 100, 150, 200, 250, 300, 350, 400, 450, 500, 550, 600, 650, 700, 750, 800, 850, 900, 950, or 1000 base pairs. The insertion may be made immediately after the first codon or any downstream codon (e.g., a 250-bp insertion immediately after the tenth codon).

An insertion in certain embodiments adds one or more nucleotides into a non-protein-coding sequence located within 500 base pairs of the 5'-end of the SOU2 open reading frame. Such an insertion can affect the 5'-non-translated region of the SOU2 transcribed sequence and/or the SOU2 promoter, and may down-regulate SOU2 by reducing transcription and/or translation. The insertion in certain embodiments is within the −10 to −1, −20 to −1, −30 to −1, −40 to −1, −50 to −1, −60 to −1, −70 to −1, −80 to −1, −90 to −1, −100 to −1, −150 to −1, −200 to −1, −250 to −1, −300 to −1, −350 to −1, −400 to −1, −450 to −1, or −500 to −1 region of the non-protein-coding sequence upstream the SOU2 open reading frame, where the −1 position is the nucleotide immediately 5'-adjacent the SOU2 start codon (ATG). The insertion in any of these aforementioned regions can be at least 50, 100, 150, 200, 250, 300, 350, 400, 450, 500, 550, 600, 650, 700, 750, 800, 850, 900, 950, or 1000 base pairs, for example (e.g., 300-bp insertion within the −100 to −1 region). Alternatively, the insertion can be of any length that results in down-regulation of the SOU2 gene.

*Y. lipolytica* in the below Examples was genetically modified to have an insertion between positions −71 to −70 with respect to the ATG start codon of an SOU2 gene. This particular insertion, as well as any of the insertions disclosed herein that can be used to down-regulate SOU2 in *Yarrowia*, may be characterized with respect to nucleotide positions in SEQ ID NOs:8 or 9, or a polynucleotide sequence having at least 95%, 96%, 97%, 98%, or 99% identity thereto (accounting for natural sequence variability that might exist across different *Yarrowia* strains). For example, an insertion between positions −71 to −70 with respect to the ATG start codon of a *Yarrowia* SOU2 gene can be described as an insertion between nucleotide positions 930 and 931 of SEQ ID NO:8. As another example, an insertion between base pairs 10 and 11 of a *Yarrowia* SOU2 open reading frame can be described as an insertion between nucleotide positions 1010 and 1011 of SEQ ID NO:8, or alternatively as an insertion between nucleotide positions 10 and 11 of SEQ ID NO:9.

Other types of mutations aside from the aforementioned deletions and insertions can be used to down-regulate the endogenous polynucleotide sequence encoding Sou2 sorbitol utilization protein in alternative embodiments of the disclosed invention. For example, one or more point mutations, which exchange a single nucleotide for another (i.e., a nucleotide substitution), may be used. The point mutation may be a transition point mutation (i.e., a purine in place of another purine, or a pyrimidine in place of another pyrimidine) or transversion point mutation (i.e., a purine in place of a pyrimidine, or a pyrimidine in place of a purine). An example transition mutation is where an adenine is in place of a guanine. An example transversion mutation is where an adenine is in place of a cytosine. Any of these mutations may result, for example, in an amino acid substitution that down-regulates the function of the Sou2 protein.

In certain embodiments, the mutation may be a nonsense mutation within the SOU2 open reading frame; such a mutation changes an amino acid codon to a nonsense codon. Depending on the position of the nonsense mutation in the SOU2 open reading frame, the encoded Sou2 sorbitol utilization protein may be truncated at its carboxy terminus by one or more amino acids. Such a truncation may remove at least 1, 5, 25, 50, 75, 100, 125, 150, 175, 200, 225, 250, or 275 amino acids from the carboxy terminus, for example.

The mutation in certain embodiments may be a missense mutation within the SOU2 open reading frame, where a codon is mutated to encode a different amino acid. Such a mutation may down-regulate SOU2 by virtue of reducing or eliminating the wild type function of the Sou2 sorbitol utilization protein. For example, the proper localization and/or enzymatic activity of the Sou2 protein may be impaired.

A mutation in a codon of the SOU2 open reading frame that does not change the amino acid encoded by the codon (i.e., a silent mutation) is not a mutation as described herein that down-regulates SOU2. Nor is a mutation as described herein one that changes the amino acid encoded by a codon to a related amino acid that does not alter the wild type function of the Sou2 protein. Related amino acids in certain embodiments have side groups that share structure and/or charge, and can be grouped as follows: aliphatic (glycine, alanine, valine, leucine, isoleucine), aromatic (phenylalanine, tyrosine, tryptophan), hydroxyl group-containing (serine, threonine), sulfur group-containing (cysteine, methionine), carboxylic acid group-containing (aspartate, glutamate), amide group-containing (asparagine, glutamine), and amino group-containing (histidine, lysine, arginine).

It would be understood by one of ordinary skill in the art that any of the disclosed mutations to the endogenous SOU2 sequence can be determined to constitute a mutation by referring to the endogenous SOU2 sequence in a microbial cell that has not be modified to mutate the endogenous SOU2 sequence. For example, the SOU2 sequence in a modified *Y. lipolytica* strain can be compared to the endogenous SOU2 sequence of the counterpart wild type *Y. lipolytica* strain from which the modified strain was derived.

Any of the above deletions and insertions, as well as any other mutation described herein, may be introduced to an endogenous SOU2 sequence of a recombinant microbial cell using any means known in the art. Genetic targeting techniques may be used, for example, such as those described for modifying yeast (Longtine et al., *Yeast* 14:953-961), fungi (Meyer et al., *J. Biotechnol.* 128:770-775), algae (Zorin et al., *Gene*, 432:91-96), and bacteria (Zhong et al., *Nucleic Acids Res.* 31:1656-1664). Alternatively, random mutagenesis techniques may be used.

The down-regulation of an endogenous polynucleotide sequence encoding Sou2 sorbitol utilization protein in certain embodiments is a reduction in the transcription and/or translation of the endogenous polynucleotide sequence by at least about 20%, 30%, 40%, 50%, 60%, 70%, 80%, 90%, 95%, or 100% relative to the transcription and/or translation of a control cell. In other embodiments, the down-regulation of an endogenous polynucleotide sequence encoding Sou2 sorbitol utilization protein is reflected by a reduction of at least about 20%, 30%, 40%, 50%, 60%, 70%, 80%, 90%, 95%, or 100% in the function (e.g., protein localization and/or enzymatic activity) of the encoded Sou2 sorbitol utilization protein relative to the function of the Sou2 protein in a control cell.

The down-regulation of the endogenous polynucleotide sequence encoding the Sou2 sorbitol utilization protein in certain embodiments of the disclosed invention increases the lipid content of the recombinant microbial cell. This increase in lipid content (TFAs % DCW) can be at least about 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, or 35% over the lipid content of a control cell.

The down-regulation of the endogenous polynucleotide sequence encoding the Sou2 sorbitol utilization protein in certain embodiments of the disclosed invention decreases the total amount of sugar alcohols produced by the microbial cell. The sugar alcohols may comprise arabitol and/or mannitol, for example. The decrease of the total amount of sugar alcohols can be at least about 20%, 30%, 40%, 50%, 60%, or 70% below the total amount of sugar alcohols in a control cell. The decrease of arabitol and/or mannitol can be at least about 20%, 30%, 40%, 50%, 60%, 70%, 80%, 90%, or 100% below the amount of arabitol and/or mannitol in a control cell. A 100% decrease in certain embodiments represents that arabitol and/or mannitol are below the threshold of detection.

The control cell in certain embodiments has an endogenous polynucleotide sequence encoding Sou2 sorbitol utilization protein that does not have any of the mutations disclosed herein. Such non-mutation in the control cell can be determined by comparing its polynucleotide sequence encoding Sou2 sorbitol utilization protein with that of a counterpart wild type cell. For example, where the control cell is a particular recombinant *Yarrowia* cell that has not been modified to have a mutation in an endogenous polynucleotide sequence encoding Sou2 sorbitol utilization protein, this polynucleotide sequence in the control cell should be the same or very similar to (e.g., containing silent a mutation) the polynucleotide sequence in the counterpart wild type *Yarrowia* cell from which the control was derived. Other aspects of a control cell that can be used in certain embodiments are described above.

A recombinant microbial cell that does not comprise an endogenous polynucleotide sequence encoding Sou2 sorbitol utilization protein should not be considered to comprise a down-regulation of this polynucleotide if the wild type counterpart cell from which the recombinant microbial cell was derived likewise does not comprise an endogenous polynucleotide sequence encoding Sou2 sorbitol utilization protein.

The recombinant microbial cell in certain embodiments of the disclosed invention comprises (a) at least one heterologous polynucleotide sequence encoding phospholipid:diacylglycerol acyltransferase (PDAT), (b) at least one heterologous polynucleotide sequence encoding delta-12 desaturase, and (c) at least one polynucleotide sequence encoding a dihomo-gamma-linolenic acid (DGLA) synthase multizyme. Each of these polynucleotide sequences (a-c) is operably linked to at least one regulatory sequence.

The term "phospholipid:diacylglycerol acyltransferase" (PDAT; EC 2.3.1.158) as used herein refers to an enzyme that is capable of transferring an acyl group from the sn-2 position of phospholipids such as phosphatidylcholine (PC) and phosphatidylethanolamine (PE) to the sn-3 position of 1,2-diacylglycerol (DAG). This reaction results in lysophospholipids such as lysophosphatidylcholine (LPC) and lysophosphatidylethanolamine (LPE). Although both PDAT and acyl-CoA:diacylglycerol acyltransferases (DGAT; E.C. 2.3.1.20) are involved in the terminal step of TAG biosynthesis, only PDAT may synthesize TAGs via an acyl-CoA-independent mechanism.

Dahlqvist et al. (2000, *Proc. Natl. Acad. Sci. U.S.A.* 97:6487-6492) and Oelkers et al. (2000, *J. Biol. Chem.* 275: 15609-15612) were the first to appreciate that TAG synthesis can occur in the absence of acyl-CoA, via the acyl-CoA-independent PDAT enzyme (structurally related to the lecithin:cholesterol acyltransferase family of proteins). Following this work, U.S. Pat. No. 7,267,976 (incorporated herein by reference) described the cloning, overexpression and knockout of the *Y. lipolytica* ATCC #90812 gene encoding PDAT (SEQ ID NO:31 herein), which was determined to share 47.1% amino acid sequence identity with ScPDAT. A single-amino acid insertion variant (SEQ ID NO:15 herein) of this YlPDAT was disclosed in U.S. Pat. Appl. Publ. No. 2012-0052537.

The heterologous polynucleotide sequence encoding PDAT in certain embodiments of the disclosed invention may encode an amino acid sequence comprising a *Yarrowia* PDAT. Such a PDAT may comprise the amino acid sequence of SEQ ID NO:15 or 31, for example. Alternatively, a PDAT in certain embodiments may comprise an amino acid sequence that is at least about 90%, 91%, 92%, 93%, 94%, 95%, 96%, 97%, 98%, or 99% identical to SEQ ID NO:15 or 31 and have PDAT function (above).

The term "delta-12 desaturase" (D12; EC 1.14.19.6) as used herein refers to an enzyme that is capable of introducing a carbon-carbon double bond between the 12th and 13th carbons as numbered from the carboxyl end of a fatty acid.

The heterologous polynucleotide sequence encoding delta-12 desaturase in certain embodiments of the disclosed invention may encode an amino acid sequence comprising a delta-12 desaturase as disclosed in U.S. Pat. No. 7,214,491 and U.S. Pat. Appl. Publ. No. 2007-0254299, both of which are incorporated herein by reference. Alternatively, the amino acid sequence may comprise a delta-12 desaturase from *Fusarium moniliforme* (e.g., SEQ ID NO:13), *Y. lipolytica* (e.g., SEQ ID NO:32), *Aspergillus nidulans*, *Magnaporthe grisea*, *Neurospora crassa*, *Fusarium graminearium*, *Aspergillus fumigatus* or *Aspergillus flavus*, all of which are disclosed in U.S. Pat. No. 7,504,259 (incorporated herein by reference). Alternatively, a delta-12 desaturase in certain embodiments may comprise an amino acid sequence that is at least about 90%, 91%, 92%, 93%, 94%, 95%, 96%, 97%, 98%, or 99% identical to SEQ ID NO:13 or 32 and have delta-12 desaturase function (above).

The terms "multizyme" and "fusion protein" are used interchangeably in embodiments herein and refer to a single polypeptide having at least two independent and separable enzymatic activities, wherein the first enzymatic activity is preferably linked to the second enzymatic activity (U.S. Pat. Appl. Publ. No. 2008-0254191, incorporated herein by reference). The multizyme in certain embodiments comprises two independent and separate enzymes. The "linker" between the two independent and separable enzymatic activities may be comprised of a single peptide bond, although the linker may also be comprised of one amino acid residue, such as a proline, or a polypeptide comprising at least one proline. Examples of linkers that can be used in certain embodiments are disclosed as SEQ ID NOs:4-10 in U.S. Pat. Appl. Publ. No. 2008-0254191.

A "DGLA synthase multizyme" in certain embodiments of the disclosed invention comprises a delta-9 elongase linked to a delta-8 desaturase. The DGLA synthase multizyme can convert LA to DGLA by virtue of containing both delta-9 elongase activity (converts LA to EDA) and delta-8 desaturase activity (converts EDA to DGLA). The DGLA synthase multizyme can also convert ALA to ETA, since its delta-9 elongase activity can convert ALA to ETrA and its delta-8 desaturase activity can convert ETrA to ETA.

Examples of delta-9 elongase amino acid sequences that can be comprised within the DGLA synthase multizyme are disclosed as SEQ ID NOs:254 (*Euglena anabaena* D9e, EaD9e), 319 (*Euglena gracilis* D9e, EgD9e) and 359 (*Eutreptiella* sp. CCMP389 D9e, E389D9e) in U.S. Pat. Appl. Publ. No. 2008-0254191. Examples of delta-8 desaturase amino acid sequences that can be comprised within the DGLA synthase multizyme are disclosed as SEQ ID NOs: 328 (mutant *Euglena gracilis* D8, EgD8M), 430 (*Euglena anabaena* D8, EaD8) and 514 (*Tetruetreptia pomquetensis*

CCMP1491 D8, TpomD8) in U.S. Pat. Appl. Publ. No. 2008-0254191. Each of these delta-9 elongases and delta-8 desaturases, or a variant thereof having at least about 90%, 91%, 92%, 93%, 94%, 95%, 96%, 97%, 98%, or 99% amino acid identity thereto and having either delta-9 elongase or delta-8 desaturase function, may be comprised in the DGLA synthase multizyme, for example.

In certain embodiments, the DGLA synthase multizyme comprises E389D9eS/EgD8M (SEQ ID NO:17 herein). This multizyme comprises E389D9e (SEQ ID NO:33 herein) linked to most of the amino acid sequence of EgD8M (SEQ ID NO:19 herein). Specifically, E389D9eS/EgD8M comprises, in the direction of the amino terminus to the carboxy terminus, SEQ ID NO:33—linker GAGPARPAGLP-PATYYDSLAVMGS (SEQ ID NO:34)—positions 2-422 of SEQ ID NO:19. The DGLA synthase multizyme in other embodiments may be any of those disclosed in U.S. Pat. Appl. Publ. No. 2008-0254191 (e.g., EgD9eS/EgD8M, SEQ ID NO:35 herein; EgD9eS/EaD8S; EaD9eS/EgD8M; EaD9eS/EaD8S, SEQ ID NO:36 herein; EgD9e/TpomD8; EaD9e/TpomD8). Alternatively, the DGLA synthase multizyme in certain embodiments may comprise an amino acid sequence that is at least about 90%, 91%, 92%, 93%, 94%, 95%, 96%, 97%, 98%, or 99% identical to SEQ ID NO:17, 35, or 36 (or any of the other above DGLA synthases) and have DGLA synthase function (above). The delta-9 elongase is located at the amino-terminus (N-terminus) of the multizyme polypeptide in certain embodiments.

The recombinant microbial cell in certain embodiments of the disclosed invention comprises (a) at least one heterologous polynucleotide sequence encoding delta-8 desaturase, (b) at least one heterologous polynucleotide sequence encoding malonyl-CoA synthetase (MCS), and (c) at least one heterologous polynucleotide sequence encoding acyl-CoA:lysophosphatidic acid acyltransferase (LPAAT). Each of these polynucleotide sequences (a-c) is operably linked to at least one regulatory sequence.

The term "delta-8 desaturase" (D8; EC 1.14.19.4) as used herein refers to an enzyme that is capable of introducing a carbon-carbon double bond between the 8th and 9th carbons as numbered from the carboxyl end of a fatty acid.

The heterologous polynucleotide sequence encoding delta-8 desaturase in certain embodiments of the disclosed invention may encode an amino acid sequence comprising a delta-8 desaturase sequence as disclosed in U.S. Pat. Appl. Publ. No. 2005-0273885 or U.S. Pat. Nos. 7,550,651; 7,256,033; 7,790,156; 7,943,823; 7,863,502; or 6,825,017, all of which are incorporated herein by reference. Alternatively, the amino acid sequence may comprise a delta-8 desaturase from *Euglena gracilis* (e.g., SEQ ID NO:19) or *Euglena anabaena* (e.g., SEQ ID NO:37), for example. Alternatively, a delta-8 desaturase in certain embodiments may comprise an amino acid sequence that is at least about 90%, 91%, 92%, 93%, 94%, 95%, 96%, 97%, 98%, or 99% identical to SEQ ID NO:19 or 37 and have delta-8 desaturase function (above).

The term "malonyl-CoA synthetase" (MCS, EC 6.2.1.14) as used herein refers to an enzyme that catalyzes the following enzymatic reaction: malonate+ATP+CoA→malonyl-CoA+AMP+pyrophosphate. The enzyme was first purified from malonate-grown *Pseudomonas fluorescens* (1985, Kim and Bang, *J. Biol. Chem.* 260:5098-5104), although various *Rhizobia* homologs have since been isolated from bacteroides within legume nodules (e.g., Kim and Chae, 1991, *Biochem. J.* 273:511-516; Kim and Kang, 1994 *Biochem. J.* 297:327-333). By converting malonate into malonyl-CoA, MCS can provide malonyl-CoA substrate for use in fatty acid synthesis. Thus, in addition to reducing the byproduction of malonates in a cell, MCS expression also helps to avoid carbon and energy waste within the cell, reduce the amount of base required to maintain an optimal pH range during the fermentation process, and reduce the amount of byproduct organic acids that require neutralization within the fermentation waste steam.

The heterologous polynucleotide sequence encoding MCS in certain embodiments of the disclosed invention may encode an amino acid sequence comprising an MCS sequence as disclosed in U.S. Pat. Appl. Publ. No. 2010-0159558, which is incorporated herein by reference. For example, the amino acid sequence may comprise an MCS from *Rhizobium leguminosarum* (e.g., SEQ ID NO:21). Alternatively, an MCS in certain embodiments may comprise an amino acid sequence that is at least about 90%, 91%, 92%, 93%, 94%, 95%, 96%, 97%, 98%, or 99% identical to SEQ ID NO:21 and have MCS function (above).

The term "acyl-CoA:lysophospholipid acyltransferase" or "lysophospholipid acyltransferase" ("LPLAT") herein refers to a broad class of acyltransferases that can acylate a variety of lysophospholipid substrates at the sn-2 position. More specifically, LPLATs include lysophosphatidic acid (LPA) acyltransferase (LPAAT), which can catalyze conversion of LPA to PA; LPC acyltransferase (LPCAT), which can catalyze conversion of LPC to PC; LPE acyltransferase (LPEAT), which can catalyze conversion of LPE to PE; LPS acyltransferase (LPSAT), which can catalyze conversion of LPS to PS; and LPG acyltransferase (LPGAT), which can catalyze conversion of LPG to PG. Various other designations for LPLATs are used in the art. For example, LPAAT has also been referred to as acyl-CoA:1-acyl-sn-glycerol-3-phosphate 2-O-acyltransferase, 1-acyl-sn-glycerol-3-phosphate acyltransferase, or 1-acylglycerolphosphate acyltransferase. LPCAT has also been referred to as acyl-CoA:1-acyl lysophosphatidylcholine acyltransferase. Certain LPLATs, such as *Saccharomyces cerevisiae* Ale1, have broad specificity and thus a single enzyme may be capable of catalyzing several LPLAT reactions, including LPAAT, LPCAT and LPEAT reactions (Tamaki et al., 2007, *J. Biol. Chem.* 282:34288-34298; Ståhl et al., 2008, *FEBS Letters* 582:305-309; Chen et al., 2007, *FEBS Letters* 581:5511-5516; Benghezal et al., 2007, *J. Biol. Chem.* 282:30845-30855; Riekhof et al., 2007, *J. Biol. Chem.* 282:28344-28352).

The term "lysophosphatidic acid acyltransferase" (LPAAT, EC 2.3.1.51) as used herein refers to an enzyme that catalyzes the following reaction: acyl-CoA+1-acyl-sn-glycerol 3-phosphate=CoA+1,2-diacyl-sn-glycerol 3-phosphate.

The heterologous polynucleotide sequence encoding LPAAT in certain embodiments of the disclosed invention may encode an amino acid sequence comprising an LPAAT sequence as disclosed in U.S. Pat. Appl. Publ. No. 2010-0317882 or U.S. Pat. Nos. 7,189,559 and 7,879,591, all of which are incorporated herein by reference. For example, the amino acid sequence may comprise an LPAAT from *Mortierella alpina* (e.g., SEQ ID NO:38) or *Y. lipolytica* (e.g., SEQ ID NO:23). Alternatively, an LPAAT in certain embodiments may comprise an amino acid sequence that is at least about 90%, 91%, 92%, 93%, 94%, 95%, 96%, 97%, 98%, or 99% identical to SEQ ID NO:38 or 23 and have LPAAT function (above).

Thus, a recombinant microbial cell in certain embodiments of the disclosed invention comprises one or more of the following features as described above:

(i) at least one polynucleotide sequence encoding an active LPCAT comprising at least one amino acid mutation in a membrane-bound O-acyltransferase motif;

(ii) a down-regulation of an endogenous polynucleotide sequence encoding Sou2 sorbitol utilization protein;

(iii) at least one polynucleotide sequence encoding PDAT;

(iv) at least one polynucleotide sequence encoding delta-12 desaturase;

(v) at least one polynucleotide sequence encoding a DGLA synthase multizyme;

(vi) at least one polynucleotide sequence encoding delta-8 desaturase;

(vii) at least one polynucleotide sequence encoding MCS;

(viii) at least one polynucleotide sequence encoding LPAAT; wherein each of the polynucleotide sequences of (i) and (iii)-(viii) is operably linked to at least one regulatory sequence. Each of the polynucleotides of (i) and (iii)-(viii) may be heterologous. The recombinant microbial cell in each embodiment may comprise or produce an oil comprising at least 28 percent EPA measured as a weight percent of the dry cell weight. Certain embodiments of the recombinant microbial cell comprise feature(s):

(i);
(ii);
(i) and (ii);
(i), (ii), (iii), (iv) and (v);
(i), (ii), (vi), (vii) and (viii); or
(i)-(viii).

For example, certain embodiments of the invention that have both features (i) and (ii) refer to recombinant microbial cells (e.g., recombinant Yarrowia cells) that produce an oil comprising at least 28 percent EPA measured as a weight percent of the dry cell weight and that comprise a down-regulation of an endogenous polynucleotide sequence encoding Sou2 sorbitol utilization protein, and at least one polynucleotide sequence encoding an active LPCAT enzyme comprising at least one amino acid mutation in a membrane-bound O-acyltransferase motif.

As described in U.S. Pat. Appl. Publ. No. 2010-0317072 (incorporated herein by reference), Y. lipolytica strain Y9502 was derived from strain Y8412, which in turn was derived from wild type strain ATCC #20362. Y. lipolytica strain Z5585 was derived from strain Y9502 as described in U.S. Pat. Appl. Publ. No. 2012-0052537, which is incorporated herein by reference. Certain of the recombinant Y. lipolytica strains disclosed in the below Examples are derived from Z5585, such as the strains listed in Table 13 (e.g. Z9276). Thus, in certain embodiments of the disclosed invention, the recombinant microbial cell is a Y. lipolytica comprising one of, a combination of, or all of the following heterologous features: down-regulation of a Pex protein-encoding polynucleotide (e.g., Pex3), down-regulation of a Sou2p-encoding polynucleotide, at least 3 polynucleotides encoding $C_{16/18}$ elongase (e.g., ME3), at least 5 polynucleotides encoding delta-9 elongase (e.g., EgD9e), at least 6 polynucleotides encoding delta-8 desaturase (e.g., EgD8, EgD8M, or EaD8), at least 4 polynucleotides encoding DGLA synthase (e.g., E389D9eS/EgD8M, E389D9eS/EgD8M, EgD9eS/EgD8M, EaD9eS/EaD8S), at least 2 polynucleotides encoding delta-9 desaturase (e.g., YID9), at least 5 polynucleotides encoding delta-12 desaturase (e.g., FmD12), at least 4 polynucleotides encoding delta-5 desaturase (e.g., EgD5M), at least 3 polynucleotides encoding delta-17 desaturase (e.g., PaD17), at least 2 polynucleotides encoding diacylglycerol cholinephosphotransferase YlCPT1), at least 3 polynucleotides encoding malonyl-CoA synthetase (e.g., MCS), at least 1 polynucleotide encoding choline-phosphate cytidylyl-transferase (e.g., YlPCT), at least 5 polynucleotides encoding acyl-CoA:lysophosphatidic acid acyltransferase (e.g., MaLPAAT1 or YlLPAAT1), at least 3 polynucleotides encoding phospholipid: diacylglycerol acyltransferase (e.g., YlPDAT), at least 1 polynucleotide encoding a mutant acyl CoA:lysophosphatidylcholine acyltransferase (e.g., YlLPCAT (M136X/T389X). Alternatively, the cell may comprise one copy of some or all of these polynucleotides.

Constructs or vectors comprising the polynucleotides described herein may be introduced into a host cell by any standard technique. These techniques include transformation (e.g., lithium acetate transformation [*Methods in Enzymology*, 194:186-187 (1991)]), biolistic impact, electroporation, and microinjection, for example. As an example, U.S. Pat. Nos. 4,880,741 and 5,071,764, and Chen et al. (1997, *Appl. Microbiol. Biotechnol.* 48:232-235), describe integration techniques for Y. lipolytica, based on linearized fragments of DNA.

Preferred selection methods for use herein are resistance to kanamycin, hygromycin and the amino glycoside G418, as well as ability to grow on media lacking uracil, leucine, lysine, tryptophan or histidine. In alternate embodiments, 5-fluoroorotic acid (5-fluorouracil-6-carboxylic acid monohydrate[5-FOA]) is used for selection of yeast Ura⁻ mutants (U.S. Pat. Appl. Publ. No. 2009-0093543), or a native acetohydroxyacid synthase (or acetolactate synthase; E.C. 4.1.3.18) that confers sulfonyl urea herbicide resistance (Intl. Appl. Publ. No. WO 2006/052870) is utilized for selection of transformants. A unique method of "recycling" a pair of preferred selection markers for their use in multiple sequential transformations, by use of site-specific recombinase systems, is also taught in U.S. Pat. Appl. Publ. No. 2009-0093543.

It may be desirable to manipulate a number of different genetic elements in the disclosed embodiments that control aspects of transcription, RNA stability, translation, protein stability and protein location, oxygen limitation and secretion from the host cell. More specifically, gene expression may be controlled by altering the following: the nature of the relevant promoter and terminator sequences; the number of copies of the cloned gene; whether the gene is plasmid-borne or integrated into the genome of the host cell; the final cellular location of the synthesized foreign protein; the efficiency of translation in the host organism; the intrinsic stability of the cloned gene protein within the host cell; and the codon usage within the cloned gene, such that its frequency approaches the frequency of preferred codon usage of the host cell.

Promoters useful to drive expression of heterologous genes in microbial host cells are numerous and known to those skilled in the art. Expression can be accomplished in an induced or constitutive fashion. Induced expression can be accomplished by inducing the activity of a regulatable promoter operably linked to the gene of interest, while constitutive expression can be achieved by the use of a constitutive promoter operably linked to the gene of interest. Virtually any promoter (i.e., native, synthetic, or chimeric) capable of directing expression of a gene is suitable, although transcriptional and translational regulatory regions from the host species may be particularly useful.

In general, the terminator can be derived from the 3' region of the gene from which the promoter was obtained or from a different gene. A large number of terminators are known and function satisfactorily in a variety of hosts, when utilized both in the same and different genera and species from which they were derived. The terminator usually is selected more as a matter of convenience rather than because of any particular property. Preferably, the terminator is derived from a yeast gene. The terminator can also be synthetic, as one of skill in the art can utilize available information to design and synthesize a terminator. A terminator may be unnecessary, but it is preferred.

Although not intended to be limiting, preferred promoters and terminators for use in a recombinant microbial host cell of the genus *Yarrowia* are those taught in U.S. Pat. Appl. Publ. Nos. 2009-0093543, 2010-0068789, 2011-0059496, 2012-0252079, 2012-0252093, 2013-0089910 and 2013-0089911, all of which are incorporated herein by reference.

Additional copies (i.e., more than one copy) of the PUFA biosynthetic pathway desaturases, elongases, etc. genes may be introduced into the recombinant microbial host cell to increase EPA production and accumulation. Specifically, additional copies of genes may be cloned within a single expression construct; and/or additional copies of the cloned gene(s) may be introduced into the host cell by increasing the plasmid copy number or by multiple integration of the cloned gene into the genome.

In general, once a DNA cassette (e.g., comprising a chimeric gene comprising a promoter, ORF and terminator) suitable for expression in a recombinant microbial host cell has been obtained, it is either placed in a plasmid vector capable of autonomous replication in the host cell or directly integrated into the genome of the host cell. Integration of expression cassettes can occur randomly within the host genome or can be targeted through the use of constructs containing regions of homology with the host genome sufficient to target recombination with the host locus. Although not relied on herein, all or some of the transcriptional and translational regulatory regions can be provided by the endogenous locus where constructs are targeted to an endogenous locus.

With respect to engineered recombinant *Y. lipolytica* host cells, the preferred method of expressing genes in this microbial host is by integration of a linear DNA fragment into the genome of the host. Integration into multiple locations within the genome can be particularly useful when high level expression of genes is desired. Preferred loci include those taught in U.S. Pat. Appl. Publ. No. 2009-0093543, for example.

Another aspect of the disclosed invention concerns a method for producing a microbial oil comprising a polyunsaturated fatty acid (PUFA). This method comprises:

a) culturing a recombinant microbial cell as described herein, wherein a microbial oil comprising a PUFA is produced; and b) optionally recovering the microbial oil of step (a).

In certain embodiments, the microbial oil produced by the method comprises EPA. Depending on the species of the microbial cell used in the method, the oil may be a fungal oil or yeast oil, for example. The oil in certain embodiments may be recovered or obtained from the recombinant microbial cell after about 12, 24, 36, 48, 60, 72, 84, 96, 100, 105, 110, 115, 120, 125, 130, 135, 140, 145, 150, 160, 170, 180, or 200 hours of culturing the microbial cell.

The recombinant microbial cell of the present disclosure can be grown under conditions that optimize expression of the disclosed polynucleotides and produce the greatest and the most economical yield of one or more PUFAs. In general, media conditions may be optimized by modifying the type and amount of carbon source, the type and amount of nitrogen source, the carbon-to-nitrogen ratio, the amount of different mineral ions, the oxygen level, growth temperature, pH, length of the biomass production phase, length of the oil accumulation phase and the time and method of cell harvest.

Fermentation media for growing the recombinant microbial cell described herein must contain a suitable carbon source, such as described in U.S. Pat. No. 7,238,482 and U.S. Pat. Appl. Publ. No. 2011-0059204. Preferred growth media include, for example, common commercially prepared media such as Yeast Nitrogen Base, corn steep liquors, or corn steep solids. Other defined or synthetic growth media may also be used. A suitable pH range for the fermentation is typically between about pH 4.0 to pH 8.0, wherein pH 5.5 to pH 7.5 is preferred as the range for the initial growth conditions. The fermentation may be conducted under aerobic or anaerobic conditions, where microaerobic conditions are preferred.

Typically, accumulation of high levels of PUFAs in oleaginous yeast cells requires a two-stage process, since the metabolic state must be "balanced" between growth and synthesis/storage of fats. Thus, most preferably, a two-stage fermentation process can be used for the production of EPA in *Yarrowia lipolytica*. This approach is described in U.S. Pat. No. 7,238,482, as are various suitable fermentation process designs (i.e., batch, fed-batch and continuous) and considerations during growth. In a two-stage approach, the first stage of the fermentation is for the accumulation of cell mass and is characterized by rapid cell growth and division; a standard amount of nitrogen is included in this stage of fermentation. In the second stage of the fermentation, nitrogen deprivation in the culture promotes a high level of lipid production and accumulation. The first stage may be performed for about 12, 24, 36, 48, or 60 hours, while the second stage (oleaginous) may be performed for about 12-150 hours, depending on the desired level of oil production.

The conditions of growing the disclosed recombinant microbial cell may be oleaginous; for example, oleaginous growth conditions for *Yarrowia* are described in U.S. Appl. Publ. No. 2009-0093543, which is incorporated herein by reference. Oleaginous growth conditions differ from standard growth conditions mainly in that nitrogen is absent or very limited (nitrogen-limited), but while still providing an ample or high amount of a fermentable carbon source. Example fermentable carbon sources are monosaccharides (e.g., glucose, fructose), disaccharides (e.g., sucrose), invert sucrose, oligosaccharides, polysaccharides, alkanes, fatty acids (e.g., 10-22 carbons), esters of fatty acids, glycerol, monoglycerides, diglycerides, and triglycerides. An example of an oleaginous growth medium lacking nitrogen has about 80 g/L glucose, 2.58 g/L $KH_2PO_4$ and 5.36 g/L $K_2HPO_4$. Another example is a medium in which no nitrogen-containing salt is directly added when preparing the medium. Since an oleaginous medium is nitrogen-limited, it may have at most about 0.050, 0.100, 0.125 0.150, 0.175, 0.200, 0.225, 0.250, 0.275, or 0.300 g/L of a nitrogen-containing salt (e.g., ammonium-containing salt such as $(NH_4)_2HPO_4$, $(NH_4)_2HSO_4$, $NH_4NO_3$, or $NH_4Cl$; a nitrate-containing salt such as $KNO_3$ or $NaNO_3$), amino acid, or urea. The amount of glucose in an oleaginous growth medium may be at least about 20, 30, 40, 50, 60, 70, 80, 90, 100, 110, 120, 130, 140, 150, 160, 170, 180, 190, or 200 g/L.

EXAMPLES

The present invention is further defined in the following Examples. It should be understood that these Examples, while indicating preferred aspects of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

General Methods

Standard recombinant DNA and molecular cloning techniques used herein are well known in the art and are described by Sambrook, J. and Russell, D., *Molecular Cloning: A Laboratory Manual,* 3rd Edition, Cold Spring Harbor Laboratory Press, Cold Spring Harbor, N.Y. (2001); and by Silhavy, T. J., Bennan, M. L. and Enquist, L. W., *Experiments with Gene Fusions*, Cold Spring Harbor Laboratory Press, Cold Spring Harbor, N.Y. (1984); and by Ausubel, F. M. et. al., *Short Protocols in Molecular Biology*, 5th Ed. Current Protocols, John Wiley and Sons, Inc., N.Y., 2002. Unless otherwise indicated herein comparisons of genetic sequences were performed using DNASTAR software (DNASTAR Inc., Madison, Wis.).

Materials and methods suitable for the maintenance and growth of microbial cultures are well known in the art. Techniques suitable for use in the following examples may be found as set out in *Manual of Methods for General Bacteriology* (P. Gerhardt, R. G. E. Murray, R. N. Costilow, E. W. Nester, W. A. Wood, N. R. Krieg and G. B. Phillips, Eds.), American Society for Microbiology: Washington, D.C. (1994)); or in *Manual of Industrial Microbiology and Biotechnology*, 3rd Edition (R. H. Baltz, J. E. Davies, and A. L. Demain, Eds.), ASM Press, Washington, D.C., 2010.

All reagents, restriction enzymes and materials used for the growth and maintenance of microbial cells were obtained from Aldrich Chemicals (Milwaukee, Wis.), DIFCO Laboratories (Detroit, Mich.), New England Biolabs, Inc. (Beverly, Mass.), GIBCO/BRL (Gaithersburg, Md.), or Sigma Chemical Company (St. Louis, Mo.), unless otherwise specified.

The structure of each genetic expression cassette disclosed herein is represented by the simple notation system of "X::Y::Z". Specifically, X describes the promoter, Y describes the protein-coding sequence, and Z describes the terminator. X is operably linked to Y, and Y is operably linked to Z.

Transformation and Cultivation of *Y. lipolytica*

*Y. lipolytica* strains were routinely grown at 30° C. in several media, according to the recipes shown below.

High Glucose Medium (HGM) (per liter): 80 g glucose, 2.58 g $KH_2PO_4$ and 5.36 g $K_2HPO_4$, pH 7.5 (do not need to adjust).

Synthetic Dextrose Medium (SD) (per liter): 6.7 g yeast nitrogen base with ammonium sulfate and without amino acids, and 20 g glucose.

Fermentation medium (FM) (per liter): 6.7 g yeast nitrogen base with ammonium sulfate and without amino acids, 6.0 g $KH_2PO_4$, 2.0 g $K_2HPO_4$, 1.5 g $MgSO_4.7H_2O$, 20 g glucose, and 5.0 g yeast extract (BBL, BD Diagnostic Systems, Sparks, Md.).

Transformation of *Y. lipolytica* was performed as described in U.S. Pat. Appl. Publ. No. 2009-0093543, which is incorporated herein by reference. In general, for transformation of Ura3⁻ cells, cells were transfected with a plasmid or fragment thereof carrying a URA3 gene, and then selected for transformation on plates lacking uracil.

Fatty Acid Analysis of *Y. lipolytica*

For fatty acid analysis, cells were collected by centrifugation and lipids were extracted as described in Bligh, E. G. & Dyer, W. J. (*Can. J. Biochem. Physiol.*, 37:911-917 (1959)). Fatty acid methyl esters (FAMEs) were prepared by transesterification of the lipid extract with sodium methoxide (Roughan, G., and Nishida I., *Arch Biochem Biophys.*, 276 (1):38-46 (1990)) and subsequently analyzed with an Agilent Technologies 6890N gas chromatograph fitted with a 30-m× 0.25 mm (i.d.) SUPELCO Omegawax320 (Agilent Technologies) column. The oven temperature was ramped from 160° C. to 240° C. at 30° C./min and then held for 3.8 min at 240° C.

For direct base transesterification, a *Y. lipolytica* culture (1 mL) was harvested by centrifugation (13,000×g) for 1 min. Sodium methoxide (500 µL of a 1% solution) was added to the sample, and then the sample was vortexed and rocked for 45 min. Then, 100 µL of 1.0 M NaCl and 500 µL of hexane were added, and the sample was vortexed and spun. The upper layer was removed and analyzed by gas chromatography as described above.

In general, initial fatty acid screening of new transformants of *Yarrowia* strains was performed as follows. Single colonies that were grown on minimal medium (MM) plates at 30° C. for 5 to 6 days were re-streaked onto MM plates, grown for two days at 30° C., and then inoculated into liquid MM in a multi-well plate (e.g., 24-well, 3 mL MM) and shaken at 250 rpm at 30° C. for 2 days. The cells from each well were collected by centrifugation, resuspended in HGM, and then shaken at 250 rpm for 5 days. Cells were then processed for fatty acid analysis as described above. Transformants exhibiting a desired fatty acid trait were further analyzed by "flask assay" as described below.

Analysis of Total Lipid Content and Composition in *Y. lipolytica* (Flask Assay)

For a detailed analysis of the total lipid content and composition in a particular strain of *Y. lipolytica*, flask assays were conducted as follows. Specifically, cultures were grown at a starting $OD_{600}$ of ~0.3 in 25 mL of SD medium in a 125-mL flask for 48 h. 6 mL of the culture was harvested by centrifugation for 5 min at 4300 rpm in a 50-mL conical tube. The supernatant was discarded and the cells were resuspended in 25 mL of HGM in another 125 mL flask; this culture was incubated for 120 hours (except as otherwise noted) in a shaker incubator at 250 rpm and 30° C. A 1-mL aliquot of the culture was then used for fatty acid analysis (as described above) following centrifugation for 1 min at 13,000 rpm, and a 5-mL aliquot of the culture was dried for dry cell weight determination. All flask assays referenced herein were performed following this methodology, except those performed using the "one-step flask assay".

For DCW determination, 10 mL of culture was harvested by centrifugation for 5 min at 4300 rpm. The pellet was resuspended in 10 mL of sterile water and re-harvested as above. The washed pellet was re-suspended in 1 mL of water (three times) and transferred to a pre-weighed aluminum pan. The cell suspension was dried overnight in a vacuum oven at 80° C. The weight of the cells was determined (g/L).

Total lipid content of cells (TFAs % DCW) was calculated and considered in conjunction with data tabulating the concentration of each fatty acid as a weight percent of TFAs (% TFAs) and the EPA content as a percent of the dry cell weight (EPA % DCW). Data from flask assays are presented in table format summarizing the total DCW of the cells, the total lipid content of cells (TFAs % DCW), the concentration of each fatty acid as a weight percent of TFAs (% TFAs) and the EPA content as a percent of the dry cell weight (EPA % DCW).

*Y. lipolytica* Strains Z5627 and Z5585

The generation of *Y. lipolytica* strains Z5627 and Z5585 is described in U.S. Pat. Appl. Publ. No. 2012-0052537, which is incorporated herein by reference. As described in Examples 1-4, Z5627 and Z5585 were used to derive certain strains of the disclosed invention.

Figure 2A:
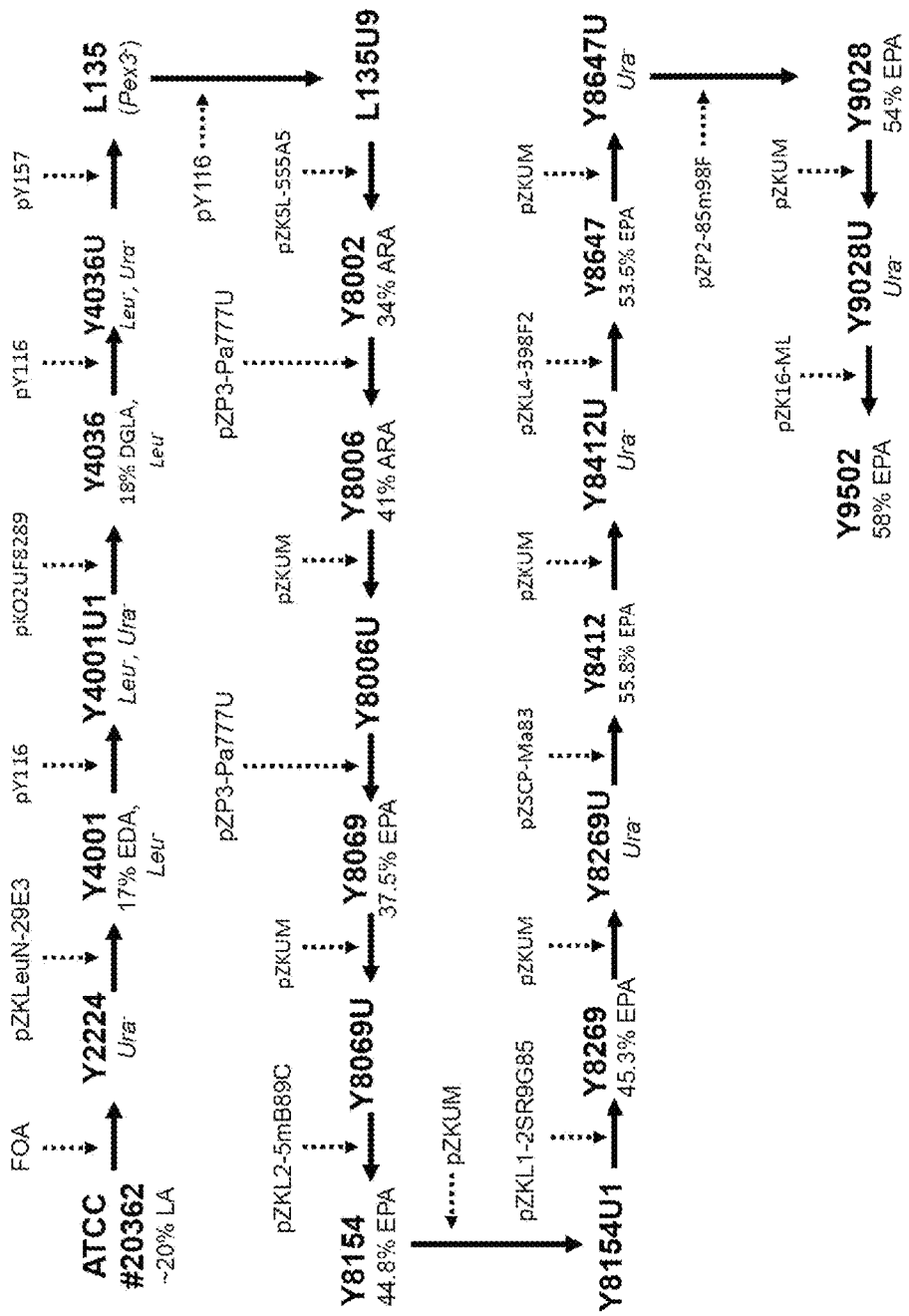
Figure 2B:
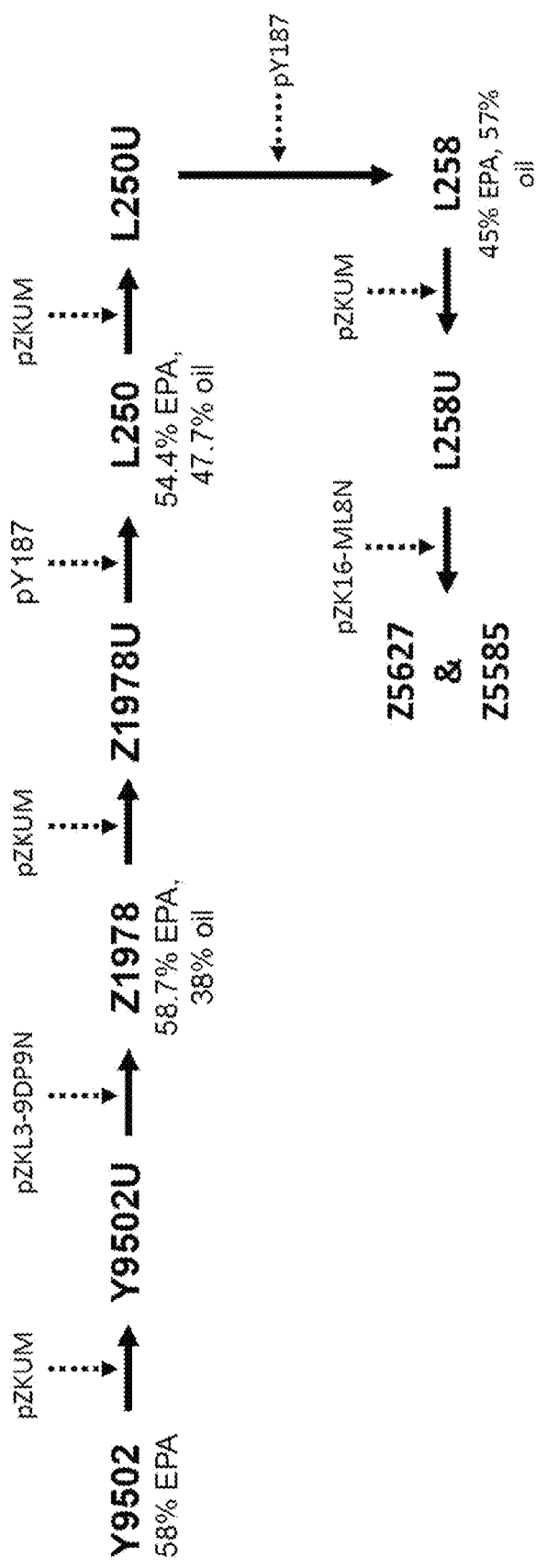

*Y. lipolytica* strains Z5627 and Z5585 were derived from multiple genetic modifications of strain Y9502, which in turn was derived after multiple genetic modifications of wild type *Y. lipolytica* strain ATCC #20362. The modification steps and intermediate strains used for generating strains Z5627 and Z5585 are shown in FIGS. 2A (ATCC #20362 to Y9502) and 2B (Y9502 to Z5627 and Z5585).

The genotype of both strains Z5627 and Z5585 with respect to wild type *Y. lipolytica* ATCC #20362 is: Ura⁺, Pex3⁻, unknown 1⁻, unknown 2⁻, unknown 3⁻, unknown 4⁻, YALI0E12947g⁻, unknown 6⁻, YALI0B21890g⁻, unknown 8⁻, unknown 10⁻, unknown 11⁻, unknown 12⁻, unknown 13⁻, unknown 14⁻, YAT1::ME3S::Pex16, GPD::ME3S::Pex20, YAT1::ME3S::Lip1, FBAINm::EgD9eS::Lip2, EXP1::EgD9eS::Lip1, GPAT::EgD9e::Lip2, YAT1::EgD9eS::Lip2, YAT1::EgD9eS-L35G::Pex20, FBAINm::EgD8M::Pex20, EXP1::EgD8M::Pex16, FBAIN::EgD8M::Lip1, GPD::EaD8S::Pex16 (2 copies), YAT1::E389D9eS/EgD8M::Lip1, YAT1::EgD9eS/EgD8M::Aco, FBAINm::EaD9eS/EaD8S::Lip2, DGAT2M::YID9::Lip1, GPDIN::YID9::Lip1, GPD::FmD12::Pex20, YAT1::FmD12::Oct, EXP1::FmD12S::Aco, GPDIN::FmD12::Pex16, EXP1::EgD5M::Pex16, FBAIN::EgD5SM::Pex20, EXP1::EgD5SM::Lip1, YAT1::EaD5SM::Oct, FBAINm::PaD17::Aco, EXP1::PaD17::Pex16, YAT1::PaD17S::Lip1, YAT1::YICPT1::Aco, EXP1::YICPT1::Oct, YAT1::MCS::Lip1, FBA::MCS::Lip1, EXP1::YIPCT::Pex16, YAT1::MaLPAAT1S::Pex16, ALK2LM1::MaLPAAT1S::Pex20, FBAINm::YILPAAT1::Lip1 (2 copies), YAT1::YIPDAT::Lip1 (2 copies).

The abbreviations listed in the above genotype are as follows: FmD12 is a *Fusarium moniliforme* delta-12 desaturase gene and FmD12S is a codon-optimized form thereof (U.S. Pat. No. 7,504,259); ME3S is a codon-optimized *Mortierella alpina* $C_{16/18}$ elongase gene (U.S. Pat. No. 7,470,532); EgD9e is a *Euglena gracilis* delta-9 elongase gene and EgD9eS is a codon-optimized form thereof (U.S. Pat. No. 7,645,604); EgD9eS-L35G is a mutant form of EgD9eS (U.S. Pat. Appl. Publ. No. 2012/0226062); EgD8M is a synthetic mutant *E. gracilis* delta-8 desaturase gene (U.S. Pat. No. 7,709,239); EaD8S is a codon-optimized *Euglena anabaena* delta-8 desaturase gene (U.S. Pat. No. 7,790,156); E389D9eS/EgD8M is a DGLA synthase created by linking a codon-optimized delta-9 elongase gene (E389D9eS) from *Eutreptiella* sp. CCMP389 (U.S. Pat. No. 7,645,604) to EgD8M (U.S. Pat. Appl. Publ. No. 2008/0254191); EgD9eS/EgD8M is a DGLA synthase created by linking EgD9eS to EgD8M (U.S. Pat. Appl. Publ. No. 2008/0254191); EaD9eS/EaD8S is a DGLA synthase created by linking a codon-optimized *E. anabaena* delta-9 elongase gene (EaD9eS) (U.S. Pat. No. 7,794,701) to EaD8S (U.S. Pat. No. 7,790,156); YIDS is a *Y. lipolytica* delta-9 desaturase gene (U.S. Pat. Appl. Publ. No. 2012/0052537); EgD5M and EgD5SM are synthetic mutant *E. gracilis* delta-5 desaturase genes comprising a mutant HPGS motif (U.S. Pat. Appl. Publ. No. 2010/0075386); EaD5SM is a synthetic mutant *E. anabaena* delta-5 desaturase gene comprising a mutant HAGG motif (U.S. Pat. Appl. Publ. No. 2010/0075386); PaD17 is a *Pythium aphanidermatum* delta-17 desaturase gene and PaD17S is a codon-optimized form thereof (U.S. Pat. No. 7,556,949); YICPT1 is a *Y. lipolytica* diacylglycerol cholinephosphotransferase gene (U.S. Pat. No. 7,932,077); MCS is a codon-optimized malonyl-CoA synthetase gene from *Rhizobium leguminosarum* bv. *viciae* 3841 (U.S. Pat. Appl. Publ. No. 2010/0159558); YIPCT is a *Y. lipolytica* choline-phosphate cytidylyl-transferase gene (U.S. Pat. Appl. Publ. No. 2012-0052537 and GenBank Accession No. XM_502978); MaLPAAT1S is a codon-optimized *M. alpina* lysophosphatidic acid acyltransferase gene (U.S. Pat. No. 7,879,591); YILPAAT1 is a *Y. lipolytica* lysophosphatidic acid acyltransferase gene (U.S. Pat. Appl. Publ. No. 2012-0052537); YIPDAT is a *Y. lipolytica* phospholipid:diacylglycerol acyltransferase gene (U.S. Pat. Appl. Publ. No. 2012-0052537); YAT1 is a *Y. lipolytica* YAT1 gene promoter (U.S. Pat. Appl. Publ. No. 2010/0068789); Pex16 is a *Y. lipolytica* Pex16 gene terminator (GenBank Accession No. U75433); GPD is a *Y. lipolytica* glyceraldehyde-3-phosphate dehydrogenase gene promoter (U.S. Pat. No. 7,459,546); GPDIN is a *Y. lipolytica* GPD gene promoter plus intron (U.S. Pat. No. 7,459,546); Pex20 is a *Y. lipolytica* Pex20 gene terminator (GenBank Accession No. AF054613); Lip1 is a *Y. lipolytica* Lip1 gene terminator (GenBank Accession No. Z50020); Lip2 is a *Y. lipolytica* Lip2 gene terminator (GenBank Accession No. AJ012632); FBA is a *Y. lipolytica* fructose-bisphosphate aldolase promoter sequence, and FBAIN and FBAINm are *Y. lipolytica* FBA promoter plus intron sequences (U.S. Pat. No. 7,202,356); DGAT2M is a *Y. lipolytica* diacylglycerol acyltransferase-2 (DGAT2) promoter sequence (U.S. Pat. Appl. Publ. No. 2012-0052537); EXP1 is a *Y. lipolytica* export protein (EXP1) gene promoter sequence (Intl. Appl. Publ. No. WO06/052870); GPAT is a *Y. lipolytica* GPAT promoter (Intl. Appl. Publ. No. WO 2006/031937); Aco is a *Y. lipolytica* Aco gene terminator (GenBank Accession No. AJ001300); Oct is a *Y. lipolytica* Oct gene terminator (GenBank Accession No. X69988); and ALK2LM1 is a *Y. lipolytica* n-alkane-hydroxylating cytochrome P450 gene (ALK2) promoter sequence plus N-terminal 66-bp coding region of the *Y. lipolytica* ALK2 gene (U.S. Pat. Appl. Publ. No. 2012-0052537).

As shown below in Table 4, which is also disclosed in U.S. Pat. Appl. Publ. No. 2012-0052537, strain Z5627 can produce oil containing about 49.5% EPA in the fatty acids of the oil. This strain can also produce, as a percentage of DCW, about 52% oil and 25.6% EPA.

As shown in Table 4, strain Z5585 can produce oil containing about 49.4% EPA in the fatty acids of the oil. This strain can also produce, as a percentage of DCW, about 56.6% oil and 28% EPA.

TABLE 4

Total Lipid Content and Composition in Various Recombinant *Y. lipolytica* Strains by Flask Assay (U.S. Pat. Appl. Publ. No. 2012-0052537)[g]

| Strain | DCW (g/L) | TFAs % DCW | % TFAs | | | | | | | | | | | | EPA % DCW |
|---|---|---|---|---|---|---|---|---|---|---|---|---|---|---|---|
| | | | 16:0 | 16:1 | 18:0 | 18:1 | 18:2 | ALA | EDA | DGLA | ARA | ETrA | ETA | EPA | |
| Z1977 | 3.8 | 34.3 | 2 | 0.5 | 1.9 | 4.6 | 11.2 | 0.7 | 3.1 | 3.3 | 0.9 | 0.7 | 2.2 | 59.1 | 20.3 |
| Z1978 | 3.9 | 38.3 | 2.4 | 0.4 | 2.4 | 4.8 | 11.1 | 0.7 | 3.2 | 3.3 | 0.8 | 0.6 | 2.1 | 58.7 | 22.5 |
| Z1979 | 3.7 | 33.7 | 2.3 | 0.4 | 2.4 | 4.1 | 10.5 | 0.6 | 3.2 | 3.6 | 0.9 | 0.6 | 2.2 | 59.4 | 20 |
| Z1980 | 3.6 | 32.7 | 2.1 | 0.4 | 2.2 | 4 | 10.8 | 0.6 | 3.1 | 3.5 | 0.9 | 0.7 | 2.2 | 59.5 | 19.5 |
| Z1981 | 3.5 | 34.3 | 2.2 | 0.4 | 2.1 | 4.2 | 10.6 | 0.6 | 3.3 | 3.4 | 1 | 0.8 | 2.2 | 58.5 | 20.1 |
| Genotype Additions with Respect to Strain Z1978: YILPAAT1, YIPDAT | | | | | | | | | | | | | | | |
| L250 | 4.4 | 51.5 | 2 | 0.7 | 2.8 | 6.1 | 16.7 | 0.9 | 3.3 | 4.9 | 0.7 | 0.6 | 3.2 | 50.4 | 26 |
| Genotype Additions with Respect to Strain Z1978: 2 YILPAAT1, 2 YIPDAT | | | | | | | | | | | | | | | |
| L258[a] | 5 | 57.1 | 2.3 | 0.9 | 3.4 | 7.8 | 18.7 | 0.9 | 4 | 5.3 | 0.8 | 0.6 | 3.2 | 45.2 | 25.8 |

TABLE 4-continued

Total Lipid Content and Composition in Various Recombinant *Y. lipolytica* Strains by Flask Assay (U.S. Pat. Appl. Publ. No. 2012-0052537)[g]

| Strain | DCW (g/L) | TFAs % DCW | % TFAs | | | | | | | | | | | | EPA % DCW |
|---|---|---|---|---|---|---|---|---|---|---|---|---|---|---|---|
| | | | 16:0 | 16:1 | 18:0 | 18:1 | 18:2 | ALA | EDA | DGLA | ARA | ETrA | ETA | EPA | |
| Genotype Additions with Respect to Strain Z1978: 2 YILPAAT1, 2 YIPDAT, EgD8M, MCS, MaLPAAT1S | | | | | | | | | | | | | | | |
| Z5565[b] | 4.8 | 56.1 | 2.1 | 0.8 | 2.8 | 6.8 | 17.3 | 0.8 | 3.8 | 5.2 | 1.1 | 0.8 | 3.4 | 47.4 | 26.6 |
| Z5567[b] | 4.9 | 56.2 | 1.9 | 0.7 | 2.6 | 6.2 | 16.7 | 0.7 | 3.8 | 5.6 | 1.1 | 1 | 3.6 | 48.3 | 27.1 |
| Z5575[b] | 4.7 | 53.8 | 1.8 | 0.7 | 2.4 | 5.7 | 15.3 | 0.6 | 3.6 | 5.9 | 1.2 | 1 | 3.6 | 50.4 | 27.1 |
| Z5576[b] | 4.9 | 55.6 | 2.3 | 0.9 | 2.8 | 6.9 | 16.9 | 0.7 | 3.6 | 5.5 | 1.2 | 0.9 | 3.3 | 47.2 | 26.2 |
| Genotype Additions with Respect to Strain Z1978: 3 YILPAAT1, 2 YIPDAT, EgD8M, MCS | | | | | | | | | | | | | | | |
| Z5620[c] | 4.5 | 52.8 | 2.1 | 0.7 | 2.8 | 6.6 | 16.1 | 0.7 | 3.6 | 5.7 | 1.1 | 0.7 | 3.3 | 49 | 25.9 |
| Z5623[c] | 4.3 | 51.7 | 2.3 | 0.8 | 2.4 | 6 | 15.9 | 0.7 | 3.8 | 5.2 | 1.1 | 0.7 | 3.1 | 50 | 25.8 |
| Z5625[c] | 4.6 | 52.7 | 2.1 | 0.7 | 2.7 | 6.2 | 16.6 | 0.7 | 3.9 | 5.4 | 1.1 | 0.8 | 3.2 | 49.1 | 25.9 |
| Genotype Additions with Respect to Strain Z1978: 2 YILPAAT1, 2 YIPDAT, ME3S, MCS, MaLPAAT1S | | | | | | | | | | | | | | | |
| Z5581[d] | 4.7 | 56.3 | 1.9 | 0.7 | 2.6 | 6.1 | 16.5 | 0.7 | 3.7 | 5.6 | 1.2 | 1 | 3.5 | 48.7 | 27.4 |
| Z5582[d] | 4.8 | 55.6 | 1.9 | 0.7 | 2.5 | 6.1 | 16.4 | 0.7 | 3.7 | 5.7 | 1.1 | 0.9 | 3.6 | 48.9 | 27.2 |
| Z5583[d] | 4.9 | 56.8 | 2 | 0.7 | 2.6 | 6.2 | 16.7 | 0.8 | 3.7 | 5.4 | 1 | 1 | 3.7 | 48.4 | 27.5 |
| Z5584[d] | 4.9 | 55.3 | 2 | 0.7 | 2.7 | 6.5 | 16.1 | 0.7 | 3.7 | 5.7 | 1.1 | 1 | 3.6 | 48.6 | 26.8 |
| Genotype Additions with Respect to Strain Z1978: 2 YILPAAT1, 2 YIPDAT, YIPCT, YID9, MaLPAAT1S | | | | | | | | | | | | | | | |
| Z5570[e] | 4.8 | 55 | 2 | 0.8 | 2.5 | 6.1 | 16.4 | 0.7 | 3.7 | 5.5 | 1.2 | 1 | 3.4 | 48.6 | 26.8 |
| Z5571[e] | 4.8 | 54.1 | 2.2 | 0.8 | 2.4 | 6.5 | 16.7 | 0.7 | 3.8 | 5.5 | 1.1 | 0.9 | 3.2 | 48.3 | 26.2 |
| Z5572[e] | 4.9 | 54 | 2.1 | 0.8 | 2.5 | 6.5 | 16.7 | 0.7 | 3.7 | 5.5 | 1.1 | 0.9 | 3.3 | 48.4 | 26.1 |
| Z5574[e] | 5 | 53.8 | 1.8 | 0.7 | 2.4 | 5.7 | 15.3 | 0.6 | 3.6 | 5.9 | 1.2 | 1 | 3.6 | 50.4 | 27.1 |
| Genotype Additions with Respect to Strain Z1978: 2 YILPAAT1, 2 YIPDAT, YICPT1, YID9, MaLPAAT1S | | | | | | | | | | | | | | | |
| Z5585[f] | 4.6 | 56.6 | 1.9 | 0.7 | 2.6 | 5.6 | 16.4 | 0.7 | 3.5 | 5.5 | 1.1 | 1 | 3.5 | 49.4 | 28 |
| Z5627[f] | 4.8 | 52 | 1.9 | 0.7 | 2.6 | 6.2 | 16.1 | 0.6 | 4 | 5.6 | 1.2 | 0.9 | 3.2 | 49.3 | 25.6 |

[a]Strain L258 was used to derive L258U (FIG. 2B), which is Ura3−.
[b]Each of strains Z5565, Z5567, Z5575 and Z5576 was derived through the one-step introduction to strain L258U of gene cassettes for expressing EgD8M, MCS and MaLPAAT1S.
[c]Each of strains Z5620, Z5623 and Z5625 was derived through the one-step introduction to strain L258U of gene cassettes for expressing YILPAAT1, EgD8M and MCS.
[d]Each of strains Z5581, Z5582, Z5583 and Z5584 was derived through the one-step introduction to strain L258U of gene cassettes for expressing ME3S, MCS and MaLPAAT1S.
[e]Each of strains Z5570, Z5571, Z5572 and Z5574 was derived through the one-step introduction to strain L258U of gene cassettes for expressing YIPCT, YID9 and MaLPAAT1S.
[f]Each of strains Z5585 and Z5627 was derived through the one-step introduction to strain L258U of gene cassettes for expressing YICPT1, YID9 and MaLPAAT1S.
[g]The values shown in the table were measured in each strain after growth in HGM for 120 hours.

Table 4 lists other strains beside Z5627 and Z5585 that were derived through multiple genetic modifications of wild type *Y. lipolytica* strain ATCC #20362. The strains in this table can produce approximately 20%-28% EPA as a percentage of DCW. Several of the strains listed in Table 4, specifically strains L250 on down to Z5627, are all descendants of intermediate strain Z1978. The genetic modifications ("genotype additions") made in each strain with respect to Z1978 are shown in Table 4. Strains Z5565 on down to Z5627 in Table 4 were directly derived through certain one-step genetic modifications of strain L258U, which is a Ura3− transformant of strain L258 (see table footnotes).

It is apparent from Table 4 that the different genetic modifications made to strain Z1978 to yield each of descendent strains Z5565 to Z5627 raised the total oil content (TFAs % DCW) from 38.3% to a range of 51.7%-56.6%. This rise in oil content was associated with an overall decrease in the percentage of EPA in the fatty acids of the oil, from 58.7% in Z1978 to a range of 47.2%-50.4% in descendent strains Z5565 to Z5627.

Thus, the increase in the total amounts of EPA produced on a dry cell weight basis obtained in strains Z5565 to Z5627 (25.6 to 28 EPA % DCW, Table 4) through the genetic modifications of strain Z1978 (22.5 EPA % DCW, Table 4) was achieved through substantially increasing oil production. Despite this significant achievement, it was not apparent from the studies disclosed in U.S. Pat. Appl. Publ. No. 2012-0052537 how to further increase total EPA content on a dry cell weight basis. For example, the steps to maintain or increase oil content while increasing the amount of EPA in the fatty acids of the oil, which would boost EPA % DCW, were unknown.

Thus, there is still a need to increase oil production while also increasing EPA content (EPA % TFAs).

Example 1

Generation of Strain Z6109 Producing at Least about 51.7% EPA of Total Fatty Acids with at Least about 54.2% Total Lipid Content This Example describes the generation of *Y. lipolytica* strain Z6109 through genetic modification of strain Z5627. The genetic modification entailed introducing an expression cassette encoding *Arabidopsis thaliana* caleosin-1 (AtClo1) into Z5627. FIG. 3A shows the modification steps and intermediate strain used for generating strain Z6109.

In order to introduce AtClo1 to Z5627, it was necessary to first render this strain to be Ura3− for subsequent selection purposes. Z5627 carries an intact URA3 coding sequence within the integrated plasmid construct pZKMP-ML9DCB, which was previously used to introduce sequences allowing for expression of MaLPAAT1S, YIDS and YICPT1 (see U.S. Pat. Appl. Publ. No. 2012-0052537). To disrupt the URA3 coding sequence of Z5627, construct pZKUM was used to integrate a Ura3− mutant sequence into the intact URA3 sequence. The construction and use of plasmid pZKUM to obtain Ura⁻ *Y. lipolytica* cells has been described (U.S. Pat. Appl. Publ. No. 2009-0093543, see Table 15 therein, which is incorporated herein by reference).

Z5627 pZKUM-transformants with a Ura⁻ phenotype were selected on minimal media (MM) plates containing 5-fluoroorotic acid (5-FOA) (U.S. Pat. Appl. Publ. No. 2009-0093543). A total of eight transformants were grown and identified to possess a Ura⁻ phenotype. These transformants were subjected to an initial fatty acid screening process as described above.

Gas chromatography (GC) analyses showed the presence of 33.5%, 35.7%, 35.9% and 34% EPA of TFAs in Z5627 pZKUM-transformants #2, #3, #4 and #6 cells from FOA-plates, respectively. These four transformants were designated as strains Z5627U1, Z5627U2, Z5627U3 and Z5627U5, respectively, and were collectively designated as strain Z5627U.

Plasmid pYRH55 (FIG. 4A, SEQ ID NO:1) was generated to integrate one synthetic *Arabidopsis thaliana* caleosin-1 (AtClo1) gene into the *Yarrowia* lipase 7 gene locus (GenBank Accession No. AJ549519). The AtClo1 coding sequence (SEQ ID NO:2, encoding SEQ ID NO:3) in pYRH55 was derived from GenBank Accession No. AEE85247 and is codon-optimized for expression in *Y. lipolytica* (see U.S. Appl. Publ. No. 2012-0301932, which is incorporated herein by reference). This codon-optimized AtClo1 is herein referred to as AtClo1 S. Table 5 describes the components contained in pYRH55.

TABLE 5

Description of Plasmid pYRH55 (SEQ ID NO: 1)

| RE$^a$ Sites and Nucleotide Positions | Description of Fragment and Chimeric Gene Components |
|---|---|
| AscI/BsiWI (1212-318) | 887-bp 5' portion of *Yarrowia* lipase 7 locus (GenBank Accession No. AJ549519, labeled as LipY-5' in FIG. 4A) |
| PacI/SphI (4682-3920) | 756-bp 3' portion of *Yarrowia* lipase 7 locus (GenBank Accession No. AJ549519, labeled as LipY-3' in FIG. 4A) |
| SwaI/BsiWI (6219-318) | FBAINm::AtClo1S::Pex20, comprising: FBAINm: *Y. lipolytica* FBAIN promoter (U.S. Pat. No. 7,202,356); AtClo1S: codon-optimized *Arabidopsis thaliana* caleosin-1 coding sequence (SEQ ID NO: 2) Pex20: Pex20 terminator sequence from *Yarrowia* Pex20 gene (GenBank Accession No. AF054613) |
| PmeI/PacI (6183-4682) | *Yarrowia* URA3 gene (GenBank Accession No. AJ306421) |

$^a$RE, restriction endonuclease

The pYRH55 plasmid was digested with AscI/SphI, and then used to transform strain Z5627U5. The transformed cells were plated onto uracil-minus MM plates and maintained at 30° C. for 5 to 6 days. Single colonies were grown as described above for initial fatty acid screening.

GC analyses showed that almost all of the selected 72 strains of Z5627U5 transformed with pYRH55 produced more than 49% EPA of TFAs. Eleven strains (#1, #11, #15, #16, #20, #21, #30, #34, #51, #53 and #54) produced about 55.3%, 50.1%, 50.9%, 51.7%, 50.8%, 49.7%, 53.4%, 54.8%, 50.3%, 53.9% and 50.6% EPA of TFAs and were designated as Z6103, Z6104, Z6105, Z6106, Z6107, Z6108, Z6109, Z6110, Z6111, Z6112 and Z6113, respectively.

Knockout of the Lip7 locus in above strains Z6103 to Z6113 was not confirmed. The genotype of strains Z6109 and its ten siblings with respect to wild type *Y. lipolytica* ATCC #20362 was: Ura⁺, Pex3⁻, unknown 1⁻, unknown 7, unknown 3⁻, unknown 4⁻, YALI0E12947g⁻, unknown 6⁻, YALI0B21890g⁻, unknown 8⁻, unknown 10⁻, unknown 11⁻, unknown 12⁻, unknown 13⁻, unknown 14⁻, unknown 15⁻, YAT1::ME3S::Pex16, GPD::ME3S::Pex20, YAT1::ME3S::Lip1, FBAINm::EgD9eS::Lip2, EXP1::EgD9eS::Lip1, GPAT::EgD9e::Lip2, YAT1::EgD9eS::Lip2, YAT1::EgD9eS-L35G::Pex20, FBAINm::EgD8M::Pex20, EXP1::EgD8M::Pex16, FBAIN::EgD8M::Lip1, GPD::EaD8S::Pex16 (2 copies), YAT1::E389D9eS/EgD8M::Lip1, YAT1::EgD9eS/EgD8M::Aco, FBAINm::EaD9eS/EaD8S::Lip2, DGAT2M::YID9::Lip1, GPDIN::YID9::Lip1, GPD::FmD12::Pex20, YAT1::FmD12::Oct, EXP1::FmD12S::Aco, GPDIN::FmD12::Pex16, EXP1::EgD5M::Pex16, FBAIN::EgD5SM::Pex20, EXP1::EgD5SM::Lip1, YAT1::EaD5SM::Oct, FBAINm::PaD17::Aco, EXP1::PaD17::Pex16, YAT1::PaD17S::Lip1, YAT1::YICPT1::Aco, EXP1::YICPT1::Oct, YAT1::MCS::Lip1, FBA::MCS::Lip1, EXP1::YIPCT::Pex16, YAT1::MaLPAAT1S::Pex16, ALK2LM1::MaLPAAT1S::Pex20, FBAINm::YILPAAT1::Lip1 (2 copies), YAT1::YIPDAT::Lip1 (2 copies), FBAINm::AtClo1 S::Pex20.

Analysis of Total Lipid Content and Composition by Flask Assay

Cells of strains Z6109 and its siblings were grown and analyzed for total lipid content and fatty acid composition by the flask assay described above. Table 6 summarizes the DCW, the TFAs % DCW, the amount of each fatty acid as a weight percent of TFAs (% TFAs) and the EPA % DCW of strains from Z6103 to Z6113.

TABLE 6

Total Lipid Content and Composition in Strain Z6109 and Its Siblings by Flask Assay

| Strain | DCW (g/L) | TFAs % DCW | % TFAs | | | | | | | | | | | | EPA % DCW | EPA Rate (g/L/h) |
|---|---|---|---|---|---|---|---|---|---|---|---|---|---|---|---|---|
| | | | 16:0 | 16:1 | 18:0 | 18:1 | LA | ALA | EDA | DGLA | ARA | ETrA | ETA | EPA | | |
| Z6103 | 4.4 | 51.1 | 2.2 | 0.8 | 2.0 | 5.5 | 14.3 | 0.5 | 3.7 | 5.7 | 1.4 | 0.6 | 3.0 | 52.0 | 26.6 | 0.0084 |
| Z6104 | 4.7 | 55.3 | 2.1 | 0.7 | 2.8 | 5.9 | 15.9 | 0.6 | 3.6 | 5.8 | 1.3 | 0.7 | 3.2 | 49.7 | 27.5 | 0.0093 |
| Z6105 | 4.7 | 55.9 | 2.0 | 0.7 | 2.7 | 5.9 | 16.0 | 0.6 | 3.7 | 5.8 | 1.3 | 0.7 | 3.2 | 49.7 | 27.8 | 0.0093 |
| Z6106 | 4.6 | 53.8 | 2.0 | 0.7 | 2.6 | 5.5 | 15.2 | 0.6 | 3.4 | 5.8 | 1.2 | 0.6 | 3.3 | 51.4 | 27.6 | 0.0091 |
| Z6107 | 4.7 | 54.2 | 2.1 | 0.7 | 2.8 | 5.8 | 16.0 | 0.7 | 3.6 | 5.8 | 1.2 | 0.6 | 3.2 | 50.0 | 27.1 | 0.0091 |
| Z6108 | 4.9 | 55.1 | 2.0 | 0.7 | 2.7 | 6.2 | 16.9 | 0.7 | 3.7 | 5.8 | 1.1 | 0.6 | 3.0 | 49.5 | 27.2 | 0.0095 |
| Z6109 | 4.5 | 54.2 | 2.2 | 0.6 | 2.4 | 4.8 | 15.9 | 0.6 | 3.9 | 5.5 | 1.5 | 0.7 | 2.9 | 51.7 | 28.0 | 0.0090 |
| Z6110 | 4.3 | 50.4 | 1.7 | 0.6 | 2.1 | 5.0 | 12.9 | 0.5 | 3.4 | 6.1 | 1.1 | 0.7 | 3.9 | 54.0 | 27.2 | 0.0083 |
| Z6111 | 4.3 | 53.2 | 2.5 | 0.9 | 2.5 | 6.5 | 16.5 | 0.6 | 3.8 | 5.3 | 1.5 | 0.7 | 2.7 | 48.4 | 25.7 | 0.0079 |
| Z6112 | 4.5 | 55.2 | 2.1 | 0.8 | 2.2 | 5.7 | 15.0 | 0.6 | 3.5 | 5.7 | 1.3 | 0.7 | 3.2 | 51.1 | 28.2 | 0.0091 |
| Z6113 | 4.9 | 54.9 | 1.9 | 0.7 | 2.6 | 5.9 | 15.5 | 0.7 | 3.9 | 5.8 | 1.4 | 0.7 | 3.0 | 49.7 | 27.3 | 0.0095 |

The results in Table 6 generally indicate that heterologous expression of AtClo1S in strain Z5627 raised oil production (i.e., TFAs % DCW) and the percentage of EPA in the total fatty acids of oil (i.e., EPA % TFAs). Specifically, while strain Z5627 yielded 52 TFAs % DCW and 49.3 EPA % TFAs (Table 4), strains Z6103 to Z6113 had average TFAs % DCW of 53.9 and EPA % TFAs of 50.7 (Table 6).

Specific strains analyzed in Table 6 had significantly higher oil and EPA levels compared to Z5627. For example, strain Z6109 had 54.2 TFAs % DCW and 51.7 EPA % TFAs. Z6109 altogether exhibited a 9.4% increase in the total amount of EPA produced (28 EPA % DCW) compared to that produced by Z5627 (25.6 EPA % DCW).

Example 2

Generation of Strain Z6903 Producing at Least about 51.4% EPA of Total Fatty Acids with at Least about 49.1% Total Lipid Content and Reduced Sugar Alcohol By-Products This Example describes the generation of *Y. lipolytica* strain Z6903 through genetic modification of strain Z5585. The genetic modification entailed knocking out the endogenous *Y. lipolytica* gene SOU2, which encodes Sou2 sorbitol utilization protein. The genetic modification further entailed introducing expression cassettes encoding phospholipid:diacylglycerol acyltransferase (PDAT), delta-12 desaturase, and a DGLA synthase multizyme (delta-9 elongase fused to delta-8 desaturase). The development of strain Z6903 was required in order to develop strain Z9276, which is described below in Example 4.

FIG. 3B shows the modification steps and intermediate strains (Z5585U21 and Z5585K2U) used for generating strain Z6903. Strains Z5585U21 and Z5585K2U were generated as follows.

Generation of Strain Z5585U21

Construct pZKUM (above) was used to disrupt the URA3 gene in strain Z5585 that was previously introduced by the plasmid pZKMP-ML9DCB, which carries sequences allowing for expression of MaLPAAT1 S, YIDS and YICPT1 (see U.S. Pat. Appl. Publ. No. 2012-0052537). A total of eight 5-FOA-resistant transformants were grown and identified to possess a Ura$^-$ phenotype. These transformants were grown as described above for initial fatty acid screening.

GC analyses showed the presence of 37.7% EPA in the TFAs of pZKUM-transformant strain #6 cells picked from an FOA plate. This transformant was designated as strain Z5585U21.

Generation of Strain Z5585K2U (Sou2$^-$)

Strain Z5585K2U was generated by knocking out the endogenous *Y. lipolytica* SOU2 gene, which encodes Sou2 sorbitol utilization protein, in strain Z5585U21.

The identification of the SOU2 gene as a genetic target to modify lipid production in *Y. lipolytica* is described below in Example 5. Briefly, during the construction of strain Z3041 (FIG. 8), which involved the genetic modification of strain Z1978, it was observed that strain Z3041 produced more DCW, more oil, and less by-products compared to its parent strain, Z2636. Genome walking and sequencing analyses showed that the promoter region of the SOU2 gene (locus YALI0D18964g, GenBank Accession No. XM_503010, FIG. 5) was disrupted in strain Z3041 by an insertion occurring within the promoter region of SOU2 (FIG. 5). Sorbitol is a sugar alcohol; other sugar alcohols such as mannitol and arabitol are produced as by-products in the *Y. lipolytica* strains disclosed herein to be engineered for enhanced lipid production.

Plasmid pZKSOU2-New (FIG. 4B, SEQ ID NO:4) was used to knock-out a large portion of the SOU2 gene in strain Z5585U21. Table 7 describes the components contained in pZKSOU2-New. This vector contains 5'- and 3'-homology arms (denoted as ySOU2-5' and ySOU2-3', respectively) containing sequences derived from the endogenous *Y. lipolytica* SOU2 locus. Stuffer sequence (non-SOU2 sequence) is located between these homology arms.

TABLE 7

Description of Plasmid pZKSOU2-New (SEQ ID NO: 4)

| RE Sites and Nucleotide Positions | Description of Fragment and Chimeric Gene Components |
|---|---|
| SphI/BsiWI (5289-1) | 1102-bp 5' portion of *Yarrowia* SOU2 locus (GenBank Accession No. XM_503010, labeled as ySOU2-5' in FIG. 4B) |
| EcoRI/SwaI (203-1076) | 873-bp 3' portion of *Yarrowia* SOU2 locus (GenBank Accession No. XM_503010, labeled as ySOU2-3' in FIG. 4B) |
| BsiWI/EcoRI (1-203) | 202-bp stuffer DNA, derived from *Yarrowia* ALK2 gene (GenBank Accession No. CR382132) |
| SwaI/PacI (1076-2573) | *Yarrowia* URA3 gene (GenBank Accession No. AJ306421) |

The knock-out strategy entailed a "pop-in/pop-out" process as delineated in the diagram and legend of FIG. 6. Briefly, the pop-in event occurred as a result of homologous recombination between the 5'-homology arm of pZKSOU2-New and corresponding sequence at the endogenous *Y. lipolytica* SOU2 locus. This particular integration event resulted in the juxtaposition of a mutated SOU2 allele with the wild type SOU2 allele, and was selected on the basis that pZKSOU2-New integration rendered the cells of strain Z5585U21 (Ura$^-$) to be Ura$^+$.

The pop-out event occurred as a result of homologous recombination between the 3'-homology arm of the integrated mutant allele and corresponding sequence at the adjacent endogenous *Y. lipolytica* SOU2 locus (FIG. 6, left-hand pop-out event). Since this pop-out event resulted in removal of the URA3 gene that had been introduced during pop-in, cells in which the pop-out event occurred leaving behind the mutant SOU2 allele could be selected on FOA plates (i.e., cells are Ura$^-$).

Plasmid pZKSOU2-New was used to transform Z5585U21. A total of 60 Ura$^+$ transformants were grown on MM plates lacking uracil. Polymerase chain reaction (PCR) amplification analyses indicated that transformants #26 and #28 had undergone recombination between the 5'-arm homologous sequences of pZSOU2-New and the endogenous SOU2 gene.

Strain #26 was picked, grown in liquid YPD media, and then plated on FOA plates to select for cells that subsequently became Ura$^-$ due to a pop-out event (FIG. 6). A total of 96 Ura$^-$ strains were analyzed by PCR amplification to determine which ones had undergone pop-out events involving recombination at the 3'-arm homology sequences which removed the pZKOSOU2-New backbone sequences (AmpR and URA3) thereby leaving behind a mutated SOU2 allele. This PCR analysis was necessary, since certain Ura$^-$ cells could alternatively have a wild type SOU2 allele if the pop-out recombination event occurred at the 5'-arm homologous sequence (FIG. 6). In 9 of the 96 Ura$^-$ strains, PCR analyses detected recombination at the 3'-arm homologous sequences indicative of a mutant SOU2 allele. Two of these 9 strains were designated as Z5585K2U1 and Z5585K2U2.

The final genotype of both strains Z5585K2U1 and Z5585K2U2 with respect to wild type *Y. lipolytica* ATCC #20362 is: Ura⁻, Pex3⁻, unknown 1⁻, unknown 2⁻, unknown 3⁻, unknown 4⁻, YALI0E12947g⁻, unknown 6⁻, YALI0B21890g⁻, unknown 8⁻, unknown 10⁻, unknown 11⁻, unknown 12⁻, unknown 13⁻, unknown 14⁻, Sou2⁻, YAT1:: ME3S::Pex16, GPD::ME3S::Pex20, YAT1::ME3S::Lip1, FBAINm::EgD9eS::Lip2, EXP1::EgD9eS::Lip1, GPAT:: EgD9e::Lip2, YAT1::EgD9eS::Lip2, YAT1::EgD9eS-L35G:: Pex20, FBAINm::EgD8M::Pex20, EXP1::EgD8M::Pex16, FBAIN::EgD8M::Lip1, GPD::EaD8S::Pex16 (2 copies), YAT1::E389D9eS/EgD8M::Lip1, YAT1::EgD9eS/EgD8M:: Aco, FBAINm::EaD9eS/EaD8S::Lip2, DGAT2M::YID9:: Lip1, GPDIN::YID9::Lip1, GPD::FmD12::Pex20, YAT1:: FmD12::Oct, EXP1::FmD12S::Aco, GPDIN::FmD12:: Pex16, EXP1::EgD5M::Pex16, FBAIN::EgD5SM::Pex20, EXP1::EgD5SM::Lip1, YAT1::EaD5SM::Oct, FBAINm:: PaD17::Aco, EXP1::PaD17::Pex16, YAT1::PaD17S::Lip1, YAT1::YICPT1::Aco, EXP1::YICPT1::Oct, YAT1::MCS:: Lip1, FBA::MCS::Lip1, EXP1::YIPCT::Pex16, YAT1:: MaLPAAT1S::Pex16, ALK2LM1::MaLPAAT1S::Pex20, FBAINm::YILPAAT1::Lip1 (2 copies), YAT1::YIPDAT:: Lip1 (2 copies).

Strain Z5585K2U1 is herein referred to as Z5585K2U.

Generation of Strain Z6903

Plasmid pZKADn-SyP298F (FIG. 7A, SEQ ID NO:5) was generated to integrate gene cassettes for expressing PDAT (SEQ ID NO:15, PDAT with an extra alanine at position 2 compared to wild type YlPDAT), delta-12 desaturase (SEQ ID NO:13), and a DGLA synthase multizyme (SEQ ID NO:17, delta-9 elongase fused to delta-8 desaturase) into the alcohol dehydrogenase 3 (ADH3) locus (GenBank Accession No. AF175273) of strain Z5585K2U. Table 8 describes the components contained in pZKADn-SyP298F.

TABLE 8

Description of Plasmid pZKADn-SyP298F (SEQ ID NO: 5)

| RE Sites and Nucleotide Positions | Description of Fragment and Chimeric Gene Components |
|---|---|
| AscI/BsiWI (6032-5255) | 777-bp 5' portion of *Yarrowia* ADH3 gene (GenBank Accession No. AF175273, labeled as yADH-5' in FIG. 7A) |
| PacI/SphI (9510-8740) | 756-bp 3' portion of *Yarrowia* ADH3 gene (GenBank Accession No. AF175273, labeled as yADH-3' in FIG. 7A) |
| SwaI/BsiWI (2697-5255) | ALK2LM1::FmD12S::Erp, comprising: ALK2LM1: *Y. lipolytica* ALK2 promoter plus N-terminal 66-bp coding region of *Y. lipolytica* ALK2 gene (U.S. Pat. Appl. Publ. No. 2012-0052537); FmD12S: codon-optimized delta-12 desaturase (SEQ ID NO: 12) derived from *Fusarium moniliforme* (U.S. Pat. No. 7,504,259); Erp: terminator sequence (SEQ ID NO: 6) from *Yarrowia* ERP gene (GenBank Accession No. XP_501960) |
| PmeI/SwaI (1-2697) | SPS19-P3::YIPDAT::Lip1, comprising: SPS19-P3: SPS19 promoter (409-bp) of *Y. lipolytica* SPS19 gene (U.S. Appl. Publ. No. 2013-0089911); YIPDAT: *Y. lipolytica* PDAT (SEQ ID NO: 14) (U.S. Pat. Appl. Publ. No. 2012-0052537); Lip1: terminator sequence from *Yarrowia* LIP1 gene (GenBank Accession No. Z50020) |
| ClaI/PmeI (11611-1) | SPS19LM::E389D9eS/EgD8M::Glo, comprising: SPS19LM: SPS19 promoter (900-bp) of *Y. lipolytica* SPS19 gene (U.S. Appl. Publ. No. 2013-0089911); E389D9eS/EgD8M (SEQ ID NO: 16): gene fusion comprising a codon-optimized delta-9 elongase derived from *Eutreptiella* sp. CCMP389 (E389D9eS), |

TABLE 8-continued

Description of Plasmid pZKADn-SyP298F (SEQ ID NO: 5)

| RE Sites and Nucleotide Positions | Description of Fragment and Chimeric Gene Components |
|---|---|
| | a linker, and a codon-optimized mutant delta-8 desaturase derived from *Euglena gracilis* (EgD8M) (U.S. Pat. Appl. Publ. No. 2008-0254191); Glo: terminator sequence (SEQ ID NO: 7) from *Yarrowia* glyoxalase (GLO) gene (GenBank Accession No. CR382130) |
| SalI/PacI (11161-9510) | *Yarrowia* URA3 gene (GenBank Accession No. AJ306421) |

The pZKADn-SyP298F plasmid was digested with AscI, and then used to transform strain Z5585K2U. The transformed cells were plated onto uracil-minus MM plates and maintained at 30° C. for 5 to 6 days. Single colonies were grown as described above for initial fatty acid screening.

GC analyses showed that 9 strains of Z5585K2U transformed with pZKADn-SyP298F produced more than 51.1% EPA of TFAs. These strains (#10, #14, #15, #61, #76, #80, #82, #83, #96) produced about 52.4%, 51.9%, 51.6%, 53.2%, 52.3%, 52.4%, 51.9%, 51.3% and 51.1% EPA of TFAs and were designated as Z6897, Z6898, Z6899, Z6900, Z6901, Z6902, Z6903, Z6904 and Z6905, respectively.

Knockout of ADH3 locus in above strains Z6897 to Z6905 was not confirmed. The genotype of strains Z6903 and its eight siblings with respect to wild type *Y. lipolytica* ATCC #20362 was: Ura⁺, Pex3⁻, unknown 1⁻, unknown 2⁻, unknown 3⁻, unknown 4⁻, YALI0E12947g⁻, unknown 6⁻, YALI0B21890g⁻, unknown 8⁻, unknown 10⁻, unknown 11⁻, unknown 12⁻, unknown 13⁻, unknown 14⁻, Sou2⁻, unknown 15, YAT1::ME3S::Pex16, GPD::ME3S::Pex20, YAT1:: ME3S::Lip1, FBAINm::EgD9eS::Lip2, EXP1::EgD9eS:: Lip1, GPAT::EgD9e::Lip2, YAT1::EgD9eS::Lip2, YAT1:: EgD9eS-L35G::Pex20, FBAINm::EgD8M::Pex20, EXP1:: EgD8M::Pex16, FBAIN::EgD8M::Lip1, GPD::EaD8S:: Pex16 (2 copies), YAT1::E389D9eS/EgD8M::Lip1, SPS19LM::E389D9eS/EgD8M::Glo YAT1::EgD9eS/ EgD8M::Aco, FBAINm::EaD9eS/EaD8S::Lip2, DGAT2M:: YID9::Lip1, GPDIN::YID9::Lip1, GPD::FmD12::Pex20, YAT1::FmD12::Oct, EXP1::FmD12S::Aco, ALK2LM1:: FmD12S::Erp, GPDIN::FmD12::Pex16, EXP1::EgD5M:: Pex16, FBAIN::EgD5SM::Pex20, EXP1::EgD5SM::Lip1, YAT1::EaD5SM::Oct, FBAINm::PaD17::Aco, EXP1:: PaD17::Pex16, YAT1::PaD17S::Lip1, YAT1::YICPT1::Aco, EXP1::YICPT1::Oct, YAT1::MCS::Lip1, FBA::MCS::Lip1, EXP1::YIPCT::Pex16, YAT1::MaLPAAT1S::Pex16, ALK2LM1::MaLPAAT1S::Pex20, FBAINm::YILPAAT1:: Lip1 (2 copies), YAT1::YIPDAT::Lip1 (2 copies), SPS19-P3::YIPDAT::Lip1.

Analysis of Total Lipid Content and Composition by Flask Assay

Cells of strains Z6903 and its siblings were grown and analyzed for total lipid content and fatty acid composition by the flask assay described above. Table 9 summarizes the DCW, the TFAs % DCW, the amount of each fatty acid as a weight percent of TFAs (% TFAs) and the EPA % DCW of strains from Z6103 to Z6113.

TABLE 9

Total Lipid Content and Composition in Strain Z6903 and Its Siblings by Flask Assay

| Strain | DCW (g/L) | TFAs % DCW | % TFAs | | | | | | | | | | | | EPA % DCW | EPA Rate (g/L/h) |
| --- | --- | --- | --- | --- | --- | --- | --- | --- | --- | --- | --- | --- | --- | --- | --- | --- |
| | | | 16:0 | 16:1 | 18:0 | 18:1 | LA | ALA | EDA | DGLA | ARA | ETrA | ETA | EPA | | |
| Z6897 | 4.4 | 47.6 | 2.0 | 0.7 | 2.2 | 5.5 | 15.9 | 0.8 | 3.7 | 5.1 | 0.8 | 0.5 | 3.6 | 52.1 | 24.8 | 0.0077 |
| Z6898 | 4.1 | 41.0 | 1.9 | 0.6 | 2.5 | 5.5 | 16.4 | 0.8 | 4.0 | 5.0 | 0.8 | 0.6 | 3.4 | 50.9 | 20.9 | 0.0061 |
| Z6899 | 4.7 | 46.1 | 1.9 | 0.8 | 1.9 | 6.0 | 15.6 | 0.8 | 3.6 | 5.1 | 0.7 | 0.5 | 3.5 | 52.5 | 24.2 | 0.0081 |
| Z6900 | 4.8 | 46.0 | 1.7 | 0.7 | 2.0 | 5.4 | 15.2 | 0.7 | 3.9 | 5.6 | 0.8 | 0.6 | 4.0 | 52.3 | 24.0 | 0.0083 |
| Z6901 | 4.9 | 48.7 | 2.0 | 0.7 | 2.3 | 5.9 | 16.3 | 0.8 | 3.9 | 5.0 | 0.9 | 0.5 | 3.6 | 51.2 | 24.9 | 0.0087 |
| Z6902 | 4.6 | 50.9 | 2.1 | 0.7 | 2.5 | 6.0 | 16.8 | 0.9 | 3.8 | 4.9 | 0.8 | 0.5 | 3.5 | 50.6 | 25.7 | 0.0084 |
| Z6903 | 4.9 | 49.1 | 2.0 | 0.7 | 2.2 | 5.7 | 16.8 | 0.8 | 3.8 | 5.0 | 0.8 | 0.5 | 3.6 | 51.4 | 25.2 | 0.0089 |
| Z6904 | 4.5 | 48.2 | 2.1 | 0.7 | 2.3 | 5.9 | 16.2 | 0.8 | 3.8 | 5.0 | 0.8 | 0.6 | 3.5 | 51.1 | 24.6 | 0.0079 |
| Z6905 | 4.8 | 52.8 | 2.0 | 0.7 | 2.7 | 6.3 | 17.6 | 0.9 | 3.7 | 4.7 | 0.7 | 0.4 | 3.2 | 50.0 | 26.4 | 0.0091 |

Table 9 shows that in strain Z6903, DCW was 4.9 g/L, TFAs % DCW was 49.1, EPA % TFAs was 51.4, and EPA % DCW was 25.2, which was the third highest EPA % DCW measurement among the analyzed strains. In strain Z6905, DCW was 4.8 g/L, TFAs % DCW was 52.8, EPA % TFAs was 50.0, and EPA % DCW was 26.4, which was the highest EPA % DCW measurement among the analyzed strains.

Strain Z6903 was further analyzed to determine the levels of the sugar alcohol by-products arabitol, mannitol and erythritol (Table 10). This analysis was also made with strain Z6109 (Example 1).

TABLE 10

Sugar Alcohols Produced by Strains Z6109 and Z6903

| | Z6109 | Z6903 |
| --- | --- | --- |
| SOU2 gene | + | − |
| Arabitol (g/L) | 4.9 | 0.0 |
| Mannitol (g/L) | 3.5 | 0.0 |
| Erythritol (g/L) | 0.8 | 2.9 |
| Total sugar alcohols (g/L) | 9.2 | 2.9 |

The results in Table 10 indicate that strain Z6903 produced no mannitol or arabitol by-products, suggesting that the Sou2 protein is essential for mannitol and arabitol biosynthesis in *Y. lipolytica*. Also, compared to strain Z6109, strain Z6903 produced about 68% less total sugar alcohol by-products. These results indicate that down-regulation of SOU2 expression in *Y. lipolytica* significantly decreases the level of sugar alcohol by-product production.

Example 3

Generation of Strain Z7418 Producing at Least about 49.8% EPA of Total Fatty Acids with at Least about 49.3% Total Lipid Content This Example describes the generation of *Y. lipolytica* strain Z7418 through genetic modification of strain Z6903. The genetic modification entailed introducing expression cassettes encoding delta-8 desaturase, malonyl-CoA synthetase (MCS), and acyl-CoA:lysophosphatidic acid acyltransferase (LPAAT). The development of strain Z7418 was required in order to develop strain Z9276, which is described below in Example 4.

FIG. 3B shows the modification steps and intermediate strain (Z6903U) used for generating strain Z7418. Strain Z6903U was generated as follows.

Generation of Strain Z6903U

Construct pZKUM (above) was used to disrupt the URA3 gene in strain Z6903 that was introduced by the plasmid pZKADn-SyP298F (above). A total of eight 5-FOA-resistant transformants were grown and identified to possess a Ura⁻ phenotype. Individual transformants were grown as described above for initial fatty acid screening.

GC analyses showed the presence of 35.0%, 32.7% and 37.7% EPA in the TFAs of pZKUM-transformant strains #5, #6 and #7 picked from an FOA plate, which were designated as Z6903U5, Z6903U6 and Z6903U7, respectively. These three transformants were collectively designated as strain Z6903U.

Generation of Strain Z7418

Plasmid pZK16-MyL8N was used to integrate gene cassettes for expressing a synthetic mutant delta-8 desaturase derived from *E. gracilis* (YAT1::EgD8M::Pex20; EgD8M is SEQ ID NO:19), a codon-optimized malonyl-CoA synthetase derived from *Rhizobium leguminosarum* bv. *viciae* 3841 (FBA::MCS::Lip1; MCS is SEQ ID NO:21), and a *Y. lipolytica* acyl-CoA:lysophosphatidic acid acyltransferase (YAT1::YILPAAT1::Lip1; YILPAAT1 is SEQ ID NO:23) into the YALI0B14795p locus (GenBank Accession No. XM_500900) of strain Z6903U. The construction of plasmid pZK16-MyL8N has been described (U.S. Pat. Appl. Publ. No. 2012-0052537, see Table 11 therein, which is incorporated herein by reference).

The pZK16-MyL8N plasmid was digested with AscI, and then used to transform strain Z6903U5. The transformed cells were plated onto uracil-minus MM plates and maintained at 30° C. for 5 to 6 days. Single colonies were grown as described above for initial fatty acid screening.

GC analyses showed that almost all of the selected 96 strains of Z6903U5 transformed with pZK16-MyL8N produced more than 50.0% EPA of TFAs. Ten strains (#8, #9, #34, #40, #43, #58, #59, #70, #79, #80) produced about 52.1%, 50.3%, 51.5%, 51.1%, 53.5%, 51.4%, 50.8%, 52.2%, 51.2% and 51.6% EPA of TFAs and were designated as Z7416, Z7417, Z7418, Z7419, Z7420, Z7421, Z7422, Z7423, Z7424 and Z7425, respectively.

Knockout of the YALI0B14795p locus in above strains Z7416 to Z7425 was not confirmed. The genotype of strains Z7418 and its nine siblings with respect to wild type *Y. lipolytica* ATCC #20362 was: Ura⁺, Pex3⁻, unknown 1⁻, unknown 2⁻, unknown 3⁻, unknown 4⁻, YALI0E12947g⁻, unknown 6⁻, YALI0B21890g⁻, unknown 8⁻, unknown 10⁻, unknown 11⁻, unknown 12⁻, unknown 13⁻, unknown 14⁻, Sou2⁻, unknown 15⁻, unknown 16⁻, YAT1::ME3S::Pex16, GPD::ME3S::Pex20, YAT1::ME3S::Lip1, FBAINm::EgD9eS::Lip2, EXP1::EgD9eS::Lip1, GPAT::EgD9e::Lip2, YAT1::EgD9eS::Lip2, YAT1::EgD9eS-L35G::Pex20, FBAINm::

EgD8M::Pex20, EXP1::EgD8M::Pex16, FBAIN::EgD8M::Lip1, YAT1::EgD8M::Pex20, GPD::EaD8S::Pex16 (2 copies), YAT1::E389D9eS/EgD8M::Lip1, SPS19LM::E389D9eS/EgD8M::Glo YAT1::EgD9eS/EgD8M::Aco, FBAINm::EaD9eS/EaD8S::Lip2, DGAT2M::YID9::Lip1, GPDIN::YID9::Lip1, GPD::FmD12::Pex20, YAT1::FmD12::Oct, EXP1::FmD12S::Aco, ALK2LM1::FmD12S::Erp, GPDIN::FmD12::Pex16, EXP1::EgD5M::Pex16, FBAIN::EgD5SM::Pex20, EXP1::EgD5SM::Lip1, YAT1::EaD5SM::Oct, FBAINm::PaD17::Aco, EXP1::PaD17::Pex16, YAT1::PaD17S::Lip1, YAT1::YICPT1::Aco, EXP1::YICPT1::Oct, YAT1::MCS::Lip1, FBA::MCS::Lip1 (2 copies), EXP1::YIPCT::Pex16, YAT1::MaLPAAT1S::Pex16, ALK2LM1::MaLPAAT1S::Pex20, FBAINm::YILPAAT1::Lip1 (2 copies), YAT1::YILPAAT1::Lip1, YAT1::YIPDAT::Lip1 (2 copies), SPS19-P3::YIPDAT::Lip1.

Analysis of Total Lipid Content and Composition by Flask Assay

Cells of strains Z7418 and its siblings were grown and analyzed for total lipid content and fatty acid composition by the flask assay described above. Table 11 summarizes the DCW, the TFAs % DCW, the amount of each fatty acid as a weight percent of TFAs (% TFAs) and the EPA % DCW of strains from Z7416 to Z7425.

Ura$^-$ phenotype. These transformants were grown as described above for initial fatty acid screening.

GC analyses showed the presence of 35.7%, 36.1%, 32.3% 35.4 and 33.6% EPA in the TFAs of B group pZKUM-transformant strains #2, #3, #6, #7 and #8 picked from an FOA-plate, which were designated as Z7418BU1, Z7418BU2, Z7418BU3, Z7418BU4 and Z7418BU5, respectively. GC analyses also showed the presence of 35.9% EPA in the TFAs of C group pZKUM-transformant strain #6 picked from an FOA-plate, which was designated as Z74180U1. GC analyses also showed the presence of 24.2%, 34.9% and 34.0% EPA in the TFAs of D group pZKUM-transformant strains #3, #4 and #7 picked from an FOA-plate, which were designated as Z7418DU1, Z7418DU2 and Z7418DU3, respectively.

Generation of Strain Z9276

Plasmid pZKMPn-YD58 (FIG. 7B, SEQ ID NO:24) was generated to integrate a gene cassette for expressing a double-mutant *Y. lipolytica* acyl CoA:lysophosphatidylcholine acyltransferase (YILPCAT [M136S/T389A], SEQ ID NO:26) into the D-arabinitol 2-dehydrogenase locus (GenBank Accession No. XP_504895) of strain Z7418U. Table 12 describes the components contained in pZKMPn-YD58.

TABLE 11

Total Lipid Content and Composition in Strain Z7418 and Its Siblings by Flask Assay

| Strain | DCW (g/L) | TFAs % DCW | _____ % TFAs _____ | | | | | | | | | | | | EPA % DCW | EPA Rate (g/L/h) |
|---|---|---|---|---|---|---|---|---|---|---|---|---|---|---|---|---|
| | | | 16:0 | 16:1 | 18:0 | 18:1 | LA | ALA | EDA | DGLA | ARA | ETrA | ETA | EPA | | |
| Z7416 | 5.7 | 48.7 | 1.9 | 0.7 | 2.4 | 5.8 | 16.5 | 0.9 | 3.7 | 4.6 | 1.1 | 0.8 | 3.8 | 50.0 | 24.3 | 0.0099 |
| Z7417 | 5.9 | 52.2 | 2.0 | 0.8 | 2.2 | 7.2 | 17.5 | 1.0 | 4.1 | 4.6 | 0.9 | 0.6 | 3.5 | 47.7 | 24.9 | 0.0106 |
| Z7418 | 5.9 | 49.3 | 1.9 | 0.7 | 2.2 | 6.0 | 16.4 | 0.9 | 3.8 | 4.7 | 1.0 | 0.8 | 3.8 | 49.8 | 24.6 | 0.0103 |
| Z7419 | 5.7 | 49.8 | 1.9 | 0.7 | 2.3 | 6.1 | 16.7 | 0.9 | 3.8 | 4.5 | 1.0 | 0.8 | 3.7 | 49.7 | 24.7 | 0.0100 |
| Z7420 | 5.2 | 51.1 | 2.0 | 0.8 | 2.4 | 6.9 | 17.4 | 1.0 | 4.1 | 4.3 | 0.9 | 0.7 | 3.4 | 48.5 | 24.8 | 0.0092 |
| Z7421 | 5.0 | 48.8 | 1.9 | 0.6 | 2.4 | 5.7 | 16.2 | 0.9 | 3.7 | 4.5 | 1.0 | 0.8 | 3.7 | 50.5 | 24.6 | 0.0088 |
| Z7422 | 5.2 | 52.5 | 2.1 | 0.8 | 2.3 | 6.9 | 17.2 | 0.9 | 4.0 | 4.4 | 0.9 | 0.7 | 3.3 | 48.4 | 25.4 | 0.0094 |
| Z7423 | 6.2 | 48.2 | 2.0 | 0.8 | 2.3 | 6.8 | 17.5 | 1.0 | 3.8 | 4.5 | 1.0 | 0.8 | 3.7 | 48.2 | 23.2 | 0.0102 |
| Z7424 | 5.9 | 49.3 | 1.9 | 0.7 | 2.3 | 5.9 | 16.6 | 0.9 | 3.7 | 4.6 | 1.0 | 0.7 | 3.8 | 49.9 | 24.6 | 0.0103 |
| Z7425 | 6.2 | 48.7 | 2.0 | 0.7 | 2.4 | 6.0 | 16.7 | 1.0 | 3.6 | 4.7 | 0.9 | 0.6 | 3.8 | 49.7 | 24.2 | 0.0107 |

Table 11 shows that in strain Z7418, DCW was 5.9 g/L, TFAs % DCW was 49.8, EPA % TFAs was 49.3, and EPA % DCW was 24.6.

Example 4

Generation of Strain Z9276 Producing at Least about 57.5% EPA of Total Fatty Acids with at Least about 56.9% Total Lipid Content This Example describes the generation of *Y. lipolytica* strain Z9276 through genetic modification of strain Z7418. The genetic modification entailed introducing an expression cassette encoding a mutant acyl CoA: lysophosphatidylcholine acyltransferase (LPCAT). The construction and analysis of this and other mutant LPCATs is described in Examples 6-9.

FIG. 3B shows the modification steps and intermediate strain (Z7418U) used for generating strain Z9276. Strain Z7418U was generated as follows.

Generation of Strain Z7418U

Construct pZKUM (above) was used to disrupt the URA3 gene in strain Z7418 that was introduced by the plasmid pZK16-MyL8N (above). A total of twenty-four 5-FOA-resistant transformants were grown and identified to possess a

TABLE 12

Description of Plasmid pZKMPn-YD58 (SEQ ID NO: 24)

| RE Sites and Nucleotide Positions | Description of Fragment and Chimeric Gene Components |
|---|---|
| AscI/BsiWI (696-1) | 695-bp 5' portion of D-arabinitol 2-dehydrogenase locus (GenBank Accession No. XP_504895, labeled as yM1DP-5' in FIG. 7B) |
| PacI/SphI (4021-3404) | 797-bp 3' portion of D-arabinitol 2-dehydrogenase locus (GenBank Accession No. XP_504895, labeled as yM1DP-3' in FIG. 7B) |
| ClaI/SwaI (6302-8930) | YAT1::YILPCAT (M136S/T389A)::Lip1, comprising: YAT1: *Y. lipolytica* YAT1 promoter (U.S. Pat. Appl. Publ. No. 2010-0068789); YILPCAT: double mutant (M136S/T389A) (SEQ ID NO: 25) of *Y. lipolytica* acyl-CoA:lysophosphatidylcholine acyltransferase (U.S. Appl. No. 61/661,623, which is incorporated herein by reference); Lip1: Lip1 terminator sequence from *Yarrowia* LIP1 gene (GenBank Accession No. Z50020) |
| SalI/PacI (5852-4201) | *Yarrowia* URA3 gene (GenBank Accession No. AJ306421) |

The pZKMPn-YD58 plasmid was digested with AscI, and then used to transform strain Z7418BU1. The transformed cells were plated onto uracil-minus MM plates and maintained at 30° C. for 5 to 6 days. Single colonies were grown as described above for initial fatty acid screening.

GC analyses showed that nine of the selected 48 strains of Z7418BU1 transformed with pZKMPn-YD58 produced more than 55.0% EPA of TFAs. These nine strains (#11, #13, #14, #15, #24, #25, #33, #37, #48) produced about 55.9%, 55.9%, 55.0%, 56.3%, 56.1%, 57.1%, 55.3%, 55.1% and 56.1% EPA of TFAs and were designated as Z9256, Z9257, Z9258, Z9259, Z9260, Z9261, Z9262, Z9263 and Z9264, respectively.

GC analyses showed that eleven of the selected 60 strains of Z7418BU2 transformed with pZKMPn-YD58 produced more than 54.7% EPA of TFAs. These eleven strains (#1, #5, #8, #10, #18, #26, #30, #35, #42, #45, #54) produced about 56.5%, 54.8%, 57.9%, 56.1%, 56.1%, 57.3%, 58.8%, 54.9%. 54.7%, 55.4% and 55.5% EPA of TFAs and were designated as Z9265, Z9266, Z9267, Z9268, Z9269, Z9270, Z9271, Z9272, Z9273, Z9274 and Z9275, respectively.

GC analyses showed that four of the selected 44 strains of Z7418DU3 transformed with pZKMPn-YD58 produced more than 55.8% EPA of TFAs. These four strains (#10, #12, #15, #16) produced about 56.5%, 55.8%, 55.9% and 56.2% EPA of TFAs and were designated as Z9276, Z9277, Z9278 and Z9279, respectively.

Knockout of the D-arabinitol 2-dehydrogenase locus in above strains Z9256 to Z9279 was not confirmed. The genotype of these strains, including Z9276, with respect to wild type *Y. lipolytica* ATCC #20362 was: Ura+, Pex3−, unknown 1−, unknown 2−, unknown 3−, unknown 4−, YALI0E12947g−, unknown 6−, YALI0B21890g−, unknown 8−, unknown 10−, unknown 11−, unknown 12−, unknown 13−, unknown 14−, Sou2−, unknown 15−, unknown 16−, unknown 17−, YAT1::ME3S::Pex16, GPD::ME3S::Pex20, YAT1::ME3S::Lip1, FBAINm::EgD9eS::Lip2, EXP1::EgD9eS::Lip1, GPAT::EgD9e::Lip2, YAT1::EgD9eS::Lip2, YAT1::EgD9eS-L35G::Pex20, FBAINm::EgD8M::Pex20, EXP1::EgD8M::Pex16, FBAIN::EgD8M::Lip1, YAT1::EgD8M::Pex20, GPD::EaD8S::Pex16 (2 copies), YAT1::E389D9eS/EgD8M::Lip1, SPS19LM::E389D9eS/EgD8M::Glo YAT1::EgD9eS/EgD8M::Aco, FBAINm::EaD9eS/EaD8S::Lip2, DGAT2M::YID9::Lip1, GPDIN::YID9::Lip1, GPD::FmD12::Pex20, YAT1::FmD12::Oct, EXP1::FmD12S::Aco, ALK2LM1::FmD12S::Erp, GPDIN::FmD12::Pex16, EXP1::EgD5M::Pex16, FBAIN::EgD5SM::Pex20, EXP1::EgD5SM::Lip1, YAT1::EaD5SM::Oct, FBAINm::PaD17::Aco, EXP1::PaD17::Pex16, YAT1::PaD17S::Lip1, YAT1::YICPT1::Aco, EXP1::YICPT1::Oct, YAT1::MCS::Lip1, FBA::MCS::Lip1 (2 copies), EXP1::YIPCT::Pex16, YAT1::MaLPAAT1S::Pex16, ALK2LM1::MaLPAAT1S::Pex20, FBAINm::YILPAAT1::Lip1 (2 copies), YAT1::YILPAAT1::Lip1, YAT1::YIPDAT::Lip1 (2 copies), SPS19-P3::YIPDAT::Lip1, YAT1::YILPCAT(M136S/T389A)::Lip1.

Analysis of Total Lipid Content and Composition by One-Step Flask Assay

Cells of strains Z9256 to Z9279, including Z9276, were grown and analyzed for total lipid content and fatty acid composition by the "one-step" flask assay, which is described as follows:

One loop of freshly streaked cells was inoculated into 3 mL One-Step Flask medium (recipe described below) and grown overnight at 250 rpm and 30° C. The $OD_{600\,nm}$ of the culture was measured and an aliquot of cells from the culture was added to a final $OD_{600\,nm}$ of 0.25 in 15 mL of One-Step Flask medium in a 125-mL flask. After one day in a shaker incubator at 250 rpm and at 30° C., 10 mL of a high glucose medium (80 g/L glucose, 1.9 g/L $KH_2PO_4$, 6.3 g/L $K_2HPO_4$, 8.4 g/L $NaHCO_3$, pH 7.2) was added into the same flask. After 5 days in a shaker incubator at 250 rpm and at 30° C., a 1-mL aliquot was used for fatty acid analysis and 10 mL dried for dry cell weight determination. The fatty acid and DCW analyses were performed as described above.

One-Step Flask Assay Media:
0.5 g/L urea, 2.5 g/L Yeast extract, 3.0 g/L $KH_2PO_4$, 1.7 g/L $Na_2PO_4.12H_2O$, 20 g/L D-glucose, 0.2 ml/L trace metal solution (100X), 0.25 g/L $MgSO_4.7H_2O$, 0.15 mg/L thiamine HCl.

Trace Metals Solution (100X):
10 g/L citric acid, 1.5 g/L $CaCl_2.2H_2O$, 10 g/L $FeSO_4.7H_2O$, 0.39 g/L $ZnSO_4.7H_2O$, 0.38 g/L $CuSO_4.5H_2O$, 0.2 g/L $CoCl_2.6H_2O$, 0.3 g/L $MnCl_2.4H_2O$.

Table 13 summarizes the DCW, the TFAs % DCW, the amount of each fatty acid as a weight percent of TFAs (% TFAs) and the EPA % DCW of strains from Z9256 to Z9279.

TABLE 13

Total Lipid Content and Composition in Strains Z9256 to Z9279, Including Z9276, by Flask Assay

| Strain | DCW (g/L) | TFAs % DCW | % TFAs[a] | | | | | | | | | | | EPA % DCW | EPA Rate (g/L/h) |
|---|---|---|---|---|---|---|---|---|---|---|---|---|---|---|---|
| | | | 16:0 | 16:1 | 18:0 | 18:1 | LA | ALA | EDA | DGLA | ARA | ETrA | ETA | EPA | | |
| Z9256 | 7.1 | 61.3 | 2.1 | 0.7 | 2.0 | 7.3 | 14.3 | 0.3 | 4.9 | 5.3 | 1.4 | 0.5 | 2.4 | 52.9 | 32.4 | 0.0165 |
| Z9257 | 7.0 | 61.0 | 1.9 | 0.6 | 2.0 | 7.3 | 14.4 | 0.3 | 4.8 | 5.3 | 1.4 | 0.6 | 2.6 | 52.7 | 32.2 | 0.0162 |
| Z9258 | 7.1 | 61.0 | 1.9 | 0.6 | 2.0 | 7.5 | 15.8 | 0.4 | 4.9 | 5.0 | 1.3 | 0.6 | 2.6 | 51.2 | 31.2 | 0.0158 |
| Z9259 | 7.0 | 61.2 | 2.0 | 0.6 | 2.0 | 7.2 | 13.5 | 0.3 | 4.8 | 5.5 | 1.5 | 0.5 | 2.4 | 53.9 | 33.0 | 0.0164 |
| Z9260 | 7.1 | 61.5 | 2.1 | 0.7 | 2.1 | 7.6 | 14.9 | 0.3 | 5.0 | 5.2 | 1.4 | 0.5 | 2.4 | 51.9 | 31.9 | 0.0161 |
| Z9261 | 6.3 | 62.0 | 1.9 | 0.6 | 1.9 | 7.9 | 13.8 | 0.3 | 4.9 | 5.1 | 1.4 | 0.5 | 2.3 | 53.5 | 33.2 | 0.0150 |
| Z9262 | 7.1 | 61.2 | 2.0 | 0.6 | 2.0 | 7.7 | 15.0 | 0.4 | 5.0 | 5.3 | 1.3 | 0.5 | 2.5 | 51.9 | 31.8 | 0.0162 |
| Z9263 | 7.3 | 59.7 | 2.0 | 0.7 | 2.0 | 7.4 | 14.7 | 0.4 | 4.9 | 5.3 | 1.3 | 0.5 | 2.5 | 52.5 | 31.4 | 0.0163 |
| Z9264 | 5.8 | 49.5 | 2.3 | 0.8 | 1.7 | 6.8 | 13.8 | 0.5 | 4.2 | 5.3 | 0.9 | 0.7 | 4.3 | 51.7 | 25.6 | 0.0106 |
| Z9265 | 5.1 | 50.6 | 1.9 | 0.8 | 1.3 | 5.6 | 10.2 | 0.3 | 3.6 | 4.7 | 1.1 | 0.7 | 2.7 | 60.0 | 30.4 | 0.0109 |
| Z9266 | 6.7 | 62.1 | 2.2 | 0.8 | 2.0 | 7.5 | 14.9 | 0.5 | 4.7 | 4.7 | 0.9 | 0.5 | 2.8 | 52.2 | 32.4 | 0.0155 |
| Z9267 | 6.2 | 53.3 | 2.4 | 0.9 | 1.9 | 5.3 | 11.3 | 0.4 | 3.6 | 4.4 | 1.2 | 0.7 | 2.4 | 57.7 | 30.8 | 0.0135 |
| Z9268 | 6.2 | 58.5 | 1.7 | 0.7 | 1.8 | 6.9 | 13.2 | 0.4 | 4.3 | 4.8 | 0.9 | 0.7 | 3.4 | 54.4 | 31.8 | 0.0141 |
| Z9269 | 5.9 | 56.1 | 1.7 | 0.7 | 1.7 | 6.9 | 13.4 | 0.5 | 4.3 | 4.8 | 0.9 | 0.6 | 3.3 | 54.5 | 30.6 | 0.0130 |
| Z9270 | 5.7 | 52.7 | 2.0 | 0.7 | 1.7 | 5.9 | 12.2 | 0.4 | 4.1 | 4.0 | 1.0 | 0.7 | 2.4 | 57.6 | 30.3 | 0.0124 |
| Z9271 | 5.7 | 51.1 | 2.1 | 0.8 | 1.7 | 4.5 | 8.8 | 0.2 | 3.3 | 4.3 | 1.3 | 0.7 | 2.2 | 62.2 | 31.8 | 0.0129 |
| Z9272 | 6.1 | 56.8 | 1.7 | 0.7 | 1.7 | 7.0 | 12.9 | 0.4 | 4.3 | 4.8 | 0.9 | 0.7 | 3.4 | 54.5 | 31.0 | 0.0135 |
| Z9273 | 5.8 | 56.2 | 2.0 | 0.8 | 1.9 | 6.8 | 11.2 | 0.3 | 4.2 | 5.0 | 1.0 | 0.6 | 3.0 | 56.8 | 31.9 | 0.0133 |
| Z9274 | 6.1 | 56.7 | 1.7 | 0.7 | 1.7 | 7.1 | 12.7 | 0.4 | 4.2 | 4.9 | 0.9 | 0.6 | 3.3 | 55.5 | 31.4 | 0.0137 |
| Z9275 | 6.2 | 57.0 | 1.7 | 0.7 | 1.7 | 6.9 | 12.8 | 0.4 | 4.3 | 4.9 | 1.0 | 0.7 | 3.4 | 54.5 | 31.1 | 0.0138 |
| Z9276 | 6.1 | 56.9 | 1.8 | 0.7 | 1.8 | 6.8 | 10.7 | 0.2 | 4.3 | 5.7 | 1.7 | 0.5 | 2.5 | 57.5 | 32.7 | 0.0143 |

TABLE 13-continued

Total Lipid Content and Composition in Strains Z9256 to Z9279, Including Z9276, by Flask Assay

| Strain | DCW (g/L) | TFAs % DCW | % TFAs[a] | | | | | | | | | | | | EPA % DCW | EPA Rate (g/L/h) |
|---|---|---|---|---|---|---|---|---|---|---|---|---|---|---|---|---|
| | | | 16:0 | 16:1 | 18:0 | 18:1 | LA | ALA | EDA | DGLA | ARA | ETrA | ETA | EPA | | |
| Z9277 | 6.3 | 57.6 | 1.7 | 0.6 | 1.7 | 7.0 | 13.6 | 0.3 | 5.0 | 5.2 | 1.6 | 0.7 | 2.6 | 53.9 | 31.0 | 0.0140 |
| Z9278 | 6.0 | 56.0 | 1.7 | 0.7 | 1.6 | 7.1 | 14.0 | 0.3 | 4.7 | 5.3 | 1.6 | 0.5 | 2.4 | 53.7 | 30.0 | 0.0129 |
| Z9279 | 5.7 | 60.9 | 2.0 | 0.8 | 1.7 | 7.3 | 13.7 | 0.4 | 4.9 | 4.7 | 1.8 | 0.5 | 1.8 | 53.7 | 32.7 | 0.0133 |
| avg | 6.3 | 57.5 | 1.9 | 0.7 | 1.8 | 6.9 | 13.2 | 0.4 | 4.5 | 5.0 | 1.2 | 0.6 | 2.7 | 54.6 | 31.4 | 0.0142 |

[a]GLA was not detected in the oil produced by any of strains Z9256-Z9279.

Table 13 shows that with the exception of Z9264, all of the strains tested produced more than 30.0% EPA as DCW. The EPA profiles in strains Z9256, Z9259 and Z9276 were notable and are summarized as follows. In strain Z9256, TFAs % DCW was 61.3%, EPA % TFAs was 52.9%, and EPA % DCW was 32.4% with an EPA productivity of 0.0165 g/L/h. In strain Z9259, TFAs % DCW was 61.2%, EPA % TFAs was 53.9%, and EPA % DCW was 33.0% with an EPA productivity of 0.0164 g/L/h. In strain Z9276, TFAs % DCW was 56.9%, EPA % TFAs was 57.5%, and EPA % DCW was 32.7% with an EPA productivity of 0.0143 g/L/h.

The average oil content on a dry cell weight basis in the strains listed in Table 13 was 57.5% (TFAs % DCW). This average oil content is higher than the oil content of strain Z5585 (56.6%, Table 4) from which the strains in Table 13 were derived. More notably, the average EPA content in the total fatty acids of the oil (EPA % TFAs) in the strains in Table 13 was 54.6%, which was about 10.5% greater than the same measurement for Z5585 (49.4%, Table 4). This increase in the EPA content in the total fatty acids of the oil, while maintaining the total amount of oil produced relative to Z5585, resulted in a higher average amount of EPA on a dry cell weight basis (31.4%) in the strains of Table 13 compared to Z5585 (28%, Table 4). This represented an increase of about 12.1%, which is consistent with the ~10.5% increase observed with oil content.

Several strains in Table 13 exhibited significant increases in oil and EPA content relative to strain Z5585. For example, the total oil content (TFAs % DCW) of strains Z9256 and Z9259 increased by about 8.3% and 8.1%, respectively, compared to the total oil content in strain Z5585 (Table 4). The EPA content in the total fatty acids of the oil (EPA % TFAs) in strains Z9256 and Z9259 was increased by about 7.1% and 9.1% compared to the same measurement in Z5585 (Table 4). These robust increases in the oil content and EPA content in the total fatty acids of the oil resulted in increases of about 15.7% and 17.9% in the total EPA content (EPA % DCW) of strains Z9256 and Z9259, respectively, compared to the total EPA content of Z5585 (Table 4).

Another strain in Table 13, Z9276, exhibited a marginal increase in oil content compared to Z5585, but had a 16.4% increase in EPA content in the total fatty acids of the oil (EPA % TFAs) compared to the same measurement in Z5585 (Table 4). This substantial increase in EPA % TFAs resulted in an increase of about 16.8% in the total EPA content (EPA % DCW) of strain Z9276 compared to the total EPA content of Z5585 (Table 4).

The genetic modifications used to produce the strains in Table 13 from strain Z5585 (Table 4) thus resulted in total oil contents (TFAs % DCW) that were mostly similar to or greater than the total oil content of Z5585. More significantly, this maintenance or increase in total oil content was not coupled to a decrease in the EPA content in the total fatty acids of the oil (EPA % TFAs), which has generally been a problem in previous efforts to increase total EPA production. This previous problem is reflected in the data in Table 4, for example, which shows that increases in oil content (TFAs % DCW) through other genetic modifications generally led to decreases in the EPA content in the total fatty acids of the oil (EPA % TFAs). Thus, previous increases in total EPA content (EPA % DCW) were driven largely in part by increasing total oil production. The strains in Table 13 on the other hand exhibited increased total EPA content (EPA % DCW) that was driven in large part by increasing EPA content in the total fatty acids of the oil while maintaining or increasing total oil content.

It was notable that almost all the strains in Table 13 had very low levels of stearic acid as a percentage of total fatty acids in the oil (18:0% TFAs). Specifically, with the exception of strain Z9261, all the strains had 2.0% or less stearic acid by weight of total fatty acids. The average level for all the strains was 1.8% stearic acid.

The average dry cell weight of the strains in Table 13 (6.3 g/L) was substantially increased compared to the dry cell weights of strain Z5585 (4.6 g/L) and the other strains listed in Table 4. This represents an average increase of about 37% compared to the dry cell weight of Z5585. Certain individual strains in Table 13, such as Z9256, Z9259 and Z9263, exhibited increases in dry cell weight of about 54.3%, 52.2% and 58.7%, respectively, compared to Z5585.

In flask assays, previous strain Z5567 (Table 4) was shown to produce about 0.45 g organic acids/g DCW, and about 0.50 g sugar alcohol/g DCW by-products. Strain Z9276 on the other hand produced 0.27 g organic acids/g DCW, and 0.18 g sugar alcohol/g DCW. Given the increased production of EPA in strain Z9276 (Table 13) versus that of Z5567 (Table 4), and the decreased production of by-products by Z9276, it is apparent that Z9276 has enhanced carbon flux toward EPA production.

In summary, the genetic modifications employed in Examples 2-4 to develop the strains of Table 13 from strain Z5585 were as follows. In Example 2, Z5585 was first modified to down-regulate expression of the Sou2 protein to yield strain Z5585K2U. Gene cassettes for over-expressing PDAT, delta-12 desaturase and a DGLA synthase multizyme were then introduced to yield strain Z6903. In Example 3, gene cassettes were introduced for over-expressing delta-8 desaturase, MCS and LPAAT, thereby yielding strain Z7418. Finally, in the present Example, a gene cassette for over-expressing a mutant LPCAT was introduced to yield the strains of Table 13. All except one of these strains can produce an oil containing at least 30 percent EPA measured as a weight percent of dry cell weight.

Example 5

Identification of the SOU2 Gene as a Genetic Target to Modify Lipid Production and Sugar Alcohol Production in *Y. lipolytica*

This Example describes that the *Y. lipolytica* SOU2 gene, which encodes Sou2 sorbitol utilization protein, can regulate the level of lipids and certain sugar alcohols in *Y. lipolytica*. Specifically, it was shown that disrupting the SOU2 gene in a *Y. lipolytica* strain increased the amount of oil, and decreased the amount of arabitol and mannitol, produced by the strain.

*lipolytica* glucose-6-phosphate dehydrogenase (YI6PDH, with 440-bp intron; U.S. Pat. Appl. Publ. No. 2011-0244512). Z3041 was produced along with sibling strains Z3030-Z3040 and Z3042-Z3050.

Analysis of Total Lipid Content and Composition by Flask Assay

Cells of strains Z3029 to Z3050, including Z3041, were grown and analyzed for total lipid content and fatty acid composition by the flask assay described above. Table 14 summarizes the DCW, the TFAs % DCW, the amount of each fatty acid as a weight percent of TFAs (% TFAs) and the EPA % DCW of strains from Z3029 to Z3050. Each value represents an average of two measurements.

TABLE 14

Total Lipid Content and Composition in Strains Z3029 to Z3050, Including Z3041, by Flask Assay

| Strain | DCW (g/L) | TFAs % DCW | 16:0 | 16:1 | 18:0 | 18:1 | LA | ALA | EDA | DGLA | ARA | ETrA | ETA | EPA | EPA % DCW |
|---|---|---|---|---|---|---|---|---|---|---|---|---|---|---|---|
| Z3029 | 3.5 | 41.5 | 1.7 | 0.8 | 1.7 | 6.1 | 12.7 | 0.7 | 3.7 | 3.9 | 0.9 | 0.6 | 2.3 | 55.3 | 23.0 |
| Z3030 | 3.3 | 38.8 | 1.9 | 0.5 | 2.6 | 5.4 | 12.4 | 0.8 | 3.3 | 3.2 | 0.7 | 0.7 | 2.5 | 57.3 | 22.2 |
| Z3031 | 3.3 | 38.7 | 2.0 | 0.5 | 2.6 | 5.5 | 12.4 | 0.8 | 3.3 | 3.2 | 0.7 | 0.7 | 2.5 | 57.1 | 22.1 |
| Z3032 | 3.2 | 38.5 | 2.3 | 0.6 | 2.4 | 5.3 | 12.4 | 0.7 | 3.3 | 3.3 | 0.7 | 0.6 | 2.3 | 57.3 | 22.1 |
| Z3033 | 3.2 | 38.2 | 2.3 | 0.7 | 2.3 | 5.4 | 12.2 | 0.7 | 3.1 | 3.4 | 0.8 | 0.5 | 2.3 | 57.2 | 21.9 |
| Z3034 | 3.3 | 38.8 | 2.0 | 0.5 | 2.6 | 5.4 | 12.4 | 0.8 | 3.4 | 3.3 | 0.7 | 0.7 | 2.6 | 56.8 | 22.0 |
| Z3035 | 3.3 | 39.1 | 1.6 | 0.6 | 1.7 | 5.3 | 11.9 | 0.6 | 3.4 | 3.9 | 0.9 | 0.6 | 2.3 | 57.2 | 22.3 |
| Z3036 | 2.9 | 31.3 | 1.2 | 0.3 | 2.2 | 3.4 | 8.3 | 0.5 | 2.5 | 3.2 | 0.5 | 1.1 | 3.4 | 63.7 | 19.9 |
| Z3037 | 3.1 | 40.0 | 1.6 | 0.6 | 1.7 | 5.1 | 11.9 | 0.6 | 3.4 | 3.9 | 0.9 | 0.6 | 2.3 | 57.6 | 23.1 |
| Z3038 | 3.2 | 39.8 | 1.8 | 0.7 | 1.7 | 5.9 | 12.9 | 0.7 | 3.6 | 3.8 | 0.9 | 0.5 | 2.3 | 55.5 | 22.1 |
| Z3039 | 3.1 | 39.2 | 1.7 | 0.6 | 1.7 | 5.4 | 12.2 | 0.6 | 3.5 | 3.8 | 0.9 | 0.5 | 2.3 | 56.9 | 22.3 |
| Z3040 | 3.0 | 38.0 | 1.4 | 0.6 | 1.5 | 4.6 | 10.9 | 0.5 | 3.1 | 4.2 | 1.0 | 0.5 | 2.4 | 59.4 | 22.5 |
| Z3041 | 3.3 | 42.1 | 1.3 | 0.5 | 1.5 | 5.8 | 12.2 | 0.7 | 4.2 | 3.6 | 0.9 | 0.9 | 2.5 | 56.8 | 23.9 |
| Z3042 | 2.5 | 34.6 | 1.9 | 0.6 | 2.1 | 4.4 | 10.8 | 0.5 | 3.1 | 3.9 | 0.8 | 0.6 | 2.6 | 58.5 | 20.2 |
| Z3043 | 3.0 | 40.0 | 1.6 | 0.6 | 1.7 | 5.2 | 12.0 | 0.6 | 3.5 | 3.9 | 0.9 | 0.5 | 2.3 | 57.4 | 22.9 |
| Z3044 | 2.9 | 36.1 | 2.1 | 0.8 | 1.6 | 5.3 | 11.8 | 0.5 | 3.3 | 3.9 | 1.0 | 0.4 | 2.2 | 56.6 | 20.4 |
| Z3045 | 3.0 | 39.3 | 1.9 | 0.5 | 2.6 | 5.2 | 12.1 | 0.8 | 3.2 | 3.2 | 0.7 | 0.7 | 2.5 | 57.5 | 22.6 |
| Z3046 | 2.9 | 35.5 | 2.2 | 0.6 | 2.0 | 4.7 | 10.7 | 0.6 | 2.7 | 3.2 | 0.8 | 0.4 | 2.0 | 59.7 | 21.2 |
| Z3047 | 3.0 | 38.1 | 2.2 | 0.6 | 2.6 | 5.2 | 12.0 | 0.7 | 3.2 | 3.4 | 0.7 | 0.5 | 2.3 | 57.2 | 21.8 |
| Z3048 | 3.1 | 39.4 | 1.9 | 0.5 | 2.5 | 5.4 | 12.4 | 0.8 | 3.3 | 3.3 | 0.7 | 0.7 | 2.5 | 57.0 | 22.5 |
| Z3049 | 2.8 | 36.5 | 2.2 | 0.6 | 2.2 | 5.1 | 11.9 | 0.7 | 3.0 | 3.4 | 0.8 | 0.5 | 2.2 | 57.9 | 21.1 |
| Z3050 | 2.9 | 40.1 | 2.1 | 0.6 | 2.3 | 5.8 | 13.0 | 0.8 | 3.5 | 3.4 | 0.8 | 0.6 | 2.4 | 55.0 | 22.1 |
| avg | 3.1 | 38.3 | 1.9 | 0.6 | 2.1 | 5.2 | 11.9 | 0.7 | 3.3 | 3.6 | 0.8 | 0.6 | 2.4 | 57.5 | 22.0 |

The SOU2 gene was identified as a genetic target to modify lipid production in *Y. lipolytica* during the development of strain Z3041 from strain Z1978. The steps involved in this process involved intermediate strains Z1978U, Z2636 and Z2636U (FIG. 8). The development of *Y. lipolytica* strain Z1978U is described in U.S. Pat. Appl. Publ. No. 2012-0052537, which is incorporated herein by reference.

Strain Z2636 was produced by transforming Z1978U with plasmid pZKT2-ML9DCB (SEQ ID NO:27, FIG. 9A), which contains cassettes for expressing *Y. lipolytica* diacylglycerol cholinephosphotransferase (YICPT1; U.S. Pat. No. 7,932, 077), *Y. lipolytica* delta-9 desaturase (YIDS; U.S. Pat. Appl. Publ. No. 2012-0052537), and an *M. alpina* acyl-CoA:lysophosphatidic acid acyltransferase nucleotide sequence that was codon-optimized for expression in *Y. lipolytica* (MaLPAAT1S; U.S. Pat. No. 7,879,591). Construct pZKUM (above) was then used to disrupt the URA3 gene in strain Z2636 that was introduced by plasmid pZKT2-ML9DCB, thereby producing the Ura⁻ strain Z2636U.

Strain Z3041 was produced by transforming Z2636U with AscI/SphI-digested plasmid pZKLY-PP2YAP (SEQ ID NO:28, FIG. 9B), which contains cassettes for expressing *Y. lipolytica* Yap1 (YIYAP1, GenBank Accession No. XM_504945), *Y. lipolytica* 6-phosphogluconolactonase (YI6PGL, U.S. Pat. Appl. Publ. No. 2011-0244512), and *Y.*

Strain Z3041 had the highest oil content (about 42.1 TFAs % DCW) compared to all of its sibling strains (Table 14). The oil content of Z3041 was also notable since most of its siblings had less than 40% oil, and the average oil content was 38.3% (Table 14). The average increase in oil content in strain Z3041 with respect to its siblings was about 10.7%. These observations suggested that the integrated sequence from pZKLY-PP2YAP in strain Z3041 provided an additional effect beyond the effects provided to all of the other strains in Table 14.

One possibility was that the integration itself provided an additional trait to Z3041 that contributed to oil synthesis. This prospect led to genome walking and sequencing analyses to determine what genetic trait(s) may have been altered in strain Z3041 to endow enhanced oil levels. The additional analyses found that the ~10.5 kbp AscI/SphI fragment of pZKLY-PP2YAP, which contains the YIYAP1, YI6PGL and YI6PDH expression cassettes, had integrated into the promoter of the SOU2 gene (locus YALI0D18964g, GenBank Accession No. XM_503010, FIG. 5). Specifically, the AscI/SphI plasmid fragment was integrated at −70 with respect to the ATG start codon of the SOU2 gene; this location is immediately downstream the presumptive TATA promoter consensus sequence. Given the location of the integration in the SOU2 promoter, the integration was predicted to down-regulate SOU2 gene expression (reduced transcription).

Aside from having increased oil content, strain Z3041 also exhibited lower levels of certain fermentation by-products compared to Z2636. Specifically, production of the sugar alcohols arabitol and mannitol in Z3041 was eliminated.

Additional studies were conducted to understand the role of the SOU2 gene in regulating oil and sugar alcohol production in *Yarrowia* (refer to Example 2). Briefly, the SOU2 gene was knocked out in strain Z5585, thereby producing strain Z5585K2U (FIG. 3). The knock-out of SOU2 entailed targeting and deleting about 522 base pairs of sequence beginning about 235 base pairs upstream the ATG start site and ending about 287 base pairs downstream the ATG start site (FIG. 5, refer to sequence between opposing triangles). SOU2 gene transcription and Sou2 protein expression were thus completely down-regulated in strain Z5585K2U and its descendent strains.

Example 6

Synthesis of Plasmid pY306-N Comprising Variant YILPCAT

This Example and Examples 7-9 are disclosed in U.S. Appl. No. 61/661,623, which is incorporated herein by reference.

The wild type *Y. lipolytica* LPCAT (YILPCAT) polynucleotide sequence and amino acid sequence are represented by SEQ ID NOs:39 and 40, respectively.

The present example describes the construction of a *Yarrowia* autonomously replicating vector comprising a variant YILPCAT sequence (plasmid pY306-N, FIG. 10, SEQ ID NO:42). The variant YILPCAT polynucleotide sequence, designated herein as YILPCAT* (SEQ ID NO:41), lacks two NcoI restriction enzyme sites that are present in the wild type YILPCAT coding region. Removal of these internal NcoI sites facilitated subsequent cloning procedures. YILPCAT* encodes wild type YILPCAT protein (SEQ ID NO:40).

As a control, the wild type YILPCAT polynucleotide sequence (SEQ ID NO:39) was cloned into a *Yarrowia* autonomously replicating vector to result in plasmid pY306 (SEQ ID NO:43), comprising a ColE1 plasmid origin of replication, an ampicillin-resistance gene, an f1 origin of replication and the *Y. lipolytica* URA3 gene (Gen Bank Accession No. AJ306421).

The variant YILPCAT* sequence was synthesized by GenScript Corporation (Piscataway, N.J.). Two internal NcoI restriction sites were removed by creation of silent mutations, while NcoI and NotI sites were added, respectively, at the 5' and 3' ends of the YILPCAT open reading frame to facilitate cloning. Specifically, an A12T mutation (i.e., a change from adenosine [A] in YILPCAT (SEQ ID NO:39) at position 12 to thymine [T] in the YILPCAT* variant) and a T918C mutation (i.e., a change from thymine [T] in YILPCAT (SEQ ID NO:39) at position 918 to cytosine [C] in the YILPCAT* variant) were introduced into the YILPCAT coding sequence. These two nucleotide substitutions were silent with respect to the amino acids encoded by the variant sequence. The nucleotide sequence encoding the variant YILPCAT lacking its internal NcoI sites (i.e., YILPCAT*) is represented by SEQ ID NO:41, while the amino acid sequence encoded thereby is represented by SEQ ID NO:40, which is wild type YILPCAT protein.

YILPCAT* was subsequently cloned into plasmid pY306, thereby producing pY306-N(SEQ ID NO:42; FIG. 10). Construct pY306-N contained the following components:

TABLE 15

| Components of Plasmid pY306-N (SEQ ID NO: 42) | |
|---|---|
| RE Sites and Nucleotide Positions | Description of Fragment and Chimeric Gene Components |
| BsiWI/BsiWI 1-2809 | YAT1::YILPCAT*::Lip1 (complementary), comprising: YAT1: *Y. lipolytica* YAT1 promoter (U.S. Pat. Appl. Publ. No. 2010/0068789); YILPCAT*: variant YILPCAT lacking two internal NcoI sites (SEQ ID NO: 41), but encoding wild type YILPCAT protein; Lip1: Lip1 terminator sequence from Yarrowia LIP1 gene (GenBank Accession No. Z50020) |
| BsiWI/EcoRI 2809-5605 | ColE1 plasmid origin of replication Ampicillin-resistance gene f1 origin of replication |
| EcoRI/PacI 5605-7021 | *Y. lipolytica* URA3 gene (GenBank Accession No. AJ306421) |

Plasmid pY306-N was used to prepare single- and double-mutants of YILPCAT protein, as described below in Examples 7 and 9, respectively.

Example 7

Designing and Synthesizing Mutant *Yarrowia* LPCAT Enzymes with Modified Motifs

Based on the premise that conserved amino acid motifs within YILPCAT are likely involved in catalysis, it was concluded that generation of mutants having variant motifs could result in the identification of an LPCAT enzyme having improved functional activity.

A series of single amino acid substitutions were designed within the conserved sequence spanning amino acid residues 132 to 148 of SEQ ID NO:40 (i.e., Motif I) and the conserved sequence spanning amino acid residues 376 to 390 of SEQ ID NO:40 (i.e., Motif II). Within Motif I, a total of 195 amino acid substitutions were designed, as shown in Table 16, by creating various substitutions at each of the 17 amino acid residues within the motif.

TABLE 16

| Single Amino Acid Substitutions within Motif I of YILPCAT Protein | | |
|---|---|---|
| Wild type residue | Single Amino Acid Substitutions | SEQ ID NO |
| M132 | M132A, M132N, M132C, M132G, M132Q, M132H, M132I, M132L, M132F, M132P, M132S, M132T, M132W, M132Y or M132V | 44 |
| V133 | V133A, V133N, V133C, V133G, V133Q, V133H, V133L, V133M, V133F, V133P, V133S, V133T, V133W or V133Y | 45 |

TABLE 16-continued

Single Amino Acid Substitutions within Motif I of YlLPCAT Protein

| Wild type residue | Single Amino Acid Substitutions | SEQ ID NO |
|---|---|---|
| L134 | L134A, L134N, L134C, L134G, L134Q, L134H, L134M, L134F, L134P, L134S, L134T, L134W, L134Y or L134V | 46 |
| C135 | C135R, C135N, C135D, C135G, C135E, C135Q, C135H, C135I, C135L, C135K, C135M, C135F, C135P, C135S, C135W or C135Y | 47 |
| M136 | M136A, M136N, M136C, M136G, M136H, M136I, M136F, M136P, M136S, M136T, M136W, M136Y or M136V | 48 |
| K137 | K137A, K137R, K137N, K137G, K137H, K137P, K137S, K137T, or K137Y | 49 |
| L138 | L138A, L138N, L138C, L138G, L138Q, L138H, L138I, L138M, L138F, L138P, L138S, L138T, L138W, or L138Y | 50 |
| S139 | S139A, S139N, S139C, S139G, S139H, S139L, S139M, S139F, S139P, S139W, or S139V | 51 |
| S140 | S140N, S140C, S140H, S140I, S140L, S140F, S140P, S140W, S140Y or S140V | 52 |
| F141 | F141A, F141N, F141G, F141H, F141I, F141M, F141P, F141S, F141T, F141W, or F141V | 53 |
| G142 | G142N, G142H, G142I, G142L, G142M, G142F, G142P, G142T, G142W, G142Y or G142V | 54 |
| W143 | W143A, W143G, W143H, W143L, W143K, W143P, W143S, W143T, or W143V | 55 |
| N144 | N144A, N144R, N144G, N144H, N144K, N144F, N144P, N144T or N144V | 56 |
| V145 | V145A, V145C, V145G, V145E, V145H, V145M, V145F, V145P, V145S, V145T, or V145W | 57 |
| Y146 | Y146R, Y146N, Y146D, Y146G, Y146E, Y146Q, Y146I, Y146L, Y146M, Y146F, Y146P, Y146W or Y146V | 58 |
| D147 | D147A, D147N, D147G, D147E, D147Q, D147H, D147F, D147S, or D147T | 59 |
| G148 | G148A, G148N, G148H, G148L, G148M, G148F, G148S, G148T or G148V | 60 |

Similarly, a total of 134 amino acid substitutions were designed within Motif II, as shown in Table 17, by creating various substitutions within 12 of the 15 amino acid residues within the motif. No substitutions were made at W379, H380 and G381, since the histidine of other LPCATs corresponding to H380 of YlLPCAT has been reported to be a likely active site residue (Lee et al., 2008, *Mol. Biol. Cell* 19:1174-1184).

TABLE 17

Single Amino Acid Substitutions within Motif II of YlLPCAT Protein

| Wild type residue | Single Amino Acid Substitutions | SEQ ID NO |
|---|---|---|
| S376 | S376A, S376G, S376H, S376L, S376F, S376P, S376T or S376V | 61 |
| A377 | A377N, A377G, A377H, A377L, A377F, A377P, A377S, A377T or A377V | 62 |
| F378 | F378A, F378N, F378C, F378G, F378H, F378L, F378P, F378S, F378T, F378W, or F378Y | 63 |
| T382 | T382A, T382N, T382G, T382Q, T382H, T382I, T382M, T382P, T382S, T382W, or T382Y | 64 |
| R383 | R383A, R383N, R383D, R383G, R383E, R383Q, R383H, R383I, R383L, R383K, R383M, R383F, R383P, R383T, R383W or R383V | 65 |
| P384 | P384A, P384R, P384G, P384H, P384I, P384L, P384K, P384M, P384F, P384S, P384T, P384W, P384Y or P384V | 66 |
| G385 | G385A, G385N, G385C, G385G, G385H, G385I, G385L, G385K, G385M, G385F, G385S, G385T, G385W, G385Y or G385V | 67 |
| Y386 | Y386A, Y386G, Y386H, Y386L, Y386F, Y386P, Y386S, Y386T or Y386V | 68 |
| Y387 | Y387A, Y387G, Y387H, Y387L, Y387F, Y387P, Y387S, Y387T, Y387W or Y387V | 69 |
| L388 | L388A, L388G, L388H, L388P, L388S, L388T, L388W, L388Y or L388V | 70 |
| T389 | T389A, T389C, T389G, T389H, T389I, T389L, T389M, T389F, T389P, T389S, T389W, T389Y or T389V | 71 |
| F390 | F390A, F390N, F390C, F390G, F390H, F390L, F390M, F390P, F390S, F390T or F390V | 72 |

Each of the 329 YlLPCAT mutants set forth above in Tables 16 and 17 were individually synthesized and cloned into NcoI/NotI-cut pY306-N vector by GenScript Corporation (Piscataway, N.J.).

Example 8

Identifying Single Amino Acid Substitutions in YlLPCAT Having Improved LPCAT Activity The present example describes the transformation of each of the 329 pY306-N vectors comprising a YlLPCAT mutant polynucleotide sequence (Example 7) into *Y. lipolytica* strain Y8406U2, followed by analysis of the lipid profiles of the transformants.

Improved LPCAT activity was indirectly evaluated, based on the observations set forth in U.S. Pat. Appl. Publ. No. 2010-0317882-A1, which is incorporated herein by reference. Specifically, improved LPCAT activity within *Y. lipolytica* strain Y8406U2 transformants comprising a mutated YlLPCAT was concluded based on an increase in the concentration of EPA as a weight % of TFAs (EPA % TFAs) and/or an increase in the conversion efficiency of the delta-9 elongase, when either factor was compared to the EPA % TFAs or the conversion efficiency of the delta-9 elongase, respectively, in *Y. lipolytica* strain Y8406U2 expressing the parent wild type YILPCAT protein.

Transformation of *Y. lipolytica* Strain Y8406U2

Strain Y8406U2 was transformed to individually express one of each of the pY306-N vectors containing a mutant YILPCAT prepared in Example 7. Y8406U2 is a Ura⁻ strain of Y8406. Details regarding the development of strains Y8406 and Y8406U2 are provided in U.S. Pat. Appl. Publ. No. 2010-0317882-A1. Following transformation, individual transformants were subjected to an initial fatty acid screening process as described above. Briefly, single colonies that were grown on MM plates at 30° C. for 5 to 6 days were re-streaked and grown for two days at 30° C. on MM plates. Single colonies were then inoculated into 3 mL MM in a 24-well plate and shaken at 250 rpm at 30° C. for 2 days. The cells from each well were collected by centrifugation, resuspended in HGM, and then shaken at 200 rpm for 5 days. Cells were then processed for fatty acid analysis as described above.

Analysis of Lipid Profiles within *Yarrowia* Transformed for Expression of Single Mutants of YILPCAT Tables 18 (Batch 1), 19 (Batch 2), 20 (Batch 3), 21 (Batch 4) and 22 (Batch 5) below show the fatty acid profiles and delta-9 elongase conversion efficiencies of individual Y8406U2 transformants comprising a plasmid for expressing a particular single-mutated YILPCAT (single amino acid substitution in Motif I or Motif II). These measurements were also made for certain controls: transformants comprising an empty vector (EV) (i.e., a replicating plasmid with no LPCAT gene [Batch #1 only]) or pY306-N (wild type YILPCAT protein expression [WT]).

More specifically, each table summarizes the number of replicates analyzed for each particular transformant (#), the average concentration of each fatty acid as a weight percent of TFAs (% TFAs), the standard deviation for EPA % TFAs (EPA SD), and the delta-9 elongase conversion efficiency (% Conv). The % Conv. was calculated for each transformant according to the following formula: (EDA+DGLA+ARA+ERA+ETA+EPA)/(C18:2+C18:3+EDA+DGLA+ARA+ERA+ETA+EPA)*100.

Comparison of each mutant's performance relative to the wild type YILPCAT control should only be made within the particular batch in which each mutant was analyzed (i.e., comparisons should not be made between Batch #1 and Batch #2, for example). Mutants shown in bold-face font and followed by a "+" were selected for further studies, as discussed below.

TABLE 18

Lipid Composition and Delta-9 Elongase Conversion Efficiency in Batch #1 Transformants Comprising a Vector Encoding YILPCAT Having a Single Amino Acid Substitution

| Mutant | # | 16:0 | 16:1 | 18:0 | 18:1 | LA | ALA | EDA | DGLA | ARA | ETrA | ETA | EPA | EPA SD | % Conv. |
|---|---|---|---|---|---|---|---|---|---|---|---|---|---|---|---|
| EV control | 6 | 2.8 | 0.5 | 2.6 | 4.6 | 19.2 | 1.8 | 2.8 | 2.6 | 0.6 | 1.4 | 2.6 | 48.7 | 0.2 | 74 |
| WT | 15 | 2.8 | 0.5 | 2.7 | 4.5 | 17.9 | 1.8 | 2.7 | 2.7 | 0.6 | 1.4 | 2.4 | 50.4 | 1.1 | 75 |
| M132A | 3 | 2.8 | 0.4 | 2.9 | 4.8 | 19.7 | 2.2 | 2.5 | 2.3 | 0.6 | 1.4 | 2.0 | 49.3 | 0.4 | 73 |
| M132I | 3 | 2.7 | 0.5 | 2.8 | 4.8 | 19.4 | 2.0 | 2.7 | 2.5 | 0.6 | 1.5 | 2.3 | 48.6 | 0.3 | 73 |
| V133M | 3 | 2.6 | 0.5 | 2.9 | 5.4 | 19.3 | 2.1 | 2.8 | 2.4 | 0.6 | 1.5 | 2.2 | 49.0 | 0.7 | 73 |
| C135I | 3 | 3.0 | 0.5 | 2.8 | 4.6 | 17.5 | 1.7 | 2.6 | 2.6 | 0.7 | 1.5 | 2.2 | 50.7 | 2.5 | 76 |
| C135M | 3 | 2.5 | 0.5 | 2.9 | 5.6 | 20.1 | 2.5 | 3.0 | 2.3 | 0.6 | 1.5 | 2.0 | 47.8 | 1.7 | 72 |
| M136A | 3 | 2.7 | 0.4 | 2.9 | 4.8 | 19.4 | 2.2 | 2.5 | 1.6 | 0.6 | 1.4 | 2.1 | 49.6 | 0.1 | 73 |
| L138A | 3 | 2.9 | 0.5 | 2.9 | 3.1 | 18.0 | 1.8 | 2.6 | 2.6 | 0.7 | 1.4 | 2.1 | 50.5 | 1.9 | 75 |
| L138C | 3 | 3.0 | 0.5 | 2.8 | 4.8 | 19.8 | 2.1 | 2.6 | 2.3 | 0.7 | 1.4 | 2.0 | 48.6 | 0.9 | 72 |
| L138M | 3 | 2.7 | 0.6 | 2.9 | 5.2 | 16.8 | 1.5 | 2.8 | 3.0 | 0.7 | 1.5 | 2.4 | 51.0 | 3.0 | 77 |
| S139A | 3 | 2.7 | 0.4 | 2.8 | 4.8 | 19.5 | 2.3 | 2.6 | 2.2 | 0.6 | 1.4 | 2.0 | 48.8 | 1.2 | 73 |
| S139C | 3 | 3.2 | 0.5 | 2.8 | 4.6 | 19.6 | 2.0 | 2.5 | 2.3 | 0.6 | 1.4 | 2.0 | 48.8 | 0.6 | 73 |
| S139L | 3 | 2.7 | 0.5 | 2.8 | 5.0 | 17.9 | 1.8 | 2.7 | 2.6 | 0.7 | 1.5 | 2.2 | 50.7 | 2.2 | 75 |
| S139M | 3 | 2.5 | 0.4 | 3.0 | 5.4 | 19.7 | 2.3 | 2.8 | 2.4 | 0.6 | 1.5 | 2.1 | 48.6 | 0.2 | 72 |
| S140I | 3 | 3.1 | 0.5 | 2.8 | 4.6 | 17.7 | 1.7 | 2.7 | 2.7 | 0.7 | 1.5 | 2.3 | 50.1 | 2.7 | 76 |
| F141M+ | 3 | 2.8 | 0.7 | 2.7 | 4.9 | 14.8 | 0.9 | 2.8 | 3.4 | 0.8 | 1.6 | 2.6 | 53.1 | 0.5 | 88 |
| G142I | 3 | 3.1 | 0.6 | 2.7 | 5.0 | 18.3 | 1.8 | 2.9 | 2.6 | 0.7 | 1.5 | 2.3 | 49.0 | 3.1 | 75 |
| G142L | 3 | 2.5 | 0.5 | 2.8 | 5.5 | 19.2 | 2.0 | 3.0 | 2.5 | 0.6 | 1.6 | 2.3 | 48.7 | 1.1 | 73 |
| W143L | 3 | 2.7 | 0.5 | 2.8 | 5.1 | 17.9 | 1.8 | 2.8 | 1.6 | 0.6 | 1.5 | 2.3 | 50.4 | 2.0 | 75 |
| N144H | 3 | 2.7 | 0.6 | 2.6 | 4.7 | 18.9 | 1.8 | 2.8 | 2.7 | 0.6 | 1.6 | 2.8 | 48.1 | 1.6 | 74 |
| N144K | 3 | 2.7 | 0.5 | 2.8 | 5.3 | 17.7 | 1.8 | 2.8 | 2.7 | 0.6 | 1.5 | 2.2 | 50.5 | 3.2 | 76 |
| V145C | 3 | 3.0 | 0.4 | 2.8 | 4.7 | 19.6 | 2.1 | 2.5 | 2.3 | 0.6 | 1.4 | 2.0 | 49.4 | 0.5 | 73 |
| V145M+ | 3 | 2.9 | 0.7 | 2.7 | 5.0 | 16.2 | 1.3 | 2.8 | 3.1 | 0.7 | 1.5 | 2.4 | 51.4 | 2.1 | 78 |
| Y146D | 3 | 3.0 | 0.5 | 2.8 | 3.3 | 19.6 | 2.0 | 2.5 | 2.4 | 0.7 | 1.4 | 2.1 | 49.0 | 0.6 | 73 |
| Y146E | 3 | 3.2 | 0.5 | 2.9 | 4.9 | 19.7 | 2.0 | 2.5 | 2.5 | 0.7 | 1.3 | 2.1 | 48.8 | 0.3 | 73 |
| Y146I | 3 | 3.0 | 0.5 | 2.8 | 5.4 | 20.0 | 2.3 | 2.8 | 2.3 | 0.6 | 1.5 | 2.1 | 47.6 | 2.3 | 72 |
| Y146L | 3 | 2.6 | 0.5 | 2.7 | 5.0 | 17.7 | 1.6 | 2.7 | 2.8 | 0.6 | 1.5 | 2.4 | 50.8 | 2.2 | 76 |
| Y146M | 3 | 2.6 | 0.5 | 2.7 | 5.2 | 18.1 | 1.9 | 2.7 | 2.7 | 0.7 | 1.5 | 2.1 | 50.7 | 1.8 | 75 |
| D147E | 3 | 3.2 | 0.5 | 2.8 | 4.7 | 18.3 | 1.7 | 2.7 | 2.7 | 0.7 | 1.5 | 2.2 | 49.5 | 0.2 | 75 |
| F378A | 3 | 2.6 | 0.4 | 2.9 | 4.8 | 19.5 | 2.3 | 2.5 | 2.2 | 0.6 | 1.4 | 2.0 | 49.9 | 0.3 | 73 |
| T382A | 3 | 2.7 | 0.5 | 2.8 | 5.1 | 19.8 | 2.2 | 2.8 | 2.4 | 0.6 | 1.4 | 2.2 | 48.3 | 1.7 | 72 |
| R383A | 3 | 2.9 | 0.6 | 2.8 | 3.6 | 17.8 | 1.5 | 2.9 | 2.8 | 0.7 | 1.4 | 2.3 | 50.2 | 1.5 | 76 |
| R383D | 3 | 3.3 | 0.5 | 2.9 | 5.0 | 19.6 | 2.0 | 2.5 | 2.4 | 0.7 | 1.4 | 2.1 | 48.7 | 0.8 | 73 |
| R383I | 3 | 3.1 | 0.5 | 2.8 | 4.6 | 18.6 | 1.7 | 2.6 | 2.6 | 0.7 | 1.5 | 2.3 | 49.2 | 0.5 | 74 |
| R383K | 3 | 2.5 | 0.5 | 2.7 | 5.4 | 20.1 | 2.4 | 3.1 | 2.3 | 0.6 | 1.5 | 2.1 | 47.7 | 2.6 | 72 |
| R383L | 3 | 2.5 | 0.4 | 2.8 | 5.0 | 19.6 | 2.1 | 2.7 | 2.4 | 0.6 | 1.5 | 2.1 | 49.4 | 0.4 | 73 |
| R383M+ | 3 | 3.0 | 0.6 | 2.8 | 5.0 | 16.5 | 1.5 | 2.7 | 3.0 | 0.7 | 1.5 | 2.2 | 52.2 | 2.8 | 78 |
| R383N | 3 | 3.0 | 0.5 | 2.8 | 4.8 | 19.3 | 2.0 | 2.5 | 2.4 | 0.6 | 1.4 | 2.1 | 49.2 | 0.5 | 73 |
| P384I | 3 | 2.8 | 0.5 | 2.9 | 4.8 | 19.3 | 2.1 | 2.6 | 2.3 | 0.6 | 1.4 | 2.1 | 49.3 | 0.4 | 73 |
| P384L | 3 | 2.5 | 0.5 | 2.8 | 5.2 | 18.8 | 1.9 | 2.8 | 2.6 | 0.6 | 1.5 | 2.3 | 49.6 | 0.6 | 74 |
| G385I | 3 | 2.4 | 0.4 | 2.9 | 5.2 | 19.4 | 2.1 | 2.7 | 2.4 | 0.6 | 1.5 | 2.1 | 49.2 | 0.3 | 73 |

TABLE 18-continued

Lipid Composition and Delta-9 Elongase Conversion Efficiency in Batch #1 Transformants Comprising a Vector Encoding YlLPCAT Having a Single Amino Acid Substitution

| Mutant | # | 16:0 | 16:1 | 18:0 | 18:1 | LA | ALA | EDA | DGLA | ARA | ETrA | ETA | EPA | EPA SD | % Conv. |
|---|---|---|---|---|---|---|---|---|---|---|---|---|---|---|---|
| G385L | 3 | 2.5 | 0.5 | 3.0 | 5.5 | 19.7 | 2.3 | 2.9 | 2.3 | 0.6 | 1.5 | 2.1 | 48.4 | 0.1 | 72 |
| Y387A | 3 | 2.7 | 0.4 | 2.9 | 4.5 | 19.6 | 2.1 | 2.5 | 2.4 | 0.7 | 1.3 | 2.0 | 49.8 | 0.2 | 73 |
| L388A | 3 | 2.6 | 0.5 | 2.8 | 4.8 | 19.9 | 2.1 | 2.5 | 2.5 | 0.7 | 1.3 | 2.3 | 48.9 | 1.4 | 73 |
| T389I | 3 | 2.5 | 0.5 | 2.8 | 5.1 | 19.7 | 2.1 | 2.7 | 2.4 | 0.6 | 1.5 | 2.2 | 48.9 | 0.8 | 73 |
| T389L | 3 | 2.5 | 0.4 | 2.9 | 5.2 | 19.9 | 2.3 | 2.7 | 2.3 | 0.6 | 1.5 | 2.0 | 48.9 | 0.3 | 72 |
| F390L | 3 | 2.5 | 0.4 | 2.9 | 5.3 | 19.7 | 2.3 | 2.7 | 2.3 | 0.6 | 1.5 | 2.1 | 48.9 | 0.4 | 72 |
| Mutant AVG | | 2.8 | 0.5 | 2.8 | 4.9 | 18.9 | 2.0 | 2.7 | 2.5 | 0.6 | 1.5 | 2.2 | 49.5 | | 74 |
| Mutant SD | | 0.2 | 0.1 | 0.1 | 0.5 | 1.2 | 0.3 | 0.2 | 0.3 | 0.0 | 0.1 | 0.2 | 1.1 | | 56 |

TABLE 19

Lipid Composition and Delta-9 Elongase Conversion Efficiency in Batch #2 Transformants Comprising a Vector Encoding YlLPCAT Having a Single Amino Acid Substitution

| Mutant | # | 16:0 | 16:1 | 18:0 | 18:1 | LA | ALA | EDA | DGLA | ARA | ETrA | ETA | EPA | EPA SD | % Conv. |
|---|---|---|---|---|---|---|---|---|---|---|---|---|---|---|---|
| WT | 5 | 3.0 | 0.6 | 2.9 | 4.9 | 15.0 | 1.2 | 2.8 | 3.2 | 0.7 | 1.5 | 2.5 | 52.9 | 1.1 | 79.7 |
| M132F | 3 | 2.6 | 0.6 | 2.8 | 5.6 | 19.2 | 1.9 | 2.8 | 2.7 | 0.6 | 1.5 | 2.5 | 48.7 | 1.3 | 73.6 |
| M132W | 3 | 2.6 | 0.6 | 2.7 | 5.5 | 18.5 | 1.7 | 2.9 | 2.7 | 0.5 | 1.6 | 2.7 | 48.6 | 0.4 | 74.4 |
| M132Y | 3 | 2.6 | 0.6 | 2.7 | 2.3 | 18.9 | 1.8 | 2.8 | 2.7 | 0.5 | 1.6 | 2.8 | 48.1 | 1.0 | 73.8 |
| V133F | 3 | 2.6 | 0.5 | 3.0 | 5.6 | 19.5 | 2.3 | 2.8 | 2.5 | 0.5 | 1.5 | 2.3 | 48.6 | 0.4 | 72.7 |
| V133W | 3 | 2.5 | 0.5 | 2.8 | 4.2 | 19.7 | 2.1 | 2.9 | 2.5 | 0.5 | 1.5 | 2.4 | 47.8 | 1.1 | 72.6 |
| L134F | 3 | 3.0 | 0.6 | 3.1 | 5.8 | 16.7 | 1.4 | 3.3 | 3.0 | 0.6 | 1.6 | 2.6 | 50.0 | 2.2 | 77.2 |
| L134V | 3 | 3.1 | 0.6 | 2.8 | 5.0 | 15.4 | 1.1 | 2.8 | 3.1 | 0.7 | 1.6 | 2.5 | 52.3 | 0.3 | 79.2 |
| L134W | 3 | 2.6 | 0.7 | 2.5 | 5.1 | 16.2 | 0.9 | 3.0 | 3.4 | 0.8 | 1.5 | 2.7 | 51.0 | 1.9 | 78.5 |
| L134Y | 3 | 2.9 | 0.6 | 2.8 | 2.1 | 16.8 | 1.3 | 2.7 | 1.9 | 0.6 | 1.7 | 2.6 | 50.8 | 0.2 | 76.9 |
| C135F | 3 | 3.0 | 0.7 | 2.7 | 5.2 | 15.1 | 1.0 | 2.8 | 3.3 | 0.7 | 1.5 | 2.6 | 52.5 | 0.5 | 79.7 |
| C135W | 3 | 2.5 | 0.5 | 2.8 | 5.1 | 18.1 | 1.5 | 2.8 | 2.7 | 0.6 | 1.5 | 2.6 | 49.9 | 0.2 | 75.4 |
| C135Y | 3 | 2.5 | 0.6 | 2.9 | 5.4 | 18.1 | 1.5 | 3.0 | 2.7 | 0.6 | 1.6 | 2.8 | 49.0 | 0.4 | 75.2 |
| M136F | 3 | 2.8 | 0.6 | 2.8 | 5.1 | 16.6 | 1.2 | 2.8 | 3.1 | 0.7 | 1.6 | 2.5 | 51.8 | 0.3 | 77.8 |
| M136S+ | 3 | 3.3 | 0.7 | 2.5 | 4.9 | 12.6 | 0.9 | 2.7 | 3.2 | 0.7 | 1.6 | 2.3 | 55.0 | 0.5 | 82.9 |
| M136T | 3 | 2.7 | 0.6 | 2.8 | 5.4 | 14.7 | 1.1 | 3.0 | 3.2 | 0.6 | 1.5 | 2.6 | 52.7 | 2.6 | 80.1 |
| M136V+ | 3 | 3.6 | 0.7 | 2.7 | 5.2 | 13.0 | 0.9 | 2.7 | 3.3 | 0.7 | 1.5 | 2.5 | 54.1 | 0.7 | 82.3 |
| M136W | 3 | 2.8 | 0.6 | 2.7 | 4.9 | 15.3 | 1.1 | 2.8 | 3.2 | 0.6 | 1.6 | 2.6 | 52.7 | 0.2 | 79.4 |
| L138F | 3 | 2.4 | 0.6 | 2.9 | 5.3 | 16.4 | 1.3 | 3.0 | 3.0 | 0.6 | 1.6 | 2.8 | 50.9 | 2.0 | 77.7 |
| L138W | 3 | 2.8 | 0.6 | 2.8 | 5.1 | 16.2 | 1.2 | 2.8 | 3.1 | 0.6 | 1.5 | 2.5 | 51.7 | 0.4 | 78.2 |
| L138Y | 3 | 2.6 | 0.6 | 2.6 | 3.5 | 16.9 | 1.5 | 2.7 | 1.8 | 0.6 | 1.5 | 2.6 | 51.2 | 1.9 | 76.7 |
| S139F | 3 | 3.1 | 0.7 | 2.7 | 3.8 | 16.0 | 1.3 | 2.8 | 3.1 | 0.7 | 1.6 | 2.6 | 50.9 | 2.7 | 78.1 |
| S139W | 3 | 2.9 | 0.6 | 2.8 | 4.9 | 14.8 | 1.1 | 2.8 | 3.2 | 0.7 | 1.5 | 2.5 | 53.2 | 0.3 | 80.1 |
| S140F | 3 | 2.8 | 0.6 | 2.7 | 5.1 | 15.6 | 1.3 | 2.8 | 3.1 | 0.6 | 1.5 | 2.5 | 52.2 | 2.3 | 78.7 |
| S140W+ | 3 | 3.2 | 0.6 | 2.7 | 5.3 | 12.8 | 0.9 | 2.7 | 3.3 | 0.7 | 1.6 | 2.4 | 54.6 | 0.4 | 82.7 |
| S140Y | 3 | 3.1 | 0.8 | 2.4 | 4.7 | 14.2 | 0.9 | 2.8 | 3.4 | 0.7 | 1.7 | 2.8 | 52.5 | 1.9 | 80.9 |
| F141V | 3 | 3.3 | 0.7 | 2.8 | 3.6 | 14.0 | 1.0 | 3.0 | 3.2 | 0.6 | 1.7 | 2.6 | 52.8 | 1.3 | 81.0 |
| F141W+ | 3 | 3.1 | 0.7 | 2.8 | 5.1 | 14.1 | 1.0 | 2.8 | 3.3 | 0.7 | 1.6 | 2.5 | 53.6 | 0.3 | 81.0 |
| G142F | 3 | 2.7 | 0.7 | 2.5 | 3.5 | 16.7 | 1.2 | 2.9 | 3.1 | 0.7 | 1.6 | 2.7 | 50.7 | 1.4 | 77.5 |
| G142V | 3 | 3.1 | 0.7 | 2.7 | 5.0 | 15.0 | 1.1 | 2.8 | 3.3 | 0.7 | 1.6 | 2.6 | 52.6 | 0.2 | 79.9 |
| G142W | 3 | 2.9 | 0.7 | 2.5 | 4.7 | 15.3 | 1.0 | 3.0 | 3.3 | 0.7 | 1.7 | 2.9 | 51.5 | 1.1 | 79.5 |
| G142Y | 3 | 2.9 | 0.6 | 2.6 | 4.9 | 17.5 | 1.5 | 2.8 | 2.9 | 0.6 | 1.6 | 2.6 | 50.1 | 1.6 | 76.1 |
| V145F | 3 | 2.9 | 0.6 | 2.6 | 5.0 | 14.9 | 1.0 | 2.8 | 3.3 | 0.7 | 1.5 | 2.6 | 52.9 | 0.1 | 80.0 |
| V145W+ | 3 | 3.0 | 1.0 | 3.0 | 5.0 | 15.0 | 1.0 | 3.0 | 3.0 | 1.0 | 2.0 | 3.0 | 53.1 | 0.1 | 80.1 |
| F378S | 3 | 2.8 | 0.6 | 2.6 | 4.9 | 16.2 | 1.2 | 2.8 | 3.0 | 0.6 | 1.5 | 2.5 | 52.2 | 0.2 | 78.3 |
| F378T | 3 | 2.7 | 0.7 | 2.6 | 4.9 | 15.8 | 1.2 | 3.0 | 3.0 | 0.6 | 1.6 | 2.8 | 51.6 | 0.1 | 78.7 |
| F378Y+ | 3 | 3.0 | 0.7 | 2.6 | 3.5 | 14.4 | 1.0 | 2.7 | 3.4 | 0.7 | 1.6 | 2.7 | 52.7 | 1.0 | 80.6 |
| T382P+ | 3 | 2.9 | 0.6 | 2.8 | 5.0 | 15.0 | 1.0 | 2.8 | 3.3 | 0.7 | 1.6 | 2.5 | 53.0 | 0.2 | 79.9 |
| T382S | 3 | 2.7 | 0.6 | 2.7 | 5.1 | 16.3 | 1.5 | 2.9 | 2.9 | 0.6 | 1.6 | 2.6 | 51.3 | 1.7 | 77.6 |
| T382W | 3 | 2.7 | 0.7 | 2.6 | 5.3 | 16.3 | 1.3 | 2.8 | 3.1 | 0.6 | 1.6 | 2.8 | 51.1 | 2.6 | 77.9 |
| T382Y+ | 2 | 3.1 | 0.7 | 2.7 | 5.0 | 14.6 | 1.0 | 2.7 | 3.3 | 0.7 | 1.6 | 2.7 | 52.8 | | 80.3 |
| R383F | 3 | 2.7 | 0.6 | 2.6 | 5.0 | 16.9 | 1.5 | 2.7 | 2.9 | 0.6 | 1.5 | 2.5 | 51.4 | 1.7 | 77.1 |
| R383P | 3 | 2.6 | 0.6 | 2.7 | 5.1 | 17.7 | 1.4 | 2.8 | 2.8 | 0.6 | 1.6 | 2.5 | 50.4 | 0.5 | 76.1 |
| R383T | 3 | 2.5 | 0.6 | 2.9 | 5.3 | 15.8 | 1.2 | 3.0 | 3.0 | 0.6 | 1.6 | 2.7 | 51.9 | 0.7 | 78.7 |
| R383V | 3 | 3.1 | 0.6 | 2.8 | 2.1 | 17.9 | 1.4 | 2.8 | 2.9 | 0.6 | 1.5 | 2.7 | 49.2 | 1.3 | 75.5 |
| R383W | 3 | 2.7 | 0.6 | 2.9 | 5.3 | 17.2 | 1.4 | 2.8 | 2.8 | 0.6 | 1.6 | 2.5 | 50.8 | 0.5 | 76.7 |
| P384F | 3 | 2.6 | 0.6 | 2.8 | 5.3 | 17.6 | 1.4 | 2.8 | 2.9 | 0.6 | 1.5 | 2.6 | 50.0 | 0.4 | 76.2 |
| P384M | 3 | 2.8 | 0.6 | 2.8 | 5.3 | 17.2 | 1.4 | 2.8 | 2.9 | 0.6 | 1.5 | 2.5 | 51.1 | 0.4 | 76.8 |
| P384T | 3 | 2.7 | 0.6 | 2.8 | 3.5 | 16.6 | 1.3 | 2.8 | 2.9 | 0.6 | 1.6 | 2.6 | 51.6 | 0.1 | 77.6 |
| P384W | 3 | 2.8 | 0.6 | 2.7 | 2.1 | 17.0 | 1.5 | 2.7 | 2.8 | 0.6 | 1.6 | 2.5 | 50.9 | 1.6 | 76.8 |
| P384Y | 3 | 2.8 | 0.7 | 2.6 | 3.7 | 17.6 | 1.4 | 2.9 | 3.0 | 0.6 | 1.7 | 2.8 | 49.2 | 0.7 | 76.1 |
| G385F | 3 | 2.5 | 0.5 | 3.0 | 5.5 | 18.5 | 1.8 | 2.8 | 2.6 | 0.6 | 1.5 | 2.5 | 48.9 | 0.1 | 74.3 |

TABLE 19-continued

Lipid Composition and Delta-9 Elongase Conversion Efficiency in Batch #2 Transformants Comprising a Vector Encoding YlLPCAT Having a Single Amino Acid Substitution

| Mutant | # | 16:0 | 16:1 | 18:0 | 18:1 | LA | ALA | EDA | DGLA | ARA | ETrA | ETA | EPA | EPA SD | % Conv. |
|---|---|---|---|---|---|---|---|---|---|---|---|---|---|---|---|
| G385M | 3 | 2.7 | 0.5 | 3.2 | 5.8 | 19.2 | 2.1 | 2.9 | 2.5 | 0.6 | 1.6 | 2.3 | 48.1 | 0.2 | 73.1 |
| G385W | 3 | 2.9 | 0.6 | 2.8 | 5.1 | 18.9 | 2.0 | 2.8 | 2.4 | 0.5 | 1.7 | 2.4 | 47.9 | 0.4 | 73.5 |
| G385Y | 3 | 2.8 | 0.5 | 2.9 | 3.9 | 19.0 | 2.0 | 2.8 | 2.6 | 0.5 | 1.6 | 2.5 | 48.4 | 0.2 | 73.6 |
| Y387V | 3 | 2.9 | 0.5 | 2.9 | 5.1 | 17.8 | 1.5 | 2.7 | 2.7 | 0.6 | 1.6 | 2.4 | 49.9 | 0.2 | 75.6 |
| Y387W | 3 | 2.8 | 0.6 | 2.8 | 3.5 | 17.0 | 1.5 | 2.6 | 2.7 | 0.6 | 1.5 | 2.4 | 51.3 | 1.7 | 76.8 |
| L388V | 3 | 3.0 | 0.6 | 3.0 | 3.7 | 18.4 | 1.7 | 2.8 | 2.7 | 0.6 | 1.7 | 2.5 | 48.8 | 0.1 | 74.5 |
| L388W | 3 | 3.0 | 0.6 | 2.8 | 2.0 | 16.6 | 1.3 | 2.7 | 2.8 | 0.6 | 1.6 | 2.5 | 51.2 | 0.5 | 77.5 |
| L388Y+ | 3 | 2.8 | 0.7 | 2.5 | 4.8 | 15.3 | 1.0 | 2.7 | 3.3 | 0.7 | 1.5 | 2.6 | 52.9 | 1.5 | 79.7 |
| T389M | 3 | 3.1 | 0.6 | 2.9 | 5.2 | 15.6 | 1.1 | 2.9 | 3.2 | 0.7 | 1.5 | 2.5 | 52.0 | 0.3 | 78.9 |
| T389W | 3 | 2.6 | 0.7 | 2.6 | 2.3 | 19.2 | 1.9 | 2.8 | 2.6 | 0.5 | 1.6 | 2.8 | 47.3 | 0.7 | 73.2 |
| T389Y | 3 | 2.7 | 0.5 | 2.8 | 3.9 | 18.7 | 1.8 | 2.9 | 2.6 | 0.5 | 1.6 | 2.6 | 48.5 | 0.2 | 74.2 |
| Mutant AVG | | 2.8 | 0.6 | 2.7 | 4.6 | 16.5 | 1.3 | 2.8 | 2.9 | 0.6 | 1.6 | 2.6 | 51.0 | | 77.5 |
| Mutant SD | | 0.2 | 0.1 | 0.2 | 1.0 | 1.7 | 0.3 | 0.1 | 0.3 | 0.1 | 0.1 | 0.1 | 1.8 | | |

TABLE 20

Lipid Composition and Delta-9 Elongase Conversion Efficiency in Batch #3 Transformants Comprising a Vector Encoding YlLPCAT Having a Single Amino Acid Substitution

| Mutant | # | 16:0 | 16:1 | 18:0 | 18:1 | LA | ALA | EDA | DGLA | ARA | ETrA | ETA | EPA | EPA SD | % Conv. |
|---|---|---|---|---|---|---|---|---|---|---|---|---|---|---|---|
| WT | 3 | 2.9 | 0.6 | 2.7 | 4.6 | 14.4 | 1.0 | 2.6 | 3.0 | 0.6 | 1.5 | 2.5 | 54.2 | 0.5 | 80.6 |
| M132C | 3 | 2.8 | 0.6 | 2.6 | 4.6 | 18.0 | 1.5 | 2.6 | 2.8 | 0.5 | 1.6 | 2.7 | 50.4 | 0.2 | 75.7 |
| M132L | 3 | 2.9 | 0.6 | 2.8 | 5.0 | 18.7 | 1.8 | 2.6 | 2.5 | 0.5 | 1.6 | 2.4 | 49.7 | 0.5 | 74.3 |
| M132Q | 3 | 2.9 | 0.4 | 2.8 | 4.7 | 19.4 | 2.2 | 2.4 | 2.4 | 0.5 | 1.3 | 2.1 | 50.1 | 0.0 | 73.1 |
| V133L | 3 | 2.9 | 0.5 | 2.7 | 5.3 | 20.4 | 2.8 | 2.8 | 2.0 | 0.4 | 1.5 | 2.1 | 48.1 | 2.2 | 71.1 |
| L134A+ | 3 | 3.1 | 0.7 | 2.5 | 4.6 | 14.2 | 1.0 | 2.6 | 3.2 | 0.6 | 1.5 | 2.5 | 54.4 | 0.7 | 81.1 |
| L134M | 3 | 3.2 | 0.6 | 2.7 | 4.6 | 15.9 | 1.5 | 2.4 | 2.8 | 0.6 | 1.4 | 2.3 | 53.3 | 2.9 | 78.3 |
| C135L | 3 | 3.3 | 0.6 | 3.0 | 4.9 | 15.9 | 1.5 | 2.4 | 2.7 | 0.6 | 1.5 | 2.2 | 52.6 | 4.4 | 78.0 |
| M136I | 3 | 3.1 | 0.6 | 2.7 | 4.7 | 16.2 | 1.7 | 2.5 | 2.6 | 0.5 | 1.5 | 2.2 | 52.4 | 3.2 | 77.5 |
| M136Y | 3 | 2.7 | 0.6 | 2.6 | 4.5 | 17.6 | 1.4 | 2.7 | 2.8 | 0.5 | 1.5 | 2.5 | 51.1 | 0.6 | 76.3 |
| K137N+ | 3 | 3.4 | 0.7 | 2.6 | 4.7 | 13.2 | 1.0 | 2.7 | 3.2 | 0.6 | 1.5 | 2.4 | 55.2 | 0.8 | 82.2 |
| K137R | 3 | 3.0 | 0.6 | 2.6 | 4.6 | 17.1 | 1.3 | 2.7 | 2.8 | 0.6 | 1.6 | 2.6 | 51.4 | 0.3 | 77.0 |
| L138Q | 3 | 3.0 | 0.5 | 2.8 | 4.6 | 18.2 | 1.8 | 2.4 | 2.6 | 0.6 | 1.4 | 2.3 | 51.0 | 1.6 | 75.0 |
| S139V | 3 | 3.1 | 0.7 | 2.6 | 4.7 | 15.8 | 1.1 | 2.6 | 3.0 | 0.6 | 1.5 | 2.4 | 53.1 | 0.5 | 78.9 |
| S140L | 3 | 3.3 | 0.6 | 2.7 | 4.8 | 15.1 | 1.5 | 2.4 | 2.8 | 0.5 | 1.5 | 2.3 | 53.8 | 3.8 | 79.2 |
| S140V | 3 | 3.2 | 0.6 | 2.8 | 4.8 | 15.8 | 1.4 | 2.5 | 2.8 | 0.6 | 1.4 | 2.3 | 53.2 | 2.9 | 78.4 |
| F141I | 3 | 3.1 | 0.6 | 2.7 | 4.8 | 16.0 | 1.6 | 2.5 | 2.7 | 0.6 | 1.5 | 2.2 | 53.0 | 3.3 | 78.0 |
| G142T | 3 | 3.2 | 0.6 | 2.7 | 5.0 | 15.9 | 1.4 | 2.5 | 2.7 | 0.6 | 1.5 | 2.3 | 52.7 | 2.3 | 78.3 |
| W143A | 3 | 3.0 | 0.5 | 2.7 | 5.3 | 19.3 | 2.4 | 2.7 | 2.1 | 0.5 | 1.5 | 2.2 | 48.8 | 3.8 | 72.7 |
| W143V | 3 | 3.2 | 0.6 | 2.7 | 4.4 | 16.4 | 1.5 | 2.5 | 2.8 | 0.6 | 1.5 | 2.4 | 52.5 | 2.2 | 77.6 |
| N144R | 3 | 3.0 | 0.6 | 2.6 | 4.6 | 15.2 | 1.2 | 2.8 | 2.9 | 0.6 | 1.5 | 2.4 | 53.5 | 0.1 | 79.5 |
| N144T+ | 3 | 3.3 | 0.7 | 2.6 | 4.7 | 13.6 | 0.9 | 2.6 | 3.2 | 0.6 | 1.5 | 2.4 | 55.2 | 0.1 | 81.9 |
| V145E | 3 | 3.1 | 0.7 | 2.6 | 4.6 | 14.3 | 1.0 | 2.5 | 3.2 | 0.6 | 1.5 | 2.5 | 54.2 | 0.7 | 80.8 |
| Y146F | 3 | 3.3 | 0.6 | 2.8 | 4.6 | 16.1 | 1.5 | 2.4 | 2.8 | 0.6 | 1.4 | 2.3 | 52.9 | 2.7 | 78.1 |
| Y146Q | 3 | 3.3 | 0.6 | 2.7 | 4.6 | 14.7 | 1.1 | 2.5 | 3.0 | 0.6 | 1.5 | 2.3 | 54.1 | 0.3 | 80.3 |
| Y146R | 3 | 3.2 | 0.5 | 2.7 | 4.6 | 16.4 | 1.6 | 2.4 | 2.6 | 0.5 | 1.5 | 2.2 | 53.0 | 3.2 | 77.6 |
| Y146V | 2 | 3.1 | 0.6 | 2.7 | 4.8 | 17.6 | 1.9 | 2.6 | 2.5 | 0.5 | 1.5 | 2.2 | 50.7 | | 75.5 |
| G148A+ | 3 | 3.2 | 0.7 | 2.6 | 4.6 | 13.4 | 0.9 | 2.5 | 3.2 | 0.6 | 1.6 | 2.5 | 54.9 | 0.3 | 82.0 |
| G148L | 3 | 3.0 | 0.6 | 2.7 | 4.8 | 16.8 | 1.7 | 2.5 | 2.6 | 0.5 | 1.5 | 2.3 | 52.2 | 2.5 | 77.0 |
| S376L | 3 | 2.7 | 0.5 | 2.8 | 4.9 | 19.2 | 2.1 | 2.6 | 2.4 | 0.5 | 1.6 | 2.3 | 49.2 | 0.3 | 73.4 |
| F378L | 3 | 3.0 | 0.5 | 2.8 | 4.5 | 16.9 | 1.3 | 2.5 | 2.7 | 0.6 | 1.5 | 2.3 | 52.3 | 0.1 | 77.2 |
| F378W | 3 | 3.0 | 0.7 | 2.5 | 4.9 | 14.9 | 1.0 | 3.0 | 3.4 | 0.6 | 1.5 | 2.7 | 53.0 | 1.0 | 80.2 |
| T382I+ | 3 | 3.3 | 0.7 | 2.6 | 4.7 | 12.9 | 0.9 | 2.4 | 3.2 | 0.6 | 1.4 | 2.4 | 55.8 | 0.5 | 82.6 |
| T382M | 3 | 2.9 | 0.5 | 2.7 | 4.5 | 16.9 | 1.7 | 2.6 | 2.6 | 0.5 | 1.5 | 2.3 | 51.9 | 2.8 | 76.8 |
| R383E | 3 | 3.1 | 0.4 | 2.9 | 4.7 | 19.7 | 2.4 | 2.3 | 2.2 | 0.5 | 1.3 | 2.1 | 49.5 | 0.5 | 72.4 |
| R383H | 3 | 2.9 | 0.6 | 2.6 | 4.8 | 16.5 | 1.2 | 2.7 | 2.9 | 0.6 | 1.6 | 2.5 | 52.1 | 0.4 | 77.8 |
| R383Q | 3 | 3.3 | 0.6 | 2.8 | 4.7 | 16.9 | 1.3 | 2.5 | 2.9 | 0.6 | 1.4 | 2.4 | 51.5 | 1.2 | 77.1 |
| P384A+ | 3 | 3.2 | 0.7 | 2.6 | 4.4 | 15.0 | 1.1 | 2.6 | 2.9 | 0.6 | 1.6 | 2.4 | 53.5 | 0.7 | 79.8 |
| P384S | 3 | 3.3 | 0.6 | 2.7 | 4.6 | 15.9 | 1.2 | 2.7 | 2.9 | 0.6 | 1.5 | 2.4 | 52.5 | 0.9 | 78.6 |
| P384T | 3 | 2.9 | 0.5 | 2.8 | 5.1 | 19.4 | 2.3 | 2.5 | 2.2 | 0.5 | 1.5 | 2.3 | 49.2 | 0.4 | 72.8 |
| P384V | 3 | 2.8 | 0.6 | 2.7 | 4.8 | 17.4 | 1.5 | 2.6 | 2.7 | 0.5 | 1.5 | 2.4 | 51.4 | 0.2 | 76.5 |
| G385A | 3 | 2.8 | 0.5 | 2.9 | 5.0 | 19.2 | 2.2 | 2.7 | 2.3 | 0.5 | 1.6 | 2.3 | 48.6 | 0.8 | 73.1 |
| G385C | 3 | 3.0 | 0.5 | 2.9 | 5.2 | 19.9 | 2.4 | 2.5 | 2.2 | 0.5 | 1.6 | 2.2 | 48.5 | 0.3 | 72.0 |
| G385V | 3 | 3.0 | 0.5 | 2.9 | 5.3 | 19.7 | 2.3 | 2.6 | 2.2 | 0.5 | 1.5 | 2.2 | 48.4 | 0.7 | 72.3 |
| Y387F | 3 | 3.1 | 0.5 | 2.8 | 4.8 | 18.3 | 1.8 | 2.4 | 2.4 | 0.5 | 1.5 | 2.2 | 50.8 | 1.5 | 74.8 |
| Y387L | 3 | 3.2 | 0.6 | 2.7 | 4.4 | 17.3 | 1.4 | 2.6 | 2.6 | 0.5 | 1.6 | 2.3 | 51.0 | 1.2 | 76.5 |
| T389A+ | 3 | 3.2 | 0.5 | 2.9 | 4.8 | 13.6 | 1.0 | 2.4 | 2.9 | 0.6 | 1.5 | 2.2 | 55.4 | 0.1 | 81.6 |

TABLE 20-continued

Lipid Composition and Delta-9 Elongase Conversion Efficiency in Batch #3 Transformants Comprising a Vector Encoding YlLPCAT Having a Single Amino Acid Substitution

| Mutant | # | 16:0 | 16:1 | 18:0 | 18:1 | LA | ALA | EDA | DGLA | ARA | ETrA | ETA | EPA | EPA SD | % Conv. |
|---|---|---|---|---|---|---|---|---|---|---|---|---|---|---|---|
| T389C+ | 3 | 3.2 | 0.6 | 2.7 | 4.4 | 13.6 | 1.0 | 2.5 | 3.1 | 0.6 | 1.5 | 2.4 | 55.3 | 0.3 | 81.8 |
| T389S+ | 3 | 3.2 | 0.6 | 2.8 | 5.0 | 13.3 | 1.0 | 2.4 | 3.1 | 0.6 | 1.5 | 2.3 | 55.2 | 0.3 | 82.0 |
| T389V | 3 | 2.9 | 0.6 | 2.8 | 4.6 | 16.0 | 1.2 | 2.7 | 2.9 | 0.6 | 1.5 | 2.4 | 52.8 | 0.4 | 78.6 |
| Mutant AVG | | 3.1 | 0.6 | 2.7 | 4.7 | 16.3 | 1.5 | 2.6 | 2.7 | 0.6 | 1.5 | 2.3 | 52.3 | 1.3 | 77.7 |
| Mutant SD | | 0.2 | 0.1 | 0.1 | 0.2 | 1.9 | 0.4 | 0.1 | 0.3 | 0.0 | 0.1 | 0.1 | 2.0 | | 3.0 |

TABLE 21

Lipid Composition and Delta-9 Elongase Conversion Efficiency in Batch #4 Transformants Comprising a Vector Encoding YlLPCAT Having a Single Amino Acid Substitution

| Mutant | # | 16:0 | 16:1 | 18:0 | 18:1 | LA | ALA | EDA | DGLA | ARA | ETrA | ETA | EPA | EPA SD | % Conv. |
|---|---|---|---|---|---|---|---|---|---|---|---|---|---|---|---|
| WT | 6 | 3.0 | 0.6 | 2.7 | 4.5 | 14.4 | 1.0 | 2.5 | 3.1 | 0.6 | 1.5 | 2.3 | 54.6 | 0.8 | 82.0 |
| M132G | 3 | 2.6 | 0.6 | 2.7 | 5.5 | 19.6 | 1.9 | 2.6 | 2.4 | 0.4 | 1.5 | 2.3 | 49.1 | 1.8 | 74.4 |
| M132H | 3 | 2.6 | 0.5 | 2.9 | 5.1 | 19.4 | 2.4 | 2.5 | 2.3 | 0.4 | 1.5 | 2.2 | 50.5 | 0.1 | 74.5 |
| M132N | 3 | 2.4 | 0.5 | 2.6 | 4.9 | 18.6 | 1.8 | 2.6 | 2.7 | 0.5 | 1.5 | 2.7 | 50.0 | 1.6 | 75.9 |
| V133A | 3 | 2.8 | 0.5 | 2.8 | 4.6 | 17.0 | 1.3 | 2.5 | 2.8 | 0.6 | 1.5 | 2.2 | 52.9 | 0.5 | 78.7 |
| V133C | 3 | 2.6 | 0.6 | 2.7 | 4.4 | 15.5 | 1.1 | 2.5 | 3.0 | 0.5 | 1.6 | 2.3 | 54.7 | 0.1 | 80.8 |
| V133G | 3 | 2.9 | 0.7 | 2.9 | 5.6 | 17.8 | 1.5 | 3.3 | 2.8 | 0.5 | 1.6 | 2.3 | 49.8 | 3.2 | 77.0 |
| V133H | 3 | 2.6 | 0.5 | 2.9 | 4.8 | 18.4 | 1.8 | 2.5 | 2.4 | 0.4 | 1.5 | 2.2 | 51.8 | 0.1 | 76.4 |
| V133N | 3 | 2.6 | 0.6 | 2.7 | 4.6 | 18.0 | 1.4 | 2.4 | 2.8 | 0.5 | 1.4 | 2.4 | 52.2 | 2.0 | 77.3 |
| V133Q | 3 | 2.7 | 0.5 | 2.9 | 4.9 | 19.2 | 2.1 | 2.4 | 2.3 | 0.4 | 1.5 | 2.0 | 51.0 | 7.9 | 75.0 |
| L134C | 3 | 2.7 | 0.7 | 2.5 | 4.6 | 13.7 | 0.9 | 2.6 | 3.4 | 0.6 | 1.6 | 2.6 | 55.0 | 1.5 | 83.2 |
| L134G+ | 3 | 3.0 | 0.7 | 2.7 | 4.4 | 14.1 | 1.0 | 2.5 | 3.0 | 0.5 | 1.7 | 2.1 | 55.3 | 0.6 | 82.6 |
| L134H | 3 | 2.5 | 0.6 | 2.6 | 4.5 | 16.7 | 1.3 | 2.5 | 2.8 | 0.5 | 1.6 | 2.6 | 53.6 | 0.3 | 79.2 |
| L134N | 3 | 2.8 | 0.5 | 2.7 | 4.6 | 16.6 | 1.4 | 2.4 | 2.7 | 0.5 | 1.5 | 2.2 | 53.5 | 2.8 | 79.0 |
| L134Q | 3 | 2.8 | 0.6 | 2.7 | 4.5 | 15.9 | 1.1 | 2.5 | 3.0 | 0.5 | 1.5 | 2.5 | 54.3 | 1.5 | 80.4 |
| C135D | 3 | 2.9 | 0.6 | 2.7 | 4.5 | 13.7 | 1.1 | 2.3 | 3.0 | 0.5 | 1.5 | 2.2 | 56.5 | 0.2 | 83.1 |
| C135E | 3 | 2.5 | 0.6 | 2.8 | 4.8 | 17.4 | 1.5 | 2.7 | 2.7 | 0.4 | 1.6 | 2.3 | 52.2 | 1.7 | 78.0 |
| C135G | 3 | 2.7 | 0.6 | 2.7 | 4.5 | 16.1 | 1.2 | 2.4 | 2.9 | 0.5 | 1.5 | 2.3 | 54.0 | 0.2 | 80.0 |
| C135H | 2 | 2.7 | 0.8 | 3.3 | 7.6 | 20.8 | 1.3 | 5.5 | 3.1 | 0.5 | 2.0 | 2.7 | 42.1 | 10.8 | 72.7 |
| C135K | 3 | 2.6 | 0.6 | 2.6 | 5.1 | 17.6 | 1.5 | 2.7 | 2.9 | 0.5 | 1.6 | 2.6 | 51.8 | 2.8 | 77.7 |
| C135N | 3 | 2.9 | 0.6 | 2.7 | 4.8 | 15.0 | 1.3 | 2.5 | 3.0 | 0.6 | 1.5 | 2.2 | 54.3 | 4.4 | 81.0 |
| C135Q | 3 | 2.8 | 0.6 | 2.8 | 4.5 | 16.2 | 1.2 | 2.5 | 2.8 | 0.5 | 1.6 | 2.3 | 54.2 | 0.5 | 79.9 |
| C135R | 3 | 2.5 | 0.5 | 2.7 | 5.1 | 19.2 | 2.0 | 2.6 | 2.6 | 0.5 | 1.5 | 2.3 | 49.9 | 0.2 | 75.0 |
| M136C | 3 | 3.0 | 0.7 | 2.6 | 4.8 | 14.6 | 1.0 | 2.9 | 3.3 | 0.6 | 1.5 | 2.3 | 54.2 | 1.3 | 81.9 |
| M136G | 2 | 3.1 | 0.6 | 2.7 | 4.5 | 12.5 | 0.9 | 2.4 | 3.1 | 0.6 | 1.5 | 2.3 | 57.0 | | 84.7 |
| M136H | 3 | 2.8 | 0.6 | 2.7 | 4.7 | 17.3 | 1.5 | 2.6 | 2.6 | 0.5 | 1.6 | 2.3 | 52.9 | 0.7 | 78.2 |
| M136N | 3 | 3.0 | 0.5 | 2.8 | 4.6 | 15.6 | 1.5 | 2.4 | 2.8 | 0.5 | 1.4 | 2.1 | 54.6 | 4.1 | 80.2 |
| K137A | 3 | 2.9 | 0.5 | 2.9 | 4.4 | 15.8 | 1.4 | 2.4 | 2.8 | 0.6 | 1.4 | 2.2 | 54.2 | 3.5 | 79.8 |
| K137G | 3 | 2.9 | 0.6 | 2.7 | 4.5 | 14.3 | 1.0 | 2.5 | 3.1 | 0.5 | 1.4 | 2.2 | 55.8 | 0.5 | 82.4 |
| K137H+ | 3 | 3.2 | 0.6 | 2.6 | 4.4 | 12.0 | 0.9 | 2.3 | 3.2 | 0.5 | 1.5 | 2.2 | 58.6 | 0.2 | 85.6 |
| L138G | 3 | 2.7 | 0.6 | 2.7 | 4.5 | 15.2 | 1.0 | 2.5 | 3.1 | 0.5 | 1.5 | 2.4 | 54.8 | 0.1 | 81.3 |
| L138H | 3 | 2.9 | 0.6 | 2.7 | 4.3 | 14.3 | 1.1 | 2.5 | 3.1 | 0.5 | 1.5 | 2.4 | 55.8 | 0.2 | 82.4 |
| L138I | 2 | 3.0 | 0.6 | 2.6 | 4.2 | 15.0 | 1.1 | 2.3 | 2.9 | 0.5 | 1.5 | 2.4 | 56.1 | | 81.7 |
| L138N | 3 | 2.9 | 0.6 | 2.6 | 4.4 | 15.3 | 1.1 | 2.4 | 3.0 | 0.6 | 1.5 | 2.3 | 54.6 | 0.9 | 81.1 |
| S139G | 3 | 2.7 | 0.6 | 2.7 | 4.5 | 15.0 | 1.0 | 2.6 | 3.1 | 0.5 | 1.5 | 2.4 | 54.8 | 1.6 | 81.4 |
| S139H | 3 | 2.8 | 0.6 | 2.6 | 4.7 | 15.5 | 1.4 | 2.5 | 2.9 | 0.5 | 1.5 | 2.4 | 54.4 | 3.9 | 80.5 |
| S139N | 3 | 2.9 | 0.6 | 2.7 | 4.4 | 15.4 | 1.1 | 2.4 | 3.0 | 0.6 | 1.5 | 2.3 | 54.7 | 0.1 | 81.0 |
| S140C | 3 | 2.9 | 0.6 | 2.8 | 4.9 | 14.9 | 1.3 | 2.6 | 3.0 | 0.5 | 1.5 | 2.1 | 54.4 | 4.3 | 81.1 |
| S140H+ | 3 | 3.1 | 0.6 | 2.6 | 4.3 | 12.1 | 0.9 | 2.4 | 3.2 | 0.5 | 1.5 | 2.3 | 58.6 | 0.5 | 85.5 |
| S140N | 3 | 3.0 | 0.6 | 2.7 | 4.3 | 13.5 | 0.9 | 2.3 | 3.1 | 0.6 | 1.5 | 2.2 | 56.6 | 0.1 | 83.5 |
| F141A | 3 | 3.0 | 0.6 | 2.8 | 4.2 | 14.3 | 1.0 | 2.4 | 3.1 | 0.6 | 1.4 | 2.2 | 55.9 | 0.2 | 82.5 |
| F141G | 3 | 2.7 | 0.5 | 2.6 | 4.7 | 16.9 | 1.3 | 2.6 | 2.8 | 0.5 | 1.5 | 2.2 | 53.3 | 0.9 | 78.8 |
| F141H | 3 | 2.4 | 0.5 | 2.6 | 4.8 | 18.0 | 1.7 | 2.6 | 2.6 | 0.4 | 1.5 | 2.5 | 52.3 | 2.2 | 77.2 |
| F141N | 3 | 2.8 | 0.6 | 2.6 | 4.8 | 16.7 | 1.4 | 2.6 | 2.7 | 0.5 | 1.6 | 2.2 | 53.2 | 0.9 | 78.9 |
| G142H | 2 | 2.8 | 0.7 | 2.6 | 4.2 | 14.3 | 0.9 | 2.4 | 3.2 | 0.5 | 1.5 | 2.7 | 55.9 | | 82.7 |
| G142N | 3 | 2.4 | 0.7 | 2.3 | 4.6 | 15.5 | 1.0 | 2.6 | 3.4 | 0.5 | 1.6 | 3.0 | 53.0 | 0.9 | 80.9 |
| W143G | 3 | 2.7 | 0.6 | 2.7 | 4.8 | 16.5 | 1.4 | 2.6 | 2.8 | 0.5 | 1.5 | 2.2 | 53.3 | 3.1 | 79.1 |
| W143H | 3 | 2.9 | 0.6 | 2.7 | 4.4 | 15.2 | 1.1 | 2.5 | 3.0 | 0.5 | 1.6 | 2.5 | 55.1 | 0.4 | 81.3 |
| W143K | 3 | 2.8 | 0.6 | 2.6 | 4.8 | 16.5 | 1.3 | 2.6 | 2.7 | 0.5 | 1.6 | 2.3 | 54.0 | 0.3 | 79.4 |
| N144A+ | 3 | 3.2 | 0.6 | 2.7 | 4.4 | 12.5 | 0.9 | 2.3 | 3.2 | 0.6 | 1.4 | 2.2 | 57.5 | 0.1 | 84.8 |
| N144G | 3 | 2.9 | 0.7 | 2.5 | 4.5 | 14.7 | 1.1 | 2.5 | 3.2 | 0.5 | 1.4 | 2.6 | 54.5 | 2.5 | 81.8 |
| V145A | 3 | 2.8 | 0.7 | 2.5 | 4.4 | 13.1 | 0.8 | 2.3 | 3.4 | 0.6 | 1.5 | 2.6 | 56.0 | 0.3 | 84.1 |
| V145G | 2 | 2.9 | 0.6 | 2.6 | 4.5 | 14.1 | 1.0 | 2.5 | 3.1 | 0.5 | 1.6 | 2.4 | 55.5 | | 82.7 |
| V145H | 3 | 3.1 | 0.6 | 2.7 | 4.6 | 15.5 | 1.2 | 2.5 | 2.9 | 0.5 | 1.6 | 2.4 | 54.5 | 1.2 | 80.7 |
| Y146G | 2 | 2.8 | 0.6 | 2.7 | 4.6 | 14.4 | 1.0 | 2.6 | 3.2 | 0.6 | 1.5 | 2.5 | 54.9 | | 82.2 |

TABLE 21-continued

Lipid Composition and Delta-9 Elongase Conversion Efficiency in Batch #4 Transformants Comprising a Vector Encoding YlLPCAT Having a Single Amino Acid Substitution

| | | | | | | % TFAs | | | | | | | | EPA | % |
|---|---|---|---|---|---|---|---|---|---|---|---|---|---|---|---|
| Mutant | # | 16:0 | 16:1 | 18:0 | 18:1 | LA | ALA | EDA | DGLA | ARA | ETrA | ETA | EPA | SD | Conv. |
| D147A | 3 | 2.8 | 0.6 | 2.6 | 4.6 | 15.6 | 1.4 | 2.5 | 2.9 | 0.5 | 1.6 | 2.3 | 53.9 | 4.0 | 80.2 |
| D147G | 3 | 2.4 | 0.6 | 3.2 | 6.5 | 20.5 | 1.9 | 4.2 | 2.7 | 0.4 | 1.8 | 2.4 | 45.2 | 7.2 | 72.9 |
| D147H+ | 3 | 3.4 | 0.6 | 2.6 | 4.2 | 13.3 | 1.0 | 2.4 | 3.0 | 0.5 | 1.5 | 2.2 | 57.5 | 0.9 | 83.9 |
| D147N | 3 | 2.9 | 0.6 | 2.7 | 4.4 | 14.5 | 1.0 | 2.5 | 3.1 | 0.6 | 1.6 | 2.3 | 55.1 | 3.2 | 82.1 |
| D147Q+ | 3 | 3.2 | 0.6 | 2.7 | 4.3 | 14.0 | 1.0 | 2.5 | 3.0 | 0.5 | 1.6 | 2.3 | 56.6 | 0.2 | 83.0 |
| G148H | 3 | 3.2 | 0.6 | 2.7 | 4.6 | 15.4 | 1.5 | 2.5 | 2.8 | 0.5 | 1.6 | 2.4 | 54.3 | 4.3 | 80.5 |
| G148N+ | 3 | 3.0 | 0.7 | 2.7 | 4.7 | 13.4 | 1.0 | 2.5 | 3.2 | 0.6 | 1.6 | 2.3 | 55.8 | 0.8 | 83.5 |
| S376A | 3 | 2.9 | 0.6 | 2.8 | 4.6 | 16.9 | 1.3 | 2.5 | 2.8 | 0.6 | 1.5 | 2.3 | 52.8 | 1.9 | 78.8 |
| S376G | 3 | 2.6 | 0.5 | 2.7 | 5.1 | 17.8 | 1.5 | 2.8 | 2.7 | 0.5 | 1.4 | 2.3 | 51.7 | 1.9 | 77.4 |
| S376H | 3 | 2.8 | 0.6 | 2.7 | 4.9 | 19.0 | 2.2 | 2.5 | 2.4 | 0.4 | 1.6 | 2.5 | 50.3 | 0.5 | 75.1 |
| A377G | 3 | 2.6 | 0.7 | 2.7 | 5.0 | 17.3 | 1.3 | 2.8 | 2.9 | 0.5 | 1.6 | 2.5 | 51.4 | 1.8 | 78.1 |
| A377H | 3 | 3.0 | 0.5 | 2.8 | 5.0 | 19.5 | 2.4 | 2.5 | 2.2 | 0.4 | 1.6 | 2.3 | 49.9 | 0.1 | 74.2 |
| A377L | 3 | 2.6 | 0.5 | 2.8 | 5.7 | 19.6 | 2.4 | 2.7 | 2.2 | 0.4 | 1.5 | 2.2 | 49.7 | 1.0 | 74.1 |
| A377N | 3 | 2.7 | 0.6 | 2.7 | 5.3 | 19.1 | 2.1 | 2.7 | 2.3 | 0.4 | 1.7 | 2.2 | 49.1 | 0.2 | 74.7 |
| F378C | 3 | 2.8 | 0.6 | 2.8 | 4.8 | 16.4 | 1.3 | 2.7 | 2.8 | 0.5 | 1.6 | 2.2 | 53.0 | 1.0 | 79.4 |
| F378G | 3 | 2.8 | 0.6 | 2.8 | 4.6 | 15.6 | 1.1 | 2.5 | 2.9 | 0.5 | 1.5 | 2.3 | 54.2 | 0.1 | 80.5 |
| F378H | 3 | 2.8 | 0.5 | 2.8 | 4.7 | 17.3 | 1.7 | 2.6 | 2.5 | 0.4 | 1.5 | 2.2 | 53.0 | 3.1 | 78.0 |
| F378N | 3 | 2.6 | 0.6 | 2.8 | 4.7 | 17.0 | 1.3 | 2.5 | 2.8 | 0.5 | 1.6 | 2.3 | 52.9 | 0.4 | 78.7 |
| T382G | 3 | 2.5 | 0.5 | 2.9 | 4.8 | 18.2 | 1.7 | 2.5 | 2.5 | 0.4 | 1.4 | 2.3 | 51.9 | 1.5 | 76.6 |
| T382H | 3 | 2.8 | 0.6 | 2.8 | 4.6 | 17.3 | 1.5 | 2.5 | 2.6 | 0.4 | 1.5 | 2.4 | 53.4 | 0.5 | 78.3 |
| T382N | 3 | 2.6 | 0.5 | 2.9 | 5.2 | 19.4 | 2.2 | 2.6 | 2.3 | 0.4 | 1.5 | 2.0 | 50.2 | 0.5 | 74.4 |
| T382Q | 2 | 2.9 | 0.7 | 3.1 | 5.7 | 16.8 | 1.0 | 3.9 | 3.2 | 0.5 | 1.8 | 2.7 | 50.0 | | 78.8 |
| R383G | 3 | 2.3 | 0.7 | 3.4 | 7.6 | 21.1 | 1.3 | 5.7 | 3.3 | 0.5 | 2.1 | 3.1 | 41.2 | 7.4 | 72.3 |
| P384G+ | 3 | 2.5 | 0.6 | 2.6 | 4.5 | 15.5 | 1.1 | 2.5 | 3.1 | 0.5 | 1.5 | 2.5 | 54.2 | 0.2 | 80.8 |
| P384H | 3 | 2.7 | 0.6 | 2.7 | 4.5 | 16.3 | 1.2 | 2.5 | 2.8 | 0.5 | 1.5 | 2.4 | 54.0 | 0.5 | 79.8 |
| P384K | 3 | 2.7 | 0.6 | 2.5 | 4.9 | 17.7 | 1.7 | 2.5 | 2.5 | 0.4 | 1.6 | 2.3 | 52.6 | 2.3 | 77.4 |
| P384R | 3 | 2.7 | 0.6 | 2.7 | 4.5 | 16.1 | 1.1 | 2.4 | 3.0 | 0.6 | 1.4 | 2.4 | 54.1 | 0.9 | 80.1 |
| G385G | 3 | 2.8 | 0.6 | 2.7 | 4.5 | 14.1 | 1.0 | 2.6 | 3.1 | 0.5 | 1.6 | 2.4 | 55.2 | 0.1 | 82.5 |
| G385H | 3 | 2.6 | 0.5 | 2.8 | 5.3 | 19.1 | 2.2 | 2.6 | 2.4 | 0.4 | 1.6 | 2.4 | 49.8 | 0.6 | 74.8 |
| G385K | 3 | 2.6 | 0.5 | 2.8 | 5.4 | 19.3 | 2.1 | 2.6 | 2.4 | 0.4 | 1.6 | 2.4 | 50.1 | 0.4 | 74.7 |
| G385N | 3 | 2.5 | 0.5 | 2.7 | 5.3 | 19.5 | 2.0 | 2.7 | 2.6 | 0.4 | 1.5 | 2.4 | 49.7 | 1.2 | 74.6 |
| Y386A | 3 | 2.7 | 0.5 | 2.9 | 4.9 | 19.2 | 2.0 | 2.5 | 2.5 | 0.5 | 1.5 | 2.2 | 50.1 | 0.3 | 74.9 |
| Y386G | 3 | 2.5 | 0.5 | 3.0 | 5.2 | 19.3 | 2.2 | 2.6 | 2.3 | 0.4 | 1.6 | 2.0 | 50.0 | 0.4 | 74.6 |
| Y386H | 3 | 2.8 | 0.5 | 2.9 | 5.2 | 19.3 | 2.2 | 2.5 | 2.3 | 0.4 | 1.6 | 2.4 | 50.0 | 0.5 | 74.6 |
| Y386L | 3 | 2.6 | 0.5 | 2.9 | 5.4 | 19.1 | 2.2 | 2.7 | 2.3 | 0.4 | 1.6 | 2.2 | 50.1 | 0.2 | 74.8 |
| Y387G | 3 | 2.5 | 0.6 | 2.6 | 5.1 | 17.9 | 1.5 | 2.8 | 2.8 | 0.5 | 1.6 | 2.5 | 51.0 | 2.1 | 77.2 |
| Y387H | 3 | 2.9 | 0.6 | 2.6 | 4.5 | 16.5 | 1.2 | 2.5 | 2.8 | 0.5 | 1.5 | 2.5 | 53.7 | 2.1 | 79.5 |
| L388G+ | 3 | 2.8 | 0.6 | 2.7 | 4.4 | 14.6 | 1.0 | 2.6 | 3.1 | 0.5 | 1.6 | 2.5 | 55.5 | 0.8 | 82.2 |
| L388H | 3 | 2.9 | 0.6 | 2.7 | 4.5 | 15.9 | 1.2 | 2.5 | 2.8 | 0.5 | 1.5 | 2.4 | 54.7 | 0.9 | 80.3 |
| T389G | 3 | 2.5 | 0.5 | 2.9 | 5.2 | 17.9 | 1.9 | 2.8 | 2.6 | 0.4 | 1.6 | 2.3 | 51.2 | 0.7 | 76.8 |
| T389H | 3 | 2.7 | 0.5 | 2.7 | 5.0 | 18.7 | 1.9 | 2.6 | 2.4 | 0.4 | 1.6 | 2.4 | 51.3 | 0.6 | 75.8 |
| F390A | 3 | 2.5 | 0.5 | 3.1 | 6.0 | 14.8 | 1.3 | 2.2 | 2.6 | 0.5 | 1.5 | 2.0 | 54.4 | 4.1 | 81.3 |
| F390C | 3 | 2.9 | 0.6 | 2.9 | 5.2 | 13.8 | 0.9 | 2.5 | 3.0 | 0.5 | 1.6 | 2.1 | 55.5 | 0.4 | 83.0 |
| F390G+ | 3 | 2.6 | 0.4 | 3.3 | 5.7 | 14.6 | 1.2 | 2.2 | 2.5 | 0.4 | 1.4 | 1.8 | 55.9 | 0.3 | 81.8 |
| F390H | 3 | 2.7 | 0.5 | 2.7 | 4.7 | 18.3 | 1.8 | 2.5 | 2.4 | 0.4 | 1.5 | 2.2 | 52.3 | 0.7 | 76.6 |
| F390N | 2 | 2.8 | 0.6 | 2.6 | 4.4 | 15.2 | 1.0 | 2.4 | 3.1 | 0.6 | 1.5 | 2.3 | 55.1 | 0.2 | 81.4 |
| Mutant AVG | | 2.8 | 0.6 | 2.7 | 4.8 | 16.4 | 1.4 | 2.6 | 2.8 | 0.5 | 1.5 | 2.3 | 53.1 | 1.5 | 79.3 |
| Mutant SD | | 0.2 | 0.1 | 0.2 | 0.6 | 2.1 | 0.4 | 0.5 | 0.3 | 0.1 | 0.1 | 0.2 | 2.9 | | 3.2 |

TABLE 22

Lipid Composition and Delta-9 Elongase Conversion Efficiency in Batch #5 Transformants Comprising a Vector Encoding YlLPCAT Having a Single Amino Acid Substitution

| | | | | | | % TFAs | | | | | | | | EPA | % |
|---|---|---|---|---|---|---|---|---|---|---|---|---|---|---|---|
| Mutant | # | 16:0 | 16:1 | 18:0 | 18:1 | LA | ALA | EDA | DGLA | ARA | ETrA | ETA | EPA | SD | Conv. |
| WT | 6 | 2.9 | 0.6 | 2.4 | 4.0 | 13.6 | 1.0 | 2.0 | 2.9 | 0.5 | 1.6 | 2.3 | 58.3 | 1.5 | 82.2 |
| M132P | 3 | 2.7 | 0.5 | 2.3 | 4.8 | 19.5 | 2.7 | 2.2 | 2.0 | 0.4 | 1.5 | 1.9 | 52.1 | 1.1 | 73.0 |
| M132S | 3 | 2.7 | 0.5 | 2.7 | 5.2 | 19.3 | 2.4 | 2.5 | 2.1 | 0.2 | 1.6 | 2.2 | 51.0 | 0.1 | 73.3 |
| M132T | 3 | 2.6 | 0.7 | 2.4 | 5.5 | 19.6 | 2.4 | 2.7 | 2.3 | 0.4 | 1.6 | 2.4 | 50.1 | 1.4 | 73.0 |
| V133P | 3 | 2.7 | 0.5 | 2.5 | 5.0 | 19.4 | 2.2 | 2.3 | 2.2 | 0.5 | 1.5 | 1.9 | 51.3 | 0.4 | 73.4 |
| V133S | 3 | 2.8 | 0.6 | 2.7 | 5.0 | 17.7 | 1.7 | 1.7 | 2.6 | 0.3 | 1.6 | 2.4 | 52.4 | 0.1 | 75.9 |
| V133T | 3 | 2.9 | 0.6 | 2.5 | 5.0 | 18.7 | 2.3 | 2.5 | 2.2 | 0.4 | 1.5 | 2.1 | 52.0 | 2.6 | 74.3 |
| V133Y | 3 | 2.5 | 0.5 | 2.5 | 4.8 | 19.0 | 2.3 | 2.2 | 2.2 | 0.4 | 1.4 | 2.2 | 52.5 | 0.2 | 74.0 |
| L134P | 3 | 2.5 | 0.5 | 2.3 | 4.4 | 18.9 | 2.4 | 2.0 | 2.1 | 0.4 | 1.5 | 2.1 | 53.2 | 0.4 | 74.2 |
| L134S | 3 | 2.8 | 0.6 | 2.7 | 5.6 | 19.9 | 2.6 | 2.6 | 2.2 | 0.2 | 1.6 | 2.1 | 49.6 | 6.0 | 72.1 |
| L134T | 3 | 2.8 | 0.5 | 2.6 | 5.3 | 20.0 | 2.8 | 2.5 | 1.9 | 0.3 | 1.5 | 1.9 | 50.6 | 0.5 | 72.0 |
| C135P | 3 | 2.5 | 0.5 | 2.3 | 4.2 | 18.2 | 2.0 | 1.9 | 2.3 | 0.4 | 1.5 | 2.3 | 54.1 | 0.6 | 75.5 |

TABLE 22-continued

Lipid Composition and Delta-9 Elongase Conversion Efficiency in Batch #5 Transformants Comprising a Vector Encoding YILPCAT Having a Single Amino Acid Substitution

| Mutant | # | 16:0 | 16:1 | 18:0 | 18:1 | LA | ALA | EDA | DGLA | ARA | ETrA | ETA | EPA | SD | % Conv. |
|---|---|---|---|---|---|---|---|---|---|---|---|---|---|---|---|
| C135S | 3 | 3.0 | 0.6 | 2.6 | 4.6 | 15.4 | 1.3 | 2.5 | 2.8 | 0.5 | 1.6 | 2.4 | 55.0 | 0.7 | 79.5 |
| M136P | 3 | 3.0 | 0.6 | 2.2 | 3.7 | 12.6 | 0.9 | 1.8 | 2.8 | 0.5 | 1.5 | 2.3 | 60.2 | 0.7 | 83.6 |
| K137P | 3 | 2.6 | 0.5 | 2.4 | 4.3 | 17.8 | 2.1 | 2.1 | 2.3 | 0.4 | 1.4 | 2.1 | 54.5 | 3.5 | 76.0 |
| K137S | 3 | 3.0 | 0.7 | 2.5 | 4.4 | 14.0 | 1.1 | 2.5 | 3.1 | 0.5 | 1.7 | 2.5 | 56.6 | 0.5 | 81.6 |
| K137T | 3 | 2.9 | 0.6 | 2.4 | 4.7 | 18.0 | 2.3 | 2.3 | 2.2 | 0.4 | 1.6 | 2.1 | 53.1 | 4.4 | 75.3 |
| K137Y | 3 | 2.7 | 0.7 | 2.0 | 4.0 | 12.0 | 0.9 | 1.8 | 3.0 | 0.5 | 1.4 | 2.4 | 60.7 | 2.8 | 84.4 |
| L138P | 3 | 2.5 | 0.4 | 2.2 | 4.5 | 19.1 | 2.6 | 1.9 | 1.9 | 0.4 | 1.4 | 2.0 | 53.7 | 0.9 | 73.9 |
| L138S | 3 | 3.0 | 0.6 | 2.5 | 4.4 | 14.7 | 1.2 | 2.5 | 2.9 | 0.5 | 1.7 | 2.3 | 56.2 | 0.9 | 80.6 |
| L138T | 3 | 3.1 | 0.7 | 2.4 | 4.4 | 14.4 | 1.1 | 2.3 | 2.8 | 0.5 | 1.7 | 2.3 | 56.7 | 0.6 | 81.0 |
| S139P | 3 | 2.6 | 0.5 | 2.5 | 4.3 | 17.3 | 2.0 | 2.0 | 2.3 | 0.4 | 1.4 | 2.1 | 54.9 | 3.2 | 76.5 |
| S140P | 3 | 3.0 | 0.6 | 2.4 | 3.9 | 13.0 | 1.0 | 1.9 | 2.9 | 0.5 | 1.5 | 2.3 | 59.7 | 0.7 | 83.1 |
| F141P | 3 | 2.5 | 0.6 | 2.0 | 4.6 | 18.8 | 2.4 | 2.1 | 1.9 | 0.3 | 1.5 | 2.1 | 53.1 | 2.1 | 74.2 |
| F141S | 3 | 2.8 | 0.7 | 2.1 | 4.4 | 15.1 | 1.7 | 2.2 | 2.5 | 0.4 | 1.7 | 2.2 | 56.6 | 5.4 | 79.6 |
| F141T | 3 | 3.1 | 0.7 | 2.4 | 4.4 | 13.9 | 1.1 | 2.3 | 3.0 | 0.3 | 1.6 | 2.4 | 57.1 | 0.1 | 81.6 |
| G142M | 3 | 3.0 | 0.6 | 2.4 | 4.6 | 16.0 | 1.6 | 2.3 | 2.6 | 0.5 | 1.5 | 2.2 | 55.3 | 3.2 | 78.5 |
| G142P | 3 | 2.8 | 0.5 | 2.5 | 4.4 | 15.7 | 1.6 | 2.4 | 2.6 | 0.4 | 1.4 | 2.2 | 55.7 | 3.6 | 79.0 |
| W143P | 3 | 2.5 | 0.5 | 2.1 | 4.1 | 17.5 | 1.6 | 2.0 | 2.3 | 0.4 | 1.5 | 2.2 | 55.5 | 0.3 | 77.0 |
| W143S | 3 | 3.0 | 0.7 | 2.5 | 4.5 | 15.4 | 1.3 | 2.5 | 2.8 | 0.4 | 1.6 | 2.3 | 55.5 | 0.2 | 79.6 |
| W143T | 3 | 2.8 | 0.6 | 2.5 | 5.3 | 19.4 | 2.6 | 2.6 | 2.1 | 0.3 | 1.6 | 2.2 | 50.1 | 0.8 | 72.9 |
| N144F | 3 | 3.1 | 0.7 | 2.3 | 4.3 | 12.2 | 0.9 | 2.1 | 3.0 | 0.5 | 1.6 | 2.3 | 59.4 | 0.6 | 84.0 |
| N144P | 3 | 2.7 | 0.5 | 2.4 | 4.2 | 16.3 | 1.3 | 2.3 | 2.7 | 0.5 | 1.5 | 2.3 | 55.7 | 0.3 | 78.7 |
| N144V | 3 | 2.8 | 0.6 | 2.0 | 3.8 | 11.6 | 0.9 | 1.7 | 2.7 | 0.5 | 1.5 | 2.2 | 61.9 | 1.0 | 85.0 |
| V145P | 3 | 2.7 | 0.5 | 2.3 | 4.3 | 17.6 | 1.5 | 2.1 | 2.4 | 0.4 | 1.4 | 2.1 | 54.7 | 1.0 | 76.8 |
| V145S | 3 | 3.0 | 0.7 | 2.2 | 4.5 | 15.4 | 1.7 | 2.3 | 2.6 | 0.5 | 1.6 | 2.3 | 55.9 | 4.0 | 79.3 |
| V145T | 3 | 3.2 | 0.7 | 2.6 | 4.5 | 14.1 | 1.2 | 2.6 | 3.0 | 0.5 | 1.6 | 2.4 | 56.0 | 0.6 | 81.3 |
| Y146N | 3 | 2.7 | 0.6 | 2.1 | 4.0 | 15.4 | 1.5 | 1.8 | 2.4 | 0.4 | 1.4 | 2.2 | 57.8 | 3.6 | 79.6 |
| Y146P | 3 | 2.6 | 0.7 | 2.3 | 4.9 | 16.4 | 1.5 | 2.5 | 2.9 | 0.5 | 1.6 | 2.6 | 53.7 | 4.5 | 78.0 |
| D147F | 3 | 3.2 | 0.6 | 2.4 | 4.5 | 15.0 | 1.6 | 2.1 | 2.6 | 0.5 | 1.6 | 2.1 | 56.2 | 4.3 | 79.8 |
| D147S | 3 | 2.9 | 0.6 | 2.2 | 4.6 | 16.1 | 1.8 | 2.4 | 2.6 | 0.5 | 1.6 | 2.2 | 55.1 | 3.3 | 78.2 |
| D147T | 3 | 2.7 | 0.5 | 2.2 | 5.0 | 20.0 | 2.9 | 2.2 | 1.8 | 0.3 | 1.5 | 1.9 | 51.5 | 0.4 | 72.1 |
| G148F | 3 | 2.9 | 0.6 | 2.4 | 4.6 | 15.3 | 1.6 | 2.3 | 2.6 | 0.4 | 1.7 | 2.3 | 55.6 | 4.4 | 79.4 |
| G148M | 3 | 2.9 | 0.6 | 2.4 | 4.5 | 16.0 | 1.6 | 2.2 | 2.6 | 0.4 | 1.6 | 2.2 | 55.2 | 1.8 | 78.5 |
| G148S | 3 | 2.8 | 0.5 | 2.5 | 5.2 | 19.9 | 2.8 | 2.4 | 1.9 | 0.3 | 1.5 | 1.9 | 51.0 | 0.6 | 72.2 |
| G148T | 3 | 2.6 | 0.5 | 2.2 | 4.8 | 19.6 | 2.7 | 2.0 | 1.8 | 0.3 | 1.4 | 1.9 | 52.7 | 0.2 | 73.0 |
| G148V | 3 | 2.7 | 0.5 | 2.2 | 3.9 | 14.7 | 1.5 | 1.7 | 2.4 | 0.4 | 1.5 | 2.1 | 58.8 | 3.9 | 80.5 |
| S376F | 3 | 2.6 | 0.5 | 2.4 | 4.9 | 18.8 | 2.3 | 2.3 | 2.3 | 0.4 | 1.6 | 2.2 | 51.8 | 0.4 | 74.1 |
| S376P | 3 | 2.6 | 0.5 | 2.5 | 5.1 | 19.2 | 2.5 | 2.4 | 2.1 | 0.4 | 1.6 | 2.0 | 51.7 | 1.5 | 73.5 |
| S376V | 3 | 2.5 | 0.5 | 2.3 | 4.1 | 17.6 | 1.9 | 2.0 | 2.3 | 0.4 | 1.4 | 2.1 | 55.4 | 1.8 | 76.5 |
| A377F | 3 | 2.6 | 0.5 | 2.6 | 5.0 | 19.2 | 2.4 | 2.4 | 2.2 | 0.4 | 1.6 | 2.2 | 51.2 | 0.9 | 73.5 |
| A377P | 3 | 2.9 | 0.6 | 2.6 | 4.9 | 17.2 | 1.6 | 2.5 | 2.4 | 0.4 | 1.7 | 2.1 | 52.7 | 0.8 | 76.8 |
| A377S | 3 | 2.8 | 0.6 | 2.4 | 4.3 | 16.2 | 1.4 | 2.3 | 2.6 | 0.4 | 1.6 | 2.3 | 55.5 | 1.4 | 78.6 |
| A377T | 3 | 2.7 | 0.5 | 2.3 | 4.6 | 18.9 | 2.4 | 2.2 | 2.0 | 0.3 | 1.6 | 2.1 | 52.6 | 1.8 | 74.0 |
| A377V | 3 | 2.4 | 0.4 | 2.4 | 4.4 | 19.0 | 2.5 | 1.9 | 1.9 | 0.4 | 1.3 | 1.9 | 54.0 | 0.9 | 74.1 |
| F378P | 3 | 2.6 | 0.5 | 2.7 | 5.2 | 18.8 | 2.2 | 2.6 | 2.3 | 0.4 | 1.6 | 2.2 | 50.9 | 0.3 | 74.0 |
| G385S | 3 | 2.5 | 0.5 | 2.5 | 5.0 | 18.7 | 2.2 | 2.4 | 2.3 | 0.4 | 1.6 | 2.4 | 51.8 | 0.8 | 74.4 |
| G385T | 3 | 2.6 | 0.6 | 2.4 | 4.8 | 18.8 | 2.4 | 1.7 | 2.1 | 0.2 | 1.6 | 2.3 | 52.2 | 1.9 | 74.0 |
| Y386F | 3 | 2.9 | 0.9 | 2.1 | 4.7 | 16.5 | 1.3 | 2.3 | 2.6 | 0.4 | 1.6 | 2.4 | 54.0 | 2.7 | 78.1 |
| Y386P | 3 | 2.3 | 0.6 | 2.4 | 5.0 | 17.9 | 1.8 | 2.6 | 2.7 | 0.4 | 1.7 | 2.9 | 51.3 | 1.0 | 75.8 |
| Y386S | 3 | 2.7 | 0.6 | 2.6 | 5.3 | 19.2 | 2.3 | 2.5 | 2.2 | 0.4 | 1.6 | 2.2 | 51.0 | 0.2 | 73.5 |
| Y386T | 3 | 2.6 | 0.6 | 2.6 | 5.5 | 19.5 | 2.2 | 2.7 | 2.3 | 0.4 | 1.7 | 2.4 | 49.7 | 1.6 | 73.1 |
| Y386V | 3 | 2.4 | 0.4 | 2.5 | 4.5 | 18.9 | 2.4 | 2.1 | 2.0 | 0.3 | 1.4 | 2.0 | 53.3 | 1.3 | 74.1 |
| Y387P | 3 | 2.8 | 0.6 | 2.7 | 4.7 | 17.1 | 1.6 | 2.5 | 2.5 | 0.4 | 1.7 | 2.3 | 53.4 | 0.1 | 77.0 |
| Y387S | 3 | 2.6 | 0.7 | 2.5 | 4.9 | 17.1 | 1.6 | 2.6 | 2.6 | 0.4 | 1.6 | 2.4 | 53.4 | 1.9 | 77.2 |
| Y387T | 3 | 2.7 | 0.6 | 2.4 | 4.7 | 17.0 | 1.5 | 2.4 | 2.6 | 0.4 | 1.5 | 2.3 | 54.0 | 0.4 | 77.3 |
| L388P | 3 | 2.5 | 0.6 | 2.5 | 5.0 | 18.3 | 1.9 | 2.5 | 2.5 | 0.3 | 1.7 | 2.5 | 51.7 | 0.8 | 75.2 |
| L388S | 3 | 2.8 | 0.6 | 2.5 | 4.8 | 17.9 | 1.9 | 2.4 | 2.3 | 0.4 | 1.5 | 2.2 | 53.0 | 1.5 | 75.7 |
| L388T+ | 3 | 2.5 | 0.6 | 2.2 | 3.8 | 14.8 | 1.1 | 1.9 | 2.7 | 0.4 | 1.4 | 2.4 | 58.6 | 0.4 | 80.8 |
| T389F | 3 | 3.0 | 0.6 | 2.7 | 4.5 | 15.9 | 1.3 | 2.5 | 2.7 | 0.4 | 1.6 | 2.4 | 54.9 | 0.1 | 79.0 |
| T389P | 3 | 2.8 | 0.6 | 2.7 | 5.1 | 17.9 | 2.1 | 2.6 | 2.4 | 0.1 | 1.6 | 2.2 | 52.4 | 1.6 | 75.4 |
| F390M | 3 | 2.5 | 0.7 | 2.2 | 4.6 | 16.1 | 1.5 | 2.3 | 2.8 | 0.4 | 1.6 | 2.7 | 54.3 | 2.1 | 78.5 |
| F390P | 3 | 2.7 | 0.5 | 2.5 | 5.1 | 19.8 | 2.8 | 1.6 | 1.9 | 0.2 | 1.5 | 2.0 | 51.3 | 0.6 | 72.2 |
| F390S+ | 3 | 2.8 | 0.5 | 2.9 | 5.9 | 12.9 | 1.1 | 2.1 | 2.4 | 0.4 | 1.5 | 1.8 | 58.0 | 0.5 | 82.6 |
| F390T+ | 3 | 2.6 | 0.5 | 2.5 | 4.4 | 14.1 | 1.1 | 1.8 | 2.4 | 0.4 | 1.4 | 2.1 | 59.2 | 0.3 | 81.6 |
| F390V | 3 | 2.4 | 0.5 | 2.2 | 4.2 | 17.2 | 1.6 | 2.0 | 2.3 | 0.4 | 1.5 | 2.3 | 55.6 | 1.5 | 77.3 |
| Mutant AVG | | 2.7 | 0.6 | 2.4 | 4.6 | 17.0 | 1.8 | 2.2 | 2.4 | 0.4 | 1.5 | 2.2 | 54.3 | 1.5 | 77.0 |
| Mutant SD | | 0.2 | 0.1 | 0.2 | 0.5 | 2.3 | 0.6 | 0.3 | 0.3 | 0.1 | 0.1 | 0.2 | 2.8 | | 3.4 |

Based on the above data, it was clear that several of the YILPCAT single-amino acid mutants functioned with approximately equal or improved activity when compared to the parent wild type YILPCAT enzyme (SEQ ID NO:40). This conclusion was made based on measuring LPCAT activity as a function of EPA % TFAs and/or % Conv. In fact, all of the mutant YILPCAT transformants had an EPA % TFAs of at least 75% of the EPA % TFAs measured in the control (transformants with wild type YlLPCAT). Also, all of the mutant YlLPCAT transformants had a % Conv. that was at least 87.6% of the % Conv. measured in the control.

Fifty-six (56) YlLPCAT mutants (comprising one of the following mutations with respect to SEQ ID NO:40: L134A, L134C, L134G, C135D, C135I, M136G, M136P, M136S, M136V, K137N, K137G, K137H, K137Y, L138A, L138H, L138M, S139L, S139W, S140N, S140H, S140P, S140W, F141A, F141M, F141W, G142H, W143L, N144A, N144K, N144F, N144T, N144V, V145A, V145G, V145E, V145M, V145F, V145W, Y146G, Y146L, Y146M, D147N, D147Q, D147H, G148A, G148N, T382I, T382P, R383M, L388G, L388Y, T389A, T389C, T389S and F390C) were found to exhibit equivalent or improved EPA % TFAs and equivalent or improved % Conv. An additional 14 YlLPCAT mutants were determined to have equivalent or improved EPA % TFAs when compared to the control (but did not have an equivalent or improved % Conv.), including mutants V133C, M136N, L138G, L138I, L138N, S139G, S139N, W143H, G148V, L388H, L388T, F390G, F390N and F390T. An additional 12 YlLPCAT mutants were determined to have equivalent or improved % Conv. when compared to the control (but did not have an equivalent or improved EPA % TFAs), including mutants C135F, M136T, S140Y, S140I, F141V, G142I, G142V, D147E, F378Y, T382Y, R383A and F390S.

A total of 26 YlLPCAT mutants, each comprising a single mutation within either Motif I or Motif II and having equivalent or improved EPA % TFAs and/or equivalent or improved % Conv. were selected for further evaluation (below, Example 9): L134A (100.4%, 100.6%), L134G (101.3%, 100.7%), M136S (104.0%, 104.0%), M136V (102.2%, 103.3%), K137H (107.3%, 104.4%), K137N (101.8%, 102.0%), S140H (107.3%, 104.3%), S140W (103.2%, 103.8%), F141M (105.4%, 106.7%), F141W (101.2%, 101.6%), N144A (105.3%, 103.4%), N144T (101.8%, 101.6%), V145M (102.0%, 104.0%), V145W (100.4%, 100.5%), D147H (105.3%, 102.3%), D147Q (103.6%, 101.2%), G148A (101.3%, 101.8%), G148N (102.2%, 101.8%), T382I (102.9%, 102.5%), T382P (100.2%, 100.2%), R383M (103.6%, 104.0%), L388G (101.6%, 100.2%), L388Y (100.0%, 99.9%), T389A (102.2%, 101.2%), T389C (102.1%, 101.5%), T389S (101.9%, 101.7%), where the first and second percentages in each parenthetical set correspond to the percentage ratio of EPA % TFAs and % Conv., respectively, in the mutant YlLPCAT transformants relative to the EPA TFAs and % Conv. in the wild type YlLPCAT control transformants. An additional 8 YlLPCAT mutants, each comprising a single mutation within either Motif I or Motif II, also were selected for further evaluation (below, Example 9): F378Y (99.6%, 101.1%), T382Y (99.8%, 100.8%), P384A (98.7%, 99.0%), P384G (99.2%, 98.6%), L388T (100.5%, 98.3%), F390G (102.4%, 99.8%), F390S (99.4%, 100.5%) and F390T (101.6%, 99.3%), where the parenthetical sets are as above.

Example 9

Identifying Double Amino Acid Substitutions in YlLPCAT Having Improved LPCAT Activity The present example describes the synthesis of double YlLPCAT mutants, wherein the double mutants comprise both a single mutation within Motif I and a single mutation within Motif II. These double mutants were transformed into *Y. lipolytica* strain Y8406U2, followed by analysis of the lipid profiles of the transformants. As in Example 8, improved LPCAT activity was indirectly evaluated based on EPA % TFAs and % Cony.

Generation of Double YlLPCAT Mutants

Preferred single mutations within Motif I (L134A, L134G, M136S, M136V, K137H, K137N, S140H, S140W, F141M, F141W, N144A, N144T, V145W, V145M, D147H, D147Q, G148A and G148N) were combined with preferred single mutations within Motif II (F378Y, T382I, T382P, T382Y, R383M, P384A, P384G, L388G, L388T, L388Y, T389A, T389C, T389S, F390G, F390S, F390T) to generate various combinations of double-mutant YlLPCAT sequences. Thus, for example, a YlLPCAT mutant comprising an S140W mutation within Motif I and a T382I mutation within Motif II is referred to herein as a YlLPCAT mutant S140W_T382I. These double mutants were individually synthesized and cloned into NcoI-NotI cut pY306-N vector by GenScript Corporation (Piscataway, N.J.); SEQ ID NO:74 represents the mutant YlLPCAT proteins encoded by the cloned sequences.

Transformation of *Y. lipolytica* Strain Y8406U2 and Analysis of Lipid Profiles within pY306-N Transformants The plasmids were transformed into *Y. lipolytica* strain Y8406U2 and transformants were subsequently grown and subjected to lipid analysis, as described in Example 8. Tables 23 (Batch 6), 24 (Batch 7), 25 (Batch 8) and 26 (Batch 10) show the fatty acid profiles and delta-9 elongase conversion efficiencies of individual transformants of Y8406U2. These measurements were also made for control transformants comprising pY306-N (wild type YlLPCAT protein expression [WT]). The Tables are formatted as described in Example 8.

Comparison of each mutant's performance relative to the wild type YlLPCAT control should only be made within the particular batch in which each mutant was analyzed (i.e., comparisons should not be made between Batch #6 and Batch #7, for example). Mutants shown in bold-face font and followed by a "+" were selected for further studies including flask assays, as discussed below.

TABLE 23

Lipid Composition and Delta-9 Elongase Conversion Efficiency in Batch #6 Transformants Comprising a Vector Encoding YlLPCAT Having Double Amino Acid Substitutions

| Mutant | # | % TFAs | | | | | | | | | | | | EPA | % |
| --- | --- | --- | --- | --- | --- | --- | --- | --- | --- | --- | --- | --- | --- | --- | --- |
| | | 16:0 | 16:1 | 18:0 | 18:1 | LA | ALA | EDA | DGLA | ARA | ETrA | ETA | EPA | SD | Conv. |
| WT | 6 | 2.7 | 0.7 | 2.3 | 5.6 | 14.4 | 0.9 | 3.0 | 3.1 | 0.7 | 1.5 | 2.7 | 52.9 | 0.2 | 80.6 |
| S140W_T382I | 3 | 2.9 | 0.8 | 2.2 | 5.8 | 13.0 | 0.8 | 2.9 | 3.2 | 0.7 | 1.5 | 2.7 | 53.7 | 1.2 | 82.4 |
| S140W_T382P+ | 3 | 2.9 | 0.8 | 2.2 | 5.7 | 12.6 | 0.8 | 2.9 | 3.3 | 0.7 | 1.5 | 2.8 | 54.3 | 0.6 | 83.0 |
| S140W_T382Y | 3 | 2.7 | 0.7 | 2.2 | 5.6 | 13.6 | 0.9 | 2.8 | 3.2 | 0.7 | 1.5 | 2.8 | 53.8 | 0.6 | 81.8 |
| S140W_R383M | 3 | 2.9 | 0.7 | 2.3 | 5.8 | 12.6 | 0.8 | 2.9 | 3.3 | 0.8 | 1.5 | 2.6 | 54.8 | 0.6 | 83.1 |
| S140W_P384A | 3 | 2.8 | 0.7 | 2.3 | 5.7 | 13.9 | 0.9 | 2.9 | 3.1 | 0.7 | 1.5 | 2.7 | 53.1 | 1.3 | 81.2 |
| S140W_L388Y | 3 | 2.5 | 0.9 | 2.1 | 6.5 | 12.7 | 0.8 | 3.0 | 3.2 | 0.6 | 1.6 | 3.2 | 52.9 | 1.9 | 82.7 |

TABLE 23-continued

Lipid Composition and Delta-9 Elongase Conversion Efficiency in Batch #6 Transformants Comprising a Vector Encoding YlLPCAT Having Double Amino Acid Substitutions

| Mutant | # | 16:0 | 16:1 | 18:0 | 18:1 | LA | ALA | EDA | DGLA | ARA | ETrA | ETA | EPA | EPA SD | % Conv. |
|---|---|---|---|---|---|---|---|---|---|---|---|---|---|---|---|
| S140W_T389A+ | 3 | 2.4 | 0.7 | 2.2 | 6.5 | 11.6 | 0.7 | 2.5 | 3.1 | 0.7 | 1.5 | 2.6 | 55.8 | 0.4 | 84.3 |
| S140W_T389C | 3 | 2.7 | 0.7 | 2.3 | 6.0 | 12.6 | 0.8 | 2.8 | 3.4 | 0.8 | 1.5 | 2.7 | 54.1 | 0.4 | 83.0 |
| S140W_T389S | 3 | 2.6 | 0.6 | 2.5 | 6.3 | 14.6 | 1.3 | 2.7 | 2.7 | 0.7 | 1.5 | 2.2 | 53.3 | 4.1 | 79.9 |
| M136V_F378Y+ | 3 | 2.5 | 0.7 | 2.2 | 4.0 | 14.7 | 1.3 | 2.8 | 2.9 | 0.7 | 1.5 | 2.6 | 52.8 | 4.3 | 79.8 |
| M136V_T382I | 3 | 2.5 | 0.7 | 2.3 | 6.1 | 14.5 | 1.2 | 2.9 | 2.9 | 0.7 | 1.6 | 2.8 | 52.1 | 4.5 | 80.0 |
| M136V_T382P | 3 | 2.7 | 0.8 | 2.2 | 5.6 | 12.8 | 0.8 | 2.9 | 3.3 | 0.8 | 1.6 | 2.8 | 54.3 | 0.4 | 82.8 |
| M136V_T382Y | 3 | 2.6 | 0.8 | 2.2 | 5.5 | 13.1 | 0.8 | 2.8 | 3.3 | 0.7 | 1.5 | 3.0 | 54.3 | 0.3 | 82.5 |
| M136V_R383M | 3 | 2.6 | 0.8 | 2.1 | 5.9 | 13.8 | 1.0 | 2.8 | 3.2 | 0.7 | 1.6 | 3.1 | 52.3 | 2.3 | 81.2 |
| M136V_P384A | 3 | 2.8 | 0.8 | 2.2 | 5.7 | 13.3 | 0.8 | 3.1 | 3.3 | 0.7 | 1.4 | 2.8 | 53.2 | 1.1 | 82.0 |
| M136V_L388Y | 3 | 2.7 | 0.8 | 2.3 | 5.5 | 14.0 | 0.9 | 3.0 | 3.3 | 0.7 | 1.6 | 2.9 | 53.0 | 1.5 | 81.3 |
| M136V_T389A+ | 3 | 2.7 | 0.7 | 2.4 | 6.1 | 11.8 | 0.8 | 2.6 | 3.0 | 0.7 | 1.4 | 2.3 | 56.2 | 0.4 | 84.0 |
| M136V_T389S+ | 3 | 2.7 | 0.7 | 2.4 | 6.1 | 11.7 | 0.8 | 2.6 | 3.0 | 0.7 | 1.4 | 2.3 | 56.5 | 0.8 | 84.2 |
| K137N_F378Y | 3 | 2.8 | 0.8 | 2.2 | 5.5 | 13.6 | 0.9 | 2.9 | 3.3 | 0.7 | 1.5 | 2.8 | 53.4 | 1.1 | 81.7 |
| K137N_T382I | 3 | 2.4 | 0.8 | 2.2 | 6.0 | 15.0 | 1.3 | 2.8 | 3.0 | 0.6 | 1.6 | 2.9 | 51.6 | 4.7 | 79.3 |
| K137N_T382P | 3 | 2.4 | 0.9 | 2.0 | 3.6 | 13.1 | 0.8 | 2.8 | 3.4 | 0.7 | 1.5 | 3.4 | 53.5 | 1.7 | 82.5 |
| K137N_T382Y | 3 | 2.3 | 0.7 | 2.2 | 2.2 | 15.6 | 1.3 | 2.7 | 2.9 | 0.6 | 1.5 | 2.8 | 51.5 | 2.6 | 78.6 |
| K137N_L388Y | 3 | 2.2 | 0.8 | 2.1 | 3.7 | 14.9 | 1.1 | 2.9 | 3.0 | 0.6 | 1.6 | 3.1 | 51.4 | 3.0 | 79.6 |
| K137N_T389C+ | 3 | 2.6 | 0.8 | 2.1 | 5.4 | 12.5 | 0.8 | 2.7 | 3.5 | 0.8 | 1.5 | 2.8 | 55.1 | 0.9 | 83.4 |
| K137N_T389S+ | 3 | 2.5 | 0.7 | 2.3 | 6.0 | 11.8 | 0.7 | 2.6 | 3.2 | 0.7 | 1.5 | 2.5 | 56.0 | 0.2 | 84.2 |
| N144T_F378Y | 3 | 2.8 | 0.8 | 2.3 | 5.5 | 12.8 | 0.8 | 2.9 | 3.3 | 0.8 | 1.5 | 2.6 | 54.4 | 0.3 | 82.8 |
| N144T_T382I | 3 | 2.4 | 0.8 | 2.1 | 4.1 | 13.7 | 1.0 | 2.9 | 3.0 | 0.7 | 1.7 | 3.2 | 52.4 | 4.3 | 81.3 |
| N144T_T382Y | 3 | 2.5 | 0.8 | 2.3 | 3.7 | 13.8 | 0.9 | 2.9 | 3.2 | 0.7 | 1.5 | 2.8 | 53.7 | 0.2 | 81.6 |
| N144T_R383M | 3 | 2.5 | 0.8 | 2.1 | 5.2 | 12.7 | 0.8 | 2.7 | 3.3 | 0.7 | 1.5 | 2.8 | 54.2 | 0.1 | 82.9 |
| N144T_T389A | 2 | 2.4 | 0.7 | 2.4 | 5.8 | 12.5 | 0.8 | 2.7 | 3.3 | 0.7 | 1.6 | 2.7 | 54.5 |  | 83.2 |
| N144T_T389C | 2 | 2.2 | 0.8 | 1.7 | 4.8 | 11.9 | 0.8 | 2.3 | 3.1 | 0.7 | 1.6 | 2.8 | 56.1 |  | 84.0 |
| N144T_T389S | 3 | 2.5 | 0.6 | 2.3 | 5.9 | 12.0 | 0.7 | 2.7 | 3.2 | 0.7 | 1.7 | 2.5 | 54.7 | 0.7 | 83.7 |
| V145W_F378Y | 3 | 2.5 | 0.8 | 2.2 | 5.6 | 13.5 | 0.9 | 2.9 | 3.3 | 0.7 | 1.5 | 2.9 | 52.6 | 1.4 | 81.7 |
| V145W_T382P | 3 | 2.5 | 0.8 | 2.2 | 2.2 | 14.4 | 0.9 | 3.2 | 3.2 | 0.7 | 1.6 | 2.8 | 52.5 | 1.0 | 80.6 |
| V145W_L388Y | 2 | 2.7 | 0.8 | 2.3 | 3.3 | 16.1 | 1.3 | 3.0 | 2.7 | 0.6 | 1.6 | 2.6 | 49.6 |  | 77.5 |
| V145W_T389A | 3 | 2.5 | 0.7 | 2.4 | 6.1 | 13.5 | 1.0 | 2.9 | 3.1 | 0.7 | 1.5 | 2.7 | 53.4 | 1.3 | 81.6 |
| V145W_T389C | 3 | 2.6 | 0.7 | 2.4 | 3.9 | 15.3 | 1.3 | 2.9 | 2.9 | 0.7 | 1.5 | 2.6 | 51.7 | 3.5 | 79.0 |
| V145W_T389S | 3 | 2.7 | 0.6 | 2.5 | 4.2 | 14.1 | 1.0 | 2.8 | 3.1 | 0.7 | 1.5 | 2.5 | 53.2 | 0.7 | 80.9 |
| Mutant AVG |  | 2.6 | 0.7 | 2.2 | 5.2 | 13.4 | 0.9 | 2.8 | 3.2 | 0.7 | 1.5 | 2.8 | 53.6 | 1.6 | 81.8 |
| Mutant SD |  | 0.2 | 0.1 | 0.1 | 1.1 | 1.1 | 0.2 | 0.2 | 0.2 | 0.0 | 0.1 | 0.2 | 1.5 | 1.4 | 1.7 |

TABLE 24

Lipid Composition and Delta-9 Elongase Conversion Efficiency in Batch #7 Transformants Comprising a Vector Encoding YlLPCAT Having Double Amino Acid Substitutions

| Mutant | # | 16:0 | 16:1 | 18:0 | 18:1 | LA | ALA | EDA | DGLA | ARA | ETrA | ETA | EPA | EPA SD | % Conv. |
|---|---|---|---|---|---|---|---|---|---|---|---|---|---|---|---|
| WT | 12 | 3.2 | 0.7 | 2.6 | 4.2 | 14.2 | 0.9 | 2.3 | 3.0 | 0.7 | 1.6 | 2.7 | 54.1 | 0.7 | 81.0 |
| M136S_F378Y | 3 | 3.4 | 0.7 | 2.6 | 4.7 | 12.0 | 0.8 | 2.1 | 3.0 | 0.7 | 1.6 | 2.5 | 56.4 | 1.3 | 84.0 |
| M136S_T382I | 3 | 3.4 | 0.8 | 2.6 | 5.2 | 11.2 | 0.8 | 2.2 | 2.9 | 0.6 | 1.6 | 2.6 | 56.3 | 1.2 | 85.0 |
| M136S_T382P | 3 | 2.9 | 0.8 | 2.3 | 4.5 | 11.5 | 0.7 | 2.1 | 3.3 | 0.6 | 1.5 | 3.1 | 56.2 | 1.6 | 85.0 |
| M136S_T382Y | 3 | 3.3 | 0.7 | 2.5 | 4.3 | 12.1 | 0.8 | 2.1 | 3.2 | 0.6 | 1.6 | 2.8 | 55.8 | 0.5 | 84.0 |
| M136S_R383M | 3 | 3.4 | 0.7 | 2.6 | 4.8 | 11.9 | 0.8 | 2.2 | 3.1 | 0.6 | 1.6 | 2.5 | 56.1 | 0.2 | 84.0 |
| M136S_P384A | 3 | 3.5 | 0.7 | 2.6 | 4.6 | 12.2 | 0.8 | 2.2 | 3.1 | 0.7 | 1.6 | 2.6 | 56.1 | 0.8 | 84.0 |
| M136S_L388Y | 3 | 3.3 | 0.7 | 2.5 | 4.3 | 12.2 | 0.8 | 2.3 | 3.2 | 0.6 | 1.6 | 2.6 | 56.1 | 1.5 | 84.0 |
| M136S_T389A+ | 3 | 3.2 | 0.6 | 2.6 | 4.6 | 11.0 | 0.8 | 2.0 | 2.7 | 0.6 | 1.6 | 2.1 | 57.9 | 0.6 | 85.0 |
| M136S_T389C+ | 3 | 3.3 | 0.6 | 2.7 | 4.8 | 11.2 | 0.8 | 2.1 | 3.0 | 0.7 | 1.6 | 2.3 | 57.3 | 0.2 | 85.0 |
| M136S_T389S+ | 3 | 2.8 | 0.6 | 2.7 | 5.3 | 11.2 | 0.7 | 2.0 | 2.9 | 0.6 | 1.6 | 2.2 | 57.7 | 0.8 | 85.0 |
| F141M_F378Y | 3 | 3.0 | 0.7 | 2.5 | 3.9 | 13.5 | 0.9 | 2.4 | 3.1 | 0.6 | 1.6 | 2.6 | 55.3 | 0.4 | 82.0 |
| F141M_T382I | 3 | 3.1 | 0.7 | 2.7 | 4.4 | 16.2 | 2.2 | 2.2 | 2.3 | 0.5 | 1.7 | 2.8 | 51.0 | 4.6 | 77.0 |
| F141M_T382P | 3 | 2.9 | 0.7 | 2.6 | 4.2 | 14.5 | 1.1 | 2.3 | 3.0 | 0.6 | 1.6 | 2.6 | 54.0 | 0.7 | 81.0 |
| F141M_T382Y | 3 | 3.0 | 0.7 | 2.5 | 4.1 | 14.1 | 0.9 | 2.3 | 3.0 | 0.7 | 1.6 | 2.7 | 54.2 | 0.3 | 81.0 |
| F141M_R383M | 3 | 3.1 | 0.7 | 2.5 | 3.9 | 13.4 | 0.9 | 2.3 | 3.1 | 0.7 | 1.5 | 2.6 | 55.3 | 0.1 | 82.0 |
| F141M_P384A | 3 | 3.1 | 0.7 | 2.5 | 3.8 | 14.3 | 0.9 | 2.3 | 3.2 | 0.6 | 1.6 | 2.6 | 54.5 | 1.0 | 81.0 |
| F141M_L388Y | 3 | 3.0 | 0.6 | 2.5 | 4.2 | 17.3 | 1.6 | 2.4 | 2.5 | 0.6 | 1.6 | 2.5 | 50.8 | 3.7 | 76.0 |
| F141M_T389A | 3 | 3.2 | 0.6 | 2.8 | 4.3 | 14.5 | 1.3 | 2.3 | 2.7 | 0.6 | 1.6 | 2.2 | 54.1 | 2.1 | 80.0 |
| F141M_T389C | 3 | 2.9 | 0.7 | 2.5 | 4.0 | 13.3 | 0.9 | 2.3 | 3.1 | 0.7 | 1.5 | 2.7 | 55.3 | 0.1 | 82.0 |
| F141M_T389S | 3 | 2.8 | 0.6 | 2.7 | 4.8 | 15.8 | 1.4 | 2.5 | 2.8 | 0.6 | 1.6 | 2.4 | 52.1 | 4.4 | 78.0 |
| F141W_F378Y | 3 | 3.2 | 0.7 | 2.6 | 4.7 | 12.8 | 0.9 | 2.3 | 3.1 | 0.6 | 1.6 | 2.5 | 55.5 | 1.2 | 83.0 |
| F141W_T382I+ | 3 | 3.0 | 0.7 | 2.5 | 4.6 | 11.7 | 0.8 | 2.1 | 3.2 | 0.7 | 1.5 | 2.5 | 57.1 | 0.5 | 84.0 |
| F141W_T382P | 3 | 3.3 | 0.8 | 2.6 | 4.2 | 13.5 | 0.9 | 2.3 | 3.2 | 0.7 | 1.5 | 2.7 | 54.8 | 1.6 | 82.0 |
| F141W_T382Y | 3 | 2.9 | 0.7 | 2.5 | 4.1 | 12.7 | 0.8 | 2.3 | 3.3 | 0.6 | 1.5 | 2.7 | 56.0 | 0.5 | 83.0 |
| F141W_R383M | 3 | 3.5 | 0.7 | 2.5 | 4.0 | 12.3 | 0.9 | 2.3 | 3.1 | 0.6 | 1.6 | 2.5 | 56.1 | 0.2 | 83.0 |

TABLE 24-continued

Lipid Composition and Delta-9 Elongase Conversion Efficiency in Batch #7 Transformants Comprising a Vector Encoding YlLPCAT Having Double Amino Acid Substitutions

| Mutant | # | 16:0 | 16:1 | 18:0 | 18:1 | LA | ALA | EDA | DGLA | ARA | ETrA | ETA | EPA | EPA SD | % Conv. |
|---|---|---|---|---|---|---|---|---|---|---|---|---|---|---|---|
| F141W_P384A | 3 | 3.5 | 0.7 | 2.6 | 4.0 | 13.9 | 1.0 | 2.4 | 3.0 | 0.6 | 1.6 | 2.6 | 54.3 | 0.4 | 81.0 |
| F141W_L388Y | 3 | 3.2 | 0.7 | 2.7 | 4.3 | 14.2 | 1.0 | 2.4 | 3.0 | 0.6 | 1.5 | 2.6 | 53.9 | 0.8 | 81.0 |
| F141W_T389A | 3 | 3.3 | 0.6 | 2.8 | 4.6 | 12.3 | 0.9 | 2.1 | 2.9 | 0.6 | 1.6 | 2.2 | 56.3 | 0.4 | 83.0 |
| F141W_T389C | 3 | 3.3 | 0.7 | 2.8 | 4.4 | 12.5 | 1.0 | 2.4 | 3.0 | 0.6 | 1.4 | 2.4 | 55.7 | 0.8 | 83.0 |
| F141W_T389S | 3 | 3.1 | 0.6 | 2.7 | 4.4 | 12.5 | 0.9 | 2.2 | 3.0 | 0.6 | 1.5 | 2.4 | 56.0 | 1.2 | 83.0 |
| V145M_F378Y | 3 | 3.3 | 0.7 | 2.6 | 4.3 | 13.7 | 1.0 | 2.4 | 3.0 | 0.6 | 1.6 | 2.6 | 54.0 | 0.4 | 81.0 |
| V145M_T382I | 3 | 3.4 | 0.8 | 2.5 | 4.1 | 13.0 | 0.9 | 2.3 | 3.2 | 0.7 | 1.5 | 2.7 | 54.9 | 1.6 | 82.0 |
| V145M_T382P | 3 | 3.1 | 0.7 | 2.7 | 4.2 | 14.7 | 1.0 | 2.4 | 3.0 | 0.7 | 1.5 | 2.6 | 53.5 | 1.0 | 80.0 |
| V145M_T382Y | 3 | 3.6 | 0.7 | 2.7 | 4.3 | 14.4 | 1.0 | 2.3 | 3.0 | 0.6 | 1.6 | 2.6 | 53.6 | 2.7 | 81.0 |
| V145M_R383M | 3 | 3.4 | 0.7 | 2.5 | 4.0 | 13.3 | 0.9 | 2.3 | 2.9 | 0.6 | 1.6 | 2.4 | 54.9 | 0.6 | 82.0 |
| V145M_P384A | 3 | 3.2 | 0.8 | 2.4 | 3.9 | 15.4 | 1.0 | 2.4 | 2.8 | 0.6 | 1.7 | 2.8 | 51.4 | 3.6 | 79.0 |
| V145M_L388Y | 3 | 3.3 | 0.7 | 2.7 | 4.3 | 15.4 | 1.1 | 2.4 | 2.7 | 0.6 | 1.5 | 2.5 | 52.2 | 0.6 | 79.0 |
| V145M_T389A | 3 | 3.6 | 0.6 | 2.8 | 4.5 | 13.6 | 1.0 | 2.3 | 2.7 | 0.6 | 1.6 | 2.3 | 54.1 | 0.0 | 81.0 |
| V145M_T389C | 3 | 3.0 | 0.7 | 2.6 | 4.1 | 13.3 | 0.9 | 2.4 | 3.1 | 0.6 | 1.5 | 2.5 | 55.4 | 0.2 | 82.0 |
| V145M_T389S | 3 | 4.1 | 1.0 | 2.2 | 3.9 | 14.5 | 1.3 | 2.1 | 2.4 | 0.6 | 1.7 | 2.1 | 51.5 | 5.3 | 79.0 |
| G148A_F378Y | 3 | 3.3 | 0.7 | 2.6 | 4.3 | 12.5 | 0.9 | 2.3 | 3.1 | 0.6 | 1.5 | 2.5 | 55.9 | 0.3 | 83.0 |
| G148A_T382I | 3 | 3.3 | 0.7 | 2.6 | 4.7 | 11.8 | 0.8 | 2.3 | 3.1 | 0.6 | 1.6 | 2.5 | 56.4 | 0.5 | 84.0 |
| G148A_T382P | 3 | 2.9 | 0.6 | 2.6 | 4.4 | 15.1 | 1.2 | 2.4 | 2.9 | 0.6 | 1.6 | 2.7 | 53.0 | 3.7 | 79.0 |
| G148A_T382Y | 3 | 2.9 | 0.7 | 2.5 | 3.9 | 12.9 | 0.8 | 2.0 | 3.0 | 0.7 | 1.5 | 2.6 | 56.1 | 1.2 | 83.0 |
| G148A_R383M | 3 | 3.4 | 0.7 | 2.6 | 4.2 | 12.5 | 0.8 | 2.3 | 3.1 | 0.6 | 1.6 | 2.6 | 55.5 | 0.9 | 83.0 |
| G148A_P384A | 3 | 2.9 | 0.8 | 2.4 | 4.3 | 13.7 | 0.8 | 2.3 | 3.2 | 0.6 | 1.7 | 3.1 | 53.7 | 0.5 | 82.0 |
| G148A_L388Y | 3 | 2.7 | 0.8 | 2.3 | 4.0 | 13.8 | 0.9 | 2.4 | 3.2 | 0.6 | 1.6 | 3.0 | 54.2 | 0.5 | 82.0 |
| G148A_T389A | 3 | 3.0 | 0.6 | 2.7 | 4.8 | 12.5 | 0.8 | 2.2 | 3.0 | 0.6 | 1.5 | 2.4 | 56.1 | 0.2 | 83.0 |
| G148A_T389C | 3 | 3.5 | 0.7 | 2.6 | 4.2 | 12.6 | 0.9 | 2.3 | 3.0 | 0.6 | 1.5 | 2.4 | 55.8 | 0.1 | 83.0 |
| G148A_T389S | 3 | 3.3 | 0.6 | 2.8 | 4.7 | 14.8 | 1.3 | 2.4 | 2.7 | 0.6 | 1.6 | 2.3 | 52.9 | 5.0 | 80.0 |
| Mutant AVG | | 3.1 | 0.7 | 2.6 | 4.4 | 13.2 | 1.0 | 2.3 | 3.0 | 0.6 | 1.6 | 2.6 | 54.9 | 1.4 | 80.0 |
| Mutant SD | | 0.3 | 0.1 | 0.1 | 0.3 | 1.3 | 0.2 | 0.1 | 0.2 | 0.0 | 0.1 | 0.2 | 1.6 | | 2.0 |

TABLE 25

Lipid Composition and Delta-9 Elongase Conversion Efficiency in Batch #8 Transformants Comprising a Vector Encoding YlLPCAT Having Double Amino Acid Substitutions

| Mutant | # | 16:0 | 16:1 | 18:0 | 18:1 | LA | ALA | EDA | DGLA | ARA | ETrA | ETA | EPA | EPA SD | % Conv. |
|---|---|---|---|---|---|---|---|---|---|---|---|---|---|---|---|
| WT | 3 | 2.6 | 0.7 | 2.6 | 4.3 | 14.4 | 1.0 | 2.6 | 3.2 | 0.6 | 1.7 | 2.8 | 53.8 | 0.8 | 81.0 |
| M136V_T389C+ | 3 | 2.8 | 0.6 | 2.6 | 4.8 | 12.1 | 0.9 | 2.3 | 3.3 | 0.6 | 1.5 | 2.6 | 56.6 | 0.5 | 84.0 |
| K137N_R383M | 3 | 2.8 | 0.7 | 2.5 | 4.4 | 12.9 | 0.9 | 2.4 | 3.3 | 0.6 | 1.5 | 2.8 | 55.8 | 0.4 | 83.0 |
| K137N_P384A | 3 | 2.6 | 0.6 | 2.7 | 4.9 | 17.7 | 1.9 | 2.8 | 2.6 | 0.6 | 1.6 | 2.5 | 49.8 | 4.2 | 75.0 |
| K137N_T389A+ | 3 | 2.6 | 0.5 | 2.7 | 4.9 | 12.4 | 0.9 | 2.2 | 3.1 | 0.7 | 1.6 | 2.3 | 56.8 | 0.6 | 83.0 |
| N144T_T382P | 3 | 2.7 | 0.6 | 2.6 | 4.3 | 14.1 | 1.0 | 2.6 | 3.3 | 0.7 | 1.6 | 2.7 | 54.4 | 0.6 | 81.0 |
| N144T_P384A | 3 | 2.6 | 0.6 | 2.5 | 4.2 | 14.4 | 1.0 | 2.5 | 3.2 | 0.7 | 1.6 | 2.7 | 54.3 | 0.6 | 81.0 |
| N144T_L388Y | 3 | 2.5 | 0.7 | 2.4 | 3.9 | 14.0 | 0.9 | 2.4 | 3.4 | 0.7 | 1.5 | 3.0 | 54.7 | 0.7 | 82.0 |
| V145W_T382I | 3 | 2.9 | 0.6 | 2.6 | 4.7 | 13.0 | 0.9 | 2.5 | 3.3 | 0.7 | 1.5 | 2.6 | 55.5 | 0.3 | 83.0 |
| V145W_T382Y | 3 | 2.6 | 0.6 | 2.6 | 4.4 | 16.5 | 1.6 | 2.5 | 2.8 | 0.6 | 1.5 | 2.6 | 52.1 | 3.3 | 77.0 |
| V145W_R383M | 3 | 2.8 | 0.6 | 2.6 | 4.7 | 16.1 | 1.5 | 2.6 | 2.8 | 0.6 | 1.6 | 2.4 | 52.3 | 3.9 | 78.0 |
| V145W_P384A | 3 | 2.6 | 0.6 | 2.6 | 4.2 | 15.6 | 1.1 | 2.7 | 3.1 | 0.7 | 1.6 | 2.7 | 52.7 | 0.3 | 79.0 |
| Mutant AVG | | 2.7 | 0.6 | 2.6 | 4.5 | 14.4 | 1.1 | 2.5 | 3.1 | 0.7 | 1.6 | 2.6 | 54.1 | 1.3 | 79.0 |
| Mutant SD | | 0.1 | 0.1 | 0.1 | 0.3 | 1.7 | 0.3 | 0.2 | 0.3 | 0.1 | 0.1 | 0.2 | 2.1 | | 2.8 |

TABLE 26

Lipid Composition and Delta-9 Elongase Conversion Efficiency in Batch #10 Transformants Comprising a Vector Encoding YlLPCAT Having Double Amino Acid Substitutions

| Mutant | # | 16:0 | 16:1 | 18:0 | 18:1 | LA | ALA | EDA | DGLA | ARA | ETrA | ETA | EPA | EPA SD | % Conv. |
|---|---|---|---|---|---|---|---|---|---|---|---|---|---|---|---|
| WT | | 2.9 | 0.7 | 2.7 | 4.2 | 14.6 | 1.1 | 2.6 | 3.0 | 0.6 | 1.5 | 2.6 | 53.1 | 1.7 | 80.1 |
| L134A_T382I+ | | 3.0 | 0.7 | 2.6 | 4.6 | 12.5 | 0.9 | 2.2 | 3.1 | 0.6 | 1.5 | 2.5 | 55.9 | 0.6 | 83.0 |
| L134A_P384G | | 2.7 | 0.6 | 2.8 | 4.2 | 15.9 | 1.2 | 2.4 | 2.8 | 0.6 | 1.5 | 2.4 | 52.7 | 0.2 | 78.5 |
| L134A_L388G | | 2.8 | 0.6 | 2.7 | 4.4 | 14.6 | 1.1 | 2.4 | 2.9 | 0.6 | 1.5 | 2.5 | 53.9 | 0.3 | 80.3 |
| L134A_L388T | | 2.7 | 0.6 | 2.8 | 4.5 | 17.3 | 1.7 | 2.4 | 2.5 | 0.5 | 1.6 | 2.3 | 51.0 | 2.7 | 76.0 |
| L134A_F390G | | 2.7 | 0.4 | 3.4 | 5.4 | 14.7 | 1.2 | 2.1 | 2.4 | 0.5 | 1.5 | 2.0 | 53.6 | 0.3 | 79.6 |
| L134A_F390S | | 2.7 | 0.5 | 3.2 | 5.6 | 15.6 | 1.7 | 2.2 | 2.3 | 0.5 | 1.5 | 1.9 | 52.5 | 4.4 | 77.9 |

TABLE 26-continued

Lipid Composition and Delta-9 Elongase Conversion Efficiency in Batch #10 Transformants Comprising a Vector Encoding YlLPCAT Having Double Amino Acid Substitutions

| Mutant | # | 16:0 | 16:1 | 18:0 | 18:1 | LA | ALA | EDA | DGLA | ARA | ETrA | ETA | EPA | EPA SD | % Conv. |
|---|---|---|---|---|---|---|---|---|---|---|---|---|---|---|---|
| L134A_F390T | | 2.7 | 0.5 | 3.0 | 4.7 | 14.4 | 1.1 | 2.3 | 2.8 | 0.5 | 1.5 | 2.4 | 54.2 | 0.5 | 80.5 |
| L134G_T382I | | 2.6 | 0.6 | 2.8 | 4.7 | 18.2 | 2.0 | 2.5 | 2.5 | 0.5 | 1.5 | 2.4 | 49.6 | 3.1 | 74.5 |
| L134G_P384G | | 2.6 | 0.6 | 2.7 | 4.2 | 16.3 | 1.3 | 2.4 | 2.7 | 0.6 | 1.5 | 2.5 | 52.4 | 0.7 | 78.0 |
| L134G_L388G | | 2.7 | 0.6 | 2.8 | 4.1 | 15.0 | 1.1 | 2.5 | 2.9 | 0.6 | 1.6 | 2.6 | 53.4 | 0.2 | 79.8 |
| L134G_L388T | | 2.7 | 0.7 | 2.6 | 4.1 | 15.5 | 1.2 | 2.5 | 2.8 | 0.6 | 1.6 | 2.6 | 52.4 | 0.5 | 78.9 |
| L134G_F390G | | 2.7 | 0.4 | 3.2 | 5.3 | 15.1 | 1.3 | 2.1 | 2.4 | 0.5 | 1.5 | 2.1 | 53.3 | 0.0 | 79.1 |
| L134G_F390S | | 2.8 | 0.5 | 3.1 | 5.4 | 15.7 | 1.7 | 2.4 | 2.3 | 0.5 | 1.6 | 2.2 | 52.0 | 3.6 | 77.8 |
| L134G_F390T | | 2.6 | 0.5 | 2.8 | 4.5 | 14.7 | 1.1 | 2.4 | 2.8 | 0.6 | 1.6 | 2.6 | 53.5 | 1.0 | 80.0 |
| K137N_P384G | | 2.9 | 0.6 | 2.7 | 4.1 | 14.4 | 1.0 | 2.4 | 3.0 | 0.6 | 1.5 | 2.6 | 54.2 | 0.3 | 80.7 |
| K137N_L388G | | 3.1 | 0.7 | 2.6 | 4.4 | 13.5 | 1.0 | 2.6 | 3.2 | 0.6 | 1.5 | 2.6 | 54.5 | 1.0 | 81.7 |
| K137N_L388T | | 3.1 | 0.6 | 2.7 | 4.2 | 13.9 | 1.0 | 2.3 | 3.0 | 0.6 | 1.5 | 2.5 | 54.8 | 0.4 | 81.3 |
| K137N_F390G+ | | 2.4 | 0.5 | 3.0 | 5.5 | 13.1 | 0.9 | 1.9 | 2.7 | 0.5 | 1.5 | 2.4 | 55.2 | 0.9 | 82.1 |
| K137N_F390S | | 2.8 | 0.5 | 3.2 | 5.5 | 13.9 | 1.1 | 2.1 | 2.6 | 0.5 | 1.5 | 2.1 | 54.5 | 1.2 | 80.9 |
| K137N_F390T | | 2.8 | 0.6 | 2.9 | 4.6 | 14.1 | 1.0 | 2.2 | 2.7 | 0.6 | 1.6 | 2.3 | 54.2 | 0.4 | 80.9 |
| K137H_T382I | | 3.1 | 0.6 | 2.8 | 4.7 | 14.8 | 1.5 | 2.2 | 2.7 | 0.5 | 1.5 | 2.3 | 53.7 | 4.7 | 79.4 |
| K137H_P384G | | 2.7 | 0.8 | 2.4 | 4.1 | 13.3 | 0.9 | 2.3 | 3.3 | 0.6 | 1.6 | 3.0 | 54.7 | 0.3 | 82.2 |
| K137H_L388G+ | | 3.2 | 0.7 | 2.5 | 4.3 | 12.5 | 0.9 | 2.2 | 3.1 | 0.6 | 1.5 | 2.5 | 56.2 | 0.6 | 83.1 |
| K137H_L388T+ | | 3.1 | 0.7 | 2.7 | 4.3 | 13.0 | 0.9 | 2.2 | 3.0 | 0.6 | 1.5 | 2.5 | 55.6 | 0.1 | 82.5 |
| K137H_F390G | | 2.8 | 0.5 | 3.3 | 5.7 | 14.6 | 1.2 | 2.0 | 2.5 | 0.5 | 1.5 | 2.1 | 53.6 | 1.2 | 79.7 |
| K137H_F390S | | 2.6 | 0.6 | 3.1 | 6.0 | 12.9 | 1.0 | 2.1 | 2.6 | 0.5 | 1.6 | 2.4 | 54.5 | 0.8 | 82.1 |
| K137H_F390T | | 2.8 | 0.5 | 2.9 | 4.9 | 14.0 | 1.0 | 2.2 | 2.8 | 0.5 | 1.5 | 2.5 | 54.4 | 0.6 | 81.0 |
| S140H_T382I+ | | 3.3 | 0.7 | 2.7 | 4.9 | 11.9 | 0.9 | 2.4 | 3.0 | 0.6 | 1.6 | 2.6 | 55.4 | 1.9 | 83.6 |
| S140H_P384G | | 3.0 | 0.7 | 2.7 | 3.8 | 14.1 | 1.0 | 2.2 | 3.0 | 0.6 | 1.6 | 2.7 | 54.5 | 0.7 | 81.1 |
| S140H_L388G+ | | 3.0 | 0.7 | 2.5 | 4.2 | 12.7 | 0.8 | 2.3 | 3.2 | 0.6 | 1.5 | 2.7 | 55.7 | 0.1 | 83.0 |
| S140H_L388T | | 3.2 | 0.7 | 2.5 | 4.1 | 13.2 | 0.9 | 2.4 | 3.0 | 0.6 | 1.7 | 2.6 | 54.7 | 0.4 | 82.1 |
| S140H_F390G | | 2.6 | 0.5 | 2.8 | 5.5 | 13.9 | 1.0 | 2.0 | 2.7 | 0.5 | 1.6 | 2.6 | 54.1 | 1.2 | 81.0 |
| S140H_F390S | | 2.8 | 0.5 | 3.1 | 5.2 | 14.1 | 1.1 | 2.2 | 2.6 | 0.5 | 1.5 | 2.2 | 54.1 | 0.4 | 80.6 |
| S140H_F390T | | 3.0 | 0.6 | 2.9 | 4.7 | 16.0 | 1.3 | 2.5 | 2.7 | 0.5 | 1.6 | 2.5 | 51.8 | 1.4 | 78.1 |
| N144A_T382I | | 3.1 | 0.6 | 2.7 | 4.8 | 14.5 | 1.5 | 2.2 | 2.7 | 0.5 | 1.6 | 2.4 | 53.8 | 5.3 | 79.8 |
| N144A_P384G | | 3.0 | 0.7 | 2.7 | 4.0 | 14.2 | 1.0 | 2.4 | 3.1 | 0.6 | 1.6 | 2.6 | 54.1 | 0.2 | 80.9 |
| N144A_L388G | | 3.4 | 0.8 | 2.7 | 4.2 | 13.2 | 1.0 | 2.2 | 3.1 | 0.6 | 1.6 | 2.5 | 54.7 | 0.2 | 82.1 |
| N144A_L388T | | 3.2 | 0.7 | 2.8 | 4.2 | 13.6 | 1.0 | 2.3 | 3.0 | 0.6 | 1.6 | 2.5 | 54.6 | 0.4 | 81.5 |
| N144A_F390G | | 2.8 | 0.5 | 3.4 | 5.9 | 13.5 | 1.1 | 1.9 | 2.4 | 0.5 | 1.5 | 1.9 | 54.6 | 0.4 | 81.2 |
| N144A_F390S+ | | 2.7 | 0.5 | 3.2 | 6.0 | 12.8 | 1.0 | 1.9 | 2.5 | 0.6 | 1.5 | 2.0 | 55.6 | 1.2 | 82.3 |
| N144A_F390T | | 2.8 | 0.6 | 2.9 | 4.7 | 13.9 | 1.0 | 2.2 | 2.8 | 0.6 | 1.5 | 2.5 | 54.5 | 1.1 | 81.1 |
| D147Q_T382I | | 3.2 | 0.7 | 2.6 | 4.4 | 12.7 | 0.9 | 2.2 | 3.1 | 0.6 | 1.6 | 2.5 | 55.6 | 0.4 | 82.7 |
| D147Q_P384G | | 2.9 | 0.6 | 2.7 | 4.1 | 16.4 | 1.3 | 2.5 | 2.7 | 0.6 | 1.7 | 2.5 | 52.0 | 0.2 | 77.8 |
| D147Q_L388G | | 3.1 | 0.7 | 2.6 | 4.0 | 15.0 | 1.1 | 2.5 | 2.9 | 0.6 | 1.7 | 2.5 | 53.4 | 0.4 | 79.8 |
| D147Q_L388T | | 2.7 | 0.7 | 2.6 | 4.0 | 15.1 | 1.1 | 2.3 | 2.9 | 0.6 | 1.6 | 2.7 | 53.1 | 0.1 | 79.7 |
| D147Q_F390G | | 2.8 | 0.5 | 3.1 | 5.2 | 16.1 | 1.5 | 2.3 | 2.4 | 0.5 | 1.7 | 2.2 | 51.7 | 1.6 | 77.7 |
| D147Q_F390S | | 2.7 | 0.5 | 3.1 | 5.1 | 14.0 | 1.1 | 2.2 | 2.5 | 0.5 | 1.5 | 2.1 | 54.7 | 0.7 | 80.9 |
| D147Q_F390T | | 2.8 | 0.5 | 2.9 | 4.5 | 15.5 | 1.2 | 2.4 | 2.7 | 0.5 | 1.6 | 2.4 | 52.8 | 0.5 | 79.0 |
| D147H_T382I+ | | 3.2 | 0.7 | 2.6 | 4.6 | 12.4 | 0.9 | 2.3 | 3.1 | 0.6 | 1.6 | 2.4 | 55.8 | 0.1 | 83.2 |
| D147H_P384G | | 2.7 | 0.7 | 2.5 | 3.9 | 15.0 | 1.0 | 2.4 | 3.1 | 0.6 | 1.8 | 2.8 | 52.9 | 0.5 | 79.9 |
| D147H_L388G | | 2.9 | 0.7 | 2.6 | 4.3 | 14.1 | 1.0 | 2.4 | 3.0 | 0.6 | 1.6 | 2.6 | 54.3 | 0.3 | 81.1 |
| D147H_L388T | | 2.8 | 0.6 | 2.6 | 4.2 | 14.4 | 1.0 | 2.4 | 3.0 | 0.6 | 1.6 | 2.6 | 54.0 | 0.2 | 80.7 |
| D147H_F390G | | 2.8 | 0.5 | 3.1 | 5.4 | 15.4 | 1.3 | 2.2 | 2.5 | 0.5 | 1.5 | 2.2 | 52.4 | 2.2 | 78.6 |
| D147H_F390S | | 2.8 | 0.5 | 3.1 | 5.6 | 13.7 | 1.1 | 2.1 | 2.6 | 0.5 | 1.5 | 2.1 | 54.5 | 0.5 | 81.1 |
| D147H_F390T | | 2.8 | 0.5 | 2.9 | 4.6 | 14.8 | 1.1 | 2.4 | 2.8 | 0.5 | 1.6 | 2.5 | 53.5 | 0.4 | 79.9 |
| G148A_P384G | | 2.7 | 0.8 | 2.5 | 4.1 | 14.6 | 0.9 | 2.4 | 3.3 | 0.6 | 1.7 | 3.1 | 53.1 | 0.4 | 80.6 |
| G148A_L388G | | 3.1 | 0.7 | 2.7 | 4.1 | 14.1 | 1.1 | 2.5 | 3.0 | 0.6 | 1.6 | 2.6 | 54.3 | 0.4 | 81.0 |
| G148A_L388T+ | | 3.2 | 0.7 | 2.9 | 4.7 | 16.7 | 1.9 | 2.8 | 2.4 | 0.5 | 1.7 | 2.5 | 50.2 | 3.4 | 76.3 |
| G148A_F390G | | 2.9 | 0.5 | 3.2 | 5.3 | 16.4 | 1.8 | 2.2 | 2.2 | 0.4 | 1.5 | 2.0 | 51.7 | 4.4 | 76.8 |
| G148A_F390S+ | | 2.6 | 0.5 | 3.3 | 5.8 | 12.3 | 1.0 | 2.1 | 2.6 | 0.5 | 1.5 | 2.0 | 56.1 | 0.3 | 82.9 |
| G148A_F390T | | 3.0 | 0.5 | 3.0 | 4.6 | 14.0 | 1.1 | 2.2 | 2.6 | 0.5 | 1.6 | 2.3 | 54.7 | 0.2 | 80.9 |
| G148N_T382I+ | | 3.6 | 0.7 | 2.7 | 4.3 | 10.6 | 0.7 | 2.2 | 3.2 | 0.6 | 1.4 | 2.5 | 58.5 | 3.2 | 85.8 |
| G148N_P384G | | 2.7 | 0.6 | 2.7 | 4.0 | 15.0 | 1.1 | 2.5 | 2.9 | 0.6 | 1.5 | 2.6 | 53.5 | 0.3 | 79.8 |
| G148N_L388G | | 2.9 | 0.7 | 2.6 | 4.5 | 15.0 | 1.1 | 2.7 | 3.2 | 0.6 | 1.6 | 2.9 | 52.2 | 3.3 | 79.7 |
| G148N_L388T | | 2.8 | 0.6 | 2.7 | 4.1 | 14.4 | 1.1 | 2.5 | 3.0 | 0.6 | 1.6 | 2.7 | 54.0 | 0.7 | 80.6 |
| G148N_F390G | | 2.5 | 0.4 | 3.2 | 5.7 | 13.6 | 1.1 | 2.0 | 2.5 | 0.5 | 1.4 | 2.0 | 55.3 | 0.3 | 81.3 |
| G148N_F390S+ | | 2.5 | 0.4 | 3.2 | 6.0 | 12.4 | 1.0 | 2.0 | 2.6 | 0.5 | 1.4 | 2.0 | 56.2 | 0.2 | 82.8 |
| G148N_F390T | | 2.7 | 0.5 | 3.0 | 4.8 | 16.2 | 1.7 | 2.4 | 2.6 | 0.5 | 1.5 | 2.5 | 52.0 | 3.8 | 77.4 |
| Mutant AVG | | 2.9 | 0.6 | 2.8 | 4.7 | 14.3 | 1.1 | 2.3 | 2.8 | 0.6 | 1.6 | 2.4 | 53.9 | 1.1 | 80.4 |

Based on the data set forth above, it is clear that most of the 167 YlLPCAT double mutants analyzed above functioned with approximately equal or improved activity when compared to the parent wild type enzyme (SEQ ID NO:40). This conclusion was made based on measuring LPCAT activity as a function of EPA % TFAs and/or % Conv.

More specifically, 106 YlLPCAT mutants comprising a single amino acid mutation within Motif I and a single amino acid mutation within Motif II were found to exhibit equivalent or improved EPA % TFAs and equivalent or improved % Conv. These mutants were L134A_T382I, L134A_L388G, L134A_F390T, M136S_F378Y, M136S_T382I, M136S_T382P, M136S_T382Y, M136S_R383M, M136S_P384A, M136S_L388Y, M136S_T389A, M136S_T389C, M136S_T389S, M136V_T382P, M136V_T382Y, M136V_P384A, M136V_L388Y, M136V_T389A, M136V_T389C, M136V_T389S, K137H_P384G, K137H_L388G, K137H_L388T, K137H_F390S, K137H_F390T, K137N_T382P, K137N_R383M, K137N_P384G, K137N_F378Y, K137N_L388G, K137N_L388T, K137N_T389A, K137N_T389C, K137N_T389S, K137N_F390G, K137N_F390S, K137N_F390T, S140H_T382I, S140H_P384G, S140H_L388G, S140H_L388T, S140H_F390G, S140H_F390S, S140W_T382I, S140W_T382P, S140W_T382Y, S140W_R383M, S140W_P384A, S140W_L388Y, S140W_T389A, S140W_T389C, F141M_F378Y, F141M_T382Y, F141M_R383M, F141M_P384A, F141M_T389C, F141W_F378Y, F141W_T382I, F141W_T382P, F141W_T382Y, F141W_R383M, F141W_P384A, F141W_T389A, F141W_T389C, F141W_T389S, N144A_P384G, N144A_L388G, N144A_L388T, N144A_F390G, N144A_F390S, N144A_F390T, N144T_F378Y, N144T_T382P, N144T_T382Y, N144T_R383M, N144T_P384A, N144T_L388Y, N144T_T389A, N144T_T389C, N144T_T389S, V145M_T382I, V145M_R383M, V145M_T389A, V145M_T382I, V145W_T382I, D147H_T382I, V145M_T389C, D147H_L388G, D147H_L388T, D147H_F390S, D147Q_T382I, D147Q_F390S, G148A_F378Y, G148A_T382I, G148A_T382Y, G148A_R383M, G148A_P384G, G148A_L388G, G148A_L388Y, G148A_T389A, G148A_T389C, G148A_F390S, G148A_F390T, G148N_T382I, G148N_L388T, G148N_F390G and G148N_F390S).

An additional 15 YILPCAT double mutants (of the 167 analyzed) had equivalent or improved EPA % TFAs when compared to the control, while an additional 6 YILPCAT double mutants (of the 167 analyzed) were determined to have equivalent or improved % Conv. when compared to the control.

Confirmation of Improved LPCAT Activity by Flask Assay

A total of 23 YILPCAT double mutants, each comprising a single amino acid mutation within Motif I and a single amino acid mutation within Motif II, and having equivalent or improved EPA % TFAs and/or equivalent or improved % Conv., were selected for further evaluation (these mutants are noted in bold and with a "+" in Tables 23-26). These mutants were: S140W_T382P, S140W_T389A, M136V_T389A, M136V_T389C, M136V_T389S, K137N_T389A, K137N_T389C, K137N_T389S, M136S_T389A, M136S_T389C, M136S_T389S, F141W_T382I, L134A_T382I, K137N_F390G, K137H_L388G, K137H_L388T, S140H_T382I, S140H_L388G, N144A_F390S, D147H_T382I, G148A_F390S, G148N_T382I and G148N_F390S. Additionally, mutants M136V_F378Y and G148A_L388T, each having slightly diminished EPA % TFAs and slightly diminished % Conv. in comparison to the control, were selected for further evaluation.

Transformants expressing these double mutant YILPCAT proteins were subjected to flask assays for a detailed analysis of the total lipid content and composition. Specifically, the double mutant strains were individually inoculated into 3 mL FM in 15-mL Falcon™ tubes and grown overnight at 30° C. and 250 rpm. The $OD_{600\,nm}$ was measured and an aliquot of the cells was added to a final $OD_{600\,nm}$ of 0.3 in 25 mL FM medium in a 125-mL flask. After 2 days in a Multitron shaking incubator at 250 rpm and at 30° C., 6 mL of the culture was harvested by centrifugation and resuspended in 25 mL HGM in the original 125-mL flask. After 5 days (120 hours) in a shaking incubator at 250 rpm and at 30° C., water was added to flasks to bring the total volume back to 25 mL (thereby accounting for evaporation). An aliquot was used for fatty acid analysis (above) and 10 mL of the culture was dried for dry cell weight determination (above).

The flask assay results are shown below in Tables 27 (Group I) and 28 (Group II). The Tables summarize the number of replicates analyzed for each particular transformant (#), the average total dry cell weight of the cells (DCW), the average total lipid content of the cells (TFAs % DCW), the average concentration of each fatty acid as a weight percent of TFAs ("% TFAs), the delta-9 elongase conversion efficiency (% Conv.) and the average EPA content as a percent of the dry cell weight (EPA % DCW).

TABLE 27

Total Lipid Content, Composition and Delta-9 Elongase Conversion Efficiency in Selected Transformants Comprising a Vector Encoding YILPCAT Having Double Amino Acid Substitutions, by Flask Assay (Group I)

| Mutant | # | DCW (g/L) | TFAs % DCW | % TFAs | | | | | | | | | | | | % Conv. | EPA % DCW |
|---|---|---|---|---|---|---|---|---|---|---|---|---|---|---|---|---|---|
| | | | | 16:0 | 16:1 | 18:0 | 18:1 | LA | ALA | EDA | DGLA | ARA | ETrA | ETA | EPA | | |
| WT | 2 | 3.7 | 26.0 | 2.7 | 0.7 | 2.6 | 4.8 | 13.7 | 1.1 | 2.5 | 3.5 | 1.0 | 0.7 | 2.9 | 53.9 | 81.3 | 14.0 |
| S140W_T382P | 2 | 3.9 | 28.6 | 2.7 | 0.7 | 2.5 | 5.2 | 11.8 | 0.9 | 2.6 | 4.0 | 1.1 | 0.9 | 3.3 | 54.2 | 83.8 | 15.5 |
| S140W_T389A | 2 | 4.0 | 28.2 | 2.7 | 0.6 | 2.8 | 6.1 | 11.7 | 0.9 | 2.4 | 3.4 | 0.9 | 0.6 | 2.5 | 55.5 | 83.7 | 15.7 |
| M136V_F378Y | 2 | 4.0 | 27.7 | 2.9 | 0.7 | 2.5 | 5.4 | 12.0 | 0.9 | 2.7 | 3.7 | 1.0 | 0.7 | 3.0 | 54.2 | 83.4 | 15.0 |
| M136V_T389A | 2 | 4.1 | 27.1 | 2.8 | 0.6 | 2.8 | 5.9 | 12.0 | 1.0 | 2.5 | 3.3 | 1.0 | 0.7 | 2.6 | 54.6 | 83.3 | 14.8 |
| M136V_T389C+ | 2 | 4.0 | 27.3 | 3.0 | 0.5 | 2.7 | 5.0 | 11.6 | 1.0 | 2.6 | 3.3 | 1.0 | 0.6 | 2.6 | 56.2 | 84.0 | 15.4 |
| M136V_T389S | 2 | 4.0 | 28.2 | 2.8 | 0.6 | 2.8 | 5.8 | 11.7 | 1.0 | 2.5 | 3.3 | 1.0 | 0.7 | 2.6 | 54.8 | 83.7 | 15.5 |
| K137N_T389A | 2 | 3.8 | 25.8 | 3.0 | 0.5 | 3.0 | 5.6 | 12.1 | 1.1 | 2.4 | 3.1 | 0.9 | 0.6 | 2.3 | 55.8 | 83.2 | 14.4 |
| K137N_T389C | 2 | 4.0 | 27.4 | 2.8 | 0.8 | 2.5 | 5.4 | 13.2 | 1.0 | 2.8 | 3.8 | 1.0 | 0.6 | 3.1 | 53.2 | 81.9 | 14.6 |
| K137N_T389S | 2 | 3.9 | 27.2 | 2.7 | 0.7 | 2.7 | 6.0 | 12.3 | 1.0 | 2.6 | 3.5 | 0.9 | 0.6 | 2.6 | 54.8 | 83.0 | 14.9 |
| M136S_T389A+ | 2 | 3.9 | 27.7 | 2.7 | 0.6 | 2.8 | 5.9 | 11.7 | 1.0 | 2.5 | 3.3 | 0.9 | 0.6 | 2.5 | 55.8 | 83.9 | 15.5 |
| M136S_T389C+ | 2 | 3.9 | 26.9 | 3.0 | 0.5 | 2.8 | 5.3 | 11.7 | 1.0 | 2.5 | 3.3 | 0.9 | 0.7 | 2.6 | 56.0 | 83.9 | 15.1 |
| M136S_T389S+ | 2 | 3.7 | 27.7 | 2.8 | 0.6 | 2.9 | 5.8 | 11.4 | 1.0 | 2.3 | 3.1 | 1.0 | 0.7 | 2.4 | 55.8 | 84.1 | 15.5 |
| F141W_T382I | 2 | 3.8 | 28.7 | 2.5 | 0.8 | 2.5 | 5.7 | 11.9 | 0.8 | 2.6 | 4.2 | 1.0 | 0.7 | 3.4 | 53.4 | 83.7 | 15.3 |

TABLE 28

Total Lipid Content, Composition and Delta-9 Elongase Conversion Efficiency in Selected Transformants
Comprising a Vector Encoding YlLPCAT Having Double Amino Acid Substitutions, by Flask Assay (Group II)

| Mutant | # | DCW (g/L) | TFAs % DCW | % TFAs | | | | | | | | | | | | % Conv. | EPA % DCW |
|---|---|---|---|---|---|---|---|---|---|---|---|---|---|---|---|---|---|
| | | | | 16:0 | 16:1 | 18:0 | 18:1 | LA | ALA | EDA | DGLA | ARA | ETrA | ETA | EPA | | |
| WT | | 2.0 | 26.0 | 3.0 | 0.7 | 2.4 | 4.2 | 13.7 | 0.9 | 2.4 | 3.4 | 0.7 | 0.5 | 3.5 | 54.7 | 82 | 14.2 |
| L134A_T382I | | 2.0 | 24.0 | 3.3 | 0.7 | 2.6 | 4.4 | 12.6 | 0.9 | 2.2 | 3.5 | 0.8 | 0.6 | 3.5 | 53.3 | 83 | 12.9 |
| K137N_F390G | | 2.1 | 27.3 | 2.1 | 0.4 | 2.5 | 6.2 | 12.4 | 0.9 | 1.9 | 3.7 | 0.8 | 0.8 | 3.8 | 54.1 | 83 | 14.8 |
| K137H_L388G | | 2.0 | 28.1 | 3.2 | 0.7 | 2.4 | 4.3 | 12.6 | 0.9 | 2.4 | 3.5 | 0.8 | 0.6 | 3.5 | 54.6 | 83 | 15.4 |
| K137H_L388T | | 2.0 | 27.4 | 2.9 | 0.7 | 2.4 | 4.4 | 13.2 | 0.9 | 2.4 | 3.6 | 0.7 | 0.6 | 3.5 | 54.8 | 82 | 15.0 |
| S140H_T382I | | 2.1 | 21.3 | 3.4 | 0.9 | 2.6 | 4.8 | 12.6 | 0.9 | 2.4 | 3.7 | 0.7 | 0.5 | 3.6 | 52.7 | 82 | 11.3 |
| S140H_L388G | | 2.0 | 26.1 | 2.7 | 0.8 | 2.2 | 4.4 | 13.0 | 0.9 | 2.5 | 3.9 | 0.7 | 0.6 | 4.0 | 54.3 | 83 | 14.2 |
| N144A_F390S+ | | 2.1 | 26.2 | 2.6 | 0.4 | 2.8 | 6.7 | 12.0 | 0.8 | 1.9 | 3.2 | 0.7 | 0.5 | 3.1 | 55.9 | 84 | 14.7 |
| D147H_T382I | | 2.1 | 26.6 | 3.0 | 0.7 | 2.3 | 4.6 | 12.4 | 0.9 | 2.4 | 3.6 | 0.8 | 0.5 | 3.7 | 54.3 | 83 | 14.4 |
| G148A_F390S+ | | 2.1 | 27.0 | 2.8 | 0.4 | 3.0 | 6.5 | 12.0 | 0.8 | 2.1 | 2.9 | 0.8 | 0.7 | 3.0 | 55.1 | 83 | 14.9 |
| G148N_T382I+ | | 1.9 | 26.5 | 3.3 | 0.7 | 2.3 | 4.7 | 12.2 | 0.8 | 2.3 | 3.5 | 0.8 | 0.6 | 3.5 | 56.7 | 84 | 15.0 |
| G148N_F390S+ | | 2.1 | 26.7 | 2.8 | 0.4 | 2.9 | 6.5 | 12.0 | 0.8 | 2.0 | 3.0 | 0.7 | 0.6 | 2.9 | 55.9 | 84 | 14.9 |
| G148A_L388T | | 2.0 | 24.7 | 2.5 | 0.6 | 2.2 | 5.4 | 11.7 | 0.9 | 2.2 | 3.6 | 0.8 | 0.5 | 3.7 | 55.1 | 84 | 13.6 |

Of the 25 YlLPCAT double mutants analyzed, each comprising a single amino acid mutation within Motif I and a single amino acid mutation within Motif II, 17 were observed to have both equivalent or improved EPA % TFAs and equivalent or improved % Conv., while the remaining 8 had equivalent or improved % Conv.

Based on the data set forth above, 22 of the 25 YlLPCAT double mutants analyzed above functioned with improved activity when compared to the parent wild type enzyme (SEQ ID NO:40).

Also, the over-expression of certain double-mutant LPCAT polypeptides resulted in increased total lipid content (TFAs % DCW) in the recombinant *Yarrowia*. For example, over-expression of mutant LPCAT polypeptides comprising the S140W_T382P, S140W_T389A, M136V_T389S and F141W_T382I, or K137H_L388G mutation pairs resulted in total lipid contents that were 8% or more increased relative to the total lipid content of the control (Tables 27 and 28). Interestingly, certain transformants had both increased total lipid content and EPA % TFAs. For example, transformants that over-expressed LPCATs with S140W_T389A, M136V_T389C, M136S_T389A, or M136S_T389S mutation pairs had at least a 5% increase in total lipid content and at least a ~3% increase in EPA % TFAs with respect to control (Tables 27 and 28). This is a significant observation since it had previously been difficult to induce a simultaneous increase in both total lipid content and EPA % TFAs. Usually, an increase in total lipid content had corresponded with a decrease in EPA % TFAs, and vice versa.

The double mutant YlLPCAT polypeptides listed in bold and with a "+" in Tables 27 and 28, i.e., M136S_T389A, M136S_T389C, M136S_T389S, M136V_T3890, N144A_F390S, G148A_F390S, G148N_T382I and G148N_F390S, are disclosed herein as SEQ ID NOs:26, 75, 76, 77, 78, 79, 80 and 81, respectively.

What is claimed is:

1. A recombinant microbial cell comprising:
   (i) a down-regulation of an endogenous polynucleotide sequence encoding Sou2 sorbitol utilization protein comprising the amino acid sequence of an Sou2 sorbitol utilization protein selected from the group consisting of *Asperqillus niger, Bifidobacterium dentium, Candida albicans, Candida dubliniensis, Candida orthopsilosis, Candida parapsilosis, Cordyceps militaris, Debaryomyces hansenii, Enterobacter hormaechei, Gaeumannomyces graminis, Glarea lozovensis, Lodderomyces elonqisporus, Maqnaporthe oryzae, Metarhizium acridum, Metarhizium anisopliae, Mycobacterium smeqmatis, Neurospora crassa, Neurospora tetrasperma, Paracoccidioides brasiliensis, Penicillium chrysoqenum, Scheffersomvces stipitis, Uncinocarpus reesii, Verticillium dahliae,* and *Yarrowia lipolytica,* and
   (ii) a polyunsaturated fatty acid (PUFA) biosynthetic pathway, wherein said down-regulation increases the lipid content of the microbial cell and/or decreases the total amount of sugar alcohols produced by the microbial cell, as compared to a suitable control cell.

2. The recombinant microbial cell of claim 1, wherein said down-regulation is due to a mutation of said endogenous polynucleotide sequence.

3. The recombinant microbial cell of claim 2, wherein said mutation is selected from the group consisting of a substitution, deletion and insertion.

4. The recombinant microbial cell of claim 3, wherein said mutation is a deletion that removes
   (i) one or more nucleotides from an open reading frame encoding said Sou2 sorbitol utilization protein, and/or
   (ii) one or more nucleotides of a non-protein-coding sequence located within 500 base pairs of the 5'-end of said open reading frame.

5. The recombinant microbial cell of claim 3, wherein said mutation is an insertion that occurs within
   (i) an open reading frame encoding said Sou2 sorbitol utilization protein, or
   (ii) a non-protein-coding sequence located within 500 base pairs of the 5'-end of said open reading frame.

6. The recombinant microbial cell of claim 1, wherein said PUFA pathway produces at least one PUFA selected from the group consisting of linoleic acid, alpha-linolenic acid, gamma-linolenic acid, stearidonic acid, eicosadienoic acid, dihomo-gamma-linolenic acid, arachidonic acid, eicosatrienoic acid, eicosatetraenoic acid, eicosapentaenoic acid, docosatetraenoic acid, omega-3 docosapentaenoic acid, omega-6 docosapentaenoic acid and docosahexaenoic acid.

7. The recombinant microbial cell of claim 6, wherein said PUFA pathway produces eicosapentaenoic acid.

8. The recombinant microbial cell of claim 1, wherein said sugar alcohols comprise arabitol or mannitol.

9. The recombinant microbial cell of claim 1, wherein said microbial cell is an oleaginous yeast cell.

10. The recombinant microbial cell of claim 9, wherein said oleaginous yeast is a *Yarrowia lipolytica* cell.

11. The recombinant microbial cell of claim 10, wherein the Sou2 sorbitol utilization protein comprises the amino acid sequence set forth in SEQ ID NO:10.

12. The recombinant microbial cell of claim 10, wherein said endogenous polynucleotide sequence comprises the nucleotide sequence set forth in SEQ ID NO:9.

13. A method of producing a microbial oil comprising a polyunsaturated fatty acid (PUFA), said method comprising:
   a) culturing the recombinant microbial cell of claim 1, wherein a microbial oil comprising a PUFA is produced; and
   b) optionally recovering the microbial oil of step (a).

14. The method of claim 13, wherein the microbial oil comprises eicosapentaenoic acid.

* * * * *